US00RE45183E

(19) United States
(12) Reissued Patent
Murray et al.

(10) Patent Number: US RE45,183 E
(45) Date of Reissued Patent: Oct. 7, 2014

(54) HETEROARYL-UREAS AND THEIR USE AS GLUCOKINASE ACTIVATORS

(71) Applicant: Novo Nordisk A/S, Bagsvaerd (DK)

(72) Inventors: Anthony Murray, Hellerup (DK); Jesper Lau, Farum (DK); Lone Jeppesen, Virum (DK); Per Vedsoe, Vaerloese (DK); Michael Ankersen, Stenloese (DK); Jane Marie Lundbeck, Glostrup (DK); Marit Kristiansen, Soeborg (DK); Maria Carmen Valcarce Lopez, Oak Ridge, NC (US); Dharma Rao Polisetti, High Point, NC (US); Govindan Subramanian, Belle Mead, NJ (US); Robert Carl Andrews, Jamestown, NC (US); Daniel P. Christen, Jamestown, NC (US); Jeremy T. Cooper, High Point, NC (US); Kalpathy Chidambareswaran Santhosh, Jamestown, NC (US)

(73) Assignee: Novo Nordisk A/S, Bagsvaerd (DK)

(21) Appl. No.: 13/940,786

(22) Filed: Jul. 12, 2013

Related U.S. Patent Documents

Reissue of:
(64) Patent No.: 7,872,139
Issued: Jan. 18, 2011
Appl. No.: 12/188,402
Filed: Aug. 8, 2008

U.S. Applications:
(63) Continuation of application No. 11/453,330, filed on Jun. 14, 2006, now Pat. No. 7,598,391, which is a continuation of application No. PCT/DK2005/000002, filed on Jan. 6, 2005.

(30) Foreign Application Priority Data

| | | |
|---|---|---|
| Jan. 6, 2004 | (DK) | 2004 00013 |
| Aug. 23, 2004 | (DK) | 2004 01272 |
| Dec. 7, 2004 | (DK) | 2004 01897 |

(51) Int. Cl.
*C07D 417/12* (2006.01)

(52) U.S. Cl.
CPC ..... *C07D 417/12* (2013.01)
USPC ..... 546/270.7; 546/209

(58) Field of Classification Search
CPC ..... C07D 417/12; C07D 417/06
USPC ..... 546/270.7, 209
See application file for complete search history.

(56) References Cited

U.S. PATENT DOCUMENTS

| | | | |
|---|---|---|---|
| 3,734,923 | A | 5/1973 | Dowding et al. |
| 3,862,163 | A | 1/1975 | Boroschewski et al. |
| 3,874,873 | A | 4/1975 | Volpp et al. |
| 3,887,709 | A | 6/1975 | Brzozowski et al. |
| 3,967,950 | A | 7/1976 | Kano et al. |
| 4,153,710 | A | 5/1979 | Brzozowski et al. |
| 4,160,833 | A | 7/1979 | Diel |
| 4,174,398 | A | 11/1979 | Regel et al. |
| 4,175,081 | A | 11/1979 | Driscoll |
| 4,183,856 | A | 1/1980 | Makisumi et al. |
| 4,241,072 | A | 12/1980 | Bolhofer |
| 4,243,404 | A | 1/1981 | Kruger et al. |
| 4,405,644 | A | 9/1983 | Kabbe et al. |
| 4,694,004 | A | 9/1987 | Nakaguti et al. |
| 4,808,722 | A | 2/1989 | Henrie |
| 5,262,415 | A | 11/1993 | Takemoto et al. |
| 5,371,086 | A | 12/1994 | Takemoto et al. |
| 5,556,969 | A | 9/1996 | Chambers et al. |
| 5,846,985 | A | 12/1998 | Murugesan |
| 5,846,990 | A | 12/1998 | Murugesan et al. |
| 5,849,732 | A | 12/1998 | Suzuki et al. |
| 5,849,769 | A | 12/1998 | Lind et al. |
| 5,891,917 | A | 4/1999 | Tang et al. |
| 5,935,993 | A | 8/1999 | Tang et al. |
| 6,001,860 | A | 12/1999 | Hamanaka |
| 6,140,343 | A | 10/2000 | DeNinno et al. |
| 6,180,635 | B1 | 1/2001 | Cheshire et al. |
| 6,225,346 | B1 | 5/2001 | Tang et al. |
| 6,268,384 | B1 | 7/2001 | Novak et al. |
| 6,271,248 | B1 | 8/2001 | Murugesan et al. |
| 6,384,220 | B2 | 5/2002 | Corbett et al. |
| 6,448,290 | B1 | 9/2002 | Ohuchida et al. |

(Continued)

FOREIGN PATENT DOCUMENTS

| | | |
|---|---|---|
| AU | 29937 | 12/1972 |
| CA | 2416229 | 9/2007 |

(Continued)

OTHER PUBLICATIONS

Atwal et al., 1996, "Cardioselective Antiischemic ATP-Sensitive Potassium Channel Openers 4 Structure-Activity Studies on Benzopyranylcyanoguanidines: Replacement of the Benzopyran Portion," Journal of Medicinal Chemistry 39:304-313.

(Continued)

*Primary Examiner* — Robert Havlin

(74) *Attorney, Agent, or Firm* — Rosemarie R. Wilk-Orescan

(57) ABSTRACT

This invention relates to compounds of formula (I)

(I)

which are activators of glucokinase and thus may be useful for the management, treatment, control, or adjunct treatment of diseases, where increasing glucokinase activity is beneficial.

1 Claim, No Drawings

(56) References Cited

U.S. PATENT DOCUMENTS

| | | | |
|---|---|---|---|
| 6,486,184 | B2 | 11/2002 | Kester et al. |
| 6,489,478 | B1 | 12/2002 | DeNinno et al. |
| 6,500,817 | B1 | 12/2002 | Fischer et al. |
| 6,559,168 | B2 | 5/2003 | Marfat et al. |
| 6,608,218 | B2 | 8/2003 | Kester et al. |
| 6,720,347 | B2 | 4/2004 | Rawlins et al. |
| 6,720,427 | B2 | 4/2004 | Sanner et al. |
| 6,784,198 | B1 | 8/2004 | Pevarello et al. |
| 6,863,647 | B2 | 3/2005 | Pevarello et al. |
| 6,875,760 | B2 | 4/2005 | Lau et al. |
| 6,903,125 | B2 | 6/2005 | Kontani et al. |
| 6,916,814 | B2 | 7/2005 | Moss et al. |
| 6,936,629 | B2 | 8/2005 | Chan Chun Kong et al. |
| 7,056,942 | B2 | 6/2006 | Hildesheim et al. |
| 7,196,104 | B2 | 3/2007 | Askew et al. |
| 7,384,967 | B2 | 6/2008 | Polisetti et al. |
| 7,582,769 | B2 | 9/2009 | Murray et al. |
| 2002/0198200 | A1 | 12/2002 | Kester et al. |
| 2003/0171411 | A1 | 9/2003 | Kodra et al. |
| 2003/0220350 | A1 | 11/2003 | Lau et al. |
| 2004/0014789 | A1 | 1/2004 | Lau et al. |
| 2004/0014968 | A1 | 1/2004 | Bizzarro et al. |
| 2007/0054897 | A1 | 3/2007 | Murray et al. |
| 2009/0216013 | A1 | 8/2009 | Murray et al. |

FOREIGN PATENT DOCUMENTS

| | | | |
|---|---|---|---|
| CN | 100506807 | C | 7/2009 |
| DE | 1901501 | | 8/1969 |
| DE | 2040580 | | 4/1971 |
| DE | 20400580 | | 4/1971 |
| DE | 2117807 | | 10/1971 |
| DE | 2129418 | | 12/1971 |
| DE | 2228890 | | 12/1972 |
| DE | 2151766 | | 4/1973 |
| DE | 2431801 | | 1/1975 |
| DE | 2264983 | | 10/1975 |
| DE | 2712630 | | 9/1978 |
| EP | 0129408 | | 12/1984 |
| EP | 0432040 | | 6/1991 |
| EP | 0885890 | | 12/1998 |
| EP | 0979823 | | 2/2000 |
| EP | 1211246 | | 6/2002 |
| EP | 1169312 | | 10/2004 |
| FR | 7.428 | M | 5/1968 |
| FR | 2001083 | | 9/1969 |
| FR | 2215967 | | 8/1974 |
| GB | 2002-536056 | | 3/1957 |
| GB | 771147 | | 3/1957 |
| GB | 1185540 | | 3/1970 |
| GB | 1195672 | | 6/1970 |
| GB | 1282308 | | 7/1972 |
| GB | 1318291 | | 5/1973 |
| HU | 0200396 | | 8/1969 |
| HU | 0200396 | | 7/2002 |
| JP | 64056660 | | 3/1989 |
| JP | 4334374 | | 11/1992 |
| JP | 6016621 | | 1/1994 |
| JP | 6102611 | | 4/1994 |
| JP | 2002-536056 | | 10/2002 |
| RU | 2021258 | | 10/1994 |
| WO | WO 91/04027 | | 4/1991 |
| WO | WO 93/24458 | | 12/1993 |
| WO | WO 94/14801 | | 7/1994 |
| WO | WO 97/24328 | | 7/1997 |
| WO | WO 99/24035 | | 5/1999 |
| WO | WO 99/24416 | | 5/1999 |
| WO | WO 99/32106 | | 7/1999 |
| WO | WO 99/32111 | | 7/1999 |
| WO | WO 99/62890 | | 12/1999 |
| WO | WO 00/17165 | | 3/2000 |
| WO | 00/26186 | A1 | 5/2000 |
| WO | WO 00/26186 | | 5/2000 |
| WO | WO 00/26203 | | 5/2000 |
| WO | WO 00/45742 | | 8/2000 |
| WO | WO 00/53591 | | 9/2000 |
| WO | WO 00/58293 | | 10/2000 |
| WO | WO 01/00206 | | 4/2001 |
| WO | WO 01/44216 | | 6/2001 |
| WO | WO 01/44217 | | 6/2001 |
| WO | WO 01/57008 | | 8/2001 |
| WO | WO 01/83465 | | 11/2001 |
| WO | WO 01/83478 | | 11/2001 |
| WO | WO 01/85706 | | 11/2001 |
| WO | WO 01/85707 | | 11/2001 |
| WO | WO 02/08209 | | 1/2002 |
| WO | WO 02/14311 | | 2/2002 |
| WO | WO 02/46173 | | 6/2002 |
| WO | WO 02/070494 | | 9/2002 |
| WO | WO 03/055482 | | 7/2003 |
| WO | WO 03/070727 | | 8/2003 |
| WO | WO 2004/002481 | | 1/2004 |
| WO | WO 2004/085388 | | 10/2004 |
| WO | WO 2005/066145 | | 7/2005 |
| WO | WO 2005/103050 | | 11/2005 |
| WO | WO 2007/006814 | | 1/2007 |
| WO | WO 2008/084043 | | 7/2008 |
| WO | WO 2008/084044 | | 7/2008 |

OTHER PUBLICATIONS

Chipkin et al., 1994, "Hormone-Fuel Interralationships . . . " Joslin's Diabetes 97-115.

Castelhano et al., 2005, "Glucokinase-Activating Ureas," Bioorganic & Medicinal Chemistry Letters 15:1501-1504.

Colowick, 1973 "The Hexokinases," The Enzymes 9:1-48.

Decombe, 1932, "Acylacetic Esters," Annali Di Chimica Applicata 18:81-187.

English Translation of Decombe, 1932, "Acylacetic Esters," Annali Di Chimica Applicata 18:81-187.

Ferre et al., 1996, "Evidence from transgenic mice that . . . " The Faseb Journal 10:1213-1218.

Gardner, 1948, "The Polyoxyphenol Series III Syntheses of . . . " Canadian Journal of Research 26b:681-693.

Girard et al., 1997, Annual Review of Nutrition 17:325-352.

Glaser et al., 1998, "Familial Hyperinsulinism . . . " The New England Journal of Medicine 338:226-230.

Grassie et al., 1950, "Preliminary Test on Possible New Stabilizers . . . " Canadian Journal of Research 28b:468-484.

Grupe et al., 1995, "Transgenic Knockouts Reveal . . . " Cell 83:69-78.

Goerdeler et al., 1980, "Acylcarbodiimides. IV. Preparation and Some Reactions of Carbamoylcarboiimides," Hcaplus, Accession No. 585914.

Heitmeier et al., 1964, "Hydroxyphenethylamino Derivatives of Various Nitrogen Heterocycles," Journal of Medicinal Chemistry 7(3):288-293.

Liang, et al., 1995, "'Variable Effects of Maturity-Onset-Diabetes- of Youth," Biochemistry 309: 167-173.

Meglasson, et al., 1984, "New Perspectives on . . . " American Journal of Physiology 246:E1-E13.

Mylari et al., 2003, "Design and Synthesis of a Novel Family of Triazine-Based Inhibitors of Sorbitol Dehydrogenase with Oral Activity: 1-{4-[3R,5S-Dimethyl-4-(4-methyl-[1,3,5]triazin-2-yl)-piperazin-1-yl]-[1,3,5]triazin-2-yl)-(R) Ethanol," Bioorganic & Medicinal Chemistry 11:4179-4188.

Printz et al., 1993, "Mammalian Glucokinase," Annual Review of Nutrition 13:463-496.

Purchase et al., 1996, "Tetrazole-Substituted Ureas as Inhibitors of Acyl-COA:Cholesterol O-Acyltransferase (ACAT) A Novel Preparation of Ureas From Weakly Nucleophilic Amines," Bioorganic & Medicinal Chemistry Letters 6(15):1753-1758.

Regel, et al., 1977, "Acylierung an C-2 Von Imidazolen Und Benzimidazolen," Liebigs Annalen Der Chemie 1:1454-158 (or 145-158).

Scheler, 1969, "Heat Developable Diazotype Material," HCAPLUS, Accession No. 444446, Nov. 5, 1968.

Sovetskaya Enthiklopedia, 1983, "Encyclopedic Dictionary," Ovetskaya Enthiklopedia pp. 130-131.

(56) References Cited

OTHER PUBLICATIONS

English Translation of Sovetskaya, Enthiklopedia, pp. 130-1 (1983).
Wawer, 1999, Magnetic Resonance in Chemistry 37(3):189-194.
White et al., 1996, "Heterocyclic Ureas: Inhibitors of Acyl-COA:Cholesterol O-Acyltransferase as Hypocholesterolemic Agents," Journal of Medicinal Chemistry 39(22):4382-4395.
Wolff, 1995, "Burger's Medicinal Chemistry and Drug Discovery," Burger'S Medicinal Chemistry and Drug Discovery 172-178.
Office Action dated Oct. 17, 2006 from the European Patent Office in EP Application No. 02 787 463.5 filed Dec. 19, 2002 by Novo Nordisk A/S.
Non-Final Office Action mailed Feb. 28, 2007 in U.S. Appl. No. 10/323,290, filed Dec. 19, 2002 by Kodra et al.
Final Office Action mailed Sep. 14, 2007 in U.S. Appl. No. 10/323,290, filed Dec. 19, 2002 by Kodra et al.
Final Office Action mailed Dec. 6, 2007 in U.S. Appl. No. 10/323,290, filed Dec. 19, 2002 by Kodra et al.
Non-Final Office Action mailed Apr. 1, 2008 in U.S. Appl. No. 10/323,290, filed Dec. 19, 2002 by Kodra et al.
Notice of Allowance mailed Jan. 28, 2009 in U.S. Appl. No 10/323,290, filed Dec. 12, 2002 by Kodra et al.
Non-Final Office Action mailed May 28, 2009 in U.S. Appl. No. 10/323,290, filed Dec. 19, 2002 by Kodra et al.
Non-Final Office Action mailed Jan. 20, 2010 in U.S. Appl. No. 10/323,290, filed Dec. 19, 2002 by Kodra et al.
Notice of Allowance mailed Oct. 28, 2005 in U.S. Appl. No. 10/679,887, filed Oct. 6, 2003 by Polisetti et al.
Notice of Allowance mailed May 17, 2006 in U.S. Appl. No. 10/679,887, filed Oct. 6, 2003 by Polisetti et al.
Notice of Allowance mailed Aug. 3, 2006 in U.S. Appl. No. 10/679,887, filed Oct. 6, 2003 by Polisetti et al.
Notice of Allowance mailed Nov. 16, 2007 in U.S. Appl. No. 10/679,887, filed Oct. 6, 2003 by Polisetti et al.
Notice of Allowance mailed Jul. 23, 2008 in U.S. Appl. No. 11/365,534, filed Mar. 1, 2006 by Polisetti et al.
Non-Final Office Action mailed Nov. 21, 2008 in U.S. Appl. No. 11/982,248, filed Oct. 31, 2007 by Polisetti et al.
Final Office Action mailed Jul. 24, 2009 in U.S. Appl. No. 11/982,248, filed Oct. 31, 2007 by Polisetti et al.
Notice of Allowance mailed Feb. 25, 2010 in U.S. Appl. No. 11/982,248, filed Oct. 31, 2007 by Polisetti et al.
Notice of Allowance mailed May 11, 2010 in U.S. Appl. No. 11/982,248, filed Oct. 31, 2007 by Polisetti et al.
Non-Final Office Action mailed Jun. 16, 2009 in U.S. Appl. No. 11/981,997, filed Oct. 31, 2007 by Polisetti et al.
Final Office Action mailed Mar. 9, 2010 in U.S. Appl. No. 11/981,997, filed Oct. 31, 2007 by Polisetti et al.
Non-Final Office Action mailed Sep. 27, 2007 in U.S. Appl. No. 11/453,330, filed Jun. 14, 2006 by Murray et al.
Notice of Allowance mailed May 9, 2008 in U.S. Appl. No. 11/453,330, filed Jun. 14, 2006 by Murray et al.
Notice of Allowance mailed Nov. 3, 2008 in U.S. Appl. No. 11/453,330, filed Jun. 14, 206 by Murray et al.
Notice of Allowance mailed May 28, 2009 in U.S. Appl. No. 11/453,330, filed Jun. 14, 2006 by Murray et al.
Non--Final Office Action mailed Sep. 21, 2009 in U.S. Appl. No. 11/994,718, filed Jul. 9, 2008 by Murray et al.
Final Office Action mailed Jun. 18, 2010 in U.S. Appl. No. 11/994,718, filed Jul. 9, 2008 by Murray et al.
Notice of Allowance mailed Jan. 2, 2009 in U.S. Appl. No. 11/994,728, filed Jul. 9, 2008 by Murray et al.
Notice of Allowance mailed Apr. 7, 2009 in U.S. Appl. No. 11/994,728, filed Jul. 9, 2008 by Murray et al.
Non-Final Office Action mailed Mar. 25, 2010 in U.S. Appl. No. 11/994,862, filed Jul. 9, 2008 by Lau et al.
Machine Translation of DE2264983.
Machine Translation of DE2228890.
Machine Translation of DE2151766.
Machine Translation of DE2040580.
Machine Translation of FR7.428M.
Machine Translation of JP6102611.
Abstract of JP 6016621.
Machine Translation of JP4334374.
Evans, et al., 1986. "Design of potent, orally effective, nonpeptidal antagonists of the peptide hormone cholecystokinin," Proceedings of the National Academy of Sciences of the United States of America, vol. 83, No. 13, Juillet 1986, USA pages.
National Institutes of Health Consensus, Ann. Int. Med., vol. 103, pp. 147-151, 1985.
Mann, G.V., N. Eng. J. Med., vol. 291(5), pp. 226-232, 1974.
http://diabetesplanner.com/articles__non__mem/diabetes__what__is__the__treatment__for.htm.
Evans, et al., 1986, "Design of potent, orally effective, nonpeptidal antagonists of the peptide hormone cholecystokinin," Proceedings of the National Academy of Sciences of the United States of America, vol. 83, No. 13, Juillet 1986, USA pages.
English Translation of Sovetskaya, Enthiklopedia, pp. 130-131 (1983).
White et al., 1996, "Heterocyclic Ureas: Inhibitors of Acyl-Coa: Cholesterol O-Acyltransferase As Hypocholesterolemic Agents," Journal of Medicinal Chemistry 39(22):4382-4395.
Notice of Allowance mailed Jan. 28, 2009 in U.S. Appl. No. 10/323,290, filed Dec. 19, 2002 by Kodra et al.
Notice of Allowance mailed Jul. 23, 2008 in U.S. Appl. No. 11/356,534, filed Mar. 1, 2006 by Polisetti et al.
Notice of Allowance mailed Nov. 3, 2008 in U.S. Appl. No. 11/453,330, filed Jun. 14, 2006 by Murray et al.
Non-Final Office Action mailed Sep. 21, 2009 in U.S. Appl. No. 11/994,718, filed Jul. 9, 2008 by Murray et al.

HETEROARYL-UREAS AND THEIR USE AS GLUCOKINASE ACTIVATORS

Matter enclosed in heavy brackets [ ] appears in the original patent but forms no part of this reissue specification; matter printed in italics indicates the additions made by reissue.

FIELD OF THE INVENTION

This invention relates to compounds that are activators of glucokinase and thus may be useful for the management, treatment, control, or adjunct treatment of diseases, where increasing glucokinase activity is beneficial.

BACKGROUND OF THE INVENTION

Diabetes is characterised by an impaired glucose metabolism manifesting itself among other things by an elevated blood glucose level in the diabetic patients. Underlying defects lead to a classification of diabetes into two major groups: Type 1 diabetes, or insulin demanding diabetes mellitus (IDDM), which arises when patients lack β-cells producing insulin in their pancreatic glands, and type 2 diabetes, or non-insulin dependent diabetes mellitus (NIDDM), which occurs in patients with an impaired β-cell function besides a range of other abnormalities.

Type 1 diabetic patients are currently treated with insulin, while the majority of type 2 diabetic patients are treated either with sulphonylureas that stimulate β-cell function or with agents that enhance the tissue sensitivity of the patients towards insulin or with insulin. Among the agents applied to enhance tissue sensitivity towards insulin, metformin is a representative example.

Even though sulphonylureas arc widely used in the treatment of NIDDM this therapy is, in most instances, not satisfactory: In a large number of NIDDM patients sulphonylureas do not suffice to normalise blood sugar levels and the patients are, therefore, at high risk for acquiring diabetic complications. Also, many patients gradually lose the ability to respond to treatment with sulphonylureas and are thus gradually forced into insulin treatment. This shift of patients from oral hypoglycemic agents to insulin therapy is usually ascribed to exhaustion of the β-cells in NIDDM patients.

In normal subjects as well as in diabetic subjects, the liver produces glucose in order to avoid hypoglycemia. This glucose production is derived either from the release of glucose from glycogen stores or from gluconeogenesis, which is a de novo intracellular synthesis of glucose. In type 2 diabetes, however, the regulation of hepatic glucose output is poorly controlled and is increased, and may be doubled after an overnight fast. Moreover, in these patients there exists a strong correlation between the increased fasting plasma glucose levels and the rate of hepatic glucose production. Similarly, hepatic glucose production will be increased in type 1 diabetes, if the disease is not properly controlled by insulin treatment.

Since existing forms of therapy of diabetes does not lead to sufficient glycemic control and therefore are unsatisfactory, there is a great demand for novel therapeutic approaches. Atherosclerosis, a disease of the arteries, is recognized to be the leading cause of death in the United States and Western Europe. The pathological sequence leading to atherosclerosis and occlusive heart disease is well known. The earliest stage in this sequence is the formation of "fatty streaks" in the carotid, coronary and cerebral arteries and in the aorta. These lesions are yellow in colour due to the presence of lipid deposits found principally within smooth-muscle cells and in macrophages of the intima layer of the arteries and aorta. Further, it is postulated that most of the cholesterol found within the fatty streaks, in turn, give rise to development of the "fibrous plaque", which consists of accumulated intimal smooth muscle cells laden with lipid and surrounded by extracellular lipid, collagen, elastin and proteoglycans. The cells plus matrix form a fibrous cap that covers a deeper deposit of cell debris and more extracellular lipid. The lipid is primarily free and esterified cholesterol. The fibrous plaque forms slowly, and is likely in time to become calcified and necrotic, advancing to the "complicated lesion" which accounts for the arterial occlusion and tendency toward mural thrombosis and arterial muscle spasm that characterize advanced atherosclerosis. Epidemiological evidence has firmly established hyperlipidemia as a primary risk factor in causing cardiovascular disease (CVD) due to atherosclerosis. In recent years, leaders of the medical profession have placed renewed emphasis on lowering plasma cholesterol levels, and low density lipoprotein cholesterol in particular, as an essential step in prevention of CVD. The upper limits of "normal" are now known to be significantly lower than heretofore appreciated. As a result, large segments of Western populations are now realized to be at particular high risk. Independent risk factors include glucose intolerance, left ventricular hypertrophy, hypertension, and being of the male sex. Cardiovascular disease is especially prevalent among diabetic subjects, at least in part because of the existence of multiple independent risk factors in this population. Successful treatment of hyperlipidemia in the general population, and in diabetic subjects in particular, is therefore of exceptional medical importance.

Hypertension (or high blood pressure) is a condition, which occurs in the human population as a secondary symptom to various other disorders such as renal artery stenosis, pheochromocytoma, or endocrine disorders. However, hypertension is also evidenced in many patients in whom the causative agent or disorder is unknown. While such "essential" hypertension is often associated with disorders such as obesity, diabetes, and hypertriglyceridemia, the relationship between these disorders has not been elucidated. Additionally, many patients display the symptoms of high blood pressure in the complete absence of any other signs of disease or disorder.

It is known that hypertension can directly lead to heart failure, renal failure, and stroke (brain hemorrhaging). These conditions are capable of causing short-term death in a patient. Hypertension can also contribute to the development of atherosclerosis and coronary disease. These conditions gradually weaken a patient and can lead to long-term death.

The exact cause of essential hypertension is unknown, though a number of factors are believed to contribute to the onset of the disease. Among such factors are stress, uncontrolled emotions, unregulated hormone release (the renin, angiotensin aldosterone system), excessive salt and water due to kidney malfunction, wall thickening and hypertrophy of the vasculature resulting in constricted blood vessels and genetic factors.

The treatment of essential hypertension has been undertaken bearing the foregoing factors in mind. Thus a broad range of beta-blockers, vasoconstrictors, angiotensin converting enzyme inhibitors and the like have been developed and marketed as antihypertensives. The treatment of hypertension utilizing these compounds has proven beneficial in the prevention of short-interval deaths such as heart failure, renal failure, and brain hemorrhaging. However, the development of atherosclerosis or heart disease due to hypertension over a long period of time remains a problem. This implies that although high blood pressure is being reduced, the underlying cause of essential hypertension is not responding to this treatment. Hypertension has been associated with elevated blood insulin levels, a condition known as hyperinsulinemia. Insulin, a peptide hormone whose primary actions are to promote glucose utilization, protein synthesis and the formation and storage of neutral lipids, also acts to promote vascular cell growth and increase renal sodium retention, among other things. These latter functions can be accomplished without affecting glucose levels and are known causes of hypertension. Peripheral vasculature growth, for example, can cause constriction of peripheral capillaries, while sodium retention increases blood volume. Thus, the lowering of insulin levels in hyperinsulinemics can prevent abnormal vascular growth and renal sodium retention caused by high insulin levels and thereby alleviates hypertension.

Cardiac hypertrophy is a significant risk factor in the development of sudden death, myocardial infarction, and congestive heart failure. Theses cardiac events are due, at least in part, to increased susceptibility to myocardial injury after ischemia and reperfusion, which can occur in out-patient as well as perioperative settings. There is an unmet medical need to prevent or minimize adverse myocardial perioperative outcomes, particularly perioperative myocardial infarction. Both non-cardiac and cardiac surgery are associated with substantial risks for myocardial infarction or death. Some 7 million patients undergoing non-cardiac surgery are considered to be at risk, with incidences of perioperative death and serious cardiac complications as high as 20-25% in some series. In addition, of the 400,000 patients undergoing coronary bypass surgery annually, perioperative myocardial infarction is estimated to occur in 5% and death in 1-2%. There is currently no drug therapy in this area, which reduces damage to cardiac tissue from perioperative myocardial ischemia or enhances cardiac resistance to ischemic episodes. Such a therapy is anticipated to be life-saving and reduce hospitalizations, enhance quality of life and reduce overall health care costs of high risk patients. Obesity is a well-known risk factor for the development of many very common diseases such as atherosclerosis, hypertension, and diabetes. The incidence of obese people and thereby also these diseases is increasing throughout the entire industrialised world. Except for exercise, diet and food restriction no convincing pharmacological treatment for reducing body weight effectively and acceptably currently exists. However, due to its indirect but important effect as a risk factor in mortal and common diseases it will be important to find treatment for obesity and/or means of appetite regulation.

The term obesity implies an excess of adipose tissue. In this context obesity is best viewed as any degree of excess adiposity that imparts a health risk. The cut off between normal and obese individuals can only be approximated, but the health risk imparted by the obesity is probably a continuum with increasing adiposity. The Framingham study demonstrated that a 20% excess over desirable weight clearly imparted a health risk (Mann G V N. Engl. J. Med 291:226, 1974). In the United States a National Institutes of Health consensus panel on obesity agreed that a 20% increase in relative weight or a body mass index (BMI=body weight in kilograms divided by the square of the height in meters) above the 85th percentile for young adults constitutes a health risk. By the use of these criteria 20 to 30 percent of adult men and 30 to 40 percent of adult women in the United States are obese. (NIH, Ann Intern Med 103:147, 1985).

Even mild obesity increases the risk for premature death, diabetes, hypertension, atherosclerosis, gallbladder disease, and certain types of cancer. In the industrialised western world the prevalence of obesity has increased significantly in the past few decades. Because of the high prevalence of obesity and its health consequences, its prevention and treatment should be a high public health priority.

When energy intake exceeds expenditure, the excess calories are stored in adipose tissue, and if this net positive balance is prolonged, obesity results, i.e. there are two components to weight balance, and an abnormality on either side (intake or expenditure) can lead to obesity. The regulation of eating behaviour is incompletely understood. To some extent appetite is controlled by discrete areas in the hypothalamus: a feeding centre in the ventrolateral nucleus of the hypothalamus (VLH) and a satiety centre in the ventromedial hypothalamus (VMH). The cerebral cortex receives positive signals from the feeding centre that stimulate eating, and the satiety centre modulates this process by sending inhibitory impulses to the feeding centre. Several regulatory processes may influence these hypothalamic centres. The satiety centre may be activated by the increases in plasma glucose and/or insulin that follow a meal. Meal-induced gastric distension is another possible inhibitory factor. Additionally the hypothalamic centres are sensitive to catecholamines, and beta-adrenergic stimulation inhibits eating behaviour. Ultimately, the cerebral cortex controls eating behaviour, and impulses from the feeding centre to the cerebral cortex are only one input. Psychological, social, and genetic factors also influence food intake.

At present a variety of techniques are available to effect initial weight loss. Unfortunately, initial weight loss is not an optimal therapeutic goal. Rather, the problem is that most obese patients eventually regain their weight. An effective means to establish and/or sustain weight loss is the major challenge in the treatment of obesity today.

SUMMARY OF THE INVENTION

The present invention provides compounds of general formula (I)

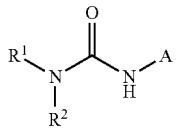

(1)

wherein the substituents are defined below, as well as further embodiments hereof described in the attached dependent claims.

The present invention also provides use of the compounds of the invention for preparation of a medicament for the treatment of various diseases, e.g. for the treatment of type 2 diabetes.

DEFINITIONS

In the structural formulas given herein and throughout the present specification, the following terms have the indicated meaning:

The term "optionally substituted" as used herein means that the moiety which is optionally substituted is either unsubstituted or substituted with one or more of the substituents specified. When the moiety in question is substituted with more than one substituent, the substituent may be the same or different.

The term "adjacent" as used herein regards the relative positions of two atoms or variables, these two atoms or variables sharing a bond or one variable preceding or succeeding the other in a variable specification. By way of example, "atom A adjacent to atom B" means that the two atoms A and B share a bond.

The term "halogen" or "halo" means fluorine, chlorine, bromine or iodine.

The term "perhalomethyl" means trifluoromethyl, trichloromethyl, tribromomethyl, or triiodomethyl.

The use of prefixes of this structure: $C_{x-y}$-alkyl, $C_{x-y}$-alkenyl, $C_{x-y}$-alkynyl, $C_{x-y}$-cycloalyl or $C_{x-y}$-cycloalkyl-$C_{x-y}$-alkenyl- and the like designates radical of the designated type having from x to y carbon atoms.

The term "alkyl" as used herein, alone or in combination, refers to a straight or branched chain saturated monovalent hydrocarbon radical having from one to ten carbon atoms, for example $C_{1-8}$-alkyl or $C_{1-6}$-alkyl. Typical $C_{1-8}$-alkyl groups and $C_{1-6}$-alkyl groups include, but are not limited to e.g. methyl, ethyl, n-propyl, isopropyl, n-butyl, sec-butyl, isobutyl, tert-butyl, n-pentyl, 2-methylbutyl, 3-methylbutyl, 4-methylpentyl, neopentyl, n-pentyl, n-hexyl, 1,2-dimethylpropyl, 2,2-dimethylpropyl, 1,2,2-trimethylpropyl and the like. The term "$C_{1-8}$-alkyl" as used herein also includes secondary $C_{3-8}$-alkyl and tertiary $C_{4-8}$-alkyl. The term "$C_{1-6}$-alkyl" as used herein also includes secondary $C_{3-6}$-alkyl and tertiary $C_{4-6}$-alkyl.

The term "alkenyl" as used herein, alone or in combination, refers to a straight or branched chain monovalent hydrocarbon radical containing from two to ten carbon atoms and at least one carbon-carbon double bond, for example $C_{2-8}$-alkenyl or $C_{2-6}$-alkenyl. Typical $C_{2-8}$-alkenyl groups and $C_{2-6}$-alkenyl groups include, but are not limited to, vinyl, 1-propenyl, 2-propenyl, iso-propenyl, 1,3-butadienyl, 1-butenyl, 2-butenyl, 3-butenyl, 2-methyl-1-propenyl, 1-pentenyl, 2-pentenyl, 3-pentenyl, 4-pentenyl, 3-methyl-2-butenyl, 1-hexenyl, 2-hexenyl, 3-hexenyl, 2,4-hexadienyl, 5-hexenyl and the like.

The term "alkynyl" as used herein alone or in combination, refers to a straight or branched monovalent hydrocarbon radical containing from two to ten carbon atoms and at least one triple carbon-carbon bond, for example $C_{2-8}$-alkynyl or $C_{2-6}$-alkynyl. Typical $C_{2-8}$-alkynyl groups and $C_{2-6}$-alkynyl groups include, but are not limited to, ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 5-hexynyl, 2,4-hexadiynyl and the like.

The term "cycloalkyl" as used herein, alone or in combination, refers to a saturated mono-, bi-, or tricarbocyclic radical having from three to twelve carbon atoms, for example $C_{3-8}$-cycloalkyl. Typical $C_{3-8}$-cycloalkyl groups include, but are not limited to, cyclopropyl, cyclobutyl, cyclopentyl, cyclohexyl, cycloheptyl, cyclooctyl, bicyclo[3.2.1]octyl, bicycle [2.2.1]heptyl, norpinyl, norbonyl, norcaryl, adamantyl and the like.

The term "cycloalkenyl" as used herein, alone or in combination, refers to an non-aromatic unsaturated mono-, bi-, or tricarbocyclic radical having from three to twelve carbon atoms, for example $C_{3-8}$-cycloalkenyl. Typical $C_{3-8}$-cycloalkyl groups include, but are not limited to cyclohexene, cycloheptene and cyclopentene, and the like.

The term "heterocyclic" or the term "heterocyclyl" as used herein, alone or in combination, refers to a saturated mono-, bi-, or tricarbocyclic group having three to twelve carbon atoms and one or two additional heteroatoms or groups selected from nitrogen, oxygen, sulphur, SO or $SO_2$, for example $C_{3-8}$-heterocyclyl. Typical $C_{3-8}$-heterocyclyl groups include, but are not limited to, tetrahydrofuryl, tetrahydrothienyl, tetrahydropyranyl, tetrahydrothiopyranyl, 1,4-dioxanyl, 1,3-dioxanyl, piperidyl, pyrrolidinyl, morpholinyl, piperazinyl, and the like.

The term "heterocycloalkenyl" as used herein, alone or in combination, refers to a non-aromatic unsaturated mono-, bi-, or tricyclic radical having from three to twelve carbon atoms, and one or two additional heteroatoms or groups selected from nitrogen, oxygen, sulphur, SO or $SO_2$, for example $C_{3-8}$-hetereocycloalkenyl. Typical $C_{3-8}$-hetreocycloalkenyl groups include, but are not limited to tetrahydropyridine, azacycloheptene, 2-pyrroline, 3-pyrroline, 2-pyrazoline, imidazoline, 4H-pyran, and the like.

The term "alkoxy" as used herein, alone or in combination, refers to the monovalent radical $R^aO$—, where $R^a$ is alkyl as defined above, for example $C_{1-8}$-alkyl giving $C_{1-8}$-alkoxy. Typical $C_{1-8}$-alkoxy groups include, but are not limited to, methoxy, ethoxy, n-propoxy, isopmpoxy, butoxy, sec-butoxy, tert-butoxy, pentoxy, isopentoxy, hexoxy, isohexoxy and the like.

The term "alkylthio" as used herein, alone or in combination, refers to a straight or branched monovalent radical comprising an alkyl group as described above linked through a divalent sulphur atom having its free valence bond from the sulphur atom, for example $C_{1-6}$-alkylthio. Typical $C_{1-6}$-alkylthio groups include, hut are not limited to, methylthio, ethylthio, propylthio, butylthio, pentylthio, hexylthio and the like.

The term "alkoxycarbonyl" as used herein refers to the monovalent radical $R^aOC(O)$ , where $R^a$ is alkyl as described above, for example $C_{1-8}$-alkoxycarbonyl. Typical $C_{1-8}$-alkoxycarbonyl groups include, but are not limited to, methoxycarbonyl, ethoxycarbonyl, propoxycarbonyl, isopropoxycarbonyl, n-butoxycarbonyl, sec-butoxycarbonyl, tertbutoxycarbonyl, 3-methylbutoxycarbonyl, n-hexoxycarbonyl and the like.

The term "aryl" as used herein refers to a carbocyclic aromatic ring radical or to a aromatic ring system radical. Aryl is also intended to include the partially hydrogenated derivatives of the carbocyclic systems.

The term "heteroaryl", as used herein, alone or in combination, refers to an aromatic ring radical with for instance 5 to 7 member atoms, or to a aromatic ring system radical with for instance from 7 to 18 member atoms, containing one or more heteroatoms selected from nitrogen, oxygen, or sulphur heteroatoms, wherein N-oxides and sulphur monoxides and sulphur dioxides are permissible heteroaromatic substitutions; such as e.g. furanyl, thienyl, thiophenyl, pyrrolyl, imidazolyl, pyrazolyl, triazolyl, tetrazolyl, thiazolyl, oxazolyl, isoxazolyl, oxadiazolyl, thiadiazolyl, isothiazolyl, pyridinyl, pyridazinyl, pyrazinyl, pyrimidinyl, quinolinyl, isoquinolinyl, benzofuranyl, benzothiophenyl, indolyl, and indazolyl, and the like. Heteroaryl is also intended to include the partially hydrogenated derivatives of the heterocyclic systems enumerated below.

Examples of "aryl" and "heteroaryl" includes, but are not limited to phenyl, biphenyl, indene, fluorene, naphthyl (1-naphthyl, 2-naphthyl), anthracene (1-anthracenyl, 2-anthracenyl, 3-anthracenyl), thiophene (2-thienyl, 3-thienyl), furyl (2-furyl, 3-furyl), indolyl, oxadiazolyl, isoxazolyl, thiadiazolyl, oxatriazolyl, thiatriazolyl, quinazolin, fluorenyl, xanthenyl, isoindanyl, benzhydryl, acridinyl, thiazolyl, pyrrolyl (1-pyrrolyl, 2-pyrrolyl, 3-pyrrolyl), pyrazolyl (1-pyrazolyl, 3-pyrazolyl, 4-pyrazolyl, 5-pyrazolyl), imidazolyl (1-imidazolyl, 2-imidazolyl, 4-imidazolyl, 5-imidazolyl), triazolyl (1,2,3 -triazol-1-yl, 1,2,3 -triazol-4-yl 1,2,3-triazol-5-yl, 1,2,4-triazol-3-yl, 1,2,4-triazol-5-yl), oxazolyl (2-oxazolyl, 4-oxazolyl, 5-oxazolyl), isooxazolyl (isooxazo-3-yl, isooxazo-4-yl, isooxaz-5-yl), isothiazolyl (isothiazo-3-yl, isothiazo-4-yl, isothiaz-5-yl) thiazolyl (2-thiazolyl, 4-thiazolyl, 5-thiazolyl), pyridyl (2-pyridyl, 3-pyridyl, 4-pyridyl), pyrimidinyl (2-pyrimidinyl, 4-pyrimidinyl, 5-pyrimidinyl, 6-pyrimidinyl), pyrazinyl, pyridazinyl (3-pyridazinyl, 4-pyridazinyl, 5-pyridazinyl), quinolyl (2-quinolyl, 3-quinolyl, 4-quinolyl, 5-quinolyl, 6-quinolyl, 7-quinolyl, 8-quinolyl), isoquinolyl (1-isoquinolyl, 3 -i soquinolyl, 4-isoquinolyl, 5-isoquinolyl, 6-isoquinolyl, 7-isoquinolyl, 8-isoquinolyl), benzo[b]furanyl (2-benzo[b]furanyl, 3-benzo[b]furanyl, 4-benzo[b]furanyl, 5-benzo[b]furanyl, 6-benzo[b]furanyl, 7-benzo[b]furanyl), 2,3-dihydro-benzo[b]furanyl (2-(2,3-dihydro-benzo[b]furanyl), 3-(2,3-dihydro-benzo[b]furanyl), 4-(2,3-dihydro-benzo[b]furanyl), 5-(2,3-dihydro-benzo[b]furanyl), 6-(2,3-dihydro-benzo[b]furanyl), 7-(2,3-dihydro-benzo[b]furanyl)), benzo[b]thiophenyl (benzo[b]thiophen-2-yl, benzo[b]thiophen-3-yl, benzo[b]thiophen-4-yl, benzo[b]thiophen-5-yl, benzo[b]thiophen-6-yl, benzo[b]thiophen-7-yl), 2,3-dihydro-benzo[b]thiophenyl (2,3-dihydro-benzo[b]thiophen-2-yl, 2,3-dihydro-benzo[b]thiophen-3-yl, 2,3-dihydro-benzo[b]thiophen-4-yl, 2,3-dihydro-benzo[b]thiophen-5-yl, 2,3-dihydro-benzo[b]thiophen-6-yl, 2,3-dihydro-benzo[b]thiophen-7-yl), indolyl (1-indolyl, 2-indolyl, 3-indolyl, 4-indolyl, 5-indolyl, 6-indolyl, 7-indolyl), indazole (1-indazolyl, 3-indazolyl, 4-indazolyl, 5-indazolyl, 6-indazolyl, 7-indazolyl), benzimidazolyl (1-benzimidazolyl, 2-benzimidazolyl, 4-benzimidazolyl, 5-benzimidazolyl, 6-benzimidazolyl, 7-benzimidazolyl, 8-benzimidazolyl), benzoxazolyl (2-benzoxazolyl, 3-benzoxazolyl, 4-benzoxazolyl, 5-benzoxazolyl, 6-benzoxazolyl, 7-benzoxazolyl), benzothiazolyl (2-benzothiazolyl, 4-benzothiazolyl, 5-benzothiazolyl, 6-benzothiazolyl, 7-benzothiazolyl), carbazolyl (1-carbazolyl, 2-carbazolyl, 3-carbazolyl, 4-carbazolyl), 5H-dibenz[b,f]azepine (5H-dibenz[b,f]azepin-1-yl, 5H-dibenz[b,f]azepine-2-yl, 5H-dibenz[b,f]azepine-3-yl, 5H-dibenz[b,f]azepine-4-yl, 5H-dibenz[bf]azepine-5-yl), 10,11-dihydro-5H-dibenz[b,f]azepine (10,11-dihydro-5H-dibenz[b,f]azepine-1-yl, 10,11-dihydro-5H-dibenz[b,f]azepine-2-yl, 10,11-dihydro-5H-dibenz[b,f]azepine-3-yl, 10,11-dihydro-5H-dibenz[b,f]azepine-4-yl, 10,11-dihydro-5H-dibenz[b,f]azepine-5-yl), benzo[1,3]dioxole (2-benzo[1,3]dioxole, 4-benzo[1,3]dioxole, 5-benzo [1,3]dioxole, 6-benzo[1,3]dioxole, 7-benzo[1,3]dioxole), purinyl, and tetrazolyl (5-tetrazolyl, N-tetrazolyl).

The present invention also relates to partly or fully saturated analogues of the ring systems mentioned above.

When two or more of the above defined terms are used in combination, such as in aryl-alkyl, heteroaryl-alkyl, cycloalkyl-$C_{1-6}$-alkyl and the like, it is to be understood that the first mentioned radical is a substituent on the latter mentioned radical, where the point of substitution, i.e. the point of attachment to another part of the molecule, is on the latter of the radicals, for example aryl-alkyl-:

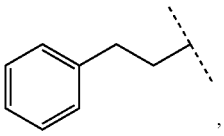

,

-continued cycloalkyl-alkyl-:

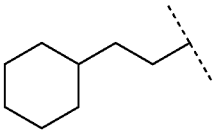

, and aryl-alkoxy-:

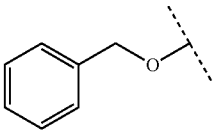

.

The term "fused arylcycloalkyl", as used herein, refers to an aryl group, as defined above, fused to a cycloalkyl group, as defined above and having the indicated number of carbon atoms, the aryl and cycloalkyl groups having two atoms in common, and wherein the cycloalkyl group is the point of substitution. Examples of "fused arylcycloalkyl" used herein include 1-indanyl, 2-indanyl, 1-(1,2,3,4-tetrahydronaphthyl),

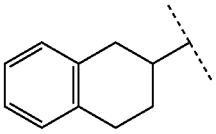

, and the like.

The term "fused heteroarylcycloalkyl", as used herein, refers to a heteroaryl group, as defined above, fused to a cycloalkyl group, as defined above and having the indicated number of carbon atoms, the aryl and cycloalkyl groups having two atoms in common, and wherein the cycloalkyl group is the point of substitution. Examples of fused heteroarylcycloalkyl used herein include 6,7-dihydro-5H-cyclopenta[b]pyridine, 5,6,7,8-tetrahydroquinoline, 5,6,7,8-tetrahydrisoquinoline, 5,6,7,8-tetrahydroquinazoline and the like The term "alkylsulfanyl", as used herein, refers to the group $R^aS$—, where $R^a$ is alkyl as described above.

The term "alkylsulfenyl", as used herein, refers to the group $R^aS(O)$—, where $R^a$ is alkyl as described above.

The term "alkylsulfonyl", as used herein, refers to the group $R^aSO_2$—, where $R^a$ is alkyl as described above.

The term "alkylsulfamoyl", as used herein, refers to the group $R^aNHSO_2$—, where $R^a$ is alkyl as described above.

The term "dialkylsulfamoyl", as used herein, refers to the group $R^aR^bNSO_2$—, where $R^a$ and $R^b$ are alkyl as described above.

The term "alkylsulfinamoyl", as used herein, refers to the group $R^aNHSO$—, where $R^a$ is alkyl as described above.

The term "dialkylsulfinamoyl", as used herein, refers to the group $R^aR^bNSO$—, where $R^a$ and $R^b$ are alkyl as described above.

The term "alkylamino", as used herein, refers to the group $R^aNH$—, where $R^a$ is alkyl as described above.

The term "acyl", as used herein, refers to the group $R^aC(O)$—, where $R^a$ is alkyl, alkenyl, alkynyl, cycloalkyl, cycloalkenyl, or heterocyclyl as described above.

The term "heteroaryloxy" as used herein, alone or in combination, refers to the monovalent radical $R^aO$—, where $R^a$ is heteroaryl as defined above.

The term "aryloxycarbonyl", as used herein, refers to the group $R^a$—O—C(O)—, where $R^a$ is aryl as described above.

The term "acyloxy", as used herein, refers to the group $R^aC(O)O$—, where $R^a$ is alkyl, alkenyl, alkynyl, cycloalkyl, cycloalkenyl, or heterocyclyl as described above.

The term "aryloxy", as used herein refers to the group $R^a$—O—, where $R^a$ is aryl as described above.

The term "aroyloxy", as used herein, refers to the group $R^aC(O)O$—, where $R^a$ is aryl as described above.

The term "heteroaroyloxy", as used herein, refers to the group $R^aC(O)O$—, where $R^a$ is heteroaryl as described above.

Whenever the terms "alkyl", "cycloalkyl", "aryl", "heteroaryl" or the like or either of their prefix roots appear in a name of a substituent (e.g. arylalkoxyaryloxy) they shall be interpreted as including those limitations given above for "alkyl" and "aryl".

As used herein, the term "oxo" shall refer to the substituent O.

As used herein, the term "mercapto" shall refer to the substituent —SH.

As used herein, the term "carboxy" shall refer to the substituent C(O)OH.

As used herein, the term "cyano" shall refer to the substituent —CN.

As used herein, the term "nitro" shall refer to the substituent —$NO_2$.

As used herein, the term "amino sulfonyl" shall refer to the substituent —$SO_2NH_2$.

As used herein, the term "sulfanyl" shall refer to the substituent —S—.

As used herein, the term "sulfenyl" shall refer to the substituent —S(O)—.

As used herein, the term "sulfonyl" shall refer to the substituent —$S(O)_2$—.

As used herein, the term "direct bond", where part of a structural variable specification, refers to the direct joining of the substituents flanking (preceding and succeeding) the variable taken as a "direct bond".

The term "lower", as used herein, refers to an group having between one and six carbons, and may be indicated with the prefix $C_{x-6}$—. Lower alkyl may thus be indicated as $C_{1-6}$-alkyl, while lower alkylene may be indicated as $C_{2-6}$-alkylene.

A radical such as $C_{x-y}$-cycloalkyl-$C_{a-b}$-alkenyl shall designate that the radical's point of attachment is in part of the radical mentioned last.

As used herein, the term "optionally" means that the subsequently described event(s) may or may not occur, and includes both event(s) which occur and events that do not occur.

As used herein, the term "substituted" refers to substitution with the named substituent or substituents, multiple degrees of substitution being allowed unless otherwise stated.

As used herein, the term "attached" or "—" (e.g. —C(O)$R^{11}$ which indicates the carbonyl attachment point to the scaffold) signifies a stable covalent bond.

As used herein, the terms "contain" or "containing" can refer to in-line substitutions at any position along the above defined alkyl, alkenyl, alkynyl or cycloalkyl substituents with one or more of any of O, S, SO, $SO_2$, N, or N-alkyl, including, for example, $CH_2$ O $CH_2$ , $CH_2$ $SO_2$ $CH_2$ , —$CH_2$—NH—$CH_3$ and so forth.

Certain of the above defined terms may occur more than once in the structural formulae, and upon such occurrence each term shall be defined independently of the other.

As used herein, the term "solvate" is a complex of variable stoichiometry formed by a solute (in this invention, a compound of formula (I)) and a solvent. Such solvents for the purpose of the present invention may not interfere with the biological activity of the solute. Solvents may be, by way of example, water, ethanol, or acetic acid.

As used herein, the term "biohydrolyzable ester" is an ester of a drug substance (in this invention, a compound of formula (I)) which either a) does not interfere with the biological activity of the parent substance but confers on that substance advantageous properties in vivo such as duration of action, onset of action, and the like, or b) is biologically inactive but is readily converted in vivo by the subject to the biologically active principle. The advantage is that, for example, the biohydrolyzable ester is orally absorbed from the gut and is transformed to (I) in plasma. Many examples of such are known in the art and include by way of example lower alkyl esters (e.g., $C_{1-4}$), lower acyloxyalkyl esters, lower alkoxyacyloxyalkyl esters, alkoxyacyloxy esters, alkyl acylamino alkyl esters, and choline esters.

As used herein, the term "biohydrolyzable amide" is an amide of a drug substance (in this invention, a compound of general formula (I)) which either a) does not interfere with the biological activity of the parent substance but confers on that substance advantageous properties in vivo such as duration of action, onset of action, and the like, or b) is biologically inactive but is readily converted in vivo by the subject to the biologically active principle. The advantage is that, for example, the biohydrolyzable amide is orally absorbed from the gut and is transformed to (I) in plasma. Many examples of such are known in the art and include by way of example lower alkyl amides, α-amino acid amides, alkoxyacyl amides, and alkylaminoalkylcarbonyl amides.

As used herein, the term "prodrug" includes biohydrolyzable amides and biohydrolyzable esters and also encompasses a) compounds in which the biohydrolyzable functionality in such a pmdrug is encompassed in the compound of formula (1) and b) compounds which may be oxidized or reduced biologically at a given functional group to yield drug substances of formula (I). Examples of these functional groups include, but are not limited to, 1,4-dihydropyridine, N-alkylcarbonyl-1,4-dihydropyridine, 1,4-cyclohexadiene, tert-butyl, and the like.

The term "pharmacologically effective amount" or shall mean that amount of a drug or pharmaceutical agent that will elicit the biological or medical response of a tissue, animal or human that is being sought by a researcher or clinician. This amount can be a therapeutically effective amount. The term "therapeutically effective amount" shall mean that amount of a drug or pharmaceutical agent that will elicit the therapeutic response of an animal or human that is being sought.

The term "treatment" and "treating" as used herein means the management and care of a patient for the purpose of combating a disease, disorder or condition. The term is intended to include the full spectrum of treatments for a given disorder from which the patient is suffering, such as the delaying of the progression of the disease, disorder or condition, the alleviation or relief of symptoms and complications, the prevention of the disease and/or the cure or elimination of the disease, disorder or condition. The patient to be treated is preferably a mammal, in particular a human being.

DESCRIPTION OF THE INVENTION

The present invention provides compounds of general formula (I)

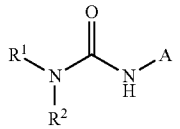

(1)

wherein $R^1$ is $C_{3-8}$-cycloalkyl, $C_{3-8}$-heterocyclyl, or fused aryl-$C_{3-8}$-cycloalkyl, each of which is optionally substituted with one or more substituents $R^3$, $R^4$, $R^5$ and $R^6$;

$R^2$ is $C_{3-8}$-cycloalkyl, $C_{3-8}$-heterocyclyl, or fused aryl-$C_{3-8}$-cycloalkyl, each of which is optionally substituted with one or more substituents $R^{30}$, $R^{31}$, $R^{32}$ and $R^{33}$, and A is heteroaryl, optionally substituted with one or more substituents $R^7$, $R^8$ or $R^9$, and $R^3$, $R^4$, $R^5$, $R^6$, $R^{30}$, $R^{31}$, $R^{32}$ and $R^{33}$ are independently selected from the group consisting of halogen, nitro, cyano, hydroxy, carboxy, —$CF_3$; or —$NR^{10}R^{11}$;

$C_{1-6}$alkyl, $C_{2-6}$alkenyl, $C_{2-6}$-alkynyl, $C_{3-8}$-cycloalkyl, $C_{3-8}$-cycloalkyl-$C_{1-6}$-alkyl, aryl, aryl-$C_{1-6}$-alkyl, heteroaryl-$C_{1-6}$alkyl, $C_{1-6}$-alkoxy, $C_{3-6}$-cycloalkyl-$C_{1-6}$-alkoxy, aryl-$C_{1-6}$-alkoxy, heteroaryl, heteroaryl-$C_{1-6}$-alkoxy, aryloxy, heteroaryloxy, $C_{1-6}$-alkylthio, arylthio, heteroarylthio, aryl-$C_{1-6}$-alkylthio, heteroaryl-$C_{1-6}$-alkylthio, alkylthio, $C_{1-6}$-alkylsulfonyl, $C_{1-6}$-alkylsulfenyl, aryl-sulfonyl, heteroarylsulfonyl, acyl, $C_{3-6}$-cycloalkyl-$C_{1-6}$-alkylthio, —C(O)—O—$C_{1-6}$-alkyl, $C_{1-6}$-alkoxy-$C_{1-6}$-alkyl, $C_{1-6}$-alkylthio-$C_{1-6}$-alkyl, carboxy-$C_{1-6}$-alkyloxy, aroyl, heteroaroyl, amino-$C_{1-6}$-alkyl, $C_{1-6}$-alkylamino-$C_{1-6}$-alkyl, di-($C_{1-6}$-alkyl)amino-$C_{1-6}$-alkyl, $C_{1-6}$alkyl-sulfamoyl, di($C_{1-6}$-alkyl)sulfamoyl, $C_{1-6}$-alkylsulfinamoyl or di($C_{1-6}$-alkyl)sulfinamoyl each of which is optionally substituted with one or more substituents independently selected from $R^{12}$; or —C(O)—$NR^{13}R^{14}$, —$C_{1-6}$-alkyl-C(O)—$NR^{13}R^{14}$; or two substituents selected from $R^3$, $R^4$, $R^5$ and $R^6$ or $R^{30}$, $R^{31}$, $R^{32}$ and $R^{33}$ attached to the same or adjacent atoms together form a radical —O—$(CH_2)_{1-3}$—O—;

$R^{10}$ and $R^{11}$ independently represent hydrogen, $C_{1-6}$-alkyl, —C(O)—$C_{1-6}$-alkyl, carboxy-$C_{1-6}$-alkyl, —C(O)—$C_{1-6}$-alkyl-C(O)OH, —$S(O)_2CH_3$, or aryl;

$R^{12}$ is halogen, cyano, hydroxy, carboxy, —$CF_3$, $C_{1-6}$-alkyl, —$S(O)_2CH_3$, or —$S(O)_2NH_2$;

$R^{13}$ and $R^{14}$ are independently selected from the group consisting of hydrogen, $C_{1-6}$-alkyl, hydroxy-$C_{1-6}$-alkyl, carboxy-$C_{1-6}$-alkyl, aryl, or heteroaryl, each of which is optionally substituted with one or more substituents independently selected from $R^{15}$; or $R^{13}$ and $R^{14}$ together with the nitrogen to which they are attached form a heterocycle such as piperazine, homopiperazine or morpholine;

$R^{15}$ is halogen, cyano, hydroxy, carboxy, —$CF_3$, $C_{1-6}$-alkyl, —$S(O)_2CH_3$, or —$S(O)_2NH_2$;

A is heteroaryl which is optionally substituted with one or more substituents independently selected from $R^7$, $R^8$ and $R^9$;

$R^7$, $R^8$ and $R^9$ are independently selected from halogen, carboxy, cyano, nitro, hydroxy, $CF_3$, SCN; or $C_{1-6}$-alkyl, $C_{2-6}$-alkenyl, $C_{2-6}$alkynyl, $C_{2-6}$-alkoxy, $C_{1-6}$-alkylthio, $C_{1-6}$-alkylamino, $C_{1-6}$alkylsulfonyl, $C_{1-6}$-alkylsulfenyl, —C(O)—O—$C_{1-6}$-alkyl, —C(O)—$C_{1-6}$-alkyl, —$C_{1-6}$alkyl-C(O)—O—$C_{1-6}$-alkyl, —$C_{1-6}$-alkyl-O—C(O)—$C_{1-6}$-alkyl, —NH—C(O)—$C_{1-6}$-alkyl, —$C_{1-6}$-alkoxy-$C_{1-6}$-alkyl, —$C_{1-6}$-alkyl-S—$C_{1-6}$-alkyl, carboxy-$C_{1-6}$-alkyl, or hydroxy-$C_{1-6}$-alkyl, each of which is optionally substituted with one or more substituents independently selected from $R^{16}$; or aryl, heteroaryl, aryl-$C_{1-6}$-alkyl, heteroaryl-$C_{1-6}$-alkyl, aryl-$C_{1-6}$-alkoxy, heteroaryl-$C_{1-6}$-alkoxy, aryl-$C_{1-6}$-alkylthio, heteroaryl-$C_{1-6}$-alkylthio, heteroaryl-thio-$C_{1-6}$-alkyl, aryloxy, heteroaryloxy, arylthio, heteroarylthio, arylsulfonyl, heteroarylsulfonyl, aryl-$C_{1-6}$-alkylamino, each of which is optionally substituted on the aryl or heteroaryl part with one or more substituents independently selected from $R^{17}$; or $C_{3-8}$-cycloalkyl, $C_{3-8}$-cycloalkenyl, $C_{3-8}$-cycloalkyl-$C_{1-6}$-alkyl, $C_{3-8}$-cycloalkenyl-$C_{1-6}$ -alkyl, $C_{3-6}$-cycloalkyl-$C_{1-6}$-alkoxy, $C_{3-6}$-cycloalkyl-$C_{1-6}$-alkylthio, each of which is optionally substituted on the cycloalkyl part with one or more substituents independently selected from $R^{18}$; or —$NR^{19}R^{20}$, —$C_{1-6}$-alkyl-$NR^{19}R^{20}$, —$C_{1-6}$-alkyl-S—$R^{21}$, —$C_{1-6}$-alkyl-S(O)—$R^{21}$, —$C_{1-6}$-alkyl-$S(O)_2$—$R^{21}$ wherein each alkyl part may be substituted with one or more substituents independently selected from $R^{25}$; or —C(O)$NR^{22}R^{23}$, —$C_{1-6}$-alkyl-C(O)$NR^{22}R^{23}$ optionally substituted with one or more substituents independently selected from $R^{26}$; or two of $R^7$, $R^8$ and $R^9$ can be taken together to form a $C_{2-5}$-alkylene bridge;

$R^{16}$, $R^{17}$, and $R^{18}$ are independently $C_{1-6}$alkyl, halogen, nitro, cyano, hydroxy, carboxy, $CF_3$, carboxy-$C_{1-6}$-alkyl, hydroxy-$C_{1-6}$-alkyl, —$C_{1-6}$-alkyl-C(O)—O—$C_{1-6}$-alkyl, —C(O)—O—$C_{1-6}$-alkyl, —$S(O)_2CH_3$, or —$S(O)_2NH_2$;

$R^{19}$ and $R^{20}$ independently represent hydrogen, $C_{1-6}$-alkyl, hydroxy-$C_{1-6}$-alkyl, carboxy-$C_{1-6}$-alkyl, aryl, heteroaryl or $R^{17}$ and $R^{18}$ together with the nitrogen to which they are attached form a heterocycle such as piperazine, homopiperazine or morpholine;

$R^{21}$ is selected from $C_{1-6}$-alkyl, carboxy-$C_{1-6}$-alkyl, $C_{1-6}$-alkylamino-$C_{1-6}$-alkyl or hydroxy-$C_{1-6}$-alkyl; or aryl, heteroaryl, aryl-$C_{1-6}$-alkyl, or heteroaryl-$C_{1-6}$-alkyl, wherein the aryl or heteroaryl part is optionally substituted with one or more substituents independently selected from $R^{24}$; or $C_{3-8}$-cycloalkyl, $C_{3-8}$-cycloalkenyl, $C_{3-8}$-cycloalkyl-$C_{1-6}$-alkyl, $C_{3-8}$-cycloalkenyl-$C_{1-6}$-alkyl.

$R^{22}$ and $R^{23}$ are independently selected from hydrogen and $C_{1-6}$-alkyl.

$R^{24}$ is halogen, nitro, cyano, hydroxy, carboxy, —$CF_3$, $C_{1-6}$-alkyl, hydroxy-$C_{1-6}$-alkyl, or carboxy-$C_{1-6}$-alkyl.

$R^{25}$ and $R^{26}$ are independently $C_{1-6}$-alkyl, halogen, nitro, cyano, hydroxy, carboxy, —$CF_3$, —$S(O)_2CH_3$, or —$S(O)_2NH_2$ as well as any salt hereof with a pharmaceutically acceptable acid or base, or any optical isomer or mixture of optical isomers, including a racemic mixture, or any tautomeric forms.

In another embodiment $R^1$ is $C_{3-8}$-cycloalkyl, tetrahydrofuryl, tetrahydrothiofuryl, tetrahydrothienyl, tetrahydropyranyl, tetrahydrothiopyranyl, 1,4-dioxanyl, 1,3-dioxanyl, piperidyl, pyrrolidinyl, morpholinyl, or piperazinyl, each of which is optionally substituted with one or more substituents $R^3$, $R^4$, $R^5$ and $R^6$.

In another embodiment $R^1$ is cyclopropyl, cyclobutyl, cyclopentyl, cyclohexyl, cyclohexenyl, cycloheptyl, cycloheptenyl, cyclooctyl, bicyclo[3.2.1]octyl, bicyclo[2.2.1]heptyl, norpinyl, norbonyl, norcaryl, adamantyl, tetrahydrofuryl, tetrahydrothiofuryl, tetrahydrothienyl, tetrahydropyranyl, tetrahydrothiopyranyl, 1,4-dioxanyl, 1,3-dioxanyl, piperidyl, pyrrolidinyl, morpholinyl, or piperazinyl, each of which is optionally substituted with one or more substituents $R^3$, $R^4$, $R^5$ and $R^6$.

In another embodiment $R^1$ is cyclopropyl, cyclobutyl, cyclopentyl, cyclohexyl, bicyclo [3.2.1]octyl, bicyclo [2.2.1] heptyl, adamantyl, tetrahydrofuryl, tetrahydrothienyl, tetrahydropyranyl, tetrahydrothiopyranyl, piperidyl, pyrrolidinyl, morpholinyl, or piperazinyl, each of which is optionally substituted with one or more substituents $R^3$, $R^4$, $R^5$ and $R^6$.

In another embodiment $R^1$ is cyclopentyl, cyclohexyl, bicyclo [2.2.1]heptyl, tetrahydrofuryl, tetrahydrothienyl, tetrahydropyranyl, tetrahydrothiopyranyl, piperidyl, pyrrolidinyl, morpholinyl, or piperazinyl, each of which is optionally substituted with one or more substituents $R^3$, $R^4$, $R^5$ and $R^6$.

In another embodiment $R^1$ is selected from

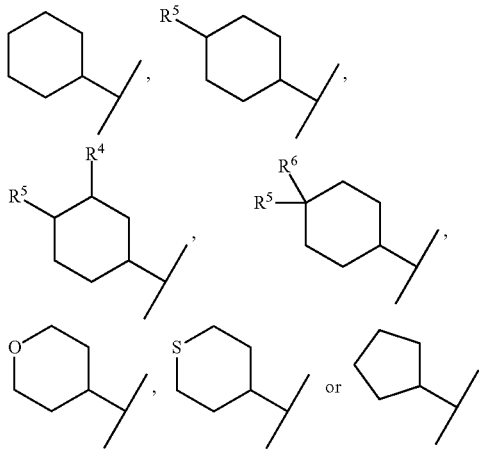

In another embodiment $R^1$ is selected from

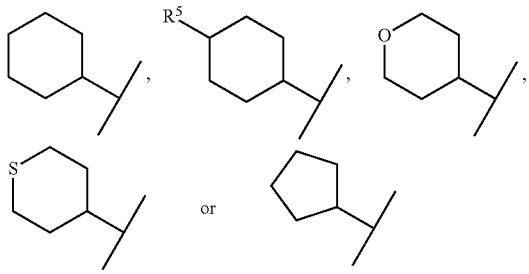

In another embodiment $R^1$ is selected from

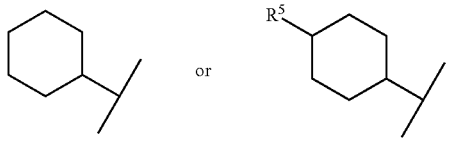

In another embodiment $R^2$ is $C_{3-8}$-cycloalkyl, tetrahydrofuryl, tetrahydrothiofuryl, tetrahydrothienyl, tetrahydropyranyl, tetrahydrothiopyranyl, 1,4-dioxanyl, 1,3-dioxanyl, piperidyl, pyrrolidinyl, morpholinyl, or piperazinyl, each of which is optionally substituted with one or more substituents $R^{30}$,$R^{31}R^{32}$ and $R^{33}$.

In another embodiment $R^2$ is cyclopropyl, cyclobutyl, cyclopentyl, cyclohexyl, cyclohexenyl, cycloheptyl, cycloheptenyl, cyclooctyl, bicyclo[3.2.1 ]octyl, bicyclo[2.2.1]heptyl, norpinyl, norbonyl, norcaryl, adamantyl, tetrahydrofuryl, tetrahydrothiofuryl, tetrahydrothienyl, tetrahydropyranyl, tetrahydrothiopyranyl, 1,4-dioxanyl, 1,3-dioxanyl, piperidyl, pyrrolidinyl, morpholinyl, or piperazinyl, each of which is optionally substituted with one or more substituents $R^{30}$, $R^{31}$, $R^{32}$ and $R^{33}$.

In another embodiment $R^2$ is cyclopropyl, cyclobutyl, cyclopentyl, cyclohexyl, bicyclo[3.2.1]octyl, bicyclo[2.2.1] heptyl, adamantyl, tetrahydrofuryl, tetrahydrothienyl, tetrahydropyranyl, tetrahydrothiopyranyl, piperidyl, pyrrolidinyl, morpholinyl, or piperazinyl, each of which is optionally substituted with one or more substituents $R^{30}$, $R^{31}$, $R^{32}$ and $R^{33}$.

In another embodiment $R^2$ is cyclopentyl, cyclohexyl, bicyclo[2.2.1]heptyl, tetrahydrofuryl, tetrahydrothienyl, tetrahydropyranyl, tetrahydrothiopyranyl, piperidyl, pyrrolidinyl, morpholinyl, or piperazinyl, each of which is optionally substituted with one or more substituents $R^{30}$, $R^{31}$, $R^{32}$ and $R^{33}$.

In another embodiment $R^2$ is selected from

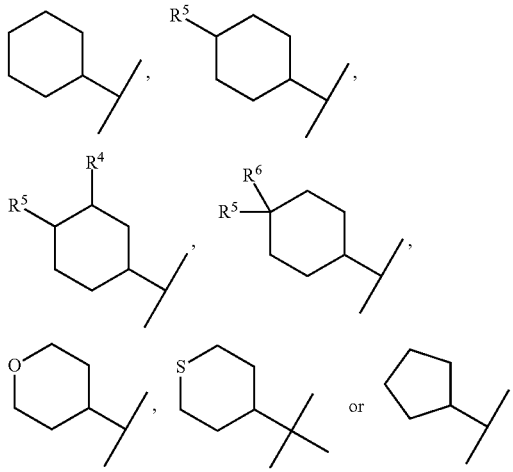

In another embodiment $R^2$ is selected from

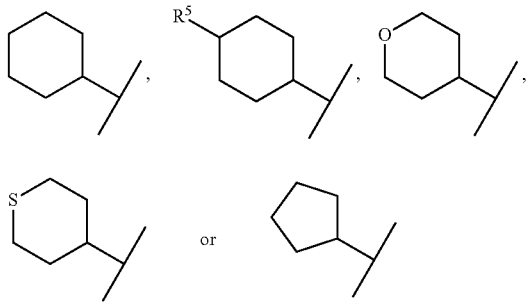

In another embodiment $R^2$ is selected from

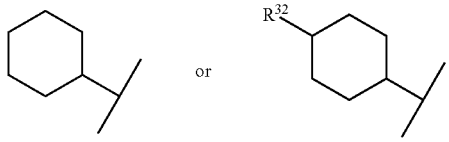

In another embodiment $R^1$ and $R^2$ are both cyclohexyl.

In another embodiment $R^3$, $R^4$, $R^5$, $R^6$, $R^{30}$, $R^{31}$, $R^{32}$ and $R^{33}$ are independently selected from the group consisting of halogen, cyano, hydroxy, carboxy, —$CF_3$; or $C_{1-6}$-alkyl, $C_{2-6}$-alkenyl, $C_{3-8}$-cycloalkyl, $C_{3-8}$-cycloalkyl-$C_{1-6}$-alkyl, aryl, aryl-$C_{1-6}$-alkyl, $C_{1-6}$-alkoxy, $C_{3-6}$-cycloalkyl-$C_{1-6}$-alkoxy, aryl-$C_{1-6}$-alkoxy, $C_{1-6}$-alkylthio, arylthio , $C_{1-6}$-alkylsulfonyl , $C_{1-6}$-alkyl-carbonyl, —C(O)—O—$C_{1-6}$-alkyl, each of which is optionally substituted with one or more substituents independently selected from $R^{12}$; or —C(O)—$NR^{13}R^{14}$, —$C_{1-6}$-alkyl-C(O)—$NR^{13}R^{14}$; or two substituents selected from $R^3$, $R^4$, $R^5$ and $R^6$ or $R^{30}$, $R^{31}$, $R^{32}$ and $R^{33}$ attached to the same or adjacent atoms together form a radical —O—$(CH_2)_{1-3}$—O—.

In another embodiment $R^3$, $R^4$, $R^5$, $R^6$, $R^{30}$, $R^{31}$, $R^{32}$ and $R^{33}$ are independently selected from the group consisting of halogen, —$CF_3$, methyl, ethyl, propyl, isopropyl, butyl, tert-butyl, cyclopropyl, cyclobutyl, cyclopentyl, cyclohexyl, phenyl, naphtyl, benzyl, phenyl-ethyl, methoxy, ethoxy, phenylthio, methylsulfonyl, ethylsulfonyl, methylcarbonyl, ethylcarbonyl, —C(O)—O—$CH_3$, —C(O)—O—$CH_2CH_3$, each of which is optionally substituted with one or more substituents independently selected from $R^{12}$; or two substituents selected from $R^3$, $R^4$, $R^5$ and $R^6$ or $R^{30}$, $R^{31}$, $R^{32}$ and $R^{33}$ attached to the same or adjacent atoms together form a radical —O—$(CH_2)_{1-3}$—O—.

In another embodiment $R^3$, $R^4$, $R^5$, $R^6$,$R^{30}$, $R^{31}$, $R^{32}$ and $R^{33}$ are independently selected from the group consisting of F, Cl, —$CF_3$, methyl, ethyl, propyl, isopropyl, butyl, or tert-butyl; or two substituents selected from $R^3$, $R^4$, $R^5$ and $R^6$ or $R^{30}$, $R^{31}$, $R^{32}$ and $R^{33}$ attached to the same or adjacent atoms together form a radical —O—$(CH_2)_{1-3}$—O—.

In another embodiment $R^{10}$ and $R^{11}$ independently represent hydrogen, methyl, ethyl, propyl, C(O) $CH_3$, —C(O)—$CH_2CH_3$, —$CH_2$C(O)OH, —$CH_2CH_2$C(O)OH, —C(O)—$CH_2$—C(O)OH, —C(O)—$CH_2CH_2$—C(O)OH, —S(O)$_2CH_3$, or phenyl.

In another embodiment $R^{10}$ and $R^{11}$ independently represent hydrogen, methyl, ethyl, —C(O)—$CH_3$, —$CH_2$C(O)OH, —C(O)—$CH_2$—C(O)OH, —S(O)$_2CH_3$, or phenyl.

In another embodiment $R^{10}$ and $R^{11}$ independently represent hydrogen, methyl, ethyl, or phenyl.

In another embodiment $R^{12}$ is halogen, cyano, hydroxy, carboxy, —$CF_3$, or $C_{1-6}$-alkyl.

In another embodiment $R^{12}$ is halogen, cyano, hydroxy, carboxy, $CF_3$, methyl, ethyl or propyl.

In another embodiment $R^{13}$ and $R^{14}$ are independently selected from the group consisting of hydrogen, $C_{1-6}$-alkyl, hydroxy-$C_{1-6}$-alkyl, carboxy-$C_{1-6}$-alkyl, phenyl, or naphtyl, each of which is optionally substituted with one or more substituents independently selected from $R^{15}$; or $R^{13}$ and $R^{14}$ together with the nitrogen to which they are attached form a heterocycle such as piperazine, homopiperazine or morpholine.

In another embodiment $R^{13}$ and $R^{14}$ are independently selected from the group consisting of hydrogen, methyl, ethyl, propyl, hydroxy-methyl, hydroxy-ethyl, carboxy-methyl, carboxy-ethyl, phenyl, or naphtyl, each of which is optionally substituted with one or more substituents independently selected from $R^{15}$; or $R^{13}$ and $R^{14}$ together with the nitrogen to which they are attached form a heterocycle such as piperazine, homopiperazine or morpholine.

In another embodiment $R^{13}$ and $R^{14}$ are independently selected from the group consisting of hydrogen, methyl, ethyl, propyl, or phenyl, each of which is optionally substituted with one or more substituents independently selected from $R^{15}$.

In another embodiment $R^{15}$ is halogen, cyano, hydroxy, carboxy, $CF_3$, methyl, ethyl, or propyl.

In another embodiment $R^{15}$ is halogen, hydroxy, carboxy, —$CF_3$, methyl, or ethyl.

In another embodiment A is thiazolyl, thiadiazolyl, pyrazinyl or 4,5,6,7-tetrahydrobenzothiazolyl optionally substituted with one or more substituents independently selected from $R^7$, $R^8$ and $R^9$.

In another embodiment A is

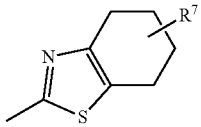

In another embodiment A is thiazolyl or thiadiazolyl optionally substituted with one or more substituents independently selected from $R^7$, $R^8$ and $R^9$.

In another embodiment A is thiazolyl, 1,2,4-thiadiazolyl, or 1,3,4-thiadiazolyl, optionally substituted with one or more substituents independently selected from $R^7$, $R^8$ and $R^9$.

In another embodiment A is

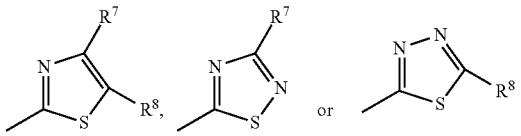

In another embodiment $R^7$, $R^8$ and $R^9$ are independently selected from halogen, carboxy, cyano, nitro, hydroxy, —$CF_3$, —SCN; or $C_{1-6}$-alkyl, $C_{2-6}$-alkenyl, $C_{1-6}$-alkoxy, $C_{1-6}$-alkylthio, $C_{1-6}$-alkylamino, $C_{1-6}$-alkylsulfonyl, $C_{1-6}$-alkylsulfenyl, —C(O)—O—$C_{1-6}$-alkyl, —C(O)—$C_{1-6}$-alkyl, —$C_{1-6}$-alkyl-C(O)—O—$C_{1-6}$-alkyl, —$C_{1-6}$-alkyl-O—C(O)—$C_{1-6}$-alkyl, —NH—C(O)—$C_{1-6}$-alkyl, —$C_{1-6}$-alkoxy-$C_{1-6}$-alkyl, $C_{1-6}$-alkyl-S $C_{1-6}$-alkyl, $C_{3-8}$-cycloalkyl-$C_{1-6}$-alkyl, $C_{3-6}$-cycloalkyl-$C_{1-6}$-alkoxy, $C_{3-6}$-cycloalkyl-$C_{1-6}$-alkylthio each of which is optionally substituted with one or more substituents independently selected from $R^{16}$; or aryl, heteroaryl, aryl-$C_{1-6}$-alkyl, heteroaryl-$C_{1-6}$-alkyl, aryl-$C_{1-6}$-alkoxy, heteroaryl-$C_{1-6}$-alkoxy, aryloxy, heteroaryloxy, heteroarylthio, each of which is optionally substituted on the aryl or heteroaryl part with one or more substituents independently selected from $R^{17}$; or $C_{3-8}$-cycloalkyl, $C_{3-8}$-cycloalkenyl, $C_{3-8}$-cycloalkyl-$C_{1-6}$-alkyl, $C_{3-8}$-cycloalkenyl-$C_{1-6}$-alkyl, each of which is optionally substituted on the cycloalkyl part with one or more substituents independently selected from $R^{18}$; or —$NR^{19}R^{20}$, —$C_{1-6}$-alkyl-$NR^{19}R^{20}$, —$C_{1-6}$-alkyl-S—$R^{21}$, —$C_{1-6}$-alkyl-S(O)—$R^{21}$, —$C_{1-6}$-alkyl-$S(O)_2$—$R^{21}$ wherein each alkyl part may be substituted with one or more substituents independently selected from $R^{25}$; or —C(O)$NR^{22}R^{23}$, —$C_{1-6}$-alkyl-C(O)$NR^{22}R^{23}$ optionally substituted with one or more substituents independently selected from $R^{26}$; or two of $R^7$, $R^8$ and $R^9$ can be taken together to form a $C_{2-5}$-alkylene bridge.

In another embodiment $R^7$, $R^8$ and $R^9$ are independently selected from halogen, carboxy, cyano, or —$CF_3$; or $C_{1-6}$-alkyl, $C_{2-6}$-alkenyl, $C_{1-6}$-alkoxy, $C_{1-6}$-alkylthio, $C_{1-6}$-alkylsulfonyl, —C(O)—O—$C_{1-6}$-alkyl, —C(O)—$C_{1-6}$-alkyl, —$C_{1-6}$-alkyl-C(O)—O—$C_{1-6}$-alkyl, —$C_{1-6}$-alkyl-O—C(O)—$C_{1-6}$-alkyl, —$C_{1-6}$-alkoxy-$C_{1-6}$-alkyl, $C_{3-8}$-cycloalkyl-$C_{1-6}$-alkyl, each of which is optionally substituted with one or more substituents independently selected from $R^{16}$; or aryl, heteroaryl, aryl-$C_{1-6}$-alkyl, heteroaryl-$C_{1-6}$-alkyl, each of which is optionally substituted on the aryl or heteroaryl part with one or more substituents independently selected from $R^{17}$; or $C_{3-8}$cycloalkyl, $C_{3-8}$-cycloalkyl-$C_{1-6}$-alkyl, each of which is optionally substituted on the cycloalkyl part with one or more substituents independently selected from $R^{18}$; or $NR^{19}R^{20}$, $C_{1-6}$-alkyl-$NR^{19}R^{20}$, wherein each alkyl part may be substituted with one or more substituents independently selected from $R^{25}$; or —C(O)$NR^{22}R^{23}$, —$C_{1-6}$-alkyl-C(O)$NR^{22}R^{23}$ optionally substituted with one or more substituents independently selected from $R^{26}$; or two of $R^7$, $R^8$ and $R^9$ can be taken together to form a $C_{2-5}$-alkylene bridge.

In another embodiment $R^7$, $R^8$ and $R^9$ are independently selected from halogen, carboxy or —$CF_3$; or $C_{1-6}$-alkyl, $C_{1-6}$-alkoxy, $C_{1-6}$-alkylthio, $C_{1-6}$-alkyl-C(O)—O—$C_{1-6}$-alkyl, —$C_{1-6}$-alkyl-O—C(O)—$C_{1-6}$-alkyl or —C(O)—O—$C_{1-6}$-alkyl, each of which is optionally substituted with one or more substituents independently selected from $R^{16}$; or phenyl, benzyl, or heteroarylthio, wherein heteroaryl is pyridyl or imidazolyl, and wherein each aryl or heteroaryl is optionally substituted on the aryl or heteroaryl part with one or more substituents independently selected from $R^{17}$; or cyclopropyl, cyclobutyl, cyclopentyl, or cyclohexyl, each of which is optionally substituted on the cycloalkyl part with one or more substituents independently selected from $R^{18}$; or two of $R^7$, $R^8$ and $R^9$ can be taken together to form a $C_{2-5}$-alkylene bridge.

In another embodiment $R^7$, $R^8$ and $R^9$ are independently selected from halogen, carboxy, —$CF_3$, —S—$CH_3$, —S—$CH_2CH_3$, methyl, ethyl, propyl, isopropyl, butyl, tert-butyl, methoxy, ethoxy, —$CH_2$—C(O)—O—$CH_3$, —$CH_2$—C(O)—O—$CH_2CH_3$, —$CH_2CH_2$—C(O)—O—$CH_3$, —$CH_2CH_2$—C(O)—O—$CH_2CH_3$. —$CH_2$—O—C(O)—$CH_3$, —$CH_2$O—C(O)—$CH_2CH_3$, —$CH_2CH_2$—O—C(O)—$CH_3$, —$CH_2CH_2$—O—C(O)—$CH_2CH_3$, —C(O)—O—$CH_3$, or —C(O)—O—$CH_2CH_3$, each of which is optionally substituted with one or more substituents independently selected from $R^{16}$; or heteroarylthio, wherein heteroaryl is pyridyl or imidazolyl, each optionally substituted on the heteroaryl part with one or more substituents independently selected from $R^{17}$.

In another embodiment $R^7$, $R^8$ and $R^9$ are independently selected from Cl, F, Br, $CF_3$, methyl, ethyl, methoxy, ethoxy, —$CH_2$—C(O)—O—$CH_2CH_3$, —C(O)—O—$CH_3$, or —C(O)—O—$CH_2CH_3$; or heteroarylthio, wherein heteroaryl is pyridyl or imidazolyl, each optionally substituted on the heteroaryl part with one or more substituents independently selected from $R^{17}$.

In another embodiment $R^{16}$, $R^{17}$, and $R^{18}$ are independently $C_{1-6}$-alkyl, halogen, hydroxy, carboxy, —$CF_3$, carboxy-$C_{1-6}$-alkyl, hydroxy-$C_{1-6}$-alkyl, —$C_{1-6}$-alkyl-C(O)—O—$C_{1-6}$-alkyl, —C(O)—O—$C_{1-6}$-alkyl, or —$S(O)_2CH_3$.

In another embodiment $R^{16}$, $R^{17}$, and $R^{18}$ are independently methyl, ethyl, propyl, halogen, hydroxy, carboxy, —$CF_3$, carboxy-methyl, carboxy-ethyl, carboxy-propyl, hydroxy-methyl, hydroxy-ethyl, hydroxy-propyl, —$CH_2$—C(O)—O—$CH_3$, —$CH_2$C(O)—O—$CH_2CH_3$, —$CH_2CH_2$—C(O)—O—$CH_3$, —$CH_2CH_2$—C(O)—O—$CH_2CH_3$, —C(O)—O—$CH_3$, —C(O)—O—$CH_2CH_3$, —C(O)—O—$CH_2CH_2CH_3$, or —$S(O)_2CH_3$.

In another embodiment $R^{16}$, $R^{17}$, and $R^{18}$ are independently methyl, ethyl, propyl, halogen, carboxy, carboxy-methyl, carboxy-ethyl, carboxy-propyl, hydroxy-methyl, hydroxy-ethyl, hydroxy-propyl, —$CH_2$—C(O)—O—$CH_3$, —$CH_2$—C(O)—O—$CH_2CH_3$, —$CH_2CH_2$—C(O)—O—$CH_3$, —$CH_2CH_2$—C(O)—O—$CH_2CH_3$, —C(O)—O—$CH_3$, —C(O)—O—$CH_2CH_3$, —C(O)—O—$CH_2CH_2CH_3$, or —$S(O)_2CH_3$.

In another embodiment $R^{19}$ and $R^{20}$ independently represent hydrogen, $C_{1-6}$-alkyl, hydroxy-$C_{1-6}$-alkyl, carboxy-$C_{1-6}$-alkyl, phenyl, or naphtyl, or $R^{17}$ and $R^{18}$ together with the nitrogen to which they are attached form a heterocycle such as piperazine, homopiperazine or morpholine.

In another embodiment $R^{19}$ and $R^{20}$ independently represent hydrogen, methyl, ethyl, propyl, carboxy-methyl, carboxy-ethyl, carboxy-propyl, hydroxy-methyl, hydroxy-ethyl, hydroxy-propyl, phenyl, or naphtyl, or $R^{17}$ and $R^{18}$ together with the nitrogen to which they are attached form a heterocycle such as piperazine, homopiperazine or morpholine.

In another embodiment $R^{21}$ is selected from $C_{1-6}$-alkyl, carboxy-$C_{1-6}$-alkyl, or hydroxy-$C_{1-6}$-alkyl; or phenyl, naphtyl, or phenyl-$C_{1-6}$-alkyl, wherein the aryl part is optionally substituted with one or more substituents independently selected from $R^{24}$; or $C_{3-8}$-cycloalkyl, or $C_{3-8}$-cycloalkyl-$C_{1-6}$-alkyl.

In another embodiment $R^{21}$ is selected from methyl, ethyl, propyl, carboxy-methyl, carboxy-ethyl, carboxy-propyl, hydroxy-methyl, hydroxy-ethyl, hydroxy-propyl; or phenyl, naphtyl, or phenyl-$C_{1-6}$-alkyl, wherein the aryl part is optionally substituted with one or more substituents independently selected from $R^{24}$; or C-$_{3-8}$-cycloalkyl, or $C_{3-8}$-cycloalkyl-$C_{1-6}$-alkyl.

In another embodiment $R^{21}$ is selected from methyl, ethyl, carboxy-methyl, carboxy-ethyl, carboxy-propyl; or phenyl, naphtyl, or phenyl-$C_{1-6}$-alkyl, wherein the aryl part is optionally substituted with one or more substituents independently selected from $R^{24}$.

In another embodiment $R^{22}$ and $R^{23}$ are independently selected from hydrogen, methyl, ethyl, or propyl.

In another embodiment $R^{24}$ is halogen, hydroxy, carboxy, —$CF_3$, methyl, ethyl, propyl, carboxy-methyl, carboxy-ethyl, carboxy-propyl, hydroxy-methyl, hydroxy-ethyl, or hydroxy-propyl.

In another embodiment $R^{25}$ and $R^{26}$ are independently $C_{1-6}$-alkyl, halogen, hydroxy, carboxy, or —$CF_3$.

In another embodiment $R^{25}$ and $R^{26}$ are independently methyl, ethyl, propyl, halogen, hydroxy, carboxy, or —$CF_3$.

In another aspect the invention provides a compound of general formula (II)

(II)

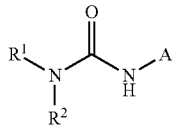

wherein $R^1$ is $C_{3-8}$-cycloalkyl, $C_{3-8}$-heterocyclyl, or fused aryl-$C_{3-8}$-cycloalkyl, each of which is optionally substituted with one or more substituents $R^3$, $R^4$, $R^5$ and $R^6$;

$R^2$ is $C_{3-8}$-cycloalkyl, $C_{3-8}$-heterocyclyl, or fused aryl-$C_{3-8}$-cycloalkyl, each of which is optionally substituted with one or more substituents $R^{30}$, $R^{31}$, $R^{32}$ and $R^{33}$, and $R^3$, $R^4$, $R^5$, $R^6$, $R^{30}$, $R^{31}$, $R^{32}$ and $R^{33}$ are independently selected from the group consisting of halogen, nitro, cyano, hydroxy, oxo, carboxy, —$CF_3$; or —$NR^{10}R^{11}$; or $C_{1-6}$-alkyl, $C_{2-6}$-alkenyl, $C_{2-6}$-alkynyl, $C_{3-8}$-cycloalkyl, $C_{3-8}$-cycloalkyl-$C_{1-6}$-alkyl, aryl, aryl-$C_{1-6}$-alkyl, heteroaryl-$C_{1-6}$-alkyl, $C_{1-6}$-alkoxy, $C_{3-6}$-cycloalkyl-$C_{1-6}$-alkoxy, aryl-$C_{1-6}$-alkoxy, heteroaryl, heteroaryl-$C_{1-6}$-alkoxy, aryloxy, heteroaryloxy, $C_{1-6}$-alkylthio, arylthio, heteroarylthio, aryl-$C_{1-6}$-alkylthio, heteroaryl-$C_{1-6}$-alkylthio, $C_{1-6}$-alkylsulfonyl, $C_{1-6}$-alkylsulfenyl, arylsulfonyl, heteroarylsulfonyl, $C_{3-6}$-cycloalkyl-$C_{1-6}$-alkylthio, —C(O)—O—$C_{1-6}$-alkyl, $C_{1-6}$-alkyl-C(O)—O—$C_{1-6}$-alkyl, $C_{1-6}$-alkoxy-$C_{1-6}$-alkyl, $C_{1-6}$-alkylthio-$C_{1-6}$-alkyl, carboxy-$C_{1-6}$-alkyloxy, amino-$C_{1-6}$-alkyl, $C_{1-6}$-alkylamino-$C_{1-6}$-alkyl, di-($C_{1-6}$-alkyl)amino-$C_{1,6}$-alkyl, $C_{1-6}$-alkylsulfamoyl, di($C_{1-6}$-alkyl)sulfamoyl, $C_{1-6}$-alkylsulfinamoyl or di($C_{1-6}$-alkyl)sulfinamoyl each of which is optionally substituted with one or more substituents independently selected from $R^{12}$; or C(O) $R^{27}$, C(O) $NR^{13}R^{14}$, $C_{1-6}$-alkyl-C(O) $NR^{13}R^{14}$; or two substituents selected from $R^3$, $R^4$, $R^5$ and $R^6$ or $R^{30}$, $R^{31}$, $R^{32}$ and $R^{33}$ attached to the same or adjacent atoms together form a radical —O—$(CH_2)_{1-3}$—O—;

$R^{10}$ and $R^{11}$ independently represent hydrogen, $C_{1-6}$-alkyl, —C(O)—$C_{1-6}$-alkyl, carboxy-$C_{1-6}$-alkyl, —C(O)—$C_{1-6}$-alkyl-C(O)OH, $S(O)_2CH_3$, or aryl;

$R^{27}$ is $C_{1-6}$-alkyl, $C_{2-6}$-alkenyl, $C_{2-6}$-alkynyl, $C_{3-8}$-cycloalkyl, $C_{3-8}$-cycloalkyl-$C_{1-6}$-alkyl, aryl, aryl-$C_{1-6}$-alkyl, heteroaryl, heteroaryl-$C_{1-6}$-alkyl, carboxy-$C_{1,6}$-alkyl, $C_{1,6}$-alkoxy-$C_{1,6}$-alkyl, $C_{1-6}$-alkylthio-$C_{1-6}$-alkyl, $R^{10}$HN—$C_{1-6}$-alkyl, $R^{10}R^{11}$—N—$C_{1-6}$-alkyl, $R^{10}R^{11}$—N—$S(O)_2$—$C_{1-6}$-alkyl, $R^{10}R^{11}$—N—C(O)—$C_{1-6}$-alkyl, $C_{1-6}$-alkyl-C(O)—NH—$C_{1-6}$-alkyl, aryl-C(O)—NH—$C_{1-6}$-alkyl, heteroaryl-C(O)—NH—$C_{1-6}$-alkyl, $C_{3-8}$-cycloalkyl-C(O)—NH—$C_{1-6}$-alkyl, $C_{1-6}$-alkyl-$S(O)_2$ NH $C_{1-6}$-alkyl, aryl-$S(O)_2$ NH $C_{1-6}$-alkyl, heteroaryl-$S(O)_2$—NH—$C_{1-6}$-alkyl, or $C_{3-8}$-cycloalkyl-$S(O)_2$—NH—$C_{1-6}$-alkyl, each of which is optionally substituted with one or more substituents independently selected from $R^{12}$;

$R^{12}$ is halogen, cyano, hydroxy, —C(O)—O—$C_{1-6}$-alkyl, carboxy, —$CF_3$, $C_{1-6}$-alkyl, —$S(O)_2CH_3$, or —$S(O)_2NH_2$;

$R^{13}$ and $R^{14}$ are independently selected from the group consisting of hydrogen, $C_{1-6}$-alkyl, hydroxy-$C_{1-6}$-alkyl, carboxy-$C_{1-6}$-alkyl, aryl, or heteroaryl, each of which is optionally substituted with one or more substituents independently selected from $R^{15}$; or $R^{13}$ and $R^{14}$ together with the nitrogen to which they are attached form a heterocycle such as piperazine, homopiperazine or morpholine;

$R^{15}$ is halogen, cyano, hydroxy, carboxy. —$CF_3$, $C_{1-6}$-alkyl, —$S(O)_2CH_3$, or —$S(O)_2NH_2$;

A is heteroaryl which is optionally substituted with one or more substituents independently selected from $R^7$, $R^8$ and $R^9$;

$R^7$, $R^8$ and $R^9$ are independently selected from halogen, carboxy, cyano, nitro, hydroxy, —$CF_3$, —SCN; or $C_{1-6}$-alkyl, $C_{2-6}$-alkenyl, $C_{2-6}$-alkynyl, $C_{1-6}$-alkoxy, $C_{1-6}$-alkylthio, $C_{1-6}$-alkylamino, $C_{1-6}$-alkylsulfonyl, $C_{1-6}$-alkylsulfenyl, —C(O)—O—$C_{1-6}$-alkyl, formyl, —C(O)—$C_{1-6}$-alkyl, —$C_{1-6}$-alkyl-C(O)—O—$C_{1-6}$-alkyl, —$C_{1-6}$-alkyl-O—C(O)—$C_{1-6}$-alkyl, —NH—C(O)—$C_{1-6}$-alkyl, —$C_{1-6}$-alkoxy-$C_{1-6}$-alkyl, —$C_{1-6}$-alkyl-S—$C_{1-6}$-alkyl, carboxy-$C_{1-6}$-alkyl, or hydroxy-$C_{1-6}$-alkyl, each of which is optionally substituted with one or more substituents independently selected from $R^{16}$; or aryl, heteroaryl, aryl-$C_{1-6}$-alkyl, heteroaryl-$C_{1-6}$-alkyl, aryl-$C_{1-6}$-alkoxy, heteroaryl-$C_{1-6}$-alkoxy, aryl-$C_{1-6}$-alkylthio, heteroaryl-$C_{1-6}$-alkylthio, heteroaryl-thio-$C_{1-6}$-alkyl, aryloxy, heteroaryloxy, arylthio. heteroarylthio, arylsulfonyl, heteroarylsulfonyl, aryl-$C_{1-6}$-alkylamino, each of which is optionally substituted on the aryl or heteroaryl part with one or more substituents independently selected from $R^{17}$; or $C_{3-8}$-cycloalkyl, $C_{3-8}$-cycloalkenyl, $C_{3-8}$-cycloalkyl-$C_{1-6}$-alkyl, $C_{3-8}$-cycloalkenyl-$C_{1-6}$-alkyl, $C_{3-6}$-cycloalkyl-$C_{1-6}$-alkoxy, $C_{3-6}$-cycloalkyl-$C_{1-6}$-alkylthio, each of which is optionally substituted on the cycloalkyl part with one or more substituents independently selected from $R^{18}$; or —$NR^{19}R^{20}$, —$C_{1-6}$-alkyl-$NR^{19}R^{20}$, —$C_{1-6}$-alkyl-S—$R^{21}$, —$C_{1-6}$-alkyl-S(O)—$R^{21}$, —$C_{1-6}$-alkyl-$S(O)_2$—$R^{21}$ or —$S(O)_2$—$NR^{19}R^{20}$, wherein each alkyl part may be substituted with one or more substituents independently selected from $R^{25}$; or —C(O)$NR^{22}R^{23}$, —$C_{1-6}$-alkyl-C(O)$NR^{22}R^{23}$ optionally substituted with one or more substituents independently selected from $R^{26}$; or two of $R^7$, $R^8$ and $R^9$ can be taken together to form a $C_{2-5}$-alkylene bridge;

$R^{16}$, $R^{17}$, and $R^{18}$ are independently $C_{1-6}$-alkyl, halogen, nitro, cyano, hydroxy, carboxy, —$CF_3$, carboxy-$C_{1-6}$-alkyl, hydroxy-$C_{1-6}$-alkyl, —$C_{1-6}$-alkyl-C(O)—O—$C_{1-6}$-alkyl, —C(O)—O—$C_{1-6}$-alkyl, —$NR^{19}R^{20}$, —$NHS(O)_2CH_3$, —C(O)$NR^{19}R^{20}$, —$S(O)_2CH_3$, or —$S(O)_2NH_2$;

$R^{19}$ and $R^{20}$ independently represent hydrogen, $C_{1-6}$-alkyl, hydroxy-$C_{1-6}$-alkyl, carboxy-$C_{1-6}$-alkyl, aryl, heteroaryl or $R^{17}$ and $R^{18}$ together with the nitrogen to which they are attached form a heterocycle such as piperazine, homopiperazine or morpholine;

$R^{21}$ is selected from $C_{1-6}$-alkyl, carboxy-$C_{1-6}$-alkyl, $C_{1-6}$-alkylamino-$C_{1-6}$-alkyl or hydroxy-$C_{1-6}$-alkyl; or aryl, heteroaryl, aryl-$C_{1-6}$-alkyl, or heteroaryl-$C_{1-6}$-alkyl, wherein the aryl or heteroaryl part is optionally substituted with one or more substituents independently selected from $R^{24}$; or $C_{3-8}$-cycloalkyl, $C_{3-8}$cycloalkenyl, $C_{3-8}$-cycloalkyl-$C_{1-6}$-alkyl, $C_{3-8}$-cycloalkenyl-$C_{1-6}$-alkyl.

$R^{22}$ and $R^{23}$ are independently selected from hydrogen, $C_{1-6}$-alkyl, $C_{3-8}$-cycloalkyl, aryl, heteroaryl or $R^{22}$ and $R^{23}$ together with the nitrogen to which they are attached form a heterocycle such as pyrrolidine, piperidine or morpholine;

$R^{24}$ is halogen, nitro, cyano, hydroxy, carboxy, —CF, $C_{1-6}$-alkyl, hydroxy-$C_{1-6}$-alkyl, or carboxy-$C_{1-6}$-alkyl.

$R^{25}$ and $R^{26}$ are independently $C_{1-6}$-alkyl, halogen, nitro, cyano, hydroxy, —C(O)—O—$C_{1-6}$-alkyl carboxy, —$C_{1-6}$-alkyl-C(O)—O—$C_{1-6}$-alkyl, carboxy-$C_{1-6}$-alkyl, —$CF_3$, —$S(O)_2CH_3$, or —$S(O)_2NH_2$ as well as any salt hereof with a pharmaceutically acceptable acid or base, or any optical isomer or mixture of optical isomers, including a racemic mixture, or any tautomeric forms.

In one embodiment $R^1$ is $C_{3-8}$-cycloalkyl, tetrahydrofuryl, tetrahydrothiofuryl, tetrahydrothienyl, tetrahydropyranyl, tetrahydrothiopyranyl, 1,4-dioxanyl, 1,3-dioxanyl, piperidyl, pyrrolidinyl, morpholinyl, or piperazinyl, each of which is optionally substituted with one or more substituents $R^3$, $R^4$, $R^5$ and $R^6$.

In another embodiment $R^1$ is cyclopropyl, cyclobutyl, cyclopentyl, cyclohexyl, cyclohexenyl, cycloheptyl, cycloheptenyl, cyclooctyl, bicyclo[3.2.1]octyl, bicyclo[2.2.1]heptyl, norpinyl, norbonyl, norcaryl, adamantyl, tetrahydrofuryl, tetrahydrothiofuryl, tetrahydrothienyl, tetrahydropyranyl, tetrahydrothiopyranyl, 1,4-dioxanyl, 1,3-dioxanyl, piperidyl, pyrrolidinyl, morpholinyl, or piperazinyl, each of which is optionally substituted with one or more substituents $R^3$, $R^4$, $R^5$ and $R^6$.

In another embodiment $R^1$ is cyclopropyl, cyclobutyl, cyclopentyl, cyclohexyl, bicyclo[3.2.1]octyl, bicyclo[2.2.1]heptyl, adamantyl, tetrahydrofuryl, tetrahydrothienyl, tetrahydropyranyl, tetrahydrothiopyranyl, piperidyl, pyrrolidinyl, morpholinyl, or piperazinyl, each of which is optionally substituted with one or more substituents $R^3$, $R^4$, $R^5$ and $R^6$.

In another embodiment $R^1$ is cyclopentyl, cyclohexyl, bicyclo[2.2,1]heptyl, tetrahydrofuryl, tetrahydrothienyl, tetrahydropyranyl, tetrahydrothiopyranyl, piperidyl, pyrrolidinyl, morpholinyl, or piperazinyl, each of which is optionally substituted with one or more substituents $R^3$, $R^4$, $R^5$ and $R^6$.

In another embodiment $R^1$ is selected from

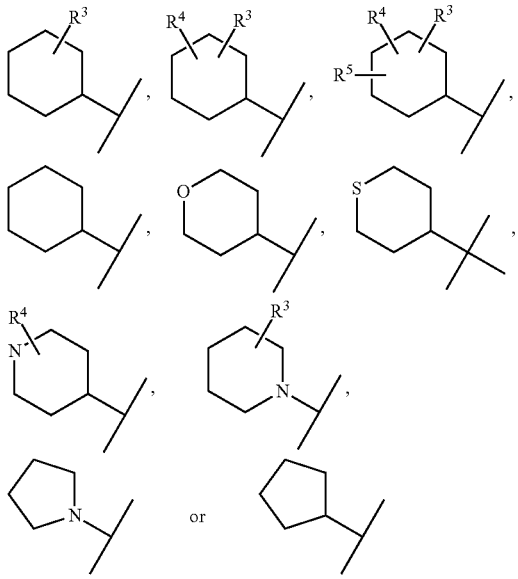

In another embodiment $R^1$ is selected from

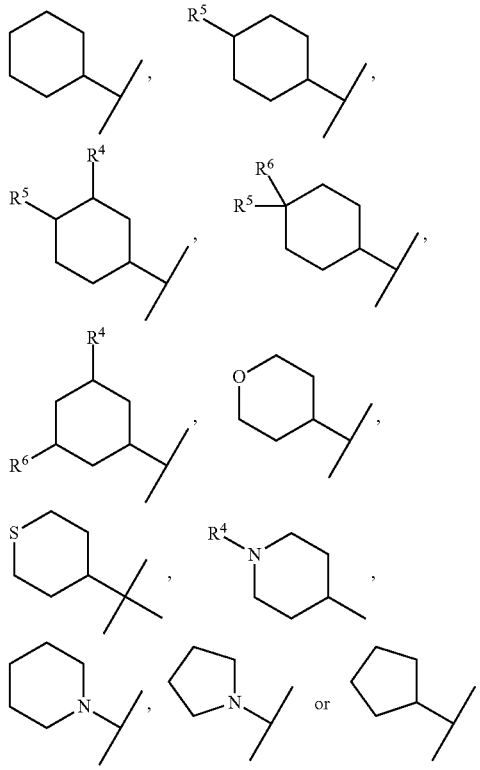

In another embodiment $R^1$ is selected from

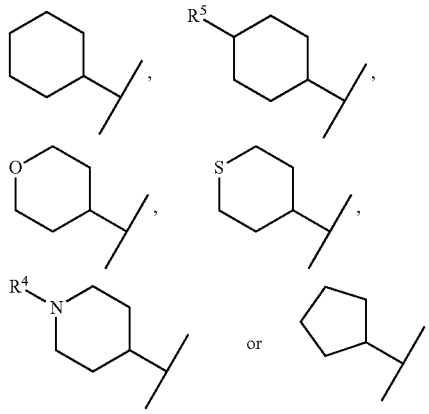

In another embodiment $R^1$ is selected from

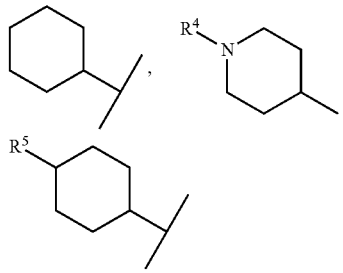

In another embodiment $R^2$ is $C_{3-8}$-cycloalkyl, tetrahydrofuryl, tetrahydrothiofuryl, tetrahydrothienyl, tetrahydropyranyl, tetrahydrothiopyranyl, 1,4-dioxanyl, 1,3-dioxanyl, piperidyl, pyrrolidinyl, morpholinyl, or piperazinyl, each of which is optionally substituted with one or more substituents $R^{30}$, $R^{31}$, $R^{32}$ and $R^{33}$.

In another embodiment $R^2$ is cyclopropyl, cyclobutyl, cyclopentyl, cyclohexyl, cyclohexenyl, cycloheptyl, cycloheptenyl, cyclooctyl, bicyclo[3.2.1]octyl, bicyclo[2.2.1]heptyl, norpinyl, norbonyl, norcaryl, adamantyl, tetrahydrofuryl, tetrahydrothiofuryl, tetrahydrothienyl, tetrahydropyranyl, tetrahydrothiopyranyl, 1,4-dioxanyl, 1,3-dioxanyl, piperidyl, pyrrolidinyl, morpholinyl, or piperazinyl, each of which is optionally substituted with one or more substituents $R^{30}$, $R^{31}$, $R^{32}$ and $R^{33}$.

In another embodiment $R^2$ is cyclopropyl, cyclobutyl, cyclopentyl, cyclohexyl, bicyclo[3.2.1]octyl, bicyclo[2.2.1]heptyl, adamantyl, tetrahydrofuryl, tetrahydrothienyl, tetrahydropyranyl, tetrahydrothiopyranyl, piperidyl, pyrrolidinyl, morpholinyl, or piperazinyl, each of which is optionally substituted with one or more substituents $R^{30}$, $R^{31}$, $R^{32}$ and $R^{33}$.

In another embodiment $R^2$ is cyclopentyl, cyclohexyl, bicyclo[2.2.1]heptyl, tetrahydrofuryl, tetrahydrothienyl, tetrahydropyranyl, tetrahydrothiopyranyl, piperidyl, pyrrolidinyl, morpholinyl, or piperazinyl, each of which is optionally substituted with one or more substituents $R^{30}$, $R^{31}$, $R^{32}$ and $R^{33}$.

In another embodiment $R^2$ is selected from

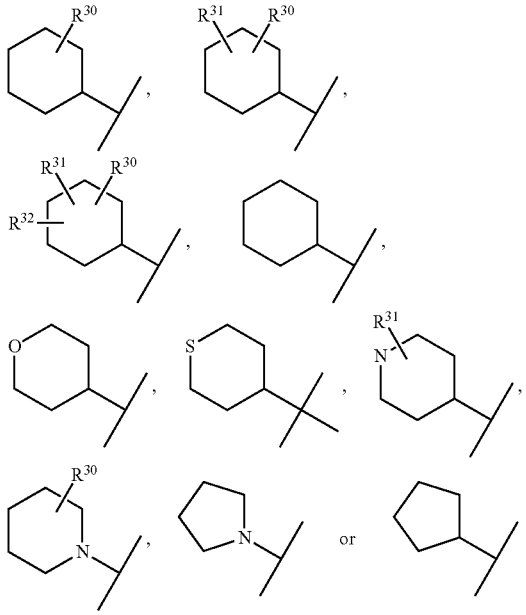

In another embodiment $R^2$ is selected from

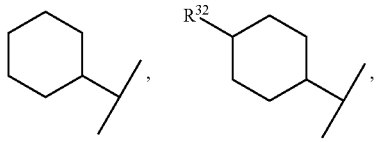

-continued

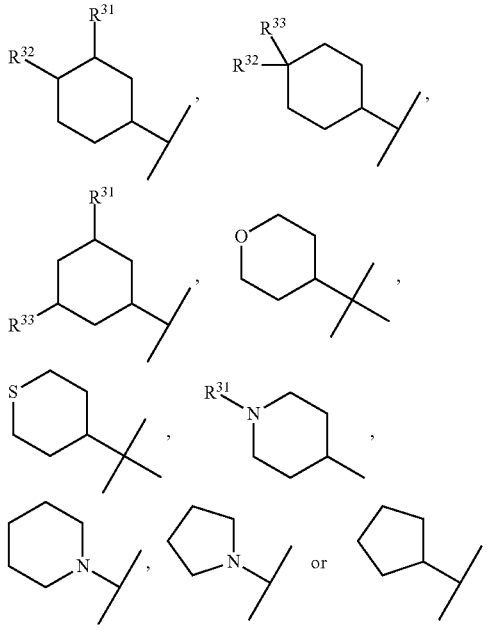

In another embodiment $R^2$ is selected from

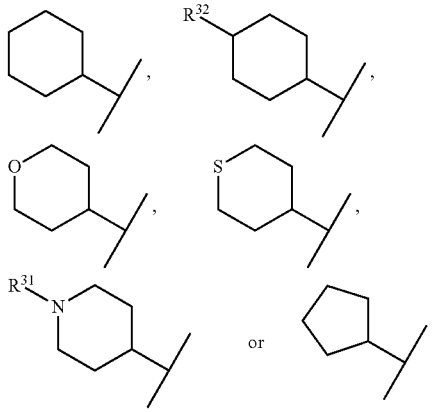

In another embodiment $R^2$ is selected from

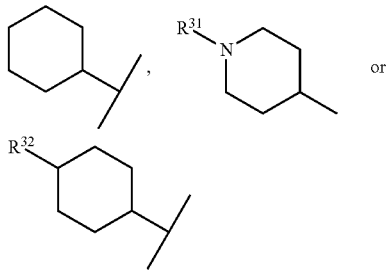

In another embodiment $R^1$ and $R^2$ are both cyclohexyl.

In another embodiment $R^3$, $R^4$, $R^5$, $R^6$, $R^{30}$, $R^{31}$, $R^{32}$ and. $R^{33}$ are independently selected from the group consisting of halogen, oxo, cyano, hydroxy, carboxy, —$CF_3$; or —$NR^{10}R^{11}$; or $C_{1-6}$-alkyl, $C_{2-6}$-alkenyl, $C_{3-8}$-cycloalkyl, $C_{3-8}$-cycloalkyl-$C_{1-6}$-alkyl, aryl, aryl-$C_{1-6}$-alkyl, $C_{1-6}$-alkoxy, $C_{3-6}$-cycloalkyl-$C_{1-6}$-alkoxy, aryl-$C_{1-6}$-alkoxy, $C_{1-6}$-alkylthio, arylthio, $C_{1-6}$-alkylsulfonyl, —C(O)—O—$C_{1-6}$-alkyl, or $C_{1-6}$-alkyl-C(O)—O—$C_{1-6}$-alkyl, each of which is optionally substituted with one or more substituents independently selected from $R^{12}$; or —C(O)—$R^{27}$, —C(O)—$NR^{13}R^{14}$, —$C_{1-6}$-alkyl-C(O)—$NR^{13}R^{14}$; or two substituents selected from $R^3$, $R^4$, $R^5$ and $R^6$ or $R^{30}$, $R^{31}$, $R^{32}$ and $R^{33}$ attached to the same or adjacent atoms together form a radical —O—$(CH_2)_{1-3}$—O—.

In another embodiment $R^3$, $R^4$, $R^5$, $R^6$, $R^{30}$, $R^{31}$, $R^{32}$ and $R^{33}$ are independently selected from the group consisting of halogen, oxo, —$CF_3$; or —$NR^{10}R^{11}$; or $C_{1-6}$alkyl, $C_{3-8}$-cycloalkyl, $C_{1-6}$-alkoxy, $C_{1-6}$-alkylthio, aryl, aryl-$C_{1-6}$-alkyl, arylthio, $C_{1-6}$-alkylsulfonyl, —C(O)—O—$C_{1-6}$-alkyl, $C_{1-6}$-alkyl-C(O)—O—$C_{1-6}$-alkyl, each of which is optionally substituted with one or more substituents independently selected from $R^{12}$; or —C(O)—$R^{27}$; or two substituents selected from $R^3$, $R^4$, $R^5$ and $R^6$ or $R^{30}$, $R^{31}$, $R^{32}$ and $R^{33}$ attached to the same or adjacent atoms together form a radical —O—$(CH_2)_{1-3}$—O—.

In another embodiment $R^3$, $R^4$, $R^5$, $R^6$, $R^{30}$, $R^{31}$, $R^{32}$ and $R^{33}$ are independently selected from the group consisting of halogen, —$CF_3$; or methyl, ethyl, propyl, isopropyl, butyl, tert-butyl, cyclopropyl, cyclobutyl, cyclopentyl, cyclohexyl, phenyl, naphtyl, benzyl, phenyl-ethyl, methoxy, ethoxy, phenylthio, methylsulfonyl, ethylsulfonyl, —C(O)—O—$CH_3$, —C(O)—O—$CH_2CH_3$, each of which is optionally substituted with one or more substituents independently selected from $R^{12}$; or —C(O)—$R^{27}$; or two substituents selected from $R^3$, $R^4$, $R^5$ and $R^6$ or $R^{30}$, $R^{31}$, $R^{32}$ and $R^{33}$ attached to the same or adjacent atoms together form a radical —O—$(CH_2)_{1-3}$—O—.

In another embodiment $R^3$, $R^4$, $R^5$, $R^6$, $R^{30}$, $R^{31}$, $R^{32}$ and $R^{33}$ are independently selected from the group consisting of F, Cl, —$CF_3$, methyl, ethyl, propyl, isopropyl, butyl, or tert-butyl; or two substituents selected from $R^3$, $R^4$, $R^5$ and $R^6$ or $R^{30}$, $R^{31}$, $R^{32}$ and $R^{33}$ attached to the same or adjacent atoms together form a radical —O—$(CH_2)_{1-3}$—O—.

In another embodiment $R^{10}$ and $R^{11}$ independently represent hydrogen, methyl, ethyl, propyl, —C(O)—$CH_3$, —C(O)—$CH_2CH_3$, —$CH_2$C(O)OH, —$CH_2CH_2$C(O)OH, —C(O)—$CH_2$—C(O)OH, —C(O)—$CH_2CH_2$—C(O)OH, —S(O)$_2CH_3$, or phenyl.

In another embodiment $R^{10}$ and $R^{11}$ independently represent hydrogen, methyl, ethyl, —C(O)—$CH_3$, —$CH_2$C(O)OH, —C(O)—$CH_2$—C(O)OH, —S(O)$_2CH_3$, or phenyl.

In another embodiment $R^{10}$ and $R^{11}$ independently represent hydrogen, methyl, ethyl, or phenyl.

In another embodiment $R^{27}$ is $C_{1-6}$-alkyl, $C_{2-6}$-alkenyl, $C_{2-6}$-alkynyl, $C_{3-8}$-cycloalkyl, $C_{3-8}$-cycloalkyl-$C_{1-6}$-alkyl, aryl, aryl-$C_{1-6}$-alkyl, heteroaryl, heteroaryl-$C_{1-6}$-alkyl, carboxy-$C_{1-6}$-alkyl, $C_{1-6}$-alkoxy-$C_{1-6}$-alkyl, $C_{1-6}$-alkylthio-$C_{1-6}$-alkyl, $R^{10}$HN—$C_{1-6}$-alkyl, $R^{10}R^{11}$—N—$C_{1-6}$-alkyl, $R^{10}R^{11}$—N—S(O)$_2$—$C_{1-6}$-alkyl, or $R^{10}R^{11}$ —N—C(O)—$C_{1-6}$-alkyl, each of which is optionally substituted with one or more substituents independently selected from $R^{12}$.

In another embodiment $R^{27}$ is $C_{1-6}$-alkyl, $C_{3-8}$-cycloalkyl, $C_{3-8}$-cycloalkyl-$C_{1-6}$-alkyl, aryl, heteroaryl, heteroaryl-$C_{1-6}$-alkyl, Carboxy-$C_{1-6}$-alkyl, $C_{1-6}$-alkoxy-$C_{1-6}$-alkyl, $R^{10}$HN—$C_{1-6}$-alkyl, $R^{10}R^{11}$—N—$C_{1-6}$-alkyl, $R^{10}R^{11}$—N—S(O)$_2$—$C_{1-6}$-alkyl, or $R^{10}R^{11}$—N—C(O)—$C_{1-6}$-alkyl, each of which is optionally substituted with one or more substituents independently selected from $R^{12}$.

In another embodiment $R^{27}$ is $C_{1-6}$-alkyl, $C_{3-8}$-cycloalkyl, $C_{3-8}$-cycloalkyl-$C_{1-6}$-alkyl, aryl or heteroaryl, each of which is optionally substituted with one or more substituents independently selected from $R^{12}$.

In another embodiment $R^{27}$ is methyl, ethyl, propyl, n-butyl, isobutyl, 1,1,1-trifluoroethyl, cyclopropyl, cyclopentyl, Cyclopropylmethyl, phenyl, pyridyl, thiophene, imidazole, or thiazole, each of which is optionally substituted with one or more substituents independently selected from $R^{12}$.

In another embodiment $R^{27}$ is methyl, ethyl, propyl, n-butyl, isobutyl, 1,1,1-trifluoroethyl, cyclopropyl, cyclopentyl, cyclopropylmethyl, phenyl, or pyridyl, thiophene, imidazole, or thiazole.

In another embodiment $R^{12}$ is halogen, cyano, hydroxy, carboxy, —$CF_3$, or $C_{1-6}$-alkyl.

In another embodiment $R^{12}$ is halogen, cyano, hydroxy, carboxy, $CF_3$, methyl, ethyl or propyl.

In another embodiment $R^{13}$ and $R^{14}$ are independently selected from the group consisting of hydrogen, $C_{1-6}$-alkyl, hydroxy-$C_{1-6}$-alkyl, carboxy-$C_{1-6}$-alkyl, phenyl, or naphtyl, each of which is optionally substituted with one or more substituents independently selected from $R^{15}$; or $R^{13}$ and $R^{14}$ together with the nitrogen to which they are attached form a heterocycle such as piperazine, homopiperazine or morpholine.

In another embodiment $R^{13}$ and $R^{14}$ are independently selected from the group consisting of hydrogen, methyl, ethyl, propyl, hydroxy-methyl, hydroxy-ethyl, carboxy-methyl, carboxy-ethyl, phenyl, or naphtyl, each of which is optionally substituted with one or more substituents independently selected from $R^{15}$; or $R^{13}$ and $R^{14}$ together with the nitrogen to which they are attached form a heterocycle such as piperazine, homopiperazine or morpholine.

In another embodiment $R^{13}$ and $R^{14}$ are independently selected from the group consisting of hydrogen, methyl, ethyl, propyl, or phenyl, each of which is optionally substituted with one or more substituents independently selected from $R^{15}$.

In another embodiment $R^{13}$ is halogen, cyano, hydroxy, carboxy, —$CF_3$, methyl, ethyl, or propyl.

In another embodiment $R^{15}$ is halogen, hydroxy, carboxy, —$CF_3$, methyl, or ethyl.

In another embodiment A is thiazolyl, thiadiazolyl, pyrazinyl, Pyridyl, 5,6-dihydro-4H-cyclopentathiazolyl, or 4,5,6,7-tetrahydrobenzothiazolyl optionally substituted with one or more substituents independently selected from $R^7$, $R^8$ and $R^9$.

In another embodiment A is

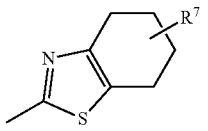

In another embodiment A is thiazolyl or thiadiazolyl optionally substituted with one ormore substituents independently selected from $R^7$, $R^8$ and $R^9$.

In another embodiment A is thiazolyl, 1,2,3-thiadiazolyl, or 1,3,4-thiadiazolyl, optionally substituted with one or more substituents independently selected from $R^7$, $R^8$ and $R^9$.

In another embodiment A is

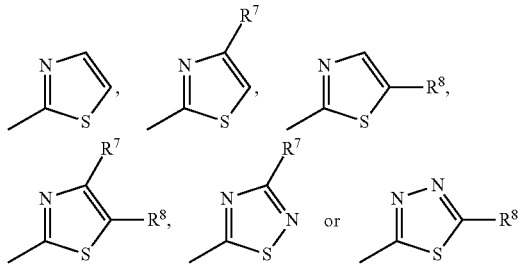

In another embodiment A is

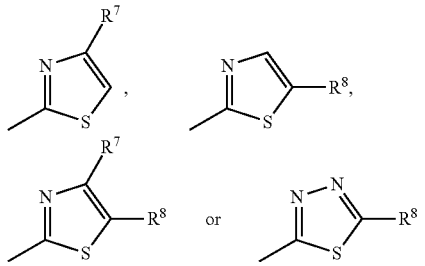

In another embodiment $R^7$, $R^8$ and $R^9$ are independently selected from halogen, carboxy, cyano, nitro, hydroxy, —$CF_3$, —SCN; or $C_{1-6}$-alkyl, $C_{2-6}$-alkenyl, $C_{1-6}$-alkoxy, $C_{1-6}$-alkylthio, $C_{1-6}$-alkylamino, $C_{1-6}$-alkylsulfonyl, $C_{1-6}$alkylsulfenyl, C(O) O $C_{1-6}$-alkyl, C(O) $C_{1-6}$-alkyl, $C_{1-6}$-alkyl -C(O)—O—$C_{1-6}$alkyl, —$C_{1-6}$-alkyl-O—C(O)—$C_{1-6}$-alkyl, —NH—C(O)—$C_{1-6}$alkyl, —$C_{1-6}$-alkoxy-$C_{1-6}$-alkyl, —$C_{1-6}$-alkyl-S—$C_{1-6}$-alkyl, $C_{3-8}$-cycloalkyl-$C_{1-6}$-alkyl, $C_{3-6}$-cycloalkyl-$C_{1-6}$-alkoxy, $C_{3-6}$-cycloalkyl-$C_{1-6}$-alkylthio each of which is optionally substituted with one or more substituents independently selected from $R^{16}$; or aryl, heteroaryl, aryl-$C_{1-6}$-alkyl, heteroaryl-$C_{1-6}$-alkyl, aryl-$C_{1-6}$-alkoxy, heteroaryl-$C_{1-6}$-alkoxy, aryloxy, heteroaryloxy, heteroarylthio, each of which is optionally substituted on the aryl or heteroaryl part with one or more substituents independently selected from $R^{17}$; or $C_{3-8}$-cycloalkyl, $C_{3-8}$-cycloalkenyl, $C_{3-8}$-cycloalkyl-$C_{1-6}$-alkyl, $C_{3-8}$-cycloalkenyl-$C_{1-6}$-alkyl, each of which is optionally substituted on the cycloalkyl part with one or more substituents independently selected from $R^{18}$; or —$NR^{19}R^{20}$, —$C_{1-6}$-alkyl-$NR^{19}R^{20}$, —$C_{1-6}$-alkyl-S—$R^{21}$, —$C_{1-6}$-alkyl-S(O)—$R^{21}$—$C_{1-6}$-alkyl-$S(O)_2$—$R^{21}$ wherein each alkyl part may be substituted with one or more substituents independently selected from $R^{25}$; or —C(O)$NR^{22}R^{23}$, —$C_{1-6}$-alkyl-C(O)$NR^{22}R^{23}$ optionally substituted with one or more substituents independently selected from $R^{26}$; or two of $R^7$, $R^8$ and $R^9$ can be taken together to form a $C_{2-5}$-alkylene bridge.

In another embodiment $R^7$, $R^8$ and $R^9$ are independently selected from halogen, carboxy, cyano, or $CF_3$; or $C_{1-6}$-alkyl, $C_{2-6}$-alkenyl, $C_{1-6}$-alkoxy, $C_{1-6}$-alkylthio, $C_{1-6}$-alkylsulfonyl, —C(O)—O—$C_{1-6}$-alkyl, —C(O)—$C_{1-6}$-alkyl, $C_{1-6}$alkyl-C(O) O $C_{1-6}$-alkyl, $C_{1-6}$-alkyl-O—C(O)—$C_{1-6}$-alkyl, —$C_{1-6}$-alkoxy-$C_{1-6}$-alkyl, $C_{3-8}$-cycloalkyl-$C_{1-6}$-alkyl, each of which is optionally substituted with one or more substituents independently selected from $R^{16}$; or aryl, heteroaryl, aryl-$C_{1-6}$-alkyl, heteroaryl-$C_{1-6}$-alkyl, each of which is optionally substituted on the aryl or heteroaryl part with one or more substituents independently selected from $R^{17}$; or $C_{3-8}$-cycloalkyl, $C_{3-8}$-cycloalkyl-$C_{1-6}$-alkyl, each of which is optionally substituted on the cycloalkyl part with one or more substituents independently selected from $R^{18}$; or —$NR^{19}R^{20}$, —$C_{1-6}$-alkyl-$NR^{19}R^{20}$, wherein each alkyl part may be substituted with one or more substituents independently selected from $R^{25}$; or —C(O)$NR^{22}R^{23}$, —$C_{1-6}$-alkyl-C(O)$NR^{22}R^{23}$ optionally substituted with one or more substituents independently selected from $R^{26}$; or two of $R^7$, $R^8$ and $R^9$ can be taken together to form a $C_{2-5}$-alkylene bridge.

In another embodiment $R^7$, $R^8$ and $R^9$ are independently selected from halogen, carboxy or —$CF_3$; or $C_{1-6}$-alkyl, $C_{1-6}$-alkoxy, $C_{1-6}$-alkylthio, —$C_{1-6}$-alkyl-C(O)—O—$C_{1-6}$-alkyl, —$C_{1-6}$-alkyl-O—C(O)—$C_{1-6}$-alkyl or —C(O)—O—$C_{1-6}$-alkyl, each of which is optionally substituted with one or more substituents independently selected from $R^{16}$; or phenyl, benzyl, or heteroarylthio, wherein heteroaryl is pyridyl or imidazolyl, and wherein each aryl or heteroaryl is optionally substituted on the aryl or heteroaryl part with one or more substituents independently selected from $R^{17}$; or cyclopropyl, cyclobutyl, cyclopentyl, or cyclohexyl, each of which is optionally substituted on the cycloalkyl part with one or more substituents independently selected from $R^{18}$; or two of $R^7$, $R^8$ and $R^9$ can be taken together to form a $C_{2-5}$-alkylene bridge.

In another embodiment $R^7$, $R^8$ and $R^9$ are independently selected from halogen, carboxy, —$CF_3$, —S—$CH_3$, —S—$CH_2CH_3$, methyl, ethyl, propyl, isopropyl, butyl, tert-butyl, methoxy, ethoxy, $CH_2$ C(O) O $CH_3$, $CH_2$ C(O)—O—$CH_2CH_3$, —$CH_2CH_2$—C(O)—O—$CH_3$, —$CH_2CH_2$—C(O)—O—$CH_2CH_3$, —$CH_2O$—C(O)—$CH_3$, —$CH_2$—O—C(O)—$CH_2CH_3$, —$CH_2CH_2$—O—C (O) $CH_3$, $CH_2CH_2$ O C(O) $CH_2CH_3$, C(O) O—$CH_3$, or —C(O)—O—$CH_2CH_3$, each of which is optionally substituted with one ormore substituents independently selected from $R^{16}$; or heteroarylthio, wherein heteroaryl is pyridyl or imidazolyl, each optionally substituted on the heteroaryl part with one or more substituents independently selected from $R^{17}$.

In another embodiment $R^7$, $R^8$ and $R^9$ are independently selected from Cl, F, Br, —$CF_3$, methyl, ethyl, methoxy, ethoxy, —$CH_2$—C(O)—O—$CH_2CH_3$, —C(O)—O—$CH_3$, or —C(O)—O—$CH_2CH_3$; or heteroarylthio, wherein heteroaryl is pyridyl or imidazolyl, each optionally substituted on the heteroaryl part with one or more substituents independently selected from $R^{17}$.

In another embodiment $R^{16}$, $R^{17}$, and $R^{18}$ are independently $C_{1-6}$-alkyl, halogen, hydroxy, carboxy, —$CF_3$, carboxy-$C_{1-6}$-alkyl, Hydroxy-$C_{1-6}$-alkyl, —$C_{1-6}$-alkyl-C(O)—O $C_{1-6}$-alkyl, C(O) O $C_{1-6}$-alkyl, or $S(O)_2CH_3$.

In another embodiment $R^{16}$, $R^{17}$, and $R^{18}$ are independently methyl, ethyl, propyl, halogen, hydroxy, carboxy, —$CF_3$, carboxy-methyl, carboxy-ethyl, carboxy-propyl, hydroxy-methyl, hydroxy-ethyl, hydroxy-propyl, —$CH_2$—C(O)—O—$CH_3$, —$CH_2$—C(O)—O—$CH_2CH_3$, —$CH_2CH_2$—C(O)—O—$CH_3$, —$CH_2CH_2$—C(O)—O—$CH_2CH_3$, —C(O)—O—$CH_3$, —C(O)—O—$CH_2CH_3$, —C(O)—O—$CH_2CH_2CH_3$, or —$S(O)_2CH_3$.

In another embodiment $R^{16}$, $R^{17}$, and $R^{18}$ are independently methyl, ethyl, propyl, halogen, carboxy, carboxy-methyl, carboxy-ethyl, carboxy-propyl, hydroxy-methyl, hydroxy-ethyl, hydroxy-propyl, —$CH_2$—C(O)—O—$CH_3$, $CH_2$ C(O) O $CH_2CH_3$, $CH_2CH_2$ C(O) O $CH_3$, —$CH_2CH_2$—C(O)—O—$CH_2CH_3$, —C(O)—O—$CH_3$, —C(O)—O—$CH_2CH_3$, —C(O)—O—$CH_2CH_2CH_3$, or —$S(O)_2CH_3$.

In another embodiment $R^{19}$ and $R^{20}$ independently represent hydrogen, $C_{1-6}$-alkyl, hydroxy-$C_{1-6}$-alkyl, carboxy-$C_{1-6}$-alkyl, phenyl, or naphtyl, or $R^{19}$ and $R^{20}$ together with the nitrogen to which they are attached form a heterocycle such as piperazine, homopiperazine or morpholine.

In another embodiment $R^{19}$ and $R^{20}$ independently represent hydrogen, methyl, ethyl, propyl, carboxy-methyl, carboxy-ethyl, carboxy-propyl, hydroxy-methyl, hydroxy-ethyl, hydroxy-propyl, phenyl, or naphtyl, or $R^{19}$ and $R^{20}$ together with the nitrogen to which they are attached form a heterocycle such as piperazine, homopiperazine or morpholine.

In another embodiment $R^{21}$ is selected from $C_{1-6}$-alkyl, carboxy-$C_{1-6}$-alkyl, or hydroxy-$C_{1-6}$-alkyl; or phenyl, naphtyl, or phenyl-$C_{1-6}$-alkyl, wherein the aryl part is optionally substituted with one or more substituents independently selected from $R^{24}$; or $C_{3-8}$-cycloalkyl, or $C_{3-8}$-cycloalkyl-$C_{1-6}$-alkyl.

In another embodiment $R^{21}$ is selected from methyl, ethyl, propyl, carboxy-methyl, carboxy-ethyl, carboxy-propyl, hydroxy-methyl, hydroxy-ethyl, hydroxy-propyl; or phenyl, naphtyl, or phenyl-$C_{1-6}$-alkyl, wherein the aryl part is optionally substituted with one or more substituents independently selected from $R^{24}$; or $C_{3-8}$-cycloalkyl, or $C_{3-8}$-cycloalkyl-$C_{1-6}$-alkyl.

In another embodiment $R^{21}$ is selected from methyl, ethyl, carboxy-methyl, carboxy-ethyl, carboxy-propyl; or phenyl, naphtyl, or phenyl-$C_{1-6}$-alkyl, wherein the aryl part is optionally substituted with one or more substituents independently selected from $R^{24}$.

In another embodiment $R^{22}$ and $R^{23}$ are independently selected from hydrogen, methyl, ethyl, or propyl.

In another embodiment $R^{24}$ is halogen, hydroxy, carboxy, $CF_3$, methyl, ethyl, propyl, carboxy-methyl, carboxy-ethyl, carboxy-propyl, hydroxy-methyl, hydroxy-ethyl, or hydroxy-propyl.

In another embodiment $R^{25}$ and $R^{26}$ are independently $C_{1-6}$-alkyl, halogen, hydroxy, carboxy, or $CF_3$.

In another embodiment $R^{25}$ and $R^{26}$ are independently methyl, ethyl, propyl, halogen, hydroxy, carboxy, or —$CF_3$.

In another aspect the invention provides a compound as described herein which is an activator of glucokinase, when tested in the Glucokinase Activation Assay (I) disclosed herein at a glucose concentration of 2 mM.

In another aspect the invention provides a compound as described herein which is an activator of glucokinase, when tested in the Glucokinase Activation Assay (I) disclosed herein at a glucose concentration of from 10 to 15 mM.

In another aspect the invention provides a compound as described herein which, at a concentration of 30 μM, is capable of providing an at least 1.5, such as at least 1.7, for instance at least 2.0 fold activation of glucokinase in the Glucokinase Activation Assay (I) disclosed herein at a glucose concentration of 2 mM.

In another aspect the invention provides a compound as described herein which, at a concentration of 30 μM, is capable of providing an at least 1.5, such as at least 1.7, for instance at least 2.0 fold activation of glucokinase in the Glucokinase Activation Assay (I) disclosed herein at a glucose concentration of from 10 to 15 mM.

In another aspect the invention provides a compound as described herein which, at a concentration of 5 μM is capable of providing an at least 1.5, such as at least 1.7, for instance at least 2.0 fold activation of glucokinase in the Glucokinase Activation Assay (I) disclosed herein at a glucose concentration Of 2 mM.

In another aspect the invention provides a compound as described herein which, at a concentration of 5 μM is capable of providing an at least 1.5, such as at least 1.7, for instance at least 2,0 fold activation of glucokinase in the Glucokinase Activation Assay (I) disclosed herein at a glucose concentration of from 10 to 15 mM.

In another aspect the invention provides a compound as described herein which provides an increase in glucokinase activity, where the increase in glucokinase activity provided by the compound increases with increasing concentrations of glucose.

In another aspect the invention provides a compound as described herein which provides an increase in glucokinase activity in Glucokinase Activation Assay (I) disclosed herein at a glucose concentration of 15 mM, which increase is significantly higher than the increase in glucokinase activity provided by the compound in Glucokinase Activation Assay (I) disclosed herein at a glucose concentration of 5 mM.

In another aspect the invention provides a compound as described herein which, at a compound concentration of 10 μM provides an increase in glucokinase activity in Glucokinase Activation Assay (I) disclosed herein at a glucose concentration of 15 mM, which increase is significantly higher than the increase in glucokinase activity provided by the compound at a compound concentration of 10 μM in Glucokinase Activation Assay (I) disclosed herein at a glucose concentration of 5 mM.

In another aspect the invention provides a compound as described herein which, at a compound concentration of 10 μM provides an increase in glucokinase activity in Glucokinase Activation Assay (I) disclosed herein at a glucose concentration of 15 mM, which increase is at least 1.1 fold higher, such as at least 1.2 fold higher, for instance at least 1.3 fold higher, such as at least 1.4 fold higher, for instance 1.5 fold higher, such as at least 1.6 fold higher, for instance at least 1.7 fold higher, such as at least 1.8 fold higher, for instance at least 1.9 fold higher, such as at least 2.0 fold higher than the increase in glucokinase activity provided by the compound at a compound concentration of 10 μM in Glucokinase Activation Assay (I) disclosed herein at a glucose concentration of 5 mM.

In another aspect the invention provides a compound as described herein, which compound increases glucose utilization in the liver without inducing any increase in insulin secretion in response to glucose.

In another aspect the invention provides a compound as described herein, which compound shows a significantly higher activity in isolated hepatocytes compared to the activity of the compound in Ins-1 cells.

In another aspect the invention provides a compound as described herein, which compound shows a significantly higher activity in isolated hepatocytes measured as described in the Glucokinase Activity Assay (II) compared to the activity of the compound in Ins-1 cells measured as described in the Glucokinase Activity Assay (III).

In another aspect the invention provides a compound as described herein, which compound shows an activity in isolated hepatocytes measured as described in the Glucokinase Activity Assay (II) which activity is at least 1.1 fold higher, such as at least 1.2 fold higher, for instance at least 1.3 fold higher, such as at least 1.4 fold higher, for instance 1.5 fold higher, such as at least 1.6 fold higher, for instance at least 1.7 fold higher, such as at least 1.8 fold higher, for instance at least 1.9 fold higher, such as at least 2.0 fold higher, for instance at least a 3.0 fold higher, such as at least a 4.0 fold higher, for instance at least 5.0 fold higher, such as at least 10 fold higher than the activity of the compound in Ins-1 cells measured as described in the Glucokinase Activity Assay (III).

In another aspect the invention provides a compound as described herein, which compound shows no activity in the Ins-1 cells measured as described in the Glucokinase Activity Assay (III).

In another aspect the invention provides a method of preventing hypoglycemia comprising administration of a compound according to the present invention.

In another aspect the invention provides the use of a compound according to the present invention for the preparation of a medicament for the prevention of hypoglycemia.

In another aspect the invention provides a compound as described herein, which is an agent useful for the treatment of an indication selected from the group consisting of hyperglycemia, IGT, insulin resistance syndrome, syndrome X, type 2 diabetes, type 1 diabetes, dyslipidemia, hypertension, and obesity.

In another aspect the invention provides a compound as described herein for use as a medicament.

In another aspect the invention provides a compound as described herein for treatment of hyperglycemia, for treatment of IGT, for treatment of Syndrome X, for treatment of type 2 diabetes, for treatment of type 1 diabetes, for treatment of dyslipidemia, for treatment of hyperlipidemia, for treatment of hypertension, for treatment of obesity, for lowering of food intake, for appetite regulation, for regulating feeding behaviour, or for enhancing the secretion of enteroincretins, such as GLP-1.

In another aspect the invention provides a pharmaceutical composition comprising, as an active ingredient, at least one compound as described herein together with one or more pharmaceutically acceptable carriers or excipients.

In one embodiment such a pharmaceutical composition may be in unit dosage form, comprising from about 0.05 mg to about 1000 mg, preferably from about 0.1 mg to about 500 mg and especially preferred from about 0.5 mg to about 200 mg of the compound according to the present invention.

In another aspect the invention provides the use of a compound according to the invention for increasing the activity of glucokinase.

In another aspect the invention provides the use of a compound according to the invention for the preparation of a medicament for the treatment of metabolic disorders, for blood glucose lowering, for the treatment of hyperglycemia, for the treatment of IGT, for the treatment of Syndrome X, for the treatment of impaired fasting glucose (IFG), for the treatment of type 2 diabetes, for the treatment of type 1 diabetes, for delaying the progression of impaired glucose tolerance (IGT) to type 2 diabetes, for delaying the progression of non-insulin requiring type 2 diabetes to insulin requiring type 2 diabetes, for the treatment of dyslipidemia, for the treatment of hyperlipidemia, for the treatment of hypertension, for lowering of food intake, for appetite regulation, for the treatment of obesity, for regulating feeding behaviour, or for enhancing the secretion of enteroincretins. In another aspect the invention provides the use of a compound according to the invention for the preparation of a medicament for the adjuvant treatment of type 1 diabetes for preventing the onset of diabetic complications.

In another aspect the invention provides the use of a compound according to the invention for the preparation of a medicament for increasing the number and/or the size of beta cells in a mammalian subject, for treatment of beta cell degeneration, in particular apoptosis of beta cells, or for treatment of functional dyspepsia, in particular irritable bowel syndrome.

In one embodiment the invention provides any of the above uses in a regimen which comprises treatment with a further antidiabetic agent.

In another embodiment the invention provides any of the above uses in a regimen which comprises treatment with a further antihyperlipidemic agent.

In another embodiment the invention provides any of the above uses in a regimen which comprises treatment with a further antiobesity agent.

In another embodiment the invention provides any of the above uses in a regimen which comprises treatment with a further antihypertensive agent.

In a further aspect the invention provides the use of a compound according to the invention or a pharmaceutical composition as described above for the treatment of metabolic disorders, for blood glucose lowering, for the treatment of hyperglycemia, for treatment of IGT, for treatment of Syndrome X, for the treatment of impaired fasting glucose (IFG), for treatment of type 2 diabetes, for treatment of type 1 diabetes, for delaying the progression of impaired glucose tolerance (IGT) to type 2 diabetes, for delaying the progression of non-insulin requiring type 2 diabetes to insulin requiring type 2 diabetes, for treatment of dyslipidemia, for treatment of hyperlipidemia, for treatment of hypertension, for the treatment or prophylaxis of obesity, for lowering of food intake, for appetite regulation, for regulating feeding behaviour, or for enhancing the secretion of enteroincretins.

In a further aspect the invention provides the use of a compound according to the invention or a pharmaceutical composition as described above for the adjuvant treatment of type 1 diabetes for preventing the onset of diabetic complications.

In a further aspect the invention provides the use of a compound according to the invention or a pharmaceutical composition as described above for increasing the number and/or the size of beta cells in a mammalian subject, for treatment of beta cell degeneration, in particular apoptosis of beta cells, or for treatment of functional dyspepsia, in particular irritable bowel syndrome.

Embodiment 1

In a further aspect the invention provides a compound of general formula (I)

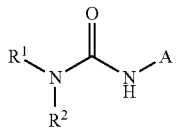

(I)

wherein $R^1$ is $C_{3-8}$-cycloalkyl, $C_{3-8}$-heterocyclyl, or fused Aryl-$C_{3-8}$-cycloalkyl, each of which is optionally substituted with one or more substituents $R^3$, $R^4$, $R^5$ and $R^6$;

$R^2$ is $C_{3-8}$-cycloalkyl, $C_{3-8}$-heterocyclyl, or fused aryl-$C_{3-8}$-cycloalkyl, each of which is optionally substituted with one or more substituents $R^{30}$, $R^{31}$, $R^{32}$ and $R^{33}$, and $R^3$, $R^4$, $R^5$, $R^6$, $R^{30}$, $R^{31}$, $R^{32}$ and $R^{33}$ are independently selected from the group consisting of halogen, nitro, cyano, hydroxy, oxo, carboxy, —$CF_3$; or —$NR^{10}R^{11}$; or $C_{1-6}$-alkyl, $C_{2-6}$-alkenyl, $C_{2-6}$-alkynyl, $C_{3-8}$-cycloalkyl, $C_{3-8}$-cycloalkyl-$C_{1-6}$-alkyl, aryl, aryl-$C_{1-6}$-alkyl, heteroaryl-$C_{1-6}$-alkyl, $C_{1-6}$-alkoxy, $C_{3-6}$-cycloalkyl-$C_{1-6}$-alkoxy, aryl-$C_{1-6}$-alkoxy, heteroaryl, heteroaryl-$C_{1-6}$-alkoxy, aryloxy, heteroaryloxy, $C_{1-6}$-alkylthio, arylthio, heteroarylthio, aryl-$C_{1-6}$-alkylthio, heteroaryl-$C_{1-6}$-alkylthio, $C_{1-6}$-alkylsulfenyl, $C_{3-6}$-cycloalkyl-$C_{1-6}$-alkylthio, $C_{1-6}$-alkylsulfenyl, $C_{3-6}$-cycloalkyl-$C_{1-6}$-alkylthio, $C_{1-6}$-alkyl-C(O)—O—$C_{1-6}$-alkyl, $C_{1-6}$-alkoxy-$C_{1-6}$-alkyl, $C_{1-6}$-alkylthio-$C_{1-6}$-alkyl, carboxy-$C_{1-6}$-alkyloxy, amino-$C_{1-6}$-alkyl, $C_{1-6}$-alkylamino-$C_{1-6}$-alkyl, di-($C_{1-6}$-alkyl)amino-$C_{1-6}$-alkyl, $C_{1-6}$-alkylsulfamoyl, di($C_{1-6}$-alkyl)sulfamoyl, $C_{1-6}$-alkylsulfinamoyl or di($C_{1-6}$-alkyl)sulfinamoyl each of which is optionally substituted with one or more substituents independently selected from $R^{12}$; or —C(O)—$R^{27}$, —$S(O)_2$—$R^{27}$, —C(O)—$NR^{13}R^{14}$, $C_{1-6}$-alkyl-C(O) $NR^{13}R^{14}$; or two substituents selected from $R^3$, $R^4$, $R^5$ and $R^6$ or $R^{30}$, $R^{31}$, $R^{32}$ and $R^{33}$ attached to the same or adjacent atoms together form a radical —O—$(CH_2)_{1-3}$—O—;

$R^{10}$ and $R^{11}$ independently represent hydrogen, $C_{1-6}$-alkyl, —C(O)—$C_{1-6}$-alkyl, carboxy-$C_{1-6}$-alkyl, —C(O)—$C_{1-6}$-alkyl-C(O)OH, —$S(O)_2CH_3$, or aryl;

$R^{27}$ is $C_{1-6}$-alkyl, $C_{1-6}$-alkoxy, $C_{2-6}$-alkenyl, $C_{2-6}$-alkynyl, $C_{3-8}$-cycloalkyl, $C_{3-8}$-cycloalkyl-$C_{1-6}$-alkyl, aryl, aryl-$C_{1-6}$-alkyl, aryl-$C_{2-6}$-alkenyl, heteroaryl, heteroaryl-$C_{1-6}$-alkyl, carboxy-$C_{1-6}$-alkyl, $C_{1-6}$-alkoxy-$C_{1-6}$-alkyl, $C_{1-6}$-alkylthio-$C_{1-6}$-alkyl, $R^{10}$HN—$C_{1-6}$-alkyl, $R^{10}R^{11}$—N—$C_{1-6}$-alkyl, $R^{10}R^{11}$—N—$S(O)_2$—$C_{1-6}$-alkyl, $R^{10}R^{11}$—N—C(O)—$C_{1-6}$-alkyl, $C_{1-6}$-alkyl-C(O)—NH—$C_{1-6}$-alkyl, aryl-C(O)—NH—$C_{1-6}$-alkyl, heteroaryl-C(O)—NH—$C_{1-6}$-alkyl, $C_{3-8}$-cycloalkyl-C(O)—NH—$C_{1-6}$-alkyl, $C_{1-6}$-alkyl-$S(O)_2$—NH—$C_{1-6}$-alkyl, aryl-$S(O)_2$—NH—$C_{1-6}$-alkyl, heteroaryl-S $(O)_2$—NH—$C_{1-6}$-alkyl, or $C_{3-8}$-cycloalkyl-$S(O)_2$—NH—$C_{1-6}$-alkyl, each of which is optionally substituted with one or more substituents independently selected from $R^{12}$;

$R^{12}$ is halogen, cyano, hydroxy, —C(O)—O—$C_{1-6}$-alkyl, carboxy, —$CF_3$, $C_{1-6}$-alkyl, $C_{1-6}$-alkoxy, —$S(O)_2CH_3$, or —$S(O)_2NH_2$;

$R^{13}$ and $R^{14}$ are independently selected from the group consisting of hydrogen, $C_{1-6}$-alkyl, hydroxy-$C_{1-6}$-alkyl, carboxy-$C_{1-6}$-alkyl, aryl, or heteroaryl, each of which is optionally substituted with one or more substituents independently selected from $R^{15}$; or $R^{13}$ and $R^{14}$ together with the nitrogen to which they are attached form a 3 to 8 membered heterocyclic ring with the said nitrogen atom, the heterocyclic ring optionally containing one or two further heteroatoms selected from nitrogen, oxygen and sulphur;

$R^{15}$ is halogen, cyano, hydroxy, carboxy, —$CF_3$, $C_{1-6}$-alkyl, —$S(O)_2CH_3$, or —$S(O)_2NH_2$;

A is heteroaryl which is optionally substituted with one or more substituents independently selected from $R^7$, $R^8$ and $R^9$;

$R^7$, $R^8$ and $R^9$ are independently selected from halogen, carboxy, cyano, nitro, hydroxy, —$CF_3$, —SCN; or $C_{1-6}$-alkyl, $C_{2-6}$-alkenyl, $C_{2-6}$-alkynyl, $C_{1-6}$-alkoxy, $C_{1-6}$-alkylthio, $C_{1-6}$-alkylamino, $C_{1-6}$-alkylsulfenyl, —C(O)—O—$C_{1-6}$-alkyl, formyl, —C(O)—$C_{1-6}$-alkyl, —$C_{1-6}$-alkyl-C(O)—O—$C_{1-6}$-alkyl, —$C_{1-6}$-alkyl-O—C(O)—$C_{1-6}$-alkyl, —NH—C(O)—$C_{1-6}$-alkyl, —$C_{1-6}$-alkoxy-$C_{1-6}$-alkyl, $C_{1-6}$-alkyl-S $C_{1-6}$-alkyl, carboxy-$C_{1-6}$-alkyl, or hydroxy-$C_{1-6}$-alkyl, each of which is optionally substituted with one or more substituents independently selected from $R^{16}$; or aryl, heteroaryl, aryl-$C_{1-6}$-alkyl, heteroaryl-$C_{1-6}$-alkyl, aryl-$C_{1-6}$-alkoxy, heteroaryl-$C_{1-6}$-alkoxy, aryl-$C_{1-6}$-alkylthio, heteroaryl-$C_{1-6}$-alkylthio, heteroaryl-thio-$C_{1-6}$-alkyl, aryloxy, heteroaryloxy, arylthio, heteroarylthio, aryl-$C_{1-6}$-alkylamino, each of which is optionally substituted on the aryl or heteroaryl part with one or more substituents independently selected from $R^{17}$; or $C_{3-8}$cycloalkyl, $C_{3-8}$-cycloalkenyl, $C_{3-8}$-cycloalkyl-$C_{1-6}$-alkyl, $C_{3-8}$-cycloalkenyl-$C_{1-6}$-alkyl, $C_{3-6}$-cycloalkyl-$C_{1-6}$-alkoxy, $C_{3-6}$-cycloalkyl-$C_{1-6}$-alkylthio, each of which is optionally substituted on the cycloalkyl part with one or more substituents independently selected from $R^{18}$; or —$NR^{19}R^{20}$, —$C_{1-6}$-alkyl-$NR^{19}R^{20}$, —$C_{1-6}$-alkyl-S—$R^{21}$, —$C_{1-6}$-alkyl-S(O)—$R^{21}$, —$C_{1-6}$-alkyl-$S(O)_2$—$R^{21}$, —$S(O)_2$—$R^{21}$ or —$S(O)_2$—$NR^{19}R^{20}$, wherein each alkyl part may be substituted with one or more substituents independently selected from $R^{25}$; or C(O)$NR^{22}R^{23}$, $C_{1-6}$-alkyl-C(O)$NR^{22}R^{23}$ optionally substituted with one or more substituents independently selected from $R^{26}$; or two of $R^7$, $R^8$ and $R^9$ can be taken together to form a $C_{2-5}$-alkylene bridge;

$R^{16}$, $R^{17}$, and $R^{18}$ are independently $C_{1-6}$-alkyl, halogen, nitro, cyano, hydroxy, carboxy, oxo, —$CF_3$, carboxy-$C_{1-6}$-alkyl, hydroxy-$C_{1-6}$-alkyl, —$C_{1-6}$-alkyl-C(O)—O—$C_{1-6}$-alkyl, —C(O)—O—$C_{1-6}$-alkyl, —$NR^{19}R^{20}$, —NHS$(O)_2CH_3$, —C(O)$NR^{19}R^{20}$, —$S(O)_2CH_3$, or —$S(O)_2NH_2$;

$R^{19}$ and $R^{20}$ independently represent hydrogen, $C_{1-6}$-alkyl, hydroxy-$C_{1-6}$-alkyl, carboxy-$C_{1-6}$-alkyl, aryl, heteroaryl, $C_{3-8}$-heterocyclyl, or —$S(O)_2$—$C_{1-6}$-alkyl, each of which is optionally substituted with one or more substituents independently selected from $R^{24}$, or $R^{19}$ and $R^{20}$ together with the nitrogen to which they are attached form a 3 to 8 membered heterocyclic ring with the said nitrogen atom, the heterocyclic ring optionally containing one or two further heteroatoms selected from nitrogen, oxygen and sulphur, the heterocyclic ring is optionally substituted with one or more substituents independently selected from $R^{24}$;

$R^{21}$ is selected from $C_{1-6}$-alkyl, carboxy-$C_{1-6}$-alkyl, $C_{1-6}$-alkylamino-$C_{1-6}$-alkyl or hydroxy-$C_{1-6}$-alkyl; or aryl, heteroaryl, aryl-$C_{1-6}$-alkyl, or heteroaryl-$C_{1-6}$-alkyl, wherein the aryl or heteroaryl part is optionally substituted with one or more substituents independently selected from $R^{24}$; or $C_{3-8}$-cycloalkyl, $C_{3-8}$-cycloalkenyl, $C_{3-8}$-cycloalkyl-$C_{1-6}$-alkyl, $C_{3-8}$-cycloalkenyl-$C_{1-6}$-alkyl;

$R^{22}$ and $R^{23}$ are independently selected from hydrogen, $C_{1-6}$-alkyl, $C_{3-8}$-cycloalkyl, aryl, heteroaryl or $R^{22}$ and $R^{23}$ together with the nitrogen to which they are attached form a 3 to 8 membered heterocyclic ring with the said nitrogen atom, the heterocyclic ring optionally containing one or two further heteroatoms selected from nitrogen, oxygen and sulphur, the heterocyclic ring is optionally substituted with one or more substituents independently selected from $R^{24}$;

$R^{24}$ is halogen, nitro, cyano, hydroxy, carboxy, —$CF_3$, $C_{1-6}$-alkyl, hydroxy-$C_{1-6}$-alkyl, carboxy-$C_{1-6}$-alkyl, —C(O)—$C_{1-6}$-alkyl, —C(O)—O—$C_{1-6}$-alkyl or —$C_{1-6}$-alkyl-C(O)—O—$C_{1-6}$-alkyl;

$R^{25}$ and $R^{26}$ are independently $C_{1-6}$-alkyl, halogen, nitro, cyano, hydroxy, —C(O)—O—$C_{1-6}$-alkyl, carboxy, —$C_{1-6}$-alkyl-C(O)—O—$C_{1-6}$-alkyl, carboxy-$C_{1-6}$-alkyl, —$CF_3$, —$S(O)_2CH_3$, or —$S(O)_2NH_2$ as well as any salt hereof with a pharmaceutically acceptable acid or base, or any optical isomer or mixture of optical isomers, including a racemic mixture, or any tautomeric forms.

Embodiment 2

A compound according to embodiment 1 wherein $R^1$ is $C_{3-8}$-cycloalkyl, indanyl, tetrahydrofuryl, tetrahydrothiofuryl, tetrahydrothienyl, tetrahydropyranyl, tetrahydrothiopyranyl, 1,4-dioxanyl, 1,3-dioxanyl, piperidyl, pyrrolidinyl, morpholinyl, or piperazinyl, each of which is optionally substituted with one or more substituents $R^3$, $R^4$, $R^5$ and $R^6$.

Embodiment 3

A compound according to any one of the embodiments 1 to 2 wherein $R^1$ is cyclopropyl, cyclobutyl, cyclopentyl, cyclohexyl, cyclohexenyl, cycloheptyl, cycloheptenyl, cyclooctyl, bicyclo[3.2.1]octyl, bicyclo[2.2.1]heptyl, norpinyl, norbonyl, norcaryl, adamantyl, indanyl, tetrahydrofuryl, tetrahydrothiofuryl, tetrahydrothienyl, tetrahydropyranyl, tetrahydrothiopyranyl, 1,4-dioxanyl, 1,3-dioxanyl, piperidyl, Pyrrolidinyl, morpholinyl, or piperazinyl, each of which is optionally substituted with one or more substituents $R^3$, $R^4$, $R^5$ and $R^6$.

Embodiment 4

A compound according to embodiment 3 wherein $R^1$ is cyclopropyl, cyclobutyl, cyclopentyl, cyclohexyl, cycloheptyl, bicyclo[3.2.1]octyl, bicyclo[2.2.1]heptyl, adamantyl, indanyl, tetrahydrofuryl, tetrahydrothienyl, tetrahydropyranyl, tetrahydrothiopyranyl, piperidyl, pyrrolidinyl, morpholinyl, or piperazinyl, each of which is optionally substituted with one or more substituents $R^3$, $R^4$, $R^5$ and $R^6$.

Embodiment 5

A compound according to embodiment 4 wherein $R^1$ is cyclopentyl, cyclohexyl, cycloheptyl, bicyclo[2.2.1]heptyl, tetrahydrofuryl, tetrahydrothienyl, tetrahydropyranyl, tetrahydrothiopyranyl, piperidyl, pyrrolidinyl, morpholinyl, or piperazinyl, each of which is optionally substituted with one or more substituents $R^3$, $R^4$, $R^5$ and $R^6$.

Embodiment 6

A compound according to embodiment 5 wherein $R^1$ is selected from

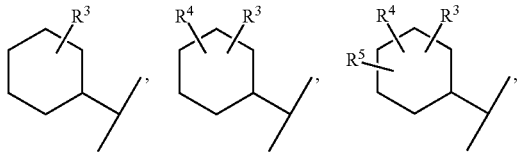

-continued

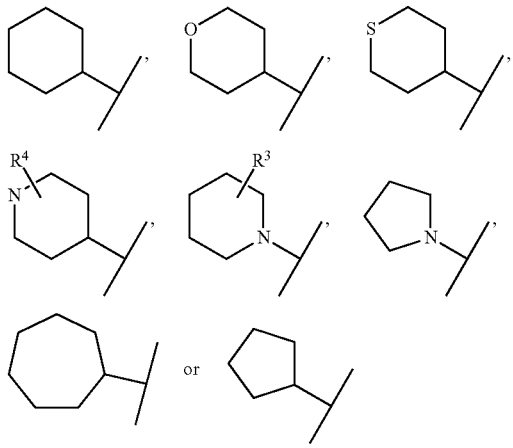

7. A compound according to embodiment 6 wherein $R^1$ is selected from

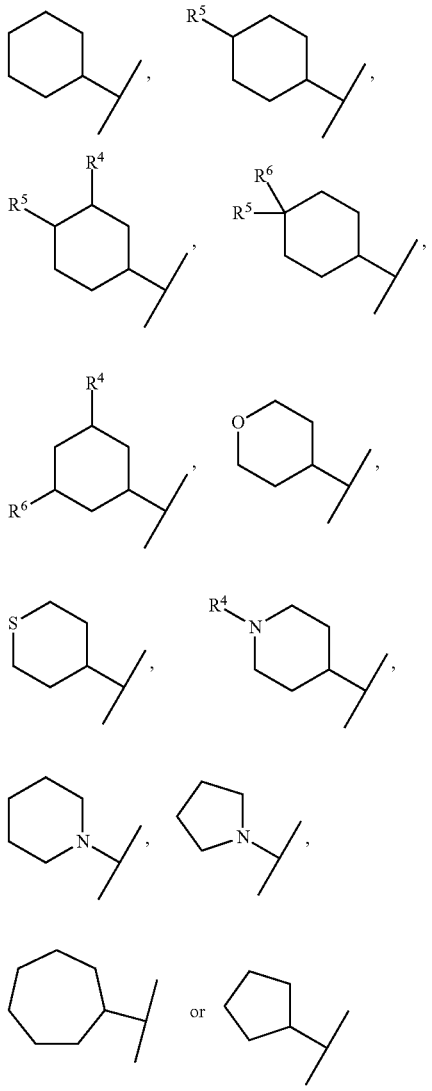

Embodiment 8

A compound according to embodiment 7 wherein $R^1$ is selected from

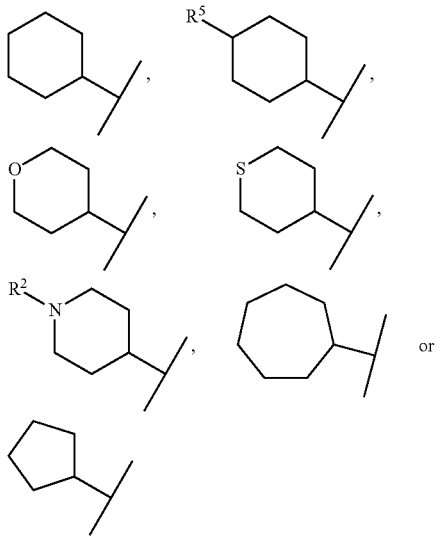

Embodiment 9

A compound according to embodiment 8 wherein $R^1$ is selected from

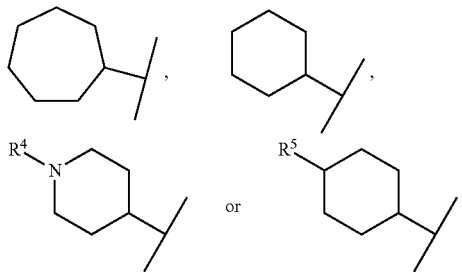

Embodiment 10

A compound according to embodiment 9 wherein $R^1$ is selected from

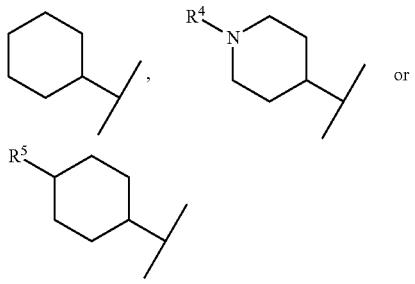

Embodiment 11

A compound according to embodiment 10 wherein $R^1$ is

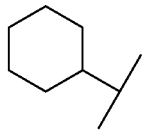

Embodiment 12

A compound according to embodiment 10 wherein $R^1$ is

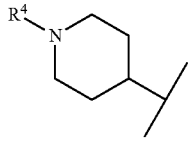

Embodiment 13

A compound according to embodiment 10 wherein $R^1$ is

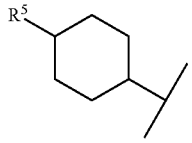

Embodiment 14

A compound according to any one of the embodiments 1 to 13 wherein $R^2$ is $C_{3-8}$-cycloalkyl, tetrahydrofuryl, tetrahydrothiofuryl, tetrahydrothienyl, tetrahydropyranyl, tetrahydrothiopyranyl, 1,4-dioxanyl, 1,3-dioxanyl, piperidyl, pyrrolidinyl, morpholinyl, or piperazinyl, each of which is optionally substituted with one or more substituents $R^{30}$, $R^{31}$, $R^{32}$ and $R^{33}$.

Embodiment 15

A compound according to embodiment 14 wherein $R^2$ is cyclopropyl, cyclobutyl, cyclopentyl, cyclohexyl, cyclohexenyl, cycloheptyl, cycloheptenyl, cyclooctyl, bicyclo[3.2.1]octyl, bicyclo[2.2.1]heptyl, norpinyl, norbonyl, norcaryl, adamantyl, tetrahydrofuryl, tetrahydrothiofuryl, tetrahydrothienyl, tetrahydropyranyl, tetrahydrothiopyranyl, 1,4-dioxanyl, 1,3-dioxanyl, piperidyl, pyrrolidinyl, morpholinyl, or piperazinyl, each of which is optionally substituted with one or more substituents $R^{30}$, $R^{31}$, $R^{32}$ and $R^{33}$.

Embodiment 16

A compound according to embodiment 15 wherein $R^2$ is cyclopropyl, cyclobutyl, cyclopentyl, cyclohexyl, bicyclo[3.2.1]octyl, bicyclo[2.2.1]heptyl, adamantyl, tetrahydrofuryl, tetrahydrothienyl, tetrahydropyranyl, tetrahydrothiopyranyl, piperidyl, pyrrolidinyl, morpholinyl, or piperazinyl, each of which is optionally substituted with one or more substituents $R^{30}$, $R^{31}$, $R^{32}$ and $R^{33}$.

Embodiment 17

A compound according to embodiment 16 wherein $R^2$ is cyclopentyl, cyclohexyl, bicyclo[2.2.1]heptyl, tetrahydrofuryl, tetrahydrothienyl, tetrahydropyranyl, tetrahydrothiopyranyl, pyrrolidinyl, morpholinyl, or piperazinyl, each of which is optionally substituted with one or more substituents $R^{30}$, $R^{31}$, $R^{32}$ and $R^{33}$.

Embodiment 18

A compound according to embodiment 17 wherein $R^2$ is selected from

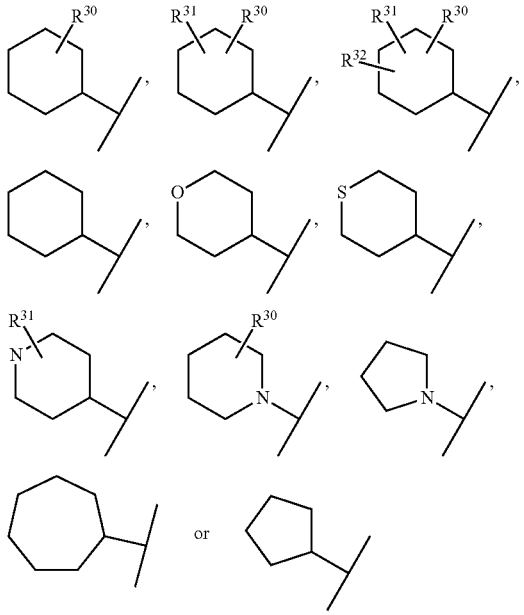

Embodiment 19

A compound according to embodiment 18 wherein $R^2$ is selected from

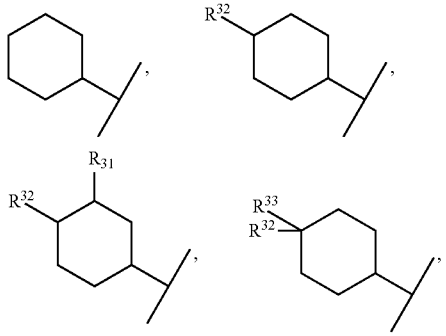

-continued

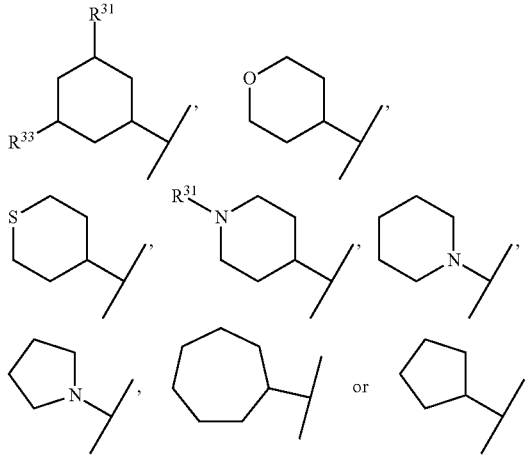

Embodiment 20

A compound according to embodiment 19 wherein $R^2$ is selected from

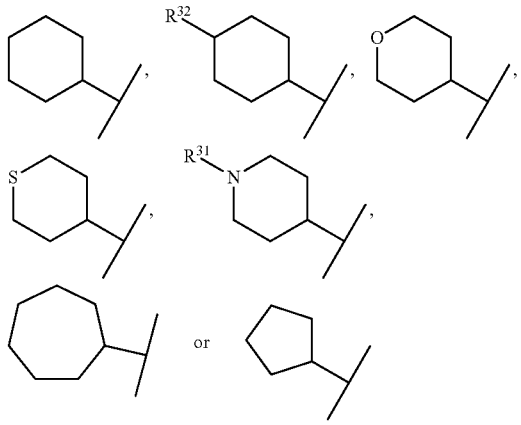

Embodiment 21

A compound according to embodiment 20 wherein $R^2$ is selected from

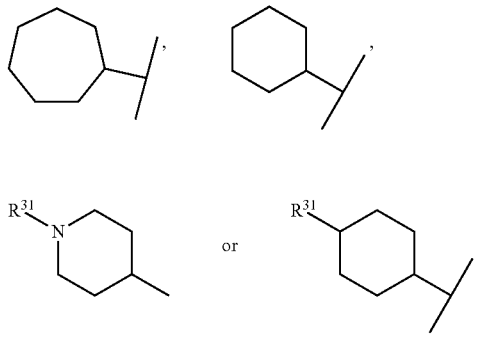

Embodiment 22

A compound according to embodiment 21 wherein $R^2$ is selected from

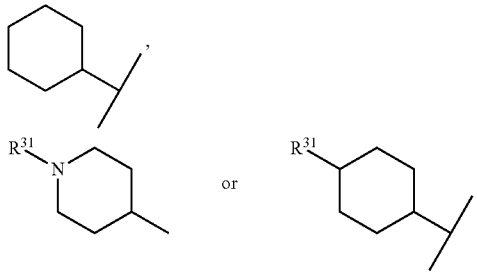

Embodiment 23

A compound according to embodiment 22 wherein $R^2$ is

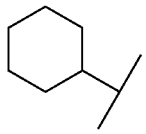

Embodiment 24

A compound according to embodiment 22 wherein $R^2$ is

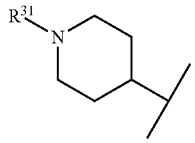

Embodiment 25

A compound according to embodiment 22 wherein $R^2$ is

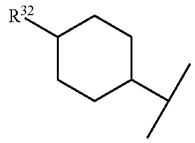

Embodiment 26

A compound according to any one of the embodiments 1 to 25 wherein $R^1$ and $R^2$ are both cyclohexyl.

Embodiment 27

A compound according to any one of the embodiments 1 to 26 wherein $R^3$, $R^4$, $R^5$, $R^6$, $R^{30}$, $R^{31}$, $R^{32}$ and $R^{33}$ are independently selected from the group consisting of halogen, oxo, cyano, hydroxy, carboxy, —$CF_3$; or —$NR^{10}R^{11}$; or $C_{1-6}$-alkyl, $C_{2-6}$-alkenyl, $C_{3-8}$-cycloalkyl, $C_{3-8}$-cycloalkyl-$C_{1-6}$-alkyl, aryl, aryl-$C_{1-6}$-alkyl, $C_{1-6}$-alkoxy, $C_{3-6}$-cycloalkyl-$C_{1-6}$-alkoxy, aryl-$C_{1-6}$-alkoxy, $C_{1-6}$-alkylthio, arylthio, —C(O)—O—$C_{1-6}$-alkyl, or $C_{1-6}$-alkyl-C(O)—O—$C_{1-6}$-alkyl, each of which is optionally substituted with one or more substituents independently selected from $R^{12}$; or —C(O)—$R^{27}$, —$S(O)_2$—$R^{27}$, —C(O)—$NR^{13}R^{14}$, —$C_{1-6}$-alkyl-C(O)—$NR^{13}R^{14}$; or two substituents selected from $R^3$, $R^4$, $R^5$ and $R^6$ or $R^{30}$, $R^{31}$, $R^{32}$ and $R^{33}$ attached to the same or adjacent atoms together form a radical —O—$(CH_2)_{1-3}$—O—.

Embodiment 28

A compound according to embodiment 27 wherein $R^3$, $R^4$, $R^5$, $R^6$, $R^{30}$, $R^{31}$, $R^{32}$ and $R^{33}$ are independently selected from the group consisting of halogen, oxo, —$CF_3$; or $NR^{10}R^{11}$; or $C_{1-6}$-alkyl, $C_{3-8}$-cycloalkyl, $C_{1-6}$-alkoxy, $C_{1-6}$-alkylthio, aryl, aryl-$C_{1-6}$-alkyl, arylthio, C(O) O $C_{1-6}$-alkyl, or $C_{1-6}$-alkyl-C(O)—O—$C_{1-6}$-alkyl, each of which is optionally substituted with one or more substituents independently selected from $R^{12}$; or —C(O)—$R^{27}$ or —$S(O)_2$—$R^{27}$; or two substituents selected from $R^3$, $R^4$, $R^5$ and $R^6$ or $R^{30}$, $R^{31}$, $R^{32}$ and $R^{33}$ attached to the same or adjacent atoms together form a radical —O—$(CH_2)_{1-3}$—O—.

Embodiment 29

A compound according to embodiment 28 wherein $R^3$, $R^4$, $R^5$, $R^6$, $R^{30}$, $R^{31}$, $R^{32}$ and $R^{33}$ are independently selected from the group consisting of halogen, —$CF_3$; or methyl, ethyl, propyl, isopropyl, butyl, tett-butyl, cyclopropyl, cyclobutyl, cyclopentyl, cyclohexyl, phenyl, naphtyl, benzyl, phenyl-ethyl, methoxy, ethoxy, propoxy, phenylthio, —C(O)—O—$CH_3$, or —C(O)—O—$CH_2CH_3$, each of which is optionally substituted with one or more substituents independently selected from $R^{12}$; or —C(O)—$R^{27}$ or —$S(O)_2$—$R^{27}$; or two substituents selected from $R^3$, $R^4$, $R^5$ and $R^6$ or $R^{30}$, $R^{31}$, $R^{32}$ and $R^{33}$ attached to the same or adjacent atoms together form a radical O $(CH_2)_{1-3}$ O .

Embodiment 30

A compound according to embodiment 29 wherein $R^3$, $R^4$, $R^5$, $R^6$, $R^{30}$, $R^{31}$, $R^{32}$ and $R^{33}$ are independently selected from the group consisting of halogen, —$CF_3$; or methyl, ethyl, propyl, isopropyl, butyl, tert-butyl, cyclopropyl, cyclobutyl, cyclopentyl, cyclohexyl, phenyl, naphtyl, benzyl, phenyl-ethyl, methoxy, ethoxy, propoxy, phenylthio, —C(O)—O—$CH_3$, or —C(O)—O—$CH_2CH_3$, each of which is optionally substituted with one or more substituents independently selected from $R^{12}$; or —C(O)—$R^{27}$ or —$S(O)_2$—$R^{27}$.

Embodiment 31

A compound according to embodiment 30 wherein $R^3$, $R^4$, $R^5$, $R^6$, $R^{30}$, $R^{31}$, $R^{32}$ and $R^{33}$ are independently selected from the group consisting of F, Cl, —$CF_3$, methyl, ethyl, propyl, isopropyl, butyl, or tert-butyl, —C(O)—$R^{27}$ or —$S(O)_2$—$R^{27}$.

Embodiment 32

A compound according to embodiment 28 wherein $R^3$, $R^4$, $R^5$, $R^6$, $R^{30}$, $R^{31}$, $R^{32}$ and $R^{33}$ are independently selected from $C_{1-6}$-alkyl or —C(O)—$R^{27}$.

Embodiment 33

A compound according to any one of the embodiments 1 to 32 wherein $R^{10}$ and $R^{11}$ independently represent hydrogen, methyl, ethyl, propyl, —C(O)—$CH_3$, —C(O)—$CH_2CH_3$, —$CH_2$C(O)OH, —$CH_2CH_2$C(O)OH, —C(O)—$CH_2$—C(O)OH, —C(O)—$CH_2CH_2$—C(O)OH, —$S(O)_2CH_3$, or phenyl.

Embodiment 34

A compound according to embodiment 33 wherein $R^{10}$ and $R^{11}$ independently represent hydrogen, methyl, ethyl, —C(O)—$CH_3$, —$CH_2$C(O)OH, —C(O)—$CH_2$—C(O)OH, —$S(O)_2CH_3$, or phenyl.

Embodiment 35

A compound according to embodiment 34 wherein $R^{10}$ and $R^{11}$ independently represent hydrogen, methyl, ethyl, or phenyl.

Embodiment 36

A compound according to any one of the embodiments 1 to 35 wherein $R^{27}$ is $C_{1-6}$-alkyl, $C_{1-6}$-alkoxy, $C_{2-6}$-alkenyl, $C_{2-6}$-alkynyl, $C_{3-8}$-cycloalkyl, $C_{3-8}$-cycloalkyl-$C_{1-6}$-alkyl, aryl, aryl-$C_{1-6}$-alkyl, aryl-$C_{2-6}$-alkenyl, hetereoaryl, heteroaryl-$C_{1-6}$-alkyl, carboxy-$C_{1-6}$-alkyl, $C_{1-6}$-alkoxy-$C_{1-6}$-alkyl, $C_{1-6}$-alkylthio-$C_{1-6}$-alkyl, $R^{10}$HN—$C_{1-6}$-alkyl, $R^{10}R^{11}$N—$C_{1-6}$-alkyl, $R^{10}R^{11}$N—$S(O)_2$—$C_{1-6}$-alkyl, or $R^{10}R^{11}$N—C(O)—$C_{1-6}$-alkyl, each of which is optionally substituted with one or more substituents independently selected from $R^{12}$.

Embodiment 37

A compound according to embodiment 36 wherein $R^{27}$ is $C_{1-6}$-alkyl, $C_{1-6}$-alkoxy, $C_{3-8}$-cycloalkyl, $C_{3-8}$-cycloalkyl-$C_{1-6}$alkyl, aryl-$C_{2-6}$-alkenyl, aryl, heteroaryl, heteroaryl-$C_{1-6}$alkyl, carboxy-$C_{1-6}$-alkyl, $C_{1-6}$-alkoxy-$C_{1-6}$-alkyl, $R^{10}$HN $C_{1-6}$-alkyl, $R^{10}R^{11}$N $C_{1-6}$-alkyl, $R^{10}R^{11}$N $S(O)_2$—$C_{1-6}$-alkyl, or $R^{10}R^{11}$N—C(O)—$C_{1-6}$-alkyl, each of which is optionally substituted with one or more substituents independently selected from $R^{12}$.

Embodiment 38

A compound according to embodiment 37 wherein $R^{27}$ is $C_{1-6}$-alkyl, $C_{1-6}$-alkoxy, $C_{3-8}$-cycloalkyl, $C_{3-8}$-cycloalkyl-$C_{1-6}$-alkyl, aryl, heteroaryl-$C_{1-6}$-alkyl, aryl-$C_{1-6}$-alkyl, $C_{1-6}$-alkoxy-$C_{1-6}$-alkyl or heteroaryl, each of which is optionally substituted with one or more substituents independently selected from $R^{12}$.

Embodiment 39

A compound according to embodiment 38 wherein $R^{27}$ is methyl, ethyl, propyl, n-butyl, isobutyl, 1,1,1-trifluoromethyl, cyclopropyl, cyclopentyl, cyclopropylmethyl, phenyl, pyridyl, thiophene, imidazole, or thiazole, each of which is optionally substituted with one or more substituents independently selected from $R^{12}$.

Embodiment 40

A compound according to embodiment 39 wherein $R^{27}$ is methyl, ethyl, propyl, n-butyl, isobutyl, 1,1,1-trifluoroethyl, cyclopropyl, cyclopentyl, cyclopropylmethyl, phenyl, or pyridyl, thiophene, imidazole, or thiazole.

Embodiment 41

A compound according to any one of the embodiments 1 to 40 wherein $R^{12}$ is halogen, cyano, hydroxy, carboxy, —$CF_3$, or $C_{1-6}$alkyl.

Embodiment 42

A compound according to embodiment 41 wherein $R^{12}$ is halogen, cyano, hydroxy, carboxy, $CF_3$, methoxy, methyl, ethyl or propyl.

Embodiment 43

A compound according to any one of the embodiments 1 to 42 wherein $R^{13}$ and $R^{14}$ are independently selected from the group consisting of hydrogen, $C_{1-6}$-alkyl, hydroxy-$C_{1-6}$-alkyl, carboxy-$C_{1-6}$-alkyl, phenyl, or naphtyl, each of which is optionally substituted with one or more substituents independently selected from $R^{15}$; or $R^{13}$ and $R^{14}$ together with the nitrogen to which they are attached form a 3 to 8 membered heterocyclic ring with the said nitrogen atom, the heterocyclic ring optionally containing one or two further heteroatoms selected from nitrogen, oxygen and sulphur.

Embodiment 44

A compound according to embodiment 43 wherein $R^{13}$ and $R^{14}$ are independently selected from the group consisting of hydrogen, methyl, ethyl, propyl, hydroxy-methyl, hydroxy-ethyl, carboxy-methyl, carboxy-ethyl, phenyl, or naphtyl, each of which is optionally substituted with one or more substituents independently selected from $R^{15}$; or $R^{13}$ and $R^{14}$ together with the nitrogen to which they are attached form a 3 to 8 membered heterocyclic ring with the said nitrogen atom, the heterocyclic ring optionally containing one or two further heteroatoms selected from nitrogen, oxygen and sulphur.

Embodiment 45

A compound according to embodiment 44 wherein $R^{13}$ and $R^{14}$ are independently selected from the group consisting of hydrogen, methyl, ethyl, propyl, or phenyl, each of which is optionally substituted with one or more substituents independently selected from $R^{15}$.

Embodiment 46

A compound according to any one of the embodiments 1 to 44 wherein $R^{15}$ is halogen, cyano, hydroxy, carboxy, —$CF_3$, methyl, ethyl, or propyl.

Embodiment 47

A compound according to embodiment 46 wherein $R^{15}$ is halogen, hydroxy, carboxy, —$CF_3$, methyl, or ethyl.

Embodiment 48

A compound according to any one of the embodiments 1 to 47 wherein A is thiazolyl, thiadiazolyl, pyrazinyl, pyridyl, benzothiazolyl, 5,6-dihydro-4H-cyclopentathiazolyl, 4,5,6,7-tetrahydro-benzothiazolo-pyridyl, 6,7-dihydro-pyranothiazolyl, or 4,5,6,7-tetrahydrobenzothiazolyl optionally substituted with one or more substituents independently selected from $R^7$, $R^8$ and $R^9$.

Embodiment 49

A compound according to embodiment 48 wherein A is

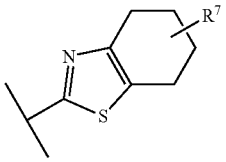

Embodiment 50

A compound according to embodiment 48 wherein A is thiazolyl or thiadiazolyl optionally substituted with one or more substituents independently selected from $R^7$, $R^3$ and $R^9$.

Embodiment 51

A compound according to embodiment 50 wherein A is thiazolyl, 1,2,4-thiadiazolyl, or 1,3,4-thiadiazolyl, optionally substituted with one or more substituents independently selected from $R^7$, $R^8$ and $R^9$.

Embodiment 52

A compound according to embodiment 51 wherein A is

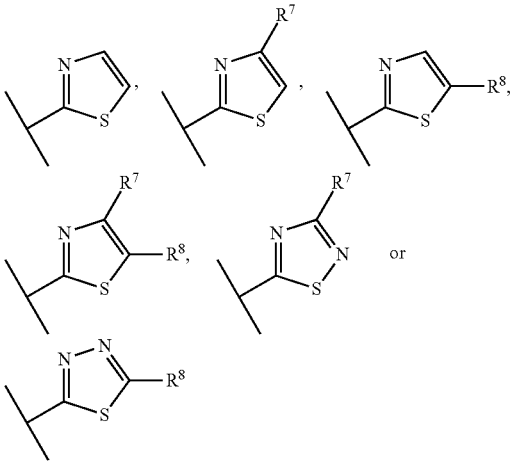

Embodiment 53

A compound according to embodiment 52 wherein A is

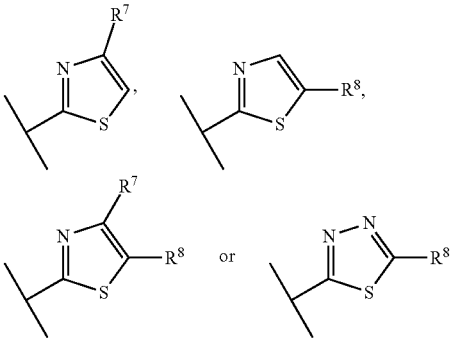

Embodiment 54

A compound according to embodiment 53 wherein A is

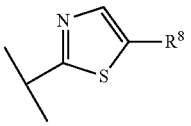

Embodiment 55

A compound according to any one of the embodiments 1 to 54 wherein $R^7$, $R^8$ and $R^9$ are independently selected from halogen, carboxy, cyano, nitro, hydroxy, —$CF_3$, —SCN; or $C_{1-6}$-alkyl, $C_{2-6}$-alkenyl, $C_{1-6}$-alkoxy, $C_{1-6}$-alkylthio, $C_{1-6}$-alkylamino, $C_{1-6}$-alkylsulfenyl, —C(O)—O—$C_{1-6}$-alkyl, —C(O)—$C_{1-6}$-alkyl, —$C_{1-6}$-alkyl-C(O)—O—$C_{1-6}$-alkyl, —$C_{1-6}$-alkyl-O—C(O)—$C_{1-6}$-alkyl, —NH—C(O)—$C_{1-6}$-alkyl, —$C_{1-6}$-alkoxy-$C_{1-6}$-alkyl, —$C_{1-6}$-alkyl-S—$C_{1-6}$-alkyl, $C_{3-8}$-cycloalkyl-$C_{1-6}$-alkyl, $C_{3-6}$-cycloalkyl-$C_{1-6}$-alkoxy, $C_{3-6}$-cycloalkyl-$C_{1-6}$-alkylthio each of which is optionally substituted with one or more substituents independently selected from $R^{16}$; or aryl, heteroaryl, aryl-$C_{1-6}$-alkyl, heteroaryl-$C_{1-6}$-alkyl, Aryl-$C_{1-6}$-alkoxy, heteroaryl-$C_{1-6}$-alkoxy, heteroarylthio-$C_{1-6}$-alkyl, aryloxy, heteroaryloxy, heteroarylthio, each of which is optionally substituted on the aryl or heteroaryl part with one or more substituents independently selected from $R^{17}$; or $C_{3-8}$-cycloalkyl, $C_{3-8}$-cycloalkenyl, $C_{3-8}$-cycloalkyl-$C_{1-6}$-alkyl, $C_{3-8}$-cycloalkenyl-$C_{1-6}$-alkyl, each of which is optionally substituted on the cycloalkyl part with one or more substituents independently selected from $R^{18}$; or —$NR^{19}R^{20}$, —$C_{1-6}$-alkyl-$NR^{19}R^{20}$, —$C_{1-6}$-alkyl-S—$R^{21}$, —$C_{1-6}$-alkyl-S(O)—$R^{21}$, —$C_{1-6}$-alkyl-$S(O)_2$—$R^{21}$, —$S(O)_2$—$R^{21}$ or —$S(O)_2$—$NR^{19}R^{20}$, wherein each alkyl part may be substituted with one or more substituents independently selected from $R^{25}$; or —C(O)$NR^{22}R^{23}$, —$C_{1-6}$-alkyl-C(O)$NR^{22}R^{23}$ optionally substituted with one or more substituents independently selected from $R^{26}$; or two of $R^7$, $R^8$ and $R^9$ can be taken together to form a $C_{2-5}$-alkylene bridge.

Embodiment 56

A compound according to embodiment 55 wherein $R^7$, $R^8$ and $R^9$ are independently selected from halogen, carboxy, cyano, or —$CF_3$; or $C_{1-6}$-alkyl, $C_{2-6}$-alkenyl, $C_{1-6}$-alkoxy, $C_{1-6}$-alkylthio, —C(O)—O—$C_{1-6}$-alkyl, —C(O)—$C_{1-6}$-alkyl, $C_{1-6}$-alkyl-C(O)—O—$C_{1-6}$-alkyl, —$C_{1-6}$-alkyl-O—C(O)—$C_{1-6}$-alkyl, —$C_{1-6}$-alkoxy-$C_{1-6}$-alkyl, $C_{3-8}$cycloalkyl-$C_{1-6}$-alkyl, each of which is optionally substituted with one or more substituents independently selected from $R^{16}$; or aryl, heteroaryl, aryl-$C_{1-6}$-alkyl, heteroaryl-$C_{1-6}$-alkyl, each of which is optionally substituted on the aryl or heteroaryl part with one or more substituents independently selected from $R^{17}$; or $C_{3-8}$-cycloalkyl, $C_{3-8}$-cycloalkyl-$C_{1-6}$-alkyl, each of which is optionally substituted on the cycloalkyl part with one or more substituents independently selected from $R^{18}$; or —$NR^{19}R^{20}$, —$C_{1-6}$-alkyl-$NR^{19}R^{20}$, —$S(O)_2$—$R^{21}$ or $S(O)_2$ $NR^{19}R^{20}$, wherein each alkyl part may be substituted with one or more substituents independently selected from $R^{25}$; or —C(O)$NR^{22}R^{23}$, —$C_{1-6}$-alkyl-C(O)$NR^{22}R^{23}$ optionally substituted with one or more substituents independently selected from $R^{26}$; or two of $R^7$, $R^8$ and $R^9$ can be taken together to form a $C_{2-5}$-alkylene bridge.

Embodiment 57

A compound according to embodiment 56 wherein $R^7$, $R^8$ and $R^9$ are independently selected from halogen, carboxy or —$CF_3$; or $C_{1-6}$-alkyl, $C_{1-6}$-alkoxy, $C_{1-6}$-alkylthio, —$C_{1-6}$-alkyl-C(O)—O—$C_{1-6}$-alkyl, —$C_{1-6}$-alkyl-O—C(O)—$C_{1-6}$-alkyl or —C(O)—O—$C_{1-6}$-alkyl, each of which is optionally substituted with one or more substituents independently selected from $R^{16}$; or phenyl, benzyl, or heteroarylthio, wherein heteroaryl is pyridyl or imidazolyl, and wherein each aryl or heteroaryl is optionally substituted on the aryl or heteroaryl part with one or more substituents independently selected from $R^{17}$; or cyclopropyl, cyclobutyl, cyclopentyl, or cyclohexyl, each of which is optionally substituted on the cycloalkyl part with one or more substituents independently selected from $R^{18}$; or C(O)$NR^{22}R^{23}$, $S(O)_2$ $R^{21}$ or $S(O)_2$ $NR^{19}R^{20}$; or two of $R^7$, $R^8$ and $R^9$ can be taken together to form a $C_{2-5}$-alkylene bridge.

Embodiment 58

A compound according to embodiment 57 wherein $R^7$, $R^8$ and $R^9$ are independently selected from halogen, carboxy, —$CF_3$, —S—$CH_3$, —S—$CH_2CH_3$, —S—$CH_2CH_2CH_3$, methyl, ethyl, propyl, isopropyl, butyl, tert-butyl, methoxy, ethoxy, —$CH_2$—C(O)—O—$CH_3$, —$CH_2$—C(O)—O—$CH_2CH_3$, —$CH_2CH_2$—C(O)—O—$CH_3$, —$CH_2CH_2$—C(O)—O—$CH_2CH_3$, —$CH_2$—O—C(O)—$CH_3$, —$CH_2$—O—C(O)—$CH_2CH_3$, —$CH_2CH_2$—O—C(O)—$CH_3$, —$CH_2CH_2$—O—C(O)—$CH_2CH_3$, —C(O)—O—$CH_3$, —C(O)—O—$CH_2CH_3$, each of which is optionally substituted with one or more substituents independently selected from $R^{16}$; or heteroarylthio, wherein heteroaryl is pyridyl or imidazolyl, each optionally substituted on the heteroaryl part with one or more substituents independently selected from $R^{17}$, or —$S(O)_2$—$R^{21}$.

Embodiment 59

A compound according to embodiment 58 wherein $R^7$, $R^8$ and $R^9$ are independently selected from Cl, F, Br, —$CF_3$, —S—$CH_3$, —S—$CH_2CH_3$, —S—$CH_2CH_2CH_3$, methyl, ethyl, methoxy, ethoxy, —$CH_2$—C(O)—O—$CH_2CH_3$, —C(O)—O—$CH_3$, or —C(O)—O—$CH_2CH_3$, each of which is optionally substituted with one or more substituents independently selected from $R^{16}$; or heteroarylthio, wherein heteroaryl is pyridyl or imidazolyl, each optionally substituted on the heteroaryl part with one or more substituents independently selected from $R^{17}$.

Embodiment 60

A compound according to any one of the embodiments 1 to 59 wherein $R^{16}$, $R^{17}$, and $R^{18}$ are independently $C_{1-6}$-alkyl, halogen, hydroxy, oxo, carboxy, —$CF_3$, carboxy-$C_{1-6}$-alkyl, hydroxy-$C_{1-6}$-alkyl, —$C_{1-6}$-alkyl-C(O)—O—$C_{1-6}$-alkyl, —C(O)—O—$C_{1-6}$-alkyl, —$NR^{19}R^{20}$, —C(O)$NR^{19}R^{20}$ or —$S(O)_2CH_3$.

Embodiment 61

A compound according to embodiment 60 wherein $R^{16}$, $R^{17}$, and $R^{18}$ are independently methyl, ethyl, propyl, halogen, hydroxy, oxo, carboxy, —$CF_3$, carboxy-methyl, carboxy-ethyl, carboxy-propyl, hydroxy-methyl, hydroxy-ethyl, hydroxy-propyl, $CH_2$ C(O) O $CH_3$, $CH_2$ C(O)—O—$CH_2CH_3$, —$CH_2CH_2$—C(O)—O—$CH_3$, —$CH_2CH_2$—C(O)—O—$CH_2CH_3$, —C(O)—O—$CH_3$, —C(O)—O—$CH_2CH_3$, —C(O)—O—$CH_2CH_2CH_3$, or $S(O)_2CH_3$.

Embodiment 62

A compound according to embodiment 61 wherein $R^{16}$, $R^{17}$, and $R^{18}$ are independently methyl, ethyl, propyl, halogen, oxo, carboxy, carboxy-methyl, carboxy-ethyl, carboxy-propyl, hydroxy-methyl, hydroxy-ethyl, hydroxy-propyl, —$CH_2$—C(O)—O—$CH_3$, —$CH_2$C(O)—O—$CH_2CH_3$, —$CH_2CH_2$—C(O)—O—$CH_3$, —$CH_2CH_2$—C(O)—O—$CH_2CH_3$, —C(O)—O—$CH_3$, —C(O)—O—$CH_2CH_3$, —C(O)—O—$CH_2CH_2CH_3$, or —$S(O)_2CH_3$.

Embodiment 63

A compound according to embodiment 60 wherein $R^{16}$, $R^{17}$, and $R^{18}$ are independently carboxy, —$NR^{19}R^{20}$, or —C(O)$NR^{19}R^{20}$.

Embodiment 64

A compound according to any one of the embodiments 1 to 63 wherein $R^{19}$ and $R^{20}$ independently represent hydrogen, $C_{1-6}$-alkyl, hydroxy-$C_{1-6}$-alkyl, carboxy-$C_{1-6}$-alkyl, phenyl, naphtyl, $C_{3-8}$-heterocyclyl, or —$S(O)_2$—$C_{1-6}$-alkyl, each of which is optionally substituted with one or more substituents independently selected from $R^{24}$; or $R^{19}$ and $R^{20}$ together with the nitrogen to which they are attached form a 3 to 8 membered heterocyclic ring with the said nitrogen atom, the heterocyclic ring optionally containing one or two further heteroatoms selected from nitrogen, oxygen and sulphur, the heterocyclic ring is optionally substituted with one or more substituents independently selected from $R^{24}$.

Embodiment 65

A compound according to embodiment 64 wherein $R^{19}$ and $R^{20}$ independently represent hydrogen, methyl, ethyl, propyl, carboxy-methyl, carboxy-ethyl, carboxy-propyl, hydroxy-methyl, hydroxy-ethyl, hydroxy-propyl, phenyl, or naphtyl, or $R^{19}$ and $R^{20}$ together with the nitrogen to which they are attached form a 3 to 8 membered heterocyclic ring with the said nitrogen atom, the heterocyclic ring optionally containing one or two further heteroatoms selected from nitrogen, oxygen and sulphur, the heterocyclic ring is optionally substituted with one or more substituents independently selected from $R^{24}$.

Embodiment 66

A compound according to embodiment 64 wherein $R^{19}$ and $R^{20}$ independently represent hydrogen, $C_{1-6}$-alkyl, or $R^{19}$ and $R^{20}$ together with the nitrogen to which they are attached form a 3 to 8 membered heterocyclic ring with the said nitrogen atom, the heterocyclic ring optionally containing one or two further heteroatoms selected from nitrogen, oxygen and sulphur, the heterocyclic ring is optionally substituted with one or more substituents independently selected from $R^{24}$.

Embodiment 67

A compound according to embodiment 66 wherein $R^{19}$ and $R^{20}$ independently represent hydrogen, methyl, ethyl, or propyl, or $R^{19}$ and $R^{20}$ together with the nitrogen to which they are attached form a 3 to 8 membered heterocyclic ring with the said nitrogen atom, wherein the heterocyclic ring is pyrrolidyl, piperidyl, piperazinyl, homopiperazinyl, or morpholinyl, the heterocyclic ring is optionally substituted with one or more substituents independently selected from $R^{24}$.

Embodiment 68

A compound according to any one of the embodiments 1 to 67 wherein $R^{21}$ is selected from $C_{1-6}$-alkyl, carboxy-$C_{1-6}$-alkyl, or hydroxy-$C_{1-6}$-alkyl; or phenyl, naphtyl, or phenyl-$C_{1-6}$-alkyl, wherein the aryl part is optionally substituted with one or more substituents independently selected from $R^{24}$; or $C_{3-8}$-cycloalkyl, or $C_{3-8}$-cycloalkyl-$C_{1-6}$-alkyl.

Embodiment 69

A compound according to embodiment 68 wherein $R^{21}$ is selected from methyl, ethyl, propyl, carboxy-methyl, carboxy-ethyl, carboxy-propyl, hydroxy-methyl, hydroxy-ethyl, hydroxy-propyl; or phenyl, naphtyl, or phenyl-$C_{1-6}$-alkyl, wherein the aryl part is optionally substituted with one or more substituents independently selected from $R^{24}$; or $C_{3-8}$-cycloalkyl, or $C_{3-8}$-cycloalkyl-$C_{1-6}$-alkyl.

Embodiment 70

A compound according to embodiment 69 wherein $R^{21}$ is selected from methyl, ethyl, carboxy-methyl, carboxy-ethyl, carboxy-propyl; or phenyl, naphtyl, or phenyl-$C_{1-6}$-alkyl, wherein the aryl part is optionally substituted with one or more substituents independently selected from $R^{24}$.

Embodiment 71

A compound according to any one of the embodiments 1 to 70 wherein $R^{22}$ and $R^{23}$ are independently selected from Hydrogen, $C_{1-6}$-alkyl, $C_{3-8}$-cycloalkyl, phenyl, naphtyl, or $R^{22}$ and $R^{23}$ together with the nitrogen to which they are attached form a 3 to 8 membered heterocyclic ring with the said nitrogen atom, the heterocyclic ring optionally containing one or two further heteroatoms selected from nitrogen, oxygen and sulphur, the heterocyclic ring is optionally substituted with one or more substituents independently selected from $R^{24}$.

Embodiment 72

A compound according to embodiment 71 wherein $R^{22}$ and $R^{23}$ are independently selected from hydrogen, methyl, ethyl, propyl, butyl, cyclopropyl, cyclobutyl, cyclopenlyl, cyclohexyl, cycloheptyl, phenyl, naphtyl, or $R^{22}$ and $R^{23}$ together with the nitrogen to which they are attached form a 3 to 8 membered hetemcyclic ring with the said nitrogen atom, wherein the heterocyclic ring is pyrrolidyl, piperidyl, piperazinyl, homopiperazinyl, or morpholinyl, the heterocyclic ring is optionally substituted with one or more substituents independently selected from $R^{24}$.

Embodiment 73

A compound according to any one of the embodiments 1 to 72 wherein $R^{24}$ is halogen, hydroxy, carboxy, —$CF_3$, $C_{1-6}$-alkyl, hydroxy-$C_{1-6}$-alkyl, carboxy-$C_{1-6}$-alkyl, C(O) $C_{1-6}$-alkyl, —C(O)—O—$C_{1-6}$-alkyl or —$C_{1-6}$-alkyl-C(O)—O—$C_{1-6}$-alkyl.

Embodiment 74

A compound according to embodiment 73 wherein $R^{24}$ is carboxy, $C_{1-6}$-alkyl, carboxy-$C_{1-6}$-alkyl, —C(O)—$C_{1-6}$-alkyl, —C(O)—O—$C_{1-6}$-alkyl or —$C_{1-6}$-alkyl-C(O)—O—$C_{1-6}$-alkyl.

Embodiment 75

A compound according to any one of the embodiments 1 to wherein $R^{25}$ and $R^{26}$ are independently $C_{1-6}$-alkyl, halogen, hydroxy, carboxy, or $CF_3$.

Embodiment 76

A compound according to embodiment 75 wherein $R^{25}$ and $R^{26}$ are independently methyl, ethyl, propyl, halogen, hydroxy, carboxy, or —$CF_3$.

Embodiment 77

A compound according to any one of the embodiments 1 to 76, which compound is an activator of glucokinase, when tested in the Glucokinase Activation Assay (I) disclosed herein at a glucose concentration of 2 mM.

Embodiment 78

A compound according to any one of the embodiments 1 to 77, which compound is an activator of glucokinase, when tested in the Glucokinase Activation Assay (I) disclosed herein at a glucose concentration of from 10 to 15 mM.

Embodiment 79

A compound according to any one of the embodiments 1 to 78, which compound, at a concentration of 30 μM, is capable of providing an at least 1.5, such as at least 1.7, for instance at least 2.0 fold activation of glucokinase in the Glucokinase Activation Assay (I) disclosed herein at a glucose concentration of 2 mM.

Embodiment 80

A compound according to any one of the embodiments 1 to 79, which compound, at a concentration of 30 μM, is capable of providing an at least 1.5, such as at least 1.7, for instance at least 2.0 fold activation of glucokinase in the Glucokinase Activation Assay (I) disclosed herein at a glucose concentration of from 10 to 15 mM.

Embodiment 81

A compound according to any one of the embodiments 1 to 80, which at a concentration of 5 μM is capable of providing an at least 1.5, such as at least 1.7, for instance at least 2.0 fold activation of glucokinase in the Glucokinase Activation Assay (I) disclosed herein at a glucose concentration of 2 mM.

Embodiment 82

A compound according to any one of the embodiments 1 to 81, which at a concentration of 5 μM is capable of providing an at least 1.5, such as at least 1.7, for instance at least 2.0 fold activation of glucokinase in the Glucokinase Activation Assay (I) disclosed herein at a glucose concentration of from 10 to 15 mM.

Embodiment 83

A compound according to any one of the embodiments 1 to 82, which compound provides an increase in glucokinase activity, where the increase in glucokinase activity provided by the compound increases with increasing concentrations of glucose.

Embodiment 84

A compound according to embodiment 83, which provides an increase in glucokinase activity in Glucokinase Activation Assay (I) disclosed herein at a glucose concentration of 15 mM, which increase is significantly higher than the increase in glucokinase activity provided by the compound in Glucokinase Activation Assay (I) disclosed herein at a glucose concentration of 5 mM.

Embodiment 85

A compound according to any one of the embodiments 83 to 84, which at a compound concentration of 10 μM provides an increase in glucokinase activity in Glucokinase Activation Assay (I) disclosed herein at a glucose concentration of 15 mM, which increase is significantly higher than the increase in glucokinase activity provided by the compound at a compound concentration of 10 μM in Glucokinase Activation Assay (I) disclosed herein at a glucose concentration of 5 mM.

Embodiment 86

A compound according to any one of the embodiments 83 to 85, which at a compound concentration of 10 μM provides an increase in glucokinase activity in Glucokinase Activation Assay (I) disclosed herein at a glucose concentration of 15 mM, which increase is at least 1.1 fold higher, such as at least 1.2 fold higher, for instance at least 1.3 fold higher, such as at least 1.4 fold higher, for instance 1.5 fold higher, such as at least 1.6 fold higher, for instance at least 1.7 fold higher, such as at least 1.8 fold higher, for instance at least 1.9 fold higher, such as at least 2.0 fold higher than the increase in glucokinase activity provided by the compound at a compound concentration of 10 μM in Glucokinase Activation Assay (I) disclosed herein at a glucose concentration of 5 mM.

Embodiment Liver Specificity

87. A compound according to any one of the embodiments 1 to 86, which compound increases glucose utilization in the liver without inducing any increase in insulin secretion in response to glucose.

Embodiment 88

A compound according to any one of the embodiments 1 to 86, which compound shows a significantly higher activity in isolated hepatocytes compared to the activity of the compound in Ins-1 cells.

Embodiment 89

A compound according to any one of the embodiments 87 to 88, which compound shows a significantly higher activity in isolated hepatocytes measured as described in the Glucokinase Activity Assay (II) compared to the activity of the compound in Ins-1 cells measured as described in the Glucokinase Activity Assay (III).

Embodiment 90

A compound according to embodiment 89, which compound shows an activity in isolated hepatocytes measured as described in the Glucokinase Activity Assay (II) which activity is at least 1.1 fold higher, such as at least 1.2 fold higher, for instance at least 1.3 fold higher, such as at least 1.4 fold higher, for instance 1.5 fold higher, such as at least 1.6 fold higher, for instance at least 1.7 fold higher, such as at least 1.8 fold higher, for instance at least 1.9 fold higher, such as at least 2.0 fold higher, for instance at least a 3.0 fold higher, such as at least a 4.0 fold higher, for instance at least 5.0 fold higher, such as at least 10 fold higher than the activity of the compound in Ins-1 cells measured as described in the Glucokinase Activity Assay (III).

Embodiment 91

A compound according to embodiment 89, which compound shows no activity in the Ins-1 cells measured as described in the Glucokinase Activity Assay (III).

Embodiment 92

A method of preventing hypoglycemia comprising administration of a compound according to any one of the embodiments 1 to 91.

Embodiment 93

The use of a compound according to any one of the embodiments 1 to 91 for the preparation of a medicament for the prevention of hypoglycemia.

Embodiment 94

A compound according to any one of embodiments 1 to 91, which is an agent useful for the treatment of an indication selected from the group consisting of hyperglycemia, IGT, insulin resistance syndrome, syndrome X, type 2 diabetes, type 1 diabetes, dyslipidemia, hypertension, and obesity.

Embodiment 95

A compound according to any one of embodiments 1 to 94 for use as a medicament.

Embodiment 96

A compound according to any one of embodiments 1 to 94 for treatment of hyperglycemia, for treatment of IGT, for treatment of Syndrome X, for treatment of type 2 diabetes, for treatment of type 1 diabetes, for treatment of dyslipidemia, for treatment of hyperlipidemia, for treatment of hypertension, for treatment of obesity, for lowering of food intake, for appetite regulation, for regulating feeding behaviour, or for enhancing the secretion of enteroincretins, such as GLP-1.

Embodiment 97

A pharmaceutical composition comprising, as an active ingredient, at least one compound according to any one of embodiments 1 to 96 together with one or more pharmaceutically acceptable carriers or excipients.

Embodiment 98

A pharmaceutical composition according to embodiment 97 in unit dosage form, comprising from about 0.05 mg to about 1000 mg, preferably from about 0.1 mg to about 500 mg and especially preferred from about 0.5 mg to about 200 mg of the compound according to any one of embodiments 1 to 96.

Embodiment 99

Use of a compound according to any one of the embodiments 1 to 96 for increasing the activity of glucokinase.

Embodiment 100

Use of a compound according to any one of embodiments 1 to 96 for the preparation of a medicament for the treatment of metabolic disorders, for blood glucose lowering, for the treatment of hyperglycemia, for the treatment of IGT, for the treatment of Syndrome X, for the treatment of impaired fasting glucose (IFG), for the treatment of type 2 diabetes, for the treatment of type 1 diabetes, for delaying the progression of impaired glucose tolerance (IGT) to type 2 diabetes, for delaying the progression of non-insulin requiring type 2 diabetes to insulin requiring type 2 diabetes, for the treatment of dyslipidemia, for the treatment of hyperlipidemia, for the treatment of hypertension, for lowering of food intake, for appetite regulation, for the treatment of obesity, for regulating feeding behaviour, or for enhancing the secretion of enteroincretins.

Embodiment 101

Use of a compound according to any one of embodiments 1 to 96 for the preparation of a medicament for the adjuvant treatment of type 1 diabetes for preventing the onset of diabetic complications.

Embodiment 102

Use of a compound according to any one of embodiments 1 to 96 for the preparation of a medicament for increasing the number and/or the size of beta cells in a mammalian subject, for treatment of beta cell degeneration, in particular apoptosis of beta cells, or for treatment of functional dyspepsia, in particular irritable bowel syndrome.

Embodiment 103

Use according to any one of the embodiments 100 to 102 in a regimen which comprises treatment with a further antidiabetic agent.

Embodiment 104

Use according to any one of the embodiments 100 to 103 in a regimen which comprises treatment with a further antihyperlipidemic agent.

Embodiment 105

Use according to any one of embodiments 100 to 104 in a regimen which comprises treatment with a further antiobesity agent.

Embodiment 106

Use according to any one of embodiments 100 to 105 in a regimen which comprises treatment with a further antihypertensive agent.

Embodiment 107

Use of a compound according to any one of the embodiments 1 to 96 or a pharmaceutical composition according to embodiment 97 or embodiment 98 for the treatment of metabolic disorders, for blood glucose lowering, for the treatment of hyperglycemia, for treatment of IGT, for treatment of Syndrome X, for the treatment of impaired fasting glucose (IFG), for treatment of type 2 diabetes, for treatment of type 1 diabetes, for delaying the progression of impaired glucose tolerance (IGT) to type 2 diabetes, for delaying the progression of non-insulin requiring type 2 diabetes to insulin requiring type 2 diabetes, for treatment of dyslipidemia, for treatment of hyperlipidemia, for treatment of hypertension, for the treatment or prophylaxis of obesity, for lowering of food intake, for appetite regulation, for regulating feeding behaviour, or for enhancing the secretion of enteroincretins.

Embodiment 108

Use of a compound according to any one of the embodiments 1 to 96 or a pharmaceutical composition according to embodiment 97 or embodiment 98 for the adjuvant treatment of type 1 diabetes for preventing the onset of diabetic complications.

Embodiment 109

Use of a compound according to any one of the embodiments 1 to 96 or a pharmaceutical composition according to embodiment 97 or embodiment 98 for increasing the number and/or the size of beta cells in a mammalian subject, for treatment of beta cell degeneration, in particular apoptosis of beta cells, or for treatment of functional dyspepsia, in particular irritable bowel syndrome.

Embodiment A1

In another aspect the invention provides a compound of general formula (I)

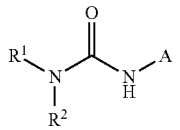

(I)

wherein $R^1$ is $C_{3-8}$-cycloalkyl, $C_{3-8}$-cycloalkenyl, $C_{3-8}$-heterocyclyl, $C_{3-8}$-heterocycloalkenyl, fused aryl-$C_{3-8}$-cycloalkyl, or fused heteroaryl-$C_{3-8}$-cycloalkyl, each of which is optionally substituted with one or more substituents $R^3$, $R^4$, $R^5$ and $R^6$;

$R^2$ is $C_{3-8}$-cycloalkyl, $C_{3-8}$-cycloalkenyl, $C_{3-8}$-heterocyclyl, $C_{3-8}$-heterocycloalkenyl, fused aryl-$C_{3-8}$-cycloalkyl or fused heteroaryl-$C_{3-8}$-cycloalkyl, each of which is optionally substituted with one or more substituents $R^{30}$, $R^{31}$, $R^{32}$ and $R^{33}$, and $R^3$, $R^4$, $R^5$, $R^6$, $R^{30}$, $R^{31}$, $R^{32}$ and $R^{33}$ are independently selected from the group consisting of halogen, nitro, cyano, hydroxy, oxo, carboxy, —$CF_3$; or —$NR^{10}R^{11}$; or $C_{1-6}$-alkyl, $C_{2-6}$-alkenyl, $C_{2-6}$-alkynyl, $C_{3-8}$-cycloalkyl, $C_{3-8}$-cycloalkyl-$C_{1-6}$-alkyl, aryl, aryl-$C_{1-6}$-alkyl, heteroaryl-$C_{1-6}$-alkyl, $C_{1-6}$-alkoxy, $C_{3-6}$-cycloalkyl-$C_{1-6}$-alkoxy, aryl-$C_{1-6}$-alkoxy, heteroaryl, heteroaryl-$C_{1-6}$-alkoxy, aryloxy, heteroaryloxy, $C_{1-6}$-alkylthio, arylthio, heteroarylthio, $C_{3-8}$cycloalkylthio, aryl-$C_{1-6}$-alkylthio, heteroaryl-$C_{1-6}$-alkylthio, $C_{1-6}$-alkylsulfenyl, $C_{3-6}$-cycloalkyl-$C_{1-6}$-alkylthio, $C_{1-6}$-alkyl-C(O)—O—$C_{1-6}$-alkyl, $C_{1-6}$-alkoxy-$C_{1-6}$-alkyl, $C_{1-6}$-alkylthio-$C_{1-6}$-alkyl, carboxy-$C_{1-6}$-alkyloxy, amino-$C_{1-6}$-alkyl, $C_{1-6}$-alkylamino-$C_{1-6}$-alkyl, di-($C_{1-6}$-alkyl)amino-$C_{1-6}$-alkyl, $C_{1-6}$-alkylsulfamoyl, di($C_{1-6}$-alkyl)sulfamoyl, $C_{1-6}$-alkylsulfinamoyl or di($C_{1-6}$-alkyl)sulfinamoyl each of which is optionally substituted with one or more substituents independently selected from $R^{12}$; or —C(O)—$R^{27}$, —$S(O)_2$—$R^{27}$, —C(O)—$NR^{13}R^{14}$, —$S(O)_2$—$NR^{13}R^{14}$, —$C_{1-6}$-alkyl-C(O)—$NR^{13}R^{14}$; or two substituents selected from $R^3$, $R^4$, $R^5$ and $R^6$ or $R^{30}$, $R^{31}$, $R^{32}$ and $R^{33}$ attached to the same or adjacent atoms together form a radical —O—$(CH_2)_{1-3}$—O—;

$R^{10}$ and $R^{11}$ independently represent hydrogen, $C_{1-6}$-alkyl, —C(O)—$C_{1-6}$-alkyl, —C(O)—O—$C_{1-6}$-alkyl, carboxy-$C_{1-6}$-alkyl, —C(O)—$C_{1-6}$-alkyl-C(O)OH, —$S(O)_2$—$C_{1-6}$-alkyl, or aryl; $R^{27}$ is $C_{1-6}$-alkyl, $C_{1-6}$-alkoxy, $C_{2-6}$-alkenyl, $C_{2-6}$-alkynyl, $C_{3-8}$-cycloalkyl, $C_{3-8}$-cycloalkyl-$C_{1-6}$-alkyl, $C_{3-8}$-cycloalkyl-$C_{2-6}$-alkenyl, aryl, aryl-$C_{1-6}$-alkyl, aryloxy-$C_{1-6}$-alkyl, aryl-$C_{2-6}$-alkenyl, heteroaryl, $C_{3-8}$-heterocyclyl, heteroaryl-$C_{1-6}$-alkyl, $C_{3-8}$-heterocyclyl-$C_{1-6}$-alkyl, Heteroaryloxy-$C_{1-6}$-alkyl, carboxy-$C_{1-6}$-alkyl, carboxy-$C_{2-6}$-alkenyl, $C_{1-6}$-alkoxy-$C_{1-6}$-alkyl, $C_{1-6}$-alkoxy-$C_{2-6}$-alkenyl, $C_{1-6}$-alkylthio-$C_{1-6}$-alkyl, $R^{10}$HN—$C_{1-6}$-alkyl, $R^{10}R^{11}$—N—$C_{1-6}$-alkyl, $R^{10}R^{11}$—N—$C_{2-6}$-alkenyl, $R^{10}R^{11}$—N—$S(O)_2$—$C_{1-6}$-alkyl, $R^{10}R^{11}$—N—C(O)—$C_{1-6}$-alkyl, $C_{1-6}$-alkyl-C(O)—NH—$C_{1-6}$-alkyl, aryl-C(O)—NH—$C_{1-6}$-alkyl, heteroaryl-C(O)—NH—$C_{1-6}$-alkyl, $C_{3-8}$-cycloalkyl-C(O)—NH—$C_{1-6}$-alkyl, $C_{1-6}$-alkyl-$S(O)_2$—NH—$C_{1-6}$-alkyl, aryl-$S(O)_2$—NH—$C_{1-6}$-alkyl, heteroaryl-$S(O)_2$—NH—$C_{1-6}$-alkyl, or $C_{3-8}$-cycloalkyl-$S(O)_2$—NH—$C_{1-6}$-alkyl, each of which is optionally substituted with one or more substituents independently selected from $R^{12}$;

$R^{12}$ is halogen, cyano, hydroxy, —C(O)—O—$C_{1-6}$-alkyl, carboxy, $CF_3$, $C_{1-6}$-alkyl, $C_{1-6}$-alkoxy, $NR^{10}R^{11}$, —$S(O)_2CH_3$, or —$S(O)_2NH_2$;

$R^{13}$ and $R^{14}$ are independently selected from the group consisting of hydrogen, $C_{1-6}$-alkyl, hydroxy-$C_{1-6}$-alkyl, carboxy-$C_{1-6}$-alkyl, aryl, or heteroaryl, each of which is optionally substituted with one or more substituents independently selected from $R^{15}$; or $R^{13}$ and $R^{14}$ together with the nitrogen to which they are attached form a 3 to 8 membered heterocyclic ring with the said nitrogen atom, the heterocyclic ring optionally containing one or two further heteroatoms selected from nitrogen, oxygen and sulphur;

$R^{15}$ is halogen, cyano, hydroxy, carboxy, —$CF_3$, $C_{1-6}$-alkyl, —$S(O)_2CH_3$, or —$S(O)_2NH_2$;

A is heteroaryl which is optionally substituted with one or more substituents independently selected from $R^7$, $R^8$ and $R^9$;

$R^7$, $R^8$ and $R^9$ are independently selected from halogen, carboxy, cyano, nitro, hydroxy, —$CF_3$, —SCN; or $C_{1-6}$-alkyl, $C_{2-6}$-alkenyl, $C_{2-6}$-alkynyl, $C_{1-6}$-alkoxy, $C_{1-6}$-alkylthio, $C_{2-6}$-alkenylthio, $C_{1-6}$-alkylamino, $C_{1-6}$-alkylsulfenyl, —C(O)—O—$C_{1-6}$-alkyl, formyl, —C(O)—$C_{1-6}$-alkyl, —$C_{1-6}$-alkyl-C(O)—O—$C_{1-6}$-alkyl, —$C_{1-6}$-alkyl-O—C(O)—$C_{1-6}$-alkyl, —NH—C(O)—$C_{1-6}$-alkyl, —$C_{1-6}$-alkoxy-$C_{1-6}$-alkyl, —$C_{1-6}$-alkyl-S—$C_{1-6}$-alkyl, carboxy-$C_{1-6}$-alkyl, or hydroxy-$C_{1-6}$-alkyl, each of which is optionally substituted with one or more substituents independently selected from $R^{16}$; or aryl, heteroaryl, aryl-$C_{1-6}$-alkyl, heteroaryl-$C_{1-6}$-alkyl, aryl-$C_{1-6}$-alkoxy, heteroaryl-$C_{1-6}$-alkoxy, aryl-$C_{1-6}$-alkylthio, heteroaryl-$C_{1-6}$-alkylthio, heteroaryl-thio-$C_{1-6}$-alkyl, heteroaryl-oxy-$C_{1-6}$-alkyl, aryloxy, heteroaryloxy, arylthio, heteroarylthio, aryl-$C_{1-6}$-alkylamino, —C(O)-aryl, or —C(O)-heteroaryl, each of which is optionally substituted on the aryl or heteroaryl part with one or more substituents independently selected from $R^{17}$; or $C_{3-8}$-cycloalkyl, $C_{3-8}$-cycloalkenyl, $C_{3-8}$-cycloalkylthio, $C_{3-8}$-cycloalkyl-$C_{1-6}$-alkyl, $C_{3-8}$-cycloalkenyl-$C_{1-6}$-alkyl, $C_{3-6}$-cycloalkyl-$C_{1-6}$-alkoxy, $C_{3-6}$-cycloalkyl-$C_{1-6}$-alkylthio, each of which is optionally substituted on the cycloalkyl part with one or more substituents independently selected from $R^{18}$; or $C_{3-8}$-heterocyclyl, $C_{3-8}$-heterocyclyl-$C_{1-6}$-alkyl, $C_{3-8}$-heterocyclyl-$C_{1-6}$-alkylthio, $C_{3-8}$-heterocyclylthio, $C_{3-8}$-heterocyclyl-amino-$C_{1-6}$-alkyl, or —C(O)—$C_{3-8}$heterocyclyl, each of which is optionally substituted with one or more substituents independently selected from $R^{16}$; or —$NR^{19}R^{20}$, —$C_{1-6}$-alkyl-$NR^{19}R^{20}$, —$C_{2-6}$-alkenyl-$NR^{19}R^{20}$, —$C_{1-6}$-alkyl-S—$R^{21}$, —$C_{1-6}$-alkyl-S(O)—$R^{21}$, $C_{1-6}$-alkyl-$S(O)_2$ $R^{21}$, $S(O)_2$ $R^{21}$ or —$S(O)_2$—

$NR^{19}R^{20}$, wherein each alkyl part may be substituted with one or more substituents independently selected from $R^{25}$; or —C(O)$NR^{22}R^{23}$—$C_{1-6}$-alkyl-C(O) $NR^{22}R^{23}$—$C_{1-6}$-alkyl-NH—$NR^{22}R^{23}$—$C_{1-6}$-alkyl-NH—C(O)—$C_{1-6}$-alkyl-$NR^{22}R^{23}$, each optionally substituted with one or more substituents independently selected from $R^{26}$; or two of $R^7$, $R^8$ and $R^9$ can be taken together to form a $C_{2-5}$-alkylene bridge; the $C_{2-5}$-alkylene bridge is optionally substituted with one or more substituents independently selected from $R^{16}$;

$R^{16}$, $R^{17}$, and $R^{18}$ are independently $C_{1-6}$-alkyl, halogen, nitro, cyano, hydroxy, carboxy, oxo, —$CF_3$, carboxy-$C_{1-6}$-alkyl, hydroxy-$C_{1-6}$-alkyl, $C_{1-6}$-alkyl-C(O) O $C_{1-6}$-alkyl, —$C_{1-6}$-alkyl-C(O)—$NR^{19}R^{20}$, —C(O)—O—$C_{1-6}$-alkyl, —C(O)—$C_{1-6}$-alkyl-C(O)—$C_{1-6}$-alkyl, —$NR^{19}R^{20}$, —NHS $(O)_2C_{1-6}$-alkyl, —C(O)$NR^{19}R^{20}$, —$S(O)_2C_{1-6}$-alkyl, or —$S(O)_2NR^{19}R^{20}$;

$R^{19}$ and $R^{20}$ independently represent hydrogen, $C_{1-6}$-alkyl, hydroxy-$C_{1-6}$-alkyl, carboxy-$C_{1-6}$-alkyl, aryl, heteroaryl, $C_{3-8}$-heterocyclyl, aryl-$C_{1-6}$-alkyl, $C_{3-8}$-heterocyclyl-$C_{1-6}$-alkyl, —C(O)—O—$C_{1-6}$-alkyl, —$C_{1-6}$-alkyl-C(O)—O—$C_{1-6}$-alkyl, —$C_{1-6}$-alkyl-$NR^{22}R^{23}$, or —$S(O)_2$—$C_{1-6}$-alkyl, each of which is optionally substituted with one or more substituents independently selected from $R^{24}$, or $R^{19}$ and $R^{20}$ together with the nitrogen to which they are attached form a 3 to 8 membered heterocyclic ring with the said nitrogen atom, the heterocyclic ring optionally containing one or two further heteroatoms selected from nitrogen, oxygen and sulphur, the heterocyclic ring is optionally substituted with one or more substituents independently selected from $R^{24}$;

$R^{21}$ is selected from $C_{1-6}$-alkyl, $C_{2-6}$-alkenyl, carboxy-$C_{1-6}$-alkyl, $C_{1-6}$-alkylamino-$C_{1-6}$-alkyl or hydroxy-$C_{1-6}$-alkyl, —$C_{1-6}$-alkyl-$NR^{22}R^{23}$; or aryl, heteroaryl, aryl-$C_{1-6}$-alkyl, or heteroaryl-$C_{1-6}$-alkyl, wherein the aryl or heteroaryl part is optionally substituted with one or more substituents independently selected from $R^{24}$; or $C_{3-8}$-cycloalkyl, $C_{3-8}$-cycloalkenyl, $C_{3-8}$-cycloalkyl-$C_{1-6}$-alkyl, $C_{3-8}$-cycloalkenyl-$C_{1-6}$-alkyl;

$R^{22}$ and $R^{23}$ are independently selected from hydrogen, $C_{1-6}$-alkyl, carboxy-$C_{1-6}$-alkyl, —$C_{1-6}$-alkyl-C(O)—O—$C_{1-6}$-alkyl, —C(O)—O—$C_{1-6}$-alkyl, —$C_{1-6}$-alkyl-$S(O)_2$—$C_{1-6}$-alkyl, $C_{3-8}$-cycloalkyl, aryl, or heteroaryl; or $R^{22}$ and $R^{23}$ together with the nitrogen to which they are attached form a 3 to 8 membered heterocyclic ring with the said nitrogen atom, the heterocyclic ring optionally containing one or two further heteroatoms selected from nitrogen, oxygen and sulphur, the heterocyclic ring is optionally substituted with one or more substituents independently selected from $R^{24}$;

$R^{24}$ is halogen, nitro, cyano, hydroxy, carboxy, oxo, —$CF_3$, $C_{1-6}$-alkyl, hydroxy-$C_{1-6}$-alkyl, carboxy-$C_{1-6}$-alkyl, —C(O)—$C_{1-6}$-alkyl, —C(O)—$C_{3-8}$-cycloalkyl, —C(O)-aryl, C(O)-heteroaryl, C(O) $C_{3-8}$-heterocyclyl —C(O)—O—$C_{1-6}$-alkyl, —$C_{1-6}$-alkyl-C(O)—O—$C_{1-6}$-alkyl, aryl, heteroaryl, aryl-$C_{1-6}$-alkyl, heteroaryl-$C_{1-6}$-alkyl, $C_{3-8}$-cycloalkyl, $C_{3-8}$-heterocyclyl, $C_{3-8}$-cycloalkyl-$C_{1-6}$-alkyl, $C_{3-8}$-heterocyclyl-$C_{1-6}$-*alkyl*, —$C_{1-6}$-alkyl-C(O)—$C_{3-8}$-heterocyclyl, —C(O)—O—$C_{1-6}$-alkyl-aryl, —NH—S $(O)_2R^2$, or —$S(O)_2R^2$, wherein each cyclic moiety is optionally substituted with one or more substituents independently selected from $R^{29}$;

$R^{25}$ and $R^{26}$ are independently $C_{1-6}$-alkyl, halogen, nitro, cyano, hydroxy, C(O) O $C_{1-6}$-alkyl, carboxy, $C_{1-6}$-alkyl-C(O)—O—$C_{1-6}$-alkyl, carboxy-$C_{1-6}$-alkyl, —$CF_3$, —$S(O)_2CH_3$, or —$S(O)_2NH_2$;

$R^{28}$ is $C_{1-6}$-alkyl, carboxy-$C_{1-6}$-alkyl, —$C_{1-6}$-alkyl-C(O)—O—$C_{1-6}$-alkyl, $C_{3-8}$-cycloalkyl, aryl, aryl-$C_{1-6}$-alkyl, heteroaryl optionally substituted with $C_{1-6}$alkyl, —$NH_2$, or —$N(CH_3)_2$;

$R^{29}$ is halogen, nitro, cyano, hydroxy, carboxy, oxo, $CF_3$, $C_{1-6}$-alkyl, or $C_{1-6}$-alkoxy;

as well as any salt hereof with a pharmaceutically acceptable acid or base, or any optical isomer or mixture of optical isomers, including a racemic mixture, or any tautomeric forms.

Embodiment A2

A compound according to embodiment A1 wherein $R^1$ is $C_{3-8}$-cycloalkyl, $C_{3-8}$-cycloalkenyl, indanyl, tetrahydrofuryl, tetrahydrothiofuryl, tetrahydrothienyl, tetrahydropyranyl, tetrahydrothiopyranyl, 1,4-dioxanyl, 1,3-dioxanyl, piperidyl, pyrrolidinyl, morpholinyl, or piperazinyl, each of which is optionally substituted with one or more substiments $R^3$, $R^4$, $R^5$ and $R^6$.

Embodiment A3

A compound according to any one of the embodiments A1 to A2 wherein $R^1$ is cyclopropyl, cyclobutyl, cyclopentyl, cyclohexyl, cyclohexenyl, cycloheptyl, cycloheptenyl, cyclooctyl, bicyclo[3.2.1]octyl, bicyclo[2.2.1]heptyl, norpinyl, norcaryl, adamantyl, indanyl, tetrahydrofuryl, tetrahydrothiofuryl, tetrahydrothienyl, tetrahydropyranyl, tetrahydrothiopyranyl, 1,4-dioxanyl, 1,3-dioxanyl, piperidyl, pyrrolidinyl, morpholinyl, or piperazinyl, each of which is optionally substituted with one or more substituents $R^3$, $R^4$, $R^5$ and $R^6$.

Embodiment A4

A compound according to embodiment A3 wherein $R^1$ is cyclopropyl, cyclobutyl, cyclopentyl, cyclohexyl, cyclohexenyl, cycloheptyl, bicyclo[3.2.1]octyl, bicyclo[2.2.1]heptyl, adamantyl, indanyl, tetrahydrofuryl, tetrahydrothienyl, tetrahydropyranyl, tetrahydrothiopyranyl, piperidyl, pyrrolidinyl, morpholinyl, or piperazinyl, each of which is optionally substituted with one or more substituents $R^3$, $R^4$, $R^5$ and $R^6$.

Embodiment A5

A compound according to embodiment A4 wherein $R^1$ is cyclopentyl, cyclohexyl, cyclohexenyl, cycloheptyl, bicyclo[2.2.1]heptyl, tetrahydrofuryl, tetrahydrothienyl, tetrahydropyranyl, tetrahydrothiopyranyl, piperidyl, pyrrolidinyl, morpholinyl, or piperazinyl, each of which is optionally substituted with one or more substituents $R^3$, $R^4$, $R^5$ and $R^6$.

Embodiment A6

A compound according to embodiment A5 wherein $R^1$ is selected from

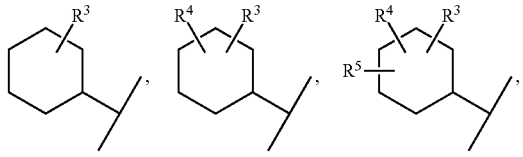

-continued
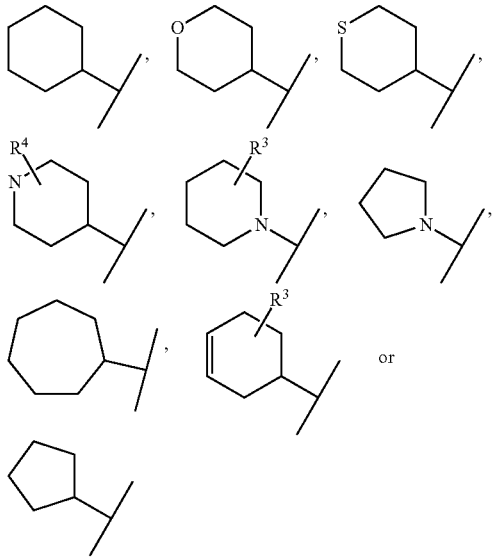
Embodiment A7
A compound according to embodiment A6 wherein $R^1$ is selected from
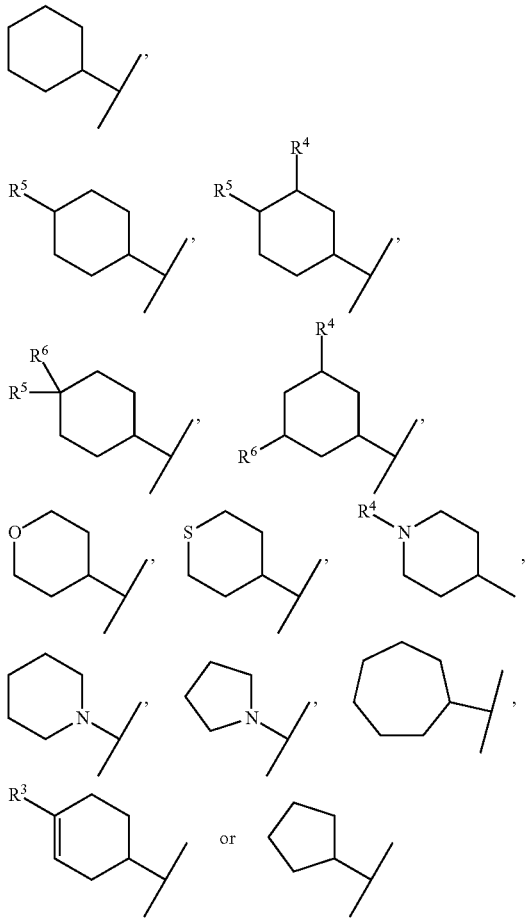
Embodiment A8
A compound according to embodiment A7 wherein $R^1$ is selected from
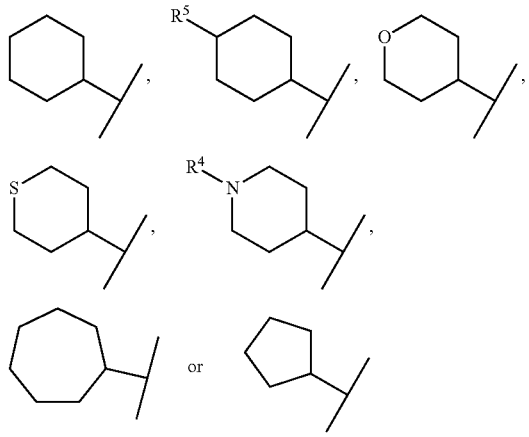
Embodiment A9
A compound according to embodiment A8 wherein $R^1$ is selected from
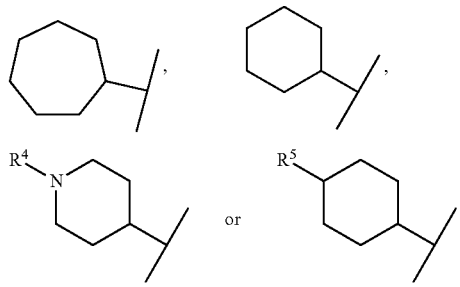
Embodiment A10
A compound according to embodiment A9 wherein $R^1$ is selected from
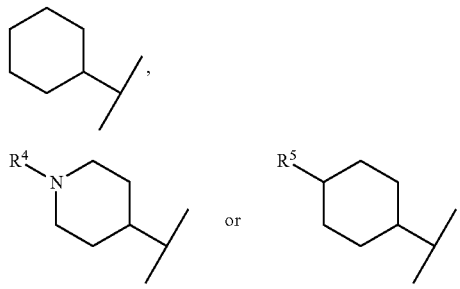

Embodiment A11

A compound according to embodiment A10 wherein $R^1$ is

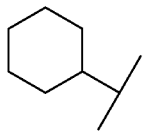

Embodiment A12

A compound according to embodiment A10 wherein $R^1$ is

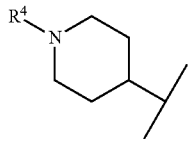

Embodiment A13

A compound according to embodiment A10 wherein $R^1$ is

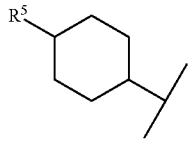

Embodiment A14

A compound according to any one of the embodiments A1 to A13 wherein $R^2$ is $C_{3-8}$-cycloalkyl, $C_{3-8}$-cycloalkenyl, tetrahydrofuryl, tetrahydrothiofuryl, tetrahydrothienyl, tetrahydropyranyl, tetrahydrothiopyranyl, 1,4-dioxanyl, 1,3-dioxanyl, piperidyl, pyrrolidinyl, morpholinyl, or piperazinyl, each of which is optionally substituted with one or more substituents $R^{30}$, $R^{31}$, $R^{32}$ and $R^{33}$.

Embodiment A15

A compound according to embodiment A14 wherein $R^2$ is cyclopropyl, cyclobutyl, cyclopentyl, cyclohexyl, cyclohexenyl, cycloheptyl, cycloheptenyl, cyclooctyl, bicyclo [3.2.1] octyl, bicyclo[2.2.1]heptyl, norpinyl, norbonyl, norcaryl, adamantyl, tetrahydrofuryl, tetrahydrothiofuryl, tetrahydrothienyl, tetrahydropyranyl, tetrahydrothiopyranyl, 1,4-dioxanyl, 1,3-dioxanyl, piperidyl, pyrrolidinyl, morpholinyl, or piperazinyl, each of which is optionally substituted with one or more substituents $R^{30}$, $R^{31}$, $R^{32}$ and $R^{33}$.

Embodiment A16

A compound according to embodiment A15 wherein $R^2$ is cyclopropyl, cyclobutyl, cyclopentyl, cyclohexyl, cyclohexenyl, bicyclo[3.2.1]octyl, bicyclo[2.2.1]heptyl, adamantyl, tetrahydrofuryl, tetrahydrothienyl, tetrahydropyranyl, tetrahydrothiopyranyl, piperidyl, pyrrolidinyl, morpholinyl, or piperazinyl, each of which is optionally substituted with one or more substituents $R^{30}$, $R^{31}$, $R^{32}$ and $R^{33}$.

Embodiment A17

A compound according to embodiment A16 wherein $R^2$ is cyclopentyl, cyclohexyl, cyclohexenyl, bicyclo[2.2.1]heptyl, tetrahydrofuryl, tetrahydrothienyl, tetrahydropyranyl, tetrahydrothiopyranyl, piperidyl, pyrrolidinyl, morpholinyl, or piperazinyl, each of which is optionally substituted with one or more substituents $R^{30}$, $R^{31}$, $R^{32}$ and $R^{33}$.

Embodiment A18

A compound according to embodiment A17 wherein $R^2$ is selected from

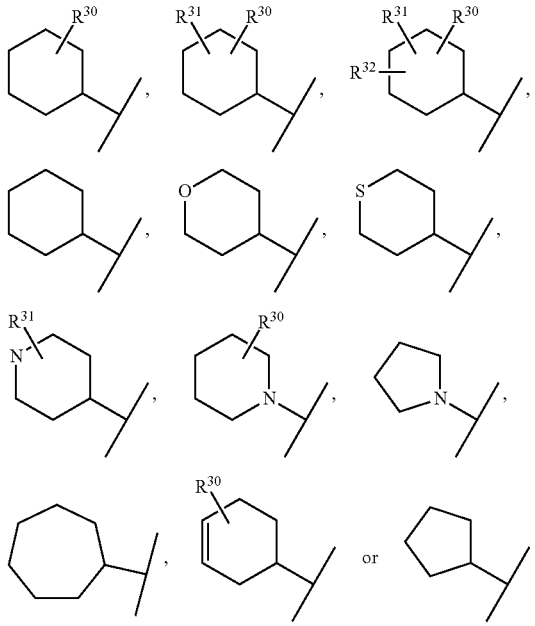

Embodiment A19

A compound according to embodiment A18 wherein $R^2$ is selected from

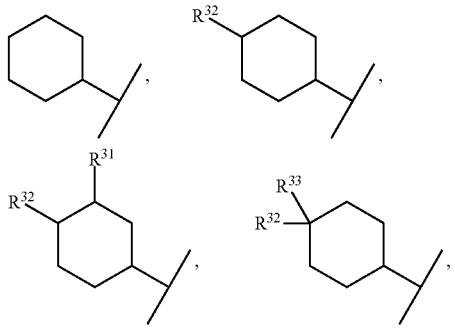

-continued

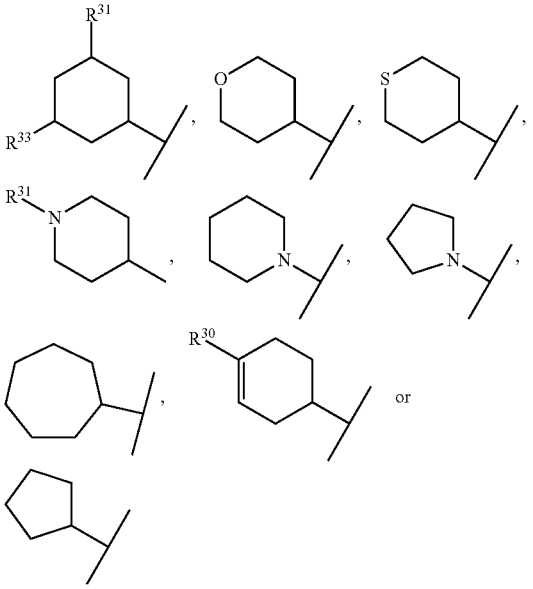

Embodiment A20

A compound according to embodiment A19 wherein $R^2$ is selected from

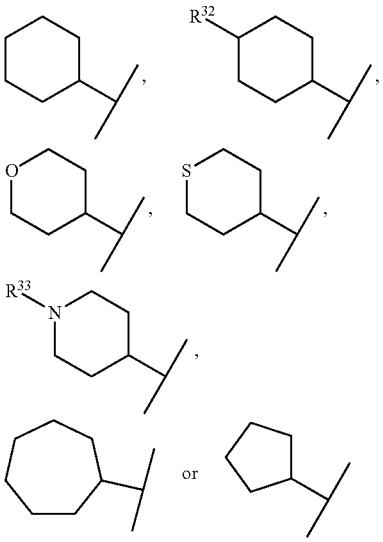

Embodiment A21

A compound according to embodiment A20 wherein $R^2$ is selected from

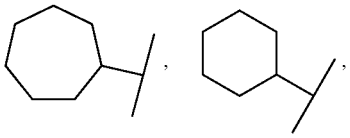

-continued

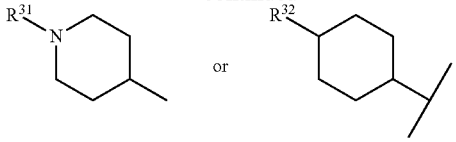

Embodiment A22

A compound according to embodiment A21 wherein $R^2$ is selected from

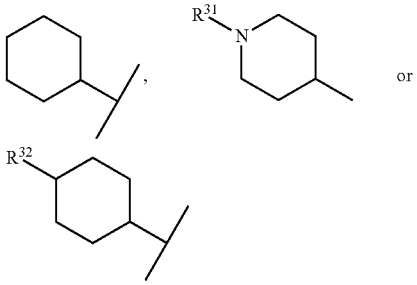

Embodiment A23

A compound according to embodiment A22 wherein $R^2$ is

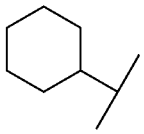

Embodiment A24

A compound according to embodiment A22 wherein $R^2$ is

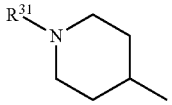

Embodiment A25

A compound according to embodiment A22 wherein $R^2$ is

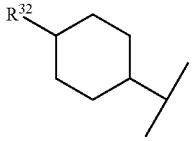

Embodiment A26

A compound according to any one of the embodiments A1 to A25 wherein $R^1$ and $R^2$ are both cyclohexyl.

Embodiment A27

A compound according to any one of the embodiments A1 to A25 wherein $R^1$ is

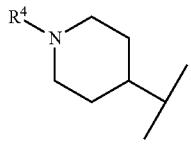

and $R^2$ is cyclohexyl.

Embodiment A28

A compound according to any one of the embodiments A1 to A27 wherein $R^3$, $R^4$, $R^5$, $R^6$, $R^{30}$, $R^{31}$, $R^{32}$ and $R^{33}$ are independently selected from the group consisting of halogen, oxo, cyano, hydroxy, carboxy, —$CF_3$; or —$NR^{10}R^{11}$; or $C_{1-6}$-alkyl, $C_{2-6}$-alkenyl, $C_{3-8}$-cycloalkyl, $C_{3-8}$-cycloalkyl-$C_{1-6}$-alkyl, aryl, aryl-$C_{1-6}$-alkyl, $C_{1-6}$-alkoxy, $C_{3-6}$-cycloalkyl-$C_{1-6}$-alkoxy, aryl-$C_{1-6}$-alkoxy, $C_{1-6}$-alkylthio, arylthio, —C(O)—O—$C_{1-6}$-alkyl, or $C_{1-6}$-alkyl-C(O)—O—$C_{1-6}$-alkyl, each of which is optionally substituted with one or more substituents independently selected from $R^{12}$; or —C(O)—$R^{27}$, —$S(O)_2$—$R^{27}$, —C(O)—$NR^{13}R^{14}$, —$S(O)_2$—$NR^{13}R^{14}$, —$C_{1-6}$-alkyl-C(O)—$NR^{13}R^{14}$; or two substituents selected from $R^3$, $R^4$, $R^5$ and $R^6$ or $R^{30}$, $R^{31}$, $R^{32}$ and $R^{33}$ attached to the same or adjacent atoms together form a radical —O—$(CH_2)_{1-3}$—O—.

Embodiment A29

A compound according to embodiment A28 wherein $R^3$, $R^4$, $R^5$, $R^6$, $R^{30}$, $R^{31}$, $R^{32}$ and $R^{33}$ are independently selected from the group consisting of halogen, oxo, —$CF_3$; or $NR^{10}R^{11}$; or $C_{1-6}$-alkyl, $C_{3-8}$-cycloalkyl, $C_{1-6}$-alkoxy, $C_{1-6}$-alkylthio, aryl, aryl-$C_{1-6}$-alkyl, arylthio, —C(O)—O—$C_{1-6}$-alkyl, or $C_{1-6}$-alkyl-C(O)—O—$C_{1-6}$-alkyl, each of which is optionally substituted with one or more substituents independently selected from $R^{12}$; or —C(O)—$R^{27}$, —$S(O)_2$—$NR^{13}R^{14}$ or —$S(O)_2$—$R^{27}$; or two substituents selected from $R^3$, $R^4$, $R^5$ and $R^6$ or $R^{30}$, $R^{31}$, $R^{32}$ and $R^{33}$ attached to the same or adjacent atoms together form a radical —O—$(CH_2)_{1-3}$—O—.

Embodiment A30

A compound according to embodiment A29 wherein $R^3$, $R^4$, $R^5$, $R^6$, $R^{30}$, $R^{31}$, $R^{32}$ and $R^{33}$ are independently selected from the group consisting of halogen, —$CF_3$; or methyl, ethyl, propyl, isopropyl, butyl, tert-butyl, cyclopropyl, cyclobutyl, cyclopentyl, cyclohexyl, phenyl, naphtyl, benzyl, phenyl-ethyl, methoxy, ethoxy, propoxy, phenylthio, —C(O)—O—$CH_3$, or —C(O)—O—$CH_2CH_3$, each of which is optionally substituted with one or more substituents independently selected from $R^{12}$; or —C(O)—$R^{27}$, —$S(O)_2$—$NR^{13}R^{14}$ or —$S(O)_2$—$R^{27}$; or two substituents selected from $R^3$, $R^4$, $R^5$ and $R^6$ or $R^{30}$, $R^{31}$, $R^{32}$ and $R^{33}$ attached to the same or adjacent atoms together form a radical —O—$(CH_2)_{1-3}$—O—.

Embodiment A31

A compound according to embodiment A30 wherein $R^3$, $R^4$, $R^5$, $R^6$, $R^{30}$, $R^{31}$, $R^{32}$ and $R^{33}$ are independently selected from the group consisting of halogen, $CF_3$; or methyl, ethyl, propyl, isopropyl, butyl, tert-butyl, cyclopropyl, cyclobutyl, cyclopentyl, cyclohexyl, phenyl, naphtyl, benzyl, phenyl-ethyl, methoxy, ethoxy, propoxy, phenylthio, C(O) O $CH_3$, or C(O) O $CH_2CH_3$, each of which is optionally substituted with one or more substituents independently selected from $R^{12}$; or C(O) $R^{27}$, $S(O)_2$ $NR^{13}R^{14}$ or $S(O)_2$ $R^{27}$.

Embodiment A32

A compound according to embodiment A31 wherein $R^3$, $R^4$, $R^5$, $R^6$, $R^{30}$, $R^{31}$, $R^{32}$ and $R^{33}$ are independently selected from the group consisting of F, Cl, —$CF_3$, methyl, ethyl, propyl, isopropyl, butyl, tert-butyl, methoxy, ethoxy, propoxy, —C(O)—$R^{27}$, —$S(O)_2$—$NR^{13}R^{14}$ or —$S(O)_2$—$R^{27}$.

Embodiment A33

A compound according to embodiment A29 wherein $R^3$, $R^4$, $R^5$, $R^6$, $R^{30}$, $R^{31}$, $R^{32}$ and $R^{33}$ are independently selected from $C_{1-6}$-alkyl, $C_{1-6}$-alkoxy, —$S(O)_2$—$R^{27}$ or —C(O)—$R^{27}$.

Embodiment A34

A compound according to any one of the embodiments A1 to A33 wherein $R^{10}$ and $R^{11}$ independently represent hydrogen, methyl, ethyl, propyl, —C(O)—$CH_3$, —C(O)—$CH_2CH_3$, —$CH_2$C(O)OH, $CH_2CH_2$C(O)OH, —C(O)—$CH_2$—C(O)OH, —C(O)—$CH_2CH_2$—C(O)OH, —$S(O)_2CH_3$, or phenyl.

Embodiment A35

A compound according to embodiment A34 wherein $R^{10}$ and $R^{11}$ independently represent hydrogen, methyl, ethyl, —C(O)—$CH_3$, —$CH_2$C(O)OH, —C(O)—$CH_2$—C(O)OH, $S(O)_2CH_3$, or phenyl.

Embodiment A36

A compound according to embodiment A35 wherein $R^{10}$ and $R^{11}$ independently represent hydrogen, methyl, ethyl, or phenyl.

Embodiment A37

A compound according to any one of the embodiments A1 to A36 wherein $R^{27}$ is $C_{1-6}$-alkyl, $C_{1-6}$-alkoxy, $C_{2-6}$-alkenyl, $C_{2-6}$-alkynyl, $C_{3-8}$-cycloalkyl, $C_{3-8}$-cycloalkyl-$C_{1-6}$-alkyl, aryl, aryl-$C_{1-6}$-alkyl, aryl-$C_{2-6}$-alkenyl, heteroaryl, heteroaryl-$C_{1-6}$-alkyl, carboxy-$C_{1-6}$-alkyl, $C_{1-6}$-alkoxy-$C_{1-6}$-alkyl, $C_{1-6}$-alkylthio-$C_{1-6}$-alkyl, $R^{10}$HN—$C_{1-6}$-alkyl, $R^{10}R^{11}N—C_{1-6}$-alkyl, $R^{10}R^{11}N—S(O)_2—C_{1-6}$-alkyl, or $R^{10}R^{11}N—C(O)—C_{1-6}$-alkyl, each of which is optionally substituted with one or more substituents independently selected from $R^{12}$.

Embodiment A38

A compound according to embodiment A37 wherein $R^{27}$ is $C_{1-6}$-alkyl, $C_{1-6}$-alkoxy, $C_{3-8}$-cycloalkyl, $C_{3-8}$-cycloalkyl-$C_{1-6}$-alkyl, aryl-$C_{2-6}$-alkenyl, aryl, heteroaryl, heteroaryl-$C_{1-6}$-alkyl, carboxy-$C_{1-6}$-alkyl, carboxy-$C_{1-6}$-alkyl, $C_{1-6}$-alkoxy-$C_{1-6}$-alkyl, $R^{10}HN—C_{1-6}$-alkyl, $R^{10}R^{11}N—C_{1-6}$-alkyl, $R^{10}R^{11}N—S(O)_2—C_{1-6}$-alkyl, or $R^{10}R^{11}N—C(O)—C_{1-6}$-alkyl, each of which is optionally substituted with one or more substituents independently selected from $R^{12}$.

Embodiment A39

A compound according to embodiment A38 wherein $R^{27}$ is $C_{1-6}$-alkyl, $C_{1-6}$-alkoxy, $C_{3-8}$-cycloalkyl, $C_{3-8}$-cycloalkyl-$C_{1-6}$-alkyl, aryl, heteroaryl-$C_{1-6}$-alkyl, aryl-$C_{1-6}$-alkyl, $C_{1-6}$-alkoxy-$C_{1-6}$-alkyl, carboxy-$C_{1-6}$-alkyl, or heteroaryl, each of which is optionally substituted with one or more substituents independently selected from $R^{12}$.

Embodiment A40

A compound according to embodiment A39 wherein $R^{27}$ is methyl, ethyl, propyl, n-butyl, isobutyl, 1,1,1-trifluoroethyl, cyclopropyl, cyclopentyl, cyclopropylmethyl, phenyl, pyridyl, thiophene, imidazole, or thiazole, each of which is optionally substituted with one or more substituents independently selected from $R^{12}$.

Embodiment A41

A compound according to embodiment A40 wherein $R^{27}$ is methyl, ethyl, propyl, n-butyl, isobutyl, 1,1,1-trifluoroethyl, cyclopropyl, cyclopentyl, cyclopropylmethyl, phenyl, or pyridyl, thiophene, imidazole, or thiazole.

Embodiment A42

A compound according to any one of the embodiments A1 to A41 wherein $R^{12}$ is halogen, cyano, hydroxy, carboxy, —$CF_3$, or $C_{1-6}$-alkyl.

Embodiment A43

A compound according to embodiment A42 wherein $R^{12}$ is halogen, cyano, hydroxy, carboxy, —$CF_3$, methoxy, methyl, ethyl or propyl.

Embodiment A44

A compound according to embodiment A43 wherein $R^{12}$ is halogen, carboxy, methyl, ethyl or propyl.

Embodiment A45

A compound according to any one of the embodiments A1 to A44 wherein $R^{13}$ and $R^{14}$ are independently selected from the group consisting of hydrogen, $C_{1-6}$-alkyl, hydroxy-$C_{1-6}$-alkyl, carboxy-$C_{1-6}$-alkyl, phenyl, or naphtyl, each of which is optionally substituted with one or more substituents independently selected from $R^{15}$; or $R^{13}$ and $R^{14}$ together with the nitrogen to which they are attached form a 3 to 8 membered heterocyclic ring with the said nitrogen atom, the heterocyclic ring optionally containing one or two further heteroatoms selected from nitrogen, oxygen and sulphur.

Embodiment A46

A compound according to embodiment A45 wherein $R^{13}$ and $R^{14}$ are independently selected from the group consisting of hydrogen, methyl, ethyl, propyl, hydroxy-methyl, hydroxy-ethyl, carboxy-methyl, carboxy-ethyl, phenyl, or naphtyl, each of which is optionally substituted with one or more substituents independently selected from $R^{15}$; or $R^{13}$ and $R^{14}$ together with the nitrogen to which they are attached form a 3 to 8 membered heterocyclic ring with the said nitrogen atom, the heterocyclic ring optionally containing one or two further heteroatoms selected from nitrogen, oxygen and sulphur.

Embodiment A47

A compound according to embodiment A46 wherein $R^{13}$ and $R^{14}$ are independently selected from the group consisting of hydrogen, methyl, ethyl, propyl, or phenyl, each of which is optionally substituted with one or more substituents independently selected from $R^{15}$.

Embodiment A48

A compound according to any one of the embodiments A1 to A46 wherein $R^{15}$ is halogen, cyano, hydroxy, carboxy, —$CF_3$, methyl, ethyl, or propyl.

Embodiment A49

A compound according to embodiment A48 wherein $R^{15}$ is halogen, hydroxy, carboxy, $CF_3$, methyl, or ethyl.

Embodiment A50

A compound according to any one of the embodiments A1 to A49 wherein A is thiazolyl, thiadiazolyl, pyrazinyl, pyridyl, benzothiazolyl, 5,6-dihydro-4H-cyclopentathiazolyl, 4,5,6,7-tetrahydro-benzothiazolo-pyridyl, 6,7-dihydro-pyranothiazolyl, or 4,5,6,7-tetrahydrobenzothiazolyl optionally substituted with one or more substituents independently selected from $R^7$, $R^8$ and $R^9$.

Embodiment A51

A compound according to embodiment A50 wherein A is

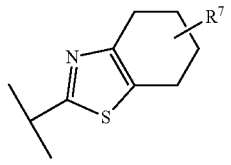

Embodiment A52

A compound according to embodiment A50 wherein A is thiazolyl or thiadiazolyl optionally substituted with one or more substituents independently selected from $R^7$, $R^8$ and $R^9$.

Embodiment A53

A compound according to embodiment A52 wherein A is thiazolyl, 1,2.4-thiadiazolyl, or 1,3,4-thiadiazolyl, optionally substituted with one or more substituents independently selected from $R^7$, $R^8$ and $R^9$.

Embodiment A54

A compound according to embodiment A53 wherein A is

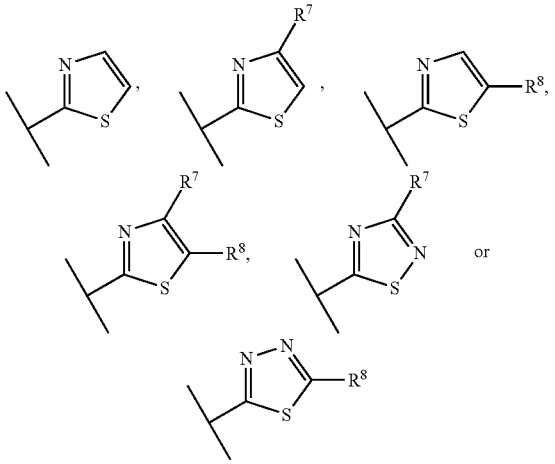

Embodiment A55

A compound according to embodiment A54 wherein A is

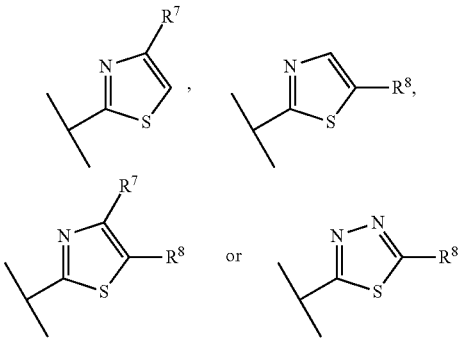

Embodiment A56

A compound according to embodiment A55 wherein A is

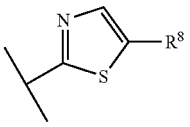

Embodiment A57

A compound according to any one of the embodiments A1 to A56 wherein $R^7$, $R^8$ and $R^9$ are independently selected from halogen, carboxy, cyano, nitro, hydroxy, —$CF_3$, —SCN; or $C_{1-6}$-alkyl, $C_{2-6}$-alkenyl, $C_{1-6}$-alkoxy, $C_{1-6}$-alkylthio, $C_{1-6}$-alkylamino, $C_{1-6}$-alkylsulfenyl, C(O) O $C_{1-6}$-alkyl, —C(O)—$C_{1-6}$-alkyl, —$C_{1-6}$-alkyl-C(O)—O—$C_{1-6}$-alkyl, —$C_{1-6}$-alkyl-O—C(O)—$C_{1-6}$-alkyl, —NH—C(O)—$C_{1-6}$-alkyl, —$C_{1-6}$-alkoxy-$C_{1-6}$-alkyl, —$C_{1-6}$-alkyl-S—$C_{1-6}$-alkyl, $C_{3-8}$-cycloalkyl-$C_{1-6}$-alkyl, $C_{3-6}$-cycloalkyl-$C_{1-6}$-alkoxy, $C_{3-6}$-cycloalkyl-$C_{1-6}$-alkylthio each of which is optionally substituted with one or more substituents independently selected from $R^{16}$; or aryl, heteroaryl, aryl-$C_{1-6}$-alkyl, heteroaryl-$C_{1-6}$-alkyl, aryl-$C_{1-6}$-alkoxy, heteroaryl-$C_{1-6}$-alkoxy, heteroarylthio-$C_{1-6}$-alkyl, aryloxy, heteroaryloxy, heteroarylthio, each of which is optionally substituted on the aryl or heteroaryl part with one or more substituents independently selected from $R^{17}$; or $C_{3-8}$-cycloalkyl, $C_{3-8}$-cycloalkenyl, $C_{3-8}$-cycloalkyl-$C_{1-6}$-alkyl, $C_{3-8}$-cycloalkenyl-$C_{1-6}$-alkyl, each of which is optionally substituted on the cycloalkyl part with one or more substituents independently selected from $R^{18}$; or $C_{3-8}$-heterocyclyl, $C_{3-8}$-heterocyclyl-$C_{1-6}$-alkyl, $C_{3-8}$-heterocyclylthio, or —C(O)—$C_{3-8}$-heterocyclyl, each of which is optionally substituted with one or more substituents independently selected from $R^{16}$; or $NR^{19}R^{20}$, $C_{1-6}$-*alkyl-NR*$^{19}R^{20}$, $C_{1-6}$-alkyl-S $R^{21}$, —$C_{1-6}$-alkyl-S(O)—$R^{21}$, —$C_{1-6}$-alkyl-$S(O)_2$—$R^{21}$, —$S(O)_2$—$R^{21}$ or —$S(O)_2$—$NR^{19}R^{20}$, wherein each alkyl part may be substituted with one or more substituents independently selected from $R^{25}$; or —C(O)$NR^{22}R^{23}$, —$C_{1-6}$-alkyl-C(O)$NR^{22}R^{23}$ optionally substituted with one or more substituents independently selected from $R^{26}$; or two of $R^7$, $R^8$ and $R^9$ can be taken together to form a $C_{2-5}$-alkylene bridge.

Embodiment A58

A compound according to embodiment A57 wherein $R^7$, $R^8$ and $R^9$ are independently selected from halogen, carboxy, cyano, or —$CF_3$; or $C_{1-6}$-alkyl, $C_{2-6}$-alkenyl, $C_{1-6}$-alkoxy, $C_{1-6}$-alkylthio, —C(O)—O—$C_{1-6}$-alkyl, —C(O)—$C_{1-6}$-alkyl, —$C_{1-6}$-alkyl-C(O)—O—$C_{1-6}$-alkyl, —$C_{1-6}$alkyl-O—C(O)—$C_{1-6}$-alkyl, —$C_{1-6}$-alkoxy-$C_{1-6}$-alkyl, $C_{3-8}$-cycloalkyl-$C_{1-6}$-alkyl, each of which is optionally substituted with one or more substituents independently selected from $R^{16}$; or aryl, heteroaryl, aryl-$C_{1-6}$-alkyl, heteroaryl-$C_{1-6}$-alkyl, each of which is optionally substituted on the aryl or heteroaryl part with one or more substituents independently selected from $R^{17}$; or $C_{3-8}$-cycloalkyl, $C_{3-8}$-cycloalkyl-$C_{1-6}$-alkyl, each of which is optionally substituted on the cycloalkyl part with one or more substituents independently selected from $R^{18}$; or $C_{3-8}$-heterocyclyl, $C_{3-8}$-heterocyclyl-$C_{1-6}$-alkyl, or C(O) $C_{3-8}$-heterocyclyl, each of which is optionally substituted with one or more substituents independently selected from $R^{16}$; or $NR^{19}R^{20}$, $C_{1-6}$-alkyl-$NR^{19}R^{20}$, $S(O)^2 R^{21}$ or —$S(O)_2$—$NR^{19}R^{20}$, wherein each alkyl part may be substituted with one or more substituents independently selected from $R^{25}$; or —$C(O)NR^{22}R^{23}$, —$C_{1-6}$-alkyl-$C(O)NR^{22}R^{23}$ optionally substituted with one or more substituents independently selected from $R^{25}$; or two of $R^7$, $R^8$ and $R^9$ can be taken together to form a $C_{2-5}$-alkylene bridge.

Embodiment A59

A compound according to embodiment A58 wherein $R^7$, $R^8$ and $R^9$ are independently selected from halogen, carboxy or —$CF_3$; or $C_{1-6}$-alkyl, $C_{1-6}$-alkoxy, $C_{1-6}$-alkylthio, —$C_{1-6}$-alkyl-C(O) O $C_{1-6}$-alkyl, $C_{1-6}$-alkyl-O C(O) $C_{1-6}$-alkyl or —C(O)—O—$C_{1-6}$-alkyl, each of which is optionally substituted with one or more substituents independently selected from $R^{16}$; or phenyl, benzyl, or heteroarylthio, wherein heteroaryl is pyridyl or imidazolyl, and wherein each aryl or heteroaryl is optionally substituted on the aryl or heteroaryl part with one or more substituents independently selected from $R^{17}$; or cyclopropyl, cyclobutyl, cyclopentyl, or cyclohexyl, each of which is optionally substituted on the cycloalkyl part with one or more substituents independently selected from $R^{18}$; or pyrrolidinyl, piperidyl, piperazinyl, or morpholinyl, each of which is optionally substituted with one or more substituents independently selected from $R^{16}$; or —$C(O)NR^{22}R^{23}$, —$S(O)_2$—$R^{21}$ or —$S(O)_2$—$NR^{19}R^{20}$; or two of $R^7$, $R^8$ and $R^9$ can be taken together to form a $C_{2-5}$-alkylene bridge.

Embodiment A60

A compound according to embodiment A59 wherein $R^7$, $R^8$ and $R^9$ are independently selected from halogen, carboxy, —$CF_3$, —S—$CH_3$, —S—$CH_2CH_3$, —S—$CH_2CH_2CH_3$, methyl, ethyl, propyl, isopropyl, butyl, tert-butyl, methoxy, ethoxy, —$CH_2$—C(O)—O—$CH_3$, —$CH_2$—C(O)—O—$CH_2CH_3$, —$CH_2CH_2$—C(O)—O—$CH_3$, —$CH_2CH_2$—C(O)—O—$CH_2CH_3$, —$CH_2$—O—C(O)—$CH_3$, —$CH_2$—O—C(O)—$CH_2CH_3$, —$CH_2CH_2$—O—C(O)—$CH_3$, —$CH_2CH_2$—O—C(O)—$CH_2CH_3$, —C(O)—O—$CH_3$, —C(O)—O—$CH_2CH_3$, each of which is optionally substituted with one or more substituents independently selected from $R^{16}$; or heteroarylthio, wherein heteroaryl is pyridyl or imidazolyl, each optionally substituted on the heteroaryl part with one or more substituents independently selected from $R^{17}$, or pyrrolidinyl, piperidyl, piperazinyl, or morpholinyl, each of which is optionally substituted with one or more substituents independently selected from $R^{16}$, or —$S(O)_2$—$R^{21}$.

Embodiment A61

A compound according to embodiment A60 wherein $R^7$, $R^8$ and $R^9$ are independently selected from Cl, F, Br, —$CF_3$, S $CH_3$, S $CH_2CH_3$, S $CH_2CH_2CH_3$, methyl, ethyl, methoxy, ethoxy, —$CH_2$—C(O)—O—$CH_2CH_3$, —C(O)—O—$CH_3$, or —C(O)—O—$CH_2CH_3$, each of which is optionally substituted with one or more substituents independently selected from $R^{16}$; or heteroarylthio, wherein heteroaryl is pyridyl or imidazolyl, each optionally substituted on the heteroaryl part with one or more substituents independently selected from $R^{17}$, or pyrrolidinyl, piperidyl, piperazinyl, or morpholinyl, each of which is optionally substituted with one or more substituents independently selected from $R^{16}$.

Embodiment A62

A compound according to any one of the embodiments A1 to A61 wherein $R^{16}$, $R^{17}$, and $R^{18}$ are independently $C_{1-6}$-alkyl, halogen, hydroxy, oxo, carboxy, —$CF_3$, carboxy-$C_{1-6}$-alkyl, hydroxy-$C_{1-6}$-alkyl, —$C_{1-6}$-alkyl-C(O)—O—$C_{1-6}$-alkyl, —C(O)—O—$C_{1-6}$-alkyl, —$NR^{19}R^{20}$, —C(O) $NR^{19}R^{20}$ or —$S(O)_2$—$C_{1-6}$-alkyl.

Embodiment A63

A compound according to embodiment A62 wherein $R^{16}$, $R^{17}$, and $R^{18}$ are independently methyl, ethyl, propyl, halogen, hydroxy, oxo, carboxy, —$CF_3$, carboxy-methyl, carboxy-ethyl, carboxy-propyl, hydroxy-methyl, hydroxy-ethyl, hydroxy-propyl, —$CH_2$—C(O)—O—$CH_3$, —$CH_2$—C(O) O $CH_2CH_3$, $CH_2CH_2$ C(O) O $CH_3$, —$CH_2CH_2$—C(O)—O—$CH_2CH_3$, —C(O)—O—$CH_3$, —C(O)—O—$CH_2CH_3$, —C(O)—O—$CH_2CH_2CH_3$, or —$S(O)_2CH_3$.

Embodiment A64

A compound according to embodiment A63 wherein $R^{16}$, $R^{17}$, and $R^{18}$ are independently methyl, ethyl, propyl, halogen, oxo, carboxy, carboxy-methyl, carboxy-ethyl, carboxy-propyl, hydroxy -methyl, hydroxy-ethyl, hydroxy-propyl, —$CH_2$—C(O)—O—$CH_3$, —$CH_2$—C(O)—O—$CH_2CH_3$, $CH_2CH_2$ C(O) O $CH_3$, $CH_2CH_2$ C(O) O $CH_2CH_3$, —C(O)—O—$CH_3$, —C(O)—O—$CH_2CH_3$, —C(O)—O—$CH_2CH_2CH_3$, or —$S(O)_2CH_3$.

Embodiment A65

A compound according to embodiment A62 wherein $R^{16}$, $R^{17}$, and $R^{18}$ are independently $C_{1-6}$-alkyl, carboxy, —$NR^{19}R^{20}$, —C(O)—O—$C_{1-6}$-alkyl or —$C(O)NR^{19}R^{20}$.

Embodiment A66

A compound according to any one of the embodiments A1 to A65 wherein $R^{19}$ and $R^{20}$ independently represent hydrogen, $C_{1-6}$-alkyl, hydroxy-$C_{1-6}$-alkyl, carboxy-$C_{1-6}$-alkyl, phenyl, naphtyl, $C_{3-8}$-heterocyclyl, phenyl-$C_{1-6}$-alkyl, $C_{3-8}$-heterocyclyl-$C_{1-6}$-alkyl, —C(O)—O—$C_{1-6}$-alkyl, —$C_{1-6}$-alkyl-C(O)—O—$C_{1-6}$-alkyl, —$C_{1-6}$-alkyl-$NR^{22}R^{23}$ or —$S(O)_2$—$C_{1-6}$-alkyl, each of which is optionally substituted with one or more substituents independently selected from $R^{24}$; or $R^{19}$ and $R^{20}$ together with the nitrogen to which they are attached form a 3 to 8 membered heterocyclic ring with the said nitrogen atom, the heterocyclic ring optionally containing one or two further heteroatoms selected from nitrogen, oxygen and sulphur, the heterocyclic ring is optionally substituted with one or more substituents independently selected from $R^{24}$.

Embodiment A67

A compound according to embodiment A66 wherein $R^{19}$ and $R^{20}$ independently represent hydrogen, methyl, ethyl, propyl, carboxy-methyl, carboxy-ethyl, carboxy-propyl, hydroxy-methyl, hydroxy-ethyl, hydroxy-propyl, phenyl, phenyl-$C_{1-6}$-alkyl, $C_{3-8}$-heterocyclyl-$C_{1-6}$-alkyl, —C(O)—O—$C_{1-6}$-alkyl, —$C_{1-6}$-alkyl-C(O)—O—$C_{1-6}$-alkyl, —$C_{1-6}$-alkyl-$NR^{22}R^{23}$, or naphtyl, or $R^{19}$ and $R^{20}$ together with the nitrogen to which they are attached form a 3 to 8 membered heterocyclic ring with the said nitrogen atom, the heterocyclic ring optionally containing one or two further heteroatoms selected from nitrogen, oxygen and sulphur, the heterocyclic ring is optionally substituted with one or more substituents independently selected from $R^{24}$.

Embodiment A68

A compound according to embodiment A66 wherein $R^{19}$ and $R^{20}$ independently represent hydrogen, $C_{1-6}$-alkyl, or $R^{19}$ and $R^{20}$ together with the nitrogen to which they are attached form a 3 to 8 membered heterocyclic ring with the said nitrogen atom, the heterocyclic ring optionally containing one or two further heteroatoms selected from nitrogen, oxygen and sulphur, the heterocyclic ring is optionally substituted with one or more substituents independently selected from $R^{24}$.

Embodiment A69

A compound according to embodiment A68 wherein $R^{19}$ and $R^{20}$ independently represent hydrogen, methyl, ethyl, or propyl, or $R^{19}$ and $R^{20}$ together with the nitrogen to which they are attached form a 3 to 8 membered heterocyclic ring with the said nitrogen atom, wherein the heterocyclic ring is pyrrolidyl, piperidyl, piperazinyl, homopiperazinyl, or morpholinyl, the heterocyclic ring is optionally substituted with one or more substituents independently selected from $R^{24}$.

Embodiment A70

A compound according to any one of the embodiments A1 to A69 wherein $R^{21}$ is selected from $C_{1-6}$-alkyl, carboxy-$C_{1-6}$-alkyl, $C_{1-6}$-alkyl-$NR^{22}R^{23}$ or hydroxy-$C_{1-6}$-alkyl; or phenyl, naphtyl, or phenyl-$C_{1-6}$-alkyl, wherein the aryl part is optionally substituted with one or more substituents independently selected from $R^{24}$; or $C_{3-8}$-cycloalkyl, or $C_{3-8}$-cycloalkyl-$C_{1-6}$-alkyl.

Embodiment A71

A compound according to embodiment A70 wherein $R^{21}$ is selected from methyl, ethyl, propyl, carboxy-methyl, carboxy-ethyl, carboxy-propyl, hydroxy-methyl, hydroxy-ethyl, hydroxy-propyl; or phenyl, naphtyl, or phenyl-$C_{1-6}$-alkyl, wherein the aryl part is optionally substituted with one or more substituents independently selected from $R^{24}$; or $C_{3-8}$-cycloalkyl, or $C_{3-8}$-cycloalkyl-$C_{1-6}$-alkyl.

Embodiment A72

A compound according to embodiment A71 wherein $R^{21}$ is selected from methyl, ethyl, carboxy-methyl, carboxy-ethyl, carboxy-propyl; or phenyl, naphtyl, or phenyl-$C_{1-6}$-alkyl, wherein the aryl part is optionally substituted with one or more substituents independently selected from $R^{24}$.

Embodiment A73

A compound according to any one of the embodiments A1 to A72 wherein $R^{22}$ and $R^{23}$ are independently selected from hydrogen, $C_{1-6}$-alkyl, carboxy-$C_{1-6}$-alkyl, —$C_{1-6}$-alkyl-C(O)—O—$C_{1-6}$-alkyl, —C(O)—O—$C_{1-6}$-alkyl, $C_{3-8}$-cycloalkyl, phenyl, naphtyl, or $R^{22}$ and $R^{23}$ together with the nitrogen to which they are attached form a 3 to 8 membered heterocyclic ring with the said nitrogen atom, the heterocyclic ring optionally containing one or two further heteroatoms selected from nitrogen, oxygen and sulphur, the heterocyclic ring is optionally substituted with one or more substituents independently selected from $R^{24}$.

Embodiment A74

A compound according to embodiment A73 wherein $R^{22}$ and $R^{23}$ are independently selected from hydrogen, methyl, ethyl, propyl, butyl, carboxymethyl, carboxyethyl, carboxypropyl, cyclopropyl, cyclobutyl, cyclopentyl, cyclohexyl, cycloheptyl, phenyl, naphtyl, or $R^{22}$ and $R^{23}$ together with the nitrogen to which they are attached form a 3 to 8 membered heterocyclic ring with the said nitrogen atom, wherein the heterocyclic ring is pyrrolidyl, piperidyl, piperazinyl, homopiperazinyl, or morpholinyl, the heterocyclic ring is optionally substituted with one or more substituents independently selected from $R^{24}$.

Embodiment A75

A compound according to embodiment A74 wherein $R^{22}$ and $R^{23}$ together with the nitrogen to which they are attached form a 3 to 8 membered heterocyclic ring with the said nitrogen atom, wherein the heterocyclic ring is pyrrolidyl, piperidyl, piperazinyl, homopiperazinyl, or morpholinyl, the heterocyclic ring is optionally substituted with one or more substituents independently selected from $R^{24}$.

Embodiment A76

A compound according to any one of the embodiments A1 to A75 wherein $R^{24}$ is halogen, hydroxy, carboxy, oxo, —$CF_3$, $C_{1-6}$-alkyl, hydroxy-$C_{1-6}$-alkyl, carboxy-$C_{1-6}$-alkyl, —C(O)—$C_{1-6}$-alkyl, —C(O)—O—$C_{1-6}$-alkyl, —$C_{1-6}$-alkyl-C(O)—O—$C_{1-6}$-alkyl, aryl, heteroaryl, aryl-$C_{1-6}$-alkyl, heteroaryl-$C_{1-6}$-alkyl, $C_{3-8}$-cycloalkyl, $C_{3-8}$-heterocyclyl, $C_{3-8}$-cycloalkyl-$C_{1-6}$-alkyl, $C_{3-8}$-heterocyclyl-$C_{1-6}$-alkyl, —C(O)—O—$C_{1-6}$-alkyl-aryl, or —$S(O)_2R^2$, wherein aryl is phenyl or naphtyl, and heteroaryl is pyridyl or pyrimidyl, and wherein each cyclic moiety is optionally substituted with one or more substituents independently selected from $R^{29}$.

Embodiment A77

A compound according to embodiment A76 wherein $R^{24}$ is halogen, hydroxy, carboxy, oxo, —$CF_3$, $C_{1-6}$-alkyl, hydroxy-$C_{1-6}$-alkyl, carboxy-$C_{1-6}$-alkyl, —C(O)—$C_{1-6}$-alkyl, —C(O)—O—$C_{1-6}$-alkyl, aryl, heteroaryl, aryl-$C_{1-6}$-alkyl, heteroaryl-$C_{1-6}$-alkyl, $C_{3-8}$-cycloalkyl, $C_{3-8}$-heterocyclyl, $C_{3-8}$-cycloalkyl-$C_{1-6}$-alkyl, $C_{3-8}$-heterocyclyl-$C_{1-6}$-alkyl, or —$S(O)_2R^{28}$, wherein aryl is phenyl or naphtyl, and heteroaryl is pyridyl or pyrimidyl, and wherein each cyclic moiety is optionally substituted with one or more substituents independently selected from $R^{29}$.

Embodiment A78

A compound according to embodiment A77 wherein $R^{24}$ halogen, carboxy, oxo, —$CF_3$, $C_{1-6}$-alkyl, carboxy-$C_{1-6}$-alkyl, —C(O)—$C_{1-6}$-alkyl, —C(O)—O—$C_{1-6}$-alkyl, aryl, aryl-$C_{1-6}$-alkyl, $C_{3-8}$-cycloalkyl, $C_{3-8}$-heterocyclyl, $C_{3-8}$-heterocyclyl-$C_{1-6}$-alkyl, or —$S(O)_2R^2$, wherein aryl is phenyl or naphtyl, and wherein each cyclic moiety is optionally substituted with one or more substituents independently selected from $R^{29}$.

Embodiment A79

A compound according to embodiment A78 wherein $R^{24}$ is carboxy, oxo, $C_{1-6}$-alkyl, carboxy-$C_{1-6}$-alkyl, —C(O)—O—$C_{1-6}$-alkyl, aryl, aryl-$C_{1-6}$-alkyl, $C_{3-8}$-cycloalkyl, $C_{3-8}$-heterocyclyl, $C_{3-8}$-heterocyclyl-$C_{1-6}$-alkyl, or —$S(O)_2R^2$, wherein aryl is phenyl or naphtyl, and wherein each cyclic moiety is optionally substituted with one or more substituents independently selected from $R^{29}$.

Embodiment A80

A compound according to any one of the embodiments A1 to A79 wherein $R^{25}$ and $R^{26}$ are independently $C_{1-6}$-alkyl, halogen, hydroxy, carboxy, or $CF_3$.

Embodiment A81

A compound according to embodiment A80 wherein $R^{25}$ and $R^{26}$ are independently methyl, ethyl, propyl, halogen, hydroxy, carboxy, or —$CF_3$.

Embodiment A82

A compound according to any one of the embodiments A1 to A81 wherein $R^{28}$ is $C_{1-6}$-alkyl, —$C_{1-6}$-alkyl-C(O)—O—$C_{1-6}$-alkyl, phenyl, phenyl-$C_{1-6}$-alkyl, heteroaryl optionally substituted with $C_{1-6}$-alkyl or —$N(CH_3)_2$, wherein heteroaryl is imidazolyl, pyridyl or pyrimidyl.

Embodiment A83

A compound according to embodiment A82 wherein $R^{28}$ is $C_{1-6}$-alkyl, —$C_{1-6}$-alkyl-C(O)—O—$C_{1-6}$-alkyl, or —$N(CH_3)_2$.

Embodiment A84

A compound according to any one of the embodiments A1 to A83 wherein $R^{29}$ is halogen, carboxy, —$CF_3$, $C_{1-6}$-alkyl, or $C_{1-6}$-alkoxy.

Embodiment A85

A compound according to any one of the embodiments A1 to A84, which compound is an activator of glucokinase, when tested in the Glucokinase Activation Assay (I) disclosed herein at a glucose concentration of 2 mM.

Embodiment A86

A compound according to any one of the embodiments A1 to A85, which compound is an activator of glucokinase, when tested in the Glucokinase Activation Assay (I) disclosed herein at a glucose concentration of from 10 to 15 mM.

Embodiment A87

A compound according to any one of the embodiments A1 to A86, which compound, at a concentration of 30 μM, is capable of providing an at least 1.5, such as at least 1.7, for instance at least 2.0 fold activation of glucokinase in the Glucokinase Activation Assay (I) disclosed herein at a glucose concentration of 2 mM.

Embodiment A88

A compound according to any one of the embodiments A1 to A87, which compound, at a concentration of 30 μM, is capable of providing an at least 1.5, such as at least 1.7, for instance at least 2.0 fold activation of glucokinase in the Glucokinase Activation Assay (I) disclosed herein at a glucose concentration of from 10 to 15 mM.

Embodiment A89

A compound according to any one of the embodiments A1 to A88, which at a concentration of 5 μM is capable of providing an at least 1.5, such as at least 1.7, for instance at least 2.0 fold activation of glucokinase in the Glucokinase Activation Assay (I) disclosed herein at a glucose concentration of 2 mM.

Embodiment A90

A compound according to any one of the embodiments A1 to A89, which at a concentration of 5 μM is capable of providing an at least 1.5, such as at least 1.7, for instance at least 2.0 fold activation of glucokinase in the Glucokinase Activation Assay (I) disclosed herein at a glucose concentration of from 10 to 15 mM.

Embodiment A91

A compound according to any one of the embodiments A1 to A90, which compound provides an increase in glucokinase activity, where the increase in glucokinase activity provided by the compound increases with increasing concentrations of glucose.

Embodiment A92

A compound according to embodiment A91, which provides an increase in glucokinase activity in Glucokinase Activation Assay (I) disclosed herein at a glucose concentration of 15 mM, which increase is significantly higher than the increase in glucokinase activity provided by the compound in Glucokinase Activation Assay (I) disclosed herein at a glucose concentration of 5 mM.

Embodiment A93

A compound according to any one of the embodiments A91 to A92, which at a compound concentration of 10 μM provides an increase in glucokinase activity in Glucokinase Activation Assay (I) disclosed herein at a glucose concentration of 15 mM, which increase is significantly higher than the increase in glucokinase activity provided by the compound at a compound concentration of 10 μM in Glucokinase Activation Assay (I) disclosed herein at a glucose concentration of 5 mM.

Embodiment A94

A compound according to any one of the embodiments A91 to A93, which at a compound concentration of 10 μM provides an increase in glucokinase activity in Glucokinase Activation Assay (I) disclosed herein at a glucose concentration of 15 mM, which increase is at least 1.1 fold higher. such as at least 1.2 fold higher, for instance at least 1.3 fold higher, such as at least 1.4 fold higher, for instance 1.5 fold higher, such as at least 1.6 fold higher, for instance at least 1.7 fold higher, such as at least 1.8 fold higher, for instance at least 1.9 fold higher, such as at least 2.0 fold higher than the increase in glucokinase activity provided by the compound at a compound concentration of 10 μM in Glucokinase Activation Assay (I) disclosed herein at a glucose concentration of 5 mM.

Embodiment A95

A compound according to any one of the embodiments A1 to A94, which compound increases glucose utilization in the liver without inducing any increase in insulin secretion in response to glucose.

Embodiment A96

A compound according to any one of the embodiments A1 to A94, which compound shows a significantly higher activity in isolated hepatocytes compared to the activity of the compound in Ins-1 cells.

Embodiment A97

A compound according to any one of the embodiments A95 to A96, which compound shows a significantly higher activity in isolated hepatocytes measured as described in the Glucokinase Activity Assay (II) compared to the activity of the compound in Ins-1 cells measured as described in the Glucokinase Activity Assay (III).

Embodiment A98

A compound according to embodiment A97, which compound shows an activity in isolated hepatocytes measured as described in the Glucokinase Activity Assay (II) which activity is at least 1.1 fold higher, such as at least 1.2 fold higher, for instance at least 1.3 fold higher, such as at least 1.4 fold higher, for instance 1.5 fold higher, such as at least 1.6 fold higher, for instance at least 1.7 fold higher, such as at least 1.8 fold higher, for instance at least 1.9 fold higher, such as at least 2.0 fold higher, for instance at least a 3.0 fold higher, such as at least a 4.0 fold higher, for instance at least 5.0 fold higher, such as at least 10 fold higher than the activity of the compound in Ins-1 cells measured as described in the Glucokinase Activity Assay (III).

Embodiment A99

A compound according to embodiment A97, which compound shows no activity in the Ins-1 cells measured as described in the Glucokinase Activity Assay (III).

Embodiment A100

A method of preventing hypoglycemia comprising administration of a compound according to any one of the embodiments A1 to 99.

Embodiment A101

The use of a compound according to any one of the embodiments A1 to A99 for the preparation of a medicament for the prevention of hypoglycemia.

Embodiment A102

A compound according to any one of embodiments A1 to A99, which is an agent useful for the treatment of an indication selected from the group consisting of hyperglycemia, IGT, insulin resistance syndrome, syndrome X, type 2 diabetes, type 1 diabetes, dyslipidemia, hypertension, and obesity.

Embodiment A103

A compound according to any one of embodiments A1 to A102 for use as a medicament.

Embodiment A104

A compound according to any one of embodiments A1 to A102 for treatment of hyperglycemia, for treatment of IGT, for treatment of Syndrome X, for treatment of type 2 diabetes, for treatment of type 1 diabetes, for treatment of dyslipidemia, for treatment of hyperlipidemia, for treatment of hypertension, for treatment of obesity, for lowering of food intake, for appetite regulation, for regulating feeding behaviour, or for enhancing the secretion of enteroincretins, such as GLP-1.

Embodiment A105

A pharmaceutical composition comprising, as an active ingredient, at least one compound according to any one of embodiments A1 to A104 together with one or more pharmaceutically acceptable carriers or excipients.

Embodiment A106

A pharmaceutical composition according to embodiment A105 in unit dosage form, comprising from about 0.05 mg to about 1000 mg, preferably from about 0.1 mg to about 500 mg and especially preferred from about 0.5 mg to about 200 mg of the compound according to any one of embodiments A1 to 104.

Embodiment A107

Use of a compound according to any one of the embodiments A1 to A104 for increasing the activity of glucokinase.

Embodiment A108

Use of a compound according to any one of embodiments A1 to A104 for the preparation of a medicament for the treatment of metabolic disorders, for blood glucose lowering, for the treatment of hyperglycemia, for the treatment of IGT, for the treatment of Syndrome X, for the treatment of impaired fasting glucose (IPG), for the treatment of type 2 diabetes, for the treatment of type 1 diabetes, for delaying the progression of impaired glucose tolerance (IGT) to type 2 diabetes, for delaying the progression of non-insulin requiring type 2 diabetes to insulin requiring type 2 diabetes, for the treatment of dyslipidemia, for the treatment of hyperlipidemia, for the treatment of hypertension, for lowering of food intake, for appetite regulation, for the treatment of obesity, for regulating feeding behaviour, or for enhancing the secretion of enteroincretins.

Embodiment A109

Use of a compound according to any one of embodiments A1 to A104 for the preparation of a medicament for the adjuvant treatment of type 1 diabetes for preventing the onset of diabetic complications.

Embodiment A110

Use of a compound according to any one of embodiments A1 to A104 for the preparation of a medicament for increasing the number and/or the size of beta cells in a mammalian subject, for treatment of beta cell degeneration, in particular apoptosis of beta cells, or for treatment of functional dyspepsia, in particular irritable bowel syndrome.

Embodiment A111

Use according to any one of the embodiments A108 to A110 in a regimen which comprises treatment with a further antidiabetic agent.

Embodiment A112

Use according to any one of the embodiments A108 to A111 in a regimen which comprises treatment with a further antihyperlipidemic agent.

Embodiment A113

Use according to any one of embodiments A108 to A112 in a regimen which comprises treatment with a further antiobesity agent.

Embodiment A114

Use according to any one of embodiments A108 to A113 in a regimen which comprises treatment with a further antihypertensive agent.

Embodiment A115

Use of a compound according to any one of the embodiments A1 to A104 or a pharmaceutical composition according to embodiment A105 or embodiment A106 for the treatment of metabolic disorders, for blood glucose lowering, for the treatment of hyperglycemia, for treatment of IGT, for treatment of Syndrome X, for the treatment of impaired fasting glucose (IFG), for treatment of type 2 diabetes, for treatment of type 1 diabetes, for delaying the progression of impaired glucose tolerance (IGT) to type 2 diabetes, for delaying the progression of non-insulin requiring type 2 diabetes to insulin requiring type 2 diabetes, for treatment of dyslipidemia, for treatment of hyperlipidemia, for treatment of hypertension, for the treatment or prophylaxis of obesity, for lowering of food intake, for appetite regulation, for regulating feeding behaviour, or for enhancing the secretion of enteroincretins.

Embodiment A116

Use of a compound according to any one of the embodiments A1 to A104 or a pharmaceutical composition according to embodiment A105 or embodiment A106 for the adjuvant treatment of type 1 diabetes for preventing the onset of diabetic complications.

Embodiment A117

Use of a compound according to any one of the embodiments A1 to A104 or a pharmaceutical composition according to embodiment A105 or embodiment A106 for increasing the number and/or the size of beta cells in a mammalian subject, for treatment of beta cell degeneration, in particular apoptosis of beta cells, or for treatment of functional dyspepsia, in particular irritable bowel syndrome.

Combination Treatment

In a further aspect of the present invention the present compounds are administered in combination with one or more further active substances in any suitable ratios. Such further active agents may be selected from antidiabetic agents, antihyperlipidemic agents, antiobesity agents, antihypertensive agents and agents for the treatment of complications resulting from or associated with diabetes.

Suitable antidiabetic agents include insulin, GLP-1 (glucagon like peptide-1) derivatives such as those disclosed in WO 98/08871 (Novo Nordisk A/S), which is incorporated herein by reference, as well as orally active hypoglycemic agents.

Suitable orally active hypoglycemic agents preferably include imidazolines, sulfonylureas, biguanides, meglitinides, oxadiazolidinediones, thiazolidinediones, insulin sensitizers, aglucosidase inhibitors, agents acting on the ATP-dependent potassium channel of the pancreatic β-cells eg potassium channel openers such as those disclosed in WO 97/26265, WO 99/03861 and WO 00/37474 (Novo Nordisk A/S) which are incorporated herein by reference, potassium channel openers, such as ormitiglinide, potassium channel blockers such as nateglinide or BTS-67582, glucagon antagonists such as those disclosed in WO 99/01423 and WO 00/39088 (Novo Nordisk A/S and Agouron Pharmaceuticals, Inc.), all of which are incorporated herein by reference, GLP-1 agonists such as those disclosed in WO 00/42026 (Novo Nordisk A/S and Agouron Pharmaceuticals, Inc.), which are incorporated herein by reference, DPP-IV (dipeptidyl peptidase-IV) inhibitors, PTPase (protein tyrosine phosphatase) inhibitors, inhibitors of hepatic enzymes involved in stimulation of gluconeogenesis and/or glycogenolysis, glucose uptake modulators, GSK-3 (glycogen synthase kinase-3) inhibitors, compounds modifying the lipid metabolism such as antihyperlipidemic agents and antilipidemic agents, compounds lowering food intake, and PPAR (peroxisome proliferator-activated receptor) and RXR (retinoid X receptor) agonists such as ALRT-268, LG-1268 or LG-1069.

In one embodiment of the present invention, the present compounds are administered in combination with a sulphonylurea eg tolbutamide, chlorpropamide, tolazamide, glibenclamide, glipizide, glimepiride, glicazide or glyburide.

In one embodiment of the present invention, the present compounds are administered in combination with a biguanide eg mefformin.

In one embodiment of the present invention, the present compounds are administered in combination with a meglitinide eg repaglinide or senaglinide/nateglinide.

In one embodiment of the present invention, the present compounds are administered in combination with a thiazolidinedione insulin sensitizer eg troglitazone, ciglitazone, pioglitazone, rosiglitazone, isaglitazone, darglitazone, englitazone, CS-011/CI-1037 or T 174 or the compounds disclosed in WO 97/41097 (DRF-2344), WO 97/41119, WO 97/41120, WO 00/41121 and WO 98/45292 (Dr. Reddy's Research Foundation), which are incorporated herein by reference.

In one embodiment of the present invention the present compounds may be administered in combination with an insulin sensitizer eg such as GI 262570, YM-440, MCC-555, JTT-501, AR-H039242, KRP-297, GW-409544, CRE-16336, AR-H049020, LY510929, MBX-102, CLX-0940, GW-501516 or the compounds disclosed in WO 99/19313 (NN622/DRF-2725). WO 00/50414, WO 00/63191, WO 00/63192, WO 00/63193 (Dr. Reddy's Research Foundation) and WO 00/23425, WO 00/23415, WO 00/23451, WO 00/23445, WO 00/23417, WO 00/23416, WO 00/63153, WO 00/63196, WO 00/63209, WO 00/63190 and WO 00/63189 (Novo Nordisk A/S), which are incorporated herein by reference.

In one embodiment of the present invention the present compounds are administered in combination with an α-glucosidase inhibitor eg voglibose, emiglitate, miglitol or acarbose.

In one embodiment of the present invention the present compounds are administered in combination with a glycogen phosphorylase inhibitor eg the compounds described in WO 97/09040 (Novo Nordisk A/S).

In one embodiment of the present invention the present compounds are administered in combination with an agent acting on the ATP-dependent potassium channel of the pancreatic β-cells eg tolbutamide, glibenclamide, glipizide, glicazide, BTS-67582 or repaglinide.

In one embodiment of the present invention the present compounds are administered in combination with nateglinide.

In one embodiment of the present invention the present compounds are administered in combination with an antihyperlipidemic agent or a antilipidemic agent eg cholestyramine, colestipol, clofibrate, gemfibrozil, lovastatin, pravastatin, simvastatin, probucol or dextrothyroxine.

Furthermore, the compounds according to the invention may be administered in combination with one or more antiobesity agents or appetite regulating agents.

Such agents may be selected from the group consisting of CART (cocaine amphetamine regulated transcript) agonists, NPY (neuropeptide Y) antagonists, MC3 (melanocortin 3) agonists, MC4 (melanocortin 4) agonists, orexin antagonists, TNF (tumor necrosis factor) agonists, CRF (corticotropin releasing factor) agonists, CRF BP (corticotropin releasing factor binding protein) antagonists, urocortin agonists, β3 adrenergic agonists such as CL-316243, AJ-9677, GW-0604, LY362884, LY377267 or AZ-40140, MSH (melanocytestimulating hormone) agonists, MCII (melanocyte-concentrating hormone) antagonists, CCK (cholecystokinin) agonists, serotonin reuptake inhibitors (fluoxetine, seroxat or citalopram), serotonin and norepinephrine reuptake inhibitors, 5HT (serotonin) agonists, bombesin agonists, galanin antagonists, growth hormone, growth factors such as prolactin or placental lactogen, growth hormone releasing compounds, TRH (thyreotropin releasing hormone) agonists, UCP 2 or 3 (uncoupling protein 2 or 3) modulators, leptin agonists, DA (dopamine) agonists (bromocriptin, doprexin), lipase/amylase inhibitors, PPAR modulators, RXR modulators, TR β agonists, adrenergic CNS stimulating agents, AGRP (agouti related protein) inhibitors, H3 histamine antagonists such as those disclosed in WO 00/42023, WO 00/63208 and WO 00/64884, which are incorporated herein by reference, exendin-4, GLP-1 agonists, ciliary neurotrophic factor, and oxyntomodulin. Further antiobesity agents are bupropion (antidepressant), topiramate (anticonvulsant), ecopipam (dopamine D1/D5 antagonist) and naltrexone (opioid antagonist).

In one embodiment of the present invention the antiobesity agent is leptin.

In one embodiment of the present invention the antiobesity agent is a serotonin and norepinephrine reuptake inhibitor eg sibutramine.

In one embodiment of the present invention the antiobesity agent is a lipase inhibitor eg orlistat.

In one embodiment of the present invention the antiobesity agent is an adrenergic CNS stimulating agent eg dexamphetamine, amphetamine, phentermine, mazindol phendimetrazine, diethylpropion, fenfluramine or dexfenfluramine.

Furthermore, the present compounds may be administered in combination with one or more antihypertensive agents. Examples of antihypertensive agents are β-blockers such as alprenolol, atenolol, timolol, pindolol, propranolol and metoprolol, ACE (angiotensin converting enzyme) inhibitors such as benazepril, captopril, enalapril, fosinopril, lisinopril, quinapril and ramipril, calcium channel blockers such as nifedipine, felodipine, nicardipine, isradipine, nimodipine, diltiazem and verapamil, and α-blockers such as doxazosin, urapidil, prazosin and terazosin. Further reference can be made to Remington: The Science and Practice of Pharmacy, 19th Edition, Gennaro, Ed., Mack Publishing Co., Easton, Pa., 1995.

In one embodiment of the present invention, the present compounds are administered in combination with insulin, insulin derivatives or insulin analogues.

In one embodiment of the invention the insulin is an insulin derivative is selected from the group consisting of B29-$N^{\epsilon}$-myristoyl-des(B30) human insulin, B29-$N^{\epsilon}$-palmitoyl-des (B30) human insulin, B29-$N^{\epsilon}$-myristoyl human insulin, B29-$N^{\epsilon}$-palmitoyl human insulin, B28-$N^{\epsilon}$-myristoyl $Lys^{B28}$ $Pro^{B29}$ human insulin, B28-$N^{\epsilon}$-palmitoyl $Lys^{B28}$ $Pro^{B29}$ human insulin, B30-$N^{\epsilon}$-myristoyl-$Thr^{B29}Lys^{B30}$ human insulin, B30-$N^{\epsilon}$-palmitoyl -$Thr^{B29}Lys^{B30}$ human insulin, B29-$N^{\epsilon}$-(N-palmitoyl-γ-glutamyl)-des(B30) human insulin, B29-$N^{\epsilon}$-(N-lithocholyl-γ-glutamyl)-des(B30) human insulin. B29-$N^{\epsilon}$-(ω-carboxyheptadecanoyl)-des(B30) human insulin and B29-$N^{\epsilon}$-(ω-carboxyheptadecanoyl) human insulin.

In another embodiment of the invention the insulin derivative is B29-$N^{\epsilon}$-myristoyl-des(B30) human insulin.

In a further embodiment of the invention the insulin is an acid-stabilised insulin. The acid-stabilised insulin may be selected from analogues of human insulin having one of the following amino acid residue substitutions:

A21G
A21G, B28K, B29P
A21G, B28D
A21G, B28E
A21G, B3K, B29E
A21G, desB27
A21G, B9E
A21G, B9D
A21G, B10E insulin.

In a further embodiment of the invention the insulin is an insulin analogue. The insulin analogue may be selected from the group consisting of An analogue wherein position B28 is Asp, Lys, Leu, Val, or Ala and position B29 is Lys or Pro; and des(B28-B30), des(B27) or des(B30) human insulin.

In another embodiment the analogue is an analogue of human insulin wherein position B28 is Asp or Lys, and position B29 is Lys or Pro.

In another embodiment the analogue is des(B30) human insulin.

In another embodiment the insulin analogue is an analogue of human insulin wherein position B28 is Asp.

In another embodiment the analogue is an analogue wherein position B3 is Lys and position B29 is Glu or Asp.

In another embodiment the GLP-1 derivative to be employed in combination with a compound of the present invention refers to GLP-1 (1-37), exendin-4 (1-39), insulinotropic fragments thereof, insulinotropic analogues thereof and insulinotropic derivatives thereof. Insulinotropic fragments of GLP-1 (1-37) are insulinotropic peptides for which the entire sequence can be found in the sequence of GLP-1 (1-37) and where at least one terminal amino acid has been deleted. Examples of insulinotropic fragments of GLP-1 (1-37) are GLP-1 (7-37) wherein the amino acid residues in positions 1-6 of GLP-1 (1-37) have been deleted, and GLP-1 (7-36) where the amino acid residues in position 1-6 and 37 of GLP-1 (1-37) have been deleted. Examples of insulinotropic fragments of exendin-4 (1-39) are exendin-4 (1-38) and exendin-4 (1-31). The insulinotropic property of a compound may be determined by in vivo or in vitro assays well known in the art. For instance, the compound may be administered to an animal and monitoring the insulin concentration over time. Insulinotropic analogues of GLP-1 (1-37) and exendin-4 (1-39) refer to the respective molecules wherein one or more of the amino acids residues have been exchanged with other amino acid residues and/or from which one or more amino acid residues have been deleted and/or from which one or more amino acid residues have been added with the proviso that said analogue either is insulinotropic or is a prodrug of an insulinotropic compound. Examples of insulinotropic analogues of GLP-1 (1-37) are e.g. $Met^{8}$-GLP-1 (7-37) wherein the alanine in position 8 has been replaced by methionine and the amino acid residues in position 1 to 6 have been deleted, and $Arg^{34}$-GLP-1 (7-37) wherein the valine in position 34 has been replaced with arginine and the amino acid residues in position 1 to 6 have been deleted. An example of an insulinotropic analogue of exendin-4 (1-39) is $Ser^{2}Asp^{3}$-exendin-4 (1-39) wherein the amino acid residues in position 2 and 3 have been replaced with serine and aspartic acid, respectively (this particular analogue also being known in the art as exendin-3). Insulinotropic derivatives of GLP-1 (1-37), exendin-4 (1-39) and analogues thereof are what the person skilled in the art considers to be derivatives of these peptides, i.e. having at least one substituent which is not present in the parent peptide molecule with the proviso that said derivative either is insulinotropic or is a prodrug of an insulinotropic compound. Examples of substituents are amides, carbohydrates, alkyl groups and lipophilic substituents. Examples of insulinotropic derivatives of GLP-1 (1-37), exendin-4 (1-39) and analogues thereof are GLP-1 (7-36)-amide, $Arg^{34}$, $Lys^{26}(N^{\epsilon}$-(γ-Glu($N^{\epsilon}$-hexadecanoyl)))-GLP-1 (7-37) and $Tyr^{31}$-exendin-4 (1-31)-amide. Further examples of GLP-1(1-37), exendin-4 (1-39), insulinotropic fragments thereof, insulinotropic analogues thereof and insulinotropic derivatives thereof are described in WO 98/08871, WO 99/43706, U.S. Pat. No. 5,424,286 and WO 00/09666.

In another aspect of the present invention, the present compounds are administered in combination with more than one of the above-mentioned compounds e.g. in combination with metformin and a sulphonylurea such as glyburide; a sulphonylurea and acarbose; nateglinide and mefformin; acarbose and metformin; a sulfonylurea, metformin and troglitazone; insulin and a sulfonylurea; insulin and metformin; insulin, mefformin and a sulfonylurea; insulin and troglitazone; insulin and lovastatin; etc.

It should be understood that any suitable combination of the compounds according to the invention with diet and/or exercise, one or more of the above-mentioned compounds and optionally one or more other active substances are considered to be within the scope of the present invention. In one embodiment of the present invention, the pharmaceutical composition according to the present invention comprises e.g. a compound of the invention in combination with metformin and a sulphonylurea such as glyburide; a compound of the invention in combination with a sulphonylurea and acarbose; nateglinide and metformin; acarbose and metformin; a sulfonylurea, mefformin and troglitazone; insulin and a sulfonylurea; insulin and metformin; insulin, metformin and a sulfonylurea; insulin and troglitazone; insulin and lovastatin; etc.

Pharmaceutical Compositions

The compounds of the present invention may be administered alone or in combination with pharmaceutically acceptable carriers or excipients, in either single or multiple doses. The pharmaceutical compositions according to the invention may be formulated with pharmaceutically acceptable carriers or diluents as well as any other known adjuvants and excipients in accordance with conventional techniques such as those disclosed in Remington: The Science and Practice of Pharmacy, $19^{th}$ Edition, Gennaro, Ed., Mack Publishing Co., Easton, Pa., 1995.

The pharmaceutical compositions may be specifically formulated for administration by any suitable route such as the oral, rectal, nasal, pulmonary, topical (including buccal and sublingual), transdermal, intracisternal, intraperitoneal, vaginal and parenteral (including subcutaneous, intramuscular, intrathecal, intravenous and intradermal) route, the oral route being preferred. It will be appreciated that the preferred route will depend on the general condition and age of the subject to be treated, the nature of the condition to be treated and the active ingredient chosen.

Pharmaceutical compositions for oral administration include solid dosage forms such as hard or soft capsules, tablets, troches, dragees, pills, lozenges, powders and granules. Where appropriate, they can be prepared with coatings such as enteric coatings or they can be formulated so as to provide controlled release of the active ingredient such as sustained or prolonged release according to methods well known in the art.

Liquid dosage forms for oral administration include solutions, emulsions, aqueous or oily suspensions, syrups and elixirs.

Pharmaceutical compositions for parenteral administration include sterile aqueous and non-aqueous injectable solutions, dispersions, suspensions or emulsions as well as sterile powders to be reconstituted in sterile injectable solutions or dispersions prior to use. Depot injectable formulations are also contemplated as being within the scope of the present invention.

Other suitable administration forms include suppositories, sprays, ointments, cremes, gels, inhalants, dermal patches, implants etc.

A typical oral dosage is in the range of from about 0.001 to about 100 mg/kg body weight per day, preferably from about 0.01 to about 50 mg/kg body weight per day, and more preferred from about 0.05 to about 10 mg/kg body weight per day administered in one or more dosages such as 1 to 3 dosages. The exact dosage will depend upon the frequency and mode of administration, the sex, age, weight and general condition of the subject treated, the nature and severity of the condition treated and any concomitant diseases to be treated and other factors evident to those skilled in the art.

The formulations may conveniently be presented in unit dosage form by methods known to those skilled in the art. A typical unit dosage form for oral administration one or more times per day such as 1 to 3 times per day may contain from 0.05 to about 1000 mg, preferably from about 0.1 to about 500 mg, and more preferred from about 0.5 mg to about 200 mg. For parenteral routes such as intravenous, intrathecal, intramuscular and similar administration, typically doses are in the order of about half the dose employed for oral administration. The compounds of this invention are generally utilized as the free substance or as a pharmaceutically acceptable salt thereof. Examples are an acid addition salt of a compound having the utility of a free base and a base addition salt of a compound having the utility of a free acid. The term "pharmaceutically acceptable salts" refers to non-toxic salts of the compounds of this invention which are generally prepared by reacting the free base with a suitable organic or inorganic acid or by reacting the acid with a suitable organic or inorganic base. When a compound according to the present invention contains a free base such salts are prepared in a conventional manner by treating a solution or suspension of the compound with a chemical equivalent of a pharmaceutically acceptable acid. When a compound according to the present invention contains a free acid such salts are prepared in a conventional manner by treating a solution or suspension of the compound with a chemical equivalent of a pharmaceutically acceptable base. Physiologically acceptable salts of a compound with a hydroxy group include the anion of said compound in combination with a suitable cation such as sodium or ammonium ion. Other salts which are not pharmaceutically acceptable may be useful in the preparation of compounds of the present invention and these form a further aspect of the present invention.

For parenteral administration, solutions of the novel compounds of the formula (I) in sterile aqueous solution, aqueous propylene glycol or sesame or peanut oil may be employed. Such aqueous solutions should be suitably buffered if necessary and the liquid diluent first rendered isotonic with sufficient saline or glucose. The aqueous solutions are particularly suitable for intravenous, intramuscular, subcutaneous and intraperitoneal administration. The sterile aqueous media employed are all readily available by standard techniques known to those skilled in the art.

Suitable pharmaceutical carriers include inert solid diluents or fillers, sterile aqueous solution and various organic solvents. Examples of solid carriers are lactose, terra alba, sucrose, cyclodextrin, talc, gelatine, agar, pectin, acacia, magnesium stearate, stearic acid and lower alkyl ethers of cellulose. Examples of liquid carriers are syrup, peanut oil, olive oil, phospholipids, fatty acids, fatty acid amines, polyoxyethylene and water. Similarly, the carrier or diluent may include any sustained release material known in the art, such as glyceryl monostearate or glyceryl distearate, alone or mixed with a wax. The pharmaceutical compositions formed by combining the novel compounds of the present invention and the pharmaceutically acceptable carriers are then readily administered in a variety of dosage forms suitable for the disclosed routes of administration. The formulations may conveniently be presented in unit dosage form by methods known in the art of pharmacy.

Formulations of the present invention suitable for oral administration may be presented as discrete units such as capsules or tablets, each containing a predetermined amount of the active ingredient, and which may include a suitable excipient. Furthermore, the orally available formulations may be in the form of a powder or granules, a solution or suspension in an aqueous or non-aqueous liquid, or an oil-in-water or water-in-oil liquid emulsion.

Compositions intended for oral use may be prepared according to any known method, and such compositions may contain one or more agents selected from the group consisting of sweetening agents, flavoring agents, coloring agents, and preserving agents in order to provide pharmaceutically elegant and palatable preparations. Tablets may contain the active ingredient in admixture with non-toxic pharmaceutically-acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example corn starch or alginic acid; binding agents, for example, starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. Nos. 4,356,108; 4,166,452; and 4,265,874, incorporated herein by reference, to form osmotic therapeutic tablets for controlled release.

Formulations for oral use may also be presented as hard gelatin capsules where the active ingredient is mixed with an inert solid diluent, for example, calcium carbonate, calcium phosphate or kaolin, or a soft gelatin capsules wherein the active ingredient is mixed with water or an oil medium, for example peanut oil, liquid paraffin, or olive oil.

Aqueous suspensions may contain the active compounds in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide such as lecithin, or condensation products of an alkylene oxide with fatty acids, for example polyoxyethylene stearate, or condensation products of ethylene oxide with long chain aliphatic alcohols, for example, heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as a liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active compound in admixture with a dispersing or wetting agent, suspending agent and one or more preservatives. Suitable dispersing or wetting agents and suspending agents are exemplified by those already mentioned above. Additional excipients, for example, sweetening, flavoring, and coloring agents may also be present. The pharmaceutical compositions of the present invention may also be in the form of oil-in-water emulsions. The oily phase may be a vegetable oil, for example, olive oil or arachis oil, or a mineral oil, for example a liquid paraffin, or a mixture thereof. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectible aqueous or oleaginous suspension. This suspension may be formulated according to the known methods using suitable dispersing or wetting agents and suspending agents described above. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution, and isotonic sodium chloride solution. In addition, sterile, fixed oils are conveniently employed as solvent or suspending medium. For this purpose, any bland fixed oil may be employed using synthetic mono- or diglycerides. In addition, fatty acids such as oleic acid find use in the preparation of injectables.

The compositions may also be in the form of suppositories for rectal administration of the compounds of the present invention. These compositions can be prepared by mixing the drug with a suitable non-irritating excipient which is solid at ordinary temperatures but liquid at the rectal temperature and will thus melt in the rectum to release the drug. Such materials include cocoa butter and polyethylene glycols, for example.

For topical use, creams, ointments, jellies, solutions of suspensions, etc., containing the compounds of the present invention are contemplated. For the purpose of this application, topical applications shall include mouth washes and gargles.

The compounds of the present invention may also be administered in the fonn of liposome delivery systems, such as small unilamellar vesicles, large unilamellar vesicles, and multilamellar vesicles. Liposomes may be formed from a variety of phospholipids, such as cholesterol, stearylamine, or phosphatidylcholines.

In addition, some of the compounds of the present invention may form solvates with water or common organic solvents. Such solvates are also encompassed within the scope of the present invention.

Thus, in a further embodiment, there is provided a pharmaceutical composition comprising a compound according to the present invention, or a pharmaceutically acceptable salt, solvate, or prodrug thereof, and one or more pharmaceutically acceptable carriers, excipients, or diluents.

If a solid carrier is used for oral administration, the preparation may be tableted, placed in a hard gelatine capsule in powder or pellet form or it can be in the form of a troche or lozenge. The amount of solid carrier will vary widely but will usually be from about 25 mg to about 1 g. If a liquid carrier is used, the preparation may be in the form of a syrup, emulsion, soft gelatine capsule or sterile injectable liquid such as an aqueous or non-aqueous liquid suspension or solution.

A typical tablet that may be prepared by conventional tabletting techniques may contain:

| Core: | |
|---|---|
| Active compound (as free compound or salt thereof) | 5.0 mg |
| Lactosum Ph. Eur. | 67.8 mg |

-continued

| Core: | |
|---|---|
| Cellulose, microcryst. (Avicel) | 31.4 mg |
| Amberlite ® IRP88* | 1.0 mg |
| Magnesii stearas Ph. Eur. | q.s. |
| Coating: | |
| Hydroxypropyl methylcellulose | approx. 9 mg |
| Mywacett 9-40 T** | approx. 0.9 mg |

*Polacrillin potassium NF, tablet disintegrant, Rohm and Haas.

**Acylated monoglyceride used as plasticizer for film coating.

If desired, the pharmaceutical composition of the present invention may comprise a compound according to the present invention in combination with further active substances such as those described in the foregoing.

The present invention also provides a method for the synthesis of compounds useful as intermediates in the preparation of compounds of formula (I) along with methods for the preparation of compounds of formula (I). The compounds can be prepared readily according to the following reaction Schemes (in which all variables are as defined before, unless so specified) using readily available starting materials, reagents and conventional synthesis procedures. In these reactions, it is also possible to make use of variants which are themselves known to those of ordinary skill in this art, but are not mentioned in greater detail.

The compounds of this invention can be prepared by routes outlined in the reaction Scheme 1. Reaction of a suitable primary amine (I) with a ketone (II) under reductive amination conditions according to methods known in the literature affords secondary amine (III). Compound (III) can be converted to the corresponding urea (V) by reaction with, for example, carbonyl diimidazole and a suitable amino heterocycle (IV) under standard conditions for the synthesis of ureas. For intermediates where $R^1$ or $R^2$ contains an additional amino functionality, a suitable protection group (for example Boc or Cbz) may be employed, allowing for deprotection and further manipulation (eg. amide coupling, reductive amination etc) using standard procedures described in the literature.

For intermediates where $R^1$ or $R^2$ contains an additional alcohol functionality, a suitable protection group (for example benzyl, tert-butyldimethylsilyl) may be employed, allowing for deprotection and further manipulation (eg. ether coupling) using standard procedures described in the literature.

For intermediates where $R^1$, $R^2$ or A contains an additional carboxy functionality, a suitable precursor (eg. alkyl ester) may be employed, allowing for deprotection and further manipulation (eg. acid or base hydrolysis, conversion to amides via reaction with amines) using standard procedures described in the literature. Additional manipulation of compound (V) can be performed as described within the general procedures outlined within the example section.

Scheme 1

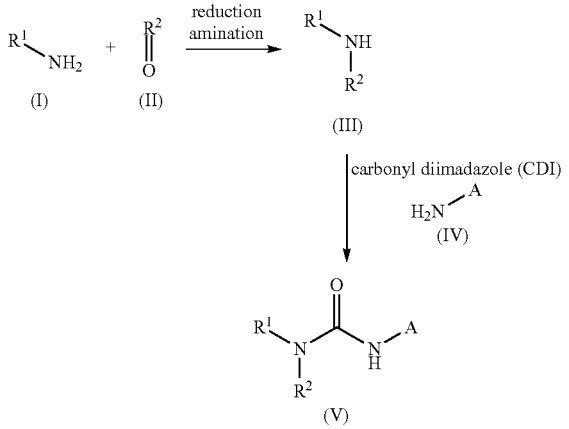

EXAMPLES

HPLC-MS (Method A)

The following instrumentation is used:

Hewlett Packard series 1100 G1312A Bin Pump

Hewlett Packard series 1100 Column compartment

Hewlett Packard series 1100 G1315A DAD diode array Detector

Hewlett Packard series 1100 MSD

Sedere 75 Evaporative Light Scattering detector

The instrument is controlled by HP Chemstation software.

The HPLC pump is connected to two eluent reservoirs containing:

| | |
|---|---|
| A: | 0.01% TFA in water |
| B: | 0.01% TFA in acetonitrile |

The analysis is performed at 40° C. by injecting an appropriate volume of the sample (preferably 1 μl) onto the column which is eluted with a gradient of acetonitrile.

The HPLC conditions, detector settings and mass spectrometer settings used are given in the following table.

| | |
|---|---|
| Column | Waters Xterra MS C-18 × 3 mm id 5 μm |
| Gradient | 5%-100% acetonitrile linear during 7.5 min at 1.5 mL/min |
| Detection | 210 nm (analogue output from DAD) |
| | ELS (analogue output from ELS) |
| MS | ionisation mode API-HS |
| | Scan 100-1000 amu step 0.1 amu |

After the DAD the flow is divided yielding approximately 1 mL/min to the ELS and 0.5 mL/min to the MS.

NMR

Proton NMR spectra were recorded at ambient temperature using a Brucker Avance DPX 200 (200 MHz), Brucker Avance DPX 300 (300 MHz) and Brucker Avance DPX 400 (400 MHz) with tetramethylsilane as an internal standard. Chemical shifts (δ) are given in ppm General Procedure (A)

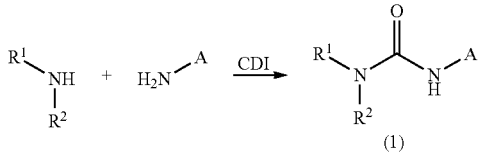

The aminoheterocycle ($NH_2A$) wherein A is defined as above, can be converted using standard literature procedures (for example WO 2004/002481) to an acyl imidazonium intermediate with carbonyl diimidazole (CDI) in a solvent such as dichloromethane, dichloroethane, tetrahydrofuran, or DMF. Treatment with $R^1R^2NH$, wherein $R^1$ and $R^2$ are as defined above, gives the compound of formula (I). The aminoheterocycle ($NH_2A$) or secondary amine ($R^1R^2NH$) can be either commercially available compounds or compounds that can be prepared following procedures described in the literature or prepared as described in the relevant example and general procedures.

General Procedure (B)

The desired amines $R^1R^2NH$ described in General procedure (A), wherein $R^1$ and $R^2$ are as defined above are commercially available, or can be prepared by a reductive amination with a suitable primary amine and a ketone as shown below, following procedures described in the literature (Org. Prep. Proced. Int. 1979, 11, 201).

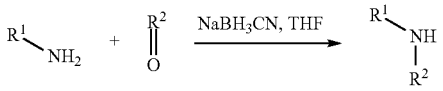

(2)

General Procedure (C)

Preparation of 1,1-dicycloalkyl-3-heteroaryl-urea

A mixture of 1,1'-carbonyldiimidazole (98 mg, 0.6 mmol), amino heteroaryl compound (0.6 mmol) and 4-(N,N-dimethylamino)pyridine (5 mg) in dichloroethane (5 ml) was heated at 80° C. for 1 h. The reaction mixture was cooled to room temperature and was added solution of a dicycloalkylamine (0.5 mmol) in dichloroethane (2 ml). The resulting suspension was heated at 80° C. for 3 h and concentrated. The residue was purified by column chromatography (silica, $CH_2Cl_2$ then 5-10% ethyl acetate in $CH_2Cl_2$) to afford the desired urea 50-60% yield.

General Procedure (D)

Synthesis of 1,1-dicycloalkyl-3-(5-thiaalkyl -thiazol-2-yl) ureas

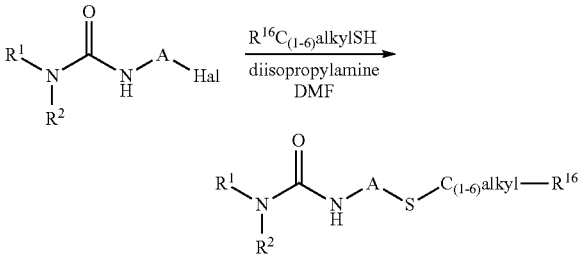

Hal=Halogen $R^1$ and $R^2$, A and $R^{17}$ as defined in compound claims

Representative Example

A mixture of 3-(5-bromo-thiazol-2-yl)-1,1-dicycloalkylurea (Example 49) (1 mmol), alkylthiol (2 mmol) and DIEA (2 mmol) in DMF (5 mL) was heated at 80° C. for 3 h. The mixture was poured into water (20 mL) and was extracted with ethyl acetate (3×25 mL). The organic layer was washed with water (2×30 mL), brine (1×30 mL), dried (anhydrous $Na_2SO_4$) and concentrated in vacuo to furnish a residue containing 3-(5-alkylthio-thiazol-2-yl)-1,1-dicyclohexyl-urea. The crude product was purified by column chromatography (silica, $CH_2Cl_2$ then 5-20% ethyl acetate in $CH_2Cl_2$) to afford 3-(5-alkylthio-thiazol-2-yl)-1,1-dicyclohexyl-urea in 35-45% yield.

General Procedure (E)

Synthesis of 1,1-dicycloalkyl-3-(5-thiaheteroaryl-thiazol-2-yl)urcas

A mixture of arylthiol (2 mmol) and tert.BuOK (2 mmol) in DMF (5 mL) was stirred for 15 min. To this solution was added 3-(5-bromo-thiazol-2-yl)-1,1-dicyclohexyl-urea (Example 49) (1 mmol) and was heated at 80° C. for 3 h. The mixture was poured into water (20 mL) and was extracted with ethyl acetate (3×25 mL). The organic layer was washed with water (2×30 mL), brine (1×30 mL), dried (anhydrous $Na_2SO_4$) and concentrated in vacuo to furnish a residue containing (5-arylthio-2-thiazolyl)-1,1-dicyclohexyl-urea. The crude product was purified by column chromatography (silica, $CH_2Cl_2$ then 5-20% ethyl acetate in $CH_2Cl_2$ and 2% MeOH in $CH_2Cl_2$) to afford the desired urea in 25-45% yield.

General Procedure (F)

Hydrolysis of Esters

Ester (1 mmol) was dissolved in 1:1 mixture of THF and methanol (5 mL). To this solution was added 2 M solution of LiOH (2 mL, 4 mmol). The mixture was stirred for 4-6 h and was concentrated. The residue was diluted with water (10 mL) and the aqueous layer was washed with ethyl acetate (2×10 mL). The water layer was acidified with HCl to pH 6.0 and the precipitated acid was extracted with ethyl acetate (2×50 mL). The organic layer was washed with water (2×20 mL), dried ($Na_2SO_4$) and concentrated in vacuo to furnish corresponding carboxylic acid in almost quantitative yield.

General Procedure (G)

Synthesis of Acyl- or Sulfonyl-piperidinyl-(thiazolyl)-cycloalkyl ureas.

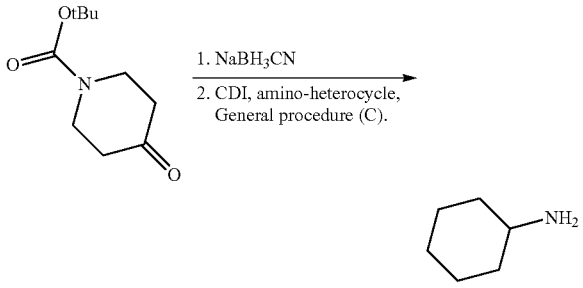

-continued

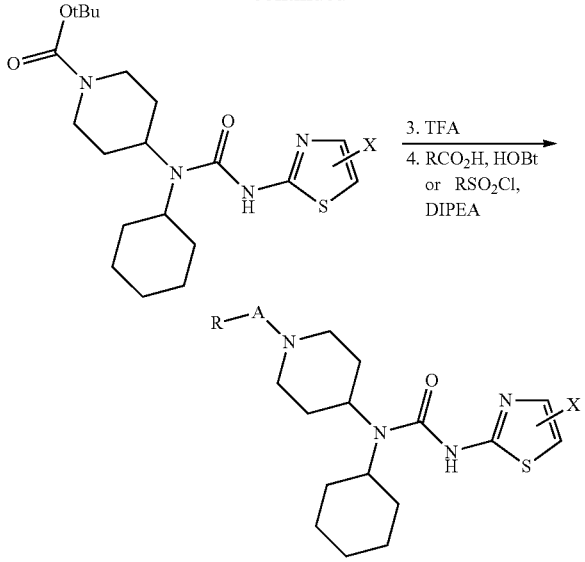

A = CO or $SO_2$
R = Alkyl, ary etc

Step 1. To N-Boc-piperidone (10 g) in a mixture of MeOH (50 ml) and THF (50 ml) is added an equimolar amount of cycloalkylamine (4.5 g) at room temperature. Sodium cyanoborohydride (6.3 g, 2 eq) is added and the reaction stirred at room temperature overnight. The crude product is filtered through celite, concentrated in vacuo, redissolved/suspended in ether, stirred for 1 h, and decanted. This procedure is repeated 4 times and the combined ether-phases are concentrated in vacuo to afford 4-cycloalkylamino-piperidine-1-carboxylic acid tert-butyl ester as a pale yellow oil which is used directly in step 2.

Step 2. A equimolar mixture of 1,1-carbonyldiimidazole, aminoheteroaryl compound (for example 5-methylaminothiazole) and DMAP (5 mol %) in dichloroethane is heated for 4 h at 80° C. then cooled to room temperature. The amine product (1 equivalent) from Step 1 is added and the reaction is stirred overnight. Work up and chromatography (5% ethyl acetate in hexane) affords the desired Boc protected urea.

Step 3. Boc deprotection is performed using trifluoroacetic acid in DCM for 2 h at room temperature. Excess TFA and DCM are removed in vacuo to give the crude amine which is used directly in the next Step.

Step 4. Acylation with either an HOBt activated carboxylic acid or a sulfonylchloride affords the required amide or sulfonamide respectively via established literature procedures.

Step 5. If the substituent on the aminoheteroaryl moiety contains an ester functionality this can be hydrolysed using lithium hydroxide in methanol to give the corresponding acid.

General Procedure (H)

Synthesis of 5-thioalkyl/5-thioalkylamino substituted thiazolyl ureas.

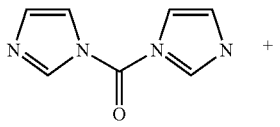

-continued

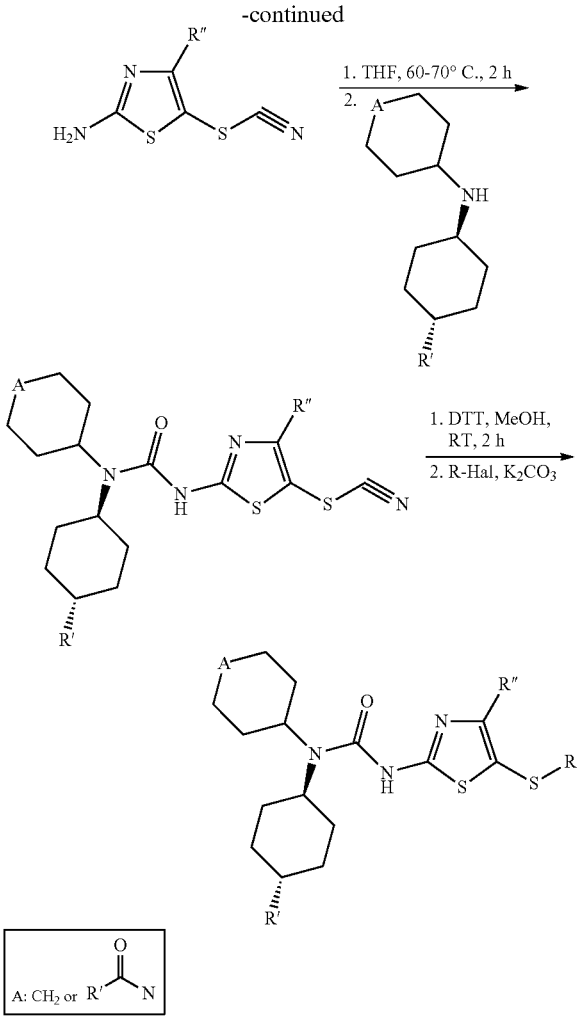

Step 1. A equimolar mixture of 1,1-carbonyldiimidazole, the appropriate 5-thiocyanato-thiazol-2-ylamine (commercially available or prepared as described in J. Am. Chem. Soc 71, 4007, 1949 or J. Med. Chem., 20, 572, 1977) and DMAP (5 mol %) in THF is heated for 2 h at 60-70° C. and then cooled to room temperature. The secondary amine (1 equivalent; prepared as described in General procedure (C) or General Procedure (I) is added and the reaction is stirred overnight at room temperature. The reaction mixture was quenched with water and organic phase was isolated. The aqueous phase was extracted with $CH_2Cl_2$, and the combined organic phases were dried and concentrated in vacuo. The crude product was purified by flash chromatography (heptane: $CH_2Cl_2$ 20:80→0:100 or heptane: $CH_2Cl_2$:EtOAc 20:80:0→0:0:100) afforded the desired (5-thiocyanato-thiazol-2-yl)urea.

Step 2. An equimolar mixture of 1,4-dithiothreitol (DTT) and the appropriate (5-thiocyanato-thiazol-2-yl)urea (prepared as described in Step 1) in MeOH (4 mL/mmol) was stirred in a nitrogen atmosphere at room temperature for 2 h. Addition of $K_2CO_3$ (3 equiv) and the appropriate alkyl halide (1-3 equivalents). The reaction mixture was stirred at room temperature over night and quenched with water. Addition of $CH_2Cl_2$. The organic phase was isolated and the aqueous phase was extracted with $CH_2Cl_2$, and the combined organic phases were concentrated in vacuo. The crude product was dissolved in MeOH or MeCN and purified by reverse phase preparative HPLC (Gilson) to give the desired product.

General Procedure (I)

Synthesis of N-acylated cycloalkyl-cycloalkylamino-amines.

Step 1. A equimolar mixture of 4-piperidone monohydrate hydrochloride, diisopropylethylamine and the appropriate acyl chloride in $CH_2Cl_2$ (1 mL/mmol) was stirred at room temperature overnight. The reaction mixture was added to $CH_2Cl_2$ and the organic phase was washed with 1N NaOH (twice), 1N HCl and brine and subsequently concentrated in vacuo to give the acylated piperidone which was used directly in Step 2.

Step 2. A equimolar mixture the acylated piperidone (prepared in Step 1) and the appropriate cycloalkylamine in THF: MeOH (1:1, 2 mL/mmol) and 3 Å molsieves was added sodium cyanoborohydride (2 equiv) and the mixture was stirred at room temperature overnight to give the crude secondary amine which is filtered through celite, concentrated in vacuo, redissolved/suspended in ether, stirred for 1 h, and decanted. The procedure is repeated 4 times and the combined ether-phases are concentrated in vacuo to afford the desired N-acylated cycloalkylpiperidin-4-yl amine.

General Procedure (J) for the Synthesis of Alkyl/Arylsulfones:

Aryl/alkyl-sulfanyl derivative of dialkyl-thiazolyl urea (0.5 mmol) was dissolved in $CH_2Cl_2$ (6 mL) and was cooled to 0° C. in an ice bath. To this solution was added peroxy acetic acid (10 mmol) in $CH_2Cl_2$ (5 mL). The mixture was stirred for 4 h at 0° C. and was diluted with $CH_2Cl_2$ (50 mL). The organic layer was washed with saturated solution of $NaHCO_3$ (2×30 mL), water (3×30 mL), brine (1×30 mL), dried (anhydrous $Na_2SO_4$) and concentrated in vacuo. The crude mixture was purified by column chromatography with $CH_2Cl_2$ then 5-20% ethyl acetate in $CH_2Cl_2$ to give the corresponding sulfone.

General Procedure (K) for the Synthesis of Amides.

A solution of 2-(3,3-dicycloalkylureido)-thiazole-4-carboxylic acid or 2-(3,3-dicycloalkylureido)-thiazole-5-carboxylic acid (0.60 mmol), DIEA (0.25 mL, 1.50 mmol) and TFFH (270 mg, 0.6 mmol) in THF (5 mL) was stirred for 30 Min. To this mixture was added amine or amino acid-ester (0.6 mmol) and the reaction mixtures was stirred for 12 h at rt. The reaction mixture was concentrated and purified by flash chromatography using $CH_2Cl_2$ and ethyl acetate (4:1) to afford the corresponding amide.

General Procedure (L) for the Synthesis of Alkyl/Aryl-Thiazolyl Ureas

To a solution of 1,1-dicycloalkyl-3-(4-hydroxymethylthiazol-2-yl)urea (1 mmol) in DCM (5 mL) was added $PBr_3$ (1.2 mmol) at 0° C. and stirred for 2 h. The mixture was slowly quenched with ice water and was extracted with DCM (3×20 mL). The organic layer was washed with water (2×20 mL), brine (1×20 mL), dried over sodium sulfate and concentrated to afford 1,1-dicycloalkyl-3-(4-bromomethyl-thiazol-2-yl) urea. This crude bromide was used as such for the next step.

A mixture of aryl thiol (2 mmol) and potassium tert-butoxide (2 mmol) in DMF (5 mL) was stirred for 15 min. To this solution was added 1,1-dicycloalkyl-3-(4-bromomethyl-thiazol-2-yl)urea (1 mmol) and was heated at 80° C. for 3 h. The mixture was poured into water (20 mL) and was extracted with ethyl acetate (3×25 mL). The organic layer was washed with water (2×30 mL), brine (1×30 mL), dried (anhydrous $Na_2SO_4$) and concentrated in vacuo to furnish a residue containing aryl/alkyl-thiazolyl urea. The crude product was purified by column chromatography (silica, $CH_2Cl_2$ then 5-20% ethyl acetate in $CH_2Cl_2$ and 2% MeOH in $CH_2Cl_2$) to afford the desired urea.

General Procedure (M) for the Removal of Boc-Group to Form Amine Hydrochlorides

To the Boc-protected amine (0.5 mmol) was added 4 M solution of HCl in dioxane (2 mL). The mixture was stirred for 30 min. The mixture was concentrated and the residue was washed with anhydrous ether and concentrated to get amine hydrochloride in almost quantitative yield.

General Procedure (N) for the Acylation of Amines

A solution of amine/amine hydrochloride (0.5 mmol) in DCM was cooled to 0° C. To this solution was added acyl chloride (0.6 mmol) followed by DIEA (1.5 mmol). The mixture was stirred for 2 h and concentrated. The residue was purified by column chromatography (silica, $CH_2Cl_2$ then 5-20% ethyl acetate in $CH_2Cl_2$ and 2% MeOH in $CH_2Cl_2$) to afford the desired product.

General Procedure (P) for Reductive Amination

To a mixture of 1,1-dialkyl-3-(5-formyl-thiazol-2-yl)-urea (0.30 mmol) and dry powdered molecular sieves in $CH_2Cl_2$ (2 mL) was added the appropriate alkyl-amino hydrochloride (0.36 mmol). The mixture was stirred for 20 minutes. To this was added sodium triacetoxyborohydride (0.39 mmol) and the reaction was stirred for six to 12 hours at ambient temperature. The reaction was quenched with saturated aqueous $Na_2HCO_3$ (10 mL), extracted once with $CH_2Cl_2$ (10 mL) and once with ethyl acetate (10 mL). The combined organic extractions were dried over $MgSO_4$. After concentration to a crude oil, the desired thiazole urea was purified by column chromatography (silica gel and 5% ethyl acetate in $CH_2Cl_2$, then 1% MeOH and 10% ethyl acetate in $CH_2Cl_2$ followed by 2% MeOH and 10% ethyl acetate in $CH_2Cl_2$) to afford the product in 14 to 65% yield.

General Procedure (Q) for the Preparation of Sulfonamides

Amine hydrochloride (0.20 mmol) and diisopropyl ethylamine (DIEA, 0.40 mmol) were combined in $CH_2Cl_2$ (3 mL) and stirred at ambient temperature. The desired sulfonyl chloride (0.30 mmol) was added and the reaction was stirred until complete (15-45 minutes). The volatile components were removed with reduced pressure and the residue was purified by column chromatography (silica gel and 5% ethyl acetate in $CH_2Cl_2$, then 1% MeOH and 10% ethyl acetate in $CH_2Cl_2$) to afford the product in 44 to 87% yield.

Example 1

1,1-Dicyclohexyl-3-thiazol 2 yl urea

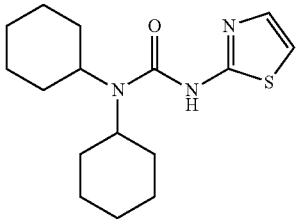

To a solution of aminothiazole (50 mg, 0.5 mmol) in dichloromethane was added carbonyldiimidazole (81 mg, 0.5 mmol) and the solution stirred 2 h at room temperature. Dicyclohexylamine (1 eq) was then added and the reaction stirred overnight at room temperature. The reaction mixture is then diluted with ethyl acetate (8 mL), washed successively with 10% sodiumhydrogensulphate (3 mL), water (3 mL), dried over magnesium sulphate, concentrated in vacuo, and the residue purified by HPLC (Gilson 1, X-terra column; 0-100% $CH_3CN/H_2O/0$, 1% TFA; 15 min; flow 50 ml/min) to give the title product (52 mg).

$^1$H NMR (DMSO-$d_6$): δ 7.28-7.35 (1H, m), 6.91-6.98 (1H, m), 3.35-3.60 (2H, m), 1.01-2.11 (20H, m); HPLC-MS (Method A): m/z=308 (M+1); $R_f$=4.07 min.

Example 2

3-(5-Chloro-thiazol-2-yl)-1,1-dicyclohexyl-urea

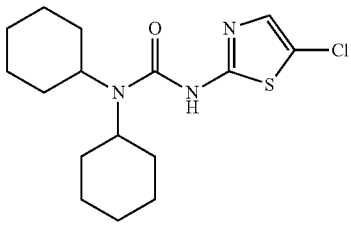

Prepared as described in general procedure (A) using 5-chloro-2-aminothiazole and dicyclohexylamine.

$^1$H NMR ($CDCl_3$): δ 8.20 (1H, bs), 7.15 (1H, s), 3.30-3.50 (2H, m), 0.80-2.00 (20H, m); HPLC-MS (Method A): m/z=342.1 (M+); Rt=5.41 min.

Example 3

1,1-Dicyclohexyl-3-(4-methyl-thiazol-2-yl)-urea

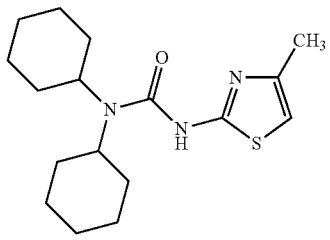

Prepared as described in general procedure (A) using 4-methyl-2-aminothiazole and dicyclohexylamine $^1$H NMR ($CDCl_3$): δ 8.10 (1H, bs), 6.40 (1H, s), 3.35-3.55 (2H, m), 1.60-1.96 (14H, m), 1.05-1.50 (6H, m); HPLC-MS (Method A): m/z=322.2 (M+1); $R_t$=4.42 min.

Example 4

1,1-Dicyclohexyl-3-(5-methyl-thiazol-2-yl)-urea

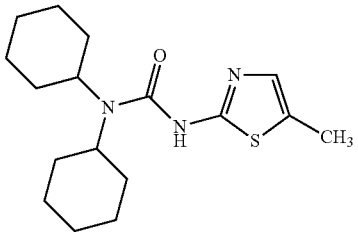

Prepared as described in general procedure (A) using 5-methyl-2-aminothiazole and dicyclohexylamine. $^1$H NMR ($CDCl_3$): δ 7.93 (1H, bs), 6.92 (1H, s), 3.39-3.51 (2H, m), 1.58-1.92 (14H, m), 1.05-1.45 (6H, m); HPLC-MS (Method A): m/z=322 (M+1); $R_t$=4.22 min.

Example 5

1,1-Dicyclohexyl-3-(5-methyl-[1,3,4]thiadiazol-2-yl)-urea

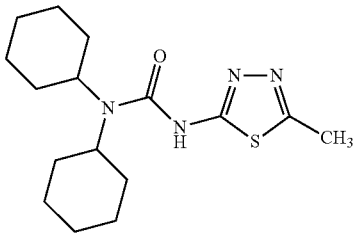

Prepared as described in general procedure (A) using 5-methyl-2-amino-1,3,4-thiadiazole and dicyclohexylamine.

$^1$H NMR ($CDCl_3$): δ 8.31 (1H, bs), 3.35-3.55 (2H, m), 2.63 (3H, s), 1.55-1.95 (14H, m), 1.09-1.45 (6H, m); HPLC-MS (Method A): m/z=323.2 (M+1); $R_t$=4.46 min.

Example 6

2-(3,3-Dicyclohexyl-ureido)-4-methyl-thiazole-5-carboxylic acid ethyl ester

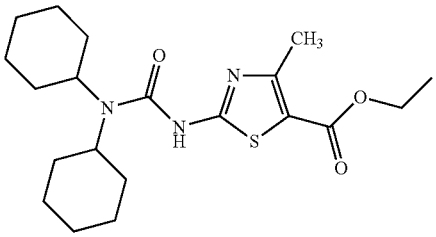

Prepared as described in general procedure (A) using 4-methyl-5-carboxyethyl-2-aminothiazole and dicyclohexylamine. $^1$ HNMR ($CDCl_3$): δ 8.05 (1H, bs), 4.25 (2H, q), 3.31-3.49 (2H, m), 2.55 (3H, s), 1.55-1.95 (14H, m),1.11-1.45 (9H, m); HPLC-MS (Method A): m/z=394.2 (M+); $R_t$=5.61 min.

Example 7

1-(4-Methyl-cyclohexyl)-1-(tetrahydro-pyran-4-yl)-3-thiazol-2-yl-urea

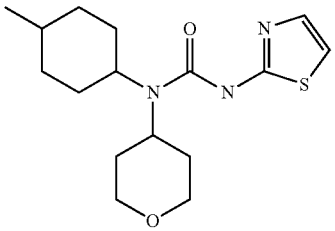

Prepared as described in general procedures (A) and (B) using aminothiazole and (4-methyl-cyclohexyl)-(tetrahydro-pyran-4-yl)-amine.

HPLC-MS (Method A): m/z=324 (M+1); $R_t$=3.36 min.

Example 8

1-(4-tert-Butyl-cyclohexyl)-3-(5-chloro-thiazol-2-yl)-1-cyclopentyl-urea

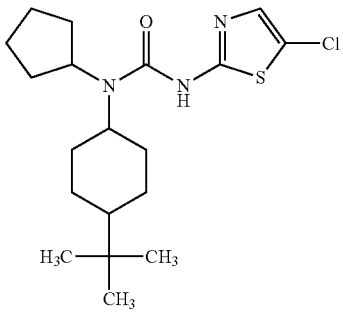

Prepared as described in general procedures (A) and (B) using 5-chloro-2-aminothiazole and (4-tert-butyl-cyclohexyl)-cyclopentyl-amine HPLC-MS (Method A): m/z=384 (M+); $R_t$=6.28 min.

Example 9

1-Cyclopentyl-1-(4-isopropyl-cyclohexyl)-3-thiazol-2-yl-urea

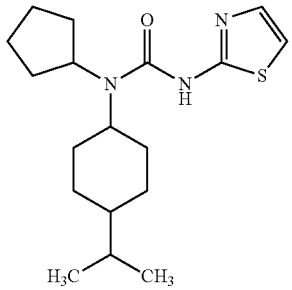

Prepared as described in general procedures (A) and (B) using aminothiazole and (4-isopropyl-cyclohexyl)-cyclopentyl-amine HPLC-MS (Method A): m/z=336 (M+); $R_t$=4.97 min.

Example 10

1-Bicyclo[2.2.1]hept-2-yl-3-(5-chloro-thiazol-2-yl)-1-cyclopentyl-urea

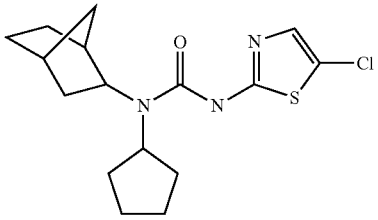

Prepared as described in general procedures (A) and (B) using 5-chloro-2-aminothiazole and bicyclo[2.2.1]hept-2-yl-cyclopentyl-amine HPLC-MS (Method A): m/z=340 (M+); $R_t$=5.48 min.

Example 11

1-(3,5-Dimethyl-cyclohexyl)-1-(4-methyl-cyclohexyl)-3-thiazol-2-yl-urea

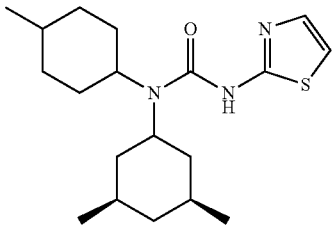

Prepared as described in general procedures (A) and (B) using aminothiazole and (3,5-dimethyl-cyclohexyl)-(4-methyl-cyclohexyl)-amine.

HPLC-MS (Method A): m/z=350 (M+); $R_t$=5.13 min.

Example 12

4-(1-Cyclopentyl-3-thiazol-2-yl-ureido)-cyclohexan-ecarboxylic acid ethyl ester

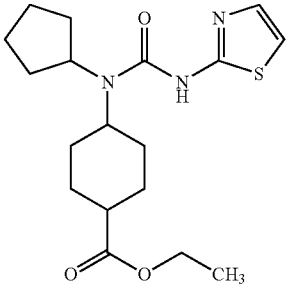

Prepared as described in general procedures (A) and (B) using aminothiazole and 4-cyclopentylamino-cyclohexan-ecarboxylic acid ethyl ester.

HPLC-MS (Method A): m/z=366 (M+1); $R_t$=3.84 min.

Example 13

3-(5-Chloro-thiazol-2-yl)-1-(4methyl-cyclohexyl)-1-(4-trifluoromethyl-cyclohexyl)-urea

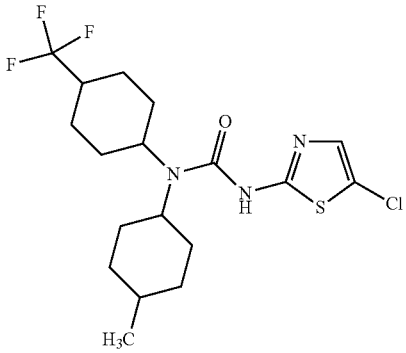

Prepared as described in general procedures (A) and (B) using 5-chloro-2-aminothiazole and (4-methyl-cyclohexyl)-(4-trifluoromethyl-cyclohexyl)-amine.

HPLC-MS (Method A): m/z=424 (M+1); $R_t$=5.41 min.

Example 14

3-(5-Chloro-thiazol-2-yl)-1-(4-methyl-cyclohexyl)-1-(tetrahydro-pyran-4-yl)-urea

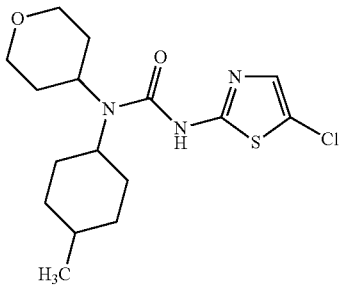

Prepared as described in general procedures (A) and (B) using 5-chloro-2-aminothiazole and (4-methyl-cyclohexyl)-(tetrahydro-pyran-4-yl)-amine.

HPLC-MS (Method A): m/z=358 (M+); $R_t$=4.64 min.

Example 15

3-(5-Chloro-thiazol-2-yl)-1-(4-methyl-cyclohexyl)-1-(tetrahydro-thiopyran-4-yl)-urea

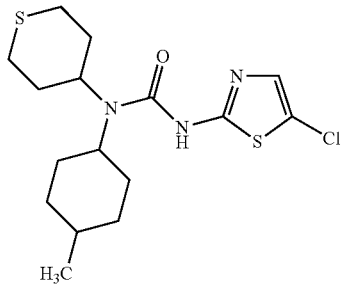

Prepared as described in general procedures (A) and (B) using 5-chloro-2-aminothiazole and (4-methyl-cyclohexyl)-(tetrahydro-thiopyran-4-yl)-amine.

HPLC-MS (Method A): m/z=374 (M+); $R_t$=4.91 min.

Example 16

3-(5-Chloro-thiazol-2-yl)-1-(1,4-dioxa-spiro[4.5]dec-8-yl)-1-(4-methyl-cyclohexyl)-urea

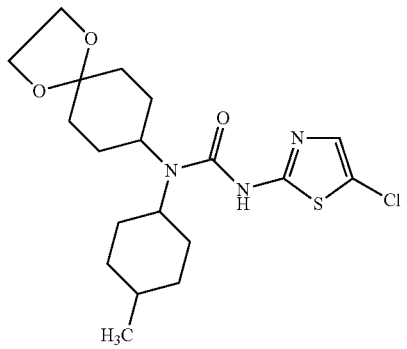

Prepared as described in general procedures (A) and (B) using 5-chloro-2-aminothiazole and (1,4-dioxa-spiro[4.5]dec-8-yl)-(4-methyl-cyclohexyl)-amine HPLC-MS (Method A): m/z=414 (M+); $R_t$=4.70 min.

Example 17

3-(5-Chloro-thiazol-2-yl)-1,1-bis-(4-methyl-cyclohexyl)-urea

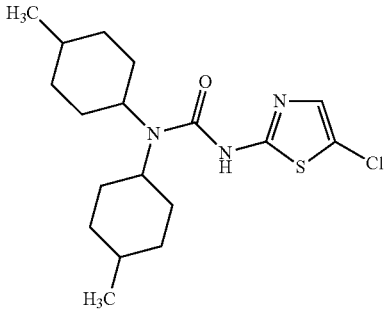

Prepared as described in general procedures (A) and (B) using 5-chloro-2-aminothiazole and bis-(4-methyl-cyclohexyl)-amine.

HPLC-MS (Method A): m/z=370 (M+); $R_t$=5.78 min.

Example 18

3-(5-Chloro-thiazol-2-yl)-1-cyclopentyl-1-(4-methyl-cyclohexyl)-urea

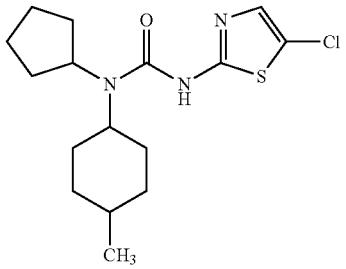

Prepared as described in general procedures (A) and (B) using 5-chloro-2-aminothiazole and cyclopentyl-(4-methyl-cyclohexyl)-amine HPLC-MS (Method A): m/z=342 (M+1); $R_t$=5.59 min.

Example 19

1-(4-Methyl-cyclohexyl)-3-thiazol-2-yl-1-(4-trifluoromethyl-cyclohexyl)-urea

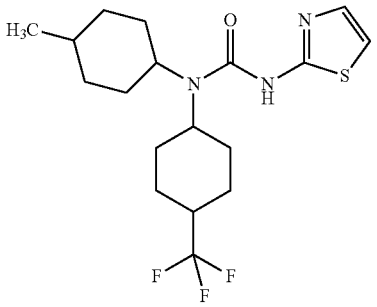

Prepared as described in general procedures (A) and (B) using 5-chloro-2-aminothiazole and (4-methyl-cyclohexyl)-(4-trifluoromethyl-cyclohexyl)-amine HPLC-MS (Method A): m/z=390 (M+1); $R_t$4.67 min.

Example 20

3-(5-Chloro-thiazol-2-yl)-1,1-dicyclopentyl-urea

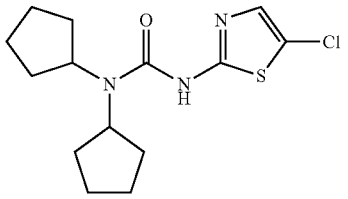

Prepared as described in general procedure (A) using 5-chloro-2-aminothiazole and dicyclopentylamine.

HPLC-MS (Method A): m/z=314 (M+); $R_t$=5.03 min.

Example 21

3-(5-Chloro-thiazol-2-yl)-1-cyclopentyl-1-(tetrahydro-thiopyran-4-yl)-urea

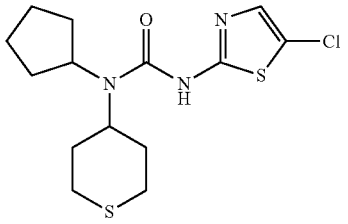

Prepared as described in general procedures (A) and (B) using 5-chloro-2-aminothiazole and cyclopentyl-(tetrahydro-thiopyran-4-yl)-amine.

HPLC-MS (Method A): m/z=346 (M+1); $R_t$=4.82 min.

Example 22

3-(5-Chloro-thiazol-2-yl)-1-cyclopentyl-1-(tetrahydro-pyran-4-yl)-urea

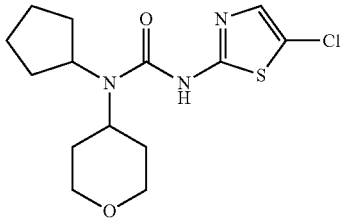

Prepared as described in general procedures (A) and (B) using 5-chloro-2-aminothiazole and cyclopentyl-(tetrahydro-pyran-4-yl)-amine.

HPLC-MS (Method A): m/z=330 (M+); $R_t$=4.09 min.

Example 23

1,1-Bis-(4-methyl-cyclohexyl)-3-thiazol-2-yl-urea

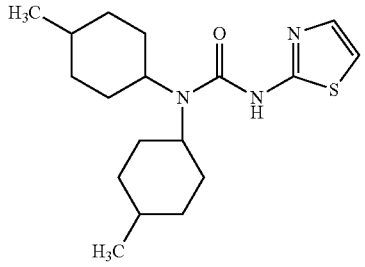

Prepared as described in general procedures (A) and (B) using aminothiazole and bis-(4-methyl-cyclohexyl)-amine.

HPLC-MS (Method A): m/z=336 (M+1); $R_t$=4.88 min.

Example 24

4-[3-(5-Chloro-thiazol-2-yl)-1-(4-methyl-cyclohexyl)-ureido]-cyclohexanecarboxylic acid ethyl ester

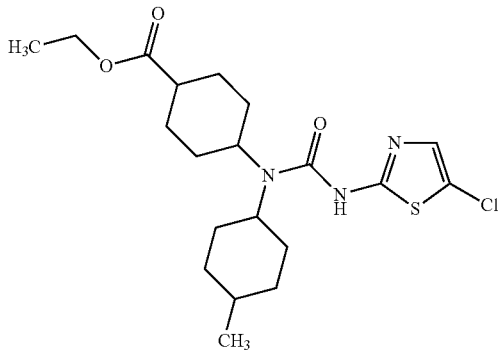

Prepared as described in general procedures (A) and (B) using 5-chloro-2-aminothiazole and 4-(4-methyl-cyclohexylamino)-cyclohexanecarboxylic acid ethyl ester HPLC-MS (Method A): m/z=429 (M+1); $R_t$=5.21 min.

Example 25

1-(4-tert-Butyl-cyclohexyl)-1-(4-methyl-cyclohexyl)-3-thiazol-2-yl-urea

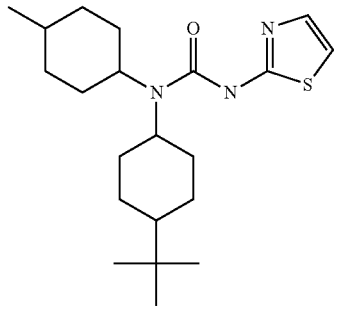

Prepared as described in general procedures (A) and (B) using 5-chloro-2-aminothiazole and (4-tert-butyl-cyclohexyl)-(4-methyl-cyclohexyl)-amine HPLC-MS (Method A): m/z=378 (M+1); $R_t$=5.84 min.

Example 26

4-[3-(5-Chloro-thiazol-2-yl)-1-cyclopentyl-ureido]-cyclohexanecarboxylic acid ethyl ester

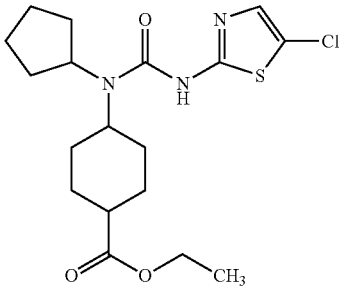

Prepared as described in general procedures (A) and (B) using 5-chloro-2-aminothiazole and 4-Cyclopentylamino-cyclohexanecarboxylic acid ethyl ester.

HPLC-MS (Method A): m/z=400 (M+); $R_t$=5.08 min.

Example 27

1-(4-Isopropyl-cyclohexyl)-1-(4-methyl-cyclohexyl)-3-thiazol-2-yl-urea

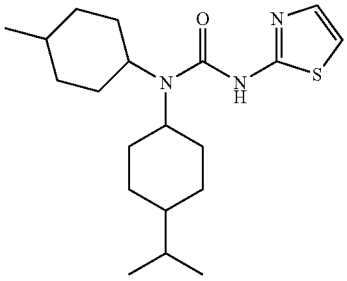

Prepared as described in general procedures (A) and (B) using aminothiazole and (4-isopropyl-cyclohexyl)-(4-methyl-cyclohexyl)-amine.

HPLC-MS (Method A): m/z=364 (M+1); $R_t$=5.52 min.

Example 28

1-Bicyclo[2.2.1]hept-2-yl-3-(5-chloro-thiazol-2-yl)-1-(4-methyl-cyclohexyl)-urea

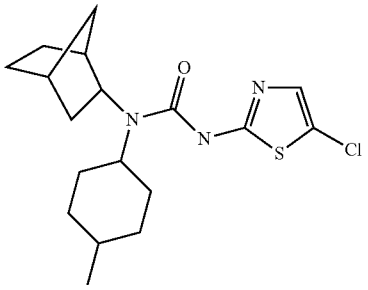

Prepared as described in general procedures (A) and (B) using 5-chloro-2-aminothiazole and bicyclo[2.2.1]hept-2-yl-(4-methyl-cyclohexyl)-amine.

HPLC-MS (Method A): m/z=368 (M+); $R_t$=5.95 min

Example 29

3-(5-Chloro-thiazol-2-yl)-1-(4-isopropyl-cyclohexyl)-1-(4-methyl-cyclohexyl)-urea

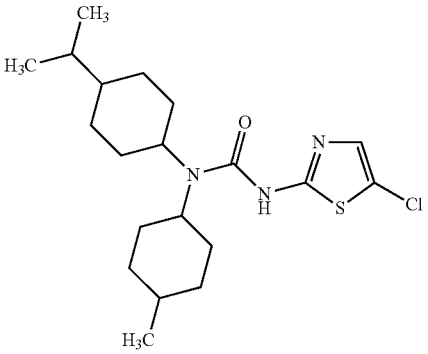

Prepared as described in general procedures (A) and (B) using 5-chloro-2-aminothiazole and (4-isopropyl-cyclohexyl)-(4-methyl-cyclohexyl)-amine.

HPLC-MS (Method A): m/z=399 (M+1); $R_t$=6.19 min.

Example 30

3-(5-Chloro-thiazol-2-yl)-1-cyclopentyl-l-(1,4-dioxa-spiro[4.5]dec-8-yl)-urea

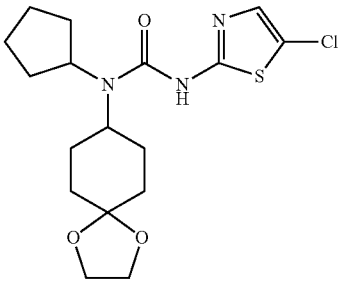

Prepared as described in general procedures (A) and (B) using 5-chloro-2-aminothiazole and cyclopentyl-(1,4-dioxa-spiro[4.5]dec-8-yl)-amine HPLC-MS (Method A): m/z=386 (M+); $R_t$=4.55 min.

Example 31

1-Cyclopentyl-1-(4-methyl-cyclohexyl)-3-thiazol-2-yl-urea

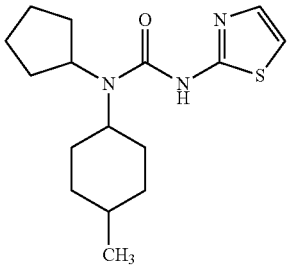

Prepared as described in general procedures (A) and (B) using aminothiazole and cyclopentyl-(4-methyl-cyclohexyl)-amine.

HPLC-MS (Method A): m/z=308 (M+1); $R_t$=4.25 min.

Example 32

1-(4-Methyl-cyclohexyl)-1-(tetrahydro-thiopyran-4-yl)-3-thiazol-2-yl-urea

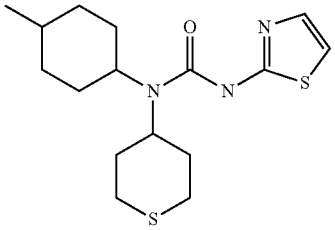

Prepared as described in general procedures (A) and (B) using aminothiazole and (4-methyl-cyclohexyl)-(tetrahydro-thiopyran-4-yl)-amine.

HPLC-MS (Method A): m/z=340 (M+1); $R_t$=4.04 min.

Example 33

3-(5-Chloro-thiazol-2-yl)-1-(3,5-dimethyl-cyclohexyl)-1-(4-methyl-cyclohexyl)-urea

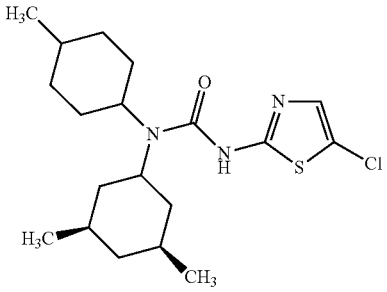

Prepared as described in general procedures (A) and (B) using 5-chloro-2-aminothiazole and (3,5-dimethyl-cyclohexyl)-(4-methyl-cyclohexyl)-amine.

HPLC-MS (Method A): m/z=385 (M+1); $R_t$=6.00 min.

Example 34

4-[1-(4-Methyl-cyclohexyl)-3-thiazol-2-yl-ureido]-cyclohexanecarboxylic acid ethyl ester

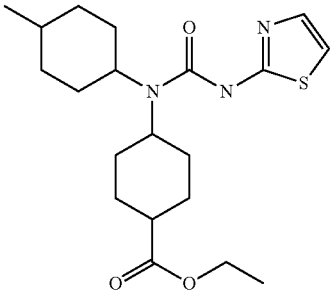

Prepared as described in general procedures (A) and (B) using aminothiazole and 4-(4-methyl-cyclohexylamino)-cyclohexanecarboxylic acid ethyl ester HPLC-MS (Method A): m/z=394 (M+1); $R_t$=4.43 min.

Example 35

3-(5-Chloro-thiazol-2-yl)-1-cyclopentyl-1-(3,5-dimethyl-cyclohexyl)-urea

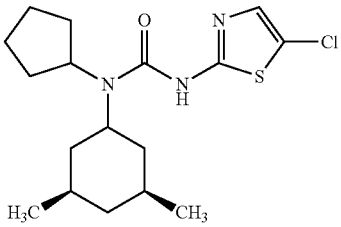

Prepared as described in general procedures (A) and (B) using 5-chloro-2-aminothiazole and (3,5-dimethyl-cyclohexyl)-(4-methyl-cyclopentyl)-amine.

HPLC-MS (Method A): m/z=356 (M+1); $R_t$=5.86 min.

Example 36

1-(4-tert-Butyl-cyclohexyl)-3-(5-chloro-thiazol-2-yl)-1-(4-methyl-cyclohexyl)-urea

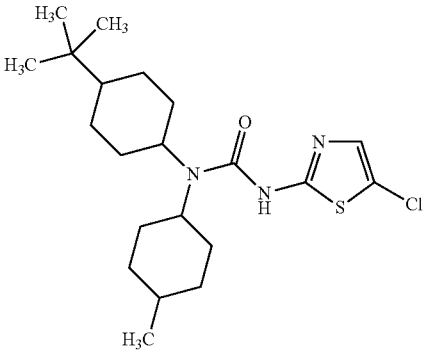

Prepared as described in general procedures (A) and (B) using 5-chloro-2-aminothiazole and (4-tert-butyl-cyclohexyl)-(4-methyl-cyclohexyl)-amine HPLC-MS (Method A): m/z=412 (M+1); $R_t$=6.44 min.

Example 37

3-(5-Chloro-thiazol-2-yl)-1-cyclopentyl-1-(4-isopropyl-cyclohexyl)-urea

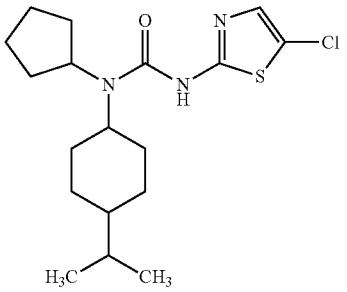

Prepared as described in general procedures (A) and (B) using 5-chloro-2-aminothiazole and (4-tert-butyl-cyclohexyl)-cyclopentyl-amine HPLC-MS (Method A): m/z=370 (M+1); $R_t$=6.20 min.

Example 38

1-(4-Methyl-cyclohexyl)-3-(5-methyl-thiazol-2-yl)-1-(tetrahydro-pyran-4-yl)-urea

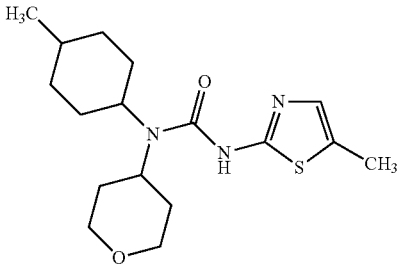

Prepared as described in general procedures (A) and (B) using 5-methyl-2-aminothiazole and (4-methyl-cyclohexyl)-(tetrahydro-pyran-4-yl)-amine.

HPLC-MS (Method A): m/z=338 (M+1); $R_t$=3.50 min.

Example 39

1-(4-Methyl-cyclohexyl)-3-(5-methyl-thiazol-2-yl)-1-(tetrahydro-thiopyran-4-yl)-urea

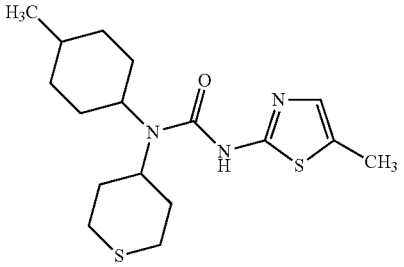

Prepared as described in general procedures (A) and (B) using 5-methyl-2-aminothiazole and (4-methyl-cyclohexyl)-(tetrahydro-thiopyran-4-yl)-amine.

HPLC-MS (Method A): m/z=354 (M+1); $R_t$=4.15 min.

Example 40

1-(4-tert-Butyl-cyclohexyl)-1-(4-methyl-cyclohexyl)-3-(5-methyl-thiazol-2-yl)-urea

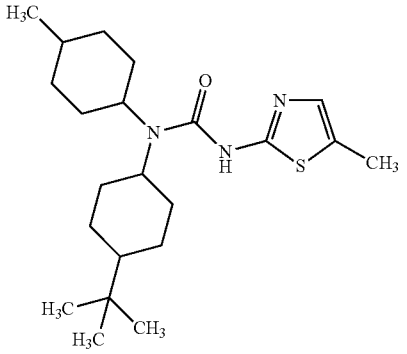

Prepared as described in general procedures (A) and (B) using 5-methyl-2-aminothiazole and (4-tert-butyl-cyclohexyl)-(4-methyl-cyclohexyl)-amine HPLC-MS (Method A): m/z=392 (M+1); $R_t$=5.81 min.

Example 41

4-[1-(4-Methyl-cyclohexyl)-3-(5-methyl-thiazol-2-yl)-ureido]-cyclohexanecarboxylic acid ethyl ester

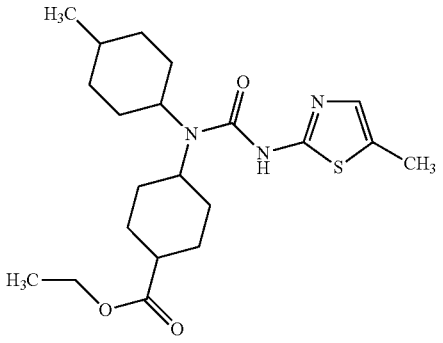

Prepared as described in general procedures (A) and (B) using 5-methyl-2-aminothiazole and 4-(4-methyl-cyclohexylamino)-cyclohexanecarboxylic acid ethyl ester.

HPLC-MS (Method A): m/z=408 (M+1); $R_t$=4.44 min.

Example 42

1-(2,3-Dioxa-spiro[4.5]dec-8-yl)-1-(4-methyl-cyclohexyl)-3-(5-methyl-thiazol-2-yl)-urea

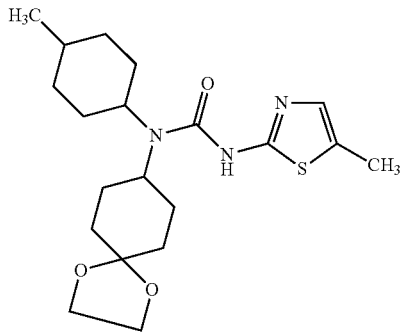

Prepared as described in general procedures (A) and (B) using 5-methyl-2-aminothiazole and (1,4-Dioxa-spiro[4.5]dec-8-yl)-(4-methyl-cyclohexyl)-amine HPLC-MS (Method A): m/z=3.94 (M+1); $R_t$=3.88 min.

Example 43

1-(4-Isopropyl-cyclohexyl)-1-(4-methyl-cyclohexyl)-3-(5-methyl-thiazol-2-yl)-urea

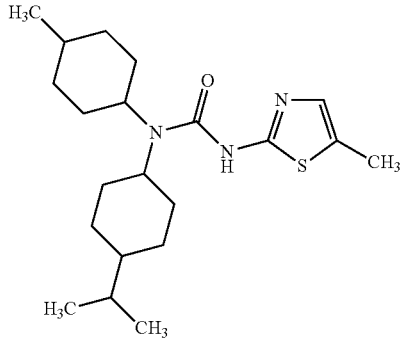

Prepared as described in general procedures (A) and (B) using 5-methyl-2-aminothiazole and (4-tert-butyl-cyclohexyl)-(4-methyl-cyclohexyl)-amine HPLC-MS (Method A): m/z=378 (M+1); $R_t$=5.57 min.

Example 44

1-(4-Methyl-cyclohexyl)-3-(5-methyl-thiazol-2-yl)-1-(4-trifluoromethyl-cyclohexyl)-urea

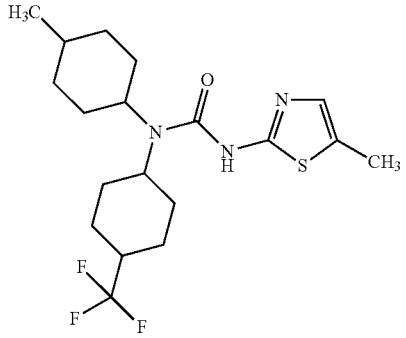

Prepared as described in general procedures (A) and (B) using 5-methyl-2-aminothiazole and (4-methyl-cyclohexyl)-(4-trifluoromethyl-cyclohexyl)-amine HPLC-MS (Method A): m/z=404 (M+1); $R_t$=4.81 min.

Example 45

1,1-Bis-(4-methyl-cyclohexyl)-3-(5-methyl-thiazol-2-yl)-urea

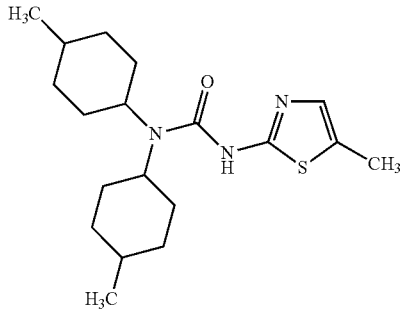

Prepared as described in general procedure (A) and (B) using 5-methyl-2-aminothiazole and bis-(4-methyl-cyclohexyl)-amine.

HPLC-MS (Method A): m/z=350 (M+1); $R_t$=4.89 min.

Example 46

[5-(3,3-Dicyclohexyl-ureido)-[1,3,4]thiadiazol-2-yl]-acetic acid ethyl ester

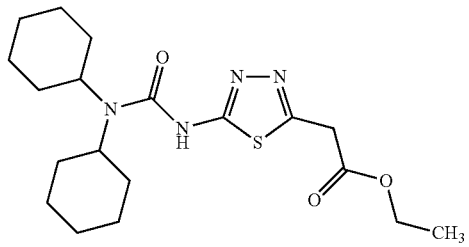

Prepared as described in general procedure (A) using dicyclohexylamine and 2-amino[1,3,4]thiadiazol-2-yl]-5-acetic acid ethyl ester.

HPLC-MS (Method A): m/z=395 (M+1); $R_t$=4.37 min.

Example 47

2-(3,3-Dicyclohexyl-ureido)-4,5,6,7-tetrahydro-benzothiazole-4-carboxylic acid ethyl ester

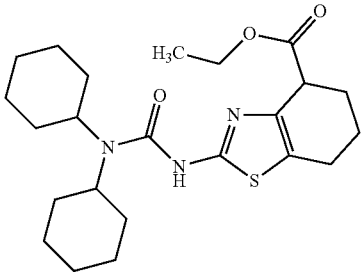

Prepared as described in general procedure (A) using dicyclohexylamine and 2-amino -4,5,6,7-tetrahydro-benzothiazole-4-carboxylic acid ethyl ester (prepared as described in Tet. Lett. 2001, 8911)

HPLC-MS (Method A): m/z=435 (M+1); $R_t$=4.81 min.

Example 48

1,1-Dicyclohexyl-3-(3-methyl-[1,2,4]thiadiazol-5-yl)-urea

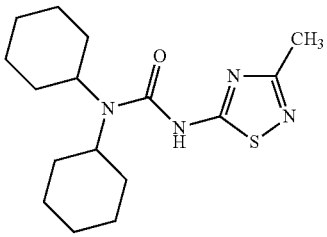

Prepared as described in general procedure (A) using dicyclohexylamine and 3-methyl-5-amino-[1,2,4]thiadiazole HPLC-MS (Method A): m/z=323 (M+1): $R_t$=4.24 min.

Example 49

3-(5-Bromo-thiazol-2-yl)-1,1-dicyclohexyl-urea

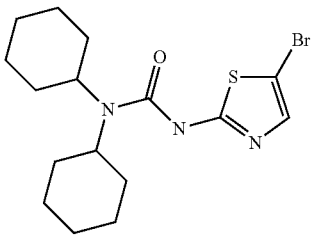

Prepared as described in general procedure (C) using dicyclohexylamine and 2-amino-5-bromothiazole.

$^1$H NMR ($CDCl_3$): δ 0.80-2.00 (m, 20H), 3.38 (m, 2H), 7.23 (s, 1H), 8.18 (br, 1H); HPLC-MS m/z=387 (M+1).

Example 50

2-(3,3-Dicyclohexyl-ureido)-thiazole-5-carboxylic acid methyl ester

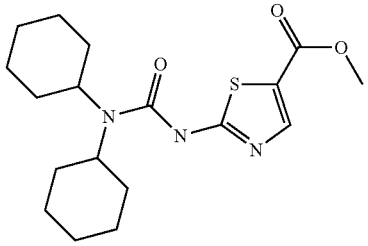

Prepared as described in general procedure (C) using dicyclohexylamine and 2-aminothiazole-5-carboxylic acid methyl ester.

$^1$H NMR ($CDCl_3$): δ 1.02-1.90 (m, 20H), 3.41 (m, 2H), 3.84 (s, 3H), 8.02 (s, 1H), 8.08 (br, 1H); HPLC-MS: m/z=366 (M+1).

Example 51

2-(3,3-Dicyclohexyl-ureido)-thiazole-5-carboxylic acid

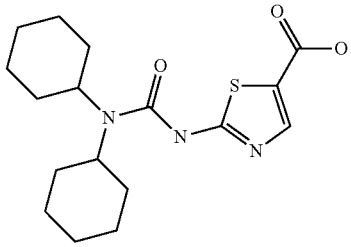

Prepared as described in general procedure (F) from 2-(3,3-dicyclohexyl-ureido)-thiazole-5-carboxylic acid methyl ester.

$^1$H NMR (DMSO-$d_6$): δ 1.02-1.87 (m, 20H), 3.42 (m, 2H), 7.92 (s, 1H), 11.02 (br, 1H); HPLC-MS: m/z=352 (M+1).

Example 52

1,1-Dicyclohexyl-3-(5-methylsulfanyl-[1,3,4]thiadiazol-2-yl)-urea

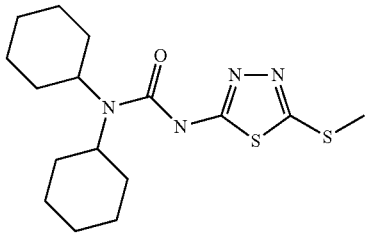

Prepared as described in general procedure Ⓒ using dicyclohexylamine and 2-amino-5-methylsulfanyl-1,3,4-thiadiazole.

$^1$H NMR ($CDCl_3$): δ 1.12-1.32 (m, 6H), 1.61-1.88 (m, 14H), 2.66 (s, 3H), 3.39 (m, 2H), 9.02 (br, 1H); HPLC-MS: m/z=355 (M+1).

Example 53

1,1-Dicyclohexyl-3-(5-methanesulfonyl-[1,3,4]thiadiazol-2-yl)-urea

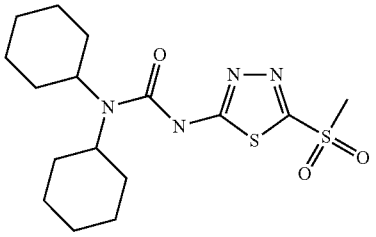

1,1-Dicyclohexyl-3-(5-methanesulfanyl-[1,3,4]thiadiazol-2-yl)-urea (0.5 mmol) was dissolved in $CH_2Cl_2$ (6 mL) and was cooled to 0° C. in an ice bath. To this solution was added peracetic acid (10 mmol) in $CH_2Cl_2$ (5 mL). The mixture was stirred for 4 h at 0° C. and was diluted with $CH_2Cl_2$ (50 mL). The organic layer was washed with saturated solution of $NaHCO_3$ (2×30 mL), water (3×30 mL), brine (1×30 mL), dried (anhydrous $Na_2SO_4$) and concentrated in vacuo. The crude mixture was purified by column chromatography with $CH_2Cl_2$ then 5-20% ethyl acetate in $CH_2Cl_2$ to give 1,1-dicyclohexyl-3-(5-methanesulfonyl-[1,3,4]thiadiazol-2-yl)-urea (155 mg).

$^1$H NMR ($CDCl_3$): δ 1.17-1.35 (m, 6H), 1.64-1.85 (m, 14H), 3.32 (s, 3H), 3.41 (m, 2H), 9.33 (br, 1H); HPLC-MS: m/z=387 (M+1).

Example 54

[2-(3,3-Dicyclohexyl-ureido)-thiazol-5-ylsulfanyl]-acetic acid methyl ester

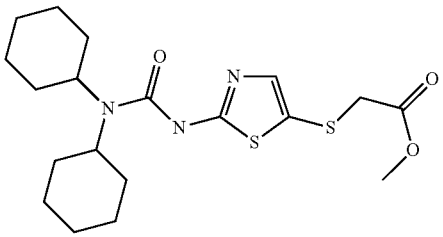

Prepared as described in general procedure (D) using 3-(5-bromo-thiazol-2-yl)-1,1-dicyclohexyl-urea and methyl thioglycolate $^1$H NMR ($CDCl_3$): δ 1.14-1.36 (m, 6H), 1.60-1.86 (m, 14H), 3.42 (m, 4H), 3.71 s, 3H), 7.40 (s, 1H), 7.86 (br, 1H); HPLC-MS: m/z=412 (M+1).

Example 55

[2-(3,3-Dicyclohexyl-ureido)-thiazol-5-ylsulfanyl]-acetic acid

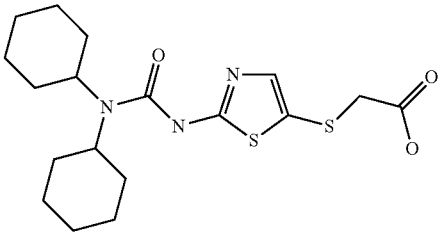

Prepared as described in general procedure (F) from [2-(3,3-dicyclohexyl-ureido)-thiazol-5-ylsulfanyl]-acetic acid methyl ester.

$^1$H NMR (DMSO-$d_6$): δ 1.12-1.96 (m, 20H), 3.38 (m, 2H), 3.45 s, 2H), 7.34 (s, 1H), 11.6 (br, 1H): HPLC-MS: m/z=398 (M+1).

Example 56

1,1-Dicyclohexyl-3-[5-(pyridin-2-ylsulfanyl)-thiazol-2-yl]-urea

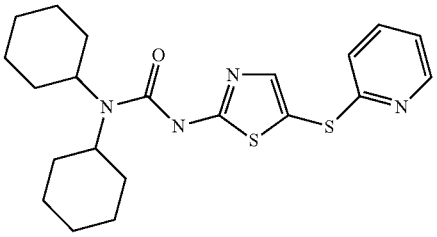

Prepared as described in general procedure (E) using 3-(5-bromo-thiazol-2-yl)-1,1-dicyclohexyl-urea and 2-mercapto-pyridine.

HPLC-MS: m/z=417 (M+1).

Example 57

2-[2-(3,3-Dicyclohexyl-ureido)-thiazol-5-ylsulfanyl]-1H-imidazole-4-carboxylic acid ethyl ester

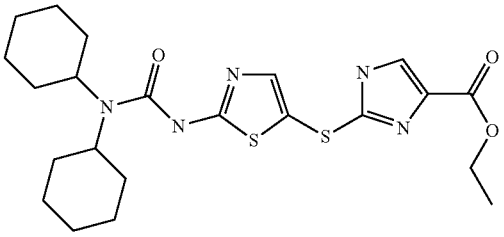

Prepared as described in general procedure (E) using 3-(5-hromo-thiazol-2-yl)-1,1-dicyclohexyl-urea and ethyl-2-mercapto-1H-imidazole-4-carboxylate.

$^1$H NMR ($CDCl_3$): δ 1.09 (t, 3H), 1.23-1.33 (m, 6H), 1.60-1.82 (m, 14H), 3.34 (m, 4H), 4.29 (q, 2H), 7.50 (s, 1H), 7.64 (s, 1H), 7.89 (br, 1H), 7.94 (br, 1H); HPLC-MS: m/z=478 (M+1).

Example 58

2-[2-(3,3-Dicyclohexyl-ureido)-thiazol-5-ylsulfanyl]-1H-imidazole-4-carboxylic acid

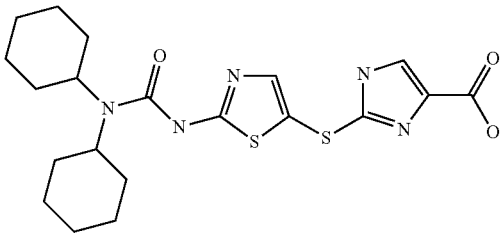

Prepared as described in general procedure (F) from 2-[2-(3,3-dicyclohexyl-ureido)-thiazol-5-ylsulfanyl]-1H-imidazole-4-carboxylic acid ethyl ester.

$^1$H NMR (DMSO-$d_6$): δ 1.04-1.96 (m, 2H), 3.40 (m, 2H), 7.56 (s, 2H), 7.79 (br, 1H), 11.2 (br, 1H); HPLC-MS: m/z=450 (M+1).

Example 59

2-[2-(3,3-Dicyclohexyl-ureido)-thiazol-5-ylsulfanyl]-3-methyl-3H-imidazole-4-carboxylic acid ethyl ester

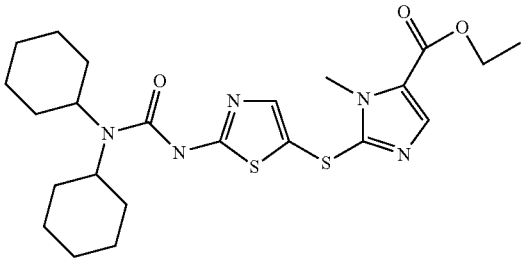

Prepared as described in general procedure (E) using 3-(5-bromo-thiazol-2-yl)-1,1-dicyclohexyl-urea and ethyl-2-mercapto-1-methyl-1H-imidazole-4-carboxylate.

$^1$H NMR ($CDCl_3$): δ 1.16 (t, 3H), 1.29-1.34 (m, 6H), 1.68-1.84 (m, 14H), 3.38 (m, 4H), 3.97 (s, 3H), 4.29 (q, 2H), 7.55 (s, 1H), 7.67 (s, 1H), 7.93 (br, 1H); HPLC-MS: m/z=492 (M+1).

Example 60

2-[2-(3,3-Dicyclohexyl-ureido)-thiazol-5-ylsulfanyl]-3-methyl-3H-imidazole-4-carboxylic acid

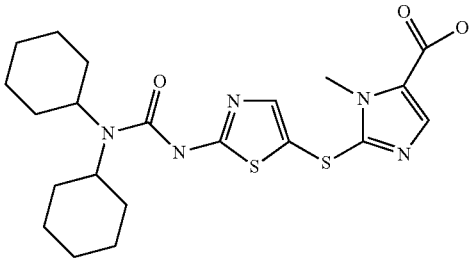

Prepared as described in general procedure (F) from 2-[2-(3,3-dicyclohexyl-ureido)-thiazol-5-ylsulfanyl]-3-methyl-3H-imidazole-4-carboxylic acid ethyl ester.

$^1$H NMR (DMSO-$d_6$) δ 1.17-1.89 (m, 20H), 3.38 (m, 2H), 3.88 (s, 3H), 7.57 (s, 1H), 7.61 (s, 1H); HPLC-MS: m/z=464 (M+1).

Example 61

1,1-Dicyclohexyl-3-[5-(1-methyl-1H-imidazol-2-ylsulfanyl)-thiazol-2-yl]-urea

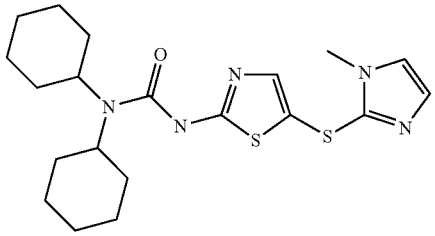

Prepared as described in general procedure (E) using 3-(5-bromo-thiazol-2-yl)-1,1-dicyclohexyl-urea and 2-mercapto-1-methyl-1H-imidazole.

$^1$H NMR ($CDCl_3$): δ 1.09-1.31 (m, 6H), 1.64-1.80 (m, 14H), 3.35 (m, 4H), 3.73 (s, 3H), 6.88 (d, 1H), 6.99 (d, 1H), 7.47 (s, 1H), 8.14 (br, 1H); HPLC-MS: m/z=420 (M+1).

Example 62

1,1-Dicyclohexyl-3-pyrazin-2-yl-urea

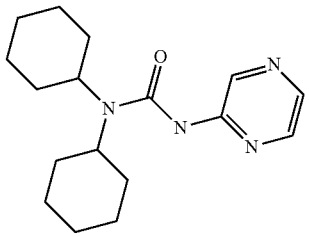

Prepared as described in general procedure (C), using dicyclohexylamino and 2-aminopyrazine.

$^1$H NMR ($CDCl_3$): δ 1.15-1.36 (m. 6H), 1.65-1.86 (m, 14H), 3.49 (m, 2H), 6.99 (br, 1H), 8.12 (d, 1H), 8.19 (d, 1H), 9.33 (s, 1H); HPLC-MS: m/z=303 (M+1).

Example 63

2-(3,3-Dicyclohexyl-ureido)-thiazole-4-carboxylic acid ethyl ester

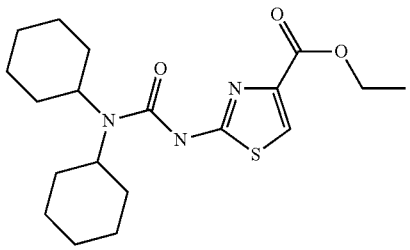

Prepared as described in general procedure (C) using dicyclohexylamine and ethyl-2-amino-4-thiazolecarboxylate.

$^1$H NMR ($CDCl_3$): δ 8.12 (1H, s), 4.21 (3H, q), 3.30-3.45 (2H, m), 1.25-1.90 (23H, m); HPLC-MS: m/z=380 (M+1).

Example 64

2-(3,3-Dicyclohexyl-ureido)-thiazole-4-carboxylic acid

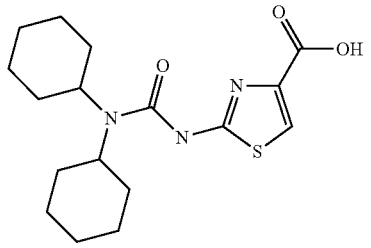

Prepared as described in the general procedure (F) from 2-(3,3-dicyclohexyl-ureido)-thiazole-4-carboxylic acid ethyl ester.

$^1$H NMR ($CDCl_3$): δ 11.41 (1H, s), 7.92 (1H, s), 3.95 (2H, m), 1.15-1.90 (20H, m); HPLC-MS: m/z=352 (M+1).

Example 65

Acetic acid 2-(3,3-dicyclohexyl-ureido)-thiazol-4-ylmethyl ester

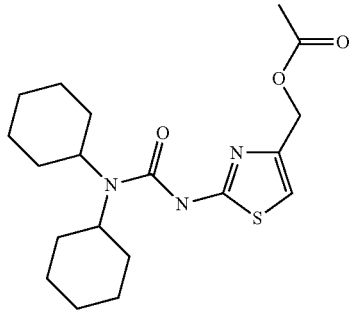

Prepared as described in general procedure (C) using dicyclohexylamine and acetic acid-2-aminothiazol-4-yl methyl ester.

$^1$H NMR ($CDCl_3$): δ 7.95 (1H, s), 6.81 (1H, s), 5.05 (2H, s), 3.40 (2H, m), 2.12 (3H, s), 1.15-1.90 (20H, m); HPLC-MS: m/z=380 (M+1).

Example 66

1,1-Dicyclohexyl-3-(4-hydroxymethyl-thiazol-2-yl) urea

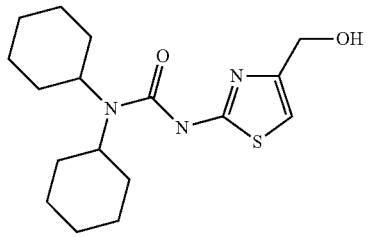

Acetic acid-2-(3,3-dicyclohexyl-ureido)-thiazol-4-yl methyl ester (2.4 g, 6.3 mmol) was stirred with a solution of potassium carbonate (0.9 g, 6.5 mmol) in 2:1 methanol/water at room temperature for 4 hours. The mixture was extracted with ethyl acetate (3×50 mL) and the combined organic extracts was dried over sodium sulphate, filtered and concentrated to obtain 1,1-dicyclohexyl-3-(4-hydroxymethyl-thiazol-2-yl)urea (2.0 g).

$^1$H NMR ($CDCl_3$): δ 8.95 (1H, s), 6.63 (1H, s), 4.60 (2H, s), 3.46 (2H, m), 1.15-1.90 (20H, m); HPLC-MS: m/z=338 (M+1).

Example 67

Ethyl {2-[dicyclohexylureido]-5-imidazol-1-yl-thiazol-4-yl}-acetic acid

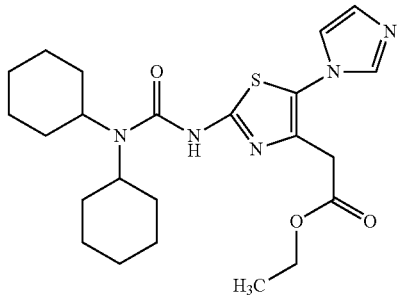

Prepared as described in general procedure (A) using dicyclohexylamine and 5-chloro-(2-amino-4-thiazolyl)acetic acid ethyl ester (prepared by chlorination of 2-aminothiazole-4-acetic acid ethyl ester using N-chlorosucccinamide in acetic acid at room temperature for 3 h).

HPLC-MS: m/z=460 (M+1).

Example 68

Ethyl {5-Chloro-2-[3-dicyclohexyl ureido]-thiazol-4-yl}-acetate

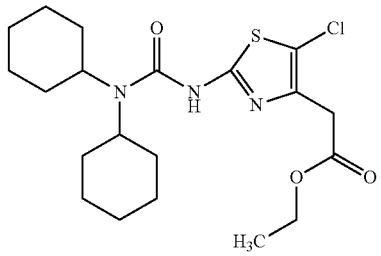

Prepared as described in general procedure (A) using dicyclohexylamine and 5-chloro-(2-amino-4-thiazolyl)acetic acid ethyl ester (prepared by chlorination of 2-aminothiazole-4-acetic acid ethyl ester using N-chlorosucccinamide in acetic acid at room temperature for 3 h).

HPLC-MS: m/z=428 (M+1).

Example 69

1,1-Dicyclohexyl-3-(4,5-dimethyl-thiazol-2-yl)-urea

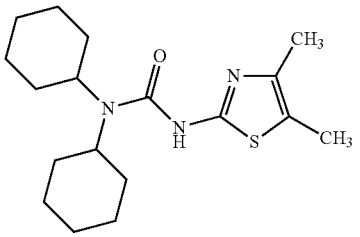

Prepared as described in general procedure (A) using dicyclohexylamine and 3,4-dimethyl-2-aminothiazole HPLC-MS: m/z=336 (M+1) .

Example 70

1,1-Dicyclohexyl-3-[1,2.4]thiadiazol-5-urea

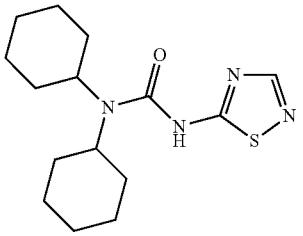

Prepared as described in general procedure (A) using dicyclohexylamine and 5-amino-1,2,4-thiadiazole HPLC-MS: m/z=309 (M+1).

Example 71

1,1-Dicyclohexyl-3-(4,5,6,7-tetrahydro-benzothiazol-2-yl)-urea

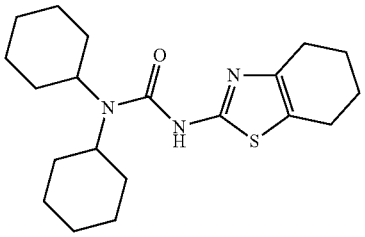

Prepared as described in general procedure (A) using dicyclohexylamine 2-amino-4,5,6,7-tetrahydro-benzothiazole HPLC-MS: m/z=362 (M+1).

Example 72

1,1-Dicyclohexyl-3-(5,6-dihydro-4H-cyclopentathiazol-2-yl)-urea

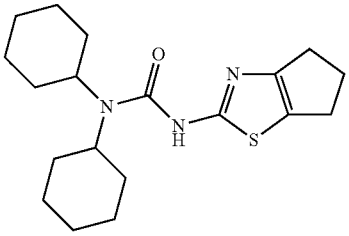

Prepared as described in general procedure (A) using dicyclohexylamine and 2-amino-5,6-dihydro-4H-cyclopentathiazole HPLC-MS: m/z=349 (M+1).

Example 73

3-(5-Chloro-pyridin-2-yl)-1,1-dicyclohexyl-urea

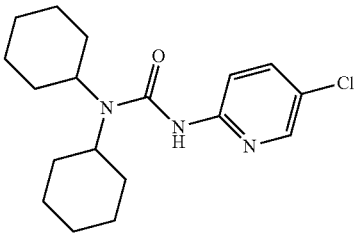

Prepared as described in general procedure (A) using dicyclohexylamine and 2-amino-5-chloropyridine HPLC-MS: m/z=336 (M+1).

Example 74

[2-(3,3-Dicyclohexylrareido)-5-chloro-thiazol-4-yl]-acetic acid

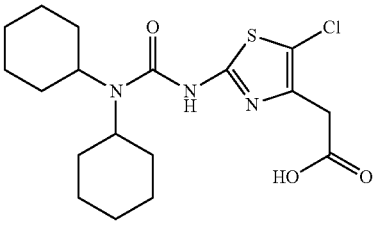

Prepared from Ethyl {5-Chloro-2-[3-dicyclohexylureido]-thiazol-4-yl}-acetate using general procedure (F).

HPLC-MS: m/z=400 (M+1).

Example 75

1,1-Dicyclohexyl-3-(3-methoxy-[1,2,4]thiadiazol-5-yl)-urea

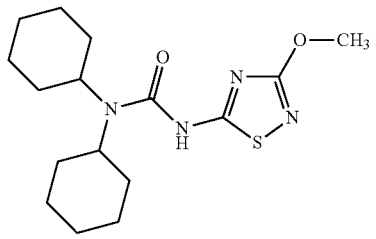

Prepared as described in general procedure (A) using dicyclohexylamine and 3-methoxy-5-amino-1,2,4-thiadiazole HPLC-MS: m/z=339 (M+1).

Example 76

1,1-Dicyclohexyl-3-(3-methylsulfanyl-[1,2,4]-thiadiazol-5-yl)-urea

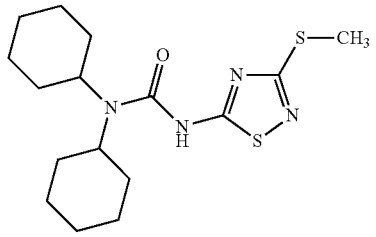

Prepared as described in general procedure (A) using dicyclohexylamine and 3-thiomethoxy-5-amino-1,2,4-thiadiazole HPLC-MS: m/z=355 (M+1).

Example 77

General Procedure A

[5-(3,3-Dicyclohexyl-ureido)-[1,3,4]thiadiazol-2-yl]-acetic acid

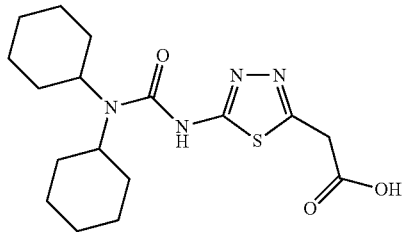

Prepared from [5-(3,3-Dicyclohexyl-ureido)-[1,3,4]thiadiazol-2-yl]-acetic acid ethyl ester as described in general procedure (F).

HPLC-MS: m/z=367 (M+1).

Example 78

1-Cyclohexyl-1-(tetrahydro-pyran-4-yl)-3-thiazol-2-yl-urea

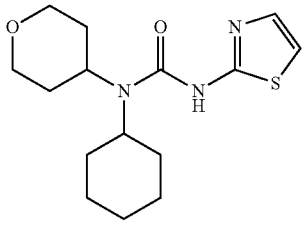

Prepared as described in general procedures (A) and (B) using aminothiazole and cyclohexyl-(ietrahydro-pyran-4-yl)-amine.

HPLC-MS: m/z=310 (M+1).

Example 79

1-Cyclohexyl-1-(tetrahydro-thiopyran-4-yl)-3-thiazol-2-yl-urea

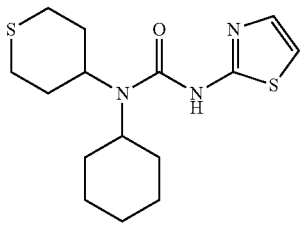

Prepared as described in general procedures (A) and (B) using aminothiazole and cyclohexyl-(tetrahydro-thiopyran-4-yl)-amine.

HPLC-MS: m/z=326 (M+1).

Example 80

4-(1-Cyclohexyl-3-thiazol-2-yl-ureido)-cyclohexan-ecarboxylic acid ethyl ester

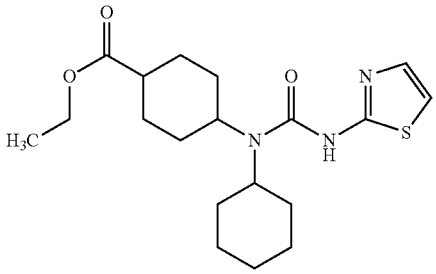

Prepared as described in general procedures (A) and (B) using aminothiazole and 4-cyclohexylamino-cyclohexan-ecarboxylic acid ethyl ester HPLC-MS: m/z=380 (M+1).

Example 81

3-[4-(1-Cyclohexyl-3-thiazol-2-yl-ureido)-cyclohexyl]-propionic acid ethyl ester

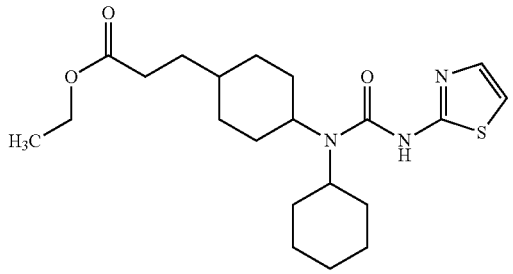

Prepared as described in general procedures (A) and (B) using aminothiazole and 3-(4-cyclohexylamino-cyclohexyl)-propionic acid ethyl ester HPLC-MS: m/z=408 (M+1).

Example 82

1-Cyclohexyl-1-(4-oxo-cyclohexyl)-3-thiazol-2-yl-urea

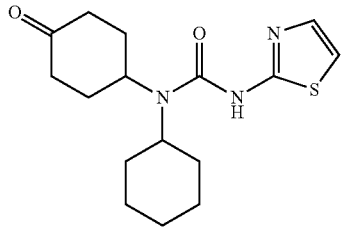

Prepared as described in general procedures (A) and (B) using aminothiazole and 4-cyclohexylamino-cyclohexanone HPLC-MS: m/z=322 (M+1).

Example 83

3-(5-Chloro-thiazol-2-yl)-1-cyclohexyl-1-(tetrahydro-pyran-4-yl)-urea

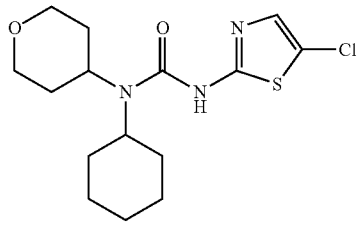

Prepared as described in general procedures (A) and (B) using 5-chloro-2-aminothiazole and cyclohexyl-(tetrahydro-pyran-4-yl)-amine HPLC-MS: m/z=344 (M+1).

Example 84

3-(5-Chloro-thiazol-2-yl)-1-cyclohex-yl-1-(tetrahydro-thiopyran-4-yl)-urea

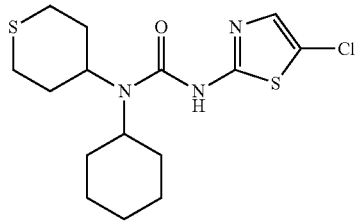

Prepared as described in general procedures (A) and (B) using 5-chloro-2-aminothiazole and cyclohexyl-(tetrahydro-thiopyran-4-yl)-amine HPLC-MS: m/z=360 (M+1).

Example 85

4-[3-(5-Chloro-thiazol-2-yl)-1-cyclohexyl-ureido]-cyclohexanecarboxylic acid ethyl ester

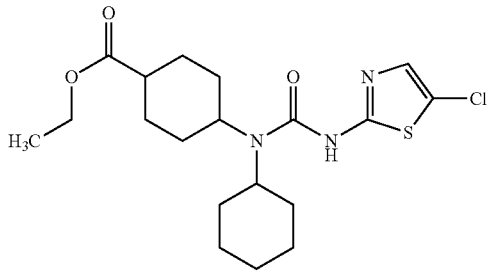

Prepared as described in general procedures (A) and (B) using 5-chloro-2-aminothiazole and 4-cyclohexylamino-cyclohexanecarboxylic acid ethyl ester HPLC-MS: m/z=414 (M+1).

Example 86

3-{4-[3-(5-Chloro-thiazol-2-yl)-1-cyclohexyl-ureido]-cyclohexyl}-propionic acid ethyl ester

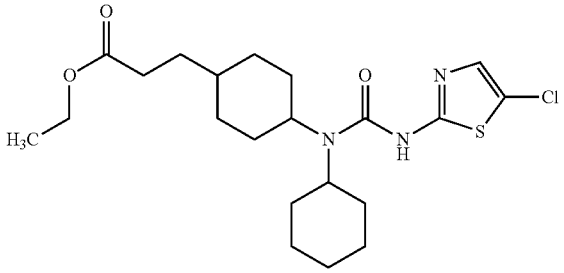

Prepared as described in general procedures (A) and (B) using 5-chloro-2-aminothiazole and 3-(4-cyclohexylamino-cyclohexyl)-propionic acid ethyl ester HPLC-MS: m/z=442 (M+1).

Example 87

2-[3-(5-Chloro-thiazol-2-yl)-1-cyclohexyl-ureido]-cyclohexanecarboxylic acid methyl ester

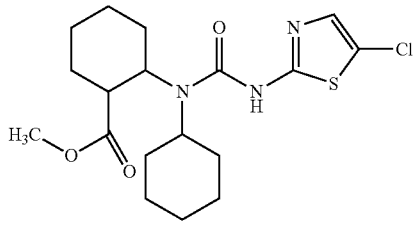

Prepared as described in general procedures (A) and (B) using 5-chloro-2-aminothiazole and 2-cyclohexylamino-cyclohexanecarboxylic acid ethyl ester HPLC-MS: m/z=400 (M+1).

Example 88

3-(5-Chloro-thiazol-2-yl)-1-cyclohexyl-1-(4-oxo-cyclohexyl)-urea

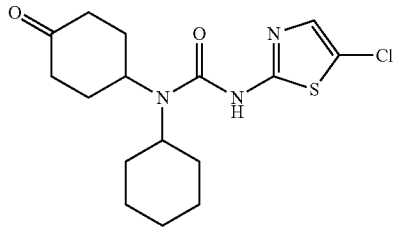

Prepared as described in general procedures (A) and (B) using 5-chloro-2-aminothiazole and 4-cycluhexylamino-cyclohexanone HPLC-MS: m/z=356 (M+1).

Example 89

1-Cyclohexyl-3-(5-methyl-thiazol-2-yl)-1-(tetrahydro-pyran-4-yl)-urea

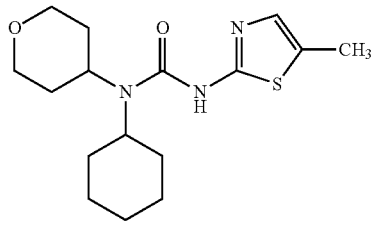

Prepared as described in general procedures (A) and (B) using 5-methyl-2-aminothiazole and cyclohexyl-(tetrahydro-pyran-4-yl)-amine HPLC-MS: m/z=324 (M+1).

Example 90

1-Cyclohexyl-3-(5-methyl-thiazol-2-yl)-1 -(tetrahydro-thiopyran-4-yl)-urea

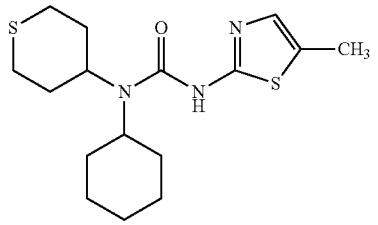

Prepared as described in general procedures (A) and (B) using 5-methyl-2-aminothiazole and cyclohexyl-(tetrahydrothiopyran-4-yl)-amine HPLC-MS: m/z=340 (M+1).

Example 91

4-[1-Cyclohexyl-3-(5-methyl-thiazol-2-yl)-ureido]-cyclohexanecarboxylic acid ethyl ester

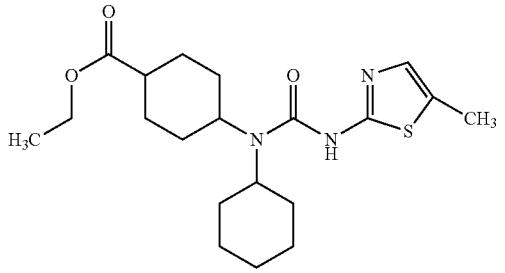

Prepared as described in general procedures (A) and (B) using 5-methyl-2-aminothiazole and 4-cyclohexylamino-cyclohexanecarboxylic acid ethyl ester HPLC-MS: m/z=394 (M+1).

Example 92

3-{4-[1-Cyclohexyl-3-(5-methyl-thiazol-2-yl)-ureido]-cyclohexyl}-propionic acid ethyl ester

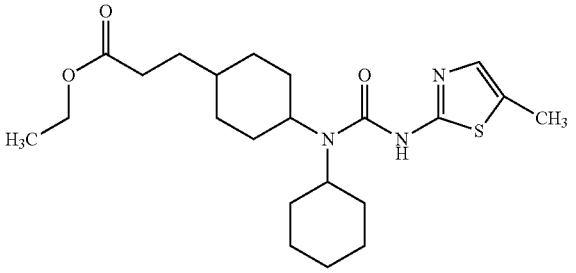

Prepared as described in general procedures (A) and (B) using 5-methyl-2-aminothiazole and 3-(4-cyclohexylamino-cyclohexyl)-propionic acid ethyl ester HPLC-MS: m/z=422 (M+1).

Example 93

General Procedures A and B

1-Cyclohexyl-3-(5-methyl-thiazol-2-yl)-1-(4-oxo-cyclohexyl)-urea

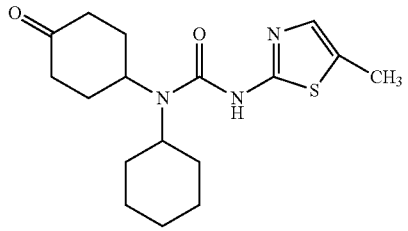

Prepared as described in general procedures (A) and (B) using 5-methyl-2-aminothiazole and 4-cyclohexylamino-cyclohexanone HPLC-MS: m/z=336 (M+1).

Example 94

1-Cyclohexyl-1-piperidin-1-yl-3-thiazol-2-yl-urea

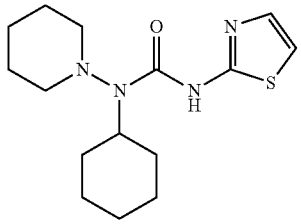

Piperidin-1-yl-amine (0.25 g, 2.5 mmol) and cyclohexanone (0.25 g, 2.5 mmol) was dissolved in MeOH (5 mL) and acetic acid ((0.25 mL). Approximately ⅔ of the $NaCNBH_3$ (0.46 g, 7.49 mmol) was added and the reaction mixture was stirred for 1 h before the last ⅓ was introduced. The reaction mixture was stirred 16 h before the volatiles were removed in vacuo. The residue was separated between EtOAc (50 mL) and semi saturated sodium carbonate (50 mL). The organic phase was dried ($MgSO_4$), filtered and concentrated in vacuo. The residue was dissolved in 1,2-dichloroethane (5 mL) (Solution 1).

Another flask was charged with 2-aminothiazole (0.25 g, 2.5 mmol) in 1,2-dichloroethane (10 mL) and CDI (0.40 g, 2.5 mmol)) was added. The mixture was stirred for 1 h before) solution 1 was added. The reaction mixture was stirred for 16 h before the solvent was removed in vacuo. The product was separated between EtOAc (50 mL) and HCl (1N, 50 mL) and the organic phase was washed with brine (50 mL) and dried ($MgSO_4$) to give 520 mg of 1-Cyclohexyl-1-piperidin-1-yl-3-thiazol-2-yl-urea.

$^1$H NMR ($CDCl_3$): δ 9.85 (s, 1H), 7.35 (d, 1H), 6.83 (d, 1H), 3.30-3.15 (m, 1H), 2.90-2.85 (m, 2H), 2.75-2.65 (m, 2H), 2.45-2.35 (m, 2H), 1.90-1.60 (m, 12H), 1.35-1.10 (m, 5H) HPLC-MS (Method A): m/z=309 (M+1); $R_t$=3.91 min.

Example 95

1-Cyclohexyl-1-pyrrolidin-1-yl-3-thiazol-2-yl-urea

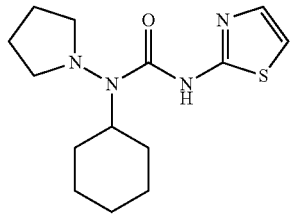

Procedure as in Example 94 using pyrrolidin-1-yl-amine and cyclohexanone

HPLC-MS (Method A): m/z=295 (M+1); $R_t$=3.60 min.

Example 96

[2-(3,3-Dicyclohexyl-ureido)-5-methyl-thiazol-4-yl]-acetic acid ethyl ester

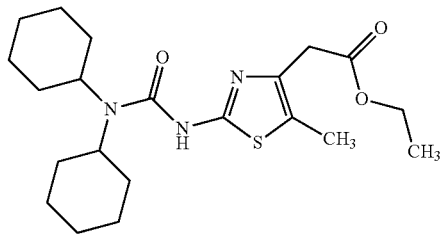

Prepared as described in general procedure (A) using dicyclohexylamine and 5-methyl-(2-amino-4-thiazolyl)acetic acid ethyl ester HPLC-MS: m/z=409 (M+1).

Example 97

[2-(3,3-Dicyclohexyl-ureido)-5-ethyl-thiazol-4-yl]-acetic acid ethyl ester

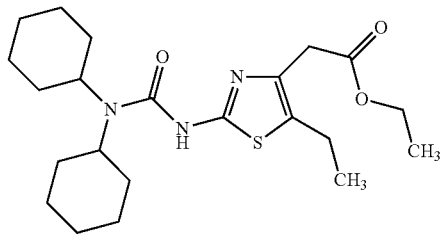

Prepared as described in general procedure (A) using dicyclohexylamine and 5-ethyl-(2-amino-4-thiazolyl)acetic acid ethyl ester HPLC-MS: m/z=422 (M+1).

Example 98

General Procedure A

[2-(3,3-Dicyclohexyl-ureido)-5-methyl-thiazol-4-yl]-acetic acid

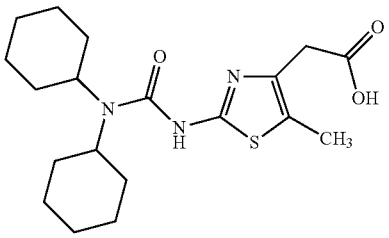

Prepared from [2-(3,3-dicyclohexyl-ureido)-5-methyl-thiazol-4-yl]-acetic acid ethyl ester using general procedure (F).

HPLC-MS: m/z=380 (M+1).

Example 99

4-[3-(5-Chloro-thiazol-2-yl)-1-(4-methyl-cyclohexyl)-ureido]-cyclohexanecarboxylic acid ethyl ester

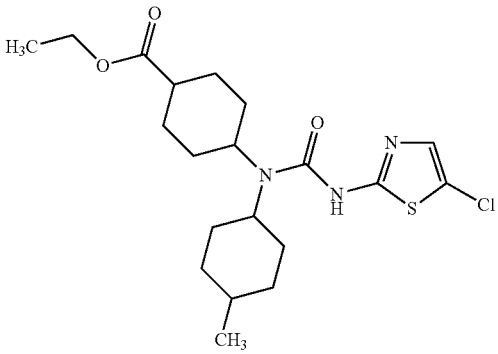

Prepared as described in general procedures (A) and (B) using 5-chloro-2-aminothiazole and 4-(4-methyl-cyclohexylamino)-cyclohexanecarboxylic acid ethyl ester HPLC-MS: m/z=428 (M+1).

Example 100

General Procedure A 1,1-Dicyclohexyl-3-(5-cyclopropyl-[1,3,4]thiadiazol-2-yl)-urea

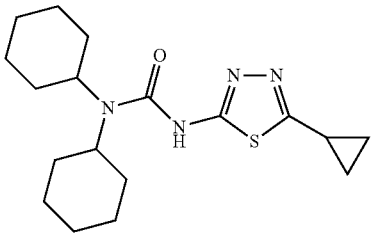

Prepared as described in general procedure (A) using dicyclohexylamine and 2-amino-5-cyclopropyl-1,3,4-thiadiazole HPLC-MS: m/z=349 (M+1).

Example 101

General Procedure A 1,1-Dicyclohexyl-3-(5-ethylsulfanyl-[1,3,4]thiadiazol-2-yl)-urea

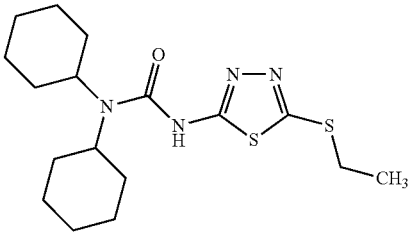

Prepared as described in general procedure (A) using dicyclohexylamine and 2-amino-5-ethylthio-1,3,4-thiadiazole HPLC-MS: m/z=369 (M+1).

Example 102

General Procedure A 1,1-Dicyclohexyl-3-(5-trifluoromethyl-[1,3,4]thiadiazol-2-yl)-urea

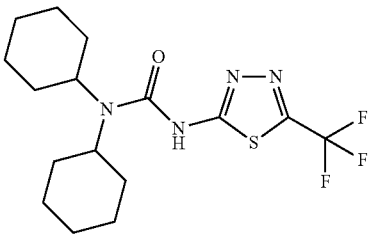

Prepared as described in general procedure (A) using dicyclohexylamine and 2-amino-5-trifluoromethyl-1,3,4-thiadiazole HPLC-MS: m/z=377 (M+1).

Example 103

3-(5-Chloro-thiazol-2-yl)-1-cyclohexyl-1-piperidin-1-yl-urea

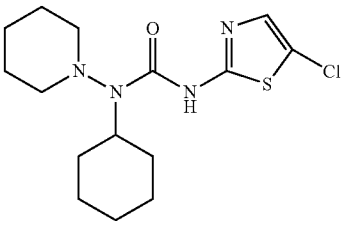

1-Cyclohexyl-1-piperidin-1-yl-3-thiazol-2-yl-urea (50 mg, 0.16 mmol), prepared in an identical manner to Example 94 was dissolved in DCM (1 mL) and NCS (26 mg, 0.19 mmol)) was added. The reaction mixture was stirred for 3 days before DCM (20 mL) and water (20 mL) was added. The organic phase was dried ($MgSO_4$) and the solvent was removed in vacuo. MeCN (1 mL) was added whereupon the product precipitated. The product was filtered off and dried. Yield: 20 mg.

HPLC-MS (Method A): m/z=344 (M+1); $R_t$=5.35 min.

Example 104

3-(5-Chloro-thiazol-2-yl)-1-cyclohexyl-1-morpholin-4-yl-urea

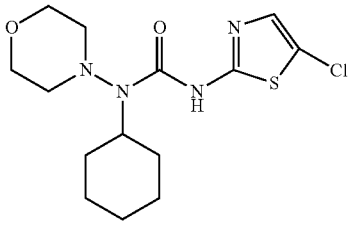

Procedure in an identical manner to Example 94 using morpholin-4-yl-amine and cyclohexanone HPLC-MS (Method A): m/z=346 (M+1); $R_t$=4.32 min Example 105

[2-(3,3-Dicyclohexyl-ureido)-5-ethyl-thiazol-4-yl]-acetic acid

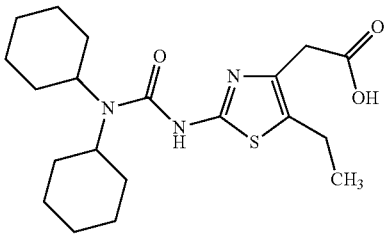

Prepared from Example 97 using general procedure (F).

HPLC-MS: m/z=394 (M+1).

Example 106

[5-(3,3-Dicyclohexyl-ureido)-[1,3,4]thiadiazol-2-ylsulfanyl]-acetic acid ethyl ester

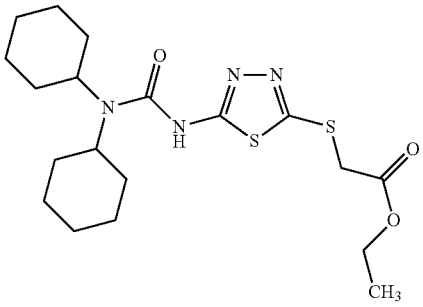

Prepared as described in general procedure (A) using dicyclohexylamine and ethyl 2-[5-amino-1,3,4-thiadiazol-2-yl) thio]acetate HPLC-MS: m/z=427 (M+1)

Example 107

6-(3,3-Dicyclohexyl-ureido)-nicotinic acid methyl ester

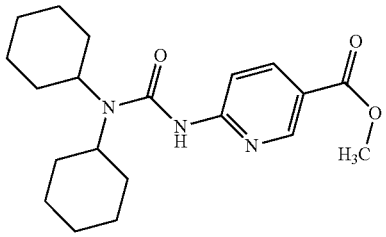

Prepared as described in general procedure (A) using dicyclohexylamine and methyl-6-amino nicotinate.

HPLC-MS: m/z=360 (M+1).

Example 108

[2-(3,3-Dicyclohexyl-ureido)-5-(pyrimidin-2-ylsulfanyl)-thiazol-4-yl]-acetic acid ethyl ester

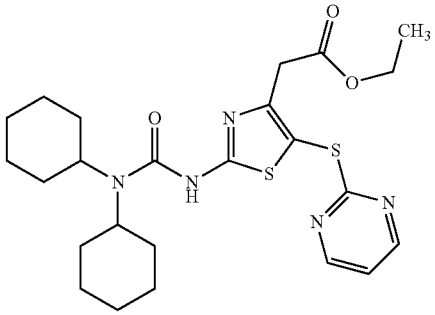

Prepared as described in general procedure (E) using ethyl {5-Chloro-2-[3-dicyclohexylureido]-thiazol-4-yl}-acetate (Example 68) and 2-mercaptopyrimidine.

HPLC-MS: m/z=504 (M+1).

Example 109

[2-(3,3-Dicyclohexyl-ureido)-5-phenylsulfanyl-thiazol-4-yl]-acetic acid ethyl ester

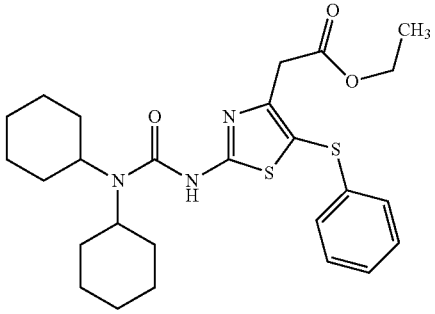

Prepared as described in general procedure (E) using ethyl {5-chloro-2-[3-dicyclohexylureido]-thiazol-4-yl}-acetate (Example 68) and thiophenol.

HPLC-MS: m/z=502 (M+1).

Example 110

5-(3,3-Dicyclohexyl-ureido)-[1,3,4]thiadiazole-2-carboxylic acid

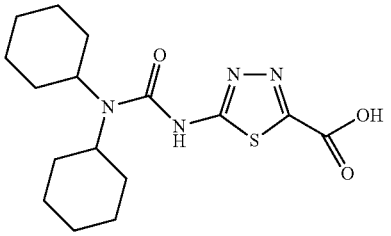

5-(3,3-Dicyclohexyl-ureido)-[1,3,4]thiadiazole-2-carboxylic acid ethyl ester was prepared from dicyclohexane and 5-amino-1,3,4-thiadiazole carboxylic acid ethyl ester using general procedures (A) and (B). Ester hydrolysis using lithium hydroxide in methanol gave the title compound.

HPLC-MS: m/z=309 (M+-$CO_2$).

Example 111

[5-(3,3-Dicyclohexyl-ureido)-[1,3,4]thiadiazol-2-ylsulfanyl]-acetic acid

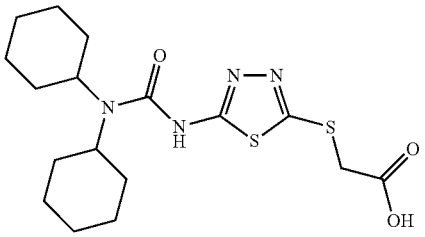

Hydrolysis of [5-(3,3-Dicyclohexyl-ureido)-[1,3,4]thiadiazol-2-ylsulfanyl]-acetic acid ethyl ester using general procedure (F) gave the title compound.

Example 112

1,1-Dicyclohexyl-3-(5-phenyl-[1,3,4]thiadiazol-2-yl)-urea

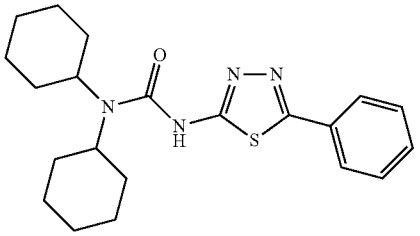

Prepared as described in general procedure (A) using dicyclohexylamine and 2-amino-5-phenyl-[1,3,4]-thiadiazole HPLC-MS: m/z=385 (M+1).

Example 113

[5-Bromo-2-(3,3-dicyclohexyl-ureido)-thiazol-4-yl]-acetic acid ethyl ester

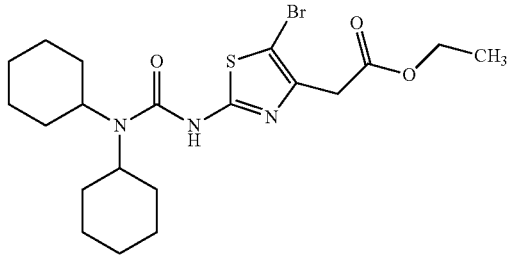

[2-(3,3-Dicyclohexyl-ureido)-thiazol-4-yl]-acetic acid ethyl ester was prepared from dicyclohexylamine and (2-amino-4-thiazolyl)acetic acid ethyl ester as described in general procedure (A). To this compound was added 1.3 equivalents of N-bromosuccinimide suspended in acetic acid, and the mixture was stirred for 3 h at RT. The reaction mixture was concentrated in vacuo, redissolved in dichloromethane, washed with 10% sodium sulphate, water, aqueous sodium bicarbonate, brine and then dried over magnesium sulphate. Flash chromatography afforded the title compound.

HPLC-MS: m/z=472 (M+1).

Example 114

3-(5-Chloro-thiazol-2-yl)-1-cyclohexyl-1-(tetrahydro-furan-(3R)-yl)-urea

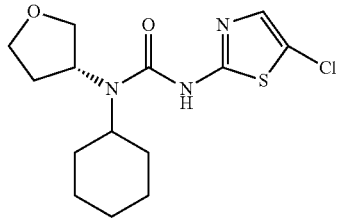

Prepared as described in general procedure (A) and (B) using (R)-cyclohexyl-(tetrahydrofuran-3-yl)-amine and 5-chloro-2-amino thiazole HPLC-MS: m/z=330 (M+1).

Example 115

[2-(3,3-Dicyclohexyl-ureido)-5-(pyrimidin-2-ylsulfanyl)-thiazol-4-yl]-acetic acid

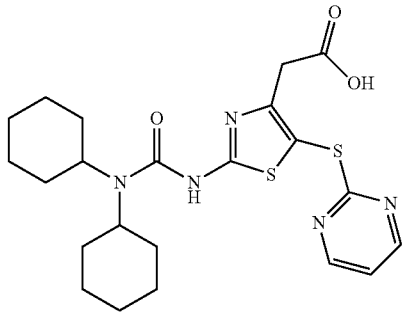

Hydrolysis of [2-(3,3-Dicyclohexyl-ureido)-5-(pyrimidin-2-ylsulfanyl)-thiazol-4-yl]-acetic acid ethyl ester using general procedure (F) gave the title compound.

HPLC-MS: m/z=476 (M+1).

Example 116

{2-[3-Cyclopentyl-3-(4-methyl-cyclohexyl)-ureido]-5-ethyl-thiazol-4-yl}-acetic acid

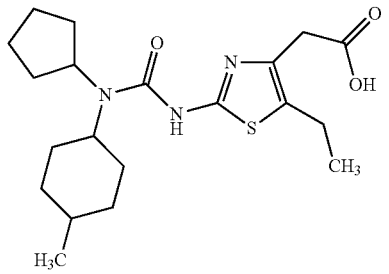

{2-[3-Cyclopentyl-3-(4-methyl-cyclohexyl)-ureido]-5-ethyl-thiazol-4-yl}-acetic acid ethyl ester was prepared from cyclopentyl-(4-methyl-cyclohexyl)-amine and 5-ethyl-2-aminothiazole-4-acetic acid ethyl ester using general procedures (A) and (B). Hydrolysis using general procedure (F) gave the title compound.

HPLC-MS: m/z=394 (M+1).

Example 117

{2-[3,3-Bis-(4-methyl-cyclohexyl)-ureido]-5-ethyl-thiazol-4-yl}-acetic acid

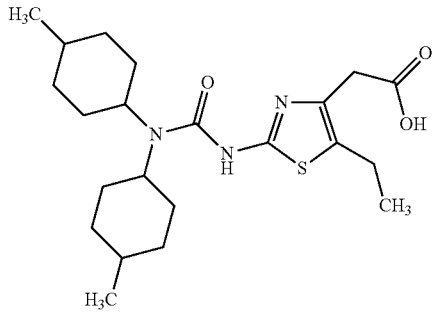

{2-[3-Cyclopentyl-3-(4-methyl-cyclohexyl)-ureido]-5-ethyl-thiazol-4-yl}-acetic acid ethyl ester was prepared from bis-(4-methyl-cyclohexyl)-amine and 5-ethyl-2-aminothiazole-4-acetic acid ethyl ester using general procedures (A) and (B). Hydrolysis using general procedure (F) gave the title compound.

HPLC-MS: m/z=422 (M+1).

Example 118

3-(5-Chloro-thiazol-2-yl)-1-(4-methyl-cyclohexyl)-1-(4-oxo-cyclohexyl)-urea

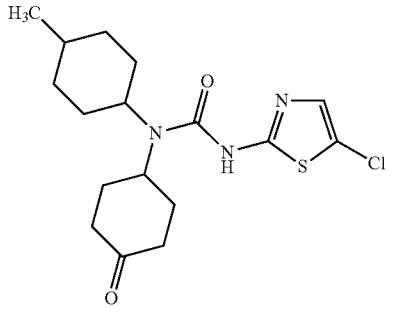

Prepared as described in general procedure (A) and (B) using 4-(4-Methyl-cyclohexylamino)-cyclohexanone and 5-chloro-2-amino thiazole HPLC-MS: m/z=370 (M+1).

Example 119

1-(1-Acetyl-piperidin-4-yl)-1-cyclohexyl-3-(5-Chloro-thiazol-2-yl)-urea

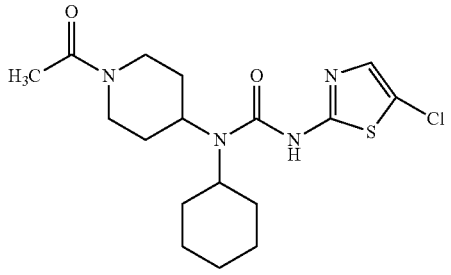

Prepared as described in general procedure (A) and (B) using 1-(4-cyclohexylamino-piperidin-1-yl)-ethanone and 5-chloro-2-amino thiazole HPLC-MS: m/z=365 (M+1).

Example 120

1-(1-Acetyl-piperidin-4-yl)-1-cyclohexyl-3-thiazol-2-yl-urea

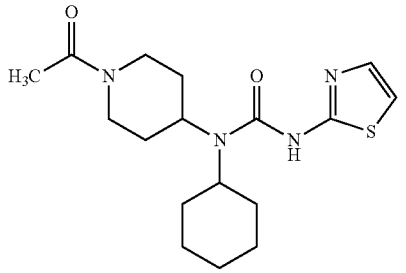

Prepared as described in general procedure (A) and (B) using 1-(4-cyclohexylamino-piperidin-1-yl)-ethanone and 2-amino thiazole HPLC-MS: m/z=351 (M+1).

Example 121

{2-[3-(1-Acetyl-piperidin-4-yl)-3-cyclohexyl-ureido]-thiazol-5-ylsulfanyl}-acetic acid ethyl ester

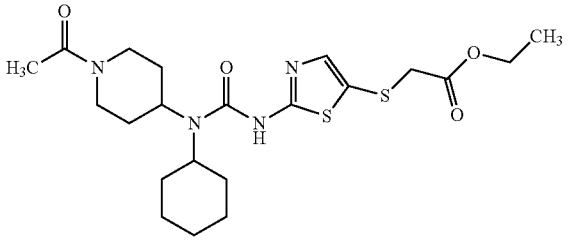

Prepared as described in general procedure (A) and (B) using 1-(4-cyclohexylamino-piperidin-1-yl)-ethanone and 5-aminothiazol-2-mercaptoacetic acid ethyl ester HPLC-MS: m/z=469 (M+1).

Example 122

1-(1-Acetyl-piperidin-4-yl)-1-cyclohexyl-3-(5-methyl-thiazol-2-yl)-urea

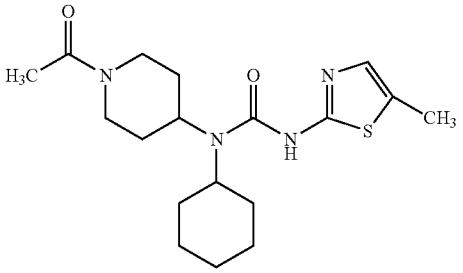

Prepared as described in general procedure (A) and (B) using 1-(4-cyclohexylamino-piperidin-1-yl)-ethanone and 5-methyl-2-amino thiazole HPLC-MS: m/z=365 (M+1).

Example 123

{2-[3-Cyclohexyl-3-(tetrahydro-furan-(3R)-yl)-ureido]-thiazol-5-ylsulfanyl}-acetic acid ethyl ester

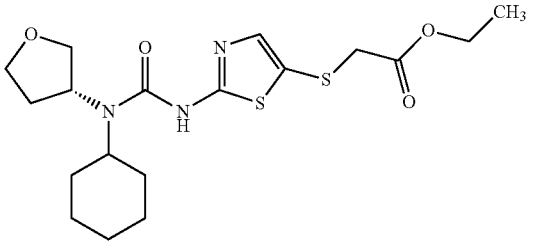

Prepared as described in general procedure (A) and (B) using (R)-cyclohexyl-(tetrahydro-furan-3-yl)-amine and ethyl-2-[5-aminothiazol-2-yl-thio]acetate HPLC-MS: m/z=414 (M+1).

Example 124

{5-[3-(1-Acetyl-piperidin-4-yl)-3-cyclohexyl-ureido]-[1,3,4]thiadiazol-2-ylsulfanyl}-acetic acid ethyl ester

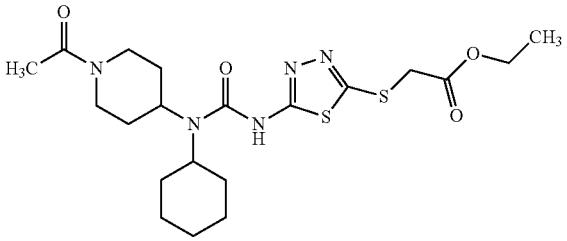

Prepared as described in general procedure (A) and (B) using 1-(4-cyclohexylamino-piperidin-1-yl)-ethanone and ethyl-2-[5-amino-1,3,4-thiadiazol-2-yl-thio]acetate.

HPLC-MS: m/z=470 (M+1).

Example 125

1-(1-Acetyl-piperidin-4-yl)-1-cyclohexyl-3-(5-cyclopropyl-[1,3,4]thiadiazol-2-yl)-urea

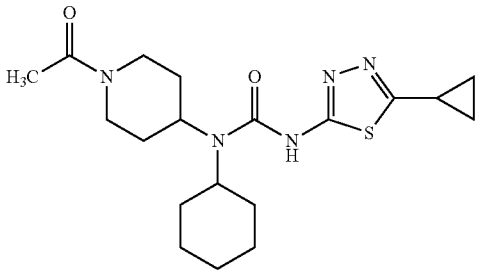

Prepared as described in general procedure (A) and (B) using 1-(4-cyclohexylamino-piperidin-1-yl)-ethanone and 2-amino-5-cyclopropyl-1,3,4-thiadiazole HPLC-MS: m/z=392 (M+1).

Example 126

1-(1-Acetyl-piperidin-4-yl)-1-cyclohexyl-3-(5-trifluoromethyl-[1,3,4]thiadiazol-2-yl)-urea

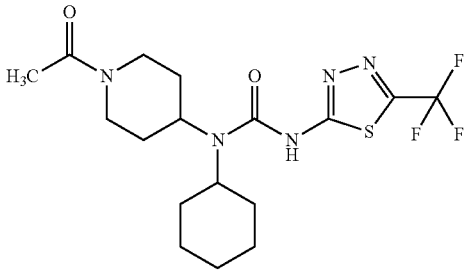

Prepared as described in general procedure (A) and (B) using 1-(4-cyclohexylamino-piperidin-1-yl)-ethanone and 2-amino-5-trifluoromethyl-1,3,4-thiadiazole HPLC-MS: m/z=420 (M+1).

Example 127

{5-[3-Cyclopentyl-3-(4-methyl-cyclohexyl)-ureido]-[1,3,4]thiadiazol-2-ylsulfanyl}-acetic acid

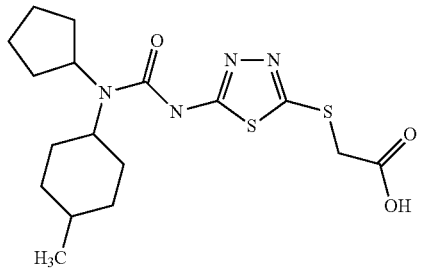

{5-[3-Cyclopentyl-3-(4-methyl-cyclohexyl)-ureido]-[1,3,4]thiadiazol-2-ylsulfanyl}-acetic acid ethyl ester was prepared using cyclopentyl-(4-methyl-cyclohexyl)-amine and ethyl-2-[5-amino-1,3,4-thiadiazol-2-yl-thio]acetate as described in general procedure (A) and (B). Hydrolysis using general procedure (F) gave the title compound.

HPLC-MS: m/z=399.4 (M+1).

Example 128

{5-[3-Cyclohexyl-3-(4-methyl-cyclohexyl)-ureido]-[1,3,4]thiadiazol-2-ylsulfanyl}-acetic acid

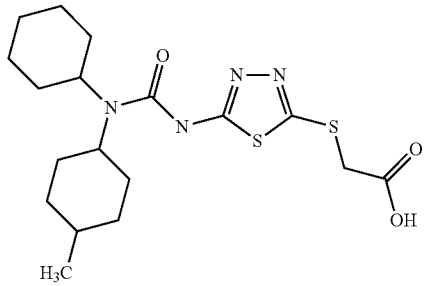

{5-[3-Cyclohexyl-3-(4-methyl-cyclohexyl)-ureido]-[1,3,4]thiadiazol-2-ylsulfanyl}-acetic acid ethyl ester was prepared using cyclohexyl-(4-methyl-cyclohexyl)-amine and ethyl-2-[5-amino-1,3,4-thiadiazol-2-yl-thio]acetate as described in general procedure (A) and (B). Hydrolysis using general procedure (F) gave the title compound.

HPLC-MS: m/z=413.5 (M+1).

Example 129

3-[6-(3,3-Dicyclohexyl-ureido)-pyridin-3-yl]-acrylic acid ethyl ester

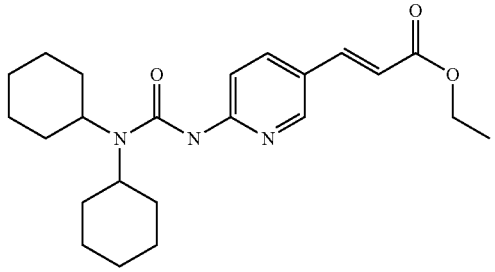

Prepared as described in general procedure (A) using dicyclohexylamine and 3-(6-aminopyridin-3-yl)-acrylic acid ethyl ester HPLC-MS: m/z=400.6 (M+1).

Example 130

{5-[3-(4-Methyl-cyclohexyl)-3-(tetrahydro-pyran-4-yl)-ureido]-[1,3,4]thiadiazol-2-ylsulfanyl}-acetic acid

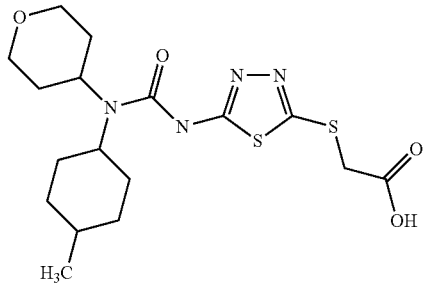

{5-[3-(4-Methyl-cyclohexyl)-3-(tetrahydro-pyran-4-yl)-ureido]-[1,3,4]thiadiazol-2-ylsulfanyl}-acetic acid ethyl ester was prepared using (4-methyl-cyclohexyl)-(tetrahydro-pyran-4-yl)-amine and ethyl-2-[5-amino-1,3,4-thiadiazol-2-yl-thio]acetate as described in general procedure (A) and (B). Hydrolysis using general procedure (F) gave the title compound.

HPLC-MS: m/z=415.5 (M+1).

Example 131

1,1-Dicyclohexyl-3-(1H-imidazol-2-yl)-urea

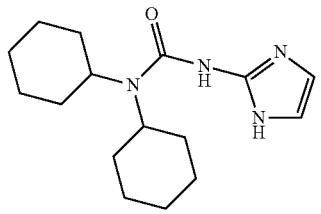

Prepared as described in general procedure (A) using dicyclohexylamine and 2-aminoimidazole HPLC-MS: m/z=292 (M+1).

Example 132

{2-[3-Cyclohexyl-3-(4-methyl-cyclohexyl)-ureido]-5-ethyl-thiazol-4-yl}-acetic acid

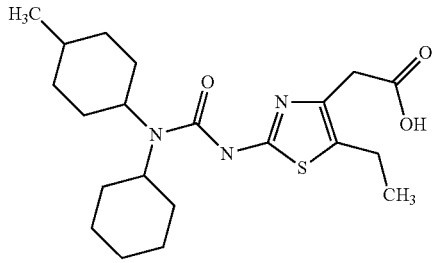

{2-[3-Cyclohexyl-3-(4-methyl-cyclohexyl)-ureido]-5-ethyl-thiazol-4-yl}-acetic acid ethyl ester was prepared from cyclohexyl-(4-methyl-cyclohexyl)-amine and (2-amino-5-ethyl-thiazol-4-yl)-acetic acid ethyl ester using general procedures (A) and (B). Hydrolysis using general procedure (F) gave the title compound.

HPLC-MS: m/z=408.6 (M+1).

Example 133

{5[3-Cyclohexyl-3-(tetrahydro-pyran-4-yl)-ureido]-[1,3,4]thiadiazol-2-ylsulfanyl}-acetic acid

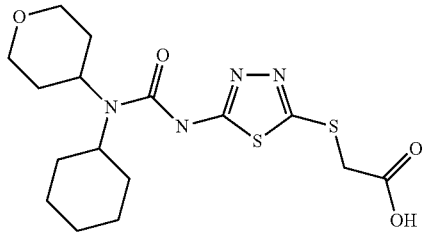

{5-[3-Cyclohexyl-3-(tetrahydro-pyran-4-yl)-ureido]-[1,3,4]thiadiazol-2-ylsulfanyl}-acetic acid ethyl ester was prepared using cyclohexyl-(tetrahydro-pyran-4-yl)-amine and ethyl-2-[5-amino-1,3,4-thiadiazol-2-yl-thio] acetate as described in general procedure (A) and (B). Hydrolysis using general procedure (F) gave the title compound.

HPLC-MS: m/z=401.4 (M+1).

Example 134

1,1-Dicyclohexyl-3-[5-(2-dimethylamino-ethylsulfanyl)-thiazol-2-yl]-urea

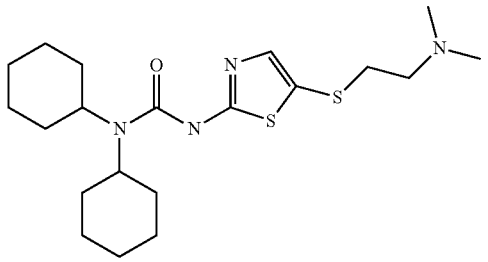

3-(5-Bromo-thiazol-2-yl)-1,1-dicyclohexyl-urea (1.25 g, 3.24 mmol) (prepared according to general procedure C) in DMF (12 mL) was added 2-dimethylamino-ethanethiole hydrochloride (0.92 g, 6.47 mmol) and NaOH (0.97 mL, 9.7 mmol) and the reaction mixture was stirred for 1 h before the flask was transferred to a refrigerator and left for 2 days. The reaction mixture was purified on a preparative HPLC. The fractions were collected and the volatiles were removed in vacuo. The residue was dissolved in EtOAc, washed with sodium carbonate and dried ($MgSO_4$). Yield 152 mg (11%). $^1$H NMR ($CDCl_3$): δ 7.35 (s, 1H), 2.76 (t, 2H), 2.41 (t, 2H), 2.12 (s, 6H), 2.0-1.0 (m, 22H) HPLC-MS: m/z=412 (M+1).

Example 135

3-5-Chloro-thiazol-2-yl)-1-cyclohexyl-1-(1,1-dioxo-tetrahydrothiophen-3-yl)-urea

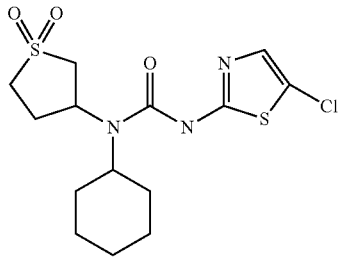

Prepared as described in general procedures (A) and (B) using cyclohexyl-(1,1-dioxo-tetrahydrothiophen-3-yl)-amine and 5-chloro-2-amino thiazole HPLC-MS: m/z=379 (M+1).

Example 136

2-[5-(3,3-Dicyclohexylureido)-[1,3,4]thiadiazol-2-ylsulfanyl]-N-thiazol-2-ylacetamide

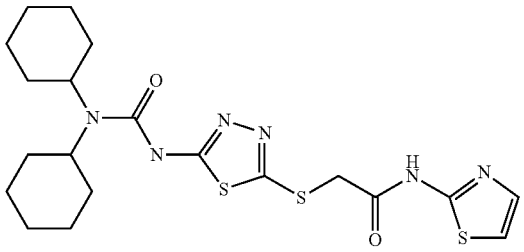

Prepared as described in general procedure (A) using dicyclohexylamine and 5-amino-1,3,4-thiadiazol-2-ylsulfanyl-N-thiazol-2-ylacetamide HPLC-MS: m/z=481 (M+1).

Example 137

1-(1-Butyryl-piperidin-4-yl)-3-(5-chloro-thiazol-2-yl)-1-cyclohexyl-urea

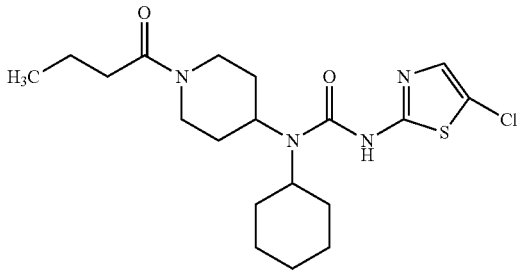

Prepared as described in general procedure (G) using 4-cyclohexylamino-piperidine-1-carboxylic acid tert-butyl ester and 5-chloro-2-aminothiazole HPLC-MS: m/z=413 (M+1).

Example 138

1-(1-Propionyl-piperidin-4-yl)-3-(5-Chloro-thiazol-2-yl)-1-cyclohexyl-urea

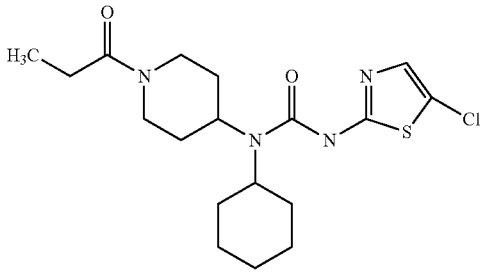

Prepared as described in general procedure (G) using 4 -cyclohexylamino-piperidine-1-carboxylic acid tert-butyl ester and 5-chloro-2-aminothiazole HPLC-MS: m/z=399 (M+1).

Example 139

{2-[3-Cyclohexyl-3-(4-oxo-cyclohexyl)-ureido]-thiazol-5-ylsulfanyl}-acetic acid ethyl ester

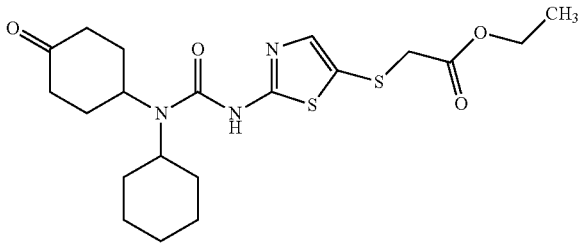

Prepared as described in general procedures (A) and (13) using 4-(4-methylcyclohexylamino)-cyclohexanone and ethyl-2-[5-aminothiazol-2-yl-thio]acetate HPLC-MS: m/z=440 (M+1).

Example 140

3-(5-Chloro-thiazol-2-yl)-1-cyclohexyl-1-(1-cyclopentanecarbonyl-piperidin-4-yl)-urea

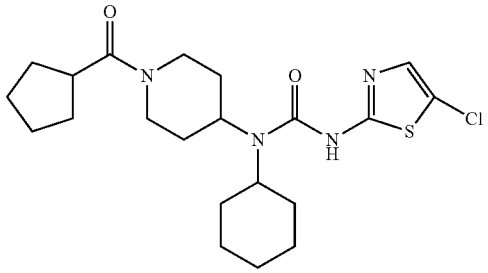

Prepared as described in general procedure (G) using 4-cyclohexylamino-piperidine-1-carboxylic acid tert-butyl ester and 5-chloro-2-aminothiazole HPLC-MS: m/z=439 (M+1).

Example 141

{2-[3-(1-Acetyl-piperidin-4-yl)-3-cyclohexyl-ureido]-thiazol-5-ylsulfanyl}-acetic acid

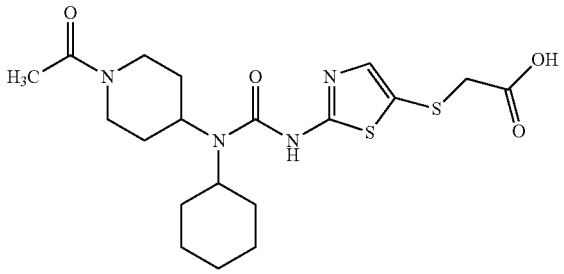

Prepared from {2-[3-(1-Acetyl-piperidin-4-yl)-3-cyclohexyl-ureido]-thiazol-5-ylsulfanyl}-acetic acid ethyl ester using general procedure (F).

HPLC-MS: m/z=441 (M+1).

Example 142

1-(1-Acetyl-piperidin-4-yl)-1-cycloheptyl-3-thiazol-2-yl-urea

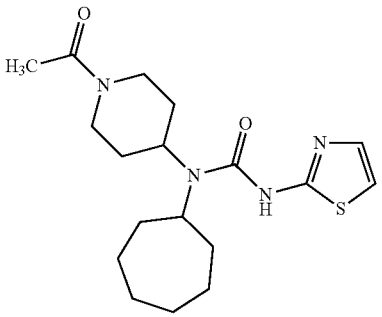

Prepared as described in general procedure (G) using 4-cycloheptylamino-piperidine-1 -carboxylic acid tert-butyl ester and 2-aminothiazole HPLC-MS: m/z=365 (M+1).

Example 143

1,1-Dicyclohexyl-3-[5-(4-methyl-piperazin-1-yl)-thiazol-2-yl]-urea

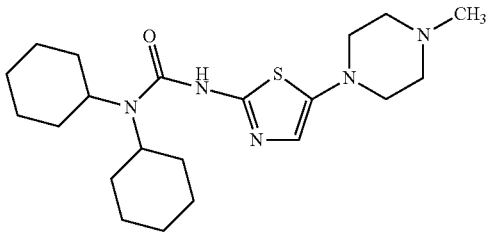

Prepared as described in general procedures (A) using dicyclohexylamine and 2-amino-5-(4-methylpiperazin-1-yl)-thiazole.

HPLC-MS: m/z=406 (M+1).

Example 144

{2-[3-Cyclohexyl-3-(4-oxo-cyclohexyl)-ureido]-thiazol-5-ylsulfanyl}-acetic acid

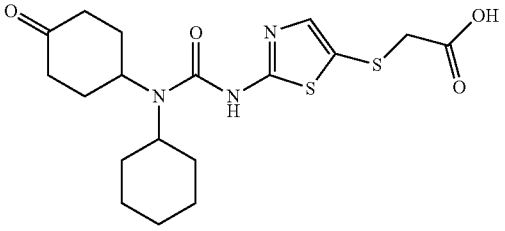

Prepared from {2-[3-Cyclohexyl-3-(4-oxo-cyclohexyl)-ureido]-thiazol-5-ylsulfanyl}-acetic acid ethyl ester using general procedure (F).

HPLC-MS: m/z=412 (M+1).

Example 145

1-(1-Acetyl-piperidin-4-yl)-3-(5-chloro-thiazol-2-yl)-1-cyclopentyl-urea

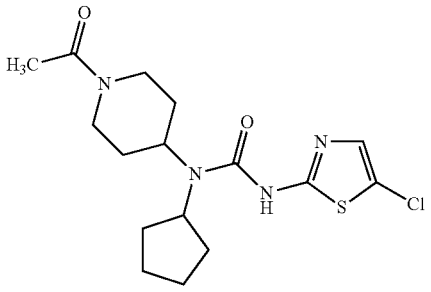

Prepared as described in general procedure (G) using 4-cyclopentylamino-piperidine-1-carboxylic acid tert-butyl ester and 5-chloro-2-aminothiazole HPLC-MS: m/z=371 (M+1).

Example 146

1-Cyclohexyl-1-(1,1-dioxo-tetrahydrothiophen-3-yl)-3-thiazol-2-yl-urea

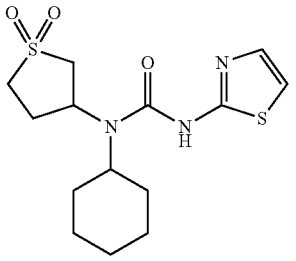

Prepared as described in general procedures (A) and (B) using cyclohexyl-(1,1-dioxo-tetrahydrothiophen-3-yl)-amine and 2-aminothiazole HPLC-MS: m/z=344 (M+1).

Example 147

{5-[3-Cyclohexyl-3-(4-oxo-cyclohexyl)-ureido]-[1,3,4]thiadiazol-2-ylsulfanyl}-acetic acid ethyl ester

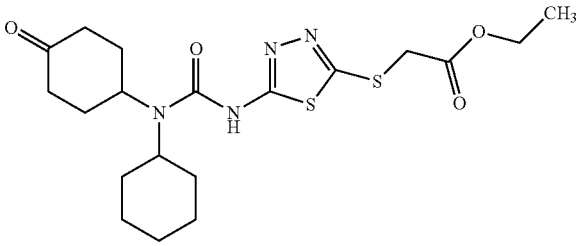

Prepared as described in general procedures (A) and (B) using 4-cyclohexylamino-cyclohexanone and ethyl-2-[5-amino-1,3,4-thiadiazol-2-yl-thio]acetate HPLC-MS: m/z=441 (M+1).

Example 148

3-[2-(3,3-Dicyclohexyl-ureido)-4-methyl-thiazol-5-ylsulfanyl]-propionic acid

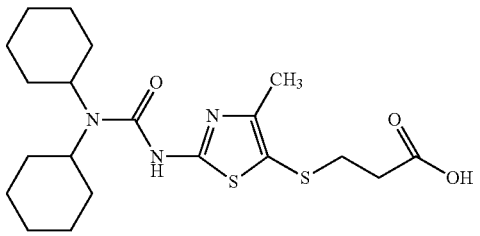

Prepared as described in general procedures (A) and (B) using 3-[2-(3,3-dicyclohexyl-ureido)-4-methyl-thiazol-5-yl-sulfanyl]-propionic acid ethyl ester and 3-(2-amino-4-methyl-thiazol-5-ylsulfanyl)-propionic acid ethyl ester HPLC-MS: m/z=426 (M+1).

Example 149

{5-[3,3-Bis-(4-methyl-cyclohexyl)-ureido]-[1,3,4]thiadiazol-2-ylsulfanyl}-acetic acid

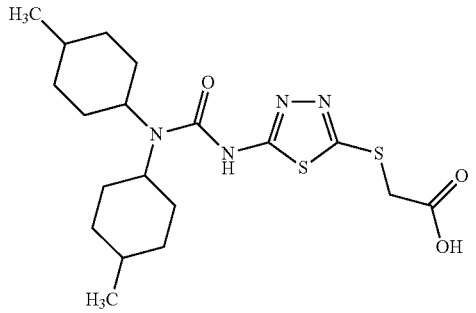

{5-[3,3-Bis-(4-methyl-cyclohexyl)-ureido]-[1,3,4]thiadiazol-2-ylsulfanyl}-acetic acid ethyl ester prepared from bis-(4-methyl-cyclohexyl)-amine and ethyl-2-[5-amino-1,3,4-thiadiazol-2-yl-thio]acetate as described in general procedures (A) and (B). Hydrolysis using general procedure (F) gave the title compound.

HPLC-MS: m/z=427 (M+1).

Example 150

4-[3-(5-Chloro-thiazol-2-yl)-1-cyclohexyl-ureido]-N-tert-butoxycarbonyl-piperidine

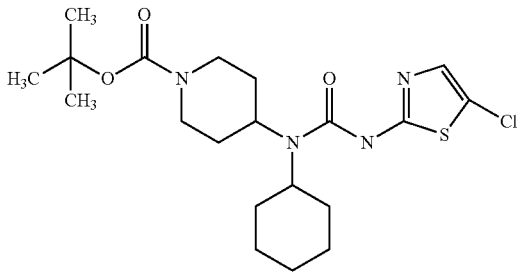

Prepared as described in general procedure (G) using 4-cyclopentylamino-piperidine-1-carboxylic acid tert-butyl ester and 5-chloro-2-aminothiazole HPLC-MS: m/z=443 (M+1).

Example 151

1-(4-Ainino-cyclohexyl)-3-(5-chloro-thiazol-2-yl)-1-cyclohexyl-urea

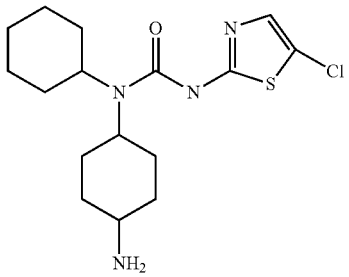

Prepared as described in general procedures (A), (B) using (4-cyclohexylamino-cyclohexyl)-carbamic acid tert-butyl ester and 5-chloro-2-aminothiazole HPLC-MS: m/z=357 (M+1).

Example 152

4-(1-Cyclohexyl-3-thiazol-2-yl-ureido)-N-tert-butoxycarbonyl-piperidine

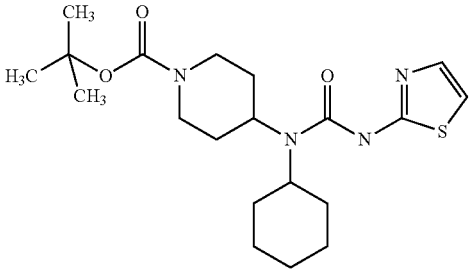

Prepared as described in general procedure (G) using 4-cyclopentylamino-piperidine-1-carboxylic acid tert-butyl ester and 2-aminothiazole HPLC-MS: m/z=409 (M+1).

Example 153

1-(1-Benzoyl-piperidin-4-yl)-3-(5-chloro-thiazol-2-yl)-1-cyclohexyl-urea

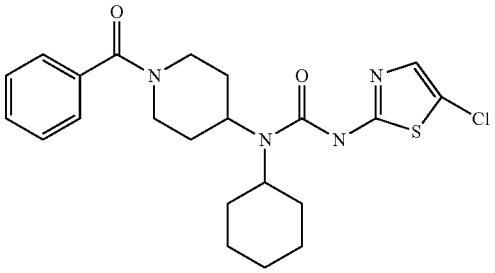

Prepared as described in general procedure (G) using 4-cyclopentylamino-piperidine-1-carboxylic acid tert-butyl ester and 5-chloro-2-aminothiazole HPLC-MS: m/z=447 (M+1).

Example 154

[2-(3,3-Dicyclohexyl-ureido)-4-methyl-thiazol-5-ylsulfanyl]-acetic acid

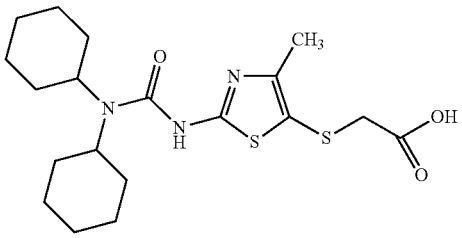

[2-(3,3-Dicyclohexyl-ureido)-4-methyl-thiazol-5-ylsulfanyl]-acetic acid ethyl ester prepared as described in general procedure (A) using dicyclohexylamine and 3-methyl-5-aminothiazole-2-mercaptoacetic acid ethyl ester. Hydrolysis using general procedure (F) gave the title compound.

HPLC-MS: m/z=412 (M+1).

Example 155

4-(3,3-Dicyclohexylureido)furazan-3-carboxylic acid

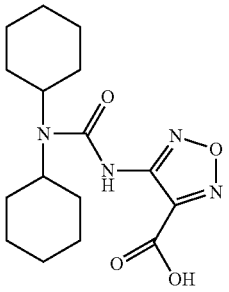

Prepared as described in general procedure (A) using dicyclohexylamine and 4-amino-3-furazanecarboxylic acid.

HPLC-MS: m/z=337 (M+1).

Example 156

[5-(3-Cyclohexyl-3-cyclopentyl-ureido)-[1,3,4]thiadiazol-2-ylsulfanyl]-acetic acid

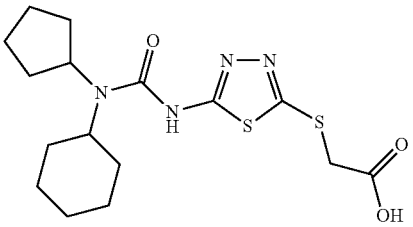

[5-(3-Cyclohexyl-3-cyclopentyl-ureido)-1,3,4thiadiazol-2-ylsulfanyl]-acetic acid ethyl ester prepared as described in general procedures (A) and (B) using cyclohexyl-cyclopentyl-amine and ethyl-2-[5-amino-1,3,4-thiadiazol-2-yl-thio] acetate. Hydrolysis using general procedure (F) gave the title compound.

HPLC-MS: m/z=385 (M+1).

Example 157

3-(5-Chloro-thiazol-2-yl)-1-cyclohexyl-1-[4-(pyridine-4-carbonyl)-piperidin-4-yl]-urea

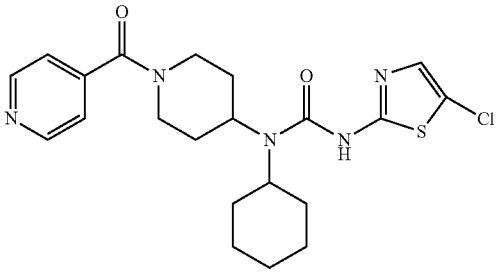

Prepared as described in general procedure (G) using 4-cyclohexylamino-piperidine-1-carboxylic acid tert-butyl ester and 5-chloro-2-aminothiazole HPLC-MS: m/z=448 (M+1).

Example 158

1-Cyclohexyl-3-(5-cyclopropyl-[1,3,4]thiadiazol-2-yl)-1-(4-oxo-cyclohexyl)-urea

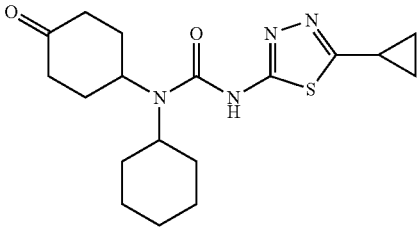

Prepared as described in general procedures (A) and (B) using 4-cyclohexylamino-cyclohexanone and 2-amino-5-cyclopropyl-1,3,4-thiadiazole HPLC-MS: m/z=363 (M+1).

Example 159

4-[5-(3,3-Dicyclohexyl-ureido)-[1,3,4]thiadiazol-2-ylsulfanyl]-butyric acid

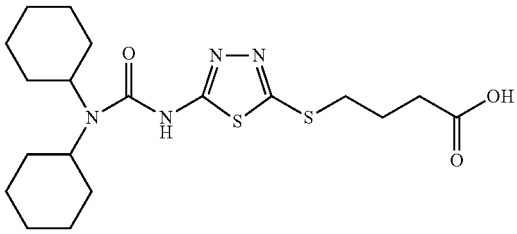

4-[5-(3,3-Dicyclohexyl-ureido)-[1,3,4]thiadiazol-2-ylsulfanyl]-butyric acid ethyl ester was pre-pared as described in general procedure (A) using dicyclohexylamine and 4-(5-amino-[1,3,4]thiadiazol-2-ylsulfanyl)-butyric acid ethyl ester. Hydrolysis using general procedure (F) gave the title compound.

HPLC-MS: m/z=427 (M+1).

Example 160

{5-[3-Cyclohexyl-3-(4-oxo-cyclohexyl)-ureido]-[1,3,4]thiadiazol-2-ylsulfanyl}-acetic acid

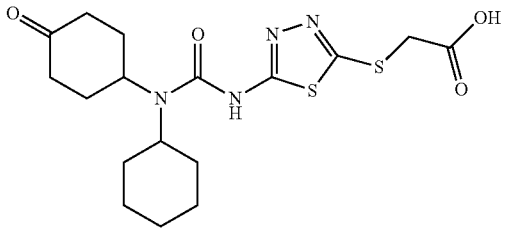

Hydrolysis of {5-[3-Cyclohexyl-3-(4-oxo-cyclohexyl)-ureido]-[1,3,4]thiadiazol-2-ylsulfanyl}-acetic acid ethyl ester using general procedure (F) gave the title compound.

HPLC-MS: m/z=413 (M+1).

Example 161

3-(5-Chloro-thiazol-2-yl)-1-cyclohexyl-1-(1,1-dioxo-tetrahydro-1-thiopyran-4-yl)-urea

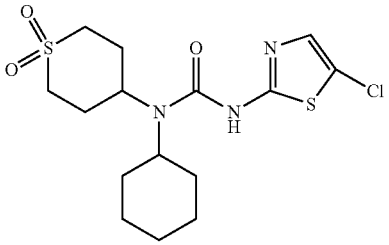

Prepared as described in general procedures (A) and (B) using cyclohexyl-(1,1-dioxo-thiomorpholine-4-yl)-amine and 5-chloro-2-aminothiazole.

HPLC-MS: 392 (M+1).

Example 162

1-Cyclohexyl-1-(4,4-dimethyl-cyclohexyl)-3-thiazol-2-yl-urea

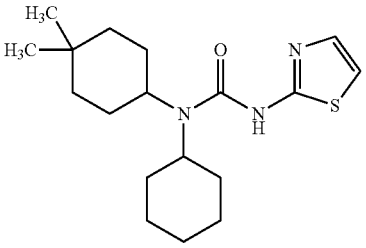

Prepared as described in general procedures (A) and (B) using cyclohexyl-(4,4-dimethyl-cyclohexyl)-amine and 2-amino thiazole HPLC-MS: m/z=336 (M+1).

Example 163

[2-(3,3-Dicyclohexylureido)benzothiazol-6-yl]acetic acid

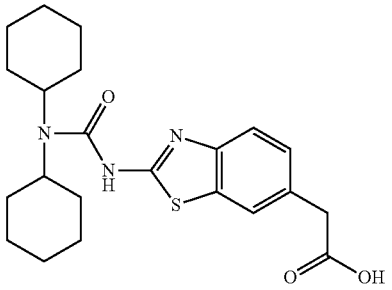

Prepared as described in general procedure (A) using dicyclohexylamine and 2-aminobenzthiazole-6-acetic acid.

HPLC-MS: m/z=416 (M+1).

Example 164

{2-[3-Cyclohexyl-3-(tetrahydro-furan-(3R)-yl)-ureido]-thiazol-5-ylsulfanyl}-acetic acid

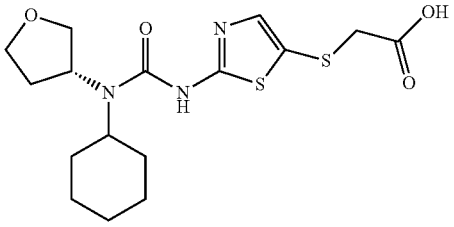

Hydrolysis of {2-[3-Cyclohexyl-3-(tetrahydro-furan-(3R)-yl)-ureido]-thiazol-5-ylsulfanyl}-acetic acid ethyl ester using general procedure (F) gave the title compound.

HPLC-MS: m/z=386 (M+1).

Example 165

3-(5-Methyl-thiazol-2-yl)-1-(4-oxo-cyclohexyl)-1-(tetrahydro-pyran-4-yl)-urea

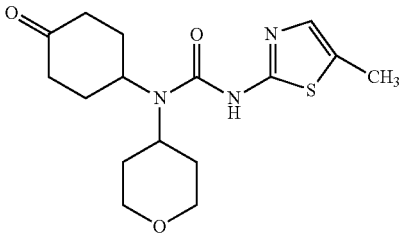

Prepared as described in general procedure (A) using 4-(tetrahydro-pyran-4-ylamino)-cyclohexanone and 2-amino-5-methylthiazole.

HPLC-MS: m/z=339 (M+1).

Example 166

[2-(3,3-Dicyclohexyl-ureido)-thiazol-4-ylmethylsulfanyl]-acetic acid

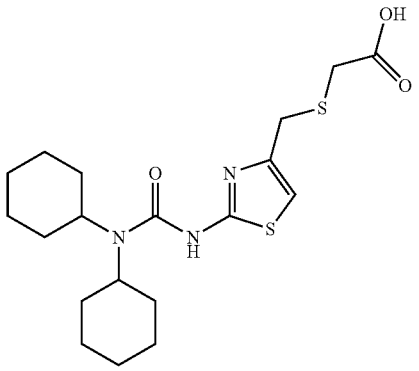

[2-(3,3-Dicyclohexyl-ureido)-thiazol-4-ylmethylsulfanyl]-acetic acid ethyl ester prepared as described in general procedure (A) using dicyclohexylamine and (2-amino-thiazol-4-ylmethylsulfanyl)-acetic acid ethyl ester (prepared by reaction of 4-chloromethyl-thiazol-2-ylamine, ethyl-2-mercaptoacetate and potassium carbonate in DMF for 1 h at room temperature). Hydrolysis using general procedure (F) gave the title compound.

HPLC-MS: m/z=412 (M+1).

Example 167

1-(4-tert-butoxycarbonylamino-cyclohexyl)-3-(5-chloro-thiazol-2-yl)-1-cyclohexyl-urea

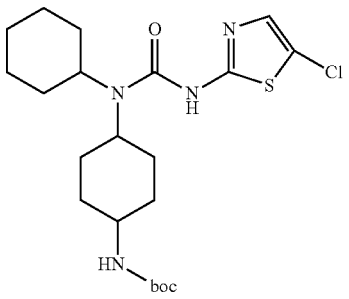

Prepared as described in general procedures (A) and (B) using (4-cyclohexylamino-cyclohexyl)-carbamic acid tert-butyl ester and 2-amino-5-chlorothiazole HPLC-MS: m/z=457 (M+1).

Example 168

1-(4-tert-butoxycarbonylamino-cyclohexyl)-3-(thiazol-2-yl)-1-cyclohexyl-urea

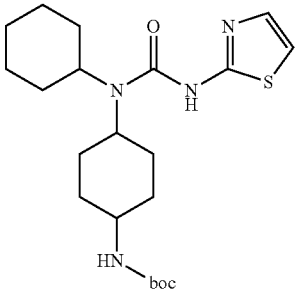

Prepared as described in general procedures (A) and (B) using (4-cyclohexylamino-cyclohexyl)-carbamic acid tert-butyl ester and 2-aminothiazole HPLC-MS: m/z=423 (M+1).

Example 169

3-(5-Chloro-thiazol-2-yl)-1-cyclohexyl-1-[1-(4-fluoro-benzyol)-piperidin-4-yl]-urea

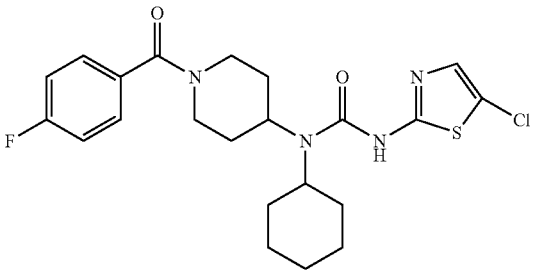

Prepared as described in general procedure (G) using 4-cyclohexylamino-piperidine-1-carboxylic acid tert-butyl ester and 5-chloro-2-aminothiazole HPLC-MS: m/z=465 (M+1).

Example 170

3-(5-Chloro-thiazol-2-yl)-1-cyclohexyl-1-[1-(4-methoxy-benzoyl)-piperidin-4-yl]-urea

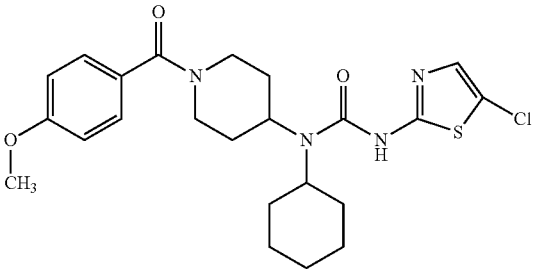

Prepared as described in general procedure (G) using 4-cyclohexylamino-piperidine-1-carboxylic acid tert-butyl ester and 5-chloro-2-aminothiazole HPLC-MS: m/z=477 (M+1).

Example 171

[5-(3,3-Dicyclopentyl-ureido)-[1,3,4]thiadiazol-2-ylsulfanyl]-acetic acid

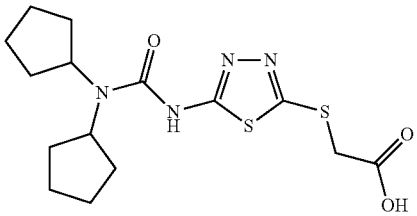

[5-(3,3-Dicyclopentyl-ureido)-[1,3,4]thiadiazol-2-ylsulfanyl]-acetic acid ethyl ester prepared as described in general procedures (A) and (B) using dicyclopentylamine and ethyl-2-[5-amino-1,3,4-thiadiazol-2-yl-thio]acetate. Hydrolysis using general procedure (F) gave the title compound.

HPLC-MS: m/z=371 (M+1).

Example 172

3-(5-Chloro-thiazol-2-yl)-1-cyclohexyl-1-[1-(2-methoxy-benzoyl)-piperidin-4-yl]-urea

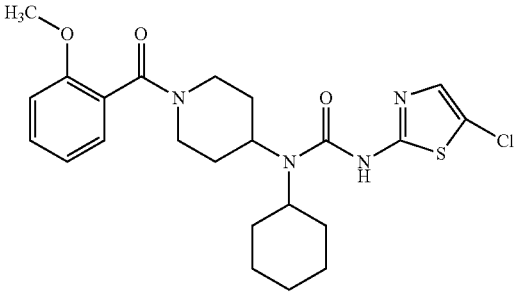

Prepared as described in general procedure (G) using 4-cyclohexylamino-piperidine-1-carboxylic acid tert-butyl ester and 5-chloro-2-aminothiazole HPLC-MS: m/z=477 (M+1).

Example 173

1,1-Dicyclohexyl-3-[4-methyl-5-(4-methyl-piperazine-1-sulfonyl)-thiazol-2-yl]-urea

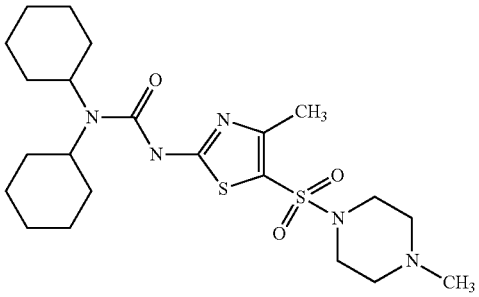

Step 1: Synthesis of 4-Methyl-5-(4-methyl-piperazine-1-sulfonyl)-thiazol-2-ylamine: N-acetamino-5-thiazolesulfonyl chloride (0.9 g; 042 mmol) was dissolved in DCM (15 ml) TEA (0.71 g; 7.07 mmol) and 1-methyl piperazine (0.42 g; 4.24 mmol) were added (Exothermic!) under stirring. The reaction mixture was stirred for 30 min. Water (15 ml) was added and extracted with DCM (3×25 ml). The organic phase was dried, filtered and evaporation in vacua gave 1.1 g white crystals of N-[5-(4-Methyl-piperazine-1-sulfonyl)-thiazol-2-yl]-acetamide.

$^1$H NMR (MeOD): δ 9.5 (br s; 1H); 3.2 (br t; 4H); 2.55 (br t; 4H); 2.50 (s; 3H); 2.32 (s; 3H); 2.29 (s; 3H).

Step 2: The above compound was hydrolysed in 6 N HCl/MeOH (1:1) in a microwave vessel (20 ml). The reaction was heated 3000@80° C.; ×4 before complete conversion. To the reaction mixture was added DCM (10 ml) and stirred for 5 min. The DCM phase was removed; TLC showed no compound in the organic phase to remove neutral starting material from the first step! Then the mixture was added base until basic pH. Extraction (3×25 ml) DCM, drying with $MgSO_4$ and evaporation gave 532 mg white crystals of 4-Methyl-5-(4-methyl-piperazine-1-sulfonyl)-thiazol-2-ylamine.

HPLC-MS: m/z=277 (M+1).

Prepared in the microwave oven (EmrysOptimizer®). 4-Methyl-5-(4-methyl-piperazine-1-sulfonyl)-thiazol-2-ylamine (0.04 g; 0.141 mmol), CDI (0.023 g; 0.141 mmol) and DMAP were mixed dichloroethane (1.5 ml) in a microwave vessel (2.5 ml). The reaction mixture was healed 600 sec at 120° C., dicyclohexylamine (0.025 g; 0.141 mmol) dissolved in dichloroethane (0.2 ml) was added through the septum and the reaction mixture was heated for additional 600 sec. at 120° C. To the reaction mixture was added water and DCM (25 ml). The water phase was extracted with DCM (3×25 ml), dried with $MgSO_4$ filtered and evaporated in vacuo to afford the title compound. (84 mg) as a yellow oil. Purification by prep. HPLC gave 3 mg (Yield: 4%)

HPLC-MS: m/z=484 (M+1).

Example 174

3-[2-(3,3-Dicyclohexyl-ureido)-thiazol-5-ylsulfanyl]-propionic acid methyl ester

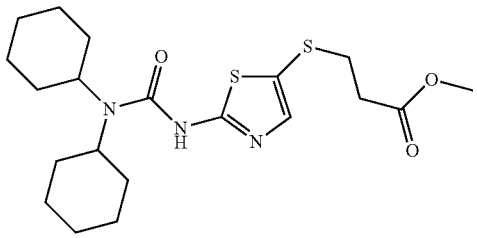

Prepared as described in general procedure (D) using 3-(5-bromo-thiazol-2-yl)-1,1-dicyclohexyl-urea and 3-mercapto-propionic acid methyl ester.

$^1$H NMR ($CDCl_3$): δ 7.52 (br, 1H), 7.34 (s, 1H), 3.67 (s, 3H), 3.41 (m, 2H), 2.91 (t, 2H), 2.61 (t, 3H), 1.05-1.84 (m, 20H) ppm; HPLC-MS: m/z 426 (M+1).

Example 175

3-[2-(3,3-Dicyclohexyl-ureido)-thiazol-5-ylsulfanyl]-propionic acid

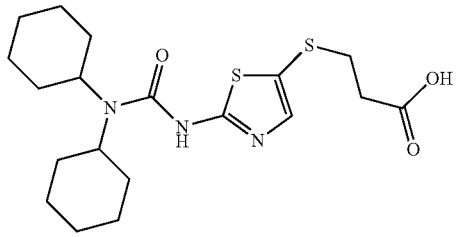

Prepared as described in the general procedure (F) from 3-[2-(3,3-dicyclohexyl-ureido)thiazol-5-ylsulfanyl]-propionic acid methyl ester.

$^1$H NMR (DMSO-$d_6$): δ 12.62 (br, 1H), 9.86 (br, 1H), 7.94 (s, 1H), 3.51 (t, 2H), 3.30 (m, 2H), 2.58 (t, 2H), 1.10-1.88 (m, 20H) ppm; HPLC-MS: m/z 412 (M+1).

Example 176

2-[2-(3,3-Dicyclohexyl-ureido)-thiazol-5-ylsulfonyl]-3-methyl-3H-imidazole-4-carboxylic acid ethyl ester

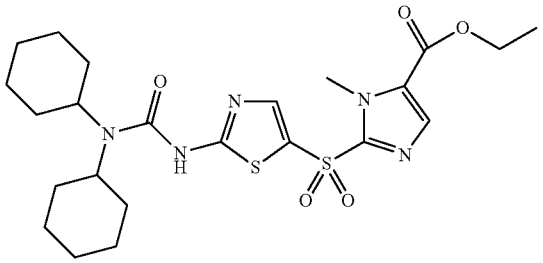

Prepared from 2-[2-(3,3-dicyclohexyl-ureido)-thiazol-5-ylsulfanyl]-3-methyl-3H-imidazole-4-carboxylic acid ethyl ester (Example 59) as described in general procedure (J).

$^1$H NMR ($CDCl_3$): δ 9.23 (br, 1H), 8.15 (br, 1H), 7.69 (s, 1H), 4.35 (q, 2H), 4.27 (s, 3H), 3.42 (m, 2H), 1.70-1.86 (m, 16H), 1.36 (t, 3H), 1.10-1.48 (m, 4H) ppm; HPLC-MS: m/z 524 (M+1).

Example 177

2-[2-(3,3-Dicyclohexyl-ureido)-thiazol-5-ylsulfonyl]-3-methyl-3H-imidazole-4-carboxylic acid

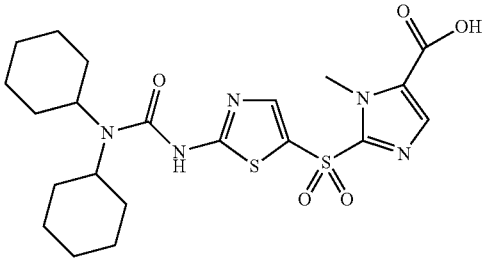

Prepared as described in general procedure (F) from 2-[2-(3,3-dicyclohexyl-ureido)-thiazol-5-ylsulfonyl]-3 -methyl-3H-imidazole-4-carboxylic acid ethyl ester (Example 176).

$^1$H NMR (DMSO-$d_6$): δ 12.82 (br, 1H), 9.42 (br, 1H), 8.22 (s, 1H), 7.68 (s, 1H), 4.19 (s, 3H), 3.42 (m, 2H),1.02-1.96 (m, 20H) ppm; HPLC-MS: m/z 496 (M+1).

Example 178

2-[2-(3,3-Dicyclohexyl-ureido)-thiazole-5-sulfonyl]-1H-imidazole-4-carboxylic acid ethyl ester

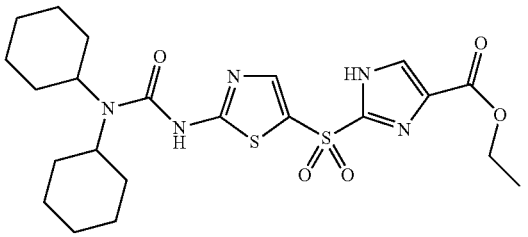

Prepared from 2-[2-(3,3-dicyclohexyl-ureido)-thiazole-5-sulfanyl]-1H-imidazole-4-carboxylic acid ethyl ester (Example 57) as described in general procedure (J).

$^1$H NMR ($CDCl_3$): δ 9.34 (br, 1H), 8.10 (br, 1H), 7.79 (s, 1H), 4.36 (q, 2H), 3.43 (m, 2H), 1.15-1.86 (m, 23H) ppm; HPLC-MS: m/z 510 (M+1).

Example 179

2-[2-(3,3-Dicyclohexyl-ureido)-thiazole-5-sulfonyl]-1H-imidazole-4-carboxylic acid

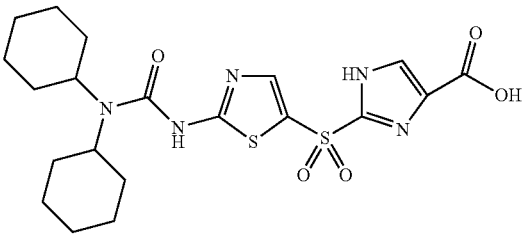

Prepared as described in general procedure (F) from 2-[2-(3,3-dicyclohexyl-ureido)-thiazole-5-sulfonyl]-1H-imidazole-4-carboxylic acid ethyl ester (Example 178).

$^1$H NMR (DMSO-$d_6$): δ 12.34 (br, 1H), 9.28 (br, 1H), 8.09 (s, 1H), 7.94 (s, 1H), 3.33 (m, 2H), 1.10-1.90 (m, 20H) ppm; HPLC-MS: m/z 482 (M+1).

Example 180

1,1-Dicyclohexyl-3-[5-(pyrimidine-2-sulfonyl)-thiazol-2-yl]-urea

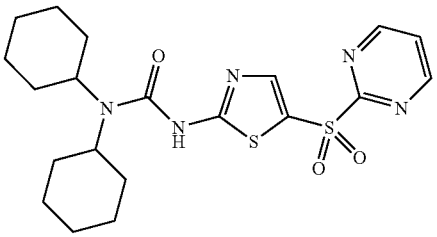

Prepared from 1,1-dicyclohexyl-3-[5-(pyrimidine-2-sulfanyl)-thiazol-2-yl]-urea as described in general procedure (J).

$^1$H NMR ($CDCl_3$): δ 9.18 (br, 1H), 8.92 (d, 2H), 8.10 (s, 1H), 7.51 (t, 1H), 3.45 (m, 2H), 1.15-1.85 (m, 20H) ppm; HPLC-MS: m/z 450 (M+1).

Example 181

[2-(3,3-Dicyclohexyl-ureido)-thiazole-5-sulfonyl]-acetic acid methyl ester

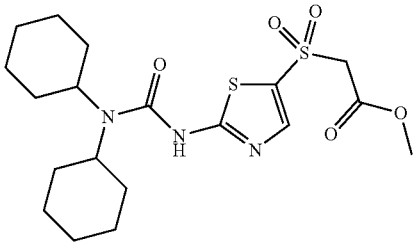

Prepared from [2-(3,3-dicyclohexyl-ureido)-thiazole-5-sulfanyl]-acetic In general procedure (J). $^1$H NMR ($CDCl_3$): δ 7.96 (br, 1H), 7.26 (s, 1H), 4.18 (s, 2H), 3.77 (s, 1H), 3.42 (m, 2H), 1.19-1.86 (m, 20H) ppm; HPLC-MS: m/z 444 (M+1).

Example 182

[2-(3,3-Dicyclohexyl-ureido)-thiazole-5-sulfonyl]-acetic acid

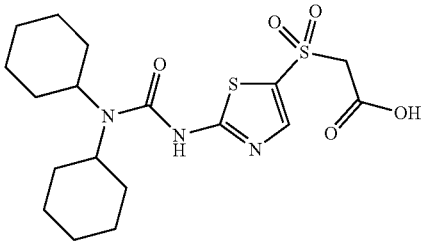

Prepared as described in the general procedure (F) from [2-(3,3-dicyclohexyl-ureido)-thiazole-5-sulfonyl]-acetic acid methyl ester (Example 181).

$^1$H NMR (DMSO-$d_6$): δ 12.12 (br, 1H), 8.22 (br, 1H), 7.95 (s, 1H), 4.46 (s, 2H), 3.42 (m, 2H), 1.08-1.90 (m, 20H) ppm; HPLC-MS: m/z 430 (M+1).

Example 183

1,1-Dicyclohexyl-3-[5-(4-methyl-4H-[1,2,4]triazole-3-sulfonyl)-thiazol-2-yl]-urea

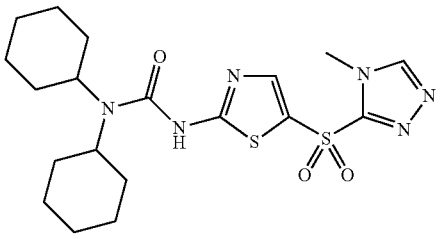

Prepared from 1,1-dicyclohexyl-3-[5-(4-methyl-4H-[1,2,4]triazole-3-sulfanyl)-thiazol-2-yl]-urea as described in general procedure (J).

$^1$H NMR ($CDCl_3$): δ 8.88 (br, 1H), 8.17 (s, 1H), 8.11 (br, 1H), 4.01 (s, 3H), 3.42 (m, 2H), 1.11-1.85 (m, 20H) ppm; HPLC-MS: m/z 453 (M+1).

Example 184

1,1-Dicyclohexyl-3-[5-(pyridine-2-sulfonyl)-thiazol-2-yl]-urea

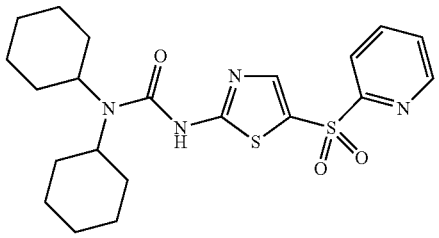

Prepared from 1,1-dicyclohexyl-3-[5-(pyridine-2-sulfanyl)-thiazol-2-yl]-urea (Example 56) as described in general procedure (J).

$^1$H NMR ($CDCl_3$): δ 8.86 (br, 1H), 8.69 (d, 1H), 8.14 (d, 1H, 8.07 (s, 1H), 7.91 (m, 1H), 7.46 (m, 1H), 3.39 (m, 2H), 1.16-1.84 (m, 20H) ppm; HPLC-MS: m/z 449 (M+1).

Example 185

2-[2-(3,3-Dicyclohexyl-ureido)-thiazol-5-ylsulfanyl]-nicotinic acid methyl ester

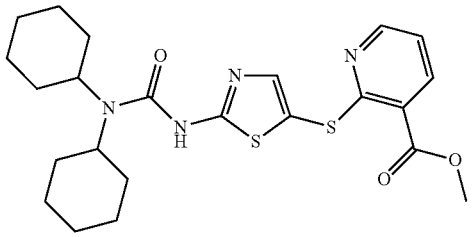

Prepared as described in general procedure (E) using 3-(5-bromo-thiazol-2-yl)-1,1-dicyclohexyl-urea and 2-mercaptonicotinic acid methylester.

HPLC-MS: m/z 475 (M+1).

Example 186

2-[2-(3,3-Dicyclohexyl-ureido)-thiazol-5-ylsulfanyl]-nicotinic acid

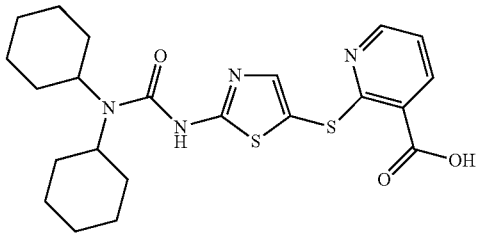

Prepared as described in the general procedure (F) from 2-[2-(3,3-dicyclohexyl-ureido)-thiazol-5-ylsulfanyl]-nicotinic acid methyl ester (Example 185).

$^1$H NMR (DMSO-$d_6$): δ 12.33 (br, 1H), 9.24 (br, 1H), 8.51 (m, 1H), 8.22 (m, 1H), 7.44 (s, 1H), 7.27 (m, 1H), 3.48 (m, 2H), 1.05-1.97 (m, 20H) ppm; HPLC-MS: m/z 461 (M+1).

Example 187

3-[2-(3,3-Dicyclohexyl-ureido)-thiazol-5-ylsulfonyl]-propionic acid methyl ester

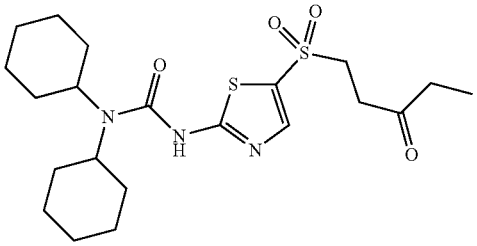

Prepared from 3-[2-(3,3-dicyclohexyl-ureido)-thiazol-5-ylsulfanyl]-propionic acid methyl ester as described in general procedure (J).

HPLC-MS: m/z 458 (M+1).

Example 188

3-[2-(3,3-Dicyclohexyl-ureido)-thiazol-5-ylsulfonyl]-propionic acid

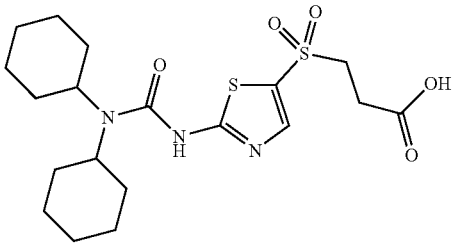

Prepared as described in the general procedure (F) from 3-[2-(3,3-dicyclohexyl-ureido)-thiazol-5-ylsulfonyl]-propionic acid methyl ester (Example 187).

HPLC-MS: m/z 444 (M+1).

Example 189

3-(5-Bromo-thiazol-2-yl)-1-cyclohexyl-1-(tetrahydro-pyran-4-yl)-urea

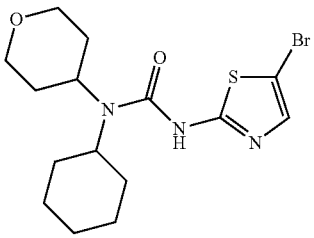

Prepared as described in general procedure (C) using cyclohexyl-(tetrahydro-pyran-4-yl)-amine and 5-bromo-2-thiazolyl amine.

$^1$H NMR ($CDCl_3$): δ 9.22 (s, 1H), 7.02 (s, 1H), 4.05 (dd, 2H), 3.87 (br, 1H), 3.48 (t, 2H), 3.40 (br, 1H), 1.26-2.28 (m, 14H) ppm; HPLC-MS: m/z 389 (M+1).

Example 190

3-(5-Bromo-thiazol-2-yl)-1-cyclohexyl-1-(tetrahydro-thiopyran-4-yl)-urea

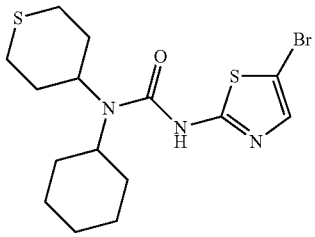

Prepared as described in general procedure (C) using cyclohexyl-(tetrahydro-thiopyran-4-yl)-amine and 5-bromo-2-thiazolyl amine. $^1$H NMR ($CDCl_3$): δ 8.11 (s, 1H), 7.24 (s, 1H), 3.57 (m, 1H), 3.38 (m, 1H), 2.75 (m, 4H), 1.14-2.17 (m, 14H) ppm; HPLC-MS: m/z 405 (M+1).

Example 191

3-(5-Bronio-thiazol-2-yl)-1-cyclohexyl-1-(1,1-dioxo-tetrahydro-thiopyran-4-yl)-urea

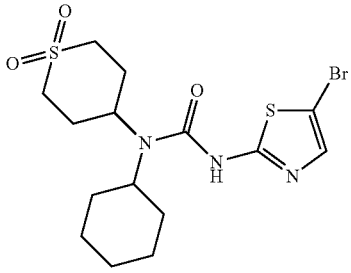

Prepared from 3-(5-bromo-thiazol-2-yl)-1-cyclohexyl-1-(tetrahydro-thiopyran-4-yl)-urea (Example 190) as described in the general procedure (J).

HPLC-MS: m/z 437 (M+1).

Example 192

{2-[3-Cyclohexyl-3-(tetrahydro-pyran-4-yl)-ureido]-thiazol-5-ylsulfanyl}-acetic acid methyl ester

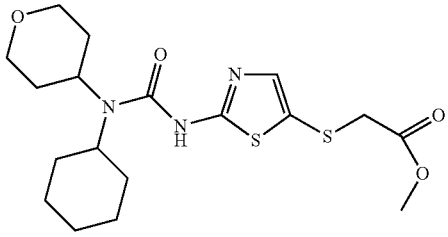

Prepared as described in general procedure (D) using 3-(5-bromo-thiazol-2-yl)-1-cyclohexyl-1-(tetrahydro-pyran-4-yl)-urea and methyl thioglycolate $^1$H NMR ($CDCl_3$): δ 8.26 (br, 1H), 7.41 (s. 1H), 4.05 (dd, 2H), 3.89 (br, 1H), 3.72 (s, 3H), 3.44 (m 2H), 3.41 (s, 2H), 3.35 (m, 1H), 1.15-2.19 (m, 14H) ppm; HPLC-MS: m/z 414 (M+1).

Example 193

{2-[3-Cyclohexyl-3-(tetrallydro-pyran-4-yl)-ureido]-thiazol-5-ylsulfanyl}-acetic acid

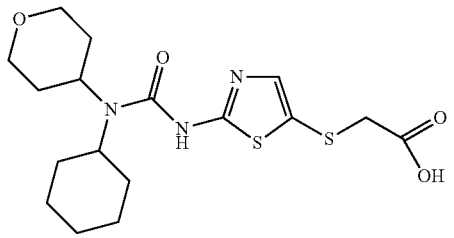

Prepared as described in general procedure (F) from {2-[3-cyclohexyl-3-(tetrahydro-pyran-4-yl)-ureido]-thiazol-5-ylsulfanyl}-acetic acid methyl ester (Example 192).

$^1$H NMR (DMSO-$d_6$): δ 12.44 (br, 1H), 8.5 (br, 1H), 7.38 (s, 1H), 3.83 (m, 2H), 3.67 (m, 1H), 3.45 (s, 2H), 3.32-3.38 (m, 3H), 1.09-2.20 (m, 14H) ppm; HPLC-MS: m/z 400 (M+1).

Example 194

{2-[3-Cyclohexyl-3-(tetrahydro-thiopyran-4-yl)-ureido]-thiazol-5-ylsulfanyl}-acetic acid methyl ester

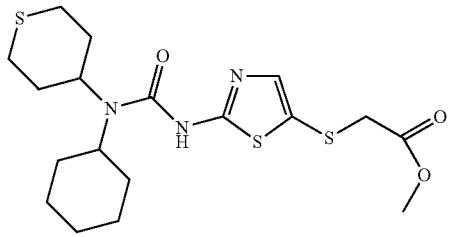

Prepared as described in general procedure (D) using 3-(5-bromo-thiazol-2-yl)-1-cyclohexyl-1-(tetrahydro-thiopyran-4-yl)-urea (Example 190) and methyl thioglycolate.

HPLC-MS: m/z 430 (M+1).

Example 195

{2-[3-Cyclohexyl-3-(tetrahydro-thiopyran-4-yl)-ureido]-thiazol-5-ylsulfanyl}-acetic acid

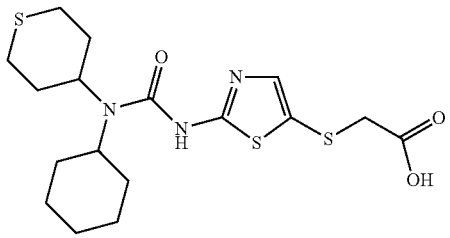

Prepared as described in general procedure (F) from {2-[3-cyclohexyl-3-(tetrahydro-thiopyran-4-yl)-ureido]-thiazol-5-ylsulfanyl}-acetic acid methyl ester.

$^1$H NMR (DMSO-$d_6$): δ 12.34 (br, 1H), 11.2 (br, 1H), 7.37 (s, 1H), 3.45 (s, 2H), 3.31 (m, 2H), 2.73 (m, 2H), 2.55 (m, 2H), 1.15-2.12 (m, 14H) ppm; HPLC-MS: m/z 416 (M+1).

Example 196

2-{2-[3-Cyclohexyl-3-(tetrahydro-pyran-4-yl)-ureido]-thiazol-5-ylsulfanyl}-1H-imidazole-4-carboxylic acid ethyl ester

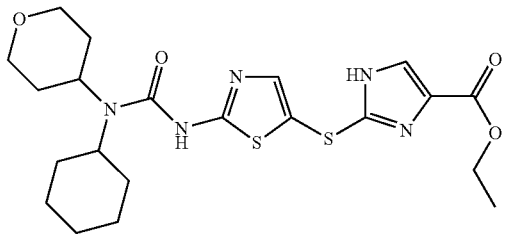

Prepared as described in general procedure (E) using 3-(5-bromo-thiazol-2-yl)-1-cyclohexyl-1-(tetrahydro-pyran-4-yl)-urea (Example 189) and ethyl-2-mercapto-1H-imidazole-4-carboxylate.

HPLC-MS: m/z 480 (M+1).

Example 197

2-{2-[3-Cyclohexyl-3-(tetrahydro-pyran-4-yl)-ureido]-thiazol-5-ylsulfanyl}-1H-imidazole-4-carboxylic acid

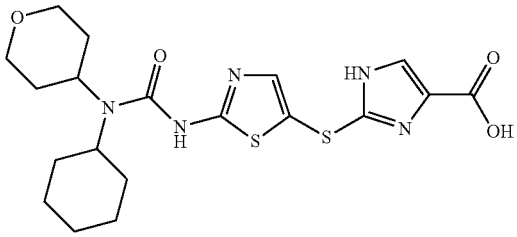

Prepared as described in general procedure (F) from 2-{2-[3-cyclohexyl-3-(tetrahydro-pyran-4-yl)-ureido]-thiazol-5-ylsulfanyl}-1H-imidazole-4-carboxylic acid ethyl ester.

$^1$H NMR (DMSO-$d_6$): δ 13.02 (br, 1H), 11.23 (br, 1H), 7.86 (s, 1H), 7.59 (s, 1H), 3.84 (m, 2H), 3.37 (m, 4H), 1.21-2.40 (m, 14H) ppm; HPLC-MS: m/z 452 (M+1).

Example 198

3-{2-[3-Cyclohexyl-3-(tetrahydro-thiopyran-4-yl)-ureido]-thiazol-5-ylsulfanyl}-propionic acid methyl ester

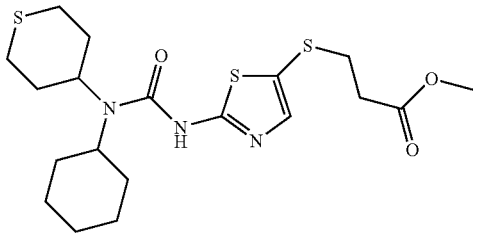

Prepared as described in general procedure (D) using 3-(5-bromo-thiazol-2-yl)-1-cyclohexyl-1-(tetrahydro-thiopyran-4-yl)-urea (Example 190) and 3-mercaptopropionic acid methyl ester.

$^1$H NMR ($CDCl_3$): δ 9.40 (br, 1H), 7.35 (s, 1H), 3.69 (s, 3H), 3.61 (br, 1H), 3.41 (br, 1H), 2.94 (t, 2H), 2.80 (t, 2H), 2.69 (dd, 2H), 2.61 (t, 2H), 1.18-2.20 (m, 14H) ppm; HPLC-MS: m/z 444 (M+1).

Example 199

3-{2-[3-Cyclohexyl-3-(tetrahydro-thiopyran-4-yl)-ureido]-thiazol-5-ylsulfanyl}-propionic acid

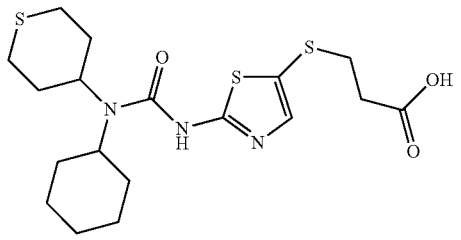

Prepared as described in the general procedure (F) from 3-{2-[3-cyclohexyl-3-(tetrahydro-thiopyran-4-yl)-ureido]-thiazol-5-ylsulfanyl}-propionic acid methyl ester (Example 198).

$^1$H NMR (DMSO-$d_6$): δ 12.40 (br, 1H), 8.42 (br, 1H), 7.35 (s, 1H), 3.82 (m, 2H), 2.82 (t, 2H), 2.76 (dd, 2H), 2.57 (dd, 2H), 2.49 (t, 2H), 1.20-2.23 (m, 14H) ppm; HPLC-MS: m/z 430 (M+1).

Example 200

2-{2-[3-Cyclohexyl-3-(tetrahydre-thiopyran-4-yl)-ureido]-thiazol-5-ylsulfanyl}-3-methyl-3H-imidazole-4-carboxylic acid ethyl ester

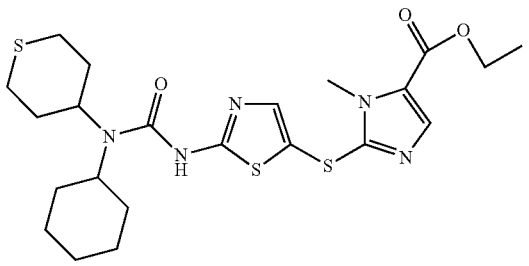

Prepared as described in general procedure (E) using 3-(5-bromo-thiazol-2-yl)-1-cyclohexyl-1-(tetrahydro-thiopyran-4-yl)-urea (Example 190) and 2-mercapto-3-methyl-3H-imidazole-4-carboxylic acid ethyl ester.

$^1$H NMR ($CDCl_3$): δ 8.20 (br, 1H), 7.73 (s, 1H), 7.66 (s, 1H), 7.53 (s, 1H), 4.29 (q, 2H), 3.96 (s, 3H), 3.58 (br, 1H), 3.39 (br, 1H), 2.65-2.78 (m, 4H), 1.18-2.24 (m, 17H) ppm; HPLC-MS: m/z 510 (M+1).

Example 201

2-{2-[3-Cyclohcxyl-3-(tetrahydro-thiopyran-4-yl)-ureido]-thiazol-5-ylsulfanyl}-3-methyl-3H-imidazole-4-carboxylic acid

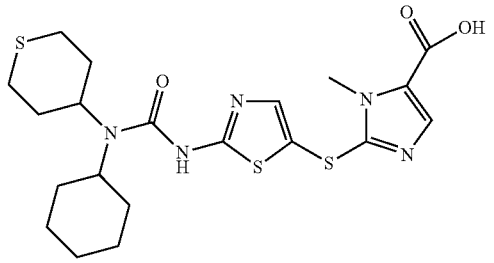

Prepared as described in general procedure (F) from 2-{2-[3-cyclohexyl-3-(tetrahydro-thiopyran-4-yl)-ureido]-thiazol-5-ylsulfanyl}-3-methyl-3H-imidazole-4-- ---carboxylic acid ethyl ester (Example 200).

$^1$H NMR (DMSO-$d_6$): δ 12.24 (br, 1H), 7.61 (br, 1H), 7.57 (s, 1H), 7.53 (s, 1H), 3.87 (s, 3H), 3.36 (m, 2H), 2.72 (t, 2H), 2.55 (d, 2H), 1.04-1.89 (m, 14H) ppm; HPLC-MS: m/z 482 (M+1).

Example 202

3-(5-Bromo-thiazol-2-yl)-1-cyclopentyl-1-(4-methyl-cyclohexyl)-urea

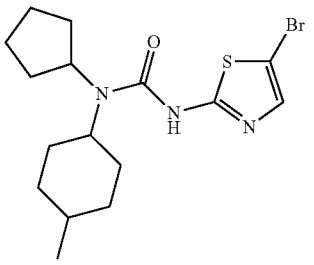

Prepared as described in general procedure (C) using cyclopentyl-(4-methyl-cyclohexyl)-amine and 5-bromo-2-thiazolyl amine.

$^1$H NMR ($CDCl_3$): δ 8.50 (br, 1H), 7.26 (1H, s), 3.83 (m, 1H), 3.48 (m, 1H), 1.07-1.90 (m, 17H, m), 0.82-1.05 (dd, 3H) ppm; HPLC-MS: m/z 387 (M+1).

Example 203

3-(5-Bromo-thiazol-2-yl)-1-(4-methyl-cyclohexyl)-1-(tetrahydro-pyran-4-yl)-urea

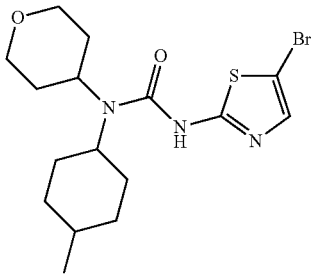

Prepared as described in general procedure (C) using (4-methyl-cyclohexyl)-(tetrahydro-pyran-4-yl)-amine and 5-bromo-2-thiazolyl amine.

$^1$H NMR ($CDCl_3$): δ 8.44 (br, 1H), 7.27 (1H, s), 4.02 (d, 2H), 3.82 (m, 2H), 3.41 (t, 2H), 3.32 (m, 1H), 1.05-2.09 (m, 13H), 0.89-1.03 (dd, 3H) ppm; HPLC-MS: m/z 403 (M+1).

Example 204

3-(5-Bromo-thiazol-2-yl)-1-cyclohexyl-1-(4-trifluoromethyl-cyclohexyl)-urea

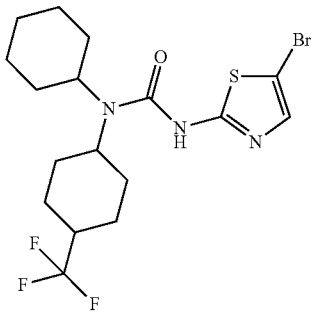

Prepared as described in general procedure (C) using cyclohexyl-(4-trifluorometlayl-cyclohexyl)-amine and 5-bromo-2-thiazolyl amine.

$^1$H NMR ($CDCl_3$): δ 8.15 (br, 1H), 7.26 (1H, s), 3.70 (m, 1H), 3.32 (m, 1H), 1.15-2.07 (m, 19H), 0.89-1.03 (dd, 3H) ppm; HPLC-MS: m/z 455 (M+1).

Example 205

{2-[3-Cyclopentyl-3-(4-methyl-cyclohexyl)-ureido]-thiazol-5-ylsulfanyl}-acetic acid methyl ester

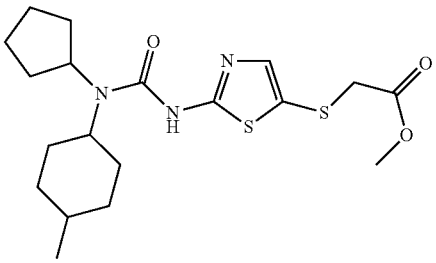

Prepared as described in general procedure (D) using 3-(5-bromo-thiazol-2-yl)-1-cyclopentyl-1-(4-methyl-cyclohexyl)-urea (Example 202) and methyl thioglycolate.

$^1$H NMR ($CDCl_3$): δ 8.44 (br, 1H), 7.39 (s, 1H), 3.83 (m, 1H), 3.70 (s, 3H), 3.49 (m, 1H), 3.41 (s, 2H), 1.12-1.87 (m, 17H), 0.87-1.01 (dd, 3H) ppm; HPLC-MS: m/z 412 (M+1).

Example 206

{2-[3-Cyclopentyl-3-(4-methyl-cyclohexyl)-ureido]-thiazol-5-ylsulfanyl}-acetic acid

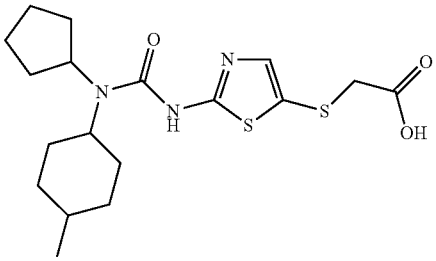

Prepared as described in general procedure (F) from {2-[3-cyclopentyl-3-(4-methyl-cyclohexyl)-ureido]-thiazol-5-ylsulfanyl}-acetic acid methyl ester (Example 205).

$^1$H NMR (DMSO-$d_6$): δ 11.94 (br, 1H), 8.42 (br 1H), 7.37 (s, 1H), 3.82 (m, 1H), 3.56 (m, 1H), 3.45 (s, 2H), 1.14-1.98 (m, 17H), 0.83-0.97 (dd, 3H) ppm; HPLC-MS: m/z 398 (M+1).

Example 207

3-{2-[3-Cyclopentyl-3-(4-methyl-cyclohexyl)-ureido]-thiazol-5-ylsulfanyl}-propionic acid methyl ester

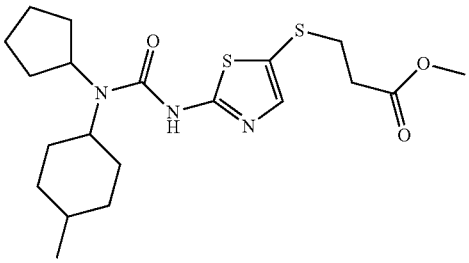

Prepared as described in general procedure (D) using 3-(5-bromo-thiazol-2-yl)-1-cyclopentyl-1-(4-methyl-cyclohexyl)-urea (Example 202) and 3-mercaptopropionic acid methyl ester.

HPLC-MS: m/z 426 (M+1).

Example 208

3-{2-[3-Cyclopentyl-3-(4-methyl-cyclohexyl)-ureido]-thiazol-5-ylsulfanyl}-propionic acid

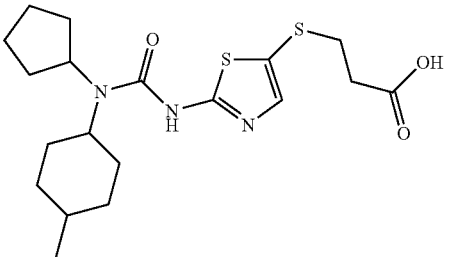

Prepared as described in the general procedure (F) from 3-{2-[3-cyclopentyl-3-(4-methyl-cyclohexyl)-ureido]-thiazol-5-ylsulfanyl}-propionic acid methyl ester (Example 207).

$^1$H NMR (DMSO-$d_6$): δ 11.44 (br, 1H), 8.54 (br 1H), 7.34 (s, 1H), 3.82 (m, 1H), 3.56 (m, 1H), 3.33 (s, 1H), 2.08 (t, 2H), 2.43 (t, 2H), 1.06-1.98 (m, 17H), 0.83-0.97 (dd, 3H) ppm; HPLC-MS: m/z 412 (M+1).

Example 209

2-{2-[3-Cyclopentyl-3-(4-methyl-cyclohexyl)-ureido]-thiazol-5-ylsulfanyl}-1H-imidazole-4-carboxylic acid ethyl ester

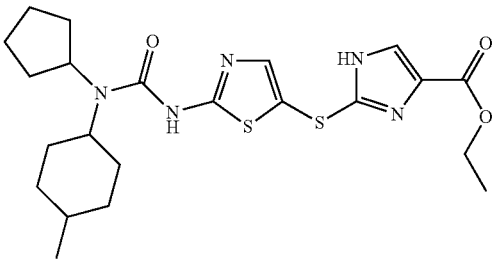

Prepared as described in general procedure (E) using 3-(5-bromo-thiazol-2-yl)-1-cyclopentyl-1-(4-methyl-cyclohexyl)-urea (Example 202) and ethyl-2-mercapto-1H-imidazole-4-carboxylate.

$^1$H NMR ($CDCl_3$): δ 9.22 (br, 1H), 7.66 (s, 1H), 7.54 (s, 1H), 4.30 (q, 2H), 3.82 (m, 1H), 3.44 (m, 1H), 1.34-1.82 (m, 20H), 0.78-0.98 (dd, 3H) ppm; HPLC-MS: m/z 478 (M+1).

Example 210

2-{2-[3-Cyclopentyl-3-(4-methyl-cyclohexyl)-ureido]-thiazol-5-ylsulfanyl}-1H-imidazole-4-carboxylic acid

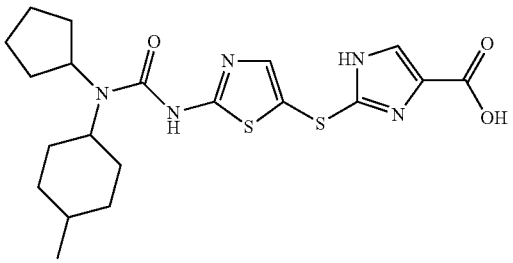

Prepared as described in general procedure (F) from 2-{2-[3-cyclopentyl-3-(4-methyl-cyclohexyl)-ureido]-thiazol-5-ylsulfanyl}-1H-imidazole-4-carboxylic acid ethyl ester.

$^1$H NMR (DMSO-$d_6$): δ 12.92 (br, 1H), 11.94 (br, 1H), 7.82 (br, 1H), 7.56 (s, 1H), 3.82 (m, 1H), 3.56 (m, 1H), 1.08-1.97 (m, 17H), 0.83-0.96 (dd, 3H) ppm; HPLC-MS: m/z 450 (M+1).

Example 211

2-{2-[3-Cyclopentyl-3-(4-methyl-cyclohexyl)-ureido]-thiazol-5-ylsulfanyl}-3-methyl-3H-imidazole-4-carboxylic acid ethyl ester

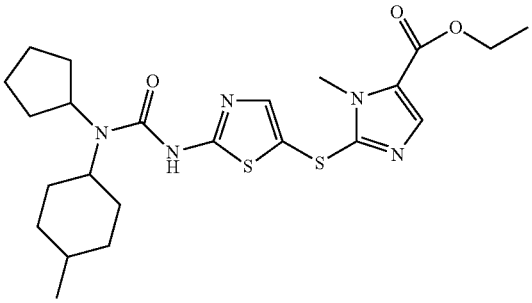

Prepared as described in general procedure (E) using 3-(5-bromo-thiazol-2-yl)-1-cyclopentyl-1-(4-methyl-cyclohexyl)-urea (Example 202) and 2-mercapto-3-methyl-3H-imidazole-4-carboxylic acid ethyl ester.

$^1$H NMR ($CDCl_3$): δ 9.24 (br, 1H), 7.68 (s, 1H), 7.56 (s, 1H), 4.28 (q, 2H), 3.98 (s, 3H), 3.83 (m, 1H), 3.50 (m, 1H), 1.01-1.84 (m, 20H), 0.82-0.98 (dd, 3H) ppm; HPLC-MS: m/z 492 (M+1).

Example 212

2-{2-[3-Cyclopentyl-3-(4-methyl-cyclohexyl)-ureido]-thiazol-5-ylsulfanyl}-3-methyl-3H-imidazole-4-carboxylic acid

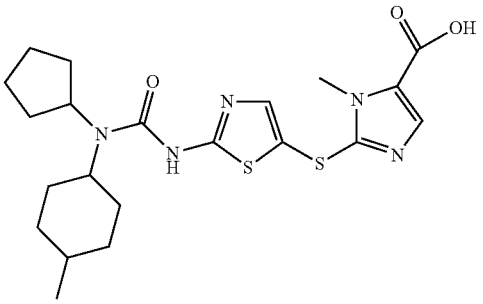

Prepared as described in general procedure (F) from 2-{2-[3-cyclopentyl-3-(4-methyl-cyclohexyl)-ureido]-thiazol-5-ylsulfanyl}-3-methyl-3H-imidazole-4-carboxylic acid ethyl ester.

$^1$H NMR (DMSO-$d_6$): δ 12.96 (br, 1H), 11.45 (br, 1H), 7.61 (br, 1H), 7.56 (s, 1H), 3.86 (s, 3H), 3.81 (m, 1H), 3.56 (m, 1H), 1.03-1.99 (m, 17H), 0.83-0.96 (dd, 3H) ppm; HPLC-MS: m/z 464 (M+1).

Example 213

{2-[3-(4-Methyl-cyclohexyl)-3-(tetrahydro-pyran-4-yl)-ureido]-thiazol-5-ylsulfanyl}-acetic acid methyl ester

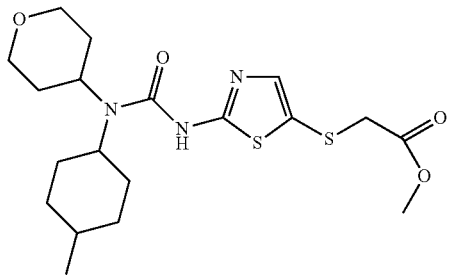

Prepared as described in general procedure (D) using 3-(5-bromo-thiazol-2-yl)-1-(4-methyl-cyclohexyl)-1-(tetrahydro-pyran-4-yl)-urea (Example 203) and methyl thioglycolate.

$^1$H NMR ($CDCl_3$): δ 8.28 (br, 1H), 7.41 (s, 1H), 4.05 (m, 2H), 3.85 (m, 2H), 3.72 (s, 3H), 3.42 (m, 2H), 3.33 (m, 1H), 1.05-2.26 (m, 13H), 0.90-1.06 (dd, 3H) ppm; HPLC-MS: m/z 428 (M+1).

Example 214

{2-[3-(4-Methyl-cyclohexyl)-3-(tetrahydro-pyran-4-yl)-ureido]-thiazol-5-ylsulfanyl}-acetic acid

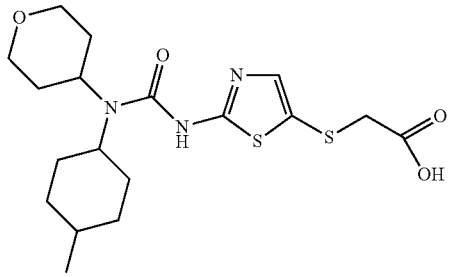

Prepared as described in general procedure (F) from {2-[3-(4-methyl-cyclohexyl)-3-(tetrahydro-pyran-4-yl)-ureido]-thiazol-5-ylsulfanyl}-acetic acid methyl ester (Example 213).

$^1$H NMR (DMSO-$d_6$): δ 12.2 (br, 1H), 7.6 (br, 1H), 7.36 (s, 1H), 3.82 (m, 2H), 3.70 (br, 1H), 3.45 (s, 2H), 3.35 (m, 3H), 1.02-2.26 (m, 13H), 0.84-0.99 (dd, 3H) ppm; HPLC-MS: m/z 414 (M+1).

Example 215

3-Methyl-2-{2-[3-(4-methyl-cyclohexyl)-3-(tetrahydro-pyran-4-yl)-ureido]-thiazol-5-ylsulfanyl}-3H-imidazole-4-carboxylic acid ethyl ester

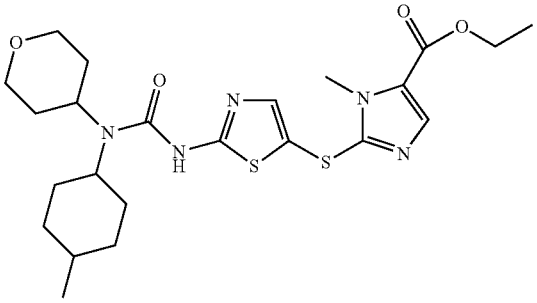

Prepared as described in general procedure (E) using 3-(5-bromo-thiazol-2-yl)-1-(4-methyl-cyclohexyl)-1-(tetrahydro-pyran-4-yl)-urea (Example 203) and 2-mercapto-3-methyl-3H-imidazole-4-carboxylic acid ethyl ester.

$^1$H NMR ($CDCl_3$): δ 9.36 (br, 1H), 8.06 (br, 1H), 7.68 (s, 1H), 7.55 (s, 1H), 4.30 (q, 2H), 4.04 (m, 2H), 3.98 (s, 3H), 3.80 (m, 1H), 3.43 (m, 2H), 3.31 (m, 1H), 1.34-1.82 (m, 13H), 0.78-0.98 (dd, 3H) ppm; HPLC-MS: m/z 508 (M+1).

Example 216

3-Methyl-2-{2-[3-(4-methyl-cyclohexyl)-3-(tetrahydro-pyran-4-yl)-ureido]-thiazol-5-ylsulfanyl}-3H-imidazole-4-carboxylic acid

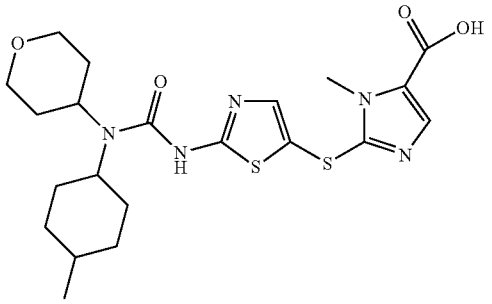

Prepared as described in general procedure (F) from 3-methyl-2-{2-[3-(4-methyl-cyclohexyl)-3-(tetrahydro-pyran-4-yl)-ureido]-thiazol-5-ylsulfanyl}-3H-imidazole-4-carboxylic acid ethyl ester (Example 215).

$^1$H NMR (DMSO-$d_6$): δ 12.26 (br, 1H), 7.8 (br, 1H), 7.61 (s, 1H), 7.54 (s, 1H), 3.87 (s, 3H), 3.81 (m, 3H), 3.48 (m, 1H), 3.36 (m, 2H), 1.03-2.20 (m, 13H), 0.83-0.96 (dd, 3H) ppm; HPLC-MS: m/z 480 (M+1).

Example 217

{2-[3-Cyclohexyl-3-(4-trifluoromethyl-cyclohexyl)-ureido]-thiazol-5-ylsulfanyl}-acetic acid methyl ester

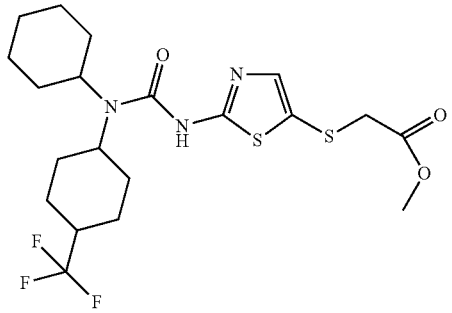

Prepared as described in general procedure (D) using 3-(5-bromo-thiazol-2-yl)-1-cyclohexyl-1-(4-trifluoromethyl-cyclohexyl)-urea (Example 204) and methyl thioglycolate.

$^1$H NMR ($CDCl_3$): δ 7.62 (br, 1H), 7.34 (s, 1H), 3.66 (s, 3H), 3.37 (s, 2H), 3.28 (m, 2H), 1.05-2.26 (m, 19H) ppm; HPLC-MS: m/z 480 (M+1).

Example 218

{2-[3-Cyclohexyl-3-(4-trifluoromethyl-cyclohexyl)-ureido]-thiazol-5-ylsulfanyl}-acetic acid

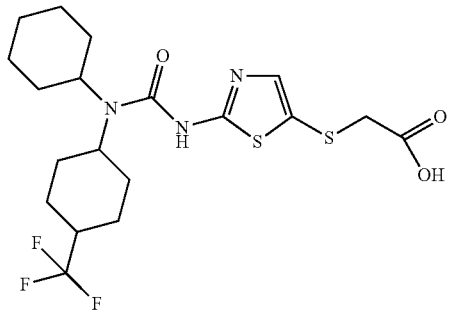

Prepared as described in general procedure (F) from {2-[3-cyclohexyl-3-(4-trifluoromethyl-cyclohexyl)-ureido]-thiazol-5-ylsulfanyl}-acetic acid methyl ester (Example 217).

$^1$H NMR (DMSO-$d_6$): δ 12.16 (br, 1H), 7.37 (s, 1H), 3.44 (s, 3H), 3.32 (m, 2H), 1.05-2.21 (m, 19H) ppm; HPLC-MS: m/z 466 (M+1).

Example 219

3-{2-[3-Cyclohexyl-3-(4-trifluoromethyl-cyclohexyl)-ureido]-thiazol-5-ylsulfanyl}-propionic acid methyl ester

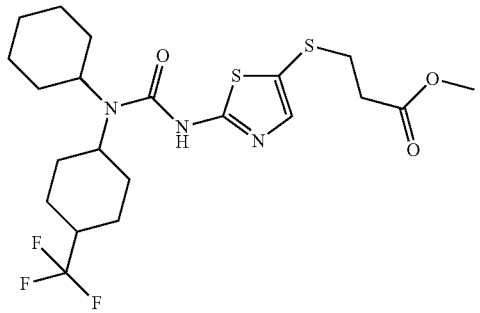

Prepared as described in general procedure (D) using 3-(5-bromo-thiazol-2-yl)-1-cyclohexyl-1-(4-trifluoromethyl-cyclohexyl)-urea (Example 204) and 3-mercaptopropionic acid methyl ester.

HPLC-MS: m/z 494 (M+1).

Example 220

[2-(3,3-Dicyclohexyl-ureido)-thiazol-5-yl]-acetic acid methyl ester

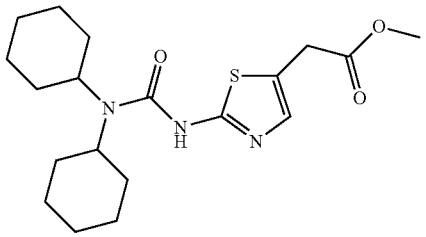

Prepared as described in general procedure (C) using dicyclohexylamine and 2-amino-thiazol-5-yl)-acetic acid methyl ester.

$^1$H NMR ($CDCl_3$): δ 7.25 (s, 1H), 7.13 (br, 1H), 3.71 (s, 5H), 3.42 (m, 2H), 1.05-1.99 (m, 20H) ppm; HPLC-MS: m/z 380 (M+1).

Example 221

[2-(3,3-Dicyclohexyl-ureido)-thiazol-5-yl]-acetic acid

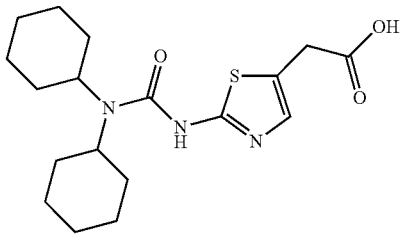

Prepared as described in the general procedure (F) from [2-(3,3-dicyclohexyl-ureido)-thiazol-5-yl]-acetic acid methyl ester (Example 220).

$^1$H NMR (DMSO-$d_6$): δ 12.16 (br, 1H), 7.29 (br, 1H), 7.10 (s, 1H), 3.65 (s, 2H), 3.44 (m, 2H), 1.05-1.97 (m, 20H) ppm; HPLC-MS: m/z 366 (M+1).

Example 222

1,1-Dicyclohexyl-3-(4-formyl-thiazol-2-yl)-urea

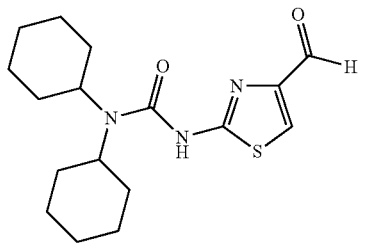

To a solution of 1,1-dicyclohexyl-3-(4-hydroxymethyl-thiazol-2-yl)urea (850 mg, 2.5 mmol) in 4:1 DCM/DMSO (8 mL) was added pyridine-sulfur trioxide (1.59 g, 10.0 mmol) and triethyl-amine (1.55 mL, 11.25 mmol) at 0° C. The mixture was stirred for 6 h and quenched with water (50 mL) and the layers were separated. The aqueous layer was extracted with DCM (2×50 mL). The combined organic layers was washed with water, saturated ammonium chloride solution, brine, dried over sodium sulfate and concentrated in vacuo to obtain 1,1-dicyclohexyl-3-(4-formyl-thiazol-2-yl)urea (800 mg, 2.38 mmol).

$^1$H NMR ($CDCl_3$): δ 9.78 (s, 1H), 8.2 (br, 1H), 7.74 (s, 1H), 3.45 (m, 2H), 1.20-1.90 (m, 20H) ppm; HPLC-MS: m/z 336 (M+1).

Example 223

[2-(3,3-Dicyclohexylureido)-thiazol-4-yl]acetic acid ethyl ester

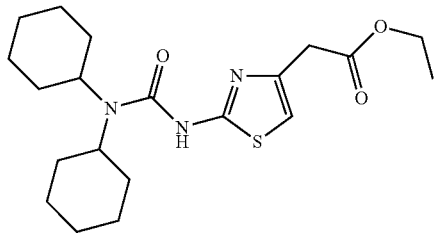

Prepared in 63% yield as described in general procedure (C) from dicyclohexylamine and ethyl-2-amino-4-thiazoleacetate.

$^1$H NMR ($CDCl_3$): δ 8.00 (br, 1H), 6.65 (s, 1H), 3.63 (s, 3H), 3.46 (m, 2H), 1.15-1.90 (m, 23H) ppm; HPLC-MS: m/z 394 (M+1).

Example 224

3-(4-Cyano-thiazol-2-yl)-1,1-dicyclohexylurea

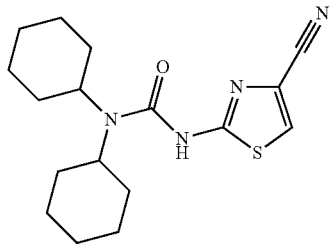

Prepared as described in general procedure (C) using dicyclohexyl amine and 4-cyano-2-thiazolyl amine.

$^1$H NMR (4:1 $CDCl_3$-$CD_3OD$): δ 8.16 (br, 1H). 7.55 (s, 1H), 3.44 (m, 2H), 1.15-1.90 (m, 20H) ppm; HPLC-MS: m/z 333 (M+1).

Example 225

1,1-Dicyclohexyl-3-[4-(methanesulfonylhydroxy-imino-methyl)-thiazol-2-yl]urea

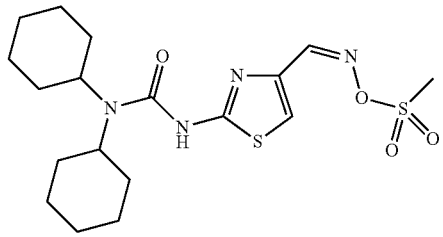

To a solution of 1,1-dicyclohexyl-3-[4-(hydroxyimino-methyl)-thiazol-2-yl]-urea (0.15 mmol) in DCM (4 mL) was added methanesulfonyl chloride (0.15 mmol) and DIEA (0.15 mL). The mixture was stirred at rt for 2 h and quenched with water (10 mL). The reaction mixture was extracted with ethyl acetate (3×10 mL). The combined organic extracts was washed with water (2×30 mL), dried over sodium sulfate, filtered and concentrated in vacuo. The crude product was purified by flash chromatography (silica, EtOAc/hexanes 1:4 to EtOAc/hexanes 1:1) to give the desired product in 30% yield.

$^1$H NMR (4:1 $CDCl_3$-$CD_3OD$): δ 8.60 (s, 1H), 7.80 (s, 1H), 6.48 (d, 1H), 3.60 (br, 2H), 3.40 (s, 3H), 1.15-1.90 (m, 20H) ppm; HPLC-MS: m/z 429 (M+1).

Example 226

1,1-Dicyclohexyl-3-[4-(1-methyl-1H-tetrazol-5-yl-sulfanyl methyl)thiazol-2-yl]urea

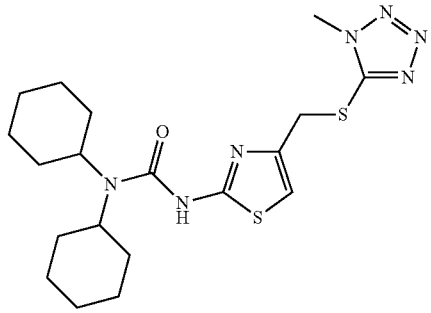

Prepared in 20% yield as described in general procedure (L) from 1,1-dicyclohexyl-3-(4-bromomethyl-thiazol-2-yl) urea and 1-methyl-5-mercaptotetrazole.

$^1$H NMR (d6-acetone): δ 6.84 (s, 1H), 4.47 (s, 2H), 3.93 (s, 3H), 3.60 (br, 2H), 2.80 (br, 1H), 1.15-1.90 (m, 20H) ppm; HPLC-MS: m/z 436 (M+1).

Example 227

2-[2-(3,3-Dicyclohexylureido)-thiazol-4-ylmethyl-sulfanyl)-1H-imidazole-4-carboxylic acid ethyl ester

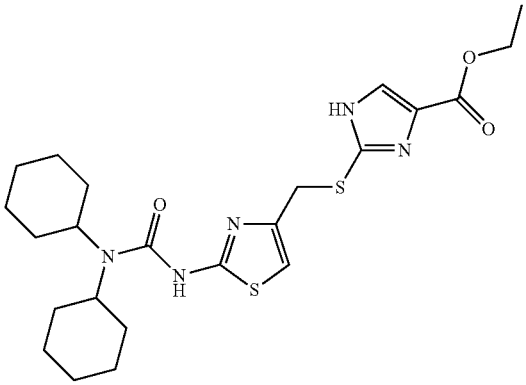

Prepared in 20% yield as described in general procedure (L) from 1,1-dicyclohexyl-3-(4-bromomethyl-thiazol-2-yl) urea and 2-mercapto-1H-imidazole-4-carboxylic acid ethyl ester.

HPLC-MS: m/z 492 (M+1).

Example 228

N-[2-(3,3-Dicyclohexylureido)-thiazol-4-ylmethyl]-methansulfonamide

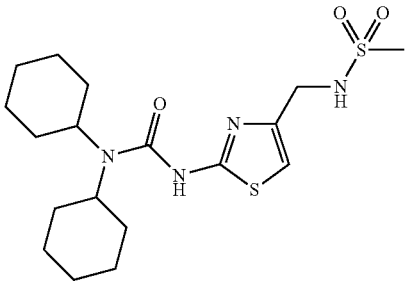

To a solution of 1,1-dicyclohexyl-3-[4-(hydroxyimino-methyl)-thiazol-2-yl]-urea (150 mg, 0.45 mmol) was added borane-THF complex (5.0 mL 1.0M) and the content was stirred for 2 h at rt. The mixture was quenched with $NaHCO_3$ solution and extracted with ethyl acetate (2×30 mL). The organic extracts was washed (2×30 mL), dried over sodium sulfate, filtered and concentrated in vacuo to get the corresponding amine. To this amine in DCM (5.0 mL) was added methansulfonyl anhydride (0.1 mL) and DIEA (0.2 mL) at 0° C. The mixture was evaporated and the crude product was purified by flash chromatography (silica, $CH_2CH_2$-EtOAc 1:4) to furnish N-[2-(3,3-dicyclohexylureido)-thiazol-4-ylmethyl]-methansulfonamide (20 mg) in 10% yield.

$^1$H NMR ($CD_3OD$): δ 6.90 (d, 1H), 4.20 (s, 2H), 3.46 (br, 1H), 3.30 (m, 2H), 2.80 (s, 2H), 1.15-1.90 (m, 20H) ppm; HPLC-MS: m/z 415 (M+1).

Example 229

1,1-Dicyclohexyl-3-[4-(pyridin-2-ylsulfanylmethyl)-thiazol-2-yl]urea

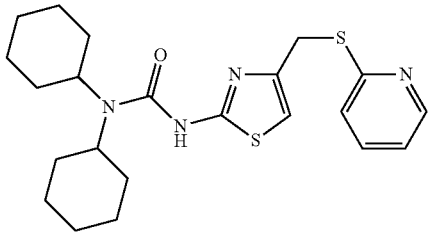

Prepared as described in general procedure (L) from 1,1-dicyclohexyl-3-(4-bromomethyl-thiazol-2-yl)urea and 2-mercaptopyridine.

$^1$H NMR (d6-DMSO): δ 8.40 (d, 1H), 7.64 (m, 1H), 7.30 (d, 1H), 7.11 (m, 1H), 6.85 (s, 1H), 4.34 (s, 2H), 3.46 (m, 2H), 1.15-1.90 (m, 20H) ppm; HPLC-MS: m/z 431 (M+1).

Example 230

1,1-Dicyclohexyl-3-[4-(1-methyl-1H-imidazol-2-ylsulfanylmethyl)-thiazol-2-yl]urea

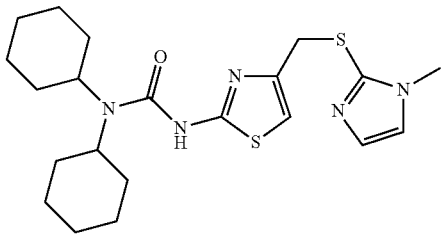

Prepared as described in general procedure (L) from 1,1-dicyclohexyl-3-(4-bromomethyl-thiazol-2-yl)urea and 2-mercapto-1-methyl-1H-imidazole.

$^1$H NMR (4:1 $CDCl_3$-$CD_3OD$): δ 7.21 (d, 1H), 7.04 (d, 1H), 6.94 (d, 1H), 6.85 (s, 1H), 3.44 (m, 2H), 3.40 (s, 2H), 3.32 (s, 3H), 1.10-1.90 (m, 20H) ppm; HPLC-MS: m/z 434 (M+1).

Example 231

{[2-(3,3-Dicyclohexylureido)-thiazole-5-carbonyl]-amino}acetic acid methyl ester

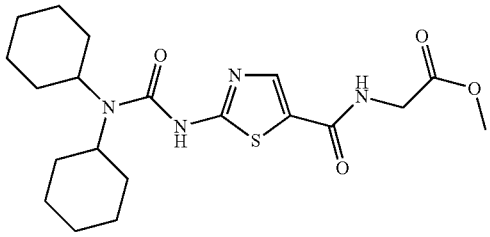

Prepared in 75% yield as described in general procedure (K) using 2-(3,3-dicyclohexylureido)-thiazole-5-carboxylic acid and glycine methyl ester hydrochloride $^1$H NMR (4:1 $CDCl_3$-$CD_3OD$): δ 8.06 (s, 1H), 7.65 (s, 1H), 4.24 (d, 2H), 3.80 (s, 3H), 3.46 (br, 2H), 1.10-1.90 (m, 20H) ppm; HPLC-MS: m/z 423 (M+1). .

Example 232

1-{[2-(3,3-Dicyclohexylureido)-thiazole-5-carbonyl]-amino}cyclopropanecarboxylic acid ethyl ester

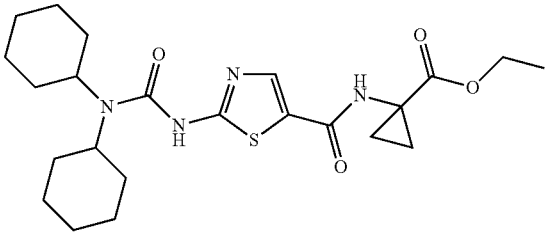

Prepared in 82% yield as described in general procedure (K) using 2-(3,3-dicyclohexylureido)-thiazole-4-carboxylic acid and 1-aminocyclopropane-1-carboxylic acid ethyl ester.

$^1$H NMR (d6-DMSO): δ 7.92 (s, 1H), 4.04 (q, 2H), 6.48 (d, 1H), 3.48 (m, 2H), 1.00-2.00 (m, 27H) ppm; HPLC-MS: m/z 463 (M+1).

Example 233

(S)-1-[2-(3,3-Dicyclohexylureido)-thiazole-5-carbonyl]-piperidine-3-carboxylic acid

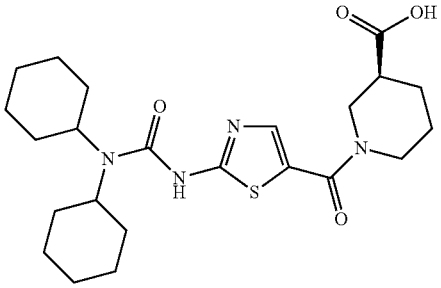

Prepared in 90% yield as described in general procedure (F) by hydrolysis of (S)-1-[2-(3,3-dicyclohexylureido)-thiazole-5-carbonyl]-piperidine-3-carboxylic acid ethyl ester (Example 234).

$^1$H NMR (d6-DMSO): δ 7.64 (s, 1H), 4.20 (d, 1H), 3.95 (d, 1H), 3.40 (m, 2H), 3.10 (m, 1H), 1.15-1.90 (m, 26H) ppm; HPLC-MS: m/z 463 (M+1).

Example 234

(S)-1-[2-(3,3-Dicyclohexylureido)-thiazole-5-carbonyl]-piperidine-3-carboxylic acid ethyl ester

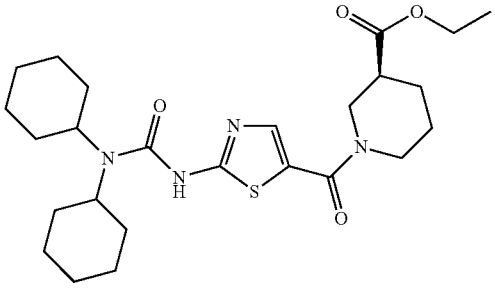

Prepared in 98% yield (120 mg) as described in general procedure (K) using 2-(3,3-dicyclohexylureido)-thiazole-4-carboxylic acid and (S)-nipecotic acid ethyl ester.

$^1$H NMR (4:1 $CDCl_3$-$CD_3OD$): δ 7.64 (s, 1H), 4.10 (d, 1H), 4.06 (q, 2H), 3.95 (d, 1H), 3.45 (m, 2H), 3.20 (t, 1H), 1.35-1.90 (m, 20H), 1.15 (t, 3H) ppm: HPLC-MS: m/z 491 (M+1).

Example 235

{[2-(3,3-Dicyclohexylureido)-thiazole-5-carbonyl]-amino}-acetic acid

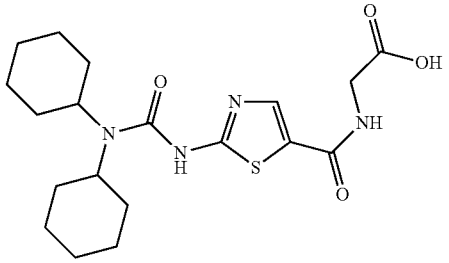

Prepared in 90% yield as described in general procedure (F) by hydrolysis of {[2-(3,3-dicyclohexylureido)-thiazole-5-carbonyl]-amino}acetic acid methyl ester (Example 231).

HPLC-MS: m/z 409 (M+1).

Example 236

3-{[2-(3,3-Dicyclohexylureido)-thiazole-5-carbonyl]-amino}-benzoic acid methyl ester

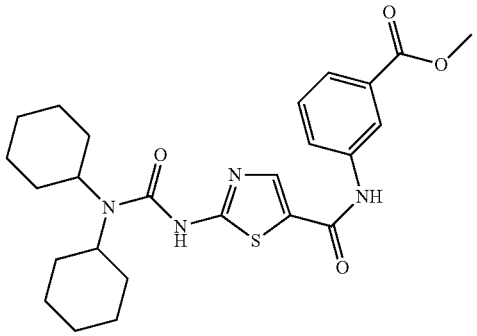

Prepared in 21% yield as described in general procedure (K) using 2-(3,3-dicyclohexylureido)-thiazole-4-carboxylic acid and methyl-3-amino benzoate.

$^1$H NMR (d6-DMSO: δ 8.60 (t, 1H), 7.94 (m, 2H), 7.70 (d, 1H), 7.50 (t, 1H), 7.40 (t, 1H), 3.60 (s, 3H), 3.46 (m, 2H), 1.15-1.90 (m, 20H) ppm; HPLC-MS: m/z 485 (M+1).

Example 237

3-(5-Bromothiazol-2-yl)-1,1-bis-4-methylcyclohexyl)urea

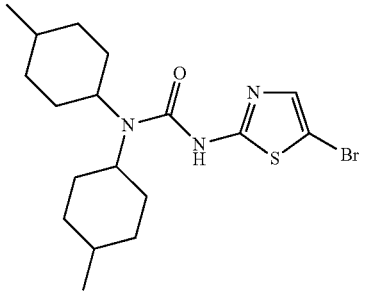

Prepared in 52% yield as described in general procedure (C) using bis(4-methylcyclohexyl)amine and 2-amino-5-bromothiazole.

$^1$H NMR (4:1 $CDCl_3$-$CD_3OD$): δ 7.95 (br, 1H), 7.24 (s, 1H), 3.46 (m, 2H), 1.15-1.90 (m, 18H), 0-95-1.10 (two d, 6H) ppm; HPLC-MS: m/z 415 (M+1).

Example 238

{2-[3,3-Bis(4-methylcyclohexyl)ureideo]thiazole-5-ylsulfanyl}acetic acid methyl ester

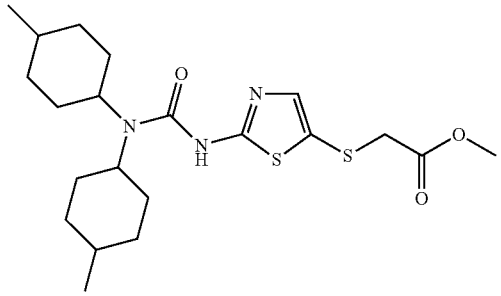

Prepared in 41% yield as described in general procedure (D) using 3-(5-bromothiazol-2-yl)-1,1-bis-4-methylcyclohexyl)urea (Example 237) and methylthioglycolate.

$^1$H NMR ($CDCl_3$): δ 8.16 (br, 1H), 7.35 (s, 1H), 3.70 (s, 3H), 3.5 (m, 2H), 1.15-1.90 (m, 18H), 0.91-1.05 (two d, 6H) ppm; HPLC-MS: m/z 440 (M+1).

Example 239

{2-[3,3-Bis(4-methylcyclohexyl)ureideo]thiazole-5-ylsulfanyl}acetic acid

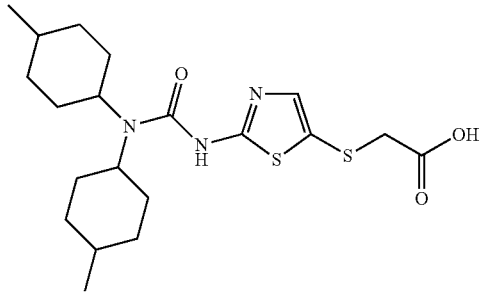

Prepared in 85% yield as described in general procedure (F) from {2-[3,3-bis(4-methylcyclohexyl)ureideo]thiazole-5-ylsulfanyl}acetic acid methyl ester (Example 238).

$^1$H NMR ($CDCl_3$): δ 8.20 (br, 1H), 7.4 (s, 1H), 3.72 (s, 3H), 3.4 (s, 2H), 3.30 (m, 2H), 1.15-1.90 (m, 18H), 0.90-1.05 (two d, 6H) ppm; HPLC-MS: m/z 426 (M+1).

Example 240

[2-(3,3-Dicyclohexylureido)thiazol-5-ylmethylsulfanyl]acetic acid methyl ester

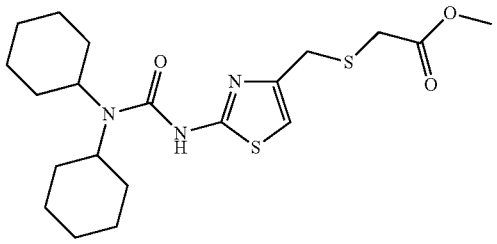

Prepared as described in general procedure (K) from 1,1-dicyclohexyl-3-(4-bromomethyl-thiazol-2-yl)urea and methyl thioglycolate.

HPLC-MS: m/z 426 (M+1).

Example 241

3-{[2-(3,3-Dicyclohexylureido)-thiazole-5-carbonyl]-amino}-propionic acid ethyl ester

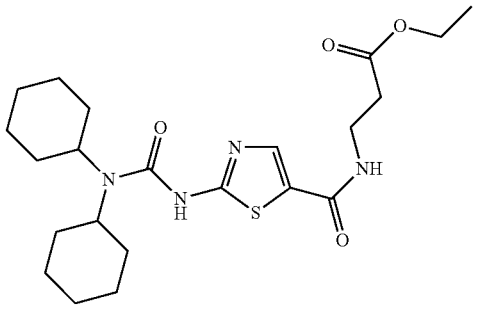

Prepared in 21% yield as described in general procedure (K) using 2-(3,3-dicyclohexylureido)-thiazole-4-carboxylic acid and beta-alanine ethyl ester hydrochloride.

HPLC-MS: m/z 451 (M+1).

Example 242

3-(5-Bromothiazol-2-yl)-1-cyclohexyl-1-(4-methylcyclohexyl)-urea

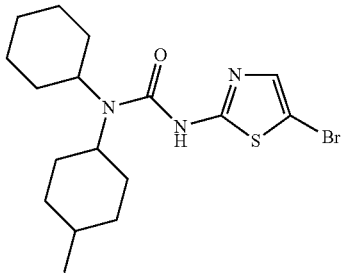

Prepared as described in general procedure (C) using 4-methylcyclohexyl-cyclohexylamine and 2-amino-5-bromothiazole.

$^1$H NMR ($CDCl_3$): δ 8.0 (s, 1H), 7.25 (s, 1H), 6.48 (d, 1H), 3.48 (m, 2H), 1.15-1.90 (m, 19H), 0.88-1.05 (two d, 3H) ppm; HPLC-MS: m/z 401 (M+1).

Example 243

3-{2-[[3,3-Bis(4-methylcyclohexyl)ureideo]thiazole-5-ylsulfanyl}propionic acid methyl ester

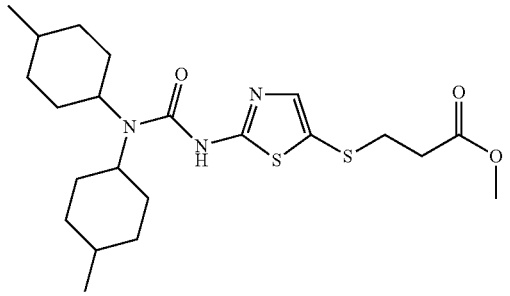

Prepared in 20% yield as described in general procedure (D) using 3-(5-bromothiazol-2-yl)-1,1-his-4-methylcyclohexyl)urea (Example 237) and 3-mercapaptoproionic acid methyl ester.

$^1$H NMR ($CDCl_3$): δ 8.16 (br, 1H), 7.35 (s, 1H), 3.70 (s, 3H), 3.5 (m, 2H), 2.92 (t, 2H), 2.61 (t, 2H), 1.15-1.90 (m, 18H), 0.91-1.05 (2d, 6H) ppm; HPLC-MS: m/z 454 (M+1).

Example 244

3-{2-[3,3-Bis(4-methylcyclohexyl)ureideo]thiazole-5-ylsulfanyl}propionic acid

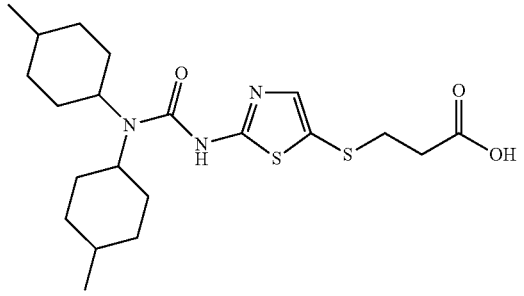

Prepared in 85% yield as described in general procedure (F) by hydrolysis of 3-{2-[[3,3-bis(4-methylcyclohexyl)ureideo]thiazole-5-ylsulfanyl}propionic acid methyl ester.

$^1$H NMR ($CDCl_3$): δ 7.27 (s, 1H), 3.75 (d, 2H), 3.0 (m, 2H), 2.26 (t, 2H), 1.15-1.90 (m, 18H), 0.91-1.05 (two d, 6H) ppm; HPLC-MS: m/z 440 (M+1).

Example 245

4-{2-[3,3-Bis(4-methylcyclohexyl)ureideo]thiazole-5-ylsulfanyl}benzoic acid ethyl ester

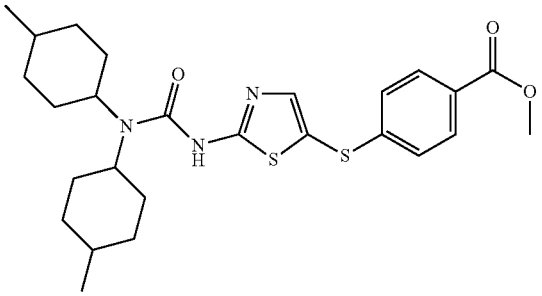

Prepared as described in general procedure (E) using 3-(5-bromothiazol-2-yl)-1,1-bis-4-methylcyclohexyl)urea (Example 237) and 4-mercapto-benzoic acid methyl ester.

$^1$H NMR ($CDCl_3$): δ 8.10 (br, 1H), 7.89 (s, 1H), 7.87 (s, 1H), 7.53 (t, 1H), 7.21 (s, 1H), 7.19 (s, 1H), 3.58 (s, 3H), 3.46 (m, 2H), 1.15-2.00 (m, 18H), 0.93-1.05 (two d, 6H) ppm; HPLC-MS: m/z 502 (M+1).

Example 246

2-{-2-[3-Cyclohexyl-3-(4-methyl-cyclohexyl)-ureido]-thiazol-5-ylsulfanyl}-3-methyl-3H-imidazole-4-carboxylic acid ethyl ester

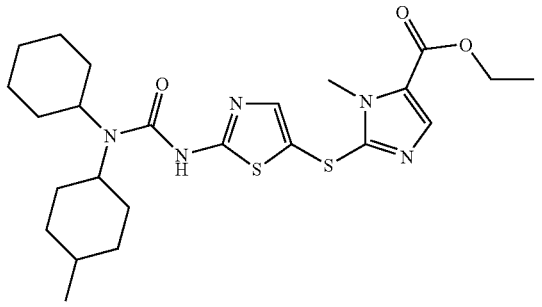

Prepared as described in general procedure (E) from 3-(5-bromothiazol-2-yl)-1-cyclohexyl-1-(4-methylcyclohexyl)-urea (Example 242) and 2-mercapto-3-methyl-3H-imidazole-4-carboxylic acid ethyl ester.

$^1$H NMR (4:1 $CDCl_3$-$CD_3OD$): δ 7.69 (s, 1H), 7.57 (s, 1H), 4.31 (q, 2H), 4.0 (s, 3H), 3.38 (m, 2H), 1.15-1.90 (m, 19H), 1.35 (t, 3H), 0.90-1.10 (two d, 3H) ppm; HPLC-MS: m/z 506 (M+1).

Example 247

{2-[3-Cyclohexyl-3-(4-methylcyclohexyl)ureideo]thiazol-5-ylsulfanyl}acetic acid methyl ester

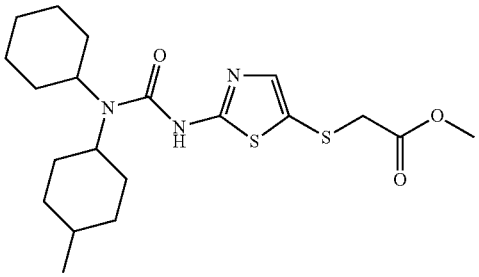

Prepared as described in general procedure (E) using 3-(5-bromothiazol-2-yl)-1-cyclohexyl-1-(4-methylcyclohexyl)-urea (Example 242) and methyl thioglycolate.

$^1$H NMR ($CDCl_3$): δ 7.43 (s, 1H), 7.48 (s, 1H), 3.77 (s, 3H), 3.79 (d, 1H), 3.50 (d, 1H), 3.46 (m, 2H). 1.15-1.90 (m, 19H) ppm: 0.90-1.05 (two d, 3H) ppm; HPLC-MS: m/z 426 (M+1).

Example 248

3-{[2-(3,3-Dicyclohexylureido)-thiazole-5-carbonyl]-amino}-propionic acid

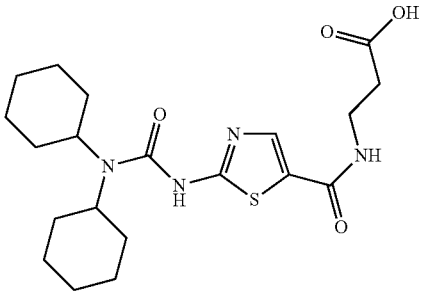

Prepared in 90% yield as described in general procedure (F) from 3-{[2-(3,3-dicyclohexyl-ureido)-thiazole-5-carbonyl]-amino}-propionic acid methyl ester (Example 241).

$^1$H NMR (d6-DMSO): δ 7.80 (s, 1H), 7.67 (s, 1H), 3.56 (t, 2H), 3.46 (m, 2H), 2.76 (t, 2H), 1.15-1.90 (m, 20H) ppm; HPLC-MS: m/z 423 (M+1).

Example 249

4-{2-[3,3-Bis(4-methylcyclohexyl)ureideo]thiazole-5-ylsulfanyl}benzoic acid

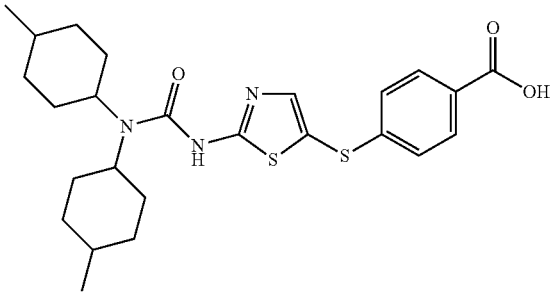

Prepared in 80% yield as described in general procedure (F) from 4-{2-[3,3-bis(4-methylcyclohexyl)ureideo]thiazole-5-ylsulfanyl}benzoic acid ethyl ester (Example 245).

$^1$H NMR ($d_6$-acetone): δ 7.84 (d, 2H), 7.35 (s, 1H), 7.18 (d, 2H), 3.40 (m, 2H), 1.15-1.90 (m, 18H), 0.95-1.05 (two d, 6H) ppm; HPLC-MS: m/z 488 (M+1).

Example 250

{2-[3-Cyclohexyl-3-(4-methylcyclohexyl)ureideo]thiazol-5-ylsulfanyl}acetic acid

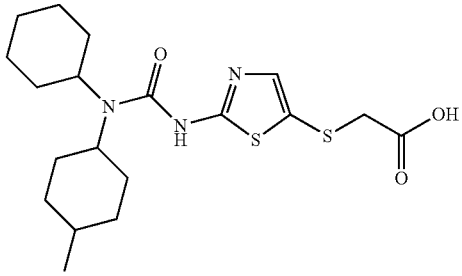

Prepared in 88% yield as described in general procedure (F) from {2-[3-cyclohexyl-3-(4-methylcyclohexyl)ureideo]thiazol-5-ylsulfanyl}acetic acid methyl ester (Example 247).

$^1$H NMR (4:1 $CDCl_3$- $CD_3OD$): δ 7.39 (s, 1H), 7.06 (s, 1H), 3.38 (obscured by MeOH peak), 1.15-1.90 (m, 19H), 0.95-1.05 (two d, 3H) ppm; HPLC-MS: m/z 412 (M+1).

Example 251

2-{-2-[3-Cyclohexyl-3-(4-methyl-cyclohexyl)-ureido]-thiazol-5-ylsulfanyl}-3-methyl-3H-imidazole-4-carboxylic acid

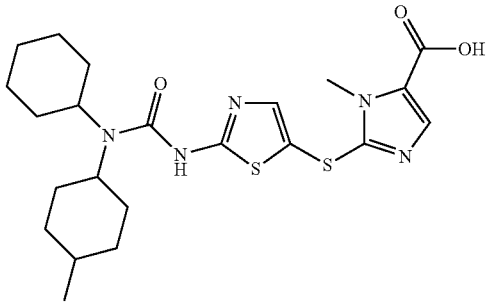

Prepared in 80% yield as described in general procedure (F) from 2-{-2-[3-cyclohexyl-3-(4-methyl-cyclohexyl)-ureido]-thiazol-5-ylsulfanyl}-3-methyl-3H-imidazole-4-carboxylic acid ethyl ester (Example 246). $^1$H NMR (4:1 $CDCl_3$-$CD_3OD$): δ 7.80 (s, 1H), 7.56 (s, 1H), 4.00 (s, 3H), 3.36 (m, 2H), 1.15-1.90 (m, 19H), 0.95-1.05 (two d, 3H) ppm; HPLC-MS: m/z 478 (M+1)

Example 252

1,1-Dicyclohexyl-3-5-formyl-thiazol-2-yl)-urea

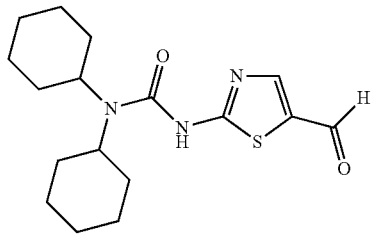

2-Amino-5-formylthiazole (215 mg, 1.67 mmol), carbonyldiimidazole (275 mg, 1.70 mmol) and a catalytic amount of DMAP were heated together in 5 mL THF at 40° C. for 2 h. To this solution was added dicyclohexylamine (0.34 mL, 1.70 mmol) and the reaction mixture was stirred for an additional 6 h at room temperature. The reaction mixture was concentrated and the crude product was purified by flash chromatography (silica, $CH_2Cl_2$-EtOAc, 4:1) to obtain 1,1-dicyclohexyl-3-(5-formyl-thiazol-2-yl)-urea.

HPLC-MS: m/z 336 (M+1).

Example 253

2-(3,3-Dicyclohexyl-ureido)-thiazole-5-carboxylic acid methoxy-methylamide

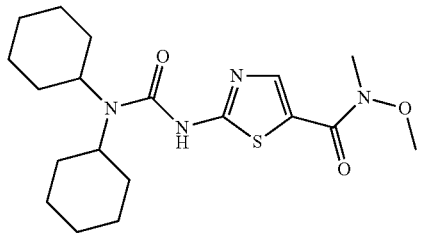

Prepared as described in general procedure (K) using 2-(3,3-dicyclohexyl-ureido)-thiazole-5-carboxylic acid and methoxy methylamine.

HPLC-MS: m/z 395 (M+1).

Example 254

1,1-Dicyclohexyl-3-[5-(pyrrolidine-1-carbonyl)-thiazol-2-yl]-urea

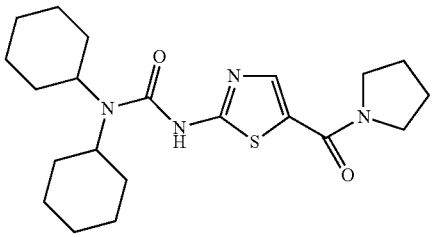

Prepared as described in general procedure (K) using 2-(3,3-dicyclohexyl-ureido)-thiazole-5-carboxylic acid and pyrrolidine.

HPLC-MS: m/z 405 (M+1).

Example 255

(4-{[2-(3,3-Dicyclohexyl-ureido)-thiazole-5-carbonyl]-amino}-phenyl)-acetic acid ethyl ester

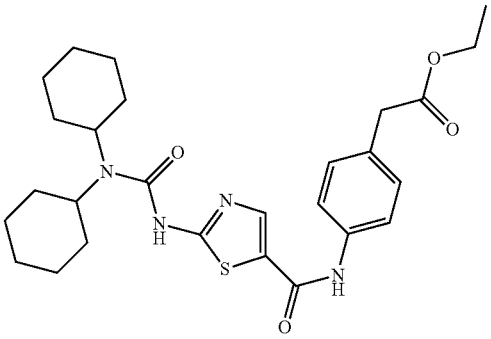

Prepared as described in general procedure (K) using 2-(3,3-dicyclohexyl-ureido)-thiazole-5-carboxylic acid and 4-aminophenylacetic acid ethylester.

HPLC-MS: m/z 513 (M+1).

Example 256

(4-{[2-(3,3-Dicyclohexyl-ureido)-thiazole-5-carbonyl]-amino}-phenyl)-acetic acid

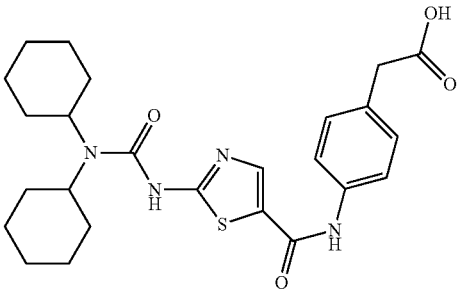

Prepared in 80% yield as described in general procedure (F) from (4-{[2-(3,3-dicyclohexyl-ureido)-thiazole-5-carbonyl]-amino}-phenyl)-acetic acid ethyl ester (Example 255).

HPLC-MS: m/z 483 (M+1).

Example 257

3-[2-(3,3-Dicyclohexylureido)-thiazol-5-yl]-acrylic acid ethyl ester

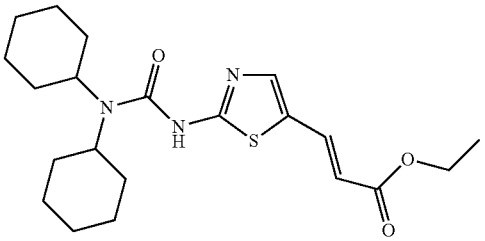

A solution of 1,1-dicyclohexyl-3-(5-formyl-thiazol-2-yl)-urea (Example 252) (90 mg, 0.27 mmol) and (carbethoxymethylene)triphenylphosphorane (102 mg, 0.30 mmol) in THF (5 mL) was stirred at 40° C. for 12 h. The reaction mixture was concentrated and the residue was purified by flash chromatography (silica, $CH_2Cl_2$-EtOAc, 4:1) to obtain 3-[2-(3,3-dicyclohexylureido)-thiazol-5-yl]-acrylic acid ethyl ester (75 mg) in 69% yield.

HPLC-MS: m/z 406 (M+1).

Example 258

3-[2-(3,3-Dicyclohexylureido)-thiazol-5-yl]-propionic acid ethyl ester

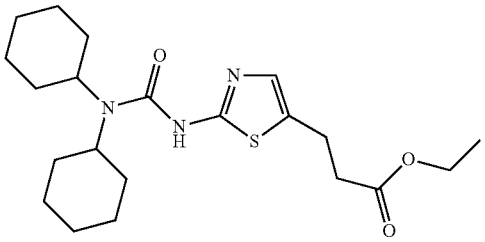

To a solution of 3-[2-(3,3-dicyclohexylureido)-thiazol-5-yl]-acrylic acid ethyl ester (Example 257) (75 mg, 0.18 mmol) in methanol was added Pd/C (150 mg). The content was degassed and was placed under hydrogen atmosphere for 12 h. The mixture was filtered through celite, and the filtrate was concentrated. The residue was further purified by flash chromatography (silica, $CH_2Cl_2$-EtOAc 4:1 to give 3-[2-(3,3-dicyclohexylureido)-thiazol-5-yl]-propionic acid ethyl ester (35 mg) in 47% yield.

HPLC-MS: m/z 408 (M+1).

Example 259

3-[2-(3,3-Dicyclohexylureido)1-thiazol-5-yl]-propionic acid

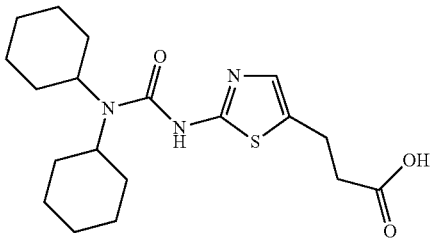

Prepared as described in general procedure (F) from 3-[2-(3,3-dicyclohexylureido)-thiazol-5-yl]-propionic acid ethyl ester (Example 258).

HPLC-MS: m/z 380 (M+1).

Example 260

1,1-Dicyclohexyl-3-(5-methylisoxazol-3-yl)urea

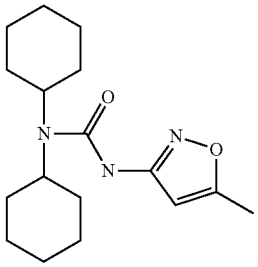

Prepared as described in general procedure (A) using dicyclohexylamine and 3-amino-5-methylisoxazole HPLC-MS: m/z=306 (M+1).

Example 261

{2-[3-(1-Acetyl-piperidin-4-yl)-3-cycloheptyl-ureido]-thiazol-5-ylsulfanyl}-acetic acid

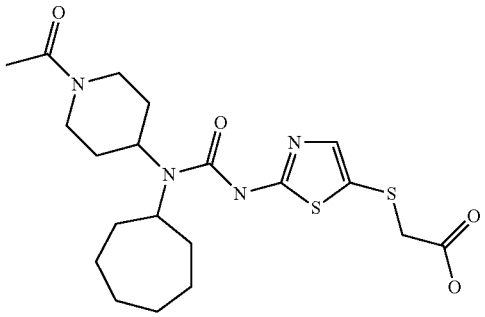

Prepared as described in general procedure (G) using 1-(4-cycloheptylamino-piperidin-1-yl)-ethanone and 5-aminothiazol-2-mercaptoacetic acid ethyl ester.

HPLC-MS: m/z=455 (M+1)

Example 262

{2-[3-(1-Acetyl-piperidin-4-yl)-3-(4-methyl-cyclohexyl)-ureido]-thiazol-5-ylsulfanyl}-acetic acid

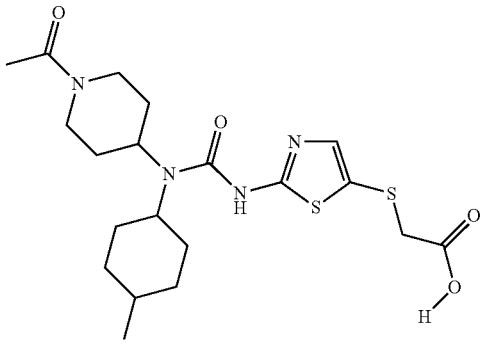

Prepared as described in general procedure (G) using 1-[4-(4-methyl-cyclohexylamino)-piperidin-1-yl]-ethanone and 5-aminothiazol-2-mercaptoacetic acid ethyl ester.

HPLC-MS: m/z=455 (M+1)

Example 263

{2-[3-(1-Acetyl-piperidin-4-yl)-3-cyclopentyl-ureido]-thiazol-5-ylsulfanyl}-acetic acid

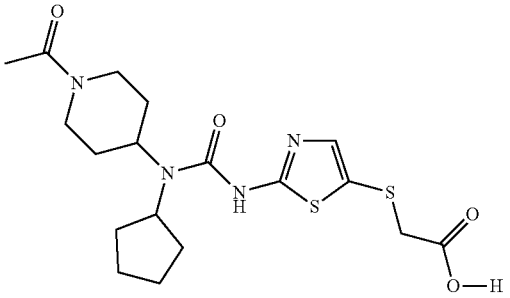

Prepared as described in general procedure (G) using 1-(4-cyclopentylamino-piperidin-1-yl)-ethanone and 5-aminothiazol-2-mercaptoacetic acid ethyl ester.

HPLC-MS: m/z=427 (M+1)

Example 264

1-(1-Acetyl-piperidin-4-yl)-1-(4-methyl-cyclohexyl)-3-thiazol-2-yl-urea

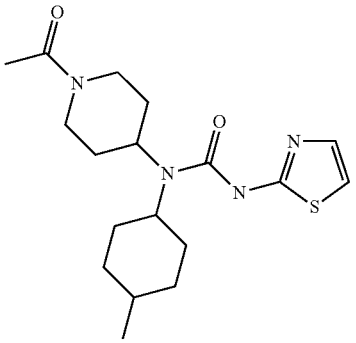

Prepared as described in general procedure (G) using 1-[4-(4-methyl-cyclohexylamino)-piperidin-1-yl]-ethanone and 2-aminothiazole.

HPLC-MS: m/z=365 (M+1)

Example 265

1-(1-Acetyl-piperidin-4-yl)-3-(5-chloro-thiazol-2-yl)-1-(4-methyl-cyclohexyl)-urea

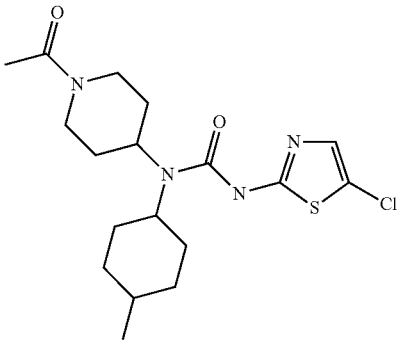

Prepared as described in general procedure (G) using 1-[4-(4-methyl-cyclohexylamino)-piperidin-1-yl]-ethanone and 2-amino-5-chlorothiazole.

HPLC-MS: m/z=399 (M+1)

Example 266

1,1-Dicyclohexyl-3-(5-methyl-4,5,6,7-tetrahydro-thiazolo[5,4-c]pyridin-2-yl)-urea

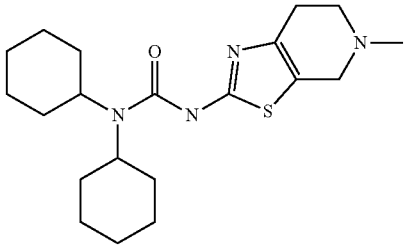

Prepared as described in general procedure (A) using dicyclohexylamine and 2-amino-5-methyl-4,5,6,7-tetrahydrothiazolo(5,4-c)pyridine HPLC-MS: m/z=378 (M+1)

Example 267

1,1-Dicyclohexyl-3-(6,7-dihydro-4H-pyrano[4,3-d]thiazol-2-yl)-urea

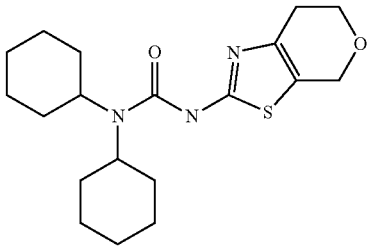

Step 1. Preparation of precursor 6,7-dihydro-4H-pyrano[4,3-d]thiazol-2-ylamine. To 4-ketotetrahydropyran (4.1 g) in ether (15 mL) at ice bath temperature was added bromine (6.5 g), dropwise over 30 min. After 20 min was added ethyl acetate and sodium carbonate. The aqueous phases was separated and extracted with ethyl acetate. The combined organic phases were dried over magnesium sulfate and concentrated in vacuo, redissolved in ethanol, and thiourea (2.8 g) was added. The mixture was warmed to reflux for 1 h, cooled and the desired product was isolated by filtration and washed with ether, dried in vacuo, and used directly in Step 2.

Step 2. Urea coupling as described in general procedure (C) gave the title compound.

HPLC-MS: m/z=365 (M+1)

Example 268

3-(5-Chloro-thiazol-2-yl)-1-cyclohexyl-1-(1-methanesulfonyl-piperidin-3-yl)-urea

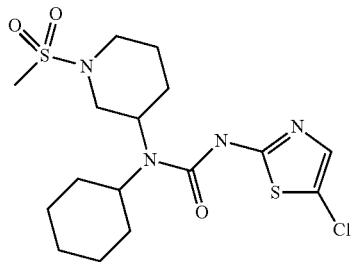

Prepared from 3-amino-1-Boc-piperidine, cyclohexanone and 2-amino-5-chlorothiazole as described in general procedure (G).

HPLC-MS: m/z=422 (M+1)

Example 269

(2-{3-Cyclohexyl-3-[1-(2,2-dimethyl-propionyl)-pyrrolidin-3-yl]-ureido}-thiazol-5-ylsulfanyl)-acetic acid

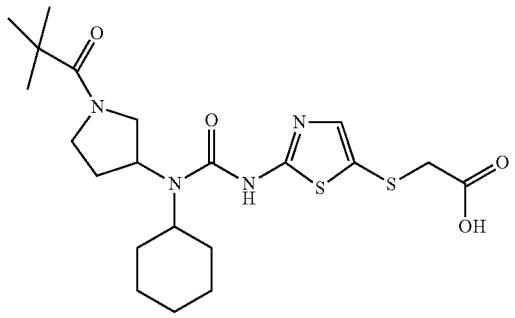

Prepared from 3-amino-1-Boc-pyrrolidine, cyclohexanone and 5-aminothiazol-2-mercaptoacetic acid ethyl ester as described in general procedure (G).

HPLC-MS: m/z=469 (M+1)

Example 270

{2-[3-Cyclohexyl-3-(1-cyclopentanecarbonyl-pyrrolidin-3-yl)-ureido]-thiazol-5-ylsulfanyl}-acetic acid

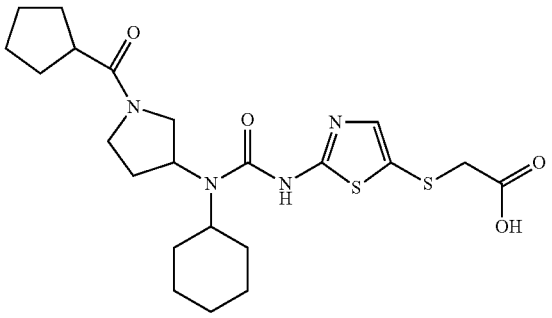

Prepared from 3-amino-1-Boc-pyrrolidine, cyclohexanone and 5-aminothiazol-2-mercaptoacetic acid ethyl ester as described in general procedure (G).

HPLC-MS : m/z=481 (M+1)

Example 271

(2-{3-Cyclohexyl-3-[1-(thiophene-2-carbonyl)-pyrrolidin-3-yl]-ureido}-thiazol-5-ylsulfanyl)-acetic acid

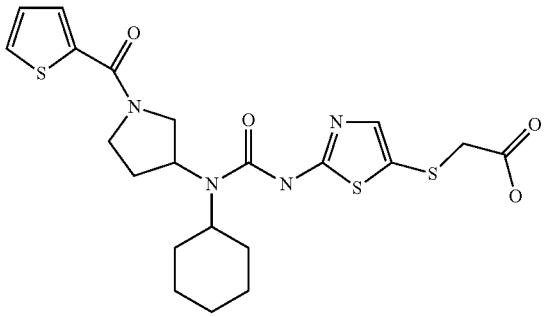

Prepared from 3-amino-1-Boc-pyrrolidine, cyclohexanone and 5-aminothiazol-2-mercaptoacetic acid ethyl ester as described in general procedure (G).

HPLC-MS: m/z=495 (M+1)

Example 272

{2-[3-(1-Benzoyl-pyrrolidin-3-yl)-3-cyclohexyl-ureido]-thiazol-5-ylsulfanyl}-acetic acid

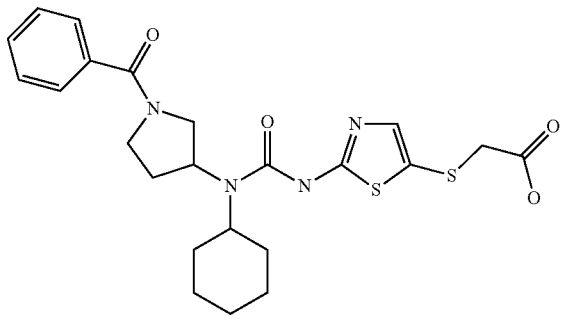

Prepared from 3-amino-1-Boc-pyrrolidine, cyclohexanone and 5-aminothiazol-2-mercaptoacetic acid ethyl ester as described in general procedure (G).

HPLC-MS: m/z=489 (M+1).

Example 273

(2-{3-Cyclohexyl-3-[1-(pyridine-3-carbonyl)-pyrrolidin-3-yl]-ureido}-thiazol-5-ylsulfanyl)-acetic acid

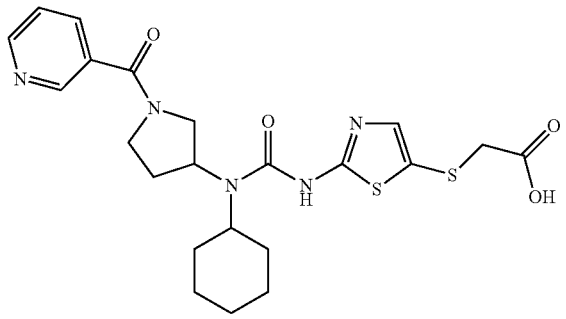

Prepared from 3-amino-1-Boc-pyrrolidine, cyclohexanone and 5-aminothiazol-2-mercaptoacetic acid ethyl ester as described in general procedure (G).

HPLC-MS: m/z=490 (M+1)

Example 274

2-[5-(3,3-Dicyclohexyl-ureido)-[1,3,4]thiadiazol-2-ylsulfanyl]-2-methyl-propionic acid

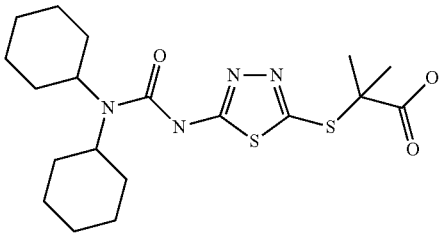

Prepared as described in general procedure (A) using dicyclohexylamine and tert-butyl 2-[(5-amino-1,3,4-thiadiazol-2-yl)thio]-2-methylpropanoate.

HPLC-MS: m/z=427 (M+1)

Example 275

N-{4-[3-(5-Chloro-thiazol-2-yl)-1-cyclohexyl-ureido]-cyclohexyl}-acetamide

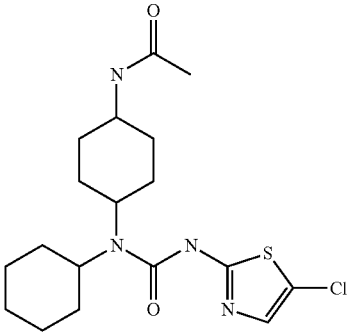

Prepared from N-Boc-aminocyclohexanone, cyclohexylamine and 5-chloro-2-aminothiazole using general procedure (G).

HPLC-MS: m/z=399 (M+1)

Example 276

N-{4-[3-(5-Chloro-thiazol-2-yl)-1-cyclohexyl-ureido]-cyclohexyl}-methanesulfonamide

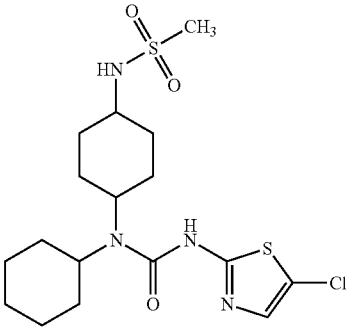

Prepared from N-Boc-aminocyclohexanone, cyclohexylamine and 5-chloro-2-aminothiazole using general procedure (G).

HPLC-MS: m/z=435 (M+1)

Example 277

1-(1-Acetyl-piperidin-3-yl)-3-(5-chloro-thiazol-2-yl)-1-cyclohexyl-urea

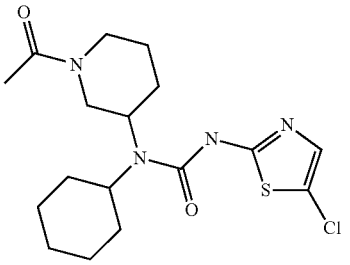

Prepared from 3-amino-1-Boc-piperidine, cyclohexanone and 5-chloro-2-aminothiazole using general procedure (G) as described in general procedure (G).

HPLC-MS: m/z=384 (M+)

Example 278

1-(1-Acetyl-piperidin-3-yl)-1-cyclohexyl-3-(5-methyl-thiazol-2-yl)-urea

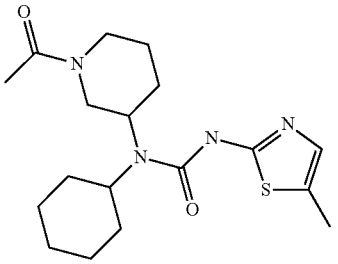

Prepared from 3-amino-1-Boc-piperidine, cyclohexanone and 5-methyl-2-aminothiazole using general procedure (G) as described in general procedure (G).

HPLC-MS: m/z=366 (M+1)

Example 279

1-(1-Acetyl-piperidin-3-yl)-1-cyclohexyl-3-thiazol-2-yl-urea

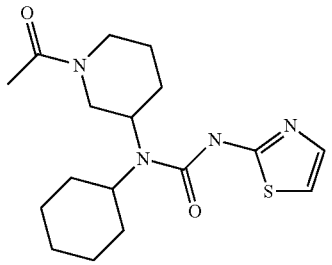

Prepared from 3-amino-1-Boc-piperidine, cyclohexanone and 2-aminothiazole using general procedure (G) as described in general procedure HPLC-MS: m/z=351 (M+1)

Example 280

{2-[3-(1-Acetyl-piperidin-4-yl)-3-cyclohexyl-ureido]-5-methyl-thiazol-4-yl}-acetic acid ethyl ester

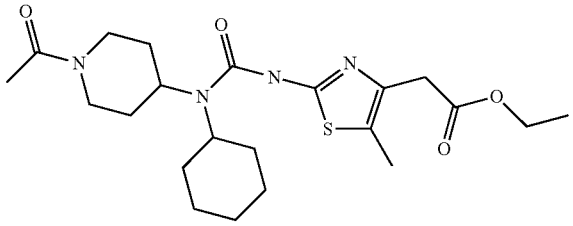

Prepared from 3-amino-1-Boc-piperidine, cyclohexanone and 5-methyl-(2-amino-4-thiazolyl)acetic acid ethyl ester using general procedure (G).

HPLC-MS: m/z=451 (M+1)

Example 281

{2-[3-(1-Acetyl-piperidin-4-yl)-3-cyclohexyl-ureido]-5-chloro-thiazol-4-yl}-acetic acid ethyl ester

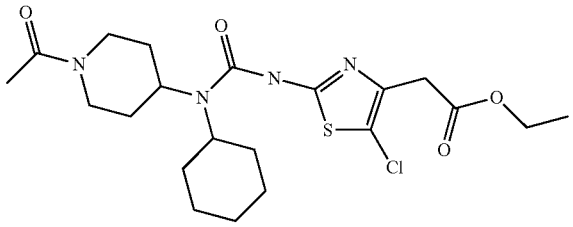

Prepared from 3-amino-1-Boc-piperidine, cyclohexanone and 5-chloro-(2-amino-4-thiazolyl)acetic acid ethyl ester using general procedure (G).

HPLC-MS: m/z=471 (M+1)

Example 282

N-[4-(1-Cyclohexyl-3-thiazol-2-yl-ureido)-cyclohexyl]-acetamide

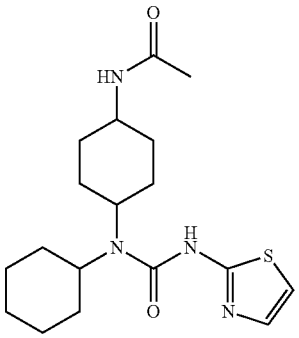

Prepared from N-Boc-aminocyclohexanone, cyclohexylamine and 2-aminothiazole using general procedure (G).

HPLC-MS: m/z=365 (M+1)

Example 283

N-[4-(1-Cyclohexyl-3-thiazol-2-yl-ureido)-cyclohexyl]-methanesulfonamide

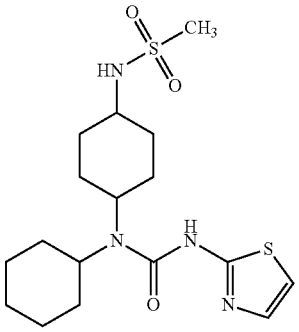

Prepared from N-Boc-aminocyclohexanone, cyclohexylamine and 2-aminothiazole using general procedure (G).

HPLC-MS: m/z=401 (M+1)

Example 284

1-(1-Acetyl-piperidin-4-yl)-1-cyclohexyl-3-[4-methyl-5-(4-methyl-piperazine-1-sulfonyl)-thiazol-2-yl]-urea

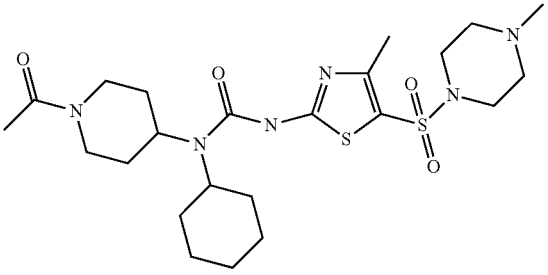

Prepared as described for Example 173 using 4-methyl-5-(4-methyl-piperazine-1-sulfonyl)-thiazol-2-ylamine and 1-(4-cyclohexylamino-piperidin-1-yl)-ethanone.

HPLC-MS: m/z=527 (M+1)

Example 285

1-Cyclobutyl-1-cyclohexyl-3-thiazol-2-yl-urea

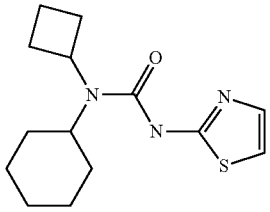

Prepared as described in general procedures (A) and (B) using cyclohexyl-cyclobutyl-amine and 2-aminothiazole HPLC-MS: m/z=281 (M+1).

Example 286

1-Cycloheptyl-1-cyclohexyl-3-thiazol-2-yl-urea

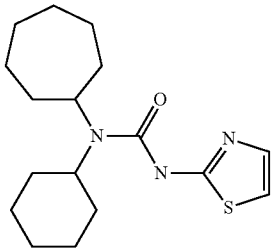

Prepared as described in general procedures (A) and (B) using cyclohexyl-cycloheptyl-amine and 2-aminothiazole HPLC-MS: m/z=322 (M+1).

Example 287

{2-[3-Cyclohexyl-3-(trans-4-methyl-cyclohexyl)-ureido]-thiazol-5-ylsulfanyl}-acetic acid

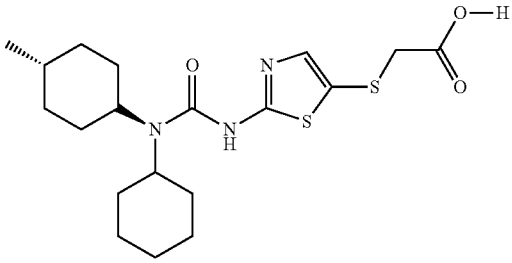

{2-[3-Cyclohexyl-3-(trans-4-methyl-cyclohexyl)-ureido]-thiazol-5-ylsulfanyl}-acetic acid ethyl ester was prepared as described in general procedures (A) and (B) using cyclohexyl-(trans-4-methyl-cyclohexyl)-amine and 5-aminothiazol-2 -mercaptoacetic acid ethyl ester. Hydrolysis using general procedure (F) gave the title compound.

HPLC-MS: m/z=412 (M+1).

Example 288

1-Cyclopentyl-3-(5-methyl-thiazol-2-yl)-1-(1-propionyl-piperidin-4-yl)-urea

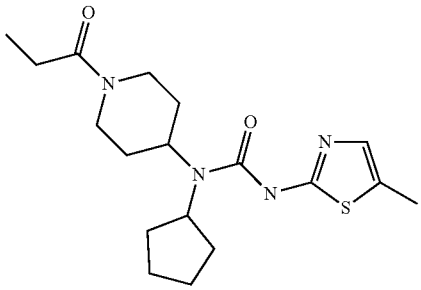

Prepared as described in general procedure (G) using 3-amino-1-Boc-piperidine, cyclopentnone and 2-amino-5-methylthiazole.

HPLC-MS: m/z=365 (M+1)

Example 289

1-(1-Butyryl-piperidin-4-yl)-1-cyclopentyl-3-(5-methyl-thiazol-2-yl)-urea

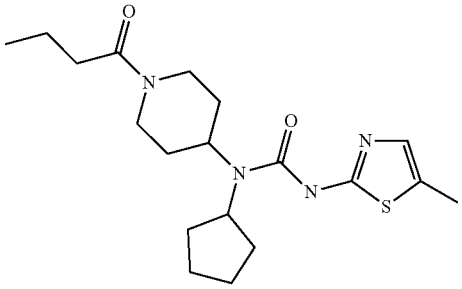

Prepared as described in general procedure (G) using 3-amino-1-Boc-piperidine, cyclopentnone and 2-amino-5-methylthiazole.

HPLC-MS: m/z=401 (M+Na)

Example 290

1-(1-Cyclopentanecarbonyl-piperidin-4-yl)-1-cyclopentyl-3-(5-methyl-thiazol-2-yl)-urea

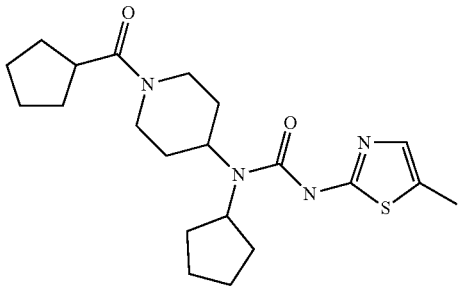

Prepared as described in general procedure (G) using 3-amino-1-Boc-piperidine, cyclopentnone and 2-amino-5-methylthiazole.

HPLC-MS: m/z=427 (M+Na)

Example 291

{2-[3-Cyclopentyl-3-(trans-4-methyl-cyclohexyl)-ureido]-thiazol-5-ylsulfanyl}-acetic acid

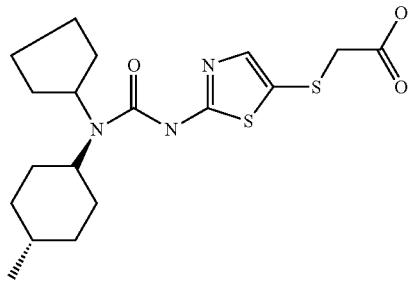

{2-[3-Cyclohexyl-3-(trans-4-methyl-cyclopentyl)-ureido]-thiazol-5-ylsulfanyl}-acetic acid ethyl ester was prepared as described in general procedures (A) and (B) using cyclopentyl-(trans-4-methyl-cyclohexyl)-amine and 5-aminothiazol-2 -mercaptoacetic acid ethyl ester. Hydrolysis using general procedure (F) gave the title compound.

HPLC-MS: m/z=398 (M+1).

Example 292

{2-[3-(1-Acetyl-piperidin-4-yl)-3-cyclohexyl-ureido]-5-methyl-thiazol-4-yl}-acetic acid

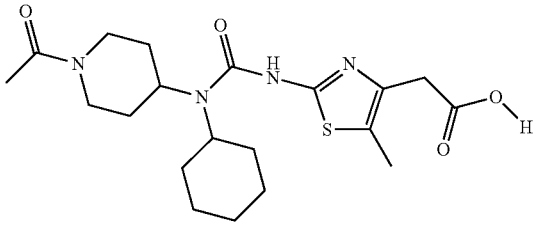

Prepared from 3-amino-1-Boc-piperidine, cyclohexanone and 5-methyl-(2-amino-4-thiazolyl)acetic acid ethyl ester using general procedure (G).

HPLC-MS: m/z=424 (M+1)

Example 293

{2-[3-(1-Acetyl-piperidin-4-yl)-3-cyclohexyl-ureido]-5-imidazol-1-yl-thiazol-4-yl}-acetic acid

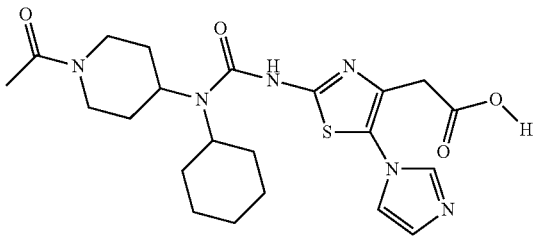

Prepared from 3-amino-1-Boc-piperidine, cyclohexanone and 5-methyl-(2-amino-4-thiazolyl)acetic acid ethyl ester using general procedure (G).

HPLC-MS: m/z=475 (M+1)

Example 294

{2-[3-(1-Acetyl-piperidin-4-yl)-3 -cyclohexyl-ureido]-5-chloro-thiazol-4-yl}-acetic acid

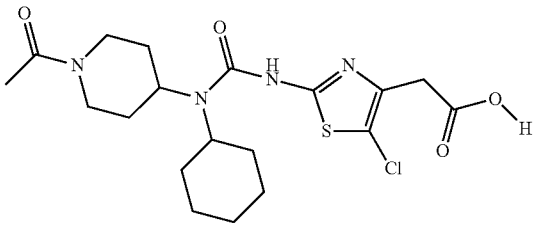

Prepared from 3-amino-1-Boc-piperidine, cyclohexanone and 5-chloro-(2-amino-4-thiazolyl)acetic acid ethyl ester using general procedure (G).

HPLC-MS: m/z=443 (M+1).

Example 295

1,1-Dicyclohexyl-3-[5-(2-dimethylamino-ethylsulfanyl)-4-methyl-thiazol-2-yl]-urea

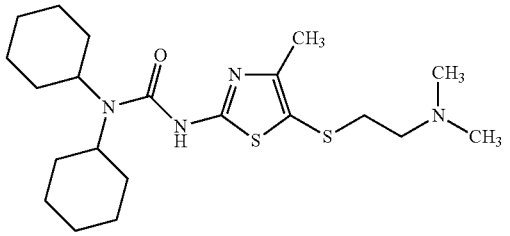

Prepared as described in general procedure (H) using 1,1-dicyclohexyl-3-(4-methyl-5-thiocyanato-thiazol-2-yl)-urea and dimethylaminoethylchloride.

HPLC-MS: m/z=425 (M+1)

Example 296

1,1-Dicyclohexyl-3-[5-(4-methyl-piperazine-1-sulfonyl)-thiazol-2-yl]-urea

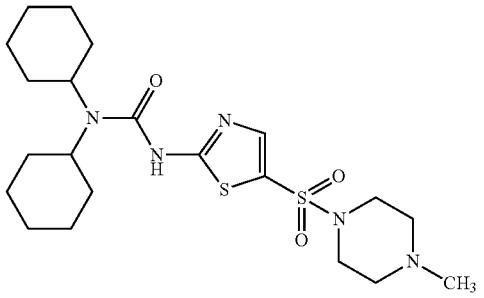

Prepared as described for Example 173 using 5-(4-methyl-piperazine-1-sulfonyl)-thiazol-2-ylamine and dicyclohexylamine.

HPLC-MS: m/z=527 (M+1)

Example 297

3-(5-Chloro-thiazol-2-yl)-1-cyclopentyl-1-(1-propionyl-piperidin-4-yl)-urea

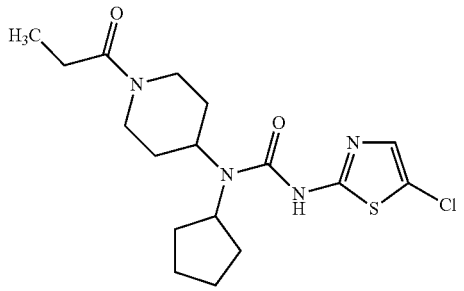

Prepared as described in general procedure (G) using 3-amino-1-Boc-piperidine, cyclopentnone and 2-amino-5-chlorothiazole HPLC-MS: m/z=385 (M+1)

Example 298

1-(1-Acetyl-piperidin-4-yl)-1-cyclohexyl-3-[5-(4-methyl-piperazine-1-sulfonyl)-thiazol-2-yl]-urea

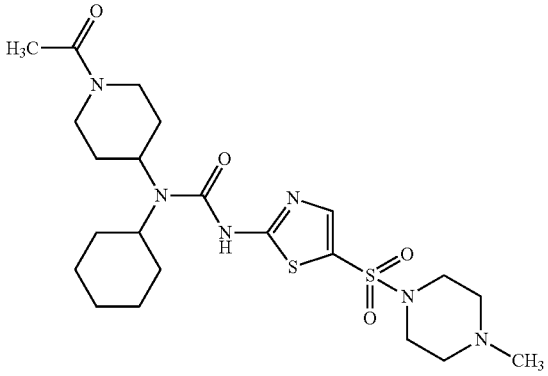

Prepared as described for Example 173 using 5-(4-methyl-piperazine-1-sulfonyl)-thiazol-2-ylamine and 1-(4-cyclohexylamino-piperidin-1-yl)-ethanone.

HPLC-MS: m/z=513 (M+1)

Example 299

1-(1-Acetyl-piperidin-4-yl)-3-(5-chloro-thiazol-2-yl)-1-(trans-4-methyl-cyclohexyl)-urea

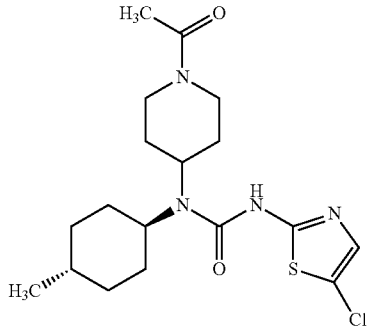

Prepared as described in general procedure (G) u sing 1-[4-(trans-4-methyl-cyclohexylamino)-piperidin-1-yl]-ethanone and 5-chloro-2-aminothiazole.

HPLC-MS: m/z=399 (M+1)

Example 300

{2-[3-(1-Acetyl-piperidin-4-yl)-3-(trans-4-methyl-cyclohexyl)-ureido]-thiazol-5-ylsulfanyl}-acetic acid

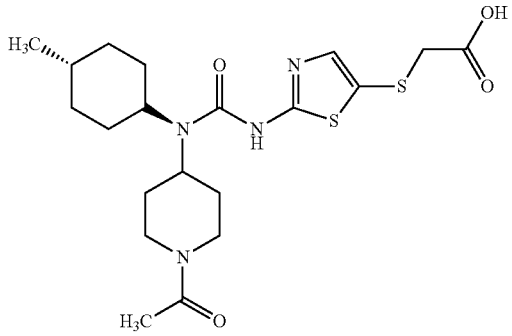

Prepared as described in general procedure (G) 1-[4-(trans-4-methyl-cyclohexylamino)-piperidin-1-yl]-ethanone and (2-amino-thiazol-5-ylsulfanyl)-acetic acid ethyl ester.

HPLC-MS: m/z=455 (M+1)

Example 301

2-(3,3-Dicyclohexyl-ureido)-5-methylsulfanyl-thiazole-4-carboxylic acid

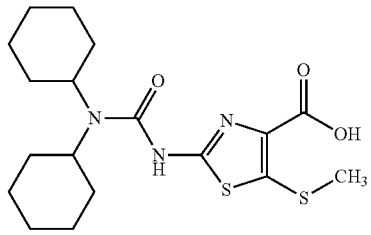

2-(3,3-Dicyclohexyl-ureido)-5-methylsulfanyl-thiazole-4-carboxylic acid ethyl ester was pre-pared as described in general procedure (H) using 2-(3,3-dicyclohexyl-ureido)-5-thiocyanato-thiazole-4-carboxylic acid ethyl ester and methyl iodide. Hydrolysis using general procedure (F) gave the title compound.

HPLC-MS: m/z=399 (M+1)

Example 302

1,1-Dicyclohexyl-3-[4-methyl-5-(2-piperidin-1-yl-ethylsulfanyl)-thiazol-2-yl]-urea

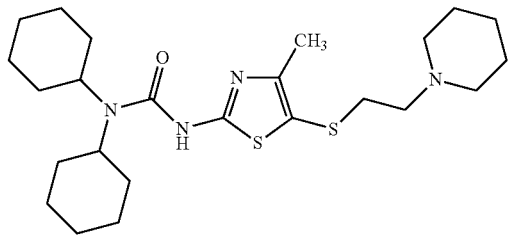

Prepared as described in general procedure (H) using 1,1-dicyclohexyl-3-(4-methyl-5-thiocyanato-thiazol-2-yl)-urea and N-(2-chloroethyl)piperidine.

HPLC-MS: m/z=580 (M+1)

Example 303

1,1-Dicyclohexyl-3-[4-methyl-5-(2-pyrrolidin-1-yl-ethylsulfanyl)-thiazol-2-yl]-urea

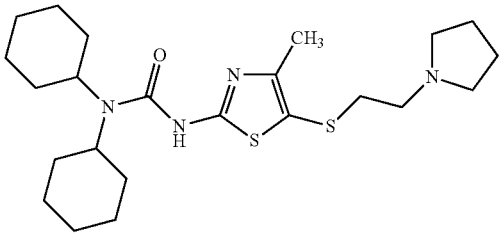

Prepared as described in general procedure (H) using 1,1-dicyclohexyl-3-(4-methyl-5-thiocyanato-thiazol-2-yl)-urea and N-(2-chloromethyl)pyrrolidine.

HPLC-MS: m/z=566 (M+1)

Example 304

1-(1-Butyryl-piperidin-4-yl)-3-(5-chloro-thiazol-2-yl)-1-cyclopentyl-urea

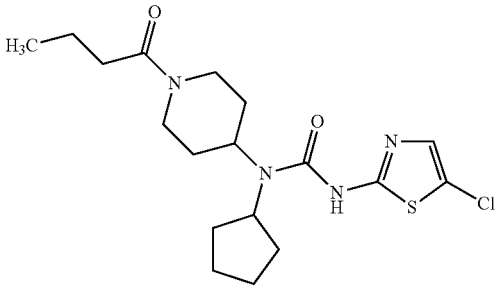

Prepared as described in general procedure (G) using 3-amino-1-Boc-piperidine, cyclopentnone and 2-amino-5-chlorothiazole HPLC-MS: m/z=421 (M+Na)

Example 305

3-(5-Chloro-thiazol-2-yl)-1-(1-cyclopentanecarbonyl-piperidin-4-yl)-1-cyclopentyl-urea

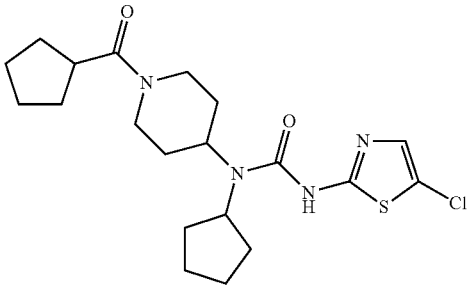

Prepared as described in general procedure (G) using 3-amino-1-Boc-piperidine, cyclopentnone and 2-amino-5-chlorothiazole HPLC-MS: m/z=425 (M+1)

Example 306

3-(5-Chloro-thiazol-2-yl)-1-cyclopentyl-1-(1-ethane-sulfonyl-piperidin-4-yl)-urea

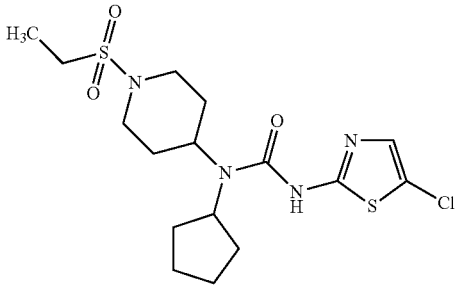

Prepared as described in general procedure (G) using 3-amino-1-Boc-piperidine, cyclopentnone and 2-amino-5-chlorothiazole HPLC-MS: m/z=421 (M+1)

Example 307

3-(5-Chloro-thiazol-2-yl)-1-cyclopentyl-1-[1-(propane-1-sulfonyl)-piperidin-4-yl]-urea

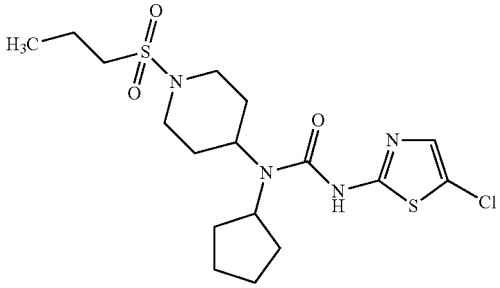

Prepared as described in general procedure (G) using 3-amino-1-Boc-piperidine, cyclopentnone 2-amino-5-chlorothiazole HPLC-MS: m/z=435 (M+1)

Example 308

1-(1-Acetyl-piperidin-4-yl)-1-cyclohexyl-3-(4-methyl-5-methylsulfanyl-thiazol-2-yl)-urea

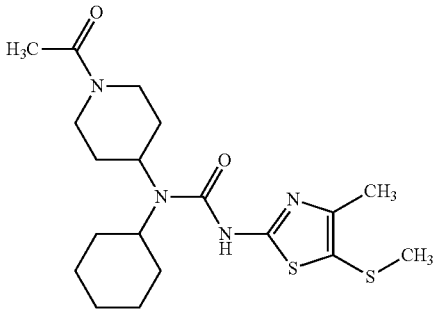

Prepared as described in general procedure (H) and (I)

HPLC-MS: m/z=412 (M+1)

Example 309

1,1-Dicyclohexyl-3-[4-methyl-5-(2-morpholin-4-yl-ethylsulfanyl)-thiazol-2-yl]-urea

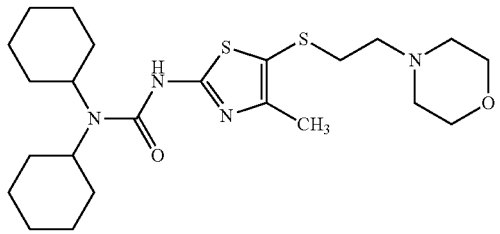

Prepared as described in general procedure (H) using 1,1-dicyclohexyl-3-(4-methyl-5-thiocyanato-thiazol-2-yl)-urea and N-(2-chloroethyl)morpholine.

HPLC-MS: m/z=582 (M+1)

Example 310

3-(5-Chloro-thiazol-2-yl)-1-cyclohexyl-1-(1-pentanoyl-piperidin-4-yl)-urea

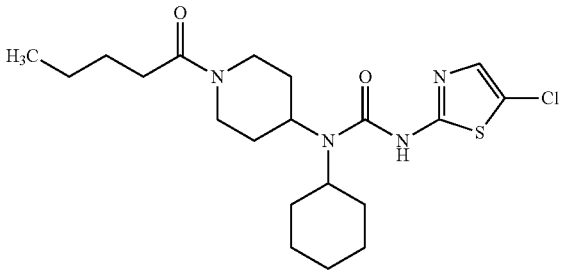

Prepared as described in general procedure (G) using 3-amino-1-Boc-piperidine, cyclohexnone and 2-amino-5-chlorothiazole HPLC-MS: m/z=427 (M+1)

Example 311

3-(5-Chloro-thiazol-2-yl)-1-cyclohexyl-1-[1-(3-methyl-butyryl)-piperidin-4-yl]-urea

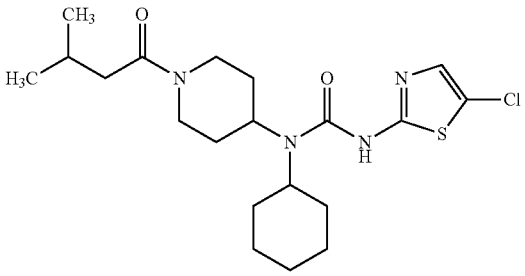

Prepared as described in general procedure (G) using 3-amino-1-Boc-piperidine, cyclohexnone and 2-amino-5-chlorothiazole HPLC-MS: m/z=427 (M+1)

Example 312

3-(5-Chloro-thiazol-2-yl)-1-cyclohexyl-1-[1-(2-methoxy-acetyl)-piperidin-4-yl]-urea

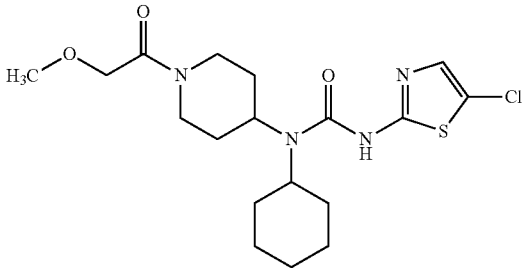

Prepared as described in general procedure (G) using 3-amino-1-Boc-piperidine, cyclohexnone and 2-amino-5-chlorothiazole HPLC-MS: m/z=415 (M+1)

Example 313

3-(5-Chloro-thiazol-2-yl)-1-cyclohexyl-1-[1-(3,3-dimethyl-butyryl)-piperidin-4-yl]-urea

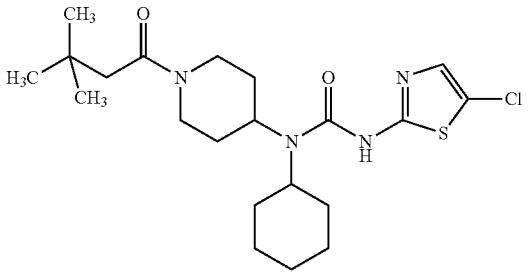

Prepared as described in general procedure (G) using 3-amino-1-Boc-piperidine, cyclohexanone and 2-amino-5-chlorothiazole HPLC-MS: m/z=463 (M+Na)

Example 314

3-(5-Chloro-thiazol-2-yl)-1-cyclohexyl-1-[1-(3-piperidin-1-yl-propionyl)-piperidin-4-yl]-urea

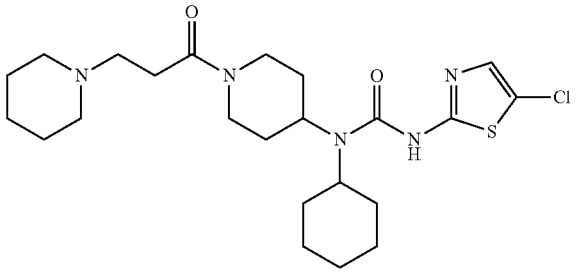

Prepared as described in general procedure (G) using 3-amino-1-Boc-piperidine, cyclohexnone and 2-amino-5-chlorothiazole HPLC-MS: m/z=483 (M+1)

Example 315

3-(5-Chloro-thiazol-2-yl)-1-cyclohexyl-1-[1-(2-pyridin-3-yl-acetyl)-piperidin-4-yl]-urea

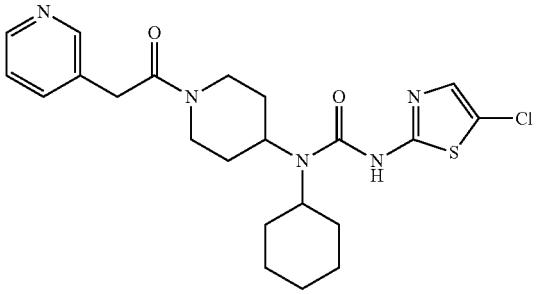

Prepared as described in general procedure (G) using 3-amino-1-Boc-piperidine, cyclohexnone and 2-amino-5-chlorothiazole HPLC-MS: m/z=462 (M+1)

Example 316

3-(5-Chloro-thiazol-2-yl)-1-cyclohexyl-1-[1-(3-cyclopentyl-propionyl)-piperidin-4-yl]-urea

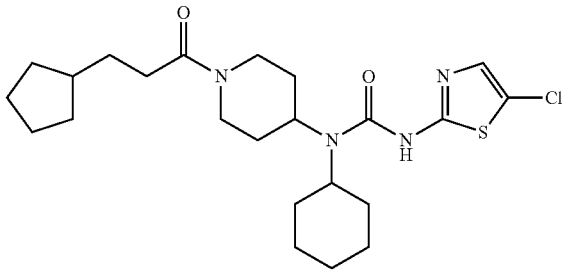

Prepared as described in general procedure (G) using 3-amino-1-Boc-piperidine, cyclohexnone and 2-amino-5-chlorothiazole HPLC-MS: m/z=490 (M+Na)

Example 317

3-(5-Chloro-thiazol-2-yl)-1-cyclohexyl-1-[1-(4-dimethylamino-butyryl)-piperidin-4-yl]-urea

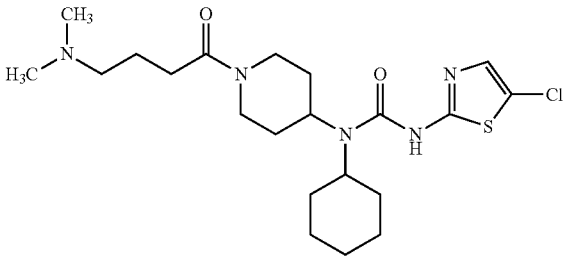

Prepared as described in general procedure (G) using 3-amino-1-Boc-piperidine, cyclohexnone and 2-amino-5-chlorothiazole HPLC-MS: m/z=456 (M+1)

Example 318

3-(5-Chloro-thiazol-2-yl)-1-cyclohexyl-1-[1-(3,3,3-trifluoro-propionyl)-piperidin-4-yl]-urea

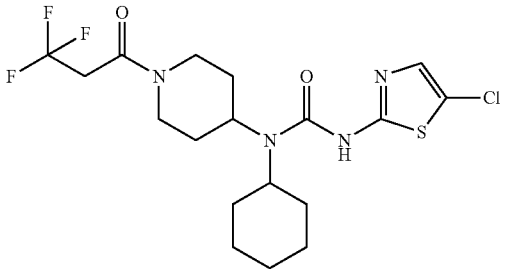

Prepared as described in general procedure (G) using 3-amino-1-Boc-piperidine, cyclohexnone and 2-amino-5-chlorothiazole HPLC-MS: m/z=453 (M+1)

Example 319

4-{4-[3-(5-Chloro-thiazol-2-yl)-1-cyclohexyl-ureido]-piperidin-1-yl}-4-oxo-butane-1-sulfonic acid amide

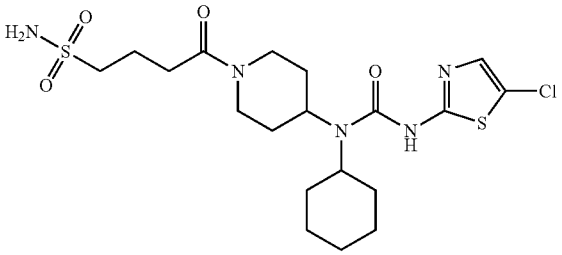

Prepared as described in general procedure (G) using 3-amino-1-Boc-piperidine, cyclohexnone and 2-amino-5-chlorothiazole HPLC-MS: m/z=492 (M+1)

Example 320

3-(5-Chloro-thiazol-2-yl)-1-cyclohexyl-1-[1-(3-methoxy-propionyl)-piperidin-4-yl]-urea

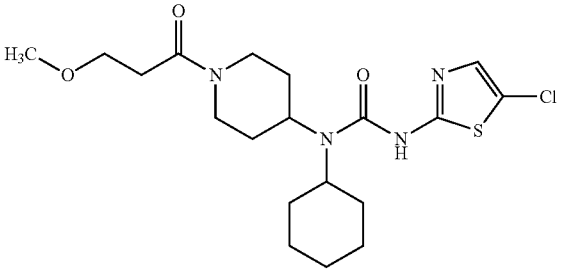

Prepared as described in general procedure (G) using 3-amino-1-Boc-piperidine, cyclohexnone and 2-amino-5-chlorothiazole HPLC-MS: m/z=429 (M+1)

Example 321

1-Cyclohexyl-3-(5-methyl-thiazol-2-yl)-1-(1-propionyl-piperidin-4-yl)-urea

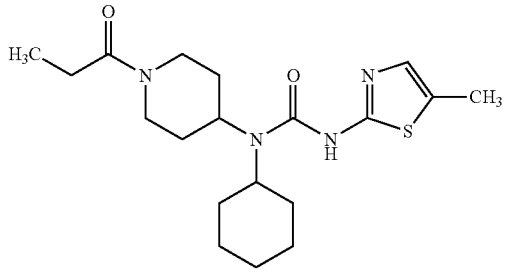

Prepared as described in general procedure (G) using 3-amino-1-Boc-piperidine, cyclohexnone and 2-amino-5-methylthiazole HPLC-MS: m/z=379 (M+1)

Example 322

1-(1-Butyryl-piperidin-4-yl)-1-cyclohexyl-3-(5-methyl-thiazol-2-yl)-urea

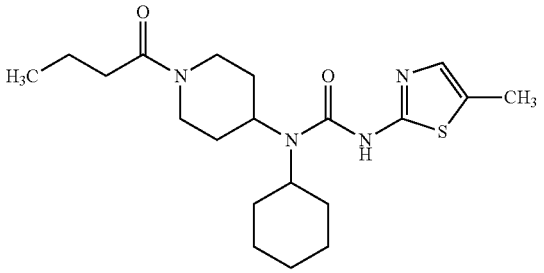

Prepared as described in general procedure (G) using 3-amino-1-Boc-piperidine, cyclohexnone and 2-amino-5-methylthiazole HPLC-MS: m/z=393 (M+1)

Example 323

1-(1-Acetyl-piperidin-4-yl)-1-(trans-4-methyl-cyclohexyl)-3-(5-methyl-thiazol-2-yl)-urea

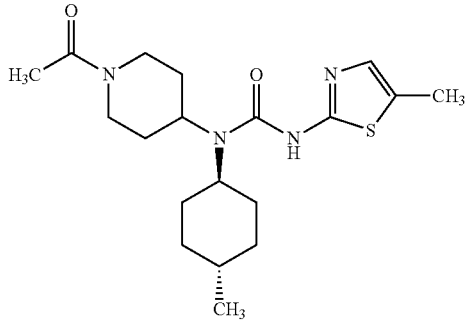

Prepared as described in general procedure (G) using 1-[4-(trans-4-methyl-cyclohexylamino)-piperidin-1-yl]-ethanone and 2-amino-5-methylthiazole HPLC-MS: m/z=379 (M+1)

Example 324

1-(trans-4-Methyl-cyclohexyl)-3-(5-methyl-thiazol-2-yl)-1-(1-propionyl-piperidin-4-yl)urea

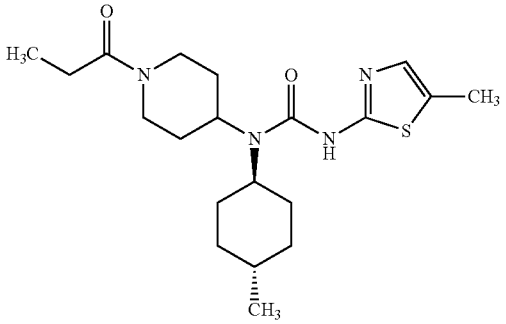

Prepared as described in general procedure (G) using 4-(4-Methyl-cyclohexylamino)-piperidine-1-carboxylic acid tert-butyl ester and 2-amino-5-methylthiazole HPLC-MS: m/z=393 (M+1)

Example 325

1-(1-Butyryl-piperidin-4-yl)-1-(trans-4-methyl-cyclohexyl)-3-(5-methyl-thiazol-2-yl)-urea

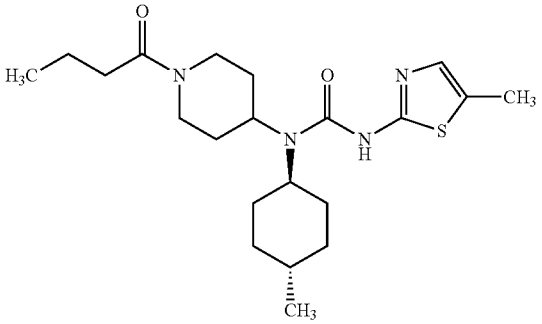

Prepared as described in general procedure (G) using 4-(4-Methyl-cyclohexylamino)-piperidine-1-carboxylic acid tert-butyl ester and 2-amino-5-methylthiazole HPLC-MS: m/z=407 (M+1)

Example 326

{2-[3-Cyclopentyl-3-(cis-4-methyl-cyclohexyl)-ureido]-thiazol-5-ylsulfanyl}-acetic acid

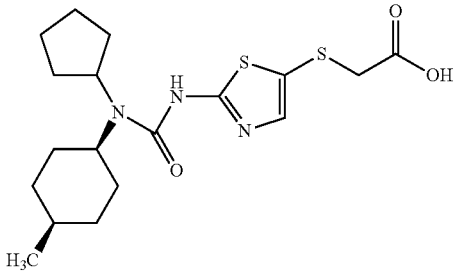

Prepared as described in general procedure (G)

HPLC-MS: m/z=398 (M+1). .

Example 327

1-[1-(3-Methoxy-propionyl)-piperidin-4-yl]-1-(trans-4-methyl-cyclohexyl)-3-(5-methyl-thiazol-2-yl)-urea

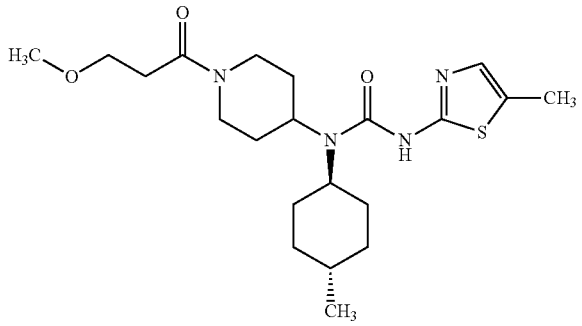

Prepared as described in general procedure (G) using 4-(4-Methyl-cyclohexylamino)-piperidine-1-carboxylic acid tert-butyl ester and 2-amino-5-methylthiazole HPLC-MS: m/z=423 (M+1)

Example 328

1-(4-Methyl- cyclohexyl)-3-(trans-5-methyl-thiazol-2-yl)-1-[1-(2,2,2-trifluoro-acetyl)-piperidin-4-yl]-urea

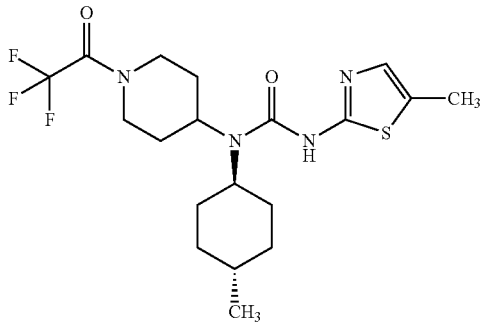

Prepared as described in general procedure (G) using 4-(4-Methyl-cyclohexylamino)-piperidine-1-carboxylic acid tert-butyl ester and 2-amino-5-methylthiazole HPLC-MS: m/z=433 (M+1)

Example 329

3-(5-Chloro-thiazol-2-yl)-1-cyclohexyl-1-indan-2-yl-urea

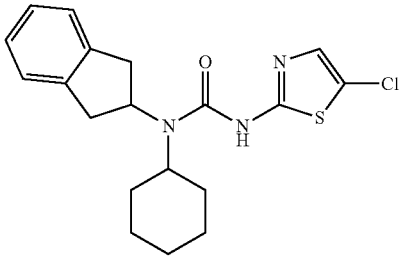

Prepared from indane, cyclohexanone and 2-amino-5-methylthiazole as described in general procedures (A) and (B)

HPLC-MS: m/z=376 (M+1)

Example 330

2-(3,3-Dicyclohexylureido)-4-methylthiazole-5-sulfonic acid piperidin-4-ylamide

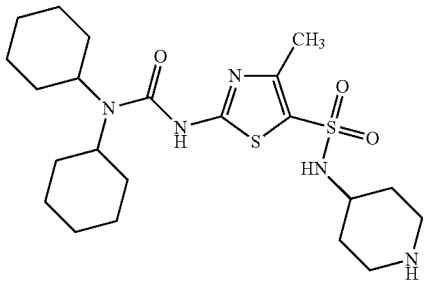

4-[2-(3,3-Dicyclohexyl-ureido)-4-methyl-thiazole-5-sulfonylamino]-piperidine-1-carboxylic acid ethyl ester was prepared as described in Example 173 using ethyl 4-amino-1-piperidine carboxylate, dicyclohexylamine and 2-acetylamino-thiazole-5-sulfonyl chloride. Reaction with 33% HBr in acetic acid followed by chromatography afforded the title compound.

HPLC-MS: m/z=484 (M+1)

Example 331

3-(5-Chloro-thiazol-2-yl)-1-cyclohexyl-1-[1-(2,2,2-trifluoro-acetyl)-piperidin-4-yl]-urea

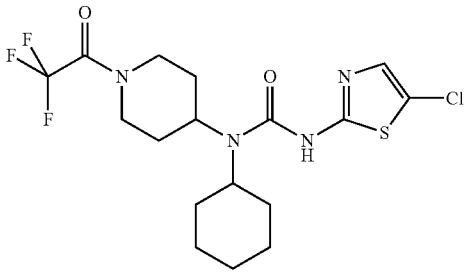

Prepared as described in general procedure (G) using 3-amino-1-Boc-piperidine, cyclohexnone and 2-amino-5-chlorothiazole HPLC-MS: m/z=437 (M+1)

Example 332

(S)-(2-{3-Cyclohexyl-3-[1-(thiophene-2-carbonyl)-pyrrolidin-3-yl]-ureido}-thiazol-5-ylsulfanyl)-acetic Acid

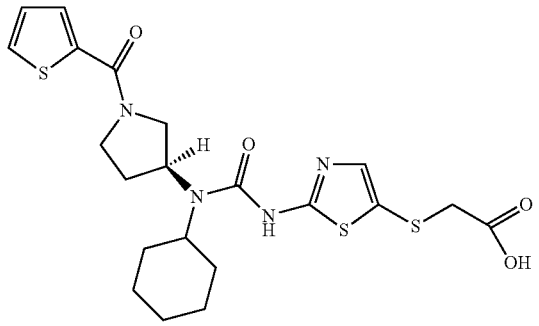

Prepared from (3S)-3-amino-1-Boc-pyrrolidine, cyclohexanone and 5-aminothiazol-2-mercaptoacetic acid ethyl ester as described in general procedure (G).

HPLC-MS: m/z=481 (M+1).

Example 333

1-(1-Benzenesulfonyl-piperidin-4-yl)-3-(5-chloro-thiazol-2-yl)-1-cyclohexyl-urea

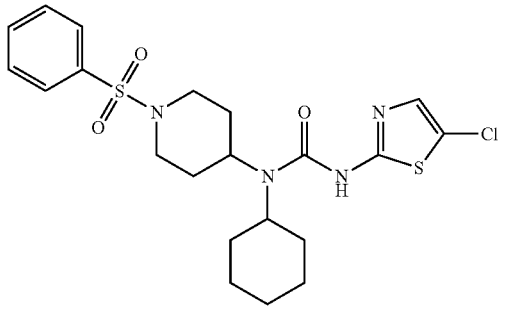

Prepared as described in general procedure (G) using 3-amino-1-Boc-piperidine, cyclohexnone and 2-amino-5-chlorothiazole HPLC-MS: m/z=483 (M+1)

Example 334

3-(5-Chloro-thiazol-2-yl)-1-cyclohexyl-1-(1-methanesulfonyl-piperidin-4-yl)-urea

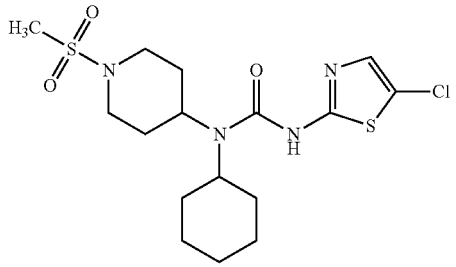

Prepared as described in general procedure (G) using 3-amino-1-Boc-piperidine, cyclohexnone and 2-amino-5-chlorothiazole HPLC-MS: m/z=421 (M+1).

Example 335

3-(5-Chloro-thiazol-2-yl)-1-cyclohexyl-1-[1-(1-methyl-1H-imidazole-4-sulfonyl)-piperidin-4-yl]-urea

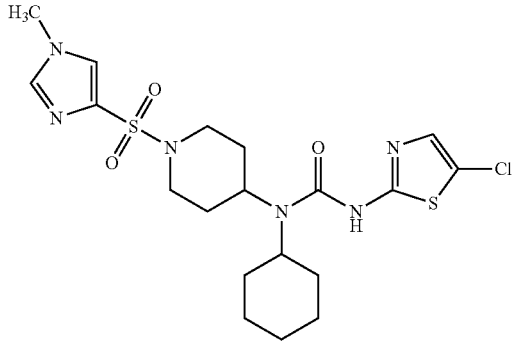

Prepared as described in general procedure (G) using 3-amino-1-Boc-piperidine, cyclohexnone and 2-amino-5-chlorothiazole HPLC-MS: m/z=487 (M+1).

Example 336

3-(5-Chloro-thiazol-2-yl)-1-cyclohexyl-1-(1-ethanesulfonyl-piperidin-4-yl)-urea

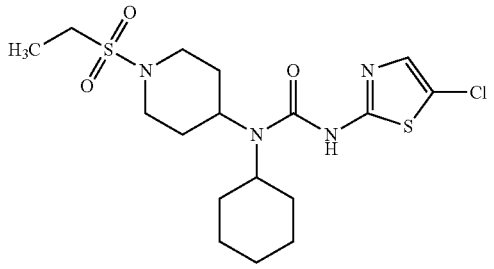

Prepared as described in general procedure (G) using 3-amino-1-Boc-piperidine, cyclohexnone and 2-amino-5-chlorothiazole HPLC-MS: m/z=435 (M+1).

Example 337 trans-3-(5-Chloro-thiazol-2-yl)-1-cyclohexyl-1-[1-(2-phenyl-ethenesulfonyl)-piperidin-4-yl]-urea

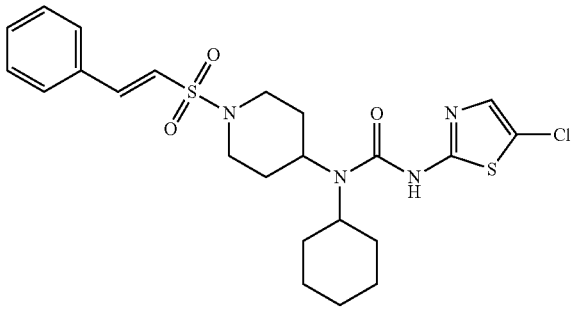

Prepared as described in general procedure (G) using 3-amino-1-Boc-piperidine, cyclohexnone and 2-amino-5-chlorothiazole HPLC-MS: m/z=509 (M+1).

Example 338

3-(5-Chloro-thiazol-2-yl)-1-cyclohexyl-1-[1-(4-methoxy-benzenesulfonyl)-piperidin-4-yl]-urea

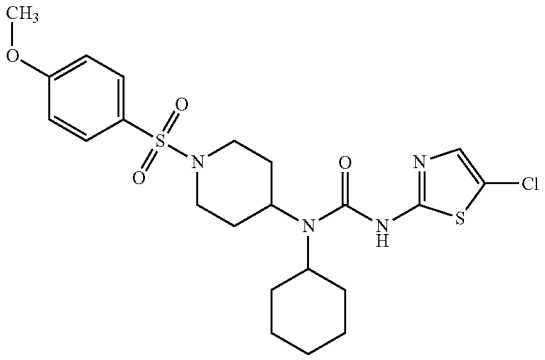

Prepared as described in general procedure (G) using 3-amino-1-Boc-piperidine, cyclohexnone and 2-amino-5-chlorothiazole HPLC-MS: m/z=513 (M+1).

Example 339

1-(1-Acetyl-piperidin-4-yl)-1-cyclohexyl-3-(5-methylsulfanyl-thiazol-2-yl)-urea

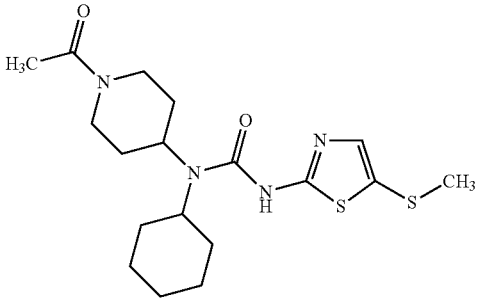

Prepared as described in general procedure (II) and (I) using 4-[1-cyclohexyl-3-(5-methylsulfanyl-thiazol-2-yl)-ureido]-piperidine-1-carboxylic acid tert-butyl ester and methyl iodide.

HPLC-MS: m/z=397 (M+1).

Example 340

1-Cyclohexyl-3-(5-methyl-thiazol-2-yl)-1-[1-(2,2,2-trifluoro-acetyl)-pyrrolidin-3-yl]-urea

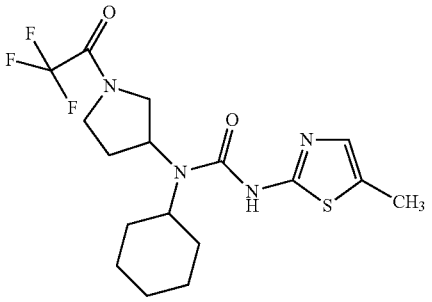

Prepared 3-amino-1-Boc-pyrrolidine and cyclohexanone as described in general procedure (G HPLC-MS: m/z=405 (M+1). ).

Example 341

1-(1-Acetyl-pyrrolidin-3-yl)-1-cyclohexyl-3-(5-methyl-thiazol-2-yl)-urea

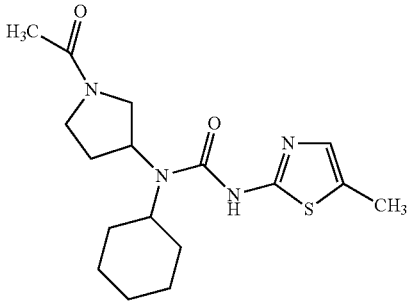

Prepared 3-amino-1-Boc-pyrrolidine, cyclohexanone and 2-amino-5-methylthiazole as described in general procedure (G).

HPLC-MS: m/z=351 (M+1).

Example 342

[2-(3-Cyclohexyl-3-indan-2-yl-ureido)-thiazol-5-ylsulfanyl]-acetic acid

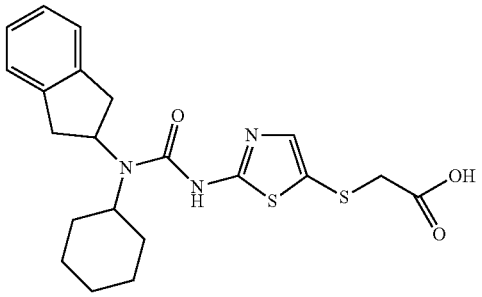

Prepared from indane, cyclohexanone and 5-aminothiazol-2-mercaptoacetic acid ethyl ester as described in general procedures (A) and (B)

HPLC-MS: m/z=432 (M+1).

Example 343

3-(5-Chloro-thiazol-2-yl)-1-(trans-4-methyl-cyclohexyl)-1-(1-propionyl-piperidin-4-yl)urea

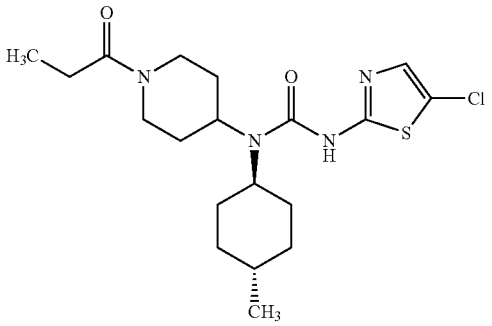

Prepared as described in general procedure (G) using 4-(4-methyl-cyclohexylamino)-piperidine-1-carboxylic acid tert-butyl ester and 2-amino-5-chlorothiazole HPLC-MS: m/z=413 (M+1).

Example 344

1-(1-Butyryl-piperidin-4-yl)-3-(5-chloro-thiazol-2-yl)-1-(trans-4-methyl-cyclohexyl)-urea

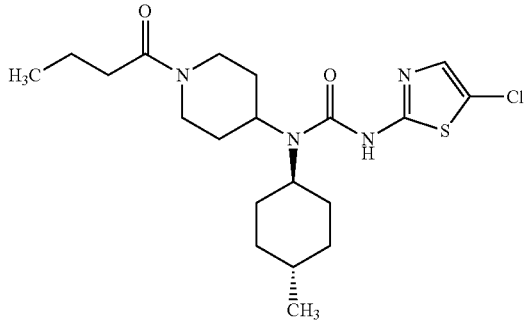

Prepared as described in general procedure (G) using 4-(4-Methyl-cyclohexylamino)-piperidine-1-carboxylic acid tert-butyl ester and 2-amino-5-chlorothiazole HPLC-MS: m/z=427 (M+1).

Example 345

1-Cyclohexyl-3-(5-methylsulfanyl-thiazol-2-yl)-1-[1-(thiophene-2-carbonyl)-piperidin-4-yl]-urea

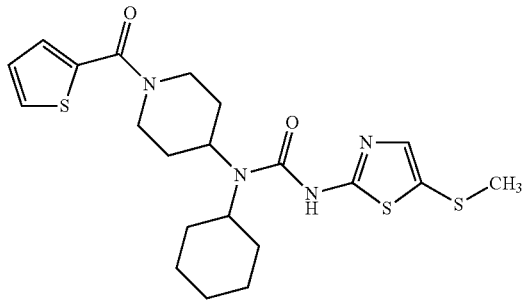

4-[1-Cyclohexyl-3-(5-methylsulfanyl-thiazol-2-yl)-ureido]-piperidine-1-carboxylic acid tert-butyl ester was prepared as described in general procedure (H) and (I) using 4-[1-cyclohexyl-3-(5-thiocyanato-thiazol-2-yl)-ureido]-piperidine-1-carboxylic acid tert-butyl ester, dithioerythritol and methyl iodide. Removal of the Boc group and N-acylation using thiophene-2 carboxylic acid as described in general procedure (G), steps 3 and 4 gave the title compound.

HPLC-MS: m/z=466 (M+1).

Example 346

1-(1-Butyryl-piperidin-4-yl)-1-cyclohexyl-3-(5-methylsulfanyl-thiazol-2-yl)-urea

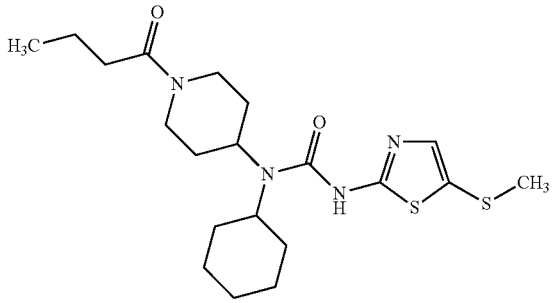

Prepared as described in general procedure (II) and (I) using 1-(1-butyryl-piperidin-4-yl)-1-(4-methyl-cyclohexyl)-3-(5-thiocyanato-thiazol-2-yl)-urea, dithioerythritol and methyliodide.

HPLC-MS: m/z=426 (M+1).

Example 347

1-(1-Acetyl-piperidin-4-yl)-1-cyclohexyl-3-[5-(2-morpholin-4-yl-ethylsulfanyl)-thiazol-2-yl]-urea

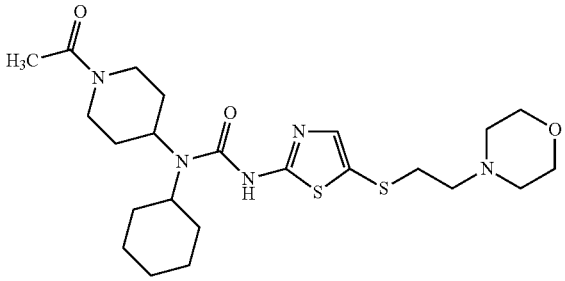

Prepared as described in general procedure (H) and (I) using 1-(1-acetyl-piperidin-4-yl)-1-cyclohexyl-3-(5-thiocyanato-thiazol-2-yl)-urea, dithioerythritol and N-(2-chloroethyl)-morpholine HPLC-MS: m/z=497 (M+1).

Example 348

1-Cyclohexyl-3-[5-(2-morpholin-4-yl-ethylsulfanyl)-thiazol-2-yl]-1-[1-(thiophene-2-carbonyl)-piperidin-4-yl]-urea

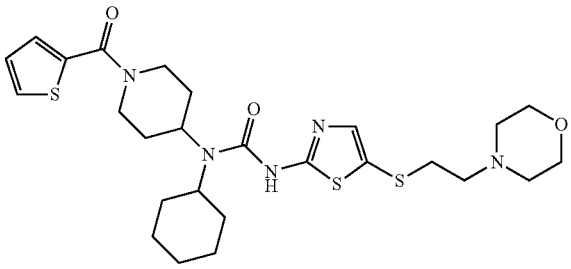

4-{1-Cyclohexyl-3-[5-(2-morpholin-4-yl-ethylsulfanyl)-thiazol-2-yl]-ureido}-piperidine-1-carboxylic acid tert-butyl ester was prepared as described in general procedure (H) and (I) using 4-[1-cyclohexyl-3-(5-thiocyanato-thiazol-2-yl)-ureido]-piperidine-1-carboxylic acid tert-butyl ester, dithioerythritol and N-(2-chloroethyl)-morpholine. Removal of the Boc group and N-acylation using thiophene-2 carboxylic acid as described in general procedure (G), steps 3 and 4 gave the title compound.

HPLC-MS: m/z=565 (M+1).

Example 349

3-(5-Chloro-thiazol-2-yl)-1-[1-(3-methyl-butyryl)-piperidin-4-yl]-1-(trans-4-methyl-cyclohexyl)-urea

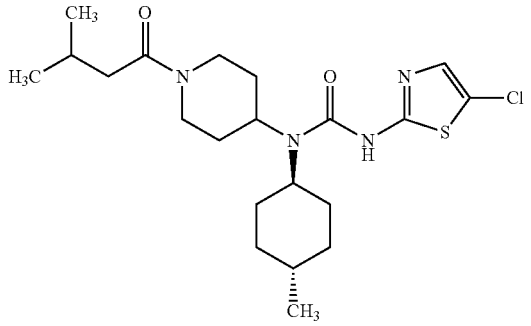

Prepared as described in general procedure (G) using 4-(4-Methyl-cyclohexylamino)-piperidine-1-carboxylic acid tert-butyl ester and 2-amino-5-chlorothiazole HPLC-MS: m/z=441 (M+1).

Example 350

3-(5-Chloro-thiazol-2-yl)-1-[1-(2-methoxy-acetyl)-piperidin-4-yl]-1-(trans-4-methyl-cyclohexyl)-urea

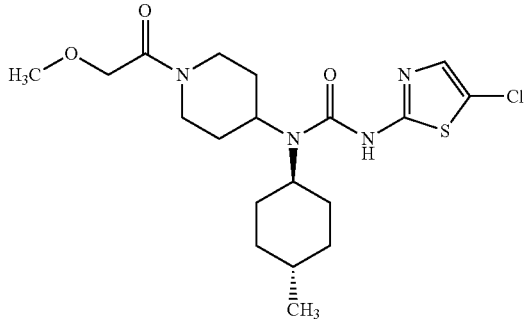

Prepared as described in general procedure (G) using 4-(4-Methyl-cyclohexylamino)-piperidine-1-carboxylic acid tert-butyl ester and 2-amino-5-chlorothiazole HPLC-MS: m/z=429 (M+1).

Example 351

1,1-Dicyclohexyl-3-[5-(2-piperidin-1-yl-ethylsulfanyl)-thiazol-2-yl]-urea

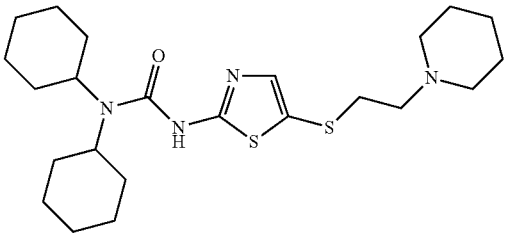

Prepared as described in general procedure (II) using 1,1-dicyclohexyl-3-(5-thiocyanato-thiazol-2-yl)-urea, dithioerythritol and 1-(2-chloroethyl)-piperidine HPLC-MS: m/z=566 (M+1).

Example 352

1,1-Dicyclohexyl-3-[5-(2-pyrrolidin-1-yl-ethylsulfanyl)-thiazol-2-yl]-urea

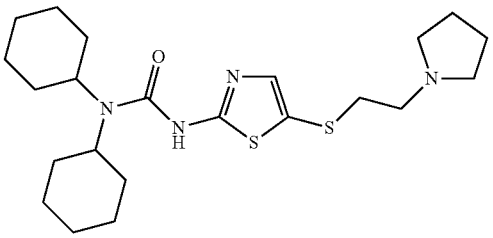

Prepared as described in general procedure (H) using 1,1-dicyclohexyl-3-(5-thiocyanato-thiazol-2-yl)-urea, dithioerythritol and 1-(2-chloroethyl)-pyrrolidine HPLC-MS: m/z=556 (M+1).

Example 353

1,1-Dicyclohexyl-3-[5-(2-morpholin-4-yl-ethylsulfanyl)-thiazol-2-yl]-urea

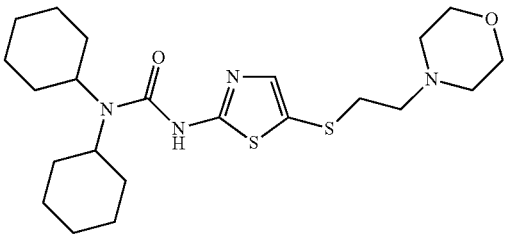

Prepared as described in general procedure (H) using 1,1-dicyclohexyl-3-(5-thiocyanato-thiazol-2-yl)-urea, dithioerythritol and N-(2-chloroethyl)-morpholine HPLC-MS: m/z=568 (M+1).

Example 354

3-(5-Chloro-thiazol-2-yl)-1-cyclohexyl-1-(6-oxo-piperidin-3-yl)-urea

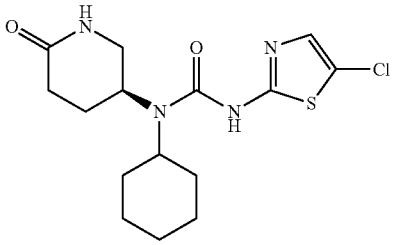

Prepared from (4S)-aminovalerolactam, cyclohexanone and 2-amino-5-chlorothiazole as described in general procedures (A) and (B).

HPLC-MS: m/z=357 (M+1).

Example 355

1-(1-Butyryl-piperidin-4-yl)-1-cycloheptyl-3-(5-methyl-thiazol-2-yl)-urea

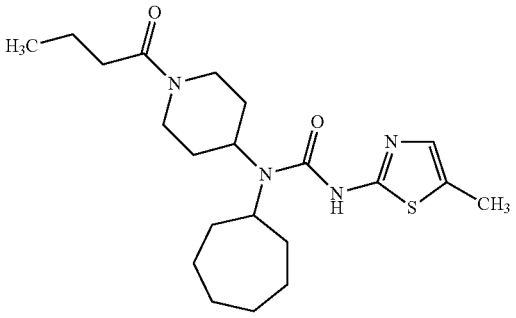

Prepared from cycloheptylamine, N-Boc-piperidone and 2-amino-5-methylthiazole as described in general procedure (G).

HPLC-MS: m/z=407 (M+1).

Example 356

1-Cycloheptyl-3-(5-methyl-thiazol-2-yl)-1-(1-propionyl-piperidin-4-yl)-urea

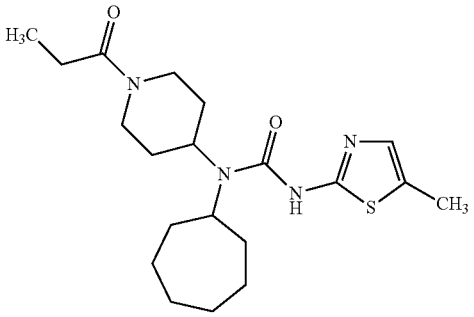

Prepared from cycloheptylamine, N-Boc-piperidone and 2-amino-5-methylthiazole as described in general procedure (G).

HPLC-MS: m/z=393 (M+1).

Example 357

1-Cycloheptyl-1-(1-cyclopentanecarbonyl-piperidin-4-yl)-3-(5-methyl-thiazol-2-yl)-urea

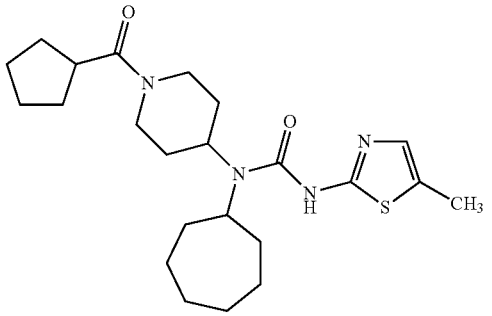

Prepared from cycloheptylamine, N-Boc-piperidone and 2-amino-5-methylthiazole as described in general procedure (G).

HPLC-MS: m/z=433 (M+1).

Example 358

1-Cycloheptyl-1-(1-methanesulfonyl-piperidin-4-yl)-3-(5-methyl-thiazol-2-yl)-urea

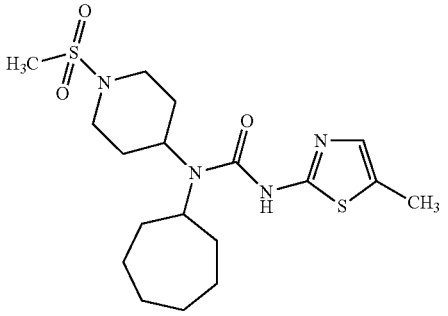

Prepared from cycloheptylamine, N-Boc-piperidone and 2-amino-5-methylthiazole as described in general procedure (G).

HPLC-MS: m/z=415 (M+1).

Example 359

1-Cycloheptyl-3-(5-methyl-thiazol-2-yl)-1-[1-(propane-1-sulfonyl)-piperidin-4-yl]-urea

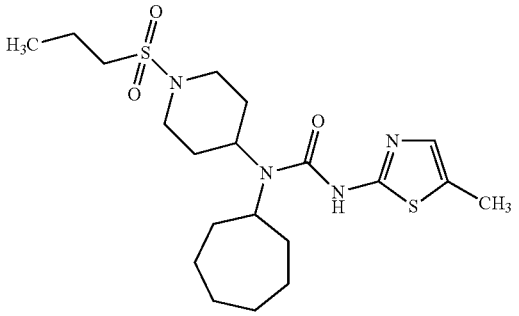

Prepared from cycloheptylamine, N-Boc-piperidone and 2-amino-5-methylthiazole as described in general procedure (G).

HPLC-MS: m/z=443 (M+1).

Example 360

3-(5-Chloro-thiazol-2-yl)-1-cyclopentyl-1-(1-methanesulfonyl-piperidin-4-yl)-urea

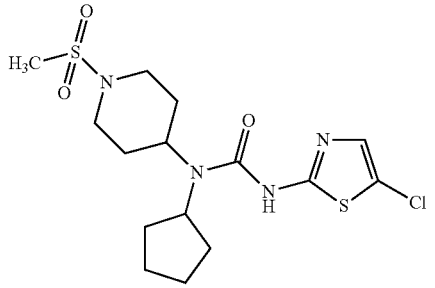

Prepared from cycloheptylamine, N-Boc-piperidone and 2-amino-5-methylthiazole as described in general procedure (G).

HPLC-MS: m/z=407 (M+1).

Example 361

1-Cycloheptyl-1-(1-ethanesulfonyl-piperidin-4-yl)-3-(5-methyl-thiazol-2-yl)-urea

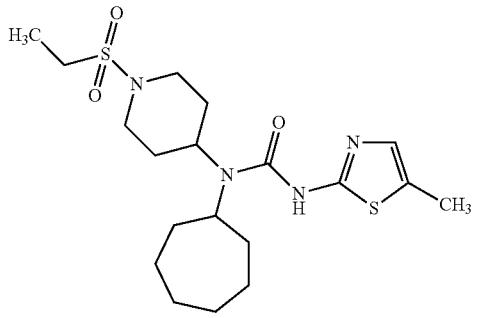

Prepared from cycloheptylamine, N-Boc-piperidone and 2-amino-5-methylthiazole as described in general procedure (G).

HPLC-MS: m/z=429 (M+1).

Example 362

[2-(3-Cyclohexyl-3-cyclopentyl-ureido)-thiazol-5-ylsulfanyl]-acetic acid

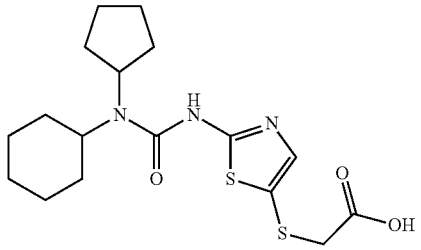

Prepared as described in general procedures (A) and (B) and (F) using cyclopentyl-cyclohexyl-amine 5-aminothiazol-2-mercaptoacetic acid ethyl ester.

HPLC-MS: m/z=384 (M+1).

Example 363

1-Cyclopentyl-3-(5-methyl-thiazol-2-yl)-1-(1-phenylmethanesulfonyl-piperidin-4-yl)-urea

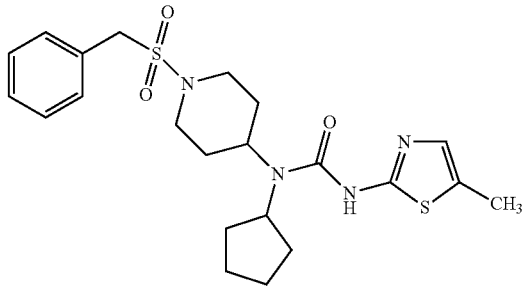

Prepared from cycloheptylamine, N-Boc-piperidone and 2-amino-5-methylthiazole as described in general procedure (G).

HPLC-MS: m/z=415 (M+1).

Example 364

[2-(3-Cycloheptyl-3-cyclohexyl-ureido)-thiazol-5-ylsulfanyl]acetic acid

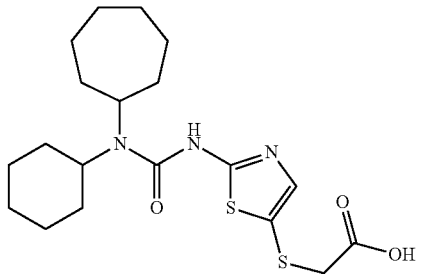

[2-(3-Cycloheptyl-3-cyclohexyl-ureido)-thiazol-5-ylsulfanyl]-acetic acid ethyl ester prepared as described in general procedure (A) using cyclohexyl-cycloheptylamine and 5-aminothiazole-2-mercaptoacetic acid ethyl ester. Hydrolysis using general procedure (F) gave the title compound.

HPLC-MS: m/z 412 (M+1).

Example 365

{2-[3-Cycloheptyl-3-(trans-4-methyl-cyclohexyl)-ureido]-thiazol-5-ylsulfanyl}-acetic acid

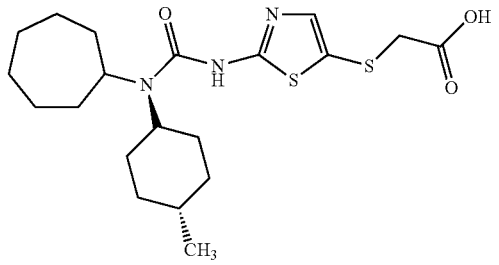

{2-[3-Cycloheptyl-3-(trans-4-methyl-cyclohexyl)-ureido]-thiazol-5-ylsulfanyl}-acetic acid ethyl ester prepared as described in general procedures (A) and (B) using cycloheptyl-(trans-4-methyl-cyclohexyl)-amine and 5-aminothiazole-2-mercaptoacetic acid ethyl ester. Hydrolysis using general procedure (F) gave the title compound.

HPLC-MS: m/z 426 (M+1).

Example 366

1-(1-Cyclopentanecarbonyl-piperidin-4-yl)-1-(trans-4-methyl-cyclohexyl)-3-(5-methyl-thiazol-2-yl)-urea

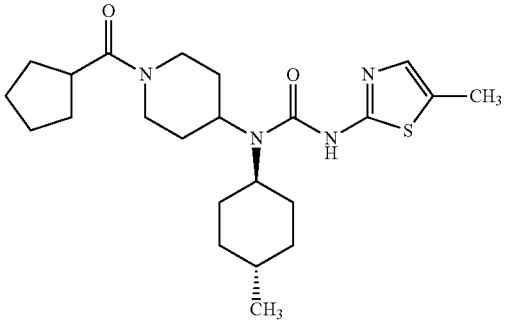

Prepared as described in general procedure (G) using 4-(trans-4-methyl-cyclohexylamino)-piperidine-1-carboxylic acid tert-butyl ester and 2-amino-5-chlorothiazole HPLC-MS: m/z 434 (M+1).

Example 367

1-(1-Acetyl-piperidin-4-yl)-3-[5-(2-diethylamino-ethylsulfanyl)-thiazol-2-yl]-1-(trans-4-methyl-cyclohexyl)-urea

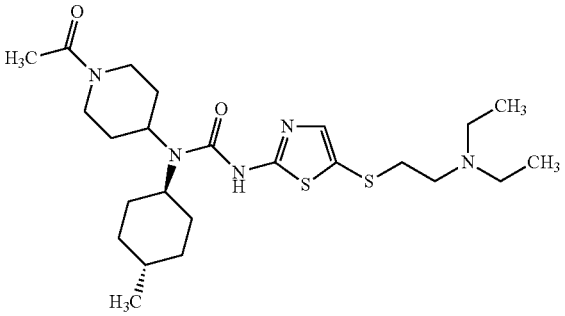

Prepared as described in general procedures (H) and (I) using 1-(1-acetyl-piperidin-4-yl)-1-(trans-4-methyl-cyclohexyl)-3-(5-thiocyanato-thiazol-2-yl)-urea, dithioerythritol and 2-diethylamino-ethanethiol HPLC-MS: m/z 496 (M+1).

Example 368

{2-[3-Cyclohexyl-3-(trans-4-propoxy-cyclohexyl)-ureido]-thiazol-5-ylsulfanyl}-acetic acid

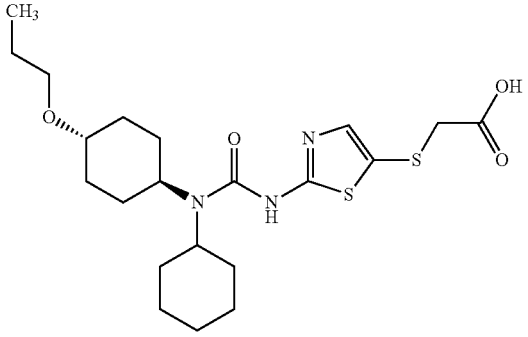

Prepared as described in general procedures (A) and (B) and (F) using trans-4-propoxy-cyclohexyl]-cyclohexyl-amine and 5-aminothiazole-2-mercaptoacetic acid ethyl ester.

HPLC-MS: m/z 456 (M+1).

Example 369

3-{2-[3-Cyclohcxyl-3-(trans-4-propoxy-cyclohexyl)-ureido]-thiazol-5-ylsulfanyl}-propionic acid

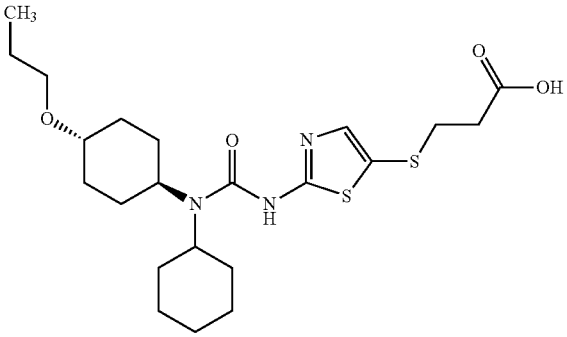

Prepared as described in general procedures (A) and (B) and (F) using trans-4-propoxy-cyclohexyl]-cyclohexyl-amine and 5-aminothiazole-2-mercaptopropionic acid ethyl ester.

HPLC-MS: m/z 470 (M+1).

Example 370

3-{2-[3-Cyclohexyl-3-(4-trifluoromethyl-cyclohexyl)-ureido]-thiazol-5-ylsulfanyl}-propionic acid

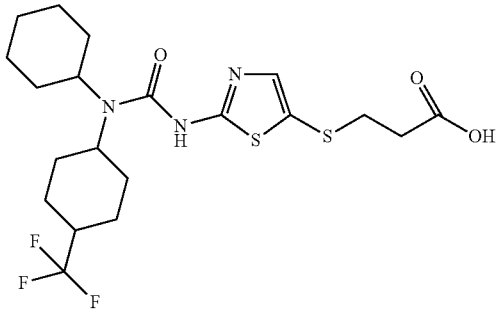

Prepared in 80% (383 mg) yield as described in the general procedure F from 3-{2-[3-cyclohexyl-3-(4-trifluoromethyl-cyclohexyl)-ureido]-thiazol-5-ylsulfanyl}-propionic acid methyl ester (494 mg, 1.0 mmol).

$^1$H NMR (Acetone-$d_6$): δ 7.39 (br 1H), 7.31 (s, 1H), 3.62 (m, 1H), 3.51 (m, 1H), 2.93 (t, 2H), 2.63 (t, 2H), 2.1 (m, 1H), 1.06-2.01 (m, 18H) ppm; HPLC-MS: m/z 480 (M+1).

Example 371

Trans-3-(5-bromo-thiazol-2-yl)-1-cyclohexyl-1-(4-methyl-cyclohexyl)-urea

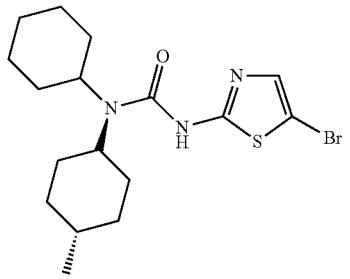

Prepared in 60% (240 mg) yield as described in general procedure C using trans-4-methylcyclohexyl-cyclohexylamine (195 mg, 1.0 mmol) and 2-amino-5-bromothiazole (179 mg, 1.0 mmol).

$^1$H NMR ($CDCl_3$): δ 8.4 (br, 1H), 7.25 (s, 1H), 3.48 (m, 2H), 1.12-1.99 (m, 19H), 0.90 (d, 3H) ppm; HPLC-MS: m/z 401 (M+1).

Example 372

Trans-1-cyclohexyl-3-(5-formyl-thiazol-2-yl)-1-(4-methyl-cyclohexyl)-urea

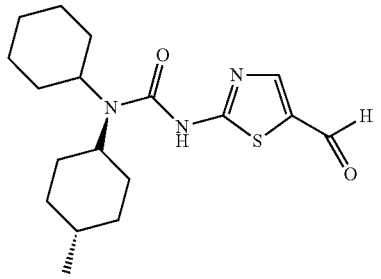

Prepared in 40% (140 mg) yield as described for 1,1-dicyclohexyl-3-5-formyl-thiazol-2-yl)-urea using cyclohexyl-(trans-4-methyl-cyclohexyl)-amine (195 mg, 1.0 mmol) and 2-amino-5-formylthiazole (128 mg, 1.0 mmol).

$^1$H NMR ($CDCl_3$): δ 9.9 (s, 1H), 8.92 (br, 1H), 7.99 (s, 1H), 3.42 (m, 2H), 1.04-1.92 (m, 19H), 0.90 (d, 3H) ppm; HPLC-MS: m/z 350 (M+1).

Example 373

1-cyclohexyl-3-(5-hydroxymethyl-thiazol-2-yl)-1-(trans-4-methyl-cyclohexyl)-urea

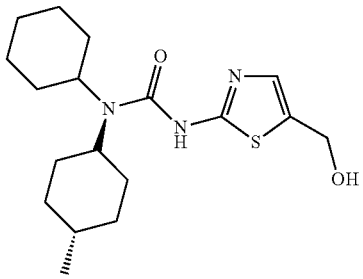

To a solution of 1-cyclohexyl-3-(5-formyl-thiazol-2-yl)-1-(trans-4-methyl-cyclohexyl)-urea (175 mg, 0.5 mmol) in MeOH (5 mL) was added sodium borohydride (38 mg, 1 mmol). The mixture was stirred at rt for 10 min and the solution was poured into water (25 mL). The aqueous layer was extracted with ethyl acetate (2×20 mL). The organic layer was washed with water (2×20 mL), brine (1×20 mL), dried (anhydrous $Na_2SO_4$) and concentrated to get trans-1-cyclohexyl-3-(5-hydroxymethyl-thiazol-2-yl)-1-(4-methyl-cyclohexyl)-urea in (90%, 158 mg) yield.

$^1$H NMR ($CDCl_3$): δ 9.20 (m, 1H), 7.22 (s, 1H), 4.74 (s, 2H), 3.63 (br, 1H), 3.43 (m, 2H), 1.04-1.85 (m, 19H), 0.89 (d, 3H) ppm: HPLC-MS: m/z 352 (M+1).

Example 374

(S)-2-tert-Butoxycarbonylamino-3-{2-[trans-3-cyclohexyl-3-(4-methyl-cyclohexyl)-ureido]-thiazol-5-ylsulfanyl}-propionic acid methyl ester

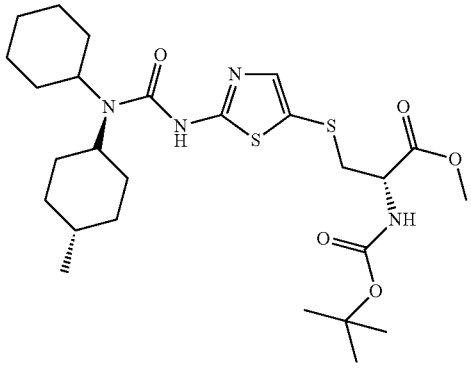

Prepared in 60% (333 mg) yield as described in general procedure (D) using trans-3-(5-bromo-thiazol-2-yl)-1-cyclohexyl-1 -(4-methyl-cyclohexyl)-urea (400 mg, 1.0 mmol) and N-(tert-butoxycarbonyl)-L-cysteine methyl ester (470 mg, 2.0 mmol).

$^1$H NMR ($CDCl_3$): δ 7.39 (br, 1H), 7.32 (s, 1H), 6.84 (d, 1H), 3.66 (s, 3H), 3.40 (m, 3H), 3.16 (m, 2H), 1.64-1.82 (m, 16H), 1.44 (s, 9H), 1.1-1.43 (m, 3H), 0.90 (d, 3H) ppm; HPLC-MS: m/z 555 (M+1).

Example 375

(S)-2-tert-Butoxycarbonylamino-3-{2-[trans-3-cyclohexyl-3-(4-methyl-cyclohexyl)-ureido]-thiazol-5-ylsulfanyl}-propionic acid

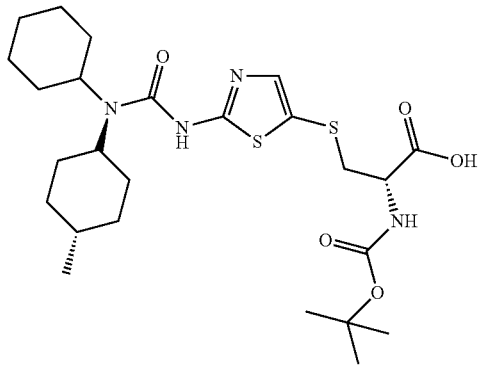

Prepared in 70% (95 mg) yield as described in general procedure (F) from (S)-2-tert-butoxycarbonylamino-3-{2-[trans-3-cyclohexyl-3-(4-methyl-cyclohexyl)-ureido]-thiazol-5-ylsulfanyl}-propionic acid methyl ester (139 mg, 0.25 mmol).

HPLC-MS: m/z 541 (M+1).

Example 376

(S)-2-{2-[3-cyclohexyl-3-(trans-4-methyl-cyclohexyl)-ureido]-thiazol-5-ylsulfanyl}-1-methoxycarbonyl-ethyl-ammonium chloride

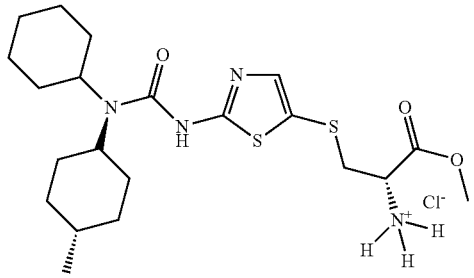

Prepared in 75% (86 mg) yield as described in general procedure (M) from (S)-2-tert-butoxycarbonylamino-3-{2-[(3-cyclohexyl-3-(trans-4-methyl-cyclohexyl)-ureido]-thiazol-5-ylsulfanyl}-propionic acid methyl ester (139 mg, 0.25 mmol).

HPLC-MS: m/z 456 (M+1).

Example 377

(S)-1-Carboxy-2-{2-[3-cyclohexyl-3-(trans-4-methyl-cyclohexyl)-ureido]-thiazol-5-ylsulfanyl}-ethyl-ammonium chloride

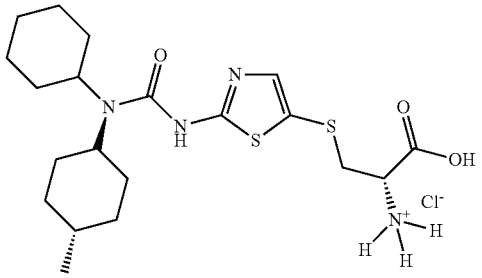

Prepared in 70% (77 mg) yield as described in general procedure (M) from (S)-2-tert-butoxycarbonylamino-3-{2-[(trans)-3-cyclohexyl-3-(4-methyl-cyclohexyl)-ureido]-thiazol-5-ylsulfanyl}-propionic acid (135 mg, 0.25 mmol).

HPLC-MS: m/z 442 (M+1).

Example 378

4-{1-Cyclohexyl-3-[5-(4-ethanesulfonyl-piperazin-1-ylmethyl)-thiazol-2-yl]-ureido}-piperidine-1-carboxylic acid tert-butyl ester

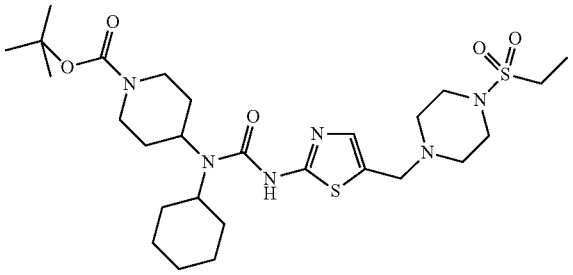

Prepared in 50% (299 mg) yield as described in general procedure (B) from 4-[1-cyclohexyl-3-(5-formyl-thiazol-2-yl)-ureido]-piperidine-1-carboxylic acid tert-butyl ester (436 mg, 1.0 mmol) and 1-ethanesulfonyl-piperazine hydrochloride (215 mg, 1.0 mmol). 4-[1-Cyclohexyl-3-(5-formyl-thiazol-2-yl)-ureido]-piperidine-1-carboxylic acid tert-butyl ester (50%, 218 mg) was prepared as described in the procedure for 1,1-dicyclohexyl-3-(5-formyl-thiazol-2-yl)-urea using 4-cyclohexylamino-piperidine-1-carboxylic acid tert-butyl ester (282 mg, 1.0 mmol) and 2-amino-5-formylthiazole (128 mg, 1.0 mmol).

HPLC-MS: m/z 599 (M+1).

Example 379

4-{1-Cyclohexyl-3-[5-(4-dimethylsulfamoyl-piperazin-1-ylmethyl)-thiazol-2-yl]-ureido}-piperidine-1-carboxylic acid tert-butyl ester

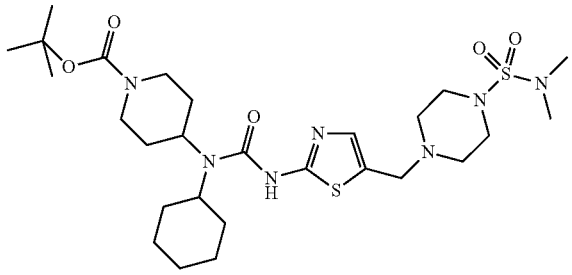

Prepared in 55% (338 mg) yield as described in general procedure (B) from 4-[1-cyclohexyl-3-(5-formyl-thiazol-2-yl)-ureido]-piperidine-1-carboxylic acid tert-butyl ester (436 mg, 1.0 mmol) and piperazine-1-sulfonic acid dimethylamide hydrochloride (230 mg, 1.0 mmol).

HPLC-MS: m/z 614 (M+1).

Example 380

4-{2-[3-Cyclohexyl-3-(1-cyclopentanecarbonyl-piperidin-4-yl)-ureido]-thiazol-5-ylmethyl}-piperazine-1-sulfonic acid dimethylamide

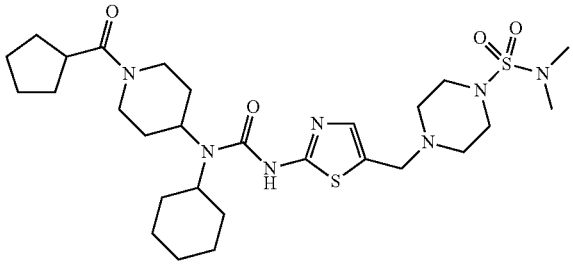

Prepared in 75% (229 mg) yield as described in general procedure (N) from 4-{1-cyclohexyl-3-[5-(4-dimethylsulfamoyl-piperazin-1-ylmethyl)-thiazol-2-yl]-ureido}-piperidinium; chloride (275 mg, 0.5 mmol) and cyclopentanecarbonyl chloride (80 mg, 0.6 mmol).

$^1$H NMR ($CDCl_3$): δ 7.52 (br, 1H), 7.09 (s, 1H), 4.76 (d, 2H), 4.04 (d, 2H), 3.76 (m, 2H), 3.64 (s, 2H), 3.26 (m, 4H), 2.87-3.10 (m, 1H), 2.81 (s, 6H), 2.52 (m, 4H), 1.15-2.14 (m, 22H) ppm;

HPLC-MS: m/z 610 (M+1).

Example 381

4-{2-[3-(1-Butyryl-piperidin-4-yl)-3-cyclohexyl-ureido]-thiazol-5-ylmethyl}-piperazine-1-sulfonic acid dimethylamide

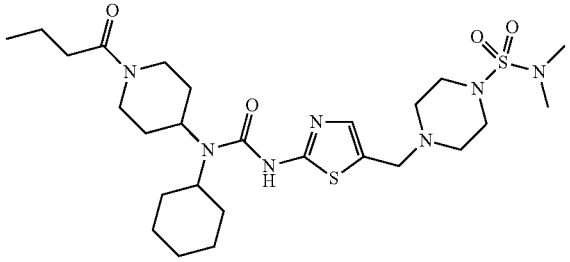

Prepared in 70% (204 mg) yield as described in general procedure (N) from 4-{(1-cyclohexyl-3-[5-(4-dimethylsulfamoyl-piperazin-1-ylmethyl)-thiazol-2-yl]-ureido}-piperidinium; chloride (275 mg) and butyryl chloride (64 mg, 0.6 mmol).

$^1$H NMR ($CDCl_3$): δ 7.30 (br, 1H), 7.11 (s, 1H), 4.75 (d, 2H), 3.94 (d, 2H), 3.78 (m, 2H), 3.65 (s, 2H), 3.27 (m, 4H), 3.06 (t, 1H), 2.83 (s, 6H), 2.52 (m, 4H), 2.32 (t, 2H), 1.05-2.21 (m, 16H), 0.95 (t, 3H) ppm; HPLC-MS: m/z 584 (M+1).

Example 382

1-Cyclohexyl-1-(1-cyclopentanecarbonyl-piperidin-4-yl)-3-[5-(4-ethanesulfonyl-piperazin-1-ylmethyl)-thiazol-2-yl]-urea

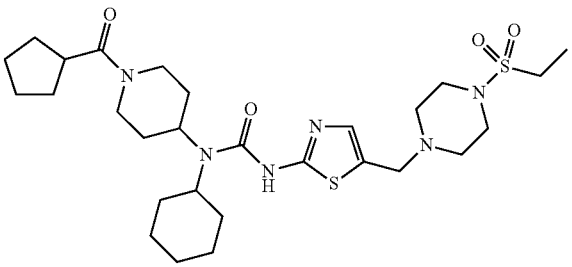

Prepared in 65% (193 mg) yield as described in general procedure (N) from 4-{1 -cyclohexyl-3-[5-(4-ethanesulfonyl-piperazin-1-ylmethyl)-thiazol-2-yl]-ureido}-piperidinium; chloride (268 mg, 0.5 mmol) and cyclopentanecarbonyl chloride (80 mg, 0.6 mmol).

$^1$H NMR ($CDCl_3$): δ 7.52 (br, 1H), 7.08 (s, 1H), 4.78 (d, 2H), 4.06 (d, 2H), 3.8 (m, 2H), 3.65 (s, 2H), 3.29 (m, 4H), 2.87-3.03 (m, 3H), 2.54 (m, 4H),1.54-2.12 ((m, 20H), 136 (t, 3H), 1.05-1.32 (m, 2H) ppm; HPLC-MS: m/z 595 (M+1).

Example 383

Trans-1-cyclohexyl-3-[5-(4 -ethanesulfonyl-piperazin-1-ylmethyl)-thiazol-2-yl]-1-(4-methyl-cyclohexyl)-urea

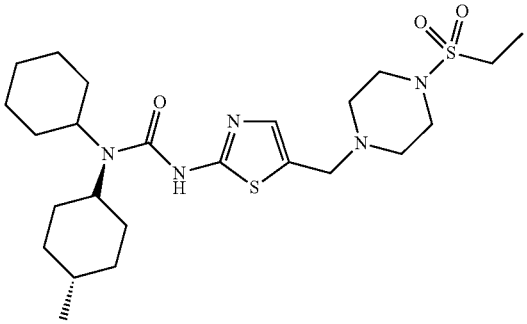

Prepared in 60% (307 mg) yield as described in general procedure (B) from trans-1-cyclohexyl-3-(5-formyl-thiazol-2-yl)-1-(4-methyl-cyclohexyl)-urea (349 mg, 1.0 mmol) and 1-ethanesulfonyl-piperazine hydrochloride (215 mg, 1.0 mmol).

$^1$H NMR ($CDCl_3$): δ 7.60 (br, 1H), 7.12 (s, 1H), 3.66 (s, 2H), 3.42 (m, 2H), 3.29 (m, 4H), 2.93 (q, 2H), 2.56 (m, 4H), 1.60-1.99 (m, 16H), 1.36 (t, 3H), 0.95-1.35 (m, 3H), 0.88 (d, 3H) ppm;

HPLC-MS: m/z 512 (M+1).

Example 384

Trans-4-{2-[3-cyclohexyl-3-(4-methyl-cyclohexyl)-ureido]-thiazol-5-ylmethyl}-piperazine-1-sulfonic acid dimethylamide

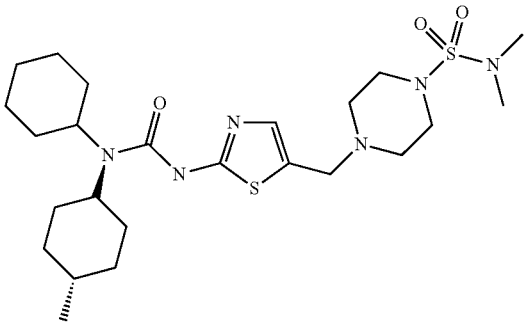

Prepared in 62% (326 mg) yield as described in general procedure (B) from trans-1-cyclohexyl-3-(5-formyl-thiazol-2-yl)-1-(4-methyl-cyclohexyl)-urea (349 mg, 1.0 mmol) and piperazine-1-sulfonic acid dimethylamide hydrochloride (230 mg, 1 mmol).

$^1$H NMR ($CDCl_3$): δ 7.58 (br, 1H), 7.11 (s, 1H), 3.65 (s, 2H), 3.46 (m, 2H), 3.25 (m, 4H), 2.82 (s, 6H), 2.52 (m, 4H), 1.01-1.99 (m, 19H), 0.89 (d, 3H) ppm; HPLC-MS: m/z 527 (M+1).

Example 385

Trans-3-(4-{2-[3-cyclohexyl-3-(4-methyl-cyclohexyl)-ureido]-thiazol-5-ylmethyl}-piperazine-1-sulfonyl)-propionic acid methyl ester

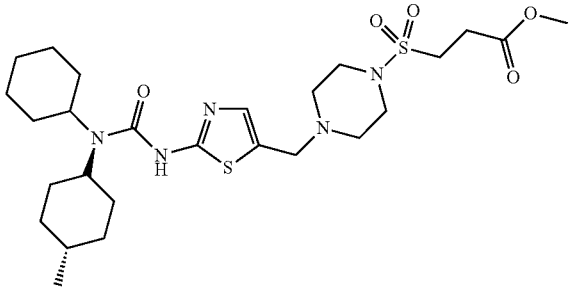

Prepared in 60% (342 mg) yield as described in general procedure (B) from trans-1-cyclohexyl-3-(5-formyl-thiazol-2-yl)-1-(4-methyl-cyclohexyl)-urea (349 mg, 1.0 mmol) and 4-(2-methoxycarbonyl-ethanesulfonyl)-piperazin-1-ium; chloride (273 mg, 1.0 mmol).

$^1$H NMR ($CDCl_3$): δ 7.22 (br, 1H), 7.10 (s, 1H), 3.73 (s, 3H), 3.65 (s, 2H), 3.41 (m, 2H), 3.28 (br, 4H), 3.23 (t, 2H), 2.83 (t, 2H), 2.54 (br, 4H), 1.02-1.94 (m, 19H), 0.88 (d, 3H) ppm; HPLC-MS: m/z 570 (M+1).

Example 386

Trans-3-(4-{2-[3-Cyclohexyl-3-(4-methyl-cyclohexyl)-ureido]-thiazol-5-ylmethyl}-piperazine-1-sulfonyl)-propionic acid

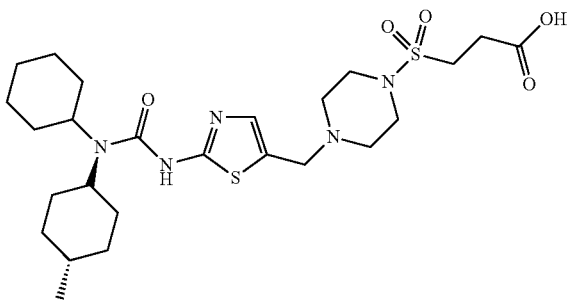

Prepared in 80% (223 mg) yield as described in general procedure (F) from trans-3-(4-{2-[3-cyclohexyl-3-(4-methyl-cyclohexyl)-ureido]-thiazol-5-ylmethyl}-piperazine-1-sulfonyl)-propionic acid methyl ester (285 mg, 0.5 mmol).

$^1$H NMR (DMSO-$d_6$): δ 7.08 (s, 1H), 6.78 (br, 1H), 3.55 (s, 2H), 3.31 (m, 2H), 3.21 (t, 2H), 3.14 (br, 4H), 2.46 (t, 2H), 2.40 (br, 4H), 1.11-1.87 (m, 19H), 0.84 (d, 3H) ppm; HPLC-MS: m/z 556 (M+1).

Example 387

Trans-3-(4-{2-[3-cycloheptyl-3-(4-methyl-cyclohexyl)-ureido]-thiazol-5-ylmethyl}-piperazine-1-sulfonyl)-propionic acid methyl ester

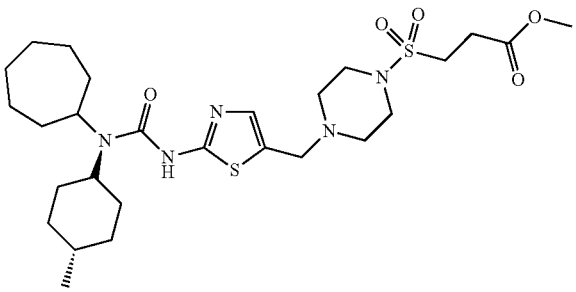

Prepared in 65% (380 mg) yield as described in general procedure (B) from trans-1-cycloheptyl-3-(5-formyl-thiazol-2-yl)-1-(4-methyl-cyclohexyl)-urea (364 mg, 1.0 mmol) and 4-(2-methoxycarbonyl-ethanesulfonyl)-piperazin-1-ium chloride (273 mg, 1 mmol).

$^1$H NMR ($CDCl_3$): δ 7.52 (br, 1H), 7.11 (s, 1H), 3.73 (s, 3H), 3.66 (s, 2H), 3.44 (m, 2H), 3.28 (br, 4H), 3.22 (t, 2H), 2.81 (t, 2H), 2.55 (br, 4H), 1.05-2.1 (m, 21H), 0.88 (d, 3H) ppm; HPLC-MS: m/z 584 (M+1).

Example 388

Trans-3-(4-{2-[3-cycloheptyl-3-(4-methyl-cyclohexyl)-ureido]-thiazol-5-ylmethyl}-piperazine-1-sulfonyl)-propionic acid

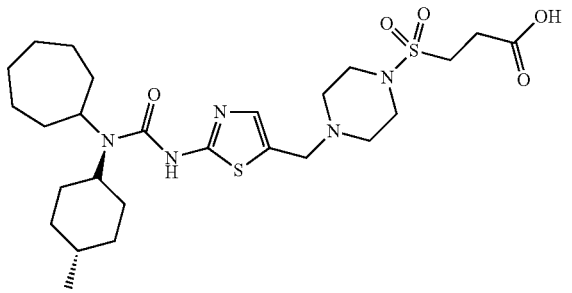

Prepared in 75% (214 mg) yield as described in general procedure (F) from trans-3-(4-{2-[3-cycloheptyl-3-(4-methyl-cyclohexyl)-ureido]-thiazol-5-ylmethyl}-piperazine-sulfonyl)-propionic acid methyl ester (293 mg, 0.5 mmol).

$^1$H NMR (DMSO-$d_6$): δ 7.07 (br, 1H), 7.05 (s, 1H), 3.55 (s, 2H), 3.49 (br, 2H), 3.21 (m, 2H), 3.14 (br, 4H), 2.431 (t, 2H), 2.41 (br, 4H), 0.88-2.12 (m, 21H), 0.84 (d, 3H) ppm; HPLC-MS: m/z 570 (M+1).

Example 389

3-(5-Bromo-thiazol-2-yl)-1-cyclohexyl-1-[1-(2-fluoro-phenyl)-piperidin-4- yl]-urea

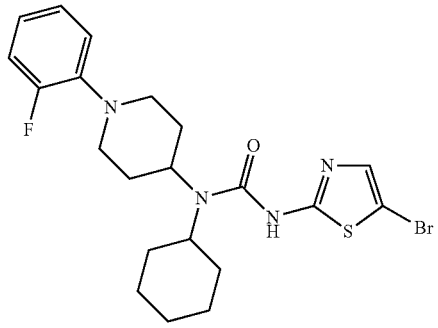

Prepared in 50% (241 mg) yield as described in general procedure (C) from cyclohexyl-[1-(2-fluoro-phenyl)-piperidin-4-yl]-amine (276 mg, 1.0 mmol) and 5-bromo-thiazol-2-ylamine (179 mg. 1.0 mmol).

$^1$H NMR ($CDCl_3$): δ 8.12 (br, 1H), 7.25 (s, 1H), 6.95-7.09 (m, 4H), 3.83 (m, 1H), 3.51 (d, 1H), 3.42 (br, 1H), 3.40 (t, 1H), 2.77 (t, 1H), 2.63 (t, 1H),1.68-2.21 (m, 10H), 1.17-1.41 (m, 2H) ppm; HPLC-MS: m/z 482 (M+1).

Example 390

3-(5-Bromo-thiazol-2-yl)-1-cyclohexyl-1-(4-phenyl-cyclohexyl)-urea

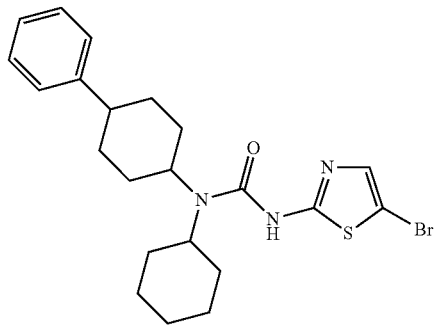

Prepared in 50% (232 mg) yield as described in general procedure (C) from cyclohexyl-(4-phenyl-cyclohexyl)-amine (257 mg, 1.0 mmol) and 5-bromo-thiazol-2-ylamine (179 mg, 1.0 mmol).

$^1$H NMR ($CDCl_3$): δ 8.20 (br, 1H), 7.06-7.25 (m, 6H), 3.68 (m, 1H), 3.42 (m, 1H), 1.56-2.51 (m, 17H), 1.14-1.35 (m, 2H) ppm: HPLC-MS: m/z 463 (M+1).

Example 391

1,1-Dicyclohexyl-3-[5-(isopropylamino-methyl)-thiazol-2-yl]-urea

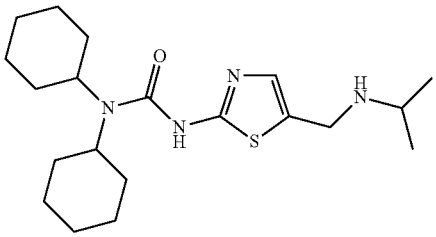

Prepared as described in general procedure (P) using 1,1-dicyclohexyl-3-(5-formyl-thiazol-2-yl)-urea (100 mg, 0.30 mmol), isopropylamine (30 μL, 0.36 mmol) and sodium triacetoxyborohydride (101 mg, 0.48 mmol) to afford 47 mg (42%) of the desired product after purification.

$^1$H NMR ($CDCl_3$): δ7.12 (s, 1H), 4.54 (s, 2H), 3.94 (br, 1H), 3.42 (br, 1H), 3.04 (m, 1H), 2.18 (m, 2H), 1.83 (m, 6H), 1.68 (m, 6H), 1.07-1.38 (m, 14H) ppm; HPLC-MS: m/z 379 (M+1).

Example 392

1,1-Dicyclohexyl-3-(5-cyclopentylaminomethyl-thiazol-2-yl)-urea

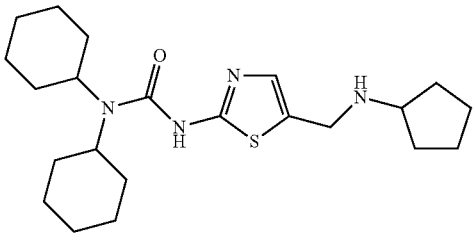

Prepared as described in general procedure (P) using 1,1-dicyclohexyl-3-(5-formyl-thiazol-2-yl)-urea (100 mg, 0.30 mmol), cyclopentylamine (45 μL, 0.45 mmol) and sodium triacetoxyborohydride (102 mg, 0.48 mmol) to afford 45 mg (37%) of the desired product after purification.

$^1$H NMR ($CDCl_3$): δ7.08 (s, 1H), 4.53 (s,1H), 3.85 (s, 2H), 3.40 (br, 1H), 3.12 (m, 1H), 2.60 (m, 2H), 1.49-1.75 (m, 8H), 1.78-1.98 (m, 8H), 1.04-1.36 (m, 14H) ppm; HPLC-MS: m/z 405 (M+1).

Example 393

4-{[2-(3,3-Dicyclohexyl-ureido)-thiazol-5-ylm-ethyl]-amino}-benzoic acid methyl ester

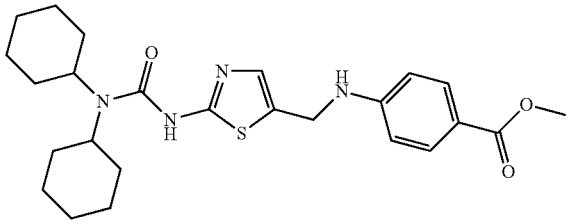

Prepared as described in general procedure (P) using 1,1-dicyclohexyl-3-(5-formyl-thiazol-2-yl)-urea (160 mg. 0.48 mmol), acetic acid (27 μL, 0.48 mmol), methyl 4-amino benzoate (144 mg, 0.95 mmol) and sodium triacetoxyborohydride (303 mg, 1.43 mmol) to afford 106 mg (47%) of the desired product after purification.

$^1$H NMR ($CDCl_3$): δ8.17 (br, 1H), 7.86 (d, 2H), 7.23 (s, 1H), 6.60 (d, 2H), 4.47 (s, 3H), 3.85 (m, 3H), 3.42 (m, 2H), 1.78-1.84 (m, 8H), 1.62-1.74 (m, 6H), 1.24-1.38 (m, 4H), 1.10-1.22 (m., 2H) ppm; HPLC-MS: m/z 471 (M+1).

Example 394

(4-{[2-(3,3-Dicyclohexyl-ureido)-thiazol-5-ylm-ethyl]-amino}-phenyl)-acetic acid ethyl ester

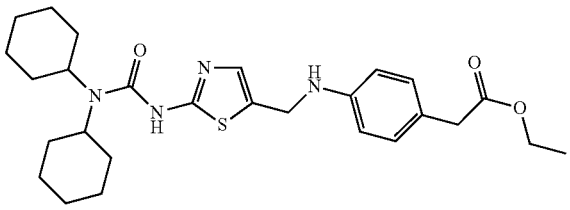

Prepared as described in general procedure (P) using 1,1-dicyclohexyl-3-(5-formyl-thiazol-2-yl)-urea (100 mg, 0.298 mmol), acetic acid (17 μL, 0.29 mmol), (4-amino-phenyl)-acetic acid ethyl ester (14 mg, 0.45 mmol) and sodium triacetoxyborohydride (101 mg, 0.48 mmol) to afford 43 mg (30%) of the desired product after purification.

$^1$H NMR ($CDCl_3$): δ7.19 (s, 1H), 7.07 (d, 2H), 6.58 (d, 2H), 4.38 (br, 2H), 4.11 (q, 2H), 3.47 (s, 2H), 3.40 (br, 1H), 1.77-1.86 (m, 8H), 1.60-1.74 (m, 6H), 1.09-1.35 (m, 11H) ppm; HPLC-MS: m/z 499 (M+1).

Example 395

4-({[2-(3,3-Dicyclohexyl-ureido)-thiazol-5-ylmethyl]-amino}-methyl)-benzoic acid methyl ester

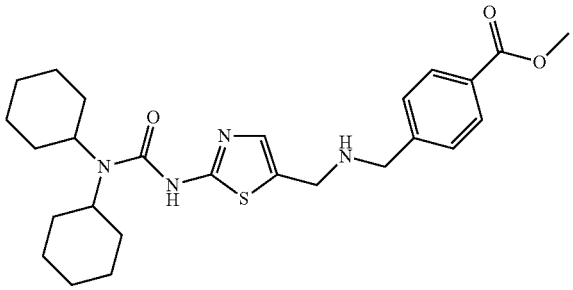

Prepared as described in general procedure (P) using 1,1-dicyclohexyl-3-(5-formyl-thiazol-2-yl)-urea (150 mg. 0.42 mmol), acetic acid (24 μL, 0.42 mmol), 4-aminomethyl-benzoic acid methyl ester (170 mg, 0.84 mmol) and sodium triacetoxyborohydride (268 mg, 1.27 mmol) to afford 74 mg (36%) of the desired product after purification.

HPLC-MS: m/z 485 (M+1).

Example 396

{[2-(3,3-Dicyclohexyl-ureido)-thiazol-5-ylmethyl]-amino}-acetic acid methyl ester

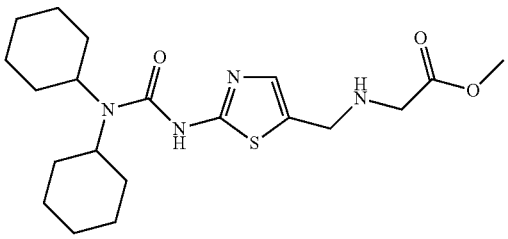

Prepared as described in general procedure (P) using 1,1-dicyclohexyl-3-(5-formyl-thiazol-2-yl)-urea (31 mg, 0.095 mmol), glycine methyl ester hydrochloride (24 mg, 0.20 mmol) and sodium triacetoxyborohydride (61 mg, 0.286 mmol) to afford 15 mg (39%) of the desired product after purification.

$^1$H NMR ($CDCl_3$): δ7.14 (s, 1H), 3.93 (s, 2H), 3.72 (s, 3H), 3.42 (m, 3H), 3.00 (br, 1H), 1.78-1.40 (m, 6H), 1.53-1.75 (m, 10H), 1.11-1.40 (m, 6H) ppm; HPLC-MS: m/z 409 (M+1).

Example 397

1-[2-(3,3-Dicyclohexyl-ureido)-thiazol-5-ylmethyl]-pyrrolidine-2(R)-carboxylie acid benzyl ester

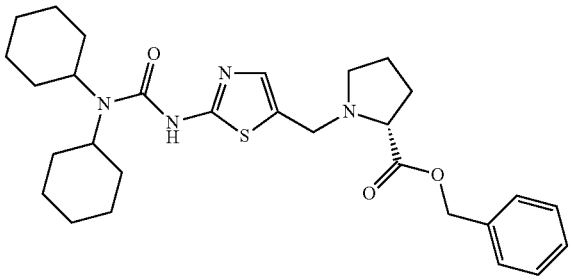

Prepared as described in general procedure (P) using 1,1-dicyclohexyl-3-(5-formyl-thiazol-2-yl)-urea (75 mg. 0.223 mmol), pyrrolidine-2(R)-carboxylic acid benzyl ester hydrochloride (73 mg, 0.31 mmol) and sodium triacetoxyborohydride (71 mg, 0.335 mmol) to afford 92 mg (78%) of the desired product after purification.

$^1$H NMR ($CDCl_3$): δ7.49 (m, 2H), 7.37 (m,. 3H), 7.04 (s, 1H), 5.16 (q, 2H), 4.54 (m, H), 3.87 (dd, 2H), 3.39 (m, 3H), 3.08 (m, 1H), 2.85 (m, 1H), 2.61 (m, 1H), 1.91-2.12 (m, 1H), 1.80-1.88 (m, 6H), 1.64-1.76 (m, 8H), 1.12-1.40 (m. 6H) ppm; HPLC-MS: m/z 525 (M+1).

Example 398

1-[2-(3,3-Dicyclohexyl-ureido)-thiazol-5-yl-methyl]-pyrrolidine-2(R)-carboxylic acid

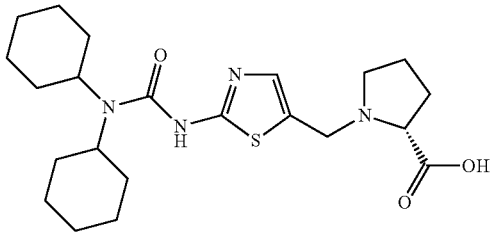

1-[2-(3,3-Dicyclohexyl-ureido)-thiazol-5-ylmethyl]-pyrrolidine-2(R)-carboxylic acid benzyl ester (50 mg, 0.095 mmol) was combined with palladium on carbon (25 mg) in MeOH. Vacuum was applied to degas the mixture. The reaction was subjected to hydrogen and vigorous stirring until no ester could be detected (36 h). After filtering and concentration, 35 mg (84%) pure acid was obtained by trituration.

HPLC-MS: m/z 435 (M+1).

Example 399

1,1-Dicyclohexyl-3-[5-(3-oxo-piperazin-1-ylm-ethyl)-thiazol-2-yl]-urea

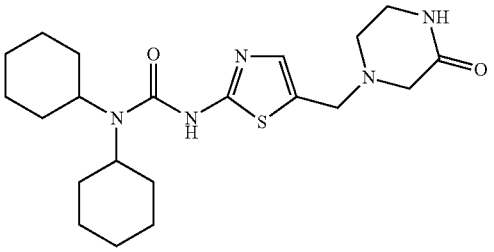

Prepared as described in general procedure (P) using 1,1-dicyclohexyl-3-(5 formyl-thiazol-2-yl)-urea (40 mg, 0.12 mmol). 2-piperazinonc (18 mg, 0.18 mmol), acetic acid (7 μL, 0.12 mmol) and sodium triacetoxyborohydride (38 mg, 0.18 mmol) to afford 20 mg (40%) of the desired product after purification.

$^1$H NMR ($CDCl_3$): δ7.14 (s, 1H), 6.35 (s, 1H), 4.62 (br, 1H), 3.72 (s, 2H), 3.43 (m. 2H), 3.34 (m, 2H), 3.18 (s, 2H), 2.69 (m, 2H), 1.79-1.87 (m, 6H), 1.62-1.73 (m, 6H), 1.12-1.39 (m, 8H) ppm; HPLC-MS: m/z 420 (M+1).

Example 400

1,1-Dicyclohexyl-3-[5-(3-oxo-pyrazolidin-1-ylm-ethyl)-thiazol-2-yl]-urea

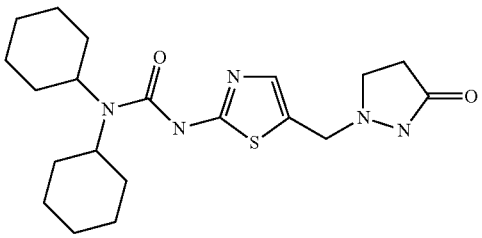

Prepared as described in general procedure (P) using 1,1-dicyclohexyl-3-(5-formyl-thiazol-2-yl)-urea (42 mg. 0.125 mmol), 3-pyrazolidinone hydrochloride (23 mg, 0.188 mmol) and sodium triacetoxyborohydride (40 mg, 0.188 mmol) to afford 8 mg (16%) of the desired product after purification.

$^1$H NMR ($CDCl_3$): δ8.07 (s, 1H), 7.40 (s, 1H), 4.45 (m, 2H), 3.42 (m, 2H), 3.07 (m, 3H), 2.89 (m, 2H), 2.19 (2H), 1.83 (m, 4H), 1.68 (6H), 1.12-1.40 (8H) ppm; HPLC-MS: m/z 406 (M+1).

Example 401

{[2-(3,3-Dicyclohexyl-ureido)-thiazol-5-ylmethyl]-amino}-acetic acid tert-butyl ester

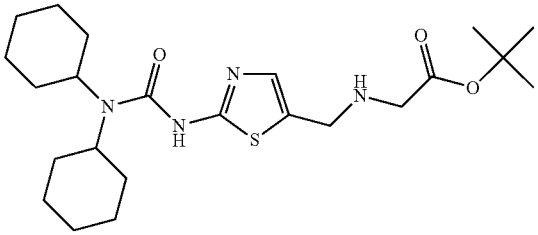

Prepared as described in general procedure (P) using 1,1-dicyclohexyl-3-(5-formyl-thiazol-2-yl)-urea (67 mg, 0.20 mmol), glycine tert-butyl ester hydrochloride (50 mg, 0.30 mmol) and sodium triacetoxyborohydride (59 mg, 0.28 mmol) to afford 62 mg (68%) of the desired product after purification.

$^1$H NMR ($CDCl_3$): δ7.14 (s, 1H), 3.91 (s, 2H), 3.43 (m, 2H), 3.30 (s, 2H), 2.68 (br, 1H), 1.59-1.93 (m, 12H), 1.46 (s, 9H), 1.10-1.39 (m, 8H) ppm; HPLC-MS: m/z 451 (M+1).

Example 402

{[2-(3,3-Dicyclohexyl-ureido)-thiazol-5-ylmethyl]-amino}-acetic acid

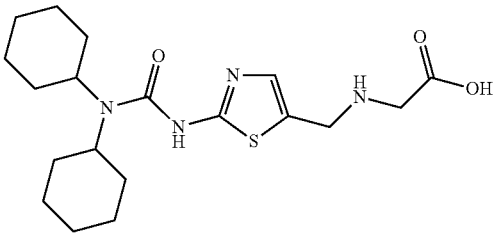

{[2-(3,3-Dicyclohexyl-ureido)-thiazol-5-ylmethyl]-amino}-acetic acid tert-butyl ester (14 mg, 0.03 mmol) was dissolved in methylene chloride. Hydrogen chloride (100 μL, 4N in dioxane) was added and the reaction was stirred at ambient temperature until no ester could be detected. The reaction was diluted with diethyl ether and concentrated. The resulting residue was dissolved in a minimum amount of methylene chloride, precipitated with diethyl ether and decanted. This was repeated to afford 9 mg (69%) of the desired compound. HPLC-MS: m/z 395 (M+1).

Example 403

1-[2-(3,3-Dicyclohexyl-ureido)-thiazol-5-ylmethyl]-pyrrolidine-3-carboxylic acid benzyl ester

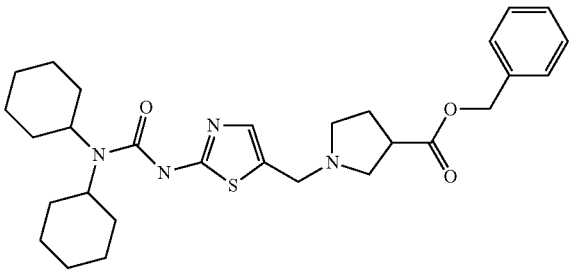

Prepared as described in general procedure (P) using 1,1-dicyclohexyl-3-(5-formyl-thiazol-2-yl)-urea (67 mg. 0.20 mmol), pyrrolidine-3-carboxylic acid benzyl ester hydrochloride (50 mg, 0.25 mmol) and sodium triacetoxyborohydride (55 mg, 0.26 mmol) to afford 52 mg (50%) of the desired product after purification.

$^1$H NMR ($CDCl_3$): δ 7.34 (m, 5H), 7.11 (s, 1H), 5.12 (d, 2H), 3.74 (s, 2H), 3.42 (m, 2H), 2.95-3.09 (m, 2H), 2.65-2.78 (m, 2H), 2.53 (m, 1H) 2.00-2.15 (m, 2H),1.61-1.88 (m, 12H), 1.10-1.37 (m, 8H) ppm; HPLC-MS: m/z 525 (M+1).

Example 404

1-[2-(3,3-Dicyclohexyl-ureido)-thiazol-5-ylmethyl]-pyrrolidine-3-carboxylic acid

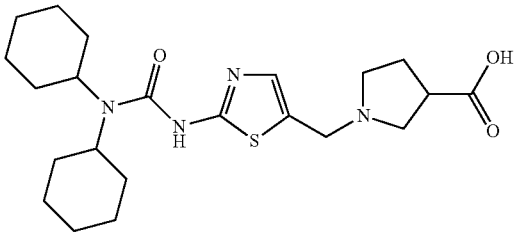

1-[2-(3,3-Dicyclohexyl-ureido)-thiazol-5-ylmethyl]-pyrrolidine-3-carboxylic acid benzyl ester (30 mg, 0.057 mmol) was combined with palladium on carbon (20 mg) in MeOH. Vacuum was applied to degas the mixture. The reaction was subjected to hydrogen and vigorous stirring until no ester could be detected (24 h). After filtering and concentration, the pure acid was obtained by trituration.

HPLC-MS: m/z 435 (M+1).

Example 405

1,1-Dicyclohexyl-3-(5-morpholin-4-ylmethyl-thiazol-2-yl)-urea

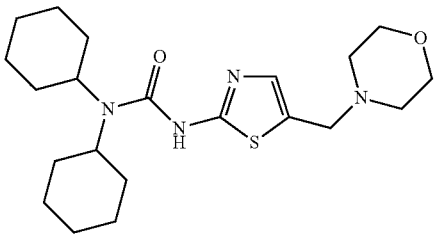

Prepared as described in general procedure (P) using 1,1-dicyclohexyl-3-(5-formyl-thiazol-2-yl)-urea (100 mg, 0.30 mmol), acetic acid (18 μL, 0.30 mmol), morpholine (78 μL, 0.90 mmol) and sodium triacetoxyborohydride (70 mg, 0.33 mmol) to afford 42 mg (34%) of the desired product after purification.

$^1$H NMR ($CDCl_3$): δ7.02 (s, 1H), 3.70 (m, 4H), 3.62 (s, 2H), 3.44 (m, 2H), 2.48 (m, 4H), 1.78-1.89 (m, 8H), 1.60-1.74 (m, 8H), 1.11-1.40 (m, 4H) ppm; HPLC-MS: m/z 407 (M+1).

Example 406

4-[2-(3,3-Dicyclohexyl-ureido)-thiazol-5-ylmethyl]-morpholine-2-carboxylic acid

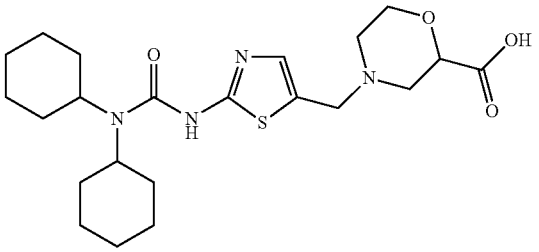

Prepared 11 mg (58%) following the general procedures (P) and (F) using 1,1-dicyclohexyl-3-(5-formyl-thiazol-2-yl)-urea (70 mg, 0.21 mmol) and morpholine-2-carboxylic acid benzyl ester hydrochloride (77 mg, 0.30 mmol).

HPLC-MS: m/z 451 (M+1).

Example 407

1,1-Dicyclohexyl-3-(5-thiomorpholin-4-ylmethyl-thiazol-2-yl)-urea

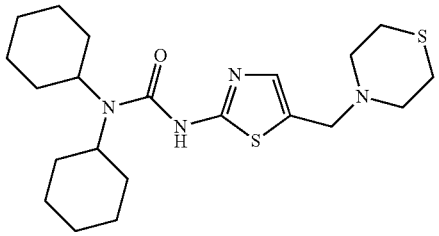

Prepared as described in general procedure (P) using 1,1-dicyclohexyl-3-(5-formyl-thiazol-2-yl)-urea (60 mg, 0.18 mmol), acetic acid (11 μL, 0.18 mmol), thiomorpholine (21 μL, 0.22 mmol) and sodium triacetoxyborohydride (38 mg, 0.20 mmol) to afford 7 mg (9%) of the desired product after purification.

$^1$H NMR ($CDCl_3$): δ 7.15 (s, 1H), 3.90 (m, 4H), 3.74 (s, 2H), 3.48 (m, 2H), 2.67 (m, 4H), 1.79-1.92 (m, 8H), 1.62-1.77 (m, 8H),1.12-1.42 (m, 4H) ppm; HPLC-MS: m/z 423 (M+1).

Example 408

1,1-Dicyclohexyl-3-[5-(1,1-dioxo-thiomorpholin-4-ylmethyl)-thiazol-2-yl]-urea

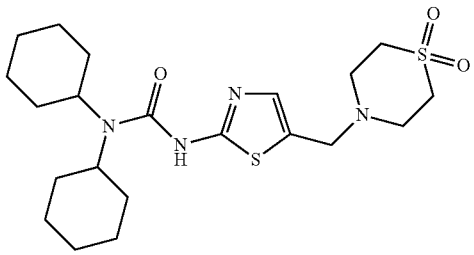

Prepared as described in general procedure (P) using 1,1-dicyclohexyl-3-(5-formyl-thiazol-2-yl)-urea (67 mg, 0.20 mmol), 1,1-dioxo-thiomorpholine hydrochloride (52 mg, 0.30 mmol) and sodium triacetoxyborohydride (51 mg, 0.24 mmol) to afford 16 mg (18%) of the desired product after purification.

$^1$H NMR ($CDCl_3$): δ7.12 (s, 1H), 3.76 (s, 2H), 3.42 (m, 2H), 3.03 (m, 8H), 1.78-1.96 (m, 6H), 1.61-1.78 (m, 6H), 1.09-1.45 (m, 8H) ppm; HPLC-MS: m/z 455 (M+1).

Example 409

1,1-Dicyclohexyl-3-[5-(4-oxo-piperidin-1-ylmethyl)-thiazol-2-yl]-urea

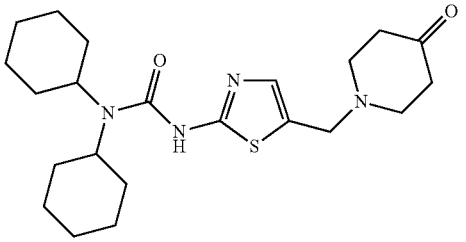

Prepared as described in general procedure (P) using 1,1-dicyclohexyl-3-(5-formyl-thiazol-2-yl)-urea (34 mg, 0.10 mmol), 4-piperidone hydrochloride (46 mg, 0.30 mmol) and sodium triacetoxyborohydride (25 mg, 0.12 mmol) to afford 5 mg (12%) of the desired product after purification.

$^1$H NMR ($CDCl_3$): δ7.99 (br, 1H), 7.11 (s, 1H), 3.91 (m, 2H), 3.74 (s, 2H), 3.42 (m, 2H), 2.77 (m, 2H), 2.44 (m, 2H), 1.79-1.91 (m, 8H), 1.62-1.75 (m, 8H), 1.09-1.41 (m, 4H) ppm; HPLC-MS: m/z 419 (M+1).

Example 410

1,1-Dicyclohexyl-3-[5-(4-propionyl-piperazin-1-ylmethyl)-thiazol-2-yl]-urea

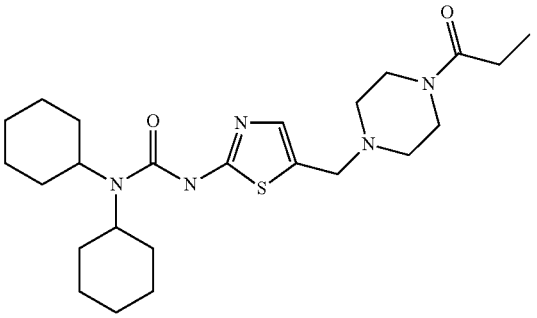

Prepared as described in general procedure (P) using 1,1-dicyclohexyl-3-(5-formyl-thiazol-2-yl)-urea (60 mg, 0.18 mmol), 1-piperazinyl-1-propanone (39 mg, 0.22 mmol), catalytic acetic acid and sodium triacetoxyborohydride (47 mg, 0.22 mmol) to afford 12 mg (15%) of the desired product after purification.

HPLC-MS: m/z 463 (M+1).

Example 411

4-[2-(3,3-Dicyclohexyl-ureido)-thiazol-5-ylmethyl]-piperazine-1-carboxylic acid tert-butyl ester

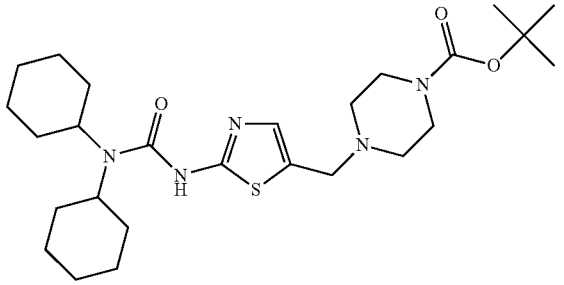

Prepared as described in general procedure P using 1,1-dicyclohexyl-3-(5-formyl-thiazol-2-yl)-urea (1.0 g, 3.0 Mmol), piperazine-1-carboxylic acid tert-butyl ester (838 mg, 4.5 mmol), acetic acid (40 μL, 0.6 mmol) and sodium triacetoxyborohydride (765 mg, 3.6 mmol) to afford 835 mg (55%) of the desired product after purification.

$^1$H NMR ($CDCl_3$): δ7.98 (br, 1H), 7.12 (s, 1H), 3.61 (s, 2H), 3.53 (m, 2H), 3.17 (m, 4H), 2.46 (m, 4H), 1.58-1.92 (m, 12H), 1.47 (s, 9H), 1.07-1.44 (m, 8H) ppm; HPLC-MS: m/z 506 (M+1).

Example 412

1,1-Dicyclohexyl-3-[5-(4-methanesulfonyl-piperazin-1-ylmethyl)-thiazol-2-yl]-urea

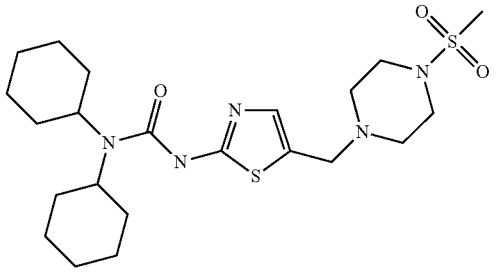

Prepared as described in general procedure (P) using 1,1-dicyclohexyl-3-(5-formyl-thiazol-2-yl)-urea (50 mg, 0.15 mmol), 4-methanesulfonyl-piperazine hydrochloride (45 mg, 0.23 mmol) and sodium triacetoxyborohydride (40 mg, 0.19 mmol) to afford 28 mg (38%) of the desired product after purification.

$^1$H NMR ($CDCl_3$): δ7.92 (br, 1H), 7.05 (s, 1H), 3.64 (s, 2H), 3.38 (m, 2H), 3.21 (m, 4H), 2.76 (s, 3H), 2.58 (m, 4H), 1.76-1.84 (m, 6H), 1.60-1.72 (m, 6H), 1.10-1.43 (m, 8H) ppm; HPLC-MS: m/z 484 (M+1).

Example 413

1,1-Dicyclohexyl-3-[5-(4-ethanesulfonyl-1-piperazinyl methyl)-thiazol-2-yl]-urea

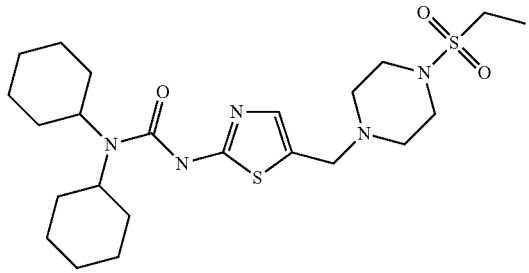

Prepared as described in general procedure (P) using 1,1-dicyclohexyl-3-(5-formyl-thiazol-2-yl)-urea (100 mg, 0.30 mmol), ethanesulfonyl-piperazine hydrochloride (128 mg, 0.60 mmol) and sodium triacetoxyborohydride (83 mg, 0.39 mmol) to afford 66 mg (44%) of the desired product after purification.

$^1$H NMR ($CDCl_3$): δ 7.98 (br, 1H), 7.10 (s, 1H), 3.66 (s, 2H), 3.42 (m, 2H), 3.29 (m, 4H), 2.94 (q, 2H), 2.56 (m, 4H), 1.65-1.92 (m, 12H), 1.16-1.44 (m, 11H) ppm; HPLC-MS: m/z 498 (M+1).

Example 414

1,1-Dicyclohexyl-3-{5-[4-(propane-1-sulfonyl)-piperazin-1-ylmethyl]-thiazol-2-yl}-urea

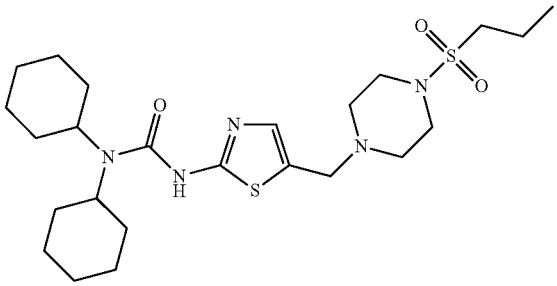

Prepared as described in general procedure (P) using 1,1-dicyclohexyl-3-(5-formyl-thiazol-2-yl)-urea (50 mg, 0.15 mmol), 1-propanesulfonyl-piperazine hydrochloride (52 mg, 0.23 mmol) and sodium triacetoxyborohydride (48 mg. 0.23 mmol) to afford 21 mg (27%) of the desired product after purification.

$^1$H NMR ($CDCl_3$): δ7.99 (s, 1H), 7.11 (s, 1H), 3.68 (s, 2H), 3.38 (m, 2H), 3.27 (m, 4H), 2.89 (m, 2H), 2.55 (m, 4H), 1.77-1.91 (m, 8H), 1.48-1.76 (m, 10H), 113-1.40 (m, 8H), 1.07 (t, 3H) ppm; HPLC-MS: m/z 512 (M+1).

Example 415

1,1-Dicyclohexyl-3-{5-[4-(propane-2-sulfonyl)-piperazin-1-ylmethyl]-thiazol-2-yl}-urea

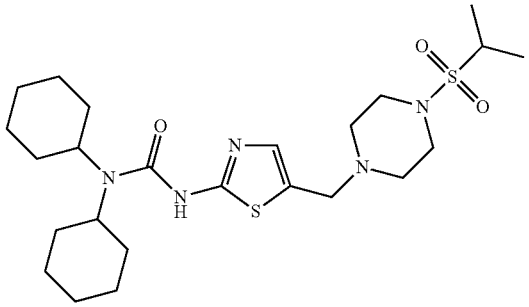

Prepared as described in general procedure (Q) using 1,1-dicyclohexyl-3-(5-piperazin-1-ylmethyl-thiazol-2-yl)-urea hydrochloride (36 mg, 0.08 mmol), DIEA (42 μL, 0.24 mmol) and propane-2-sulfonyl chloride (18 μL, 0.16 mmol) to afford 18 mg (44%) of the desired product after purification.

$^1$H NMR ($CDCl_3$): δ7.10 (s, 1H), 3.65 (s, 2H), 3.39 (m, 6H), 3.27 (m, 4H), 3.16 (m, 1H), 2.52 (m, 4H), 1.59-1.96 (m, 12H), 1.04-1.40 (m, 14H) ppm; HPLC-MS: m/z 512 (M+1).

Example 416

3-{5-[4-(Butane-1-sulfonyl)-piperazin-1-ylmethyl]-thiazol-2-yl}-1,1-dicyclohexyl-urea

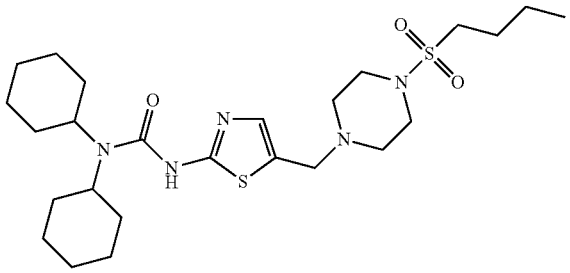

Prepared as described in general procedure (Q) using 1,1-dicyclohexyl-3-(5-piperazin-1-ylmethyl-thiazol-2-yl)-urea hydrochloride (30 mg, 0.06 mmol), DIEA (32 μL, 0.18 mmol) and butane-1-sulfonyl chloride (16 μL, 0.12 mmol) to afford 19 mg (61%) of the desired product after purification.

$^1$H NMR ($CDCl_3$): δ7.13 (s, 1H), 3.63 (s, 2H), 3.42 (m, 2H), 3.28 (m, 4H), 2.88 (m, 2H), 2.48 (m, 4H), 1.31-1.94 (m, 22H), 0.78-1.06 (m, 4H) ppm; HPLC-MS: m/z 526 (M+1).

Example 417

3-[5-(4-Benzenesulfonyl-piperazin-1-ylmethyl)-thiazol-2-yl]-1,1-dicyclohexyl-urea

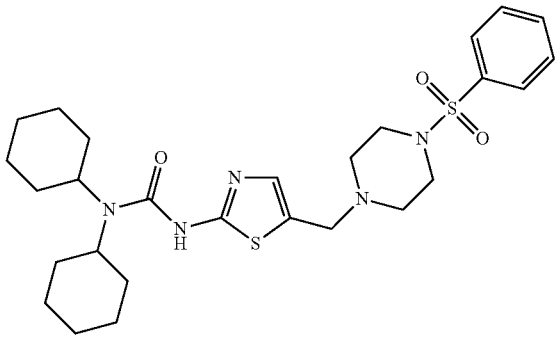

Prepared as described in general procedure (Q) using 1,1-dicyclohexyl-3 -(5-piperazin-1 -ylmethyl-thiazol-2-yl)-urea hydrochloride (36 mg, 0.08 mmol), DIEA (42 μL, 0.24 mmol) and benzenesulfonyl chloride (20 μL, 0.16 mmol) to afford 37 mg (68%) of the desired product after purification.

$^1$H NMR ($CDCl_3$): δ7.74 (d, 2H), 7.62 (m, 1H), 7.55 (m, 2H), 7.08 (s, 1H), 3.60 (s, 2H), 3.41 (m, 2H), 3.00 (m, 4H), 2.55 (m, 4H), 1.78-1.86 (m, 8H), 1.63-1.72 (m, 8H), 1.23-1.38 (m, 4H) ppm; HPLC-MS: m/z 546 (M+1).

Example 418

1,1-Dicyclohexyl-3-[5-(4-phenylmethanesulfonyl-piperazin-1-ylmethyl)-thiazol-2-yl]-urea

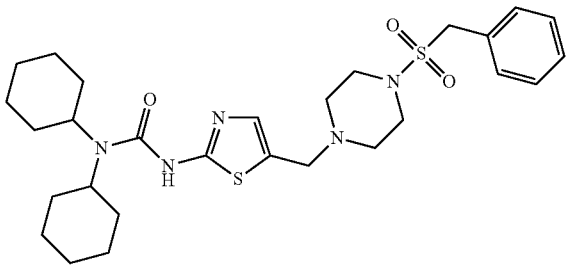

Prepared as described in general procedure (Q) using 1,1-dicyclohexyl-3-(5-piperazin-1-ylmethyl-thiazol-2-yl)-urea hydrochloride (26 mg, 0.05 mmol), DIEA (26 μL, 0.15 mmol) and alpha-toluenesulfonyl chloride (20 mg. 0.10 mmol) to afford 8 mg (29%) of the desired product after purification.

$^1$H NMR ($CDCl_3$): δ8.05 (br, 1H), 7.38 (m, 5H), 7.08 (s, 1H), 4.19 (s, 2H), 3.56 (s, 2H), 3.43 (m, 2H), 3.12 (m, 4H), 2.43 (m, 4H), 1.77-1.88 (m, 6H), 1.56-1.75 (m, 6H), 1.10-1.39 (m, 8H) ppm: HPLC-MS: m/z 560 (M+1).

Example 419

1,1-Dicyclohexyl-3-{5-[4-(1-methyl-1H-imidazole-4-sulfonyl)-piperazin-1-ylmethyl]-thiazol-2-yl}-urea

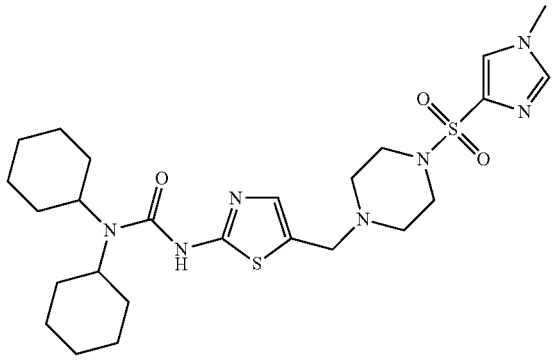

Prepared as described in general procedure (Q) using 1,1-dicyclohexyl-3-(5-piperazin-1-ylmethyl-thiazol-2-yl)-urea hydrochloride (27 mg, 0.055 mmol), DIEA (29 μL, 0.17 mmol) and N-methylimidazole-4-sulfonyl chloride (20 mg, 0.11 mmol) to afford 20 mg (66%) of the desired product after purification.

$^1$H NMR ($CDCl_3$): δ8.04 (br, 1H), 7.53 (s, 1H), 7.41 (s, 1H), 7.09 (s, 1H), 3.90 (m, 1H), 3.79 (s, 3H), 3.73 (s, 2H), 3.42 (m, 2H), 3.15 (m, 4H), 2.56 (m, 4H), 1.44-1.91 (m, 12H), 1.08-1.44 (m, 6H), 0.86 (m, 2H) ppm: HPLC-MS: m/z 550 (M+1).

Example 420

Propane-2-sulfonic acid {1-[2-(3,3-dicyclohexyl-ureido)-thiazol-5-ylmethyl]-piperidin-4-yl}-amide

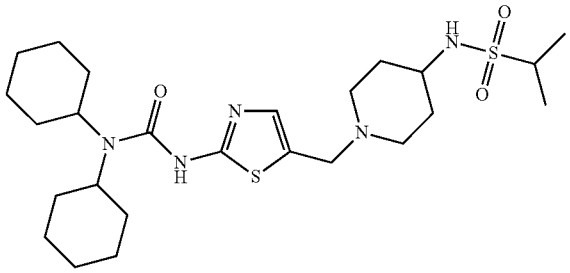

Prepared as described in general procedure (P) using 1,1-dicyclohexyl-3-(5-formyl-thiazol-2-yl)-urea (21 mg, 0.07 mmol), propane-2-sulfonic acid piperidin-4-yl amide hydrochloride (17 mg, 0.077 mmol) and sodium triacetoxyborohydride (19 mg, 0.09 mmol) to afford 4 mg (11%) of the desired product after purification.

HPLC-MS: m/z 526 (M+1).

Example 421

4-[2-(3,3-Dicyclohexyl-ureido)-thiazol-5-ylmethyl]-piperazine-1-sulfonic acid dimethylamide

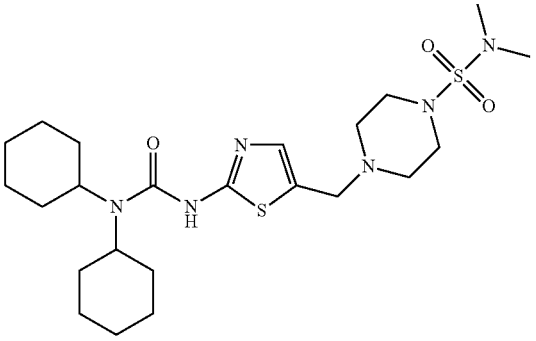

Prepared as described in general procedure (P) using 1,1-dicyclohexyl-3-(5-formyl-thiazol-2-yl)-urea (84 mg, 0.25 mmol), piperazine-1-sulfonic acid dimethyl amide hydrochloride (115 mg, 0.50 mmol) and sodium triacetoxyborohydride (70 mg, 0.33 mmol) to afford 54 mg (42%) of the desired product after purification.

$^1$H NMR ($CDCl_3$): δ7.09 (s, 1H), 3.64 (s, 2H), 3.42 (m, 2H), 3.25 (m, 4H), 2.81 (s, 6H), 2.51 (m, 4H), 1.77-1.91 (m, 6H), 1.61-1.73 (m, 6H), 1.09-1.41 (m, 8H) ppm; HPLC-MS: m/z 513 (M+1).

Example 422

4-[2-(3,3-Dicyclohexyl-ureido)-thiazole-5-carbonyl]-piperazine-1-carboxylic acid tert-butyl ester

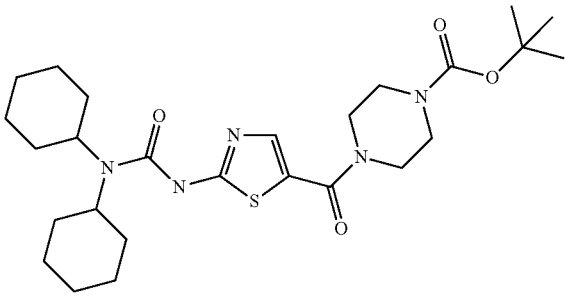

2-(3,3-Dicyclohexyl-ureido)-thiazole-5-carboxylic acid (176 mg, 0.50 mmol), piperazine carboxylic acid tert-butyl ester (140 mg, 0.75 mmol), and HBTU (285 mg, 0.75 mmol) were weighed out and added to a 25 mL reaction flask. DMF (5 mL) and DIEA (175 μL, 1.0 mmol) were added. The reaction was stirred under nitrogen at ambient temperature overnight. The reaction was diluted with EtOAc (10 mL) and quenched with saturated aqueous $NH_4Cl$ (10 mL). After separation and extraction with EtOAc (2×5 mL) the combined organic portions were dried over $MgSO_4$. Purification with silica gel and 10% EtOAc in $CH_2Cl_2$ afforded 187 mg (72%) of the desired compound.

$^1$H NMR ($CDCl_3$): δ8.08 (s, 1H), 7.67 (s, 1H), 3.70 (m, 4H), 3.18 (m, 6H), 1.63-1.89 (m, 14H), 1.48 (s, 9H), 1.12-1.39 (m, 6H) ppm; HPLC-MS: m/z 520 (M+1).

Example 423

4-[2-(3,3-Dicyclohexyl-ureido)-thiazole-5-carbonyl]-piperazine-1-sulfonic acid dimethylamide

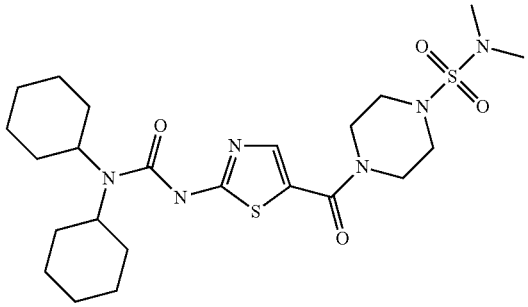

2-(3,3-Dicyclohexyl-ureido)-thiazole-5-carboxylic acid (53 mg, 0.15 mmol), piperazine sulfonic acid dimethylamide hydrochloride (44 mg, 0.19 mmol), and HBTU (74 mg, 0.19 mmol) were weighed out and added to a 10 mL reaction flask. DMF (1.5 mL) and DIEA (65 μL, 0.38 mmol) were added. The reaction was stirred under nitrogen at ambient temperature overnight. The reaction was diluted with EtOAc (5 mL) and quenched with saturated aqueous $NH_4Cl$ (5 mL). After separation and extraction with EtOAc (2×5 mL) the combined organic portions were dried over $MgSO_4$. Purification with silica gel (10% EtOAc and 1% MeOH in $CH_2Cl_2$) afforded 53 mg (67%) of the desired compound.

$^1$H NMR ($CDCl_3$): δ8.13 (br, 1H), 7.67 (s, 1H), 3.80 (m, 4H), 3.46 (m, 2H), 3.30 (m, 4H), 2.86 (s, 6H), 1.62-1.93 (m, 14H), 1.13-1.42 (m, 6H) ppm; HPLC-MS: m/z 527 (M+1).

Example 424

{1-[2-(3,3-dicyclohexyl-ureido)-thiazol-5-ylmethyl]-pyrrolidin-3-yl}-sulfonic acid dimethylamide

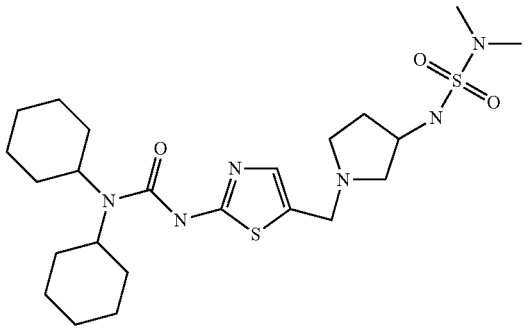

Prepared as described in general procedure (P) using 1,1-dicyclohexyl-3-(5-formyl-thiazol-2-yl)-urea (40 mg, 0.12 mmol), pyrrolidine-3-amino sulfonic acid dimethylamide hydrochloride (34 mg, 0.15 mmol) and sodium triacetoxyborohydride (32 mg, 0.15 mmol) to afford 36 mg (59%) of the desired product after purification.

$^1$H NMR ($CDCl_3$): δ8.31 (br, 1H), 7.21 (s, 1H), 5.69 (br, 1H), 3.87 (m, 1H), 3.70 (m, 2H), 3.40 (m, 2H), 2.90 (m, 1H), 2.76 (s, 6H), 2.55 (m, 1H), 2.25 (m, 2H), 1.61-1.93 (m, 16H), 1.10-1.41 (m, 6H) ppm; HPLC-MS: m/z 513 (M+1).

Example 425

Ethanesulfonic acid {1-[2-(3,3-dicyclohexyl-ureido)-thiazol-5-ylmethyl]-pyrrolidin-3-yl}-amide

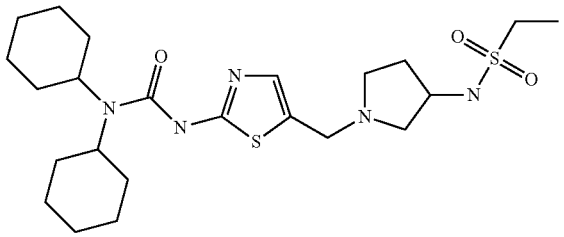

Prepared as described in general procedure (P) using 1,1-dicyclohexyl-3-(5-formyl-thiazol-2-yl)-urea (50 mg, 0.15 mmol), ethanesulfonic acid pyrrolidin-3-yl amide hydrochloride (41 mg, 0.19 mmol) and sodium triacetoxyborohydride (40 mg, 0.19 mmol) to afford 35 mg (47%) of the desired product after purification.

$^1$H NMR ($CDCl_3$): δ8.46 (br, 1H), 7.23 (s, 1H), 6.22 (br, 1H), 3.96 (m, 1H), 3.69 (s, 2H), 3.39 (m, 2H), 3.00 (q, 2H), 2.93 (m, 1H), 2.76 (1H), 2.56 (1H), 2.21-2.34 (m, 2H), 1.60-1.95 (m, 19H), 1.33 (t, 3H), 1.18 (m, 2H) ppm; HPLC-MS: m/z 498 (M+1).

Example 426

1,1-Dicyclohexyl-3-{5-[(1-ethanesulfonyl-pyrrolidin-3-ylamino)-methyl]-thiazol-2-yl}-urea

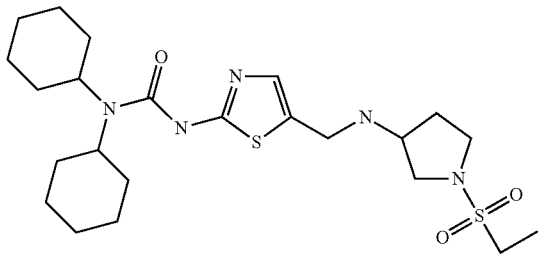

Prepared as described in general procedure (P) using 1,1-dicyclohexyl-3-(5-formyl-thiazol-2-yl)-urea (50 mg, 0.15 mmol), 3-amino-1-pyrrolidine ethane sulfonamide hydrochloride (41 mg, 0.19 mmol) and sodium triacetoxyhorohydride (40 mg, 0.19 mmol) to afford 15 mg (20%) of the desired product after purification.

$^1$H NMR ($CDCl_3$): δ8.28 (br, 1H), 7.13 (s, 1H), 4.63 (m, 1H), 3.89 (s, 2H), 3.37-3.62 (m, 6H), 3.17 (m, 1H), 3.03 (m, 3H), 2.09 (m, 2H),1.63-1.88 (m, 12H), 1.39 (t, 3H), 1.12-1.38 (m, 6H) ppm; HPLC-MS: m/z 498 (M+1).

Example 427

4-[3-(5-Formyl-thiazol-2-yl)-1-(4-methyl-cyclohexyl)-ureido]-piperidine-1-carboxylic acid tert-butyl ester

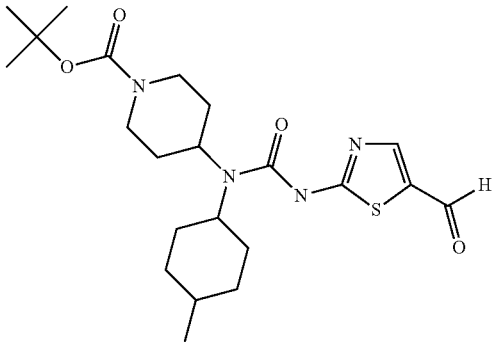

Prepared in a manner similar to general procedure (C) using 5-formyl-2-aminothiazole (1.88 g, 14.6 mmol), 4-(4-methyl-cyclohexylamino)-piperidine-1-carboxylic acid tert-butyl ester (4.32 mg, 14.6 mmol), catalytic DMAP, CDI (2.60 g, 1.1 mmol) and THF with heating to 65° C. afforded 1.77 g (27%) of the desired product after purification.

$^1$H NMR ($CDCl_3$): δ9.91 (s, 1H), 8.01 (s, 1H), 3.74 (m, 1H), 3.33 (m, 1H), 2.75 (m, 4H), 2.04 (m, 4H),1.53-1.82 (m, 8), 1.46 (s, 9H), 1.62-1.83 (m, 4H), 0.85-1.15 (m, H) ppm; HPLC-MS: m/z 451 (M+1).

Example 428

4-[3-[5-(4-Ethanesulfonyl-piperazin-1-ylmethyl)-thiazol-2-yl]-1-(4-methyl-cyclohexyl)-ureido]-piperidine-1-carboxylic acid tert-butyl ester

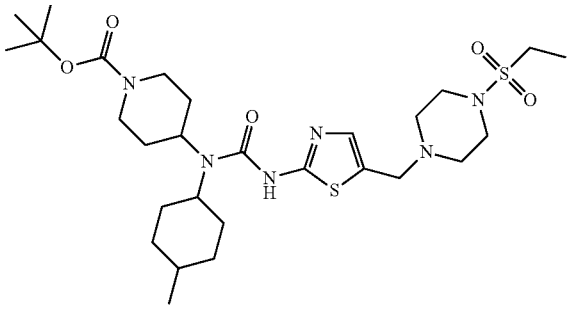

Prepared as described in general procedure (P) using 4-[3-(5-formyl-thiazol-2-yl)-1-(4-methyl-cyclohexyl)-ureido]-piperidine-1-carboxylic acid tert-butyl ester (200 mg, 0.45 mmol), piperazine ethane sulfonamide hydrochloride (125 mg, 0.58 mmol), triethyl amine (80 μL, 0.58 mmol) and sodium triacetoxyborohydride (113 mg, 0.53 mmol) to afford 160 mg (58%) of the desired product after purification.

$^1$H NMR ($CDCl_3$): δ9.37 (br, 1H), 7.16 (s, 1H), 4.21 (m, 2H), 3.70 (s, 2H), 3.35 (m, 5H), 2.96 (m, 2H), 2.79 (m, 2H), 2.61 (m, 4H), 1.82-2.21 (m, 6H), 1.63 (m, 6H), 1.47 (s, 9H), 1.38 (m, 4H), 1.05 (d, 3H), 0.92 (m, 1H) ppm; HPLC-MS: m/z 613 (M+1).

Example 429

1-(1-Cyclopentanecarbonyl-piperidin-4-yl)-3-[5-(4-ethanesulfonyl-piperazin-1-ylmethyl)-thiazol-2-yl]-1-(4-methyl-cyclohexyl)-urea

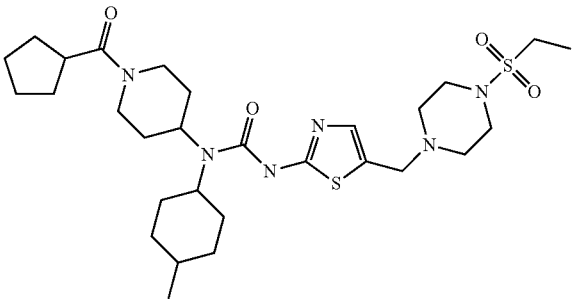

Prepared as described in general procedure (N) using 3-[5-(4-ethanesulfonyl-piperazin-1-ylmethyl)-thiazol-2-yl]-1-(4-methyl-cyclohexyl)-1-piperidin-4-yl-urea hydrochloride (48 mg, 0.078 mmol), TEA (24 μL, 0.17 mmol) and cyclopentane carbonylchloride (11 μL, 0.086 mmol) and to afford 19 mg (40%) of the desired product after purification.

$^1$H NMR ($CDCl_3$): δ8.22 (br, 1H), 7.10 (s, 1H), 4.78 (m, 1H), 4.07 (m, 1H), 3.68 (m, 3H), 3.31 (m, 4H), 2.97 (m, 3H), 2.56 (m, 4H), 2.14 (m, 2H), 1.45-2.05 (m, 21H), 1.37 (t, 3H), 0.87-1.10 (m, 4H) ppm; HPLC-MS: m/z 609 (M+1).

Example 430

3-[5-(4-Ethanesulfonyl-piperazin-1-ylmethyl)-thiazol-2-yl]-1-[1-(4-fluoro-benzoyl)-piperidin-4-yl]-1-(4-methyl-cyclohexyl)-urea

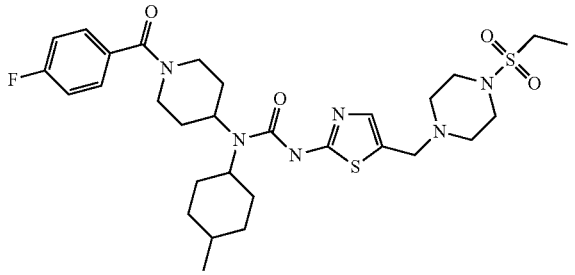

Prepared as described in general procedure (N) using 3-[5-(4-ethanesulfonyl-piperazin-1-ylmethyl)-thiazol-2-yl]-1-(4-methyl-cyclohexyl)-1-piperidin-4-yl-urea hydrochloride (46 mg, 0.075 mmol), TEA (26 μL, 0.19 mmol) and 4-fluorobenzoyl chloride (10 μL, 0.083 mmol) and to afford 41 mg (86%) of the desired product after purification.

$^1$H NMR ($CDCl_3$): δ8.07 (s, 1H), 7.45 (m, 2H), 7.11 (m, 3H), 3.86 (m, 1H), 3.65 (s, 2H), 3.32 (m, 5H), 2.73-3.13 (m, 6H), 2.55 (m, 4H), 2.38 (m, 2H), 1.99 (m, 2H), 1.48-1.87 (m, 8H), 1.37 (t, 3H), 0.90-1.13 (m, 4H) ppm; HPLC-MS: m/z 635 (M+1).

Example 431

4-[3-[5-(4-Dimethylsulfamoyl-piperazin-1-ylmethyl)-thiazol-2-yl]-1-(4-methyl-cyclohexyl)-ureido]-piperidine-1-carboxylic acid tert-butyl ester

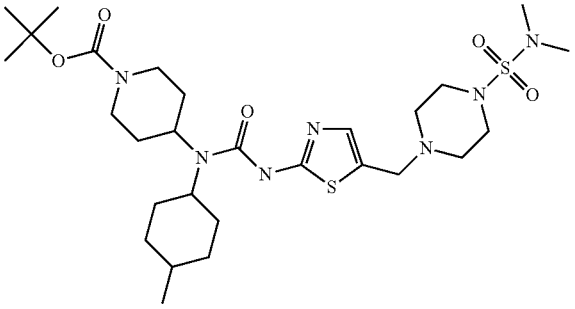

Prepared as described in general procedure (P) using 4-[3-(5-formyl-thiazol-2-yl)-1-(4-methyl-cyclohexyl)-ureido]-piperidine-1-carboxylic acid tert-butyl ester (202 mg, 0.45 mmol), piperazine sulfonic acid dimethylamide hydrochloride (132 mg, 0.58 mmol), triethyl amine (80 μL, 0.58 mmol) and sodium triacetoxyborohydride (118 mg, 0.53 mmol) to afford 110 mg (39%) of the desired product after purification.

$^1$H NMR ($CDCl_3$): δ8.43 (br, 1H), 7.11 (s, 1H), 4.24 (m, 2H), 3.65 (m, 3H), 3.26 (m, 4H), 2.82 (s, 6H), 2.74 (m, 2H), 2.52 (m, 4H), 2.08 (m, 2H), 1.57-2.03 (m, 8H), 1.49 (s, 9H), 1.26 (m, 2H), 1.05 (d, 3H), 0.82-0.97 (m, 2H) ppm; HPLC-MS: m/z 628 (M+1).

Example 432

4-{2-[3-(1-Cyclopentanecarbonyl-piperidin-4-yl)-3-(4-methyl-cyclohexyl)-ureido]-thiazol-5-ylmethyl}-piperazine-1-sulfonic acid dimethylamide

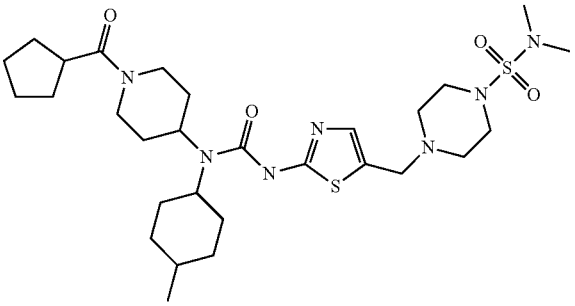

Prepared as described in general procedure (N) using 4-{2-[3-(4-methyl-cyclohexyl)-3-piperidin-4-yl-ureido]-thiazol-5-ylmethyl}-piperazine-1-sulfonic acid dimethylamide hydrochloride (50 mg, 0.088 mmol), TEA (31 FμL, 0.22 mmol) and cyclopentane carbonyl chloride (13 μL, 0.11 mmol) to afford 27 mg (49%) of the desired product after purification.

$^1$H NMR ($CDCl_3$): δ8.62 (br, 1H), 7.10 (s, 1H), 4.78 (d, 1H), 4.07 (d, 1H), 3.76 (m, 1H), 3.65 (s, 2H), 3.27 (m, 4H), 3.05 (m, 1H), 2.91 (m, 1H), 2.82 (s, 6H), 2.53 (m, 4H), 1.38-2.19 (m, 21H), 1.05 (d, 3H), 0.81-0.98 (m, 2H) ppm; HPLC-MS: m/z 624 (M+1).

Example 433

4-{2-[3-[1-(4-Fluoro-benzoyl)-piperidin-4-yl]-3-(4-methyl-cyclohexyl)-ureido]-thiazol-5-ylmethyl}-piperazine-1-sulfonic acid dimethylamide

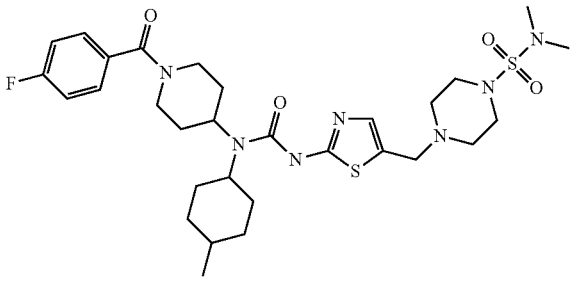

Prepared as described in general procedure (N) using 4-{2-[3-(4-methyl-cyclohexyl)-3-piperidin-4-yl-ureido]-thiazol-5-ylmethyl}-piperazine-1-sulfonic acid dimethylamide hydrochloride (47 mg, 0.083 mmol), TEA (26 μL, 0.19 mmol) and 4-fluorobenzoyl chloride (10 μL, 0.083 mmol) to afford 39 mg (73%) of the desired product after purification.

$^1$NMR ($CDCl_3$): δ8.17 (br, 1H). 7.46 (m, 2H), 7.10 (m, 3H), 4.82 (m, 1H), 3.73 (m, 1H), 3.65 (s, 2H), 3.27 (m, 5H), 3.03 (m, 1H), 2.82 (s, 6H), 2.53 (m, 4H), 2.32 (m, 2H), 2.00 (m, 2H), 1.36-1.87 (m, 6H), 1.15 (m, 4H), 1.05 (d. 3H), 0.80-0.99 (m, 1H) ppm; HPLC-MS: m/z 650 (M+1).

Example 434

TTP-00212496

{4-[2-(3,3-Dicyclohexyl-ureido)-1-thiazole-5-carbonyl]-piperazin-1-yl}-acetic acid ethyl ester

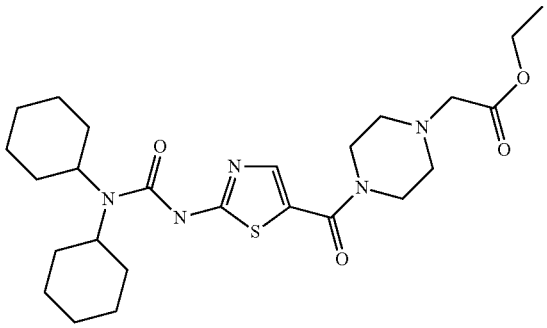

2-(3,3-Dicyclohexyl-ureido)-thiazole-5-carboxylic acid (53 mg, 0.15 mmol), 1-morpholin-4-yl-2-piperazin-1-yl-ethanone (39 mg, 0.23 mmol), and HBTU (74 mg, 0.19 mmol) were weighed out and added to a 25 mL reaction flask. DMF (2 mL) and DIEA (52 μL, 0.30 mmol) were added. The reaction was stirred under nitrogen at ambient temperature overnight. The reaction was diluted with EtOAc (10 mL) and quenched with saturated aqueous $NH_4Cl$ (10 mL). After separation and extraction with EtOAc (2×5 mL) the combined organic portions were dried over $MgSO_4$. Purification with silica gel chromatography (10% EtOAc and 1% MeOH in $CH_2Cl_2$) afforded 37 mg (49%) of the desired compound.

HPLC-MS: m/z 506 (M+1).

Example 435

{4-[2-(3,3-Dicyclohexyl-ureido)-thiazole-5-carbonyl]-piperazin-1-yl}-acetic acid

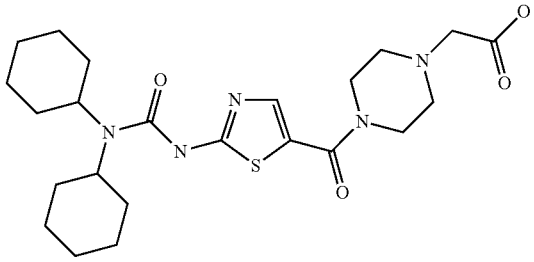

Prepared as described in general procedure (F) using {4-[2-(3,3-dicyclohexyl-ureido)-thiazole-5-carbonyl]-piperazin-1-yl}-acetic acid ethyl ester (16 mg, 0.32 mmol) afforded 6 mg (39%) of the desired compound.

HPLC-MS: m/z 478 (M+1).

Example 436

1,1-Dicyclohexyl-3-{5-[4-(2-morpholin-4-yl-2-oxo-ethyl)-piperazine-1-carbonyl]-thiazol-2-yl}-urea

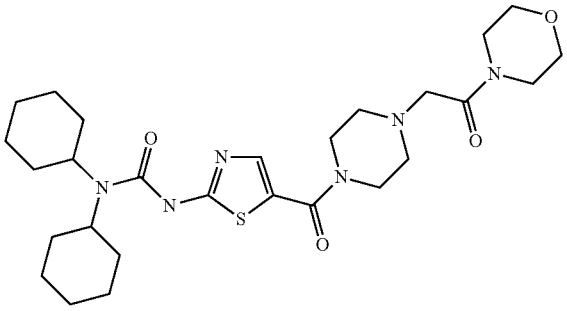

2-(3,3-Dicyclohexyl-ureido)-thiazole-5-carboxylic acid (53 mg, 0.15 mmol), 1-morpholin-4-yl-2-piperazin-1-yl-ethanone (42 mg, 0.19 mmol), and HBTU (71 mg, 0.19 mmol) were weighed out and added to a 25 mL reaction flask. DMF (2 mL) and DIEA (65 μL, 0.37 mmol) were added. The reaction was stirred under nitrogen at ambient temperature overnight. The reaction was diluted with EtOAc (10 mL) and quenched with saturated aqueous $NH_4Cl$ (10 mL). After separation and extraction with EtOAc (2×5 mL) the combined organic portions were dried over $MgSO_4$. Purification with silica gel chromatography (10% EtOAc and 1% MeOH in $CH_2Cl_2$) afforded 17 mg (31%) of the desired compound.

$^1$H NMR ($CDCl_3$): δ8.26 (br, 1H), 7.65 (s, 1H), 3.82 (s. 2), 3.65 (m, 8H), 3.33 (m, 6H), 2.58 (m, 4H), 1.59-2.17 (m, 12H), 1.12-1.20 (m, 6H), 0.80-0.92 (m, 2H) ppm; HPLC-MS: m/z 547 (M+1).

Example 437

4-[3-{5-[4-(2-Methoxycarbonyl-acetyl)-piperazin-1-ylmethyl]-thiazol-2-yl}-1-(4-methyl-cyclohexyl)-ureido]-piperidine-1-carboxylic acid tert-butyl ester

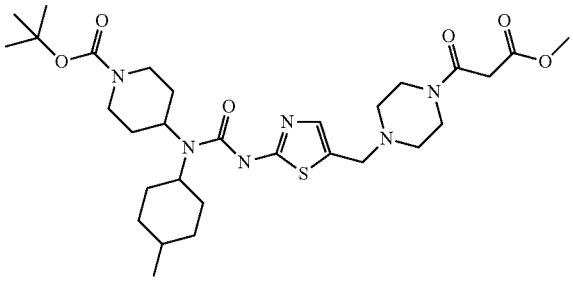

Prepared as described in general procedure (P) using 4-[3-(5-formyl-thiazol-2-yl)-1-(4-methyl-cyclohexyl)-ureido]-piperidine-1-carboxylic acid tert-butyl ester (68 mg, 0.15 mmol), 3-oxo-3-piperazin-1-yl-propionic acid methyl ester hydrochloride (54 mg, 0.19 mmol) and sodium triacetoxyborohydride (38 mg, 0.18 mmol) to afford 23 mg (25%) of the desired product after purification.

HPLC-MS: m/z 621 (M+1).

Example 438

3-(4-{2-[3-(1-Butyryl-piperidin-4-yl)-3-(4-methyl-cyclohexyl)-ureido]-thiazol-5-ylmethyl}-piperazin-1-yl)-3-oxo-propionic acid methyl ester

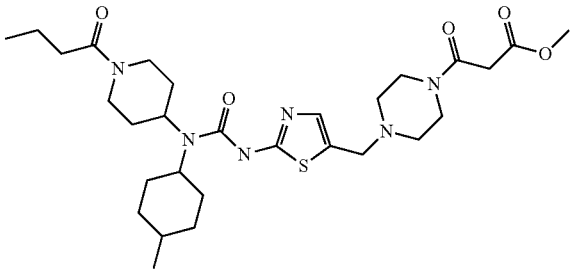

Prepared as described in general procedure (N) using 3-(4-{2-[3-(4-Methyl-cyclohexyl)-3-piperidin-4-yl-ureido]-thiazol-5-ylmethyl}-piperazin-1-yl)-3-oxo-propionic acid methyl ester hydrochloride (17 mg, 0.032 mmol), TEA (10 μL, 0.050 mmol) and 1-butyryl chloride (5 μL, 0.039 mmol) to afford 12 mg (65%) of the desired product after purification.

$^1$H NMR ($CDCl_3$): δ8.67 (br, 1H), 7.08 (s, 1H), 4.76 (m, 1H), 3.94 (m, 1H), 3.74 (s, 3H), 3.63 (m, 4H), 3.45 (s, 2H), 3.41 (m, 2H), 3.30 (m, 1H), 3.07 (m, 1H), 2.56 (m, 1H), 2.46 (m, 4H), 2.32 (t, 2H), 2.12 (m, 2H), 1.93 (m, 2H), 1.53-1.81 (m, 6H), 1.46 (m, 2H), 1.24 (m, 4H), 1.05 (m, 2H), 0.98 (t, 3H), 0.79-0.94 (m, 1H) ppm; HPLC-MS: m/z 591 (M+1).

Example 439

1-Cycloheptyl-3-[5-(4-ethanesulfonyl-piperazin-1-ylmethyl)-thiazol-2-yl]-1-(trans-4-methyl-cyclohexyl)-urea

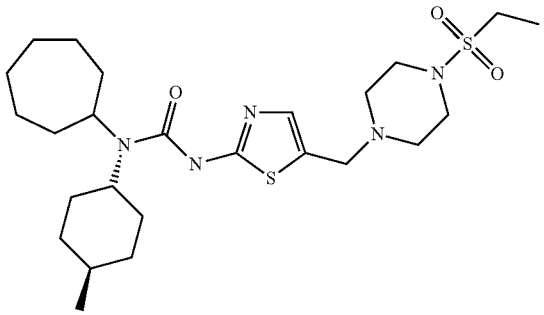

Prepared as described in general procedure (P) using 1-cycloheptyl-3-(5-formyl-thiazol-2-yl)-1-(4-trans-methyl-cyclohexyl)-urea (100 mg, 0.28 mmol), ethane sulfonyl piperazine hydrochloride (68 mg, 0.30 mmol) and sodium triacetoxyborohydride (70 mg, 0.33 mmol) to afford 18 mg (13%) of the desired product after purification.

$^1$H NMR ($CDCl_3$): δ7.89 (br, 1H), 7.11 (s, 1H), 3.78 (m, 1H), 3.66 (s, 2H), 3.41 (m, 2H), 3.29 (m, 4H), 2.93 (m, 3H), 2.55 (m, 4H), 2.08 (m, 2H), 1.46-1.83 (m, 12H), 1.37 (t, 3H), 1.20-1.35 (m, 2H), 1.08 (m, 2H), 0.90 (d, 3H), 0.82 (m, 1H) ppm; HPLC-MS: m/z 526 (M+1).

Example 440

4-{2-[3-Cycloheptyl-3-(4-trans-methyl-cyclohexyl)-ureido]-thiazol-5-ylmethyl}-piperazine-1-sulfonic acid dimethylamide

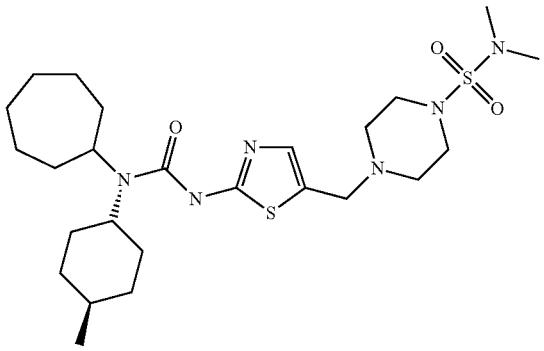

Prepared as described in general procedure (P) using 1-cycloheptyl-3-(5-formyl-thiazol-2-yl)-1-(4-trans-methyl-cyclohexyl)-urea (100 mg, 0.28 mmol), piperazine sulfonic acid dimethyl amide hydrochloride (69 mg, 0.30 mmol) and sodium triacetoxyborohydride (70 mg, 0.33 mmol) to afford 16 mg (11%) of the desired product after purification.

HPLC-MS: m/z 541 (M+1).

Example 441

1-Cycloheptyl-3-(5-hydroxymethyl-thiazol-2-yl)-1-(trans-4-methyl-cyclohexyl)-urea

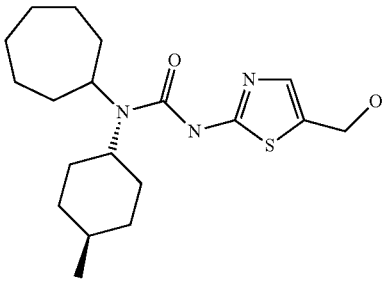

Prepared using 1-cycloheptyl-3-(5-formyl-thiazol-2-yl)-1-(4-trans-methyl-cyclohexyl)-urea (20 mg, 0.055 mmol) and lithium borohydride (45 μL, 2M in THF) in MeOH (1 mL). Purification without work-up (silica gel, 10% EtOAc and 2% MeOH in $CH_2Cl_2$) afforded 20 mg (99%) of the desired compound.

$^1$H NMR ($CDCl_3$): δ8.90 (br, 1H), 7.18 (s, 1H), 4.73 (s, 2H), 3.73 (br, 1H), 3.43 (m, 1H), 2.07 (m, 2H), 1.65-1.83 (m, 8H), 1.43-1.65 (m, 7H), 1.21-1.43 (m, 2H), 0.99-1.14 (m, 2H), 0.90 (d, 3H), 0.85-0.89 (m, 1H) ppm; HPLC-MS: m/z 366 (M+1).

Example 442

1,1-Dicyclohexyl-3-(5-hydroxymethyl-thiazol-2-yl)-urea

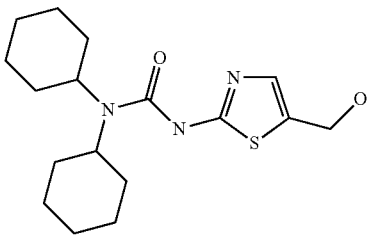

Prepared using 1,1-dicyclohexyl-3-(5-formyl-thiazol-2-yl)-urea (50 mg, 0.15 mmol) and lithium borohydride (95 μL, 2M in THF) in MeOH (1 mL). Purification without work-up (silica gel, 10% EtOAc and 2% MeOH in $CH_2Cl_2$) afforded 49 mg (97%) of the desired compound.

$^1$H NMR ($CDCl_3$): δ8.12 (br, 1H), 7.19 (s, 1H), 4.73 (s, 2H), 3.45 (m, 2H), 1.60-2.07 (m, 12H), 1.09-1.42 (m, 8H) ppm; HPLC-MS: m/z 338 (M+1).

Example 443

{[2-(3,3-Dicyclohexyl-ureido)-thiazole-4-carbonyl]-amino}-acetic acid methyl ester

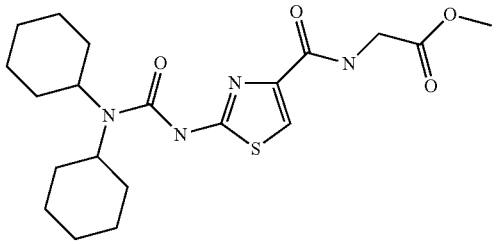

Prepared in 30% yield (76 mg) as described in general procedure (K) from 2-(3,3-dicyclohexylureido)-thiazole-4-carboxylic acid (210 mg, 0.6 mmol) and glycine methyl ester (HCl salt, 75 mg, 0.6 mmol).

$^1$H NMR ($CDCl_3$): δ 8.06 (s, 1H), 7.65 (s, 1H), 4.24 (d, 2H), 3.80 (s, 3H), 3.46 (m, 2H), 1.10-1.90 (m, 20H) ppm; HPLC-MS: m/z 423 (M+1).

Example 444

1,1-Dicyclohexyl-3-[4-(morpholine-4-carbonyl)thiazol-2-yl]-urea

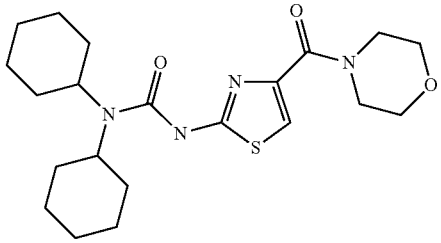

Prepared in 24% yield (61 mg) as described in general procedure (K) from 2-(3,3-dicyclohexylureido)-thiazole-4-carboxylic acid (210 mg, 0.60 mmol) and morpholine (52 mg, 0.60 mmol).

$^1$H NMR (d6-DMSO): δ 8.10 (s, 1H), 7.65 (s, 1H), 3.60 (m, 4H), 3.20 (m, 4H), 1.10-1.90 (m, 20H) ppm; HPLC-MS: m/z 421 (M+1).

Example 445

2(S)-{[2-(3,3-Dicyclohexylureido)-thiazole-4-carbonylamino)propionic acid methyl ester

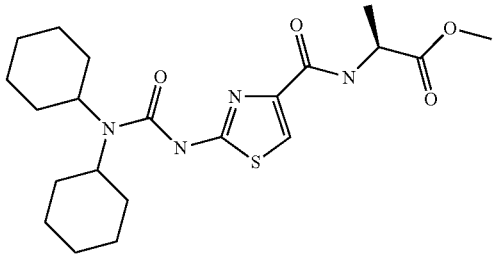

Prepared in 17% yield (44 mg) as described in general procedure (K) from 2-(3,3-dicyclohexylureido)-thiazole-4-carboxylic acid (210 mg, 0.60 mmol) and (S)-alanine methyl ester (HCl salt, 84 mg, 0.6 mmol).

$^1$H NMR ($CDCl_3$): δ 8.00 (s, 1H), 7.62 (s, 1H), 4.79 (q, 1H), 3.78 (s, 3H), 3.46 (m, 2H), 1.60-1.90 (m, 14H), 1.52 (d, 3H), 1.10-1.40 (m, 6H) ppm; HPLC-MS: m/z 437 (M+1).

Example 446

2(S)-{[2-(3,3-Dicyclohexylureido)-thiazole-4-carbonyl]-amino}propionic acid

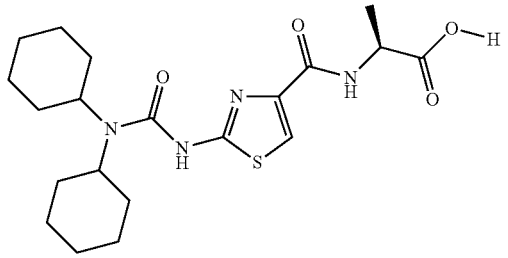

Prepared in 94% yield (36 mg) as described in general procedure (K). Hydrolysis of 2(S)-{[2-(3,3-dicyclohexylureido)-thiazole-4-carbonyl]-amino}propionic acid methyl ester (40 mg, 0.09 mmol).

$^1$H NMR (4:1 $CDCl_3$-$CD_3OD$): δ 8.00 (s, 1H), 7.62 (s, 1H), 4.66 (m, 1H), 3.44 (m, 2H), 1.60-1.90 (m, 14H), 1.55 (d, 3H), 1.10-1.40 (m, 6H) ppm; HPLC-MS: m/z 423 (M+1).

Example 447

2-{[2-(3,3-Dicyclohexylureido)-thiazole-4-carbonyl] acetic acid

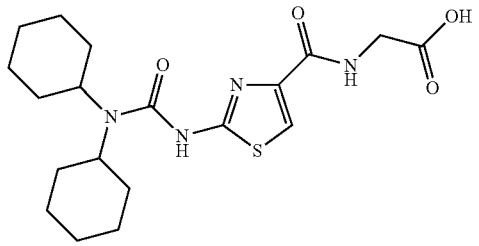

Prepared in 95% yield (56 mg) as described in general procedure (F) by hydrolysis of 2-{[2-(3,3-dicyclohexylureido)-thiazole-4-carbonyl]-amino}acetic acid methyl ester (60 mg, 0.14 mmol).

$^1$H NMR (4:1 $CDCl_3$-$CD_3OD$): δ 8.06 (s, 1H), 7.65 (s, 1H), 7.54 (t, 1H), 4.17 (d, 2H), 3.37 (m, 2H), 1.10-1.90 (m, 20H) ppm; HPLC-MS: m/z 409 (M+1).

Example 448

1,1-Dicyclohexyl-3-[4-(pyridin-2-yloxymethyl)-thiazol-4-yl]urea

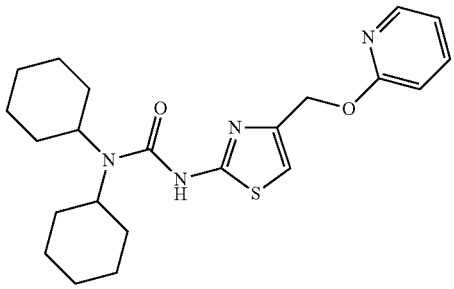

1,1-Dicyclohexyl-3-(4-hydroxymethylthiazole-2-yl)urea (180 mg, 0.5 mmol) was dissolved in 5.0 mL anhydrous DMF and treated with NaH (60 mg, 1.50 mmol) for 30 min at r.t. After addition of 2-bromopyridine (70 uL, 0.75 mmol), the resulting solution was heated for 12 h at 95 C. After cooling to r.t., the DMF solution was diluted with 20 mL water and extracted with EtOAc (2×20 mL). The combined organic extracts were washed with water (2×10 mL), dried over sodium sulfate and concentrated to a yellow oil. After flash chromatography, the desired product was obtained in 25 mg (11.5%) yield.

$^1$H NMR (d6-DMSO): δ 10.80 (s, 1H), 8.16 (d, 1H), 7.68 (m, 1H), 6.96 (m, 2H), 6.82 (d, 1H), 5.20 (s, 2H), 3.40 (m, 2H), 1.15-1.90 (m, 20H) ppm; HPLC-MS: m/z 415 (M+1).

Example 449

1,1-Dicyclohexyl-3-[4-(pyridin-2-yloxymethyl)-thiazol-4-yl]urea

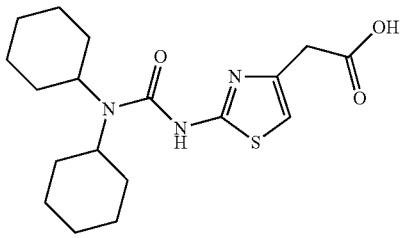

Prepared in quantitative yield (1.85 g) as described in general procedure (F) by hydrolysis of [2-(3,3-dicyclohexylureido)-thiazol-4-yl]acetic acid ethyl ester (2.0 g, 5.1 mmol).

$^1$H NMR (4:1 $CDCl_3$-$CD_3OD$): δ 6.60 (s, 1H), 3.46 (m, 4H), 1.15-1.90 (m, 20H) ppm; HPLC-MS: m/z 366 (M+1).

Example 450

{{[2-(3,3-Dicyclohexyl-ureido)-thiazol-4-ylmethyl]-carbamoyl}-methyl}carbamic acid tert-butyl ester

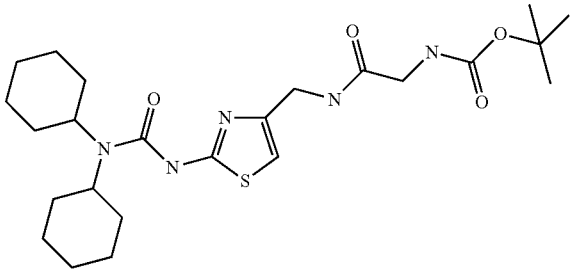

Prepared in 29% yield (40 mg) as described in general procedure (K) from 3-(4-aminomethylthiazol-2-yl)-1,1-dicyclohexyl-urea (96 mg, 0.28 mmol) and Boc-glycine (60 mg, 0.30 mmol).

$^1$H NMR ($CDCl_3$): δ 6.80 (s, 1H), 6.60 (s, 1H), 4.29 (d, 2H), 3.83 (m, 2H), 3.43 (s, 1H), 2.80 (s, 2H), 1.15-1.90 (m, 20H), 1.10 (s, 9H) ppm; HPLC-MS: m/z 494 (M+1).

Example 451

TTP-00203346

1,1-Dicyclohexyl-3-(4-morpholin-4-ylmethyl-thiazol-2-yl)-urea

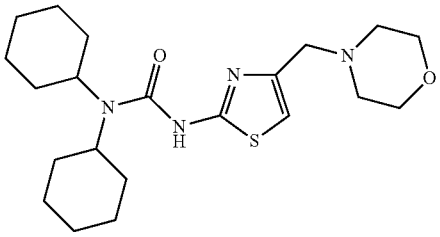

1,1-Dicyclohexyl-3-(4-morpholin-4-ylmethyl-thiazol-2-yl)-urea was prepared in 30% yield (30 mg) as described in general procedure A from 1,1-dicyclohexyl-3-(4-formyl-thiazol-2-yl)-urea (101 mg, 0.3 mmol) and morpholine (30 uL, 0.3 mmol) using sodium triacetoxyborohydride as the reducing reagent.

HPLC-MS: m/z 407 (M+1).

Example 452

1,1-Dicyclohexyl-3-{4-[2-(pyridin-2-yloxy)-ethyl]-thiazol-2-yl}-urea

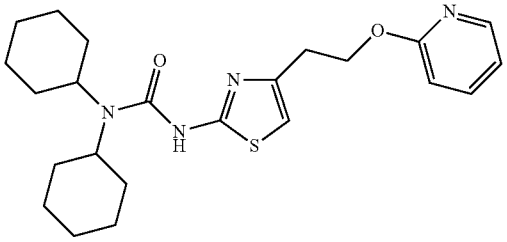

1,1-Dicyclohexyl-3-{4-[2-(pyridin-2-yloxy)-ethyl]-thiazol-2-yl}-urea was prepared from the sodium salt of 1,1-dicyclohexyl-3-[4-(2-hydroxyethyl)-thiazol-2-yl]-urea (50 mg, 0.14 mmol; 0.5 mmol NaH, DMF as solvent) and 2-bromopyridine (20 mg, 0.14 mmol). After aqueous workup, the resulting oil was purified on silica gel to give 1,1-dicyclohexyl-3-{4-[2-(pyridin-2-yloxy)-ethyl]-thiazol-2-yl}-urea in 20 mg (33%) yield.

$^1$H NMR ($CDCl_3$): δ 8.08 (d, 1H), 7.49 (t, 1H), 6.80 (t, 1H), 6.67 (d, 1H), 6.47 (s, 1H), 4.50 (t, 2H), 3.38 (m, 2H), 3.10 (t, 2H), 1.10-1.90 (m, 20H) ppm; HPLC-MS: m/z 429 (M+1).

Example 453

2-[2-(3,3-Dicyclohexylureido)-thiazol-4-ylmethyl-sulfanyl)-1H-imidazole-4-carboxylic acid

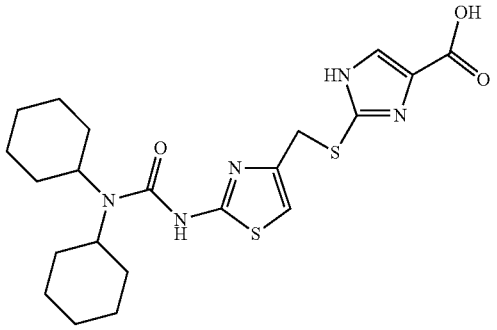

2-[2-(3,3-Dicyclohexylureido)-thiazol-4-ylmethylsulfanyl)-1H-imidaole-4-carboxylic acid ethyl ester was prepared in 20% yield as described in general procedure L from 1,1-dicyclohexyl-3-(4-bromomethyl-thiazol-2-yl)urea and 2-mercapto-1H-imidazole-4-carboxylic acid ethyl ester. The ester (30 mg, 0.06 mmol) was hydrolysed using general procedure F to give 2-[2-(3,3-dicyclohexylureido)-thiazol-4-yl-methylsulfanyl)-1H-imidaole-4-carboxylic acid in 80% yield (22 mg).

HPLC-MS: m/z 464 (M+1).

Example 454

3-{[2-(3,3-Dicyclohexylureido)-thiazole-5-carbonyl]-amino}-benzoic acid

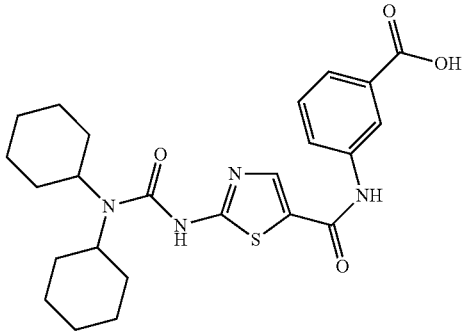

3-{[2-Dicyclohexylureido)-thiazole-5-carbonyl]-amino}-benzoic acid was prepared in 40% yield as described in general procedure F from 3- {[2-(3,3-Dicyclohexylureido)-thiazole-5-carbonyl]-amino}-benzoic acid methyl ester, which in turn was prepared in 21% yield as described in general procedure H using 2-(3,3-dicyclohexylureido)-thiazole-4-carboxylic acid and methyl-3-amino benzoate.

HPLC-MS: m/z 471 (M+1).

Example 455

4-[2-(3,3-Dicyclohexylureideo)-thiazole-5-ylsulfanyl]benzoic acid methyl ester

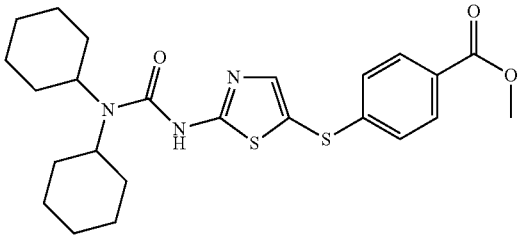

Prepared in 20% yield (47 mg) as described in general procedure (E) using 3-(5-bromothiazol-2-yl)-1,1-bis-4-methylcyclohexyl)urea and 4-mercapto-benzoic acid methyl ester.

$^1$H NMR ($CDCl_3$): δ 8.10 (s, 1H), 7.89 (d, 2H), 7.54 (s, 1H), 7.21 (d, 2H), 3.89 (s, 3H), 3.43 (m, 2H), 1.10-1.90 (m, 20H) ppm; HPLC-MS: m/z 474 (M+1).

Example 456

4-[2-(3,3-Dicyclohexylureideo)-thiazole-5-ylsulfanyl]benzoic acid

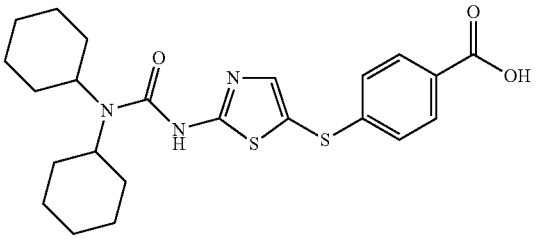

Prepared in 85% yield (24 mg) as described in general procedure (F) from 4-[2-(3,3-dicyclohexylureideo)-thiazole-5-ylsulfanyl]benzoic acid methyl ester (30 mg, 0.06 mmol).

$^1$H NMR (d6-DMSO): δ 7.83 (d, 2H), 7.67 (s, 1H), 7.22 (d, 2H), 3.60 (m, 2H),1.10-1.90 (m, 20H) ppm; HPLC-MS: m/z 460 (M+1).

Example 457

{4-[2-(3,3-Dicyclohexylureideo)-thiazole-5-ylsulfanyl]-phenyl}-acetic acid methyl ester

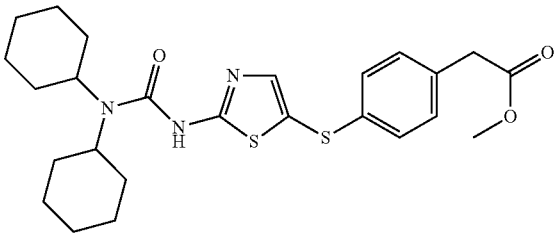

Prepared in 15% yield (37 mg) as described in general procedure (E) using 3-(5-bromothiazol-2-yl)-1,1-bis-4-methylcyclohexyl)urea and 4-mercaptobenzeneacetic acid methyl ester.

$^1$H NMR ($CDCl_3$): δ 8.00 (s, 1H), 7.49 (s, 1H), 7.21 (d, 1H), 7.19 (d, 1H), 7.16 (d, 1H), 7.13 (d, 1H), 3.67 (s, 3H), 3.55 (s, 2H), 3.42 (m, 2H), 1.10-1.90 (m, 20H) ppm; HPLC-MS: m/z 488 (M+1).

Example 458

{4-[2-(3,3-Dicyclohexylureideo)-thiazole-5-ylsulfanyl]-phenyl}-acetic acid

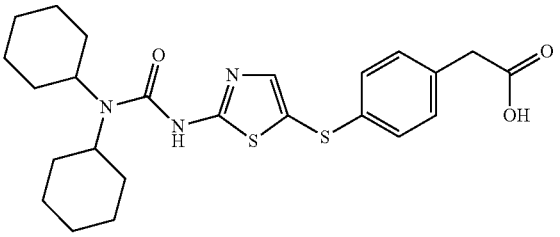

Prepared in 90% yield (18 mg) as described in general procedure (F) from {4-[2-(3,3-dicyclohexylureideo)-thiazole-5-ylsulfanyl]-phenyl}-acetic acid methyl ester (21 mg, 0.04 mmol).

$^1$H NMR (d6-DMSO): δ 7.49 (s, 1H), 7.18 (d, 2H), 7.14 (d, 2H), 3.50 (s, 2H), 3.32 (m, 2H), 1.10-1.90 (m, 20H) ppm; HPLC-MS: m/z 474 (M+1).

Example 459

3-{2-[3-Cyclohexyl-3-(4-trans-methylcyclohexyl)-ureido]-thiazol-5-yl}-acrylic acid ethyl ester

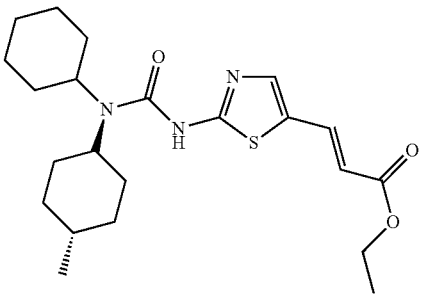

A solution of cyclohexyl-(trans-4-methylcylcohexyl)-3-(5-formyl-thiazol-2-yl)-urea (350 mg, 1.00 mmol) and (carbethoxymethylene)triphenylphosphorane (420 mg, 1.20 mmol) in THF (5 mL) was stirred at 50° C. for 12 h. The reaction mixture was concentrated and the residue was purified by hash chromatography (silica, $CH_2Cl_2$-EtOAc, 4:1) to obtain 3-{2-[3-cyclohexyl-3-(4-trans-methylcyclohexyl)-ureido]-thiazol-5-yl}-acrylic acid ethyl ester (300 mg) in 73% yield.

$^1$H NMR ($CDCl_3$): δ 8.20 (s, 1H), 7.70 (d, 1H), 7.47 (s, 1H), 6.06 (d, 1H), 4.23 (q, 2H), 3.40 (m, 2H), 1.50-2.00 (m,

12H), 1.40-1.50 (m, 2H), 1.30 (t, 3H),1.0-1.20 (M, 5H), 0.91 (d, 3H) ppm; HPLC-MS: m/z 420 (M+1).

Example 460

3-{2-[3-Cyclohexyl-3-(4-trans-methylcyclohexyl)-ureido]-thiazol-5-yl}-propionic acid

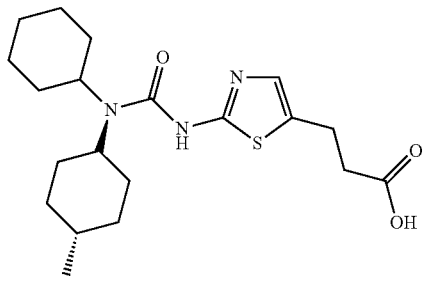

3-{2-[3-Cyclohexyl-3-(4-trans-methylcyclohexyl)-ureido]-thiazol-5-yl}-acrylic acid ethyl ester (200 mg, 0.48 mmol) was reduced with hydrogen (60 psi, pressure reaction vessel) over Pd/C (300 mg) to give 3-{2-[3-cyclohexyl-3-(4-trans-methylcyclohexyl)-ureido]-thiazol-5-yl}-propionic acid ethyl ester (110 mg) after purification (silica gel, 20% ethyl acetate in hexanes).

3-{2-[3-Cyclohexyl-3-(4-trans-methylcyclohexyl)-ureido]-thiazol-5-yl}-propionic acid ethyl ester (100 mg) was hydrolysed according to general procedure F using NaOH to give 85 mg (91% yield) of 3-{2-[3-cyclohexyl-3-(4-trans-methylcyclohexyl)-ureido]-thiazol-5-yl}-propionic acid.

$^1$H NMR (d6-DMSO): δ 6.94 (s, 1H), 4.4 (t, 2H), 3.6 (m, 2H), 2.80 (t, 2H), 1.10-1.90 (m, 19H), 0.85 (d, 3H) ppm; HPLC-MS: m/z 394 (M+1).

Example 461

2-(3,3-Dicyclohexylureido)-thiazole-5-carboxylic acid-(2-methanesulfonylethyl)amide

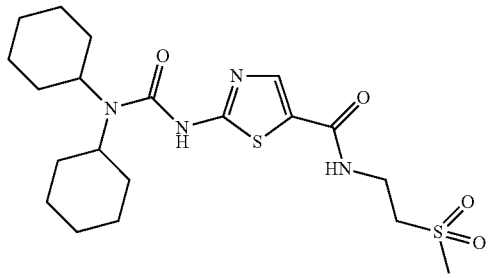

Prepared in 75% yield (170 mg) as described in general procedure (H) from 2-(3,3-dicyclohexylureido)thiazole-5-carboxylic acid (175 mg, 0.5 mmol) and 2-aminoethylmethylsulfone (HCl salt, 80 mg, 0.5 mmol).

$^1$H NMR ($CDCl_3$): δ 7.83 (s, 1H), 7.77 (d, 1H), 3.88 (t, 2H), 3.70 (t, 2H), 3.67 (m, 2H), 2.90 (s, 3H), 1.10-1.90 (m, 20H) ppm; HPLC-MS: m/z 457 (M+1).

Example 462

2-[3-Cyclohexyl-3-(4-methylcyclohexyl)-ureido]-thiazole-5-carboxylic acid methyl ester

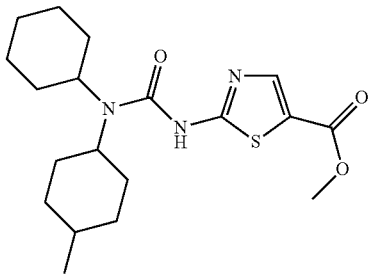

Prepared in 69% yield (8.3 g) as described in general procedure (C) from cyclohexyl-(4-methylcyclohexyl)-amine (6.2 g, 32 mmol) and methyl-2-aminothiazole-5-carboxylate (5.0 g, 31.6 mmol).

$^1$H NMR ($CDCl_3$): δ 8.00 (s, 1H), 3.82 (s, 3H), 3.36 (m, 2H), 1.15-2.00 (m, 19H), 1.02 (d, 3H) ppm; HPLC-MS: m/z 380 (M+1).

Example 463

{2-[3-Cyclohexyl-3-(4-phenyl-cyclohexyl)-ureido]-thiazol-5-ylsulfanyl}-acetic acid methyl ester

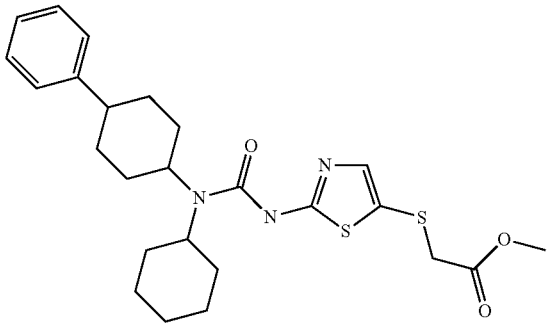

Prepared in 60% (292 mg) yield as described in general procedure (D) from 3-(5-bromothiazol-2-yl)-1-cyclohexyl-1-(4-phenyl-cy:clohexyl)-urea (463 mg, 1.0 mmol) and methylthioglycolate (212 mg, 2.0 mmol).

$^1$H NMR ($CDCl_3$): δ 8.16 (br, 1H), 7.42 (s, 1H), 7.18-7.38 (m, 5H), 3.71 (s, 3H), 3.56 (br, 1H), 3.44 (br, 1H), 3.43 (s, 2H), 2.58 (m, 1H), 1.17-2.02 (m, 18H) ppm; HPLC-MS: m/z 488 (M+1).

Example 464

{2-[3-Cyclohexyl-3-(4-phenyl-cyclohexyl)-ureido]-thiazol-5-ylsulfanyl}-acetic acid

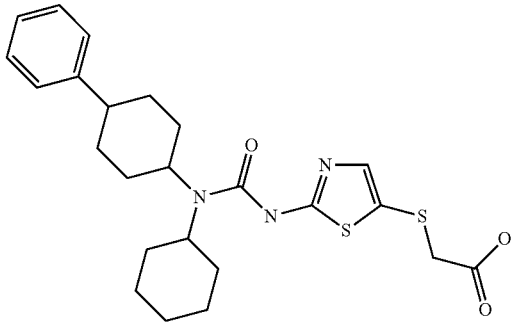

Prepared in 80% (190 mg) yield as described in general procedure (F) from {2-[3-cyclohexyl-3-(4-phenyl-cyclohexyl)-ureido]-thiazol-5-ylsulfanyl}-acetic acid methyl ester (244 mg, 0.5 mmol).

$^1$H NMR ($CDCl_3$): δ 12.02 (br, 1H), (8.32 (br, 1H), 7.14-7.39 (m, 6H), 3.45 (m, 4H), 2.19 (m, 1H), 1.07-1.96 (m, 18H) ppm; HPLC-MS: m/z 474 (M+1).

Example 465

1,1-Bis-(1-acetyl-piperidin-4-yl)-3-(5-bromo-thiazol-2-yl)-urea

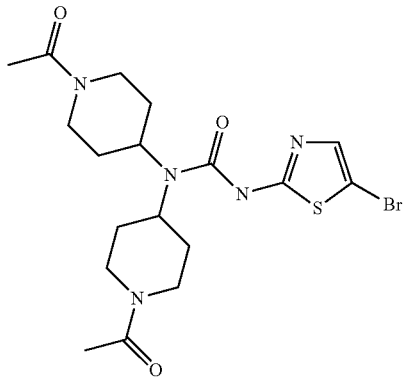

Prepared in 65% (76 mg) yield as described in general procedure (N) from 3-(5-bromothiazol-2-yl)-1,1-di-piperidin-4-yl-urea (97 mg, 0.25 mmol) and acetyl chloride (78 mg, 1 mmol).

$^1$H NMR ($CDCl_3$): δ 7.38 (br, 1H), 7.19 (s, 1H), 4.76 (m, 4H), 3.90 (m, 4H), 3.55 (m, 2H), 3.17 (m, 2H), 2.61 (m, 2H), 2.17 (m, 2H), 2.10 (s, 3H), 2.06 (s, 3H), 1.34 (m, 2H) ppm; HPLC-MS: m/z 473 (M+1).

Example 466

1-Cycloheptyl-3-(5-formylthiazol-2-yl)-1-(trans-4-methylcyclohexyl)urea

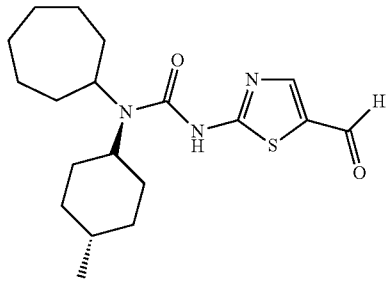

2-Amino-5-formylthiazole (2.56 g, 20.0 mmol), carbonyldiimidazole (3.25 g, 20.0 mmol) and a catalytic amount of DMAP were heated together in 60 mL THF at 50° C. for 3 h. To this solution was added cycloheptyl-(trans-4-methylcyclohexyl)amine (4.18 g, 20.0 mmol) and the reaction mixture was stirred for an additional 6 h at room temperature. The reaction mixture was concentrated and the crude product was purified by flash chromatography (silica, $CH_2Cl_2$-EtOAc, 4:1) to obtain 1,1-dicyclohexyl-3-(5-formyl-thiazol-2-yl)-urea (2.3 g, 31% yield).

HPLC-MS: m/z 364 (M+1).

Example 467

1-(1-Butyryl-piperidin-4-yl)-3-(5-chloro-thiazol-2-yl)-1-cycloheptyl-urea

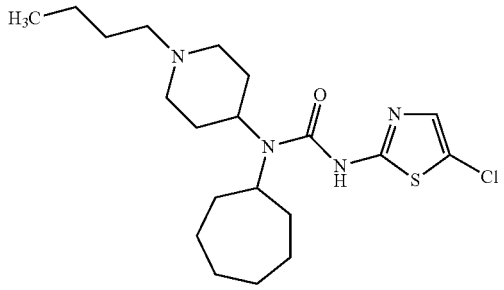

Prepared as described in general procedure (G) using 4-cycloheptylamino-piperidine-1-carboxylic acid tert-butyl ester and 5-chloro-2-aminothiazole HPLC-MS: m/z 427 (M+1).

Example 468

[2-(3-Cycloheptyl-3-cyclopentyl-ureido)-thiazol-5-ylsulfanyl]-acetic acid

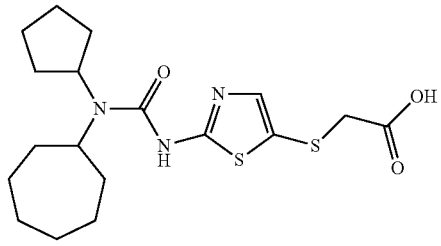

[2-(3-Cycloheptyl-3-cyclopentyl-ureido)-thiazol-5-ylsulfanyl]-acetic acid ethyl ester prepared as described in general procedures (A) and (B) using cycloheptyl-cyclopentylamine and 5-aminothiazole-2-mercaptoacetic acid ethyl ester. Hydrolysis using general procedure (F) gave the title compound.

HPLC-MS: m/z 398 (M+1).

Example 469

[2-(3-Cyclobutyl-3-cycloheptyl-ureido)-thiazol-5-ylsulfanyl]-acetic acid

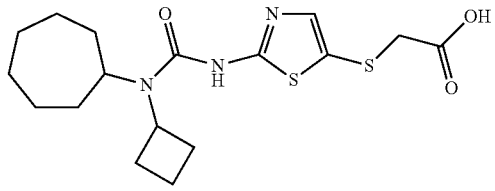

[2-(3-Cycloheptyl-3-cyclobutyl-ureido)-thiazol-5-ylsulfanyl]-acetic acid ethyl ester prepared as described in general procedures (A) and (B) using cycloheptyl-cyclobutylamine and 5-aminothiazole-2-mercaptoacetic acid ethyl ester. Hydrolysis using general procedure (F) gave the title compound.

HPLC-MS: m/z 384 (M+1).

Example 470

{2-[3-Cyclobutyl-3-(trans-4-methyl-cyclohexyl)-ureido]-thiazol-5-ylsulfanyl}-acetic acid

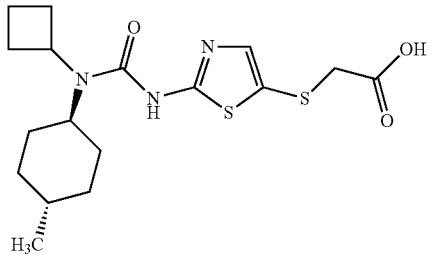

{2-[3-Cyclobutyl-3-(trans-4-methyl-cyclohexyl)-ureido]-thiazol-5-ylsulfanyl}-acetic acid ethyl ester prepared as described in general procedures (A) and (B) using cyclobutyl-(trans-4-methyl-cyclohexyl)-amine and 5-aminothiazole-2-mercaptoacetic acid ethyl ester. Hydrolysis using general procedure (F) gave the title compound.

HPLC-MS: m/z 384 (M+1).

Example 471

3-(5-Chloro-thiazol-2-yl)-1-cycloheptyl-1-(1-ethane-sulfonyl-piperidin-4-yl)-urea

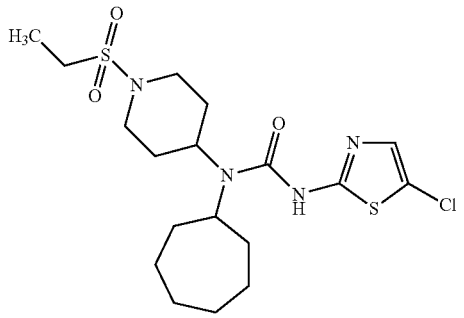

Prepared as described in general procedure (G) using 3-amino-1-Boc-piperidine, cycloheptanone and 2-amino-5-chlorothiazole HPLC-MS: m/z 449 (M+1).

Example 472

{[2-(3,3-Dicyclohexyl-ureido)-thiazol-5-yl]-methyl-amino}-acetic acid ethyl ester

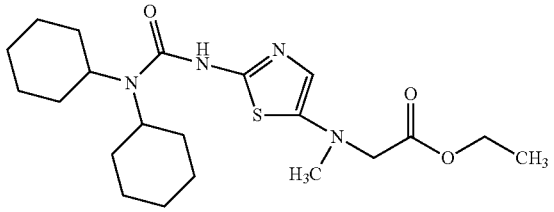

Prepared as described in general procedure (A) using dicyclohexylamine and [(2-aminothiazol-5-yl)-methyl-amino]-acetic acid ethyl ester HPLC-MS: m/z 867 (2M+Na).

Example 473

3-[2-(3-Cyclobutyl-3-cycloheptyl-ureido)-thiazol-5-ylsulfanyl]-propionic acid

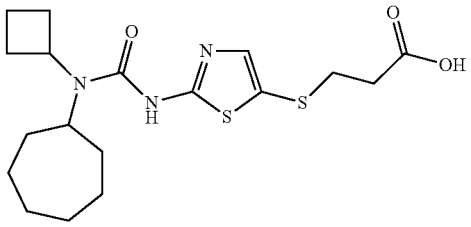

[2-(3-Cycloheptyl-3-cyclobutyl-ureido)-thiazol-5-ylsulfanyl]-propionic acid ethyl ester prepared as described in general procedure (A) using cycloheptyl-cyclobutylamine and 5-aminothiazole-2-mercaptoacetic acid ethyl ester. Hydrolysis using general procedure (F) gave the title compound HPLC-MS: m/z 398 (M+1).

Example 474

3-[2-(3-Cycloheptyl-3-cyclopentyl-ureido)-thiazol-5-ylsulfanyl]-propionic acid

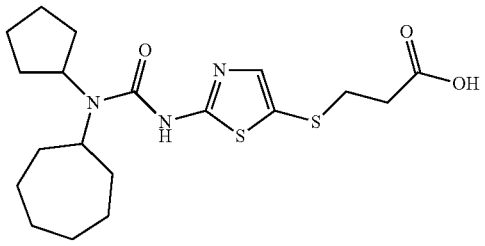

[2-(3-Cycloheptyl-3-cyclopentyl-ureido)-thiazol-5-ylsulfanyl]-propionic acid ethyl ester pre-pared as described in general procedure (A) using cycloheptyl-cyclopentylamine and 5-aminothiazole-2-mercaptoacetic acid ethyl ester. Hydrolysis using general procedure (F) gave the title compound HPLC-MS: m/z 412 (M+1).

Example 475

3-(5-Chloro-thiazol-2-yl)-1-(1-cyclobutanecarbonyl-piperidin-4-yl)-1-(trans-4-methyl-cyclohexyl)-urea

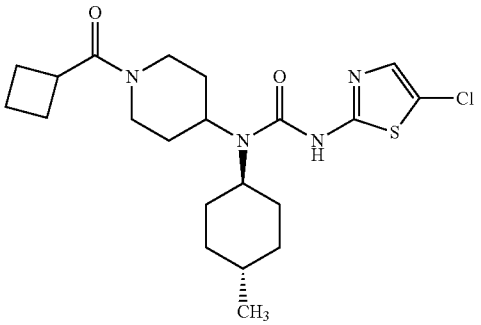

Prepared as described in general procedure (G) using 4-(trans-4-methyl-cyclohexylamino)-piperidine-1-carboxylic acid tert-butyl ester and 2-amino-5-chlorothiazole HPLC-MS: m/z 439 (M+1).

Example 476

3-(5-Chloro-thiazol-2-yl)-1-(1-cyclopentanecarbonyl-piperidin-4-yl)-1-(trans-4-methylcyclohexyl)-urea

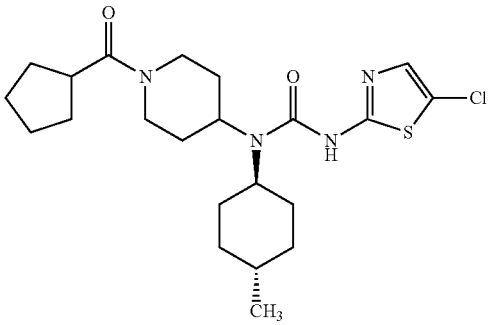

Prepared as described in general procedure (G) using 4-(trans-4-methyl-cyclohexylamino)-piperidine-1-carboxylic acid tert-butyl ester and 2-amino-5-chlorothiazole HPLC-MS: m/z 453 (M+1).

Example 477

3-(5-Chloro-thiazol-2-yl)-1-(trans-4-methyl-cyclohexyl)-1-(1-pentanoyl-piperidin-4-yl)-urea

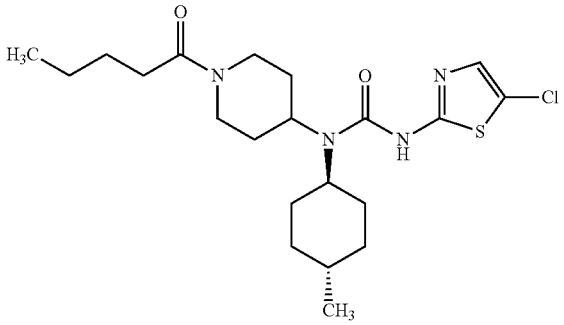

Prepared as described in general procedure (G) using 4-(trans-4-methyl-cyclohexylamino)-piperidine-1-carboxylic acid tert-butyl ester and 2-amino-5-chlorothiazole HPLC-MS: m/z 442 (M+1).

Example 478

2-(3,3-Dicyclohexyl-ureido)-thiazole-5-sulfonic acid (2-dimethylamino-ethyl)-amide

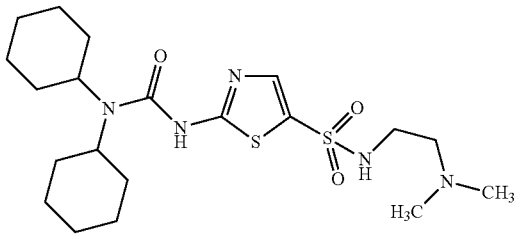

Prepared as described in Example 173 using dicyclohexylamine, N-acetamino-5-thiazolesulfonyl chloride and 2-dimethylaminoethylamine.

HPLC-MS: m/z 458 (M+1).

Example 479

2-(3,3-Dicyclohexyl-ureido)-thiazole-5-sulfonic acid (2-diethylamino-ethyl)-amide

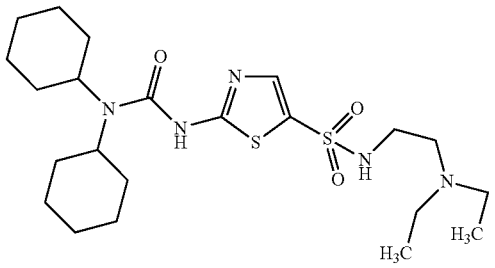

Prepared as described in Example 173 using dicyclohexylamine, N-acetamino-5-thiazolesulfonyl chloride and 2-diethylaminoethylamine HPLC-MS: m/z 486 (M+1). .

Example 480

2-(3,3-Dicyclohexyl-ureido)-thiazole-5-sulfonic acid (2-morpholin-4-yl-ethyl)-amide

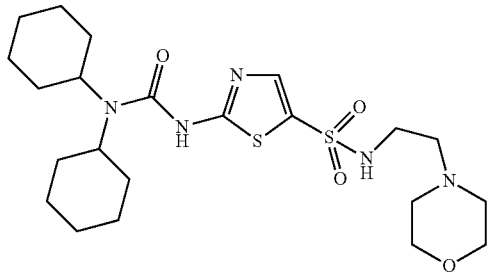

Prepared as described in Example 173 using dicyclohexylamine, N-acetamino-5-thiazolesulfonyl chloride and 1-(2-aminoethyl)piperidine.

HPLC-MS: m/z 501 (M+1).

Example 481

1-Cyclohexyl-1-(trans-4-hydroxy-cyclohexyl)-3-thiazol-2-yl-urea

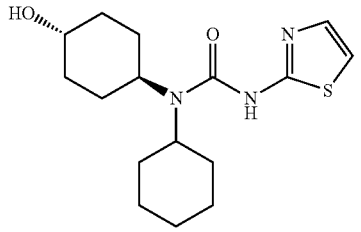

Reaction of [trans-4-(tert-butyl-dimethyl-silanyloxy)-cyclohexyl]-cyclohexyl-amine and 2-aminothiazole using general procedure (A) gave 1-[trans-4-(tert-butyl-dimethyl-silanyloxy)-cyclohexyl]-1-cyclohexyl-3-thiazol-2-yl-urea. Removal of the silyl protection group by addition of tetrabutylammoniumchloride (1.1 equiv) in THF for 1 h at room temperature followed by flash chromatography afforded the title compound.

HPLC-MS: m/z 324 (M+1).

Example 482

1,1-Dicyclohexyl-3-[5-(2-diethylamino-ethylsulfanyl)-thiazol-2-yl]-urea

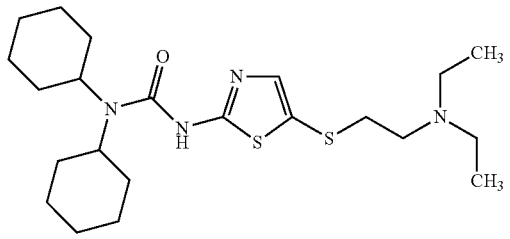

Prepared as described in general procedure (H) using 1,1-dicyclohexyl-3-(5-thiocyanato-thiazol-2-yl)-urea, dithioerythritol and 2-diethylamino-ethanethiol HPLC-MS: m/z 439 (M+1).

Example 483

1,1-Dicyclohexyl-3-[5-(3-dimethylamino-propylsulfanyl)-thiazol-2-yl]-urea

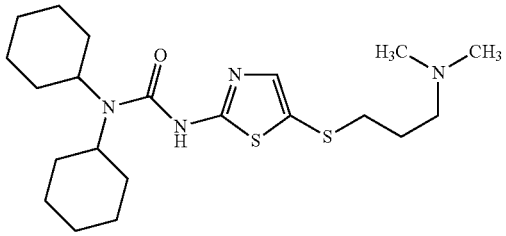

Prepared as described in general procedure (H) using 1,1-dicyclohexyl-3-(5-thiocyanato-thiazol-2-yl)-urea, dithioerythritol and 3-dimethylamino-1-propylchloride.

HPLC-MS: m/z 425 (M+1).

Example 484

1,1-Dicyclohexyl-3-[5-(4,5-dihydro-1H-imidazol-2-ylmethylsulfanyl)-thiazol-2-yl]-urea

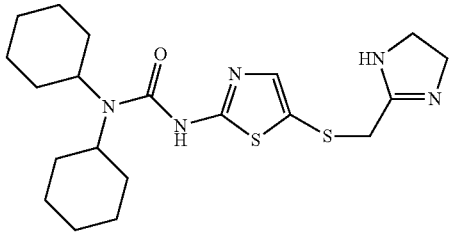

Prepared as described in general procedure (H) using 1,1-dicyclohexyl-3-(5-thiocyanato-thiazol-2-yl)-urea, dithioerythritol and 2-chloromethyl-2-imidazoline.

HPLC-MS: m/z 422 (M+1).

Example 485

3-[5-(2-Azepan-1-yl-ethylsulfanyl)-thiazol-2-yl]-1,1-dicyclohexyl-urea

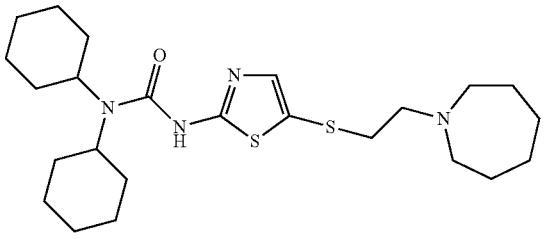

Prepared as described in general procedure (H) using 1,1-dicyclohexyl-3-(5-thiocyanato-thiazol-2-yl)-urea, dithioerythritol and 2-(hexamethyleneimino)ethylchloride HPLC-MS: m/z 465 (M+1).

Example 486

3-(5-Chloro-thiazol-2-yl)-1-cycloheptyl-1-(1-phenylmethanesulfonyl-piperidin-4-yl)-urea

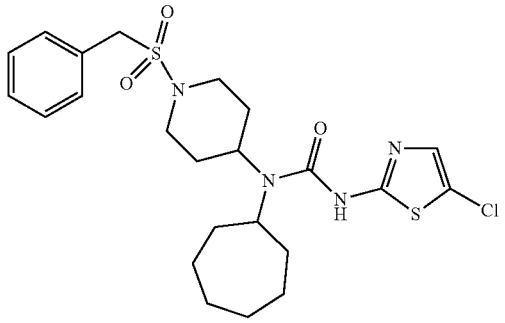

Prepared as described in general procedure (G) using 3-amino-1-Boc-piperidine, cycloheptanone and 2-amino-5-chlorothiazole HPLC-MS: m/z 511 (M+1).

Example 487

1-(1-Acetyl-piperidin-4-yl)-1-cyclohexyl-3-(5-methanesulfonyl-thiazol-2-yl)-urea

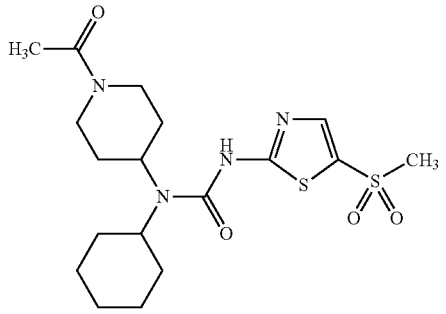

Prepared by oxidising 1-(1-acetyl-piperidin-4-yl)-1-cyclohexyl-3-(5-methylsulfanyl-thiazol-2-yl)-urea (Example 339) using montmorillonite clay, oxone (2.5 equivalents) for 16 h at room temperature in dichloromethane. The title compound was purified by HPLC.

HPLC-MS: m/z 430 (M+1).

Example 488

1,1-Dicyclohexyl-3-[4-methyl-5-(2-morpholin-4-yl-ethanesulfonyl)-thiazol-2-yl]-urea

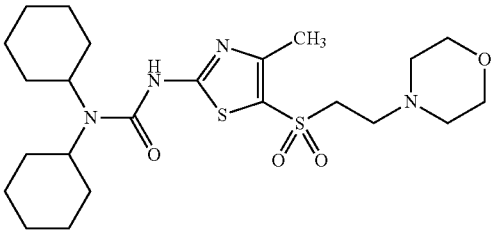

Prepared by oxidising 1,1-Dicyclohexyl-3-[4-methyl-5-(2-morpholin-4-yl-ethanesulfanyl)-thiazol-2-yl]-urea (Example 309) using montmorillonite clay, oxone (2.5 equivalents) for 16 h at room temperature in dichloromethane. The title compound was purified by HPLC.

HPLC-MS: m/z 500 (M+1).

Example 489

1,1-Dicyclohexyl-3-[4-methyl-5-(2-piperidin-1-yl-ethanesulfonyl)-thiazol-2-yl]-urea

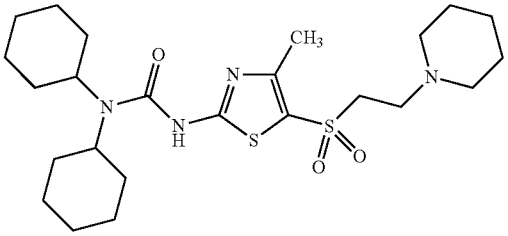

Prepared by oxidising 1,1-Dicyclohexyl-3-[4-methyl-5-(2-piperidin-1-yl-ethanesulfonyl)-thiazol-2-yl]-urea (Example 302) using montmorillonite clay, oxone (2.5 equivalents) for 16 h at room temperature in dichloromethane. The title compound was purified by HPLC.

HPLC-MS: m/z 498 (M+1).

Example 490

{2-[3-Cyclohexyl-3-(6-oxo-piperidin-3(S)-yl)-ureido]-thiazol-5-ylsulfanyl}-acetic acid

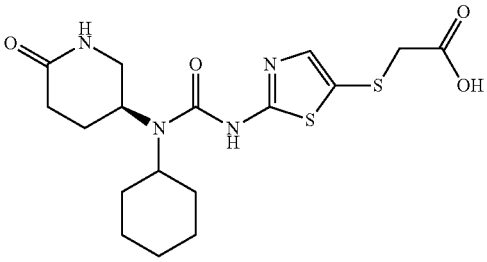

{2-[3-Cyclohexyl-3-(6-oxo-piperidin-3(S)-yl)-ureido]-thiazol-5-ylsulfanyl}-acetic acid ethyl ester was prepared as described in general procedures (A) and (B) using 5-cyclohexylamino-piperidin-2-one and (2-amino-thiazol-5-ylsulfanyl)-acetic acid ethyl ester. Hydrolysis using general procedure (F) gave the title compound.

HPLC-MS: m/z 413 (M+1).

Example 491

1,1-Dicyclohexyl-3-(5-ethenesulfonyl-4-methyl-thiazol-2-yl)-urea

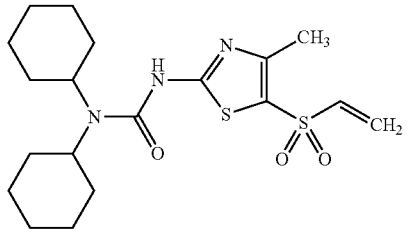

A secondary product prepared by oxidising Example 309 using montmorillonite clay, oxone (2.5 equivalents) for 16 h at room temperature in dichloromethane. The title compound was purified by HPLC.

HPLC-MS: m/z 412 (M+1).

Example 492

(2-{3-Cyclohexyl-3-[1-(thiophene-2-carbonyl)-pyrrolidin-3(R)-yl]-ureido}-thiazol-5-ylsulfanyl)-acetic acid

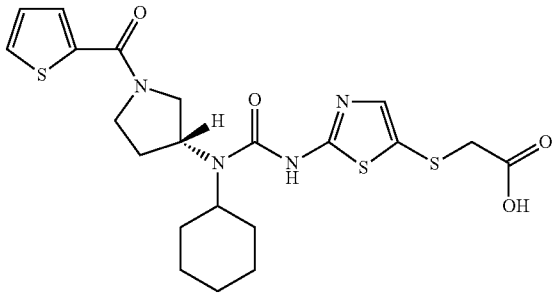

Prepared in an identical manner to Example 271 using 3(R)-amino-1-Boc-pyrrolidine.

HPLC-MS: m/z 495 (M+1).

Example 493

3-(5-Chloro-thiazol-2-yl)-1-cycloheptyl-1-[1-(propane-1-sulfonyl)-piperidin-4-yl]-urea

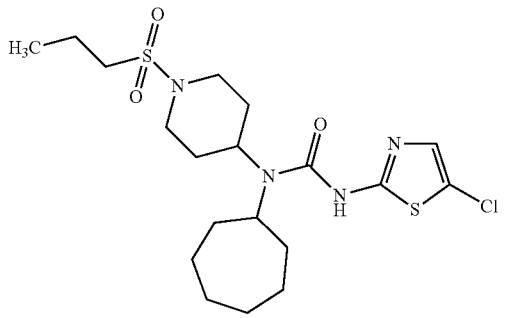

Prepared as described in general procedure (G) using 3-amino-1-Boc-piperidine, cycloheptanone and 2-amino-5-chlorothiazole HPLC-MS: m/z 463 (M+1).

Example 494

3-(5-Chloro-thiazol-2-yl)-1-cycloheptyl-1-(1-cyclopentanecarbonyl-piperidin-4-yl)-urea

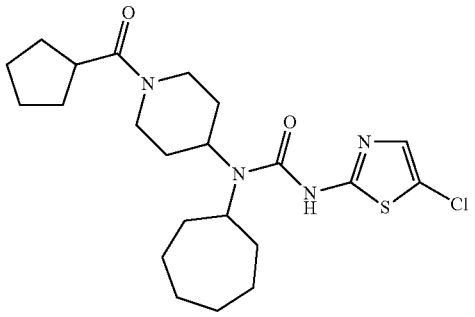

Prepared as described in general procedure (G) using 3-amino-1-Boc-piperidine, cycloheptanone and 2-amino-5-chlorothiazole HPLC-MS: m/z 453 (M+1).

Example 495

3-[2-(3 -Cyclohexyl-3-indan-2-yl-ureido)-thiazol-5-ylsulfanyl]-propionic acid

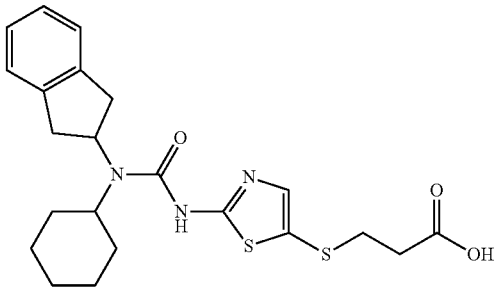

Prepared in an identical manner to Example 342 using indane, cyclohexanone and 5-aminothiazol-2-mercaptopropionic acid ethyl ester HPLC-MS: m/z 446 (M+1).

Example 496

3-{2-[3-Cyclobutyl-3-(trans-4-methyl-cyclohexyl)-ureido]-thiazol-5-ylsulfanyl}-propionic acid

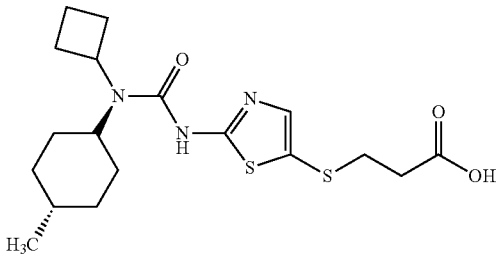

{2-[3-Cyclobutyl-3-(trans-4-methyl-cyclohexyl)-ureido]-thiazol-5-ylsulfanyl}-propionic acid ethyl ester prepared as described in general procedure (A) using cyclobutyl-(trans-4-methyl-cyclohexyl)-amine and 5-aminothiazole-2-mercaptopropionic acid ethyl ester. Hydrolysis using general procedure (F) gave the title compound.

HPLC-MS: m/z 398 (M+1).

Example 497

3-{2-[3-Cyclopentyl-3-(trans-4-methyl-cyclohexyl)-ureido]-thiazol-5-ylsulfanyl}-propionic acid

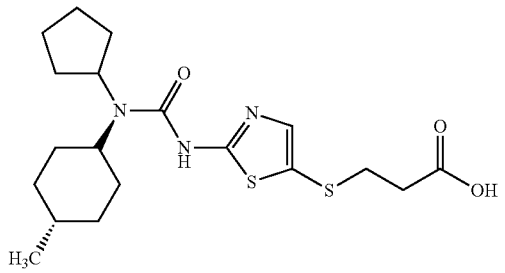

{2-[3-Cyclopentyl-3-(trans-4-methyl-cyclohexyl)-ureido]-thiazol-5-ylsulfanyl}-propionic acid ethyl ester prepared as described in general procedure (A) using cyclopentyl-(trans-4-methyl-cyclohexyl)-amine and 5-aminothiazole-2-mercaptopropionic acid ethyl ester. Hydrolysis using general procedure (F) gave the title compound.

HPLC-MS: m/z 412 (M+1).

Example 498

3-{2-[3-Cycloheptyl-3-(trans-4-methyl-cyclohexyl)-ureido]-thiazol-5-ylsulfanyl}-propionic acid

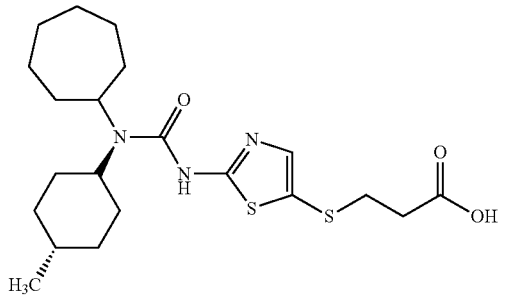

{2-[3-Cycloheptyl-3-(trans-4-methyl-cyclohexyl)-ureido]-thiazol-5-ylsulfanyl}-propionic acid ethyl ester prepared as described in general procedure (A) using cycloheptyl-(trans-4-methyl-cyclohexyl)-amine and 5-aminothiazole-2-mercaptopropionic acid ethyl ester. Hydrolysis using general procedure (F) gave the title compound.

HPLC-MS: m/z 440 (M+1).

Example 499

3-(5-Chloro-thiazol-2-yl)-1-cyclohexyl-1-(1-cyclopropanecarbonyl-piperidin-4-yl)-urea

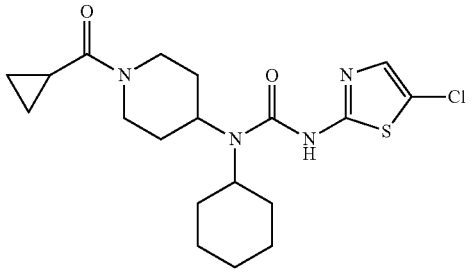

Prepared as described in general procedure (G) using 4-cyclohexylamino-piperidine-1-carboxylic acid tert-butyl ester and 5-chloro-2-aminothiazole HPLC-MS: m/z 411 (M+1).

Example 500

3-(5-Chloro-thiazol-2-yl)-1-(1-cyclobutanecarbonyl-piperidin-4-yl)-1-cyclohexyl-urea

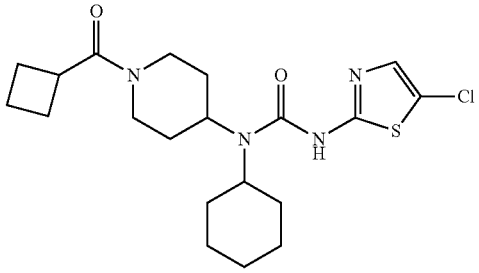

Prepared as described in general procedure (G) using 4-cyclohexylamino-piperidine-1-carboxylic acid tert-butyl ester and 5-chloro-2-aminothiazole HPLC-MS: m/z 447 (M+1).

Example 501

3-(5-Chloro-thiazol-2-yl)-1-cyclohexyl-1-[1-(2-cyclopropyl-acetyl)-piperidin-4-yl]-urea

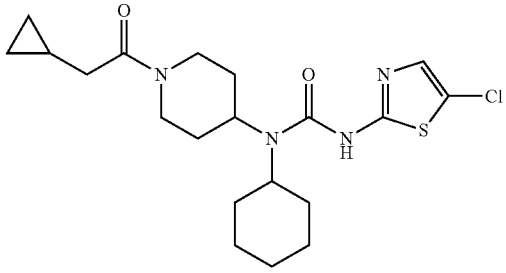

Prepared as described in general procedure (G) using 4-cyclohexylamino-piperidine-1-carboxylic acid tert-butyl ester and 5-chloro-2-aminothiazole HPLC-MS: m/z 447 (M+1).

Example 502

4-{4-[3-(5-Chloro-thiazol-2-yl)-1-cyclohexyl-ureido]-piperidin-1-yl}-4-oxo-butyric acid

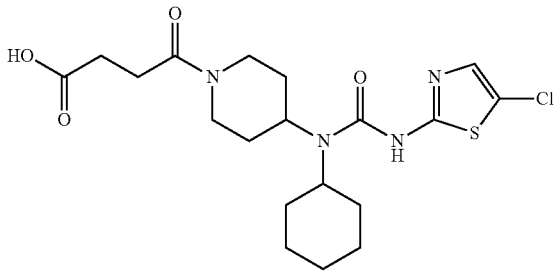

Prepared as described in general procedure (G) using 4-cyclohexylamino-piperidine-1-carboxylic acid tert-butyl ester and 5-chloro-2-aminothiazole HPLC-MS: m/z 443 (M+1).

Example 503

1,1-Dicyclohexyl-3-{5-[2-(1H-tetrazol-5-yl)-ethylsulfanyl]-thiazol-2-yl}-urea

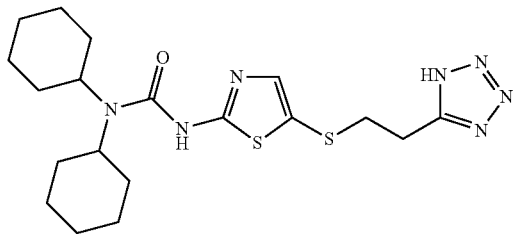

Prepared as described in general procedure (H) using 1,1-dicyclohexyl-3-(5-thiocyanato-thiazol-2-yl)-urea, dithioerythritol and 5-(2-chloroethyl)-1H-tetrazole.

HPLC-MS: m/z 437 (M+1).

Example 504

1-(1-Acetyl-piperidin-3-yl)-3(S)-(5-chloro-thiazol-2-yl)-1-cyclohexyl-urea

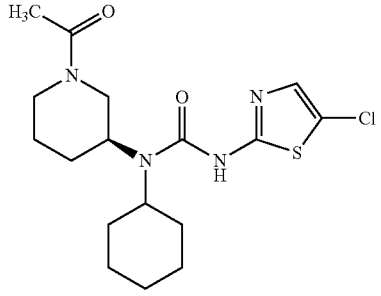

Prepared as described in general procedures (A) and (B). using 1-(3(S)-cyclohexylarnino-piperidin-1-yl)-ethanone and 5-chloro-2-aminothiazole HPLC-MS: m/z 385 (M+1).

Example 505

{2-[3-(1-Acetyl-piperidin-3(S)-yl)-3-cyclohexyl-ureido]-thiazol-5-ylsulfanyl}-acetic acid

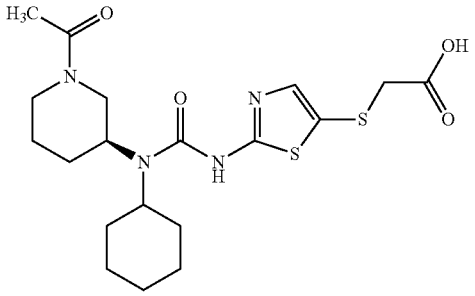

{2-[3-(1-Acetyl-piperidin-3(S)-yl)-3-cyclohexyl-ureido]-thiazol-5-ylsulfanyl}-acetic acid ethyl ester prepared as described in general procedures (A) and (B). using 1-(3(S) cyclohexylamino-piperidin-1-yl)-ethanone and (2-amino-thiazol-5-ylsulfanyl)-acetic acid ethyl ester. Hydrolysis using general procedure (F) gave the title compound.

HPLC-MS: m/z 441 (M+1).

Example 506

3-(5-Chloro-thiazol-2-yl)-1-cyclohexyl-1-(4,4-difluoro-cyclohexyl)-urea

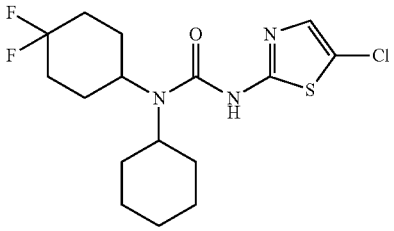

Prepared using general procedures (A) and (B) using cyclohexyl-(4,4-difluoro-cyclohexyl)-amine and 5-chloro-2-aminothiazole HPLC-MS: m/z 378 (M+1).

Example 507

3-(5-Chloro-thiazol-2-yl)-1-(1-cyclopropanecarbonyl-piperidin-4-yl)-1-(trans-4-methylcyclohexyl)-urea

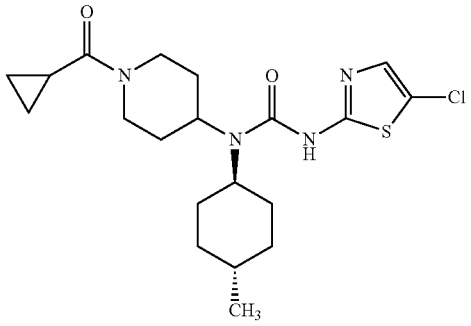

Prepared as described in general procedure (G) using 4-(trans-4-methyl-cyclohexylamino)-piperidine-1-carboxylic acid tert-butyl ester and 2-amino-5-chlorothiazole HPLC-MS: m/z 425 (M+1).

Example 508

1-(1-Acetyl-piperidin-4-yl)-1-cyclohexyl-3-[5-(2-pyrrolidin-1-yl-ethylsulfanyl)-thiazol-2-yl]-urea

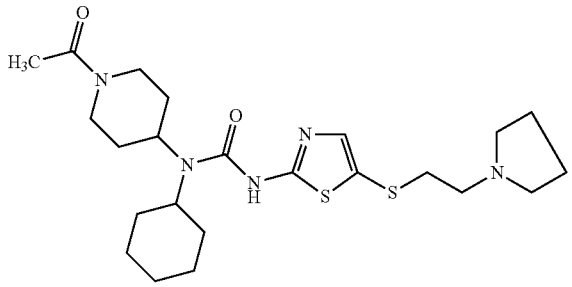

Prepared as described in general procedures (H) and (I) using 1-(1-acetyl-piperidin-4-yl)-1-cyclohexyl-3-(5-thiocyanato-thiazol-2-yl)-urea, dithioerythritol and N-(2-chloroethyl)pyrrolidine. HPLC-MS: m/z 480 (M+1).

Example 509

1-(1-Acetyl-piperidin-4-yl)-3-[5-(2-azepan-1-yl-ethylsulfanyl)-thiazol-2-yl]-1-cyclohexyl-urea

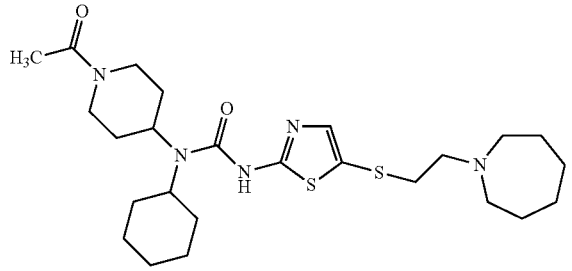

Prepared as described in general procedures (H) and (I) using 1-(1-acetyl-piperidin-4-yl)-1-cyclohexyl-3-(5-thiocyanato-thiazol-2-yl)-urea, dithioerythritol and 2-(hexamethyleneimino)ethylchloride HPLC-MS: m/z 508 (M+1).

Example 510

1-(1-Acetyl-piperidin-4-yl)-1-cyclohexyl-3-[5-(2-diethylamino-ethylsulfanyl)-thiazol-2-yl]-urea

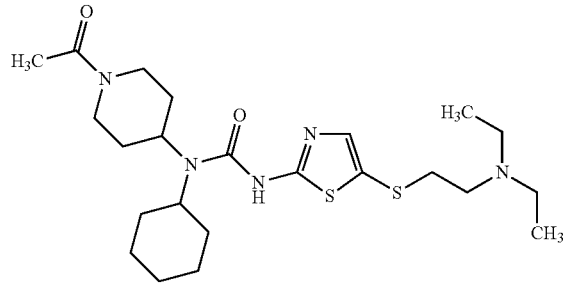

Prepared as described in general procedures (H) and (I) using 1-(1-acetyl-piperidin-4-yl)-1-cyclohexyl-3-(5-thiocyanato-thiazol-2-yl)-urea, dithioerythritol and 2-diethylamino-ethanethiol HPLC-MS: m/z 482 (M+1).

Example 511

1-(1-Acetyl-piperidin-4-yl)-1-(trans-4-methyl-cyclohexyl)-3-[5-(2-piperidin-1-yl-ethylsulfanyl)-thiazol-2-yl]-urea

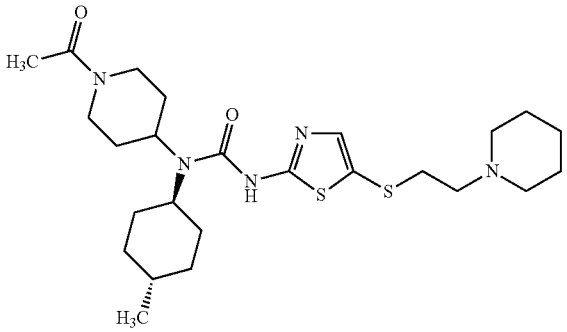

Prepared as described in general procedures (H) and (I) using 1-(1-acetyl-piperidin-4-yl)-1-(trans-4-methyl-cyclohexyl)-3-(5-thiocyanato-thiazol-2-yl)-urea, dithioerythritol and N-(2-chloroethyl)piperidine HPLC-MS: m/z 508 (M+1).

Example 512

1-(1-Acetyl-piperidin-4-yl)-1-(trans-4-methyl-cyclohexyl)-3-[5-(2-pyrrolidin-1-yl-ethylsulfanyl)-thiazol-2-yl]-urea

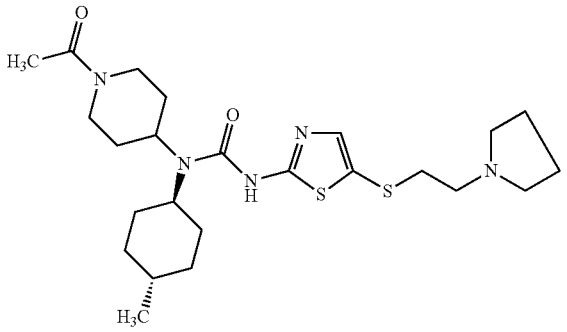

Prepared as described in general procedures (H) and (I) using 1-(1-acetyl-piperidin-4-yl)-1-(trans-4-methyl-cyclohexyl)-3-(5-thiocyanato-thiazol-2-yl)-urea, dithioerythritol and N-(2-chloroethyl)pyrrolidine HPLC-MS: m/z 494 (M+1).

Example 513

1-(1-Acetyl-piperidin-4-yl)-1-(trans-4-methyl-cyclohexyl)-3-[5-(2-morpholin-4-yl-ethylsulfanyl)-thiazol-2-yl]-urea

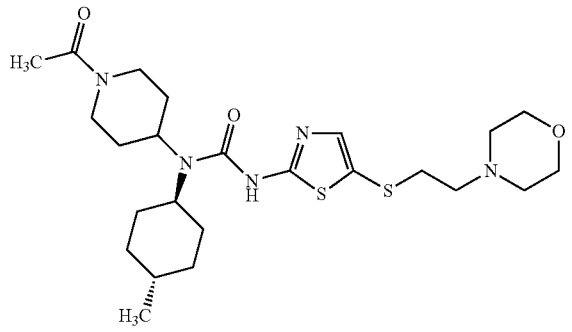

Prepared as described in general procedures (H) and (I) using 1-(1-acetyl-piperidin-4-yl)-1-(trans-4-methyl-cyclohexyl)-3-(5-thiocyanato-thiazol-2-yl)-urea, dithioerythritol and N-(2-chloroethyl)morpholine HPLC-MS: m/z 510 (M+1).

Example 514

1-(1-Acetyl-piperidin-4-yl)-3-[5-(2-azepan-1-yl-ethylsulfanyl)-thiazol-2-yl]-1-(trans-4-methyl-cyclohexyl)-urea

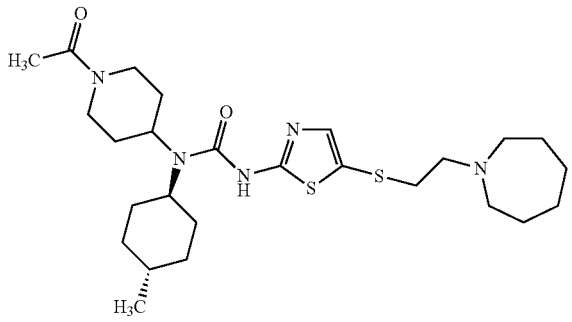

Prepared as described in general procedures (H) and (I) using 1-(1-acetyl-piperidin-4-yl)-1-(trans-4-methyl-cyclohexyl)-3-(5-thiocyanato-thiazol-2-yl)-urea, dithioerythritol and 2-(hexamethyleneimino)ethylchloride HPLC-MS: m/z 522 (M+1).

Example 515

1-(1-Acetyl-piperidin-4-yl)-3-(5-chloro-thiazol-2-yl)-1-indan-2-yl-urea

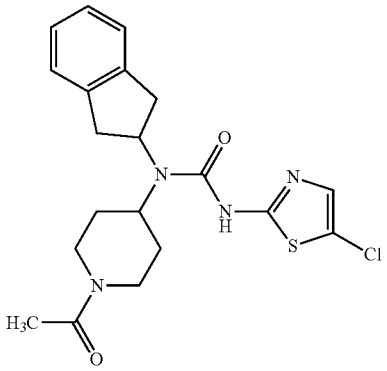

Prepared as described in general procedures (A) and (B) using indane, N-acetylpiperidin-4-one and 5-chloro-2-aminothiazole.

HPLC-MS: m/z 419 (M+1).

Example 516

{2-[3-(1-Acetyl-piperidin-4-yl)-3-indan-2-yl-ureido]-thiazol-5-ylsulfanyl}-acetic acid

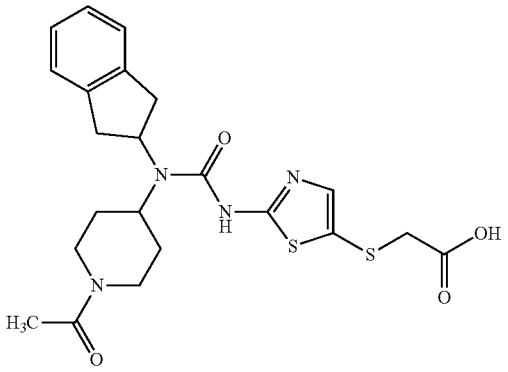

{2-[3-(1-Acetyl-piperidin-4-yl)-3-indan-2-yl-ureido]-thiazol-5-ylsulfanyl}-acetic acid ethyl ester was prepared as described in general procedures (A) and (B) using indane, N-acetylpiperidin-4-one and 5-aminothiazole-2-mercaptoacetic acid ethyl ester. Hydrolysis using general procedure (F) gave the title compound HPLC-MS: m/z 475 (M+1).

Example 517

{2-[3-Cyclohexyl-3-(4,4-difluoro-cyclohexyl)-ureido]-thiazol-5-ylsulfanyl}-acetic acid

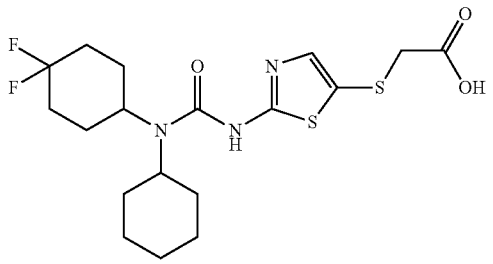

{2-[3-Cyclohexyl-3-(4,4-difluoro-cyclohexyl)-ureido]-thiazol-5-ylsulfanyl}-acetic acid ethyl ester prepared using general procedures (A) and (B) using cyclohexyl-(4,4-difluoro-cyclohexyl)-amine and 5-aminothiazole-2-mercaptoacetic acid ethyl ester. Hydrolysis using general procedure (F) gave the title compound.

HPLC-MS: m/z 434 (M+1).

Example 518

1-Cyclohexyl-3-(5-methylsulfanyl-thiazol-2-yl)-1-[1-(thiophene-2-carbonyl)-pyrrolidin-3(R)-yl]-urea

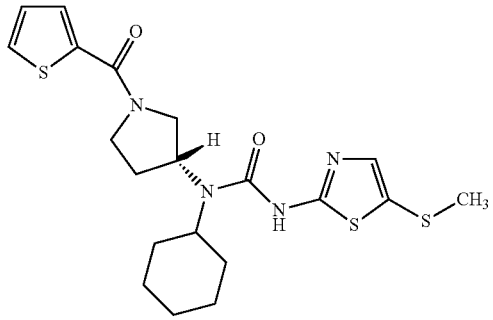

Prepared as described in general procedure (H) using 1-cyclohexyl-3-(5-thiocyanato-thiazol-2-yl)-1-[1-(thiophone-2-carbonyl)-pyrrolidin-3(R)-yl]-urea, dithioerythritol and methyliodide.

HPLC-MS: m/z 451 (M+1).

Example 519

1-Cyclohexyl-1-(trans-4-methyl-cyclohexyl)-3-[5-(2-morpholin-4-yl-ethylsulfanyl)-thiazol-2-yl]-urea

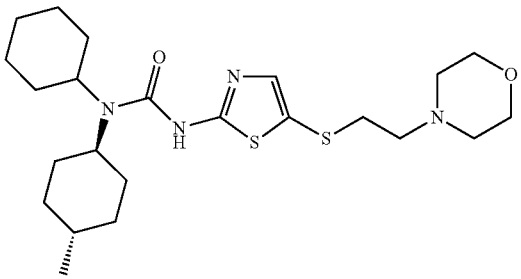

Prepared as described in general procedure (H) using 1-cyclohexyl-1-(trans-4-methyl-cyclohexyl)-3-(5-thiocyanato-thiazol-2-yl)-urea, dithioerythritol and N-(2-chloroethyl) morpholine HPLC-MS: m/z 468 (M+1).

Example 520

1-Cyclohexyl-1-(trans-4-methyl-cyclohexyl)-3-[5-(2-piperidin-1-yl-ethylsulfanyl)-thiazol-2-yl]-urea

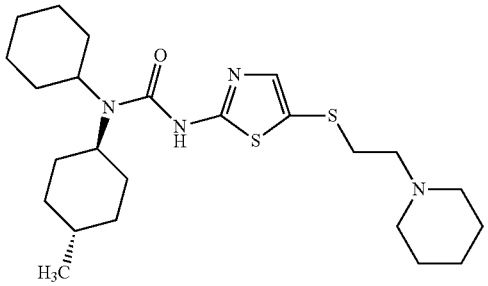

Prepared as described in general procedure (H) using 1-cyclohexyl-1-(trans-4-methyl-cyclohexyl)-3-(5-thiocyanato-thiazol-2-yl)-urea, dithioerythritol and N-(2-chloroethyl)piperidine HPLC-MS: m/z 466 (M+1).

Example 521

3-[5-(2-Azepan-1-yl-ethylsulfanyl)-thiazol-2-yl]-1-cyclohexyl-1-(trans-4-methyl-cyclohexyl)-urea

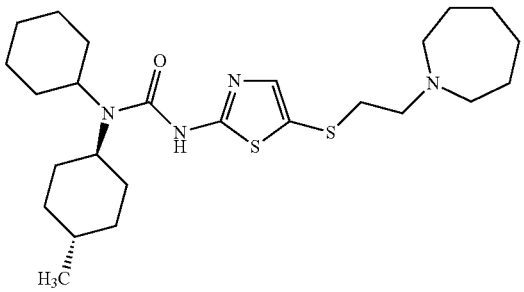

Prepared as described in general procedure (H) using 1-cyclohexyl-1-(trans-4-methyl-cyclohexyl)-3-(5-thiocyanato-thiazol-2-yl)-urea, dithioerythritol and 2-(hexamethylene-imino)ethyl chloride.

HPLC-MS: m/z 480 (M+1).

Example 522

3-{2-[3-(1-Acetyl-piperidin-4-yl)-3-(trans-4-methyl-cyclohexyl)-ureido]-thiazol-5-ylsulfanyl}-propionic acid

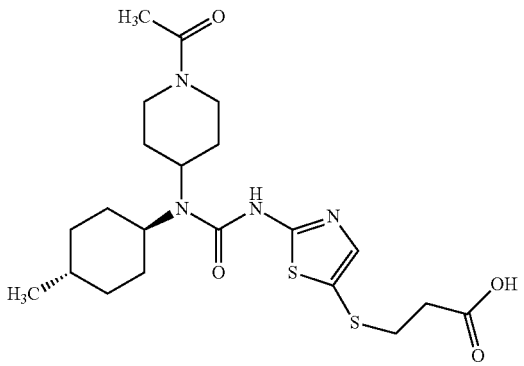

3-{2-[3-(1-Acetyl-piperidin-4-yl)-3-(4-methyl-cyclohexyl)-ureido]-thiazol-5-ylsulfanyl}-propionic acid ethyl ester prepared as described in general procedures (A) and (B) using 1-[4-(4-methyl-cyclohexylamino)-piperidin-1-yl]-ethanone and 3-(2-amino-thiazol-5-ylsulfanyl)propionic acid ethyl ester. Hydrolysis using general procedure (F) gave the title compound.

HPLC-MS: m/z 469 (M+1).

Example 523

3-{2-[3-Cyclohexyl-3-(trans-4-methyl-cyclohexyl)-ureido]-thiazol-5-ylsulfanyl}-propionic acid

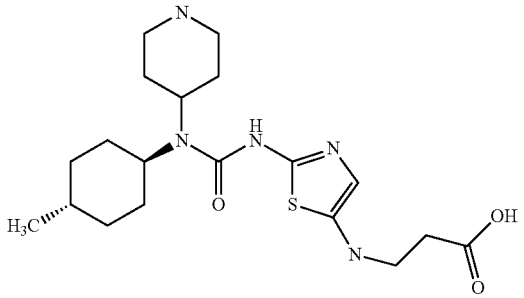

{2-[3-Cyclohexyl-3-(trans-4-methyl-cyclohexyl)-ureido]-thiazol-5-ylsulfanyl}-propionic acid ethyl ester prepared as described in general procedure (A) using cyclohexyl-(trans-4-methyl-cyclohexyl)-amine and 5-aminothiazole-2-mercaptopropionic acid ethyl ester. Hydrolysis using general procedure (F) gave the title compound.

HPLC-MS: m/z 426 (M+1).

Example 524

3-[2-(3-Cyclohexyl-3-cyclopentyl-ureido)-thiazol-5-ylsulfanyl]-propionic acid

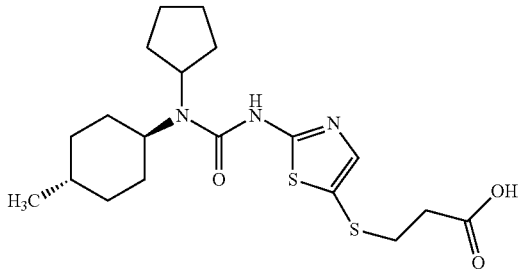

{2-[3-Cyclopentyl-3-(trans-4-methyl-cyclohexyl)-ureido]-thiazol-5-ylsulfanyl}-propionic acid ethyl ester prepared as described in general procedure (A) using cyclopentyl-(trans-4-methyl-cyclohexyl)-amine and 5-aminothiazole-2-mercaptopropionic acid ethyl ester. Hydrolysis using general procedure (F) gave the title compound.

HPLC-MS: m/z 398 (M+1).

Example 525

3-(5-Chloro-thiazol-2-yl)-1-cycloheptyl-1-(1-propionyl-piperidin-4-yl)-urea

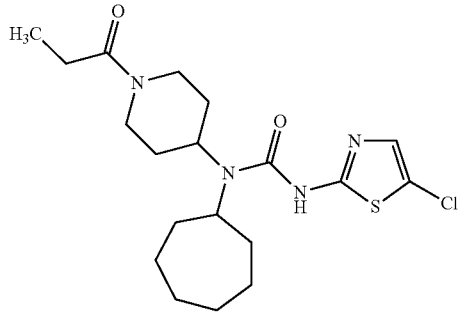

Prepared as described in general procedure (G) using 3-amino-1-Boc-piperidine, cycloheptanone and 2-amino-5-chlorothiazole HPLC-MS: m/z 413 (M+1).

Example 526

3-(5-Chloro-thiazol-2-yl)-1-cycloheptyl-1-(1-methanesulfonyl-piperidin-4-yl)-urea

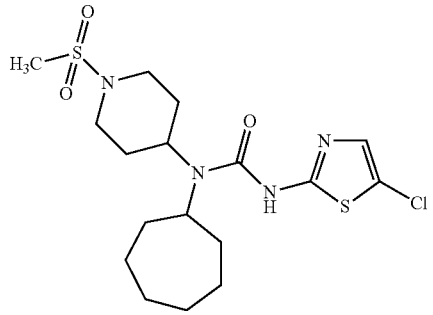

Prepared as described in general procedure (G) using 3-amino-1-Boc-piperidine, cycloheptanone and 2-amino-5-chlorothiazole HPLC-MS: m/z 435 (M+1).

Example 527

1-Cyclohexyl-3-[5-(2-diethylamino-ethylsulfanyl)-thiazol-2-yl]-1-(trans-4-methyl-cyclohexyl)-urea

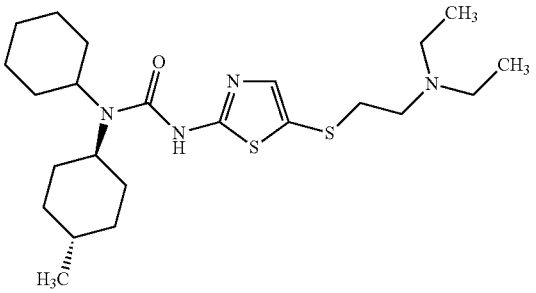

Prepared as described in general procedure (H) using 1-cyclohexyl-1-(trans-4-methyl-cyclohexyl)-3-(5-thiocyanato-thiazol-2-yl)-urea, dithioerythritol and 2-chlorotriethylamine HPLC-MS: m/z 454 (M+1).

Example 528

1-Cyclohexyl-1-(trans-4-methyl-cyclohexyl)-3-[5-(3-morpholin-4-yl-propylsulfanyl)-thiazol-2-yl]-urea

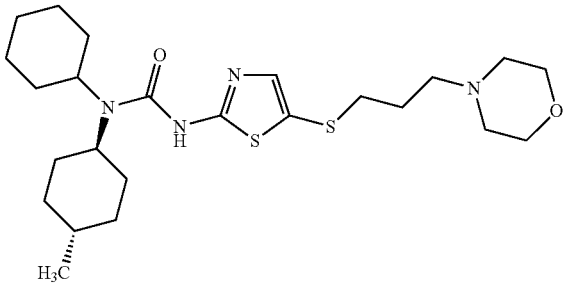

Prepared as described in general procedure (H) using 1-cyclohexyl-1-(trans-4-methyl-cyclohexyl)-3-(5-thiocyanato-thiazol-2-yl)-urea, dithioerythritol and 4-(3-chloropropyl) morpholine HPLC-MS: m/z 482 (M+1).

Example 529

1-(1-Acetyl-piperidin-4-yl)-3-[5-(4,5-dihydro-1H-imidazol-2-ylmethylsulfanyl)-thiazol-2-yl]-1-(trans-4-methyl-cyclohexyl)-urea

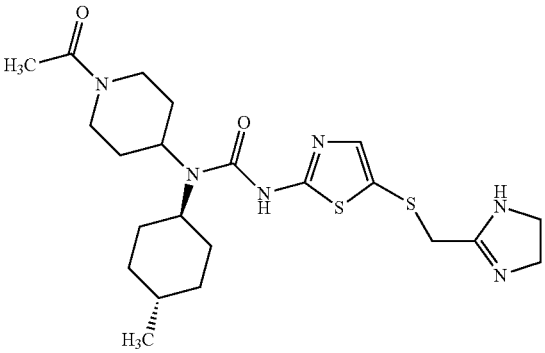

Prepared as described in general procedure (H) using 1-cyclohexyl-1-(trans-4-methyl-cyclohexyl)-3-(5-thiocyanato-thiazol-2-yl)-urea, dithioerythritol and 3-chloroethyl-2-imidazoline.

HPLC-MS: m/z 479 (M+1).

Example 530

1-(1-Acetyl-piperidin-4-yl)-3-[5-(3-amino-propylsulfanyl)-thiazol-2-yl]-1-(trans-4-methylcyclohexyl)-urea

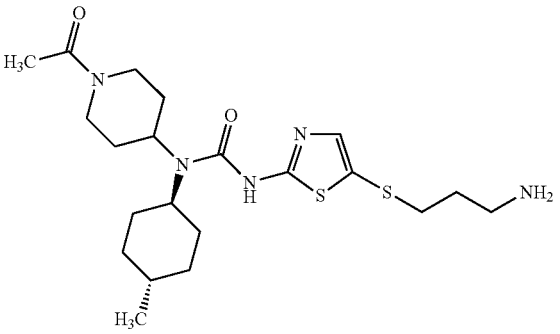

Prepared as described in general procedure (H) using 1-cyclohexyl-1-(trans-4-methyl-cyclohexyl)-3-(5-thiocyanato-thiazol-2-yl)-urea, dithioerythritol and 3-chloropropylamine HPLC-MS: m/z 454 (M+1).

Example 531

{2-[3-Cyclopentyl-3-(4-trifluoromethyl-cyclohexyl)-ureido]-thiazol-5-ylsulfanyl}-acetic acid

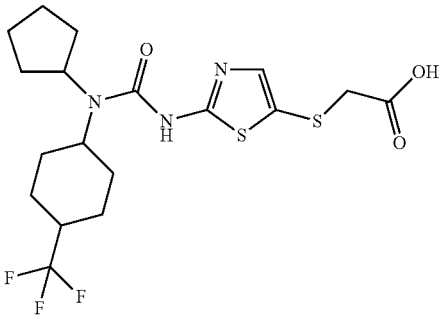

Prepared as described in general procedure (F) from {2-[3-cyclopentyl-3-(4-trifluoromethyl-cyclohexyl)-ureido]-thiazol-5-ylsulfanyl}-acetic acid methyl ester.

HPLC-MS: m/z 452 (M+1).

Example 532

1,1-Dicyclohexyl-3-[5-(2-oxo-2-piperidin-1-yl-ethylsulfanyl)-thiazol-2-yl]-urea

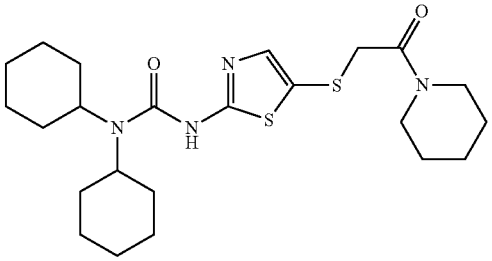

To Example 55 (0.1 mmol) in 2 mL dimethylformamide was added 1.2 equivalents of DHOBt and 1 equivalent of EDAC. After stirring for 1 h, 1 equivalent of piperidine and 1 equivalent of diisopropylethylamine was added. The reaction was diluted with 10 ml of EtOAc and 5 ml of 10% $NaHSO_4$, mixed and separated. The organic phase was washed with 3 ml of water, 3 ml of sat. $NaHCO_3$, 3 ml of brine, dried ($MgSO_4$), filtered and concentrated in vacuo. Purification by HPLC gave the title compound.

HPLC-MS: m/z 465 (M+1).

Example 533

1,1-Dicyclohexyl-3-[5-(2-morpholin-4-yl-2-oxo-ethylsulfanyl)-thiazol-2-yl]-urea

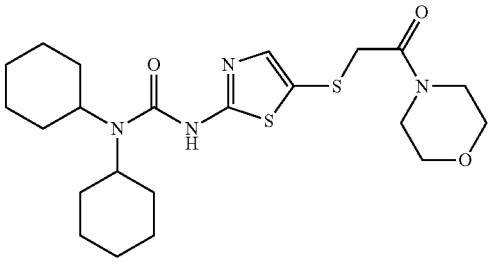

Prepared in a similar manner to Example 532 using morpholine.

HPLC-MS: m/z 467 (M+1).

Example 534

2-[2-(3,3-Dicyclohexyl-ureido)-thiazol-5-ylsulfanyl]-N,N-diethyl-acetamide

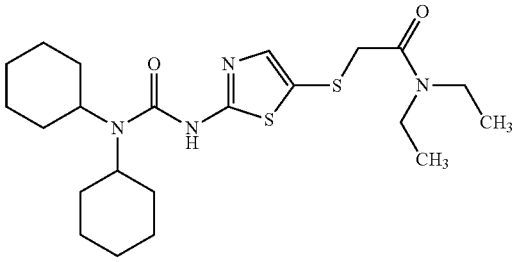

Prepared in a similar manner to Example 532 using diethylamine.

HPLC-MS: m/z 453 (M+1).

Example 535

4-{2-[2-Dicyclohexyl-ureido)-thiazol-5-ylsulfanyl]-acetyl}-piperazine-1-carboxylic acid tert-butyl ester

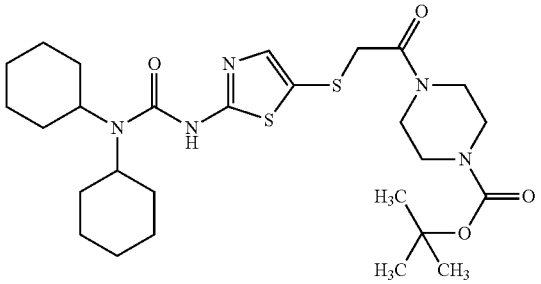

Prepared in a similar manner to

Example 532 using tert-butyl-1-piperazine carboxylate.

HPLC-MS: m/z 566 (M+1).

Example 536

N-Benzyl-2-[2-(3,3-dicyclohexyl-ureido)-thiazol-5-ylsulfanyl]-acetamide

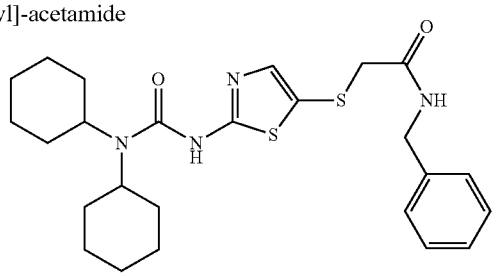

Prepared in a similar manner to Example 532 using benzylamine.

HPLC-MS: m/z 487 (M+1).

Example 537

1-(1-Butyryl-piperidin-4-yl)-1-(trans-4-methyl-cyclohexyl)-3-[5-(2-morpholin-4-yl-ethylsulfanyl)-thiazol-2-yl]-urea

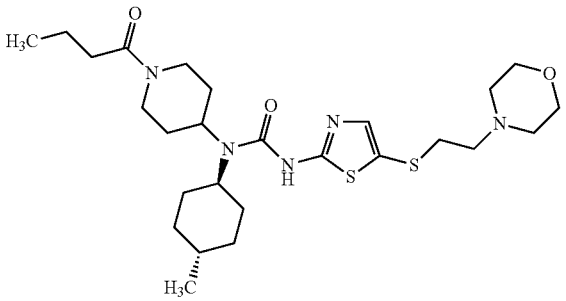

Prepared as described in general procedures (H) and (I) using 1-(1-butyryl-piperidin-4-yl)-1-(trans-4-methyl-cyclohexyl)-3-(5-thiocyanato-thiazol-2-yl)-urea, dithioerythritol and N-(2-chloroethyl)morpholine HPLC-MS: m/z 539 (M+1).

Example 538

3-[5-(2-Azepan-1-yl-ethylsulfanyl)-thiazol-2-yl]-1-(1-butyryl-piperidin-4-yl)-1-trans-4-methyl-cyclohexyl)-urea

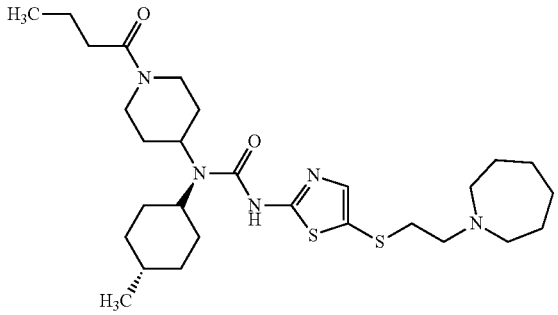

Prepared as described in general procedures (H) and (I) using 1-(1-butyryl-piperidin-4-yl)-1-(trans-4-methyl-cyclohexyl)-3-(5-thiocyanato-thiazol-2-yl)-urea, dithioerythritol and 2-(hexamethyleneimino)ethylchloride HPLC-MS: m/z 452 (M+2).

Example 539

1-(1-Butyryl-piperidin-4-yl)-1-(trans-4-methyl-cyclohexyl)-3-[5-(2-pyrrolidin-1-yl-ethylsulfanyl)-thiazol-2-yl]-urea

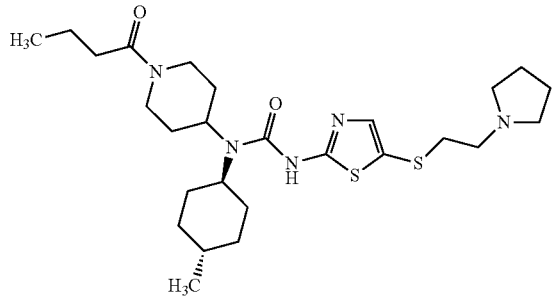

Prepared as described in general procedures (H) and (I) using 1-(1-butyryl-piperidin-4-yl)-1-(trans-4-methyl-cyclohexyl)-3-(5-thiocyanato-thiazol-2-yl)-urea, dithioerythritol and N-(2-chloroethyl)pyrrolidine.

HPLC-MS: m/z 525 (M+2).

Example 540

1-(1-Butyryl-piperidin-4-yl)-3-[5-(2-diethylamino-ethylsulfanyl)-thiazol-2-yl]-1-(trans-4-methyl-cyclohexyl)-urea

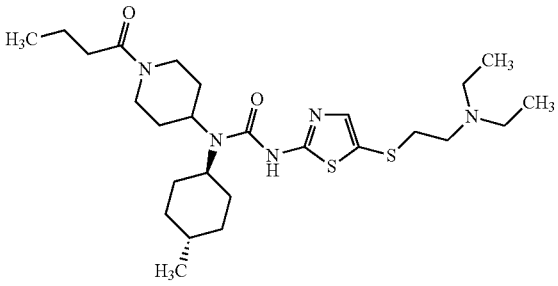

Prepared as described in general procedures (H) and (I) using 1-(1-butyryl-piperidin-4-yl)-1-(trans-4-methyl-cyclohexyl)-3-(5-thiocyanato-thiazol-2-yl)-urea, dithioerythritol and 2-diethylamino-ethanethiol HPLC-MS: m/z 526 (M+2).

Example 541

1-(1-Butyryl-piperidin-4-yl)-1-(trans-4-methyl-cyclohexyl)-3-(5-methylsulfanyl-thiazol-2-yl)-urea

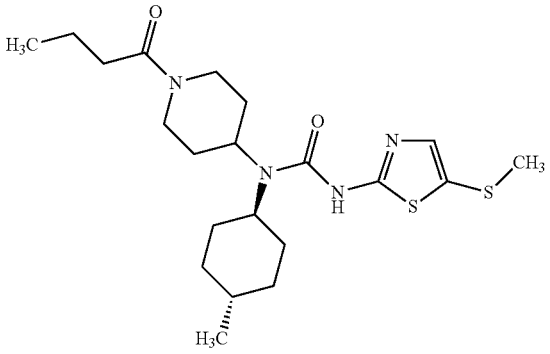

Prepared as described in general procedures (H) and (I) using 1-(1-butyryl-piperidin-4-yl)-1-(trans-4-methyl-cyclohexyl)-3-(5-thiocyanato-thiazol-2-yl)-urea, dithioerythritol and iodomethane.

HPLC-MS: m/z 441 (M+2).

Example 542

1-[1-(2-Cyclopropyl-acetyl)-piperidin-4-yl]-1-(trans-4-methyl-cyclohexyl)-3-(5-methyl-thiazol-2-yl)-urea

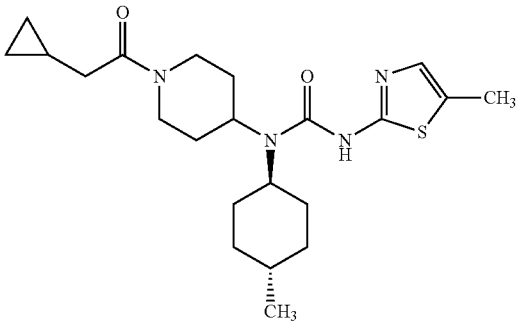

Prepared as described in general procedure (G) using 4-(trans-4-methyl-cyclohexylamino)-piperidine-1-carboxylic acid tert-butyl ester and 2-amino-5-methylthiazole HPLC-MS: m/z 419 (M+1).

Example 543

1-(1-Acetyl-pyrrolidin-3(S)-yl)-1-cyclohexyl-3-[5-(2-morpholin-4-yl-ethylsulfanyl)-thiazol-2-yl]-urea

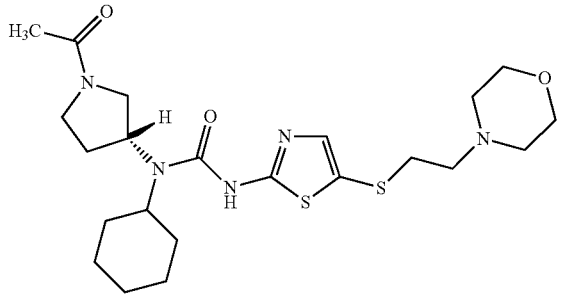

Prepared as described in general procedure (H) using 1-cyclohexyl-3-(5-thiocyanato-thiazol-2-yl)-1-[1-(acetyl)-pyrrolidin-3(S)-yl]urea, dithioerythritol and N-(2-chloroethyl) morpholine HPLC-MS: m/z 482 (M+1).

Example 544

1-(1-Acetyl-pyrrolidin-3(R)-yl)-1-cyclohexyl-3-[5-(2-pyrrolidin-1-yl-ethylsulfanyl)-thiazol-2-yl]-urea

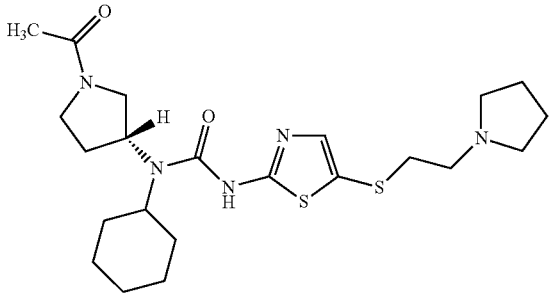

Prepared as described in general procedure (H) using 1-cyclohexyl-3-(5-thiocyanato-thiazol-2-yl)-1-[1-(acetyl)-pyrrolidin-3(R)-yl]-urea, dithioerythritol and N-(2-chloroethyl) pyrrolidine.

HPLC-MS: m/z 466 (M+1).

Example 545

1-(trans-4-Methyl-cyclohexyl)-3-(5-methyl-thiazol-2-yl)-1-[1-(3,3,3-trifluoro-propionyl)-piperidin-4-yl]-urea

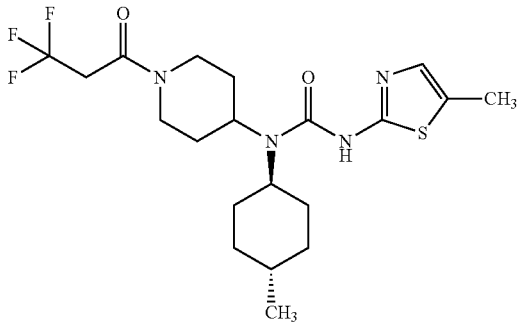

Prepared as described in general procedure (G) using 4-(trans-4-methyl-cyclohexylamino)-piperidine-1-carboxylic acid tert-butyl ester and 2-amino-5-methylthiazole HPLC-MS: m/z 447 (M+1).

Example 546

{2-[3-Cyclohexyl-3-(trans-4-hydroxy-cyclohexyl)-ureido]-thiazol-5-ylsulfanyl}-acetic acid

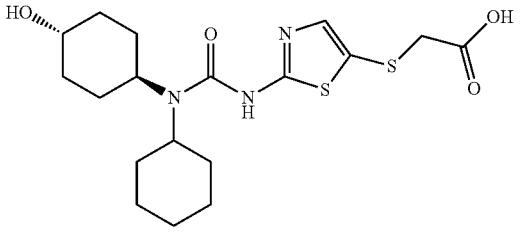

Prepared in a similar manner to Example 381 using [trans-4-(tert-butyl-dimethyl-silanyloxy)-cyclohexyl]-cyclohexylamine and 5-aminothiazole-2-mercaptoacetic acid ethyl ester.

HPLC-MS: m/z 414 (M+1).

Example 547

3-(5-Chloro-thiazol-2-yl)-1-cyclohexyl-1-(trans-4-hydroxy-cyclohexyl)-urea

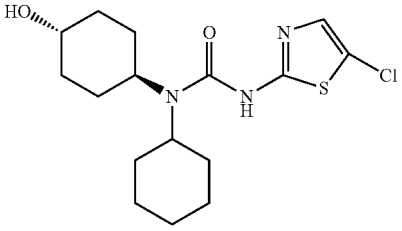

Prepared in a similar manner to Example 381 using [trans-4-(tert-butyl-dimethyl-silanyloxy)-cyclohexyl]-cyclohexylamine and 5-chloro 2-aminothiazole.

HPLC-MS: m/z 358 (M+1).

Example 548

{2-[3-Cyclohexyl-3-(trans-4-methoxy-cyclohexyl)-ureido]-thiazol-5-ylsulfanyl}-acetic acid

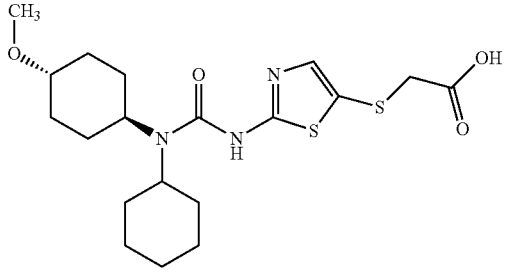

Prepared as described in general procedures (A) and (B) and (F) using trans-4-methoxy-cyclohexyl]-cyclohexyl-amine and 5-aminothiazole-2-mercaptoacetic acid ethyl ester.

HPLC-MS: m/z 428 (M+1).

Example 549

1-Cycloheptyl-3-[5-(2-diethylamino-ethylsulfanyl)-4-methyl-thiazol-2-yl]-1-(trans-4-methyl-cyclo-hexyl)-urea

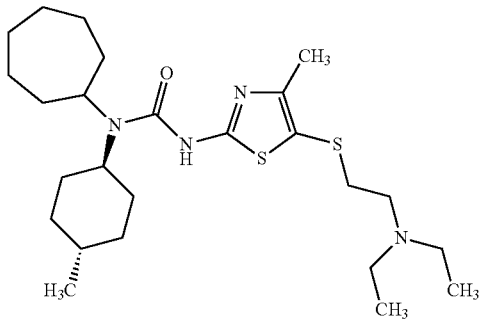

Prepared as described in general procedure (H) using dithioerythritol and N-(2-chloroethyl)morpholine HPLC-MS: m/z 481 (M+1).

Example 550

1-Cycloheptyl-1-(trans-4-methyl-cyclohexyl)-3-[4-methyl-5-(2-pyrrolidin-1-yl-ethylsulfanyl)-thiazol-2-yl]-urea

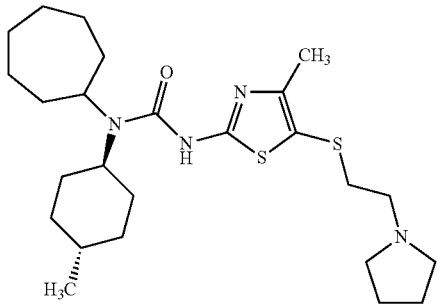

Prepared as described in general procedure (H) using dithioerythritol and N-(2-chloroethyl)pyrrolidine HPLC-MS: m/z 479 (M+1).

Example 551

1-Cycloheptyl-1-(trans-4-methyl-cyclohexyl)-3-[4-methyl-5-(2-piperidin-1-yl-ethylsulfanyl)-thiazol-2-yl]-urea

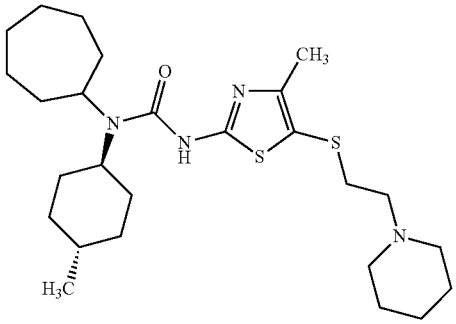

Prepared as described in general procedure (H) using dithioerythritol and N-(2-chloroethyl)piperidine HPLC-MS: m/z 493 (M+1).

Example 552

3-(5-Chloro-thiazol-2-yl)-1-(trans-4-methyl-cyclo-hexyl)-1-[1-(3,3,3-trifluoro-propionyl)-piperidin-4-yl]-urea

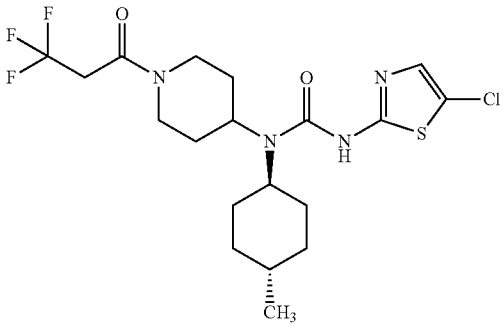

Prepared as described in general procedure (G) using 4-(trans-4-methyl-cyclohexylamino)-piperidine-1-carboxy-lic acid tert-butyl ester and 2-amino-5-chlorothiazole HPLC-MS: m/z 467 (M+1).

Example 553

3-(5-Chloro-thiazol-2-yl)-1-[1-(2-cyclopropyl-acetyl)-piperidin-4-yl]-1-(4-methyl-cyclohexyl)-urea

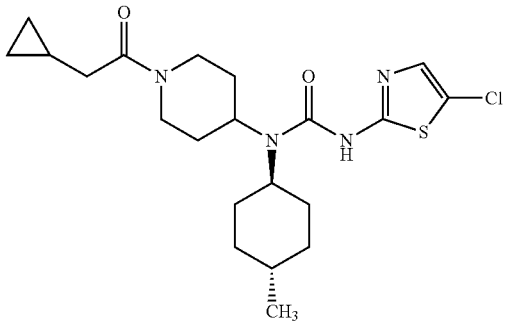

Prepared as described in general procedure (G) using 4-(trans-4-methyl-cyclohexylamino)-piperidine-1-carboxylic acid tert-butyl ester and 2-amino-5-chlorothiazole HPLC-MS: m/z 439 (M+1).

Example 554

4-[3-(5-Chloro-thiazol-2-yl)-1-(trans-4-methyl-cyclohexyl)-ureido]-piperidine-1-carboxylic acid dimethylamide

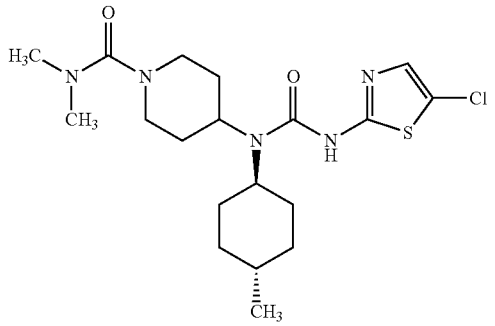

To a solution of 3-(5-chloro-thiazol-2-yl)-1-(trans-4-methyl-cyclohexyl)-1-piperidin-4-yl-urea (0.8 mmol), prepared as described in general procedure (G), steps 1-3, and 1.2 equivalents of DIPEA in 10 mL dioxane was added dimethylcarbamoyl chloride (1.2 equivalents) in 1 ml dioxane. The reaction was stirred overnight at room temperature, concentrated in vacuo and purified by flash chromatography to give the title compound.

HPLC-MS: m/z 428 (M+1).

Example 555

2-(3,3-Dicyclohexyl-ureido)-4-methyl-thiazole-5-sulfonic acid (1-methyl-piperidin-4-yl)-amide

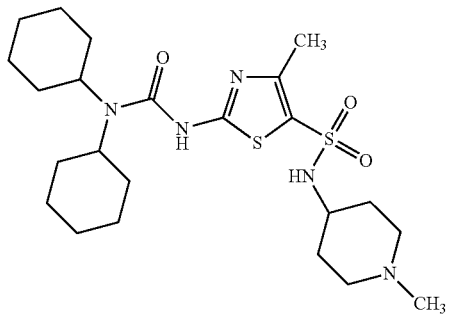

Prepared in a similar manner to Example 173 using dicyclohexylamine and 4-methyl-thiazole-5-sulfonic acid (1-methyl-piperidin-4-yl)-amide HPLC-MS: m/z 499 (M+1).

Example 556

4-[3-(5-Chloro-thiazol-2-yl)-1-(trans-4-methyl-cyclohexyl)-ureido]-piperidine-1-sulfonic acid dimethylamide

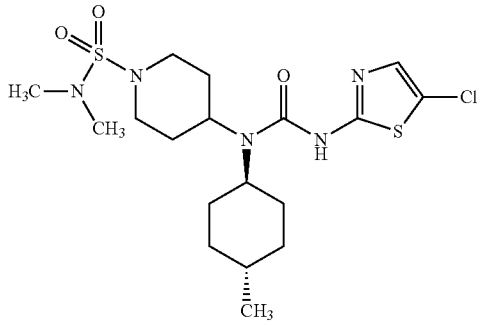

Prepared in a similar manner to Example 554 using 3-(5-chloro-thiazol-2-yl)-1-(trans-4-methyl-cyclohexyl)-1-piperidin-4-yl-urea and dimethylsulfamoyl chloride HPLC-MS: m/z 464 (M+1).

Example 557

3-(5-Chloro-thiazol-2-yl)-1-(trans-4-methyl-cyclohexyl)-1-[1-(propane-1-sulfonyl)-piperidin-4-yl]-urea

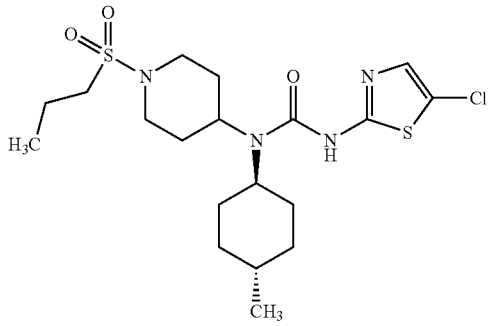

Prepared in a similar manner to Example 554 using 3-(5-chloro-thiazol-2-yl)-1-(trans-4-methyl-cyclohexyl)-1-piperidin-4-yl-urea and propanesulfonylchloride HPLC-MS: m/z 463 (M+1).

Example 558

3-(5-Chloro-thiazol-2-yl)-1-(trans-4-methyl-cyclohexyl)-1-[1-(morpholine-4-carbonyl)-piperidin-4-yl]-urea

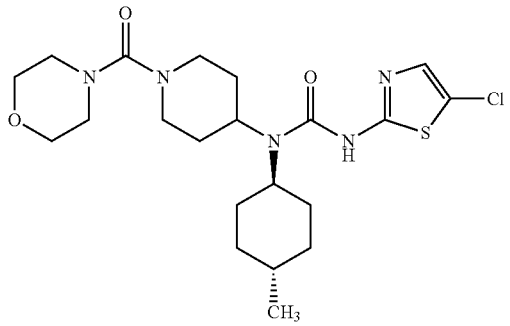

Prepared in a similar manner to Example 532 using 3-(5-chloro-thiazol-2-yl)-1-(trans-4-methyl-cyclohexyl)-1-piperidin-4-yl-urea and 4-morpholinecarbonyl chloride HPLC-MS: m/z 470 (M+1).

Example 559

N-(4-{4-[3-(5-Chloro-thiazol-2-yl)-1-(trans-4-methyl-cyclohexyl)-ureido]-piperidine-1-sulfonyl}-phenyl)-acetamide

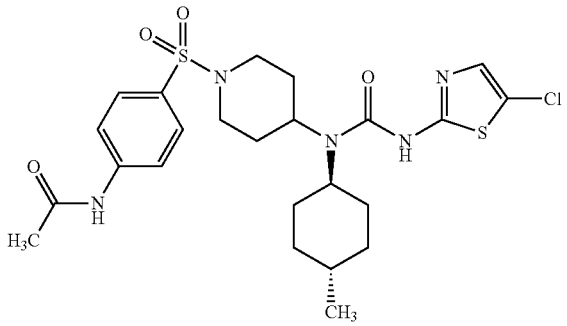

Prepared in a similar manner to Example 554 using 3-(5-chloro-thiazol-2-yl)-1-(trans-4-methyl-cyclohexyl)-1-piperidin-4-yl-urea and N-acetylsulfanilyl chloride.

HPLC-MS: m/z 554 (M+1).

Example 560

1,1-Dicyclohexyl-3-{5-[2-(4-methyl-piperazin-1-yl)-2-oxo-ethylsulfanyl]-thiazol-2-yl}-urea

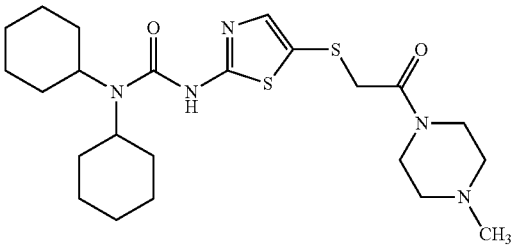

Prepared in a similar manner to Example 532 using 1-benzylpiperazine.

HPLC-MS: m/z 480 (M+1).

Example 561

3-{5-[2-(4-Benzyl-piperazin-1-yl)-2-oxo-ethylsulfanyl]-thiazol-2-yl}-1,1-dicyclohexyl-urea

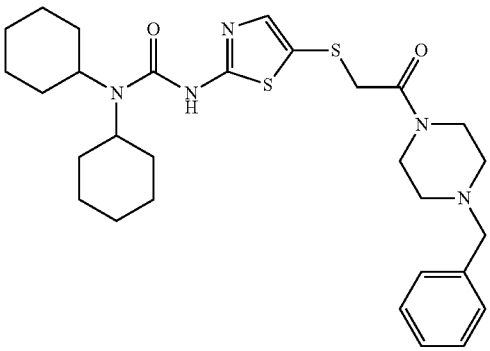

Prepared in a similar manner to Example 532 using 1-benzylpiperazine.

HPLC-MS: m/z 556 (M+1).

Example 562

1,1-Dicyclohexyl-3-{5-[2-oxo-2-(4-phenyl-piperazin-1-yl)-ethylsulfanyl]-thiazol-2-yl}-urea

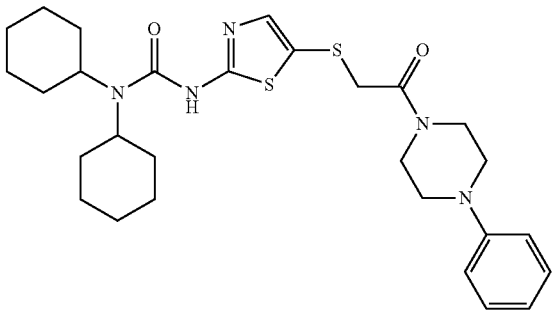

Prepared in a similar manner to Example 532 using 1-phenylpiperazine.

HPLC-MS: m/z 542 (M+1).

Example 563

1,1-Dicyclohexyl-3-{5-[2-oxo-2-(4-pyrimidin-2-yl-piperazin-1-yl)-ethylsulfanyl]-thiazol-2-yl}-urea

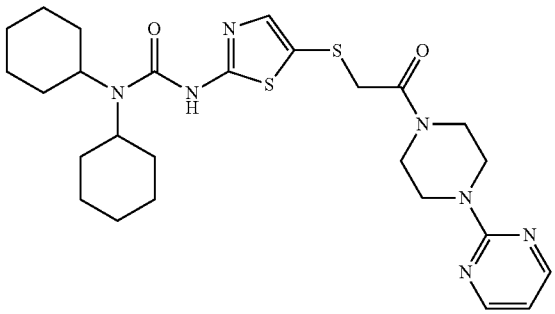

Prepared in a similar manner to Example 532 using 1-(2-pyrimidinyl)-piperazine.

HPLC-MS: m/z 544 (M+1).

Example 564

1,1-Dicyclohexyl-3-{5-[2-oxo-2-(4-pyridin-2-yl-piperazin-1-yl)-ethylsulfanyl]-thiazol-2-yl}-urea

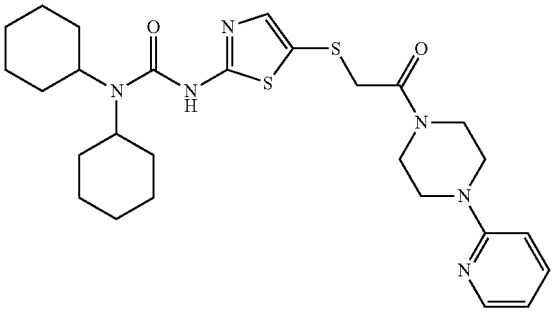

Prepared in a similar manner to Example 532 using 1-(2-pyridinyl)-piperazine.

HPLC-MS: m/z 543 (M+1).

Example 565

1,1-Dicyclohexyl-3-{5-[2-oxo-2-(4-pyridin-4-yl-piperazin-1-yl)-ethylsulfanyl]-thiazol-2-yl}-urea

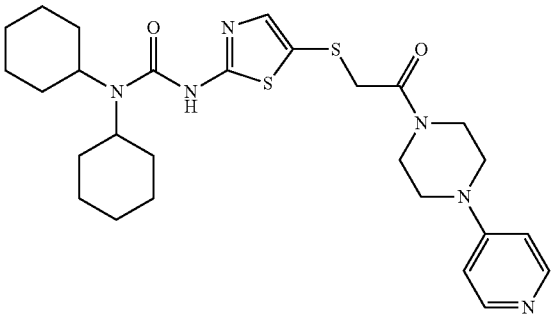

Prepared in a similar manner to Example 532 using 1-(4-pyridinyl)-piperazine. HPLC-MS: m/z 543 (M+1).

Example 566

1,1-Dicyclohexyl-3-{5-[2-(4-cyclopentyl-piperazin-1-yl)-2-oxo-ethylsulfanyl]-thiazol-2-yl}-urea

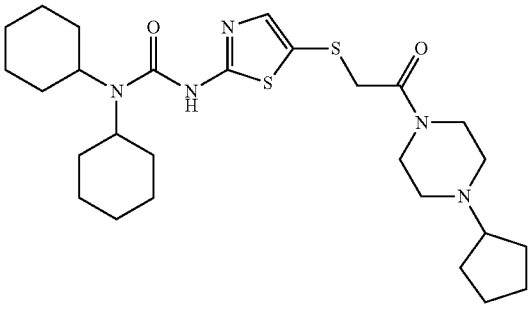

Prepared in a similar manner to Example 532 using 1-cyclopentyl-piperazine

HPLC-MS: m/z 534 (M+1).

Example 567

1,1-Dicyclohexyl-3-(5-{2-oxo-2-[4-(tetrahydro-furan-2-ylmethyl)-piperazin-1-yl]-ethylsulfanyl}-thiazol-2-yl)-urea

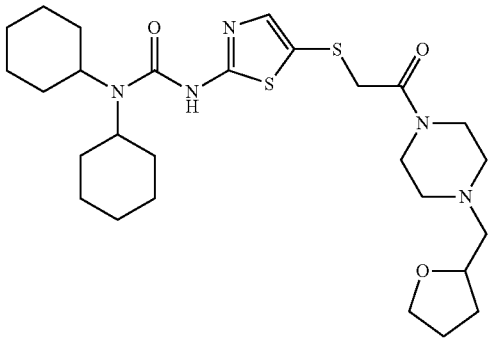

Prepared in a similar manner to Example 532 using 1-(2-tetrahydrofurfuryl)-piperazine HPLC-MS: m/z 550 (M+1).

Example 568

1,1-Dicyclohexyl-3-{5-[2-(4-ethyl-piperazin-1-yl)-2-oxo-ethylsulfanyl]-thiazol-2-yl}-urea

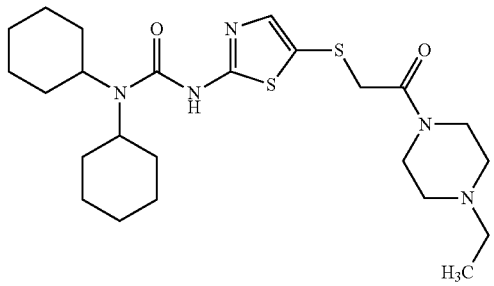

Prepared in a similar manner to Example 532 using 1-ethyl-piperazine

HPLC-MS: m/z 494 (M+1).

Example 569

4-[3-(5-Chloro-thiazol-2-yl)-1-(trans-4-methyl-cyclohexyl)-ureido]-piperidine-1-carboxylic acid diethylamide

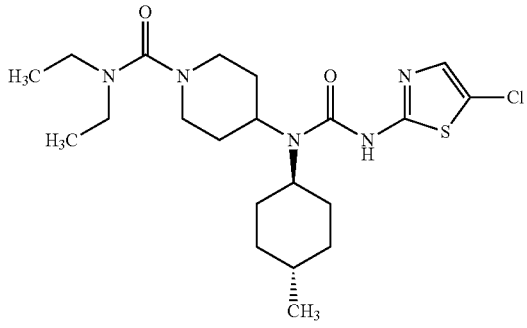

Prepared in a similar manner to Example 554 using 3-(5-chloro-thiazol-2-yl)-1-(trans-4-methyl-cyclohexyl)-1-piperidin-4-yl-urea and diethylcarbamoyl chloride HPLC-MS: m/z 456 (M+1).

Example 570

3-[2-(3-Cycloheptyl-3-cyclohexyl-ureido)-thiazol-5-ylsulfanyl]-propionic acid

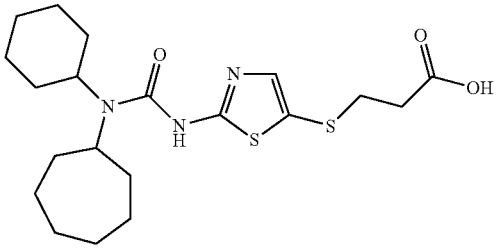

[2-(3-Cycloheptyl-3-cyclohexyl-ureido)-thiazol-5-ylsulfanyl]-propionic acid ethyl ester pre-pared as described in general procedure (A) using cycloheptyl-cyclohexylamine and 5-aminothiazole-2-mercaptoacetic acid ethyl ester. Hydrolysis using general procedure (F) gave the title compound HPLC-MS: m/z 426 (M+1).

Example 571

1-(1-Acetyl-piperidin-4-yl)-1-cyclohexyl-3-[5-(2-piperidin-1-yl-ethylsulfanyl)-thiazol-2-yl]-urea

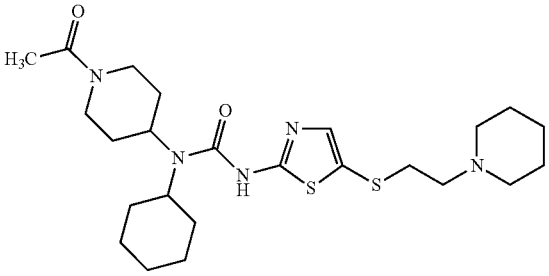

Prepared as described in general procedures (H) and (I) using 1-(1-acetyl-piperidin-4-yl)-1-cyclohexyl-3-(5-thiocyanato-thiazol-2-yl)-urea, dithioerythritol and N-(2-chloroethyl)piperidine HPLC-MS: m/z 494 (M+1).

Example 572

1-Cyclohexyl-1-(trans-4-methyl-cyclohexyl)-3-[5-(2-pyrrolidin-1-yl-ethylsulfanyl)-thiazol-2-yl]-urea

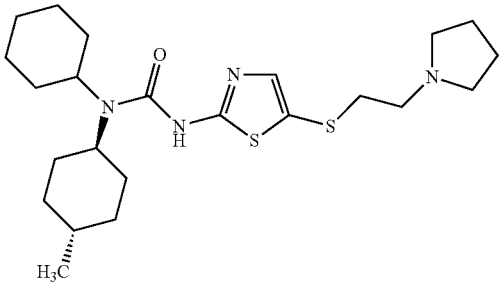

Prepared as described in general procedure (H) using 1-cyclohexyl-1-(trans-4-methyl-cyclohexyl)-3-(5-thiocyanato-thiazol-2-yl)-urea, dithioerythritol and N-(2-chloroethyl)pyrrolidine HPLC-MS: m/z 452 (M+1).

Example 573

1,1-Dicyclohexyl-3-[5-(2-oxo-2-piperazin-1-yl-ethylsulfanyl)-thiazol-2-yl]-urea

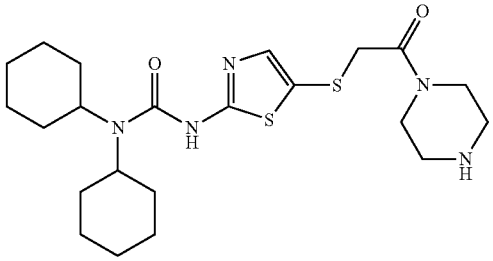

To Example 55 (0.1 mmol) in 2 mL dimethylformamide was added 1.2 equivalents of DHOBt and 1 equivalent of EDAC. After stirring for 1 h, 1 equivalent of piperazine and 1 equivalent of diisopropylethylamine was added. The reaction was diluted with 10 ml of EtOAc and 5 ml of 10% $NaHSO_4$, mixed and separated. The organic phase was washed with 3 ml of water, 3 ml of sat. $NaHCO_3$, 3 ml of brine, dried ($MgSO_4$), filtered and concentrated in vacuo. Purification by HPLC gave the title compound.

HPLC-MS: m/z 466 (M+1).

Example 574

3-(5-Chloro-thiazol-2-yl)-1-(trans-4-methyl-cyclohexyl)-1-[1-(piperidine-1-carbonyl)-piperidin-4-yl]-urea

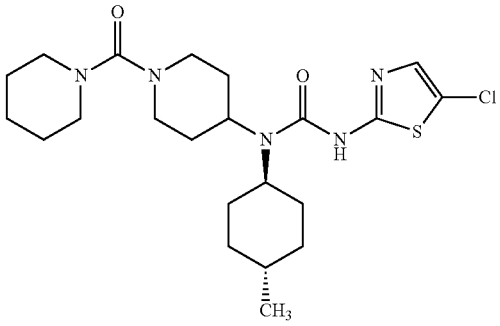

Prepared in a similar manner to Example 554 using 3-(5-chloro-thiazol-2-yl)-1-(trans-4-methyl-cyclohexyl)-1-piperidin-4-yl-urea and 1-piperidinecarbonyl chloride HPLC-MS: m/z 468 (M+).

Example 575

3-{2-[3-Cyclohexyl-3-(4,4-difluoro-cyclohexyl)-ureido]-thiazol-5-ylsulfanyl}-propionic acid

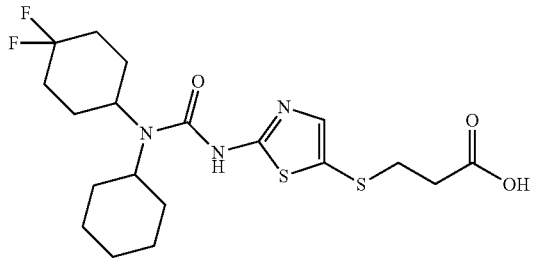

Reaction of Boc-aminocyclohexanone with DAST in DCM for 24 h at room temperature gave (4,4-Difluoro-cyclohexyl)-carbamic acid tert-butyl ester after flash chromatography. Boc deprotection using TFA followed by reductive amination with cyclohexanone using general procedure B gave cyclohexyl-(4,4-difluoro-cyclohexyl)-amine. Treatment with CDI and 5-aminothiazol-2-mercaptopropionic acid ethyl ester using general procedure (A) gave 3-{2-[3-Cyclohexyl-3-(4,4-difluoro-cyclohexyl)-ureido]-thiazol-5-ylsulfanyl}-propionic acid ethyl ester, which was hydrolysed using general procedure (F) to give the title compound.

HPLC-MS: m/z 448 (M+1).

Example 576

3-(5-Chloro-thiazol-2-yl)-1-(trans-4-methyl-cyclohexyl)-1-[1-(propane-1-sulfonyl)-piperidin-4-yl]-urea

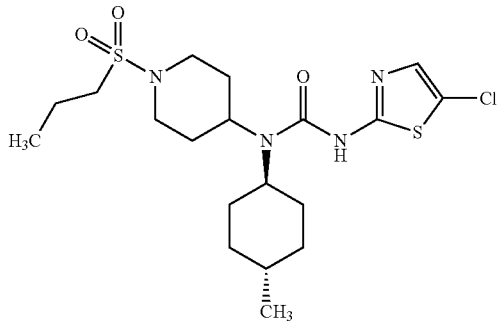

Prepared as described in general procedure (G) using 3-(5-chloro-thiazol-2-yl)-1-(trans-4-methyl-cyclohexyl)-1-piperidin-4-yl-urea and 3-chloropropane-1-sulfonyl chloride HPLC-MS: m/z 463 (M+1).

Example 577

1-(1-Acetyl-piperidin-4-yl)-1-cyclohexyl-3-(5-fluoro-thiazol-2-yl)-urea

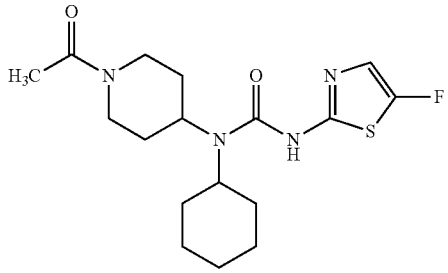

Prepared as described in general procedures (A) and (B) using 1-(4-cyclohexylamino-piperidin-1-yl)-ethanone and 5-fluoro-2-aminothiazole.

HPLC-MS: m/z 391 (M+23).

Example 578

1,1-Dicyclohexyl-3-(5-fluoro-thiazol-2-yl)-urea

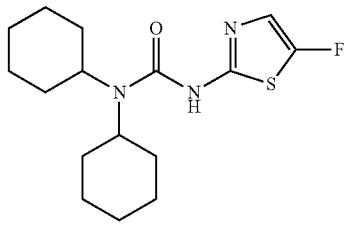

Prepared as described in general procedures (A) and (B) using dicyclohexylamine and 5-fluoro-2-aminothiazole.

HPLC-MS: m/z 326 (M+1).

Example 579

1-Cyclohexyl-3-(5-fluoro-thiazol-2-yl)-1-(trans-4-methyl-cyclohexyl)-urea

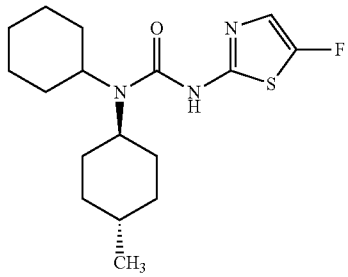

Prepared as described in general procedures (A) and (B) using cyclohexyl-(trans-4-methyl-cyclohexyl)-amine and 5-fluoro-2-aminothiazole HPLC-MS: m/z 340 (M+1).

Example 580

3-(5-Chloro-thiazol-2-yl)-1-cyclohexyl-1-(3-cyano-cyclohexyl)-urea

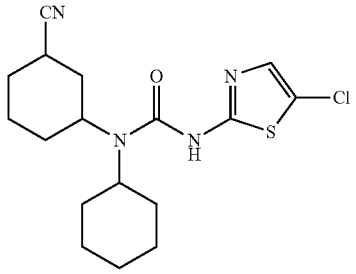

Prepared as described in general procedures (A) and (B) using cyclohexyl-(3-cyanocyclohexyl)-amine and 5-chloro-2-aminothiazole HPLC-MS: m/z 367 (M+).

Example 581

6-{4-[3-(5-Chloro-thiazol-2-yl)-1-cyclohexyl-ureido]-piperidin-1-yl}-6-oxo-hexanoic acid

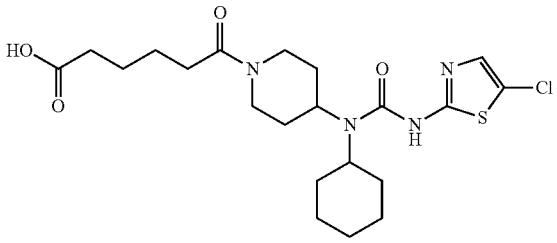

Prepared as described in general procedure (G) using 3-(5-chloro-thiazol-2-yl)-1-(trans-4-methyl-cyclohexyl)-1-piperidin-4-yl-urea and adipic acid.

HPLC-MS: m/z 471 (M+).

Example 582

1-Cyclohexyl-1-(2-methyl-cyclohexyl)-3-thiazol-2-yl-urea

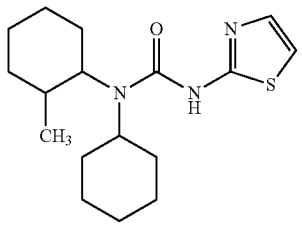

Prepared as described in general procedures (A) and (B) using cyclohexyl-(2-methylcyclohexyl)-amine and 2-aminothiazole HPLC-MS: m/z 322 (M+).

Example 583

5-{4-[3-(5-Chloro-thiazol-2-yl)-1-cyclohexyl-ureido]-piperidin-1-yl}-5-oxo-pentanoic acid

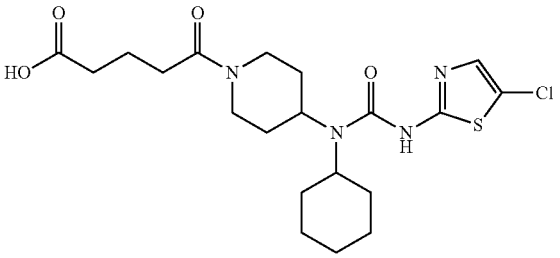

Prepared as described in general procedure (O) using 3-(5-chloro-thiazol-2-yl)-1-(trans-4-methyl-cyclohexyl)-1-piperidin-4-yl-urea and glutaric acid HPLC-MS: m/z 457 (M+).

Example 584

2-{2-[3-Cyclohexyl-3-(trans-4-methyl-cyclohexyl)-ureido]-thiazol-5-ylsulfanyl}-propionic acid

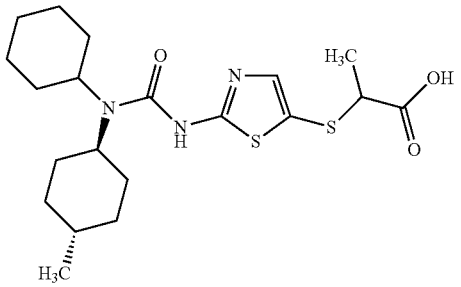

Prepared as described in general procedure (H) using 1-cyclohexyl-1-(trans-4-methyl-cyclohexyl)-3-(5-thiocyanato-thiazol-2-yl)-urea, dithioerythritol and ethyl-2-bromopropionate.

HPLC-MS: m/z 428 (M+1).

Example 585

7-{4-[3-(5-Chloro-thiazol-2-yl)-1-cyclohexyl-ureido]-piperidin-1-yl}-7-oxo-heptanoic acid

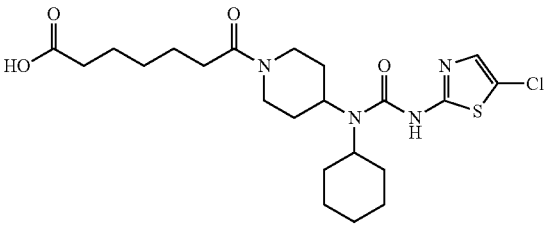

Prepared as described in general procedure (G) using 3-(5-chloro-thiazol-2-yl)-1-(trans-4-methyl-cyclohexyl)-1-piperidin-4-yl-urea and pimelic acid.

HPLC-MS: m/z 485 (M+).

Example 586

(2-{3-(trans-4-Methyl-cyclohexyl)-3-[1-(morpholine-4-carbonyl)-piperidin-4-yl]-ureido}-thiazol-5-vlsulfanyl)-acetic acid

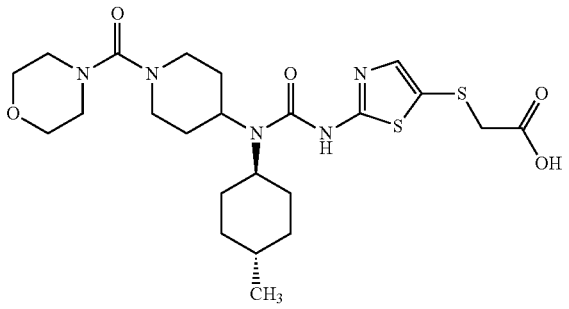

(2-{3-(trans-4-Methyl-cyclohexyl)-3-[1-(morpholine-4-carbonyl)-piperidin-4-yl]-ureido}-thiazol-5-ylsulfanyl)-acetic acid ethyl ester was prepared in a similar manner to Example 554 using {2-[3-(trans-4-methyl-cyclohexyl)-3-piperidin-4-yl-ureido]-thiazol-5-ylsulfanyl}-acetic acid ethyl ester and 4-morpholinecarbonyl chloride. Hydrolysis using general procedure (F) gave the title compound HPLC-MS: m/z 526 (M+).

Example 587

2-{2-[3-Cyclohexyl-3-(trans-4-methyl-cyclohexyl)-ureido]-thiazol-5-ylsulfanyl}-2-methyl-propionic acid

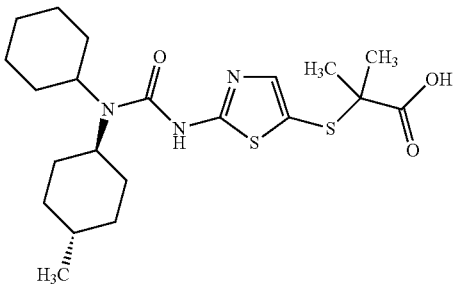

Prepared as described in general procedure (H) using 1-cyclohexyl-1-(trans-4-methyl-cyclohexyl)-3-(5-thiocyanato-thiazol-2-yl)-urea, dithioerythritol and ethyl-2-bromo-2-methyl propionate.

HPLC-MS: m/z 441 (M+1).

Example 588

1-{2-[3-Cyclohexyl-3-(trans-4-methyl-cyclohexyl)-ureido]-thiazol-5-ylsulfanyl}-cyclobutanecarboxylic acid

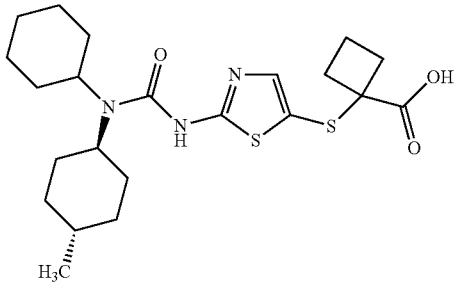

Prepared as described in general procedure (H) using 1-cyclohexyl-1-(trans-4-methyl-cyclohexyl)-3-(5-thiocyanato-thiazol-2-yl)-urea, dithioerythritol and ethyl-1-bromocyclobutane carboxylate.

HPLC-MS: m/z 453 (M+1).

Example 589

{2-[3-(1-Dimethylsulfamoyl-piperidin-4-yl)-3-(trans-4-methyl-cyclohexyl)-ureido]-thiazol-5-ylsulfanyl}-acetic acid

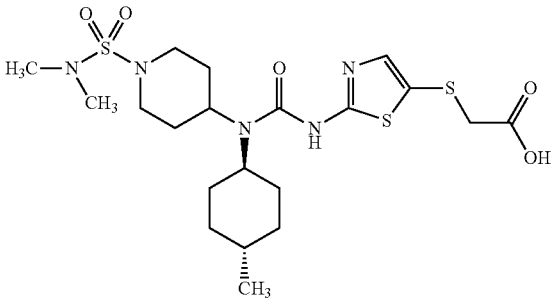

{2-[3-(1-Dimethylsulfamoyl-piperidin-4-yl)-3-(trans-4-methyl-cyclohexyl)-ureido]-thiazol-5-ylsulfanyl}-acetic acid ethyl ester was prepared in a similar manner to Example 554 using {2-[3-(trans-4-methyl-cyclohexyl)-3-piperidin-4-yl-ureido]-thiazol-5-ylsulfanyl}-acetic acid ethyl ester and dimethylsulfamoyl chloride. Hydrolysis using general procedure (F) gave the title compound.

HPLC-MS: m/z 520 (M+1).

Example 590

{2-[3-(1-Dimethylcarbamoyl-piperidin-4-yl)-3-(trans-4-methyl-cyclohexyl)-ureido]-thiazol-5-ylsulfanyl}-acetic acid

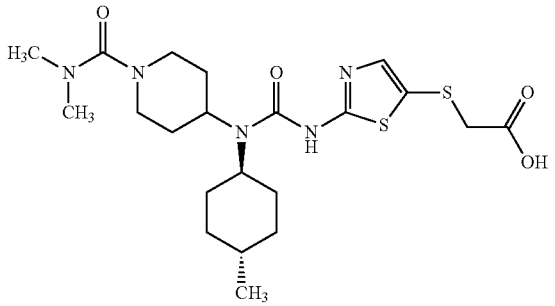

{2-[3-(1-Dimethylcarbamoyl-piperidin-4-yl)-3-(trans-4-methyl-cyclohexyl)-ureido]-thiazol-5-ylsulfanyl}-acetic acid ethyl ester was prepared in a similar manner to Example 554 using {2-[3-(trans-4-methyl-cyclohexyl)-3-piperidin-4-yl-ureido]-thiazol-5-ylsulfanyl}-acetic acid ethyl ester and dimethylcarbamoyl chloride. Hydrolysis using general procedure (F) gave the title compound.

HPLC-MS: m/z 484 (M+1).

Example 591

2-{2-[3-Cyclohexyl-3-(trans-4-methyl-cyclohexyl)-ureido]-thiazol-5-ylsulfanyl}-3-methyl-butyric acid

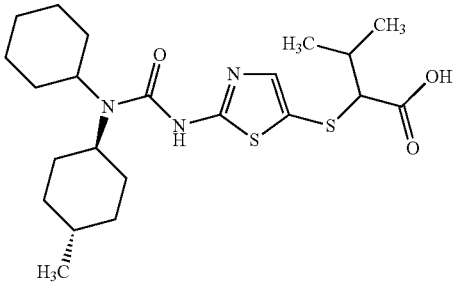

Prepared as described in general procedure (H) using 1-cyclohexyl-1-(trans-4-methyl-cyclohexyl)-3-(5-thiocyanato-thiazol-2-yl)-urea, dithioerythritol and ethyl-2-bromoisovalerate.

HPLC-MS: m/z 455 (M+1).

Example 592

1,1-Dicyclohexyl-3-(5-methylsulfanyl-pyrazin-2-yl)-urea

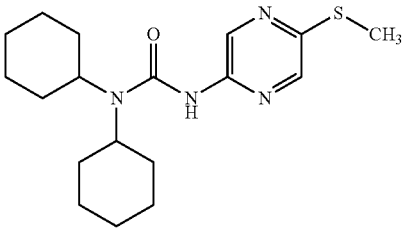

Prepared as described in general procedures (A) and (B) using dicyclohexylamine and 5-methylsulfanyl-pyrazin-2-ylamine HPLC-MS: m/z 349 (M+).

Example 593

4-[2-(3,3-Dicyclohexyl-ureido)-4-methyl-thiazole-5-sulfonylamino]-piperidine-1-carboxylic acid ethyl ester

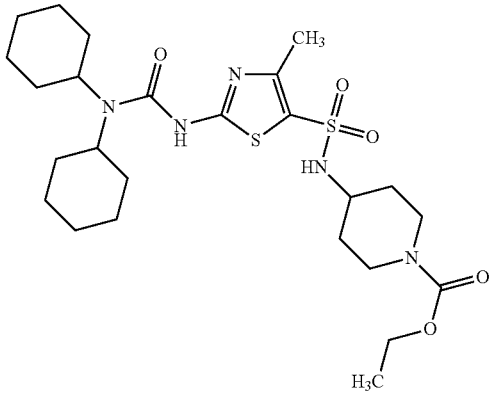

Prepared as described in Example 173 using ethyl 4-amino-1-piperidine carboxylate, dicyclohexylamine and 2-acetylamino-thiazole-5-sulfonyl chloride.

HPLC-MS: m/z 556 (M+1).

Example 594

1-Cyclohex-3-enyl-1-cyclohexyl-3-thiazol-2-yl-urea

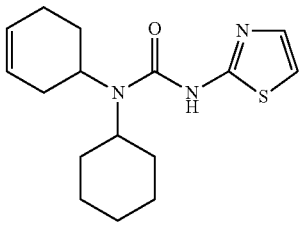

Cyclohex-3-enyl-cyclohexylamine was prepared by reductive amination of cyclohex-3-enylamine and cyclohexanone using general procedure (B). Reaction with carbonyl diimidazole and 2-aminothiazole using general procedure (A) gave the title compound.

HPLC-MS: m/z 306 (M+1).

Example 595

3-(5-Chloro-thiazol-2-yl)-1-cyclohex-3-enyl-1-cyclohexyl-urea

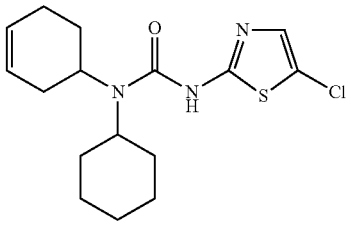

Cyclohex-3-enyl-cyclohexylamine was prepared by reductive amination of cyclohex-3-enylamine and cyclohexanone using general procedure (B). Reaction with CDI and 5-chloro-2-aminothiazole using general procedure (A) gave the title compound.

HPLC-MS: m/z 341 (M+1).

Example 596

1,1-Dicyclohexyl-3-(5-{2-[4-(4-methoxy-phenyl)-piperazin-1-yl]-2-oxo-ethylsulfanyl}-thiazol-2-yl)-urea

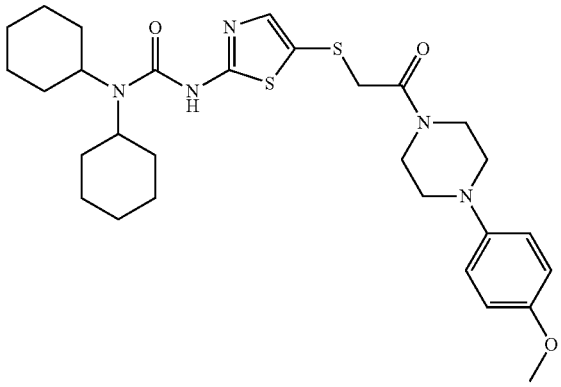

Prepared in a similar manner to Example 532 using 1-(4-methoxyphenyl)piperazine

HPLC-MS: m/z 583 (M+1).

Example 597

3-{5-[2-(4-Acetyl-piperazin-1-yl)-2-oxo-ethylsulfanyl]-thiazol-2-yl}-1,1-dicyclohexyl-urea

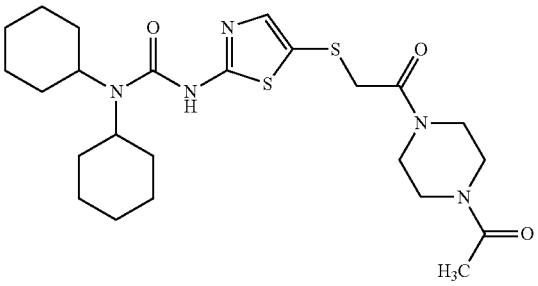

Prepared in a similar manner to Example 532 using 1-acetylpiperazine

HPLC-MS: m/z 508 (M+1).

Example 598

3-{5-[2-(4-Benzo[1,3]dioxol-5-yl-piperazin-1-yl)-2-oxo-ethylsulfanyl]-thiazol-2-yl}-1,1-dicyclohexyl-urea

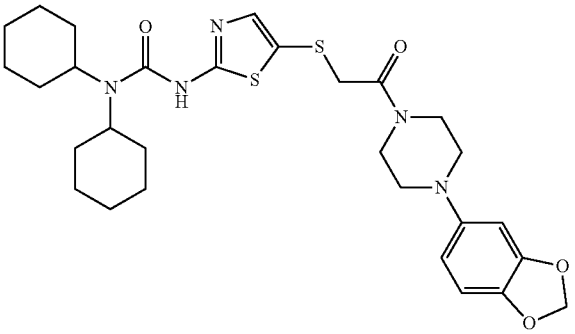

Prepared in a similar manner to Example 532 using 1-benzo[1,3]dioxol-5-yl-piperazine HPLC-MS: m/z 586 (M+1).

Example 599

1,1-Dicyclohexyl-3-(5-{2-[4-(1-methyl-piperidin-4-ylmethyl)-piperazin-1-yl]-2-oxo-ethylsulfanyl}-thiazol-2-yl)-urea

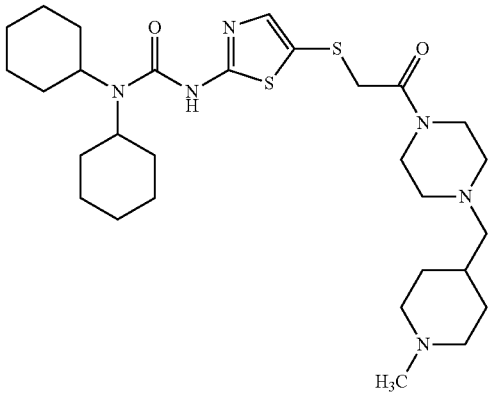

Prepared in a similar manner to Example 532 using 1-(N-methyl-4-piperidinmethyl)piperazine HPLC-MS: m/z 577 (M+1).

Example 600

1,1-Dicyclohexyl-3-(5-{2-[4-(1-methyl-piperidin-4-yl)-piperazin-1-yl]-2-oxo-ethylsulfanyl}-thiazol-2-yl)-urea

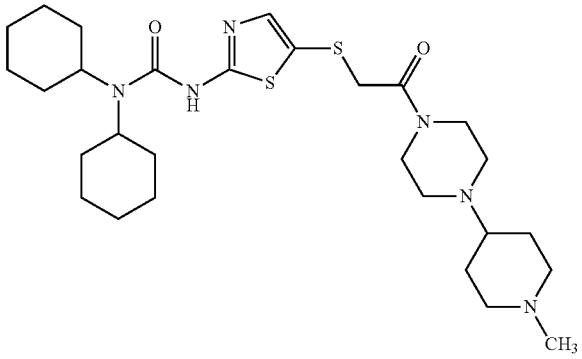

Prepared in a similar manner to Example 532 using 1-(1-methyl-4-piperidinyl)piperazine.

HPLC-MS: m/z 563 (M+1).

Example 601

3-(2-{3-(trans-4-Methyl-cyclohexyl)-3-[1-(morpholine-4-carbonyl)-piperidin-4-yl]-ureido}-thiazol-5-ylsulfanyl)-propionic acid

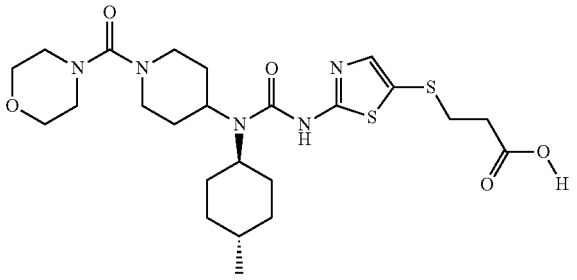

3-(2-{3-(4-Methyl-cyclohexyl)-3-[1-(morpholine-4-carbonyl)-piperidin-4-yl]-ureido}-thiazol-5-ylsulfanyl)-propionic acid ethyl ester was prepared in a similar manner to Example 554 using 3-{2-[3-(trans-4-methyl-cyclohexyl)-3-piperidin-4-yl-ureido]-thiazol-5-ylsulfanyl}-propionic acid ethyl ester and 4-morpholinecarbonyl chloride. Hydrolysis using general procedure (F) gave the title compound HPLC-MS: m/z 541 (M+1).

Example 602

3-{2-[3-(1-Dimethylsulfamoyl-piperidin-4-yl)-3-(trans-4-methyl-cyclohexyl)-ureido]-thiazol-5-ylsulfanyl}-propionic acid

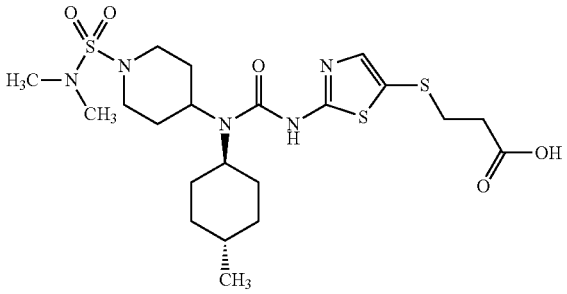

3-{2-[3-(1-Dimethylsulfamoyl-piperidin-4-yl)-3-(trans-4-methyl-cyclohexyl)-ureido]-thiazol-5-ylsulfanyl}-propionic acid ethyl ester was prepared in a similar manner to Example 554 using 3-{2-[3-(trans-4-methyl-cyclohexyl)-3-piperidin-4-yl-ureido]-thiazol-5-ylsulfanyl}-propionic acid ethyl ester and dimethylsulfamoyl chloride. Hydrolysis using general procedure (F) gave the title compound HPLC-MS: m/z 535 (M+1).

Example 603

3-{2-[3-(1-Dimethylcarbamoyl-piperidin-4-yl)-3-(trans-4-methyl-cyclohexyl)-ureido]-thiazol-5-ylsulfanyl}-propionic acid

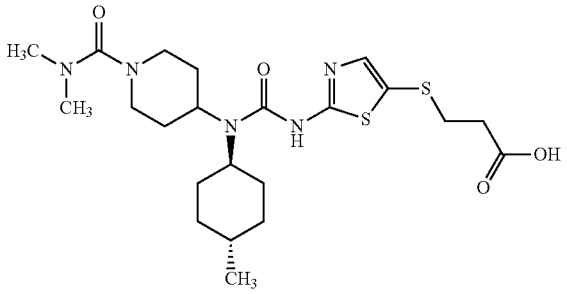

3-{2-[3-(1-Dimethylcarbamoyl-piperidin-4-yl)-3-(trans-4-methyl-cyclohexyl)-ureido]-thiazol-5-ylsulfanyl}-propionic acid ethyl ester was prepared in a similar manner to Example 554 using 3-{2-[3-(trans-4-methyl-cyclohexyl)-3-piperidin-4-yl-ureido]-thiazol-5-ylsulfanyl}-propionic acid ethyl ester and dimethylcarbamoyl chloride. Hydrolysis using general procedure (F) gave the title compound HPLC-MS: m/z 499 (M+1).

Example 604

3-(5-Bromo-thiazol-2-yl)-1-[1-(2-fluoro-phenyl)-piperidin-4-yl]-1-(4-trans-methyl-cyclohexyl)-urea

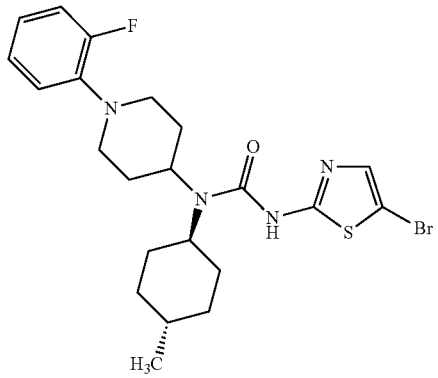

The title compound was prepared (227 mg, 46%) in a manner similar to general procedure (C) using 5-bromo-2-aminothiazole (180 mg, 1.0 mmol), [1-(2-fluoro-phenyl)-piperidin-4-yl]-(4-trans-methyl-cyclohexyl)-amine (300 mg, 1.0 mmol), catalytic DMAP and CDI (163 mg, 1.0 mmol) in dichloroethane.

$^1$H NMR ($CDCl_3$): δ 8.12 (br, 1H), 7. (s, 1H), 4 (s, 2H), 3. (m, 2H), 1. (m, 12H), 1. (m, 8H) ppm; HPLC-MS: m/z 497 (M+1).

Example 605

TTP-00214142

{2-[3-[1-(2-Fluoro-phenyl)-piperidin-4-yl]-3-(4-trans-methyl-cyclohexyl)-ureido]-thiazol-5-ylsulfanyl}-acetic acid methyl ester

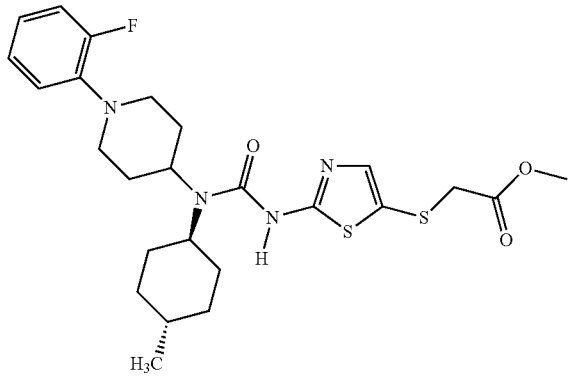

The title compound was prepared (49 mg, 27%) as described in general procedure (D) using 3-(5-bromo-thiazol-2-yl)-1-[1-(2-fluoro-phenyl)-piperidin-4-yl]-1-(4-trans-methyl-cyclohexyl)-urea (170 mg, 0.34 mmol), methyl thioglycolate (122 μL, 1.37 mmol) and powdered $K_2CO_3$ (332 mg, 2.40 mmol) as the base.

$^1$H NMR ($CDCl_3$): δ 8.28 (br, 1H), 7.41 (s, 1H), 6.92-7.09 (m, 4H), 3.85 (m, 1H), 3.72 (s, 3H), 3.52 (d, 2H), 3.40 (m, 3H), 2.75 (t, 2H), 2.25 (m, 2H), 1.98 (m, 2H), 1.77 (m, 4H), 1.42 (m, 2H), 1.08 (m, 2H), 0.91 (d, 3H) ppm; HPLC-MS: m/z 521 (M+1).

Example 606

{2-[3-[1-(2-Fluoro-phenyl)-piperidin-4-yl]-3-(4-trans-methyl-cyclohexyl)-ureido]-thiazol-5-ylsulfanyl}-acetic acid

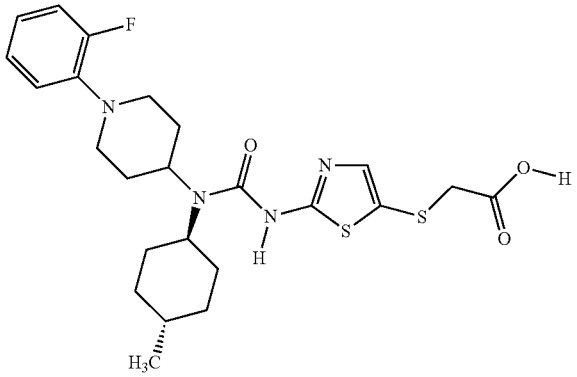

The title compound was prepared (17 mg, 58%) as described in general procedure (F) using {2-[3-[1-(2-fluorophenyl)-piperidin-4-yl]-3-(4-trans-methyl-cyclohexyl)-ureido]-thiazol-5-ylsulfanyl}-acetic acid methyl ester (30 mg, 0.057 mmol) and lithium hydroxide.

HPLC-MS: m/z 507 (M+1).

Example 607

3-{2-[3-[1-(2-Fluoro-phenyl)-piperidin-4-yl]-3-(4-trans-methyl-cyclohexyl)-ureido]-thiazol-5-ylsulfanyl}-propionic acid methyl ester

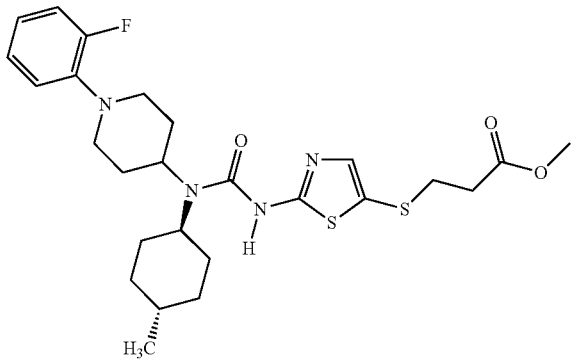

The title compound was prepared (42 mg, 36%) as described in general procedure (D) using 3-(5-bromo-thiazol-2-yl)-1-[1-(2-fluoro-phenyl)-piperidin-4-yl]-1-(4-trans-methyl-cyclohexyl)-urea (107 mg, 0.22 mmol), methyl thiopropionate (72 μL, 0.65 mmol) and powdered $K_2CO_3$ (180 mg, 1.29 mmol) as the base.

$^1$H NMR ($CDCl_3$): δ 8.33 (br, 1H), 7.35 (s, 1H), 6.91-7.11 (m, 4H), 3.88 (m, 1H), 3.69 (s, 3H), 3.53 (d, 2H), 3.41 (m,

1H), 2.93 (t, 2H), 2.77 (t, 2H), 2.62 (t, 2H), 2.26 (m, 2H), 2.00 (m, 2H), 1.60-1.88 (m, 5H), 1.45 (m, 2H), 1.10 (m, 2H), 0.92 (d, 3H) ppm; HPLC-MS: m/z 535 (M+1).

Example 608

3-{2-[3-[1-(2-Fluoro-phenyl)-piperidin-4-yl]-3-(4-trans-methyl-cyclohexyl)-ureido]-thiazol-5-ylsulfanyl}-propionic acid

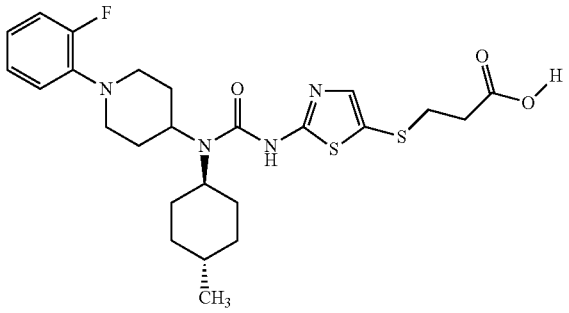

The title compound was prepared (8 mg, 60%) as described in general procedure (F) using 3-{2-[3-[1-(2-fluoro-phenyl)-piperidin-4-yl]-3-(4-trans-methyl-cyclohexyl)-ureido]-thiazol-5-ylsulfanyl}-propionic acid methyl ester (15 mg, 0.028 mmol) and lithium hydroxide.

HPLC-MS: m/z 521 (M+1).

Pharmacological Methods

Glucokinase Activity Assay (I)

Glucokinase activity is assayed spectrometrically coupled to glucose 6-phosphate dehydrogenase to determine compound activation of glucokinase. The final assay contains 50 mM Hepes, pH 7.1, 50 mM KCl, 5 mM $MgCl_2$, 2 mM dithiothreitol, 0.6 mM NADP, 1 mM ATP, 0.195 μM G-6-P dehydrogenase (from Roche, 127 671), 15 nM recombinant human glucokinase. The glucokinase is human liver glucokinase N-terminally truncated with an N-terminal His-tag ($(His)_8$-VEQILA . . . Q466) and is expressed in E. coil as a soluble protein with enzymatic activity comparable to liver extracted GK.

The purification of His-tagged human glucokinase (hGK) was performed as follows: The cell pellet from 50 ml E. coil culture was resuspended in 5 ml extraction buffer A (25 mM HEPES, pH 8.0, 1 mM $MgCl_2$, 150 mM NaCl, 2 mM mercaptoethanol) with addition of 0.25 mg/ml lysozyme and 50 μg/ml sodium azide. After 5 minutes at room temperature 5 ml of extraction buffer B (1.5 M NaCl, 100 mM $CaCl_2$, 100 mM $MgCl_2$, 0.02 mg/ml DNase 1, protease inhibitor tablet (Complete® 1697498): 1 tablet pr. 20 ml buffer) was added. The extract was then centrifugated at 15.000 g for 30 minutes. The resulting supernatant was loaded on a 1 ml Metal Chelate Affinity Chromatography (MCAC) Column charged with $Ni^{2+}$. The column is washed with 2 volumes buffer A containing 20 mM imidazole and the bound his-tagged hGK is subsequently eluted using a 20 minute gradient of 20 to 500 mM imidazole in buffer A. Fractions are examined using SDS-gel-electrophoresis, and fractions containing hGK (MW: 52 KDa) are pooled. Finally a gelfiltration step is used for final polishing and buffer exchange. hGK containing fractions are loaded onto a Superdex 75 (16/60) gelfiltration column and eluted with Buffer B (25 mM HEPES, pH 8.0, 1 mM $MgCl_2$, 150 mM NaCl, 1 mM Dithiothreitol). The purified hGK is examined by SDS-gel electrophoresis and MALDI mass spectrometry and finally 20% glycerol is added before freezing. The yield from 50 ml E. coli culture is generally approximately 2-3 mg hGK with a purity>90%.

The compound to be tested is added into the well in final 2.5% DMSO concentration in an amount sufficient to give a desired concentration of compound, for instance 1, 5, 10, 25 or 50 μM. The reaction starts after glucose is added to a final concentration of 2, 5, 10 or 15 mM. The assay uses a 96-well UV plate and the final assay volume used is 200 μl/well. The plate is incubated at 25° C. for 5 min and kinetics is measured at 340 nm in SpectraMax every 30 seconds for 5 minutes. Results for each compound are expressed as the fold activation of the glucokinase activity compared to the activation of the glucokinase enzyme in an assay without compound after having been subtracted from a "blank", which is without glucokinase enzyme and without compound. The compounds in each of the Examples exhibits activation of glucokinase in this assay. A compound, which at a concentration of at or below 30 μM gives 1.5-fold higher glucokinase activity than the result from the assay without compound, is deemed to be an activator of glucokinase.

The glucose sensitivity of the compounds are measured at a compound concentration of 10 μM and at glucose concentrations of 5 and 15 mM.

Glucokinase Activity Assay (II)

Determination of Glycogen Deposition in Isolated Rat Hepatocytes:

Hepatocytes are isolated from rats fed ad libitum by a two-step perfusion technique. Cell viability, assessed by trypan blue exclusion, is consistently greater than 80%. Cells are plated onto collagen-coated 96-well plates in basal medium (Medium 199 (5.5 mM glucose) supplemented with 0.1 μM Dexamethasone, 100 units/ml penicillin, 100 mg/ml streptomycin, 2 mM L-glutamine and 1 nM insulin) with 4% FCS at a cell density of 30,000 cells/well. The medium is replaced with basal medium 1 hour after initial plating in order to remove dead cells. Medium is changed after 24 hours to basal medium supplemented with 9.5 mM glucose and 10 nM insulin to induce glycogen synthesis, and experiments are performed the next day. The hepatocytes are washed twice with prewarmed (37° C.) buffer A (117.6 mM NaCl, 5.4 mM KCl, 0.82 mM $Mg_2SO_4$, 1.5 mM $KH_2PO_4$, 20 mM HEPES, 9 mM $NaHCO_3$, 0.1% w/v HSA, and 2.25 mM $CaCl_2$, pH 7.4 at 37° C.) and incubated in 100 μl buffer A containing 15 mM glucose and increasing concentrations of the test compound, such as for instance 1, 5, 10, 25, 50 or 100 μM, for 180 minutes. Glycogen content is measured using standard procedures (Agius, L. et al, Biochem J. 266, 91-102 (1990). A compound, which when used in this assay gives an significant increase in glycogen content compared to the result from the assay without compound, is deemed to have activity in this assay.

Glucokinase Activity Assay (III)

Stimulation of Insulin Secretion by Glucokinase Activators in INS-1E Cells

The glucose responsive β-cell line INS-1E is cultivated as described by Asfari M et al., Endocrinology. 130, 167-178 (1992). The cells are then seeded into 96 well cell culture plates and grown to a density of approximately $5\times10^4$ per well. Stimulation of glucose dependent insulin secretion is tested by incubation for 2 hours in Krebs Ringer Hepes buffer at glucose concentrations from 2.5 to 15 mM with or without addition of glucokinase activating compounds in concentrations of for instance 1, 5, 10, 25, 50 or 100 μM, and the supernatants collected for measurements of insulin concentrations by ELISA (n−4). A compound, which when used in this assay gives an significant increase in insulin secretion in response to glucose compared to the result from the assay without compound, is deemed to have activity in this assay.

While the invention has been described and illustrated with reference to certain preferred embodiments thereof, those skilled in the art will appreciate that various changes, modifications and substitutions can be made therein without departing from the spirit and scope of the present invention. For example, effective dosages other than the preferred dosages as set forth herein may be applicable as a consequence of variations in the responsiveness of the mammal being treated for glucokinase-deficiency mediated disease(s). Likewise, the specific pharmacological responses observed may vary according to and depending on the particular active compound selected or whether there are present pharmaceutical carriers, as well as the type of formulation and mode of administration employed, and such expected variations or differences in the results are contemplated in accordance with the objects and practices of the present invention.

The invention claimed is:

[1. A compound of formula (I)

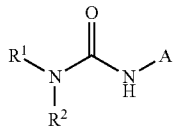

wherein $R^1$ is

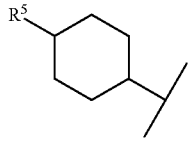

$R^2$ is

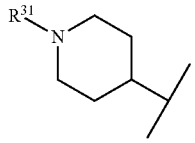

and $R^5$ and $R^{31}$ are independently selected from the group consisting of halogen, nitro, cyano, hydroxy, oxo, carboxy, —$CF_3$; or —$NR^{10}R^{11}$; or $C_{1-6}$-alkyl, $C_{2-6}$-alkenyl, $C_{2-6}$-alkynyl, $C_{3-8}$-cycloalkyl, $C_{3-8}$-cycloalkyl-$C_{1-6}$-alkyl, aryl, aryl-$C_{1-6}$-alkyl, heteroaryl-$C_{1-6}$-alkyl, $C_{1-6}$-alkoxy, $C_{3-6}$ cycloalkyl-$C_{1-6}$-alkoxy, aryl-$C_{1-6}$-alkoxy, heteroaryl, heteroaryl-$C_{1-6}$-alkoxy, aryloxy, heteroaryloxy, $C_{1-6}$-alkylthio, arylthio, heteroarylthio, $C_{3-8}$-cycloalkylthio, aryl-$C_{1-6}$-alkylthio, heteroaryl-$C_{1-6}$-alkylthio, $C_{1-6}$-alkylsulfenyl, $C_{3-6}$-cycloalkyl-$C_{1-6}$-alkylthio, $C_{1-6}$-alkyl-C(O)—O—$C_{1-6}$-alkyl, $C_{1-6}$-alkoxy-$C_{1-6}$-alkyl, $C_{1-6}$-alkylthio-$C_{1-6}$-alkyl, carboxy-$C_{1-6}$-alkyloxy, amino-$C_{1-6}$-alkyl, $C_{1-6}$-alkylamino-$C_{1-6}$-alkyl, di-($C_{1-6}$-alkyl)amino-$C_{1-6}$-alkyl, $C_{1-6}$-alkylsulfamoyl, di($C_{1-6}$-alkyl)sulfamoyl, $C_{1-6}$-alkylsulfinamoyl or di($C_{1-6}$-alkyl)sulfinamoyl each of which is optionally substituted with one or more substituents independently selected from $R^{12}$; or —C(O)—$R^{27}$, —$S(O)_2$—$R^{27}$, —C(O)—$NR^{13}R^{14}$, —$S(O)_2$—$NR^{13}R^{14}$, —$C_{1-6}$-alkyl-C(O)—$NR^{13}R^{14}$;

$R^{10}$ and $R^{11}$ independently represent hydrogen, $C_{1-6}$-alkyl, —C(O)—$C_{1-6}$-alkyl, —C(O)—O—$C_{1-6}$-alkyl, carboxy-$C_{1-6}$-alkyl, —C(O)—$C_{1-6}$-alkyl-C(O)OH, —$S(O)_2$—$C_{1-6}$-alkyl, or aryl;

$R^{27}$ is $C_{1-6}$-alkyl, $C_{1-6}$-alkoxy, $C_{2-6}$-alkenyl, $C_{2-6}$-alkynyl, $C_{3-8}$-cycloalkyl, $C_{3-8}$cycloalkyl-$C_{1-6}$-alkyl, $C_{3-8}$cycloalkyl-$C_{2-6}$-alkenyl, aryl, aryl-$C_{1-6}$-alkyl, aryloxy-$C_{1-6}$-alkyl, aryl-$C_{2-6}$-alkenyl, heteroaryl, $C_{3-8}$-heterocyclyl, heteroaryl-$C_{1-6}$-alkyl, $C_{3-8}$-heterocyclyl-$C_{1-6}$-alkyl, heteroaryloxy-$C_{1-6}$-alkyl, carboxy-$C_{1-6}$-alkyl, carboxy-$C_{2-6}$-alkenyl, $C_{1-6}$-alkoxy-$C_{1-6}$-alkyl, $C_{1-6}$-alkoxy-$C_{2-6}$-alkenyl, $C_{1-6}$-alkylthio-$C_{1-6}$-alkyl, $R^{10}$HN—$C_{1-6}$-alkyl, $R^{10}R^{11}$—N—$C_{1-6}$-alkyl, $R^{10}R^{11}$—N—$C_{2-6}$-alkenyl, $R^{10}R^{11}$—N—$S(O)_2$—$C_{1-6}$-alkyl, $R^{10}R^{11}$—N—C(O)—$C_{1-6}$-alkyl, $C_{1-6}$-alkyl-C(O)—NH—$C_{1-6}$-alkyl, aryl-C(O)—NH—$C_{1-6}$-alkyl, heteroaryl-C(O)—NH—$C_{1-6}$-alkyl, $C_{3-8}$-cycloalkyl-C(O)—NH—$C_{1-6}$-alkyl, $C_{1-6}$-alkyl-$S(O)_2$—NH—$C_{1-6}$-alkyl, aryl-$S(O)_2$—NH—$C_{1-6}$-alkyl, heteroaryl-$S(O)_2$—NH—$C_{1-6}$-alkyl, or $C_{3-8}$-cycloalkyl-$S(O)_2$—NH $C_{1-6}$-alkyl, each of which is optionally substituted with one or more substituents independently selected from $R^{12}$;

$R^{12}$ is halogen, cyano, hydroxy, —C(O)—O—$C_{1-6}$-alkyl, carboxy, —$CF_3$, $C_{1-6}$-alkyl, $C_{1-6}$-alkoxy, —$NR^{10}R^{11}$, —$S(O)_2CH_3$, or —$S(O)_2NH_2$;

$R^{13}$ and $R^{14}$ are independently selected from the group consisting of hydrogen, $C_{1-6}$-alkyl, hydroxy-$C_{1-6}$-alkyl, carboxy-$C_{1-6}$-alkyl, aryl, or heteroaryl, each of which is optionally substituted with one or more substituents independently selected from $R^{15}$; or $R^{13}$ and $R^{14}$ together with the nitrogen to which they are attached form a 3 to 8 membered heterocyclic ring with the said nitrogen atom, the heterocyclic ring optionally containing one or two further heteroatoms selected from nitrogen, oxygen and sulphur;

$R^{15}$ is halogen, cyano, hydroxy, carboxy, —$CF_3$, $C_{1-6}$-alkyl, —$S(O)_2CH_3$, or —$S(O)_2NH_2$;

A is

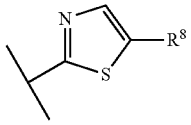

$R^8$ is selected from halogen, carboxy, cyano, nitro, hydroxy, —$CF_3$, —SCN; or $C_{1-6}$-alkyl, $C_{2-6}$-alkenyl, $C_{2-6}$-alkynyl, $C_{1-6}$-alkoxy, $C_{1-6}$-alkylthio, $C_{2-6}$-alkenylthio, $C_{1-6}$-alkylamino, $C_{1-6}$-alkylsulfenyl, C(O) O $C_{1-6}$-alkyl, formyl, —C(O)—$C_{1-6}$-alkyl, —$C_{1-6}$-alkyl-C(O)—O—$C_{1-6}$-alkyl, —$C_{1-6}$-alkyl-O—C(O)—$C_{1-6}$-alkyl, —NH—C(O)—$C_{1-6}$-alkyl, —$C_{1-6}$-alkoxy-$C_{1-6}$-alkyl, $C_{1-6}$alkyl-S $C_{1-6}$-alkyl, carboxy-$C_{1-6}$-alkyl, or hydroxy-$C_{1-6}$-alkyl, each of which is optionally substituted with one or more substituents independently selected from $R^{16}$; or aryl, heteroaryl, aryl-$C_{1-6}$-alkyl, heteroaryl-$C_{1-6}$-alkyl, aryl-$C_{1-6}$-alkoxy, heteroaryl-$C_{1-6}$-alkoxy, aryl-$C_{1-6}$-alkylthio, heteroaryl-$C_{1-6}$-alkylthio, heteroaryl-thio- $C_{1-6}$-alkyl, heteroaryl-oxy-$C_{1-6}$-alkyl, aryloxy, heteroaryloxy, arylthio, heteroarylthio, aryl-$C_{1-6}$-alkylamino, —C(O)-aryl, or —C(O)-heteroaryl, each of which is optionally substituted on the aryl or heteroaryl part with one or more substituents independently selected from $R^{17}$; or $C_{3-8}$-cycloalkyl, $C_{3-8}$-cycloalkenyl, $C_{3-8}$-cycloalkylthio, $C_{3-8}$-cycloalkyl-$C_{1-6}$-alkyl, $C_{3-8}$-cycloalkenyl-$C_{1-6}$-alkyl, $C_{3-6}$-cycloalkyl-$C_{1-6}$-alkoxy, $C_{3-6}$-cycloalkyl-$C_{1-6}$-alkylthio, each of which is optionally substituted on the cycloalkyl part with one or more substituents independently selected from $R^{18}$; or $C_{3-8}$-heterocyclyl, $C_{3-8}$-heterocyclyl-$C_{1-6}$-alkyl, $C_{3-8}$-heterocyclyl-$C_{1-6}$-alkylthio, $C_{3-8}$-heterocyclylthio, $C_{3-8}$-heterocyclyl-amino-$C_{1-6}$-alkyl, or C(O) $C_{3-8}$-heterocyclyl, each of which is optionally substituted with one or more substituents independently selected from $R^{16}$; or —$NR^{19}R^{20}$, —$C_{1-6}$-alkyl-$NR^{19}R^{20}$, —$C_{2-6}$-alkenyl-$NR^{19}R^{20}$, —$C_{1-6}$-alkyl-S—$R^{21}$, —$C_{1-6}$-alkyl-S (O) $R^{21}$, $C_{1-6}$-alkyl-$S(O)_2$ $R^{21}$, $S(O)_2$ $R^{21}$ or —$S(O)_2$—$NR^{19}R^{20}$, wherein each alkyl part may be substituted with one or more substituents independently selected from $R^{25}$; or —$C(O)NR^{22}R^{23}$, —$C_{1-6}$-alkyl-$C(O)NR^{22}R^{23}$—$C_{1-6}$-alkyl-NH—$NR^{22}R^{23}$ —$C_{1-6}$-alkyl-NH—C(O)—$C_{1-6}$-alkyl-$NR^{22}R^{23}$, each optionally substituted with one or more substituents independently selected from $R^{26}$; or $R^{16}$, $R^{17}$, and $R^{18}$ are independently $C_{1-6}$-alkyl, halogen, nitro, cyano, hydroxy, carboxy, oxo, —$CF_3$, carboxy-$C_{1-6}$-alkyl, hydroxy-$C_{1-6}$-alkyl, $C_{1-6}$-alkyl-C(O)O—$C_{1-6}$-alkyl, —$C_{1-6}$-alkyl-C(O)—$NR^{19}R^{20}$, —C(O)—O—$C_{1-6}$-alkyl, —C(O)—$C_{1-6}$-alkyl-C(O)—$C_{1-6}$-alkyl, —$NR^{19}NR^{20}$, —$NHS(O)_2C_{1-6}$-alkyl, —C(O) $NR^{19}R^{20}$, $S(O)_2C_{1-6}$-alkyl, or $S(O)_2NR^{19}R^{20}$;

$R^{19}$ and $R^{20}$ independently represent hydrogen, $C_{1-6}$-alkyl, hydroxy-$C_{1-6}$-alkyl, carboxy-$C_{1-6}$-alkyl, aryl, heteroaryl $C_{3-8}$-heterocyclyl, aryl-$C_{1-6}$-alkyl, $C_{3-8}$-heterocyclyl-$C_{1-6}$-alkyl, —C(O)—O—$C_{1-6}$-alkyl, —$C_{1-6}$-alkyl-C(O)—O—$C_{1-6}$-alkyl, —$C_{1-6}$-alkyl-$NR^{22}R^{23}$, or —$S(O)_2$—$C_{1-6}$-alkyl, each of which is optionally substituted with one or more substituents independently selected from $R^{24}$, or $R^{19}$ and $R^{20}$ together with the nitrogen to which they are attached form a 3 to 8 membered heterocyclic ring with the said nitrogen atom, the heterocyclic ring optionally containing one or two further heteroatoms selected from nitrogen, oxygen and sulphur, the heterocyclic ring is optionally substituted with one or more substituents independently selected from $R^{24}$;

$R^{21}$ is selected from $C_{1-56}$-alkyl $C_{2-6}$-alkenyl, carboxy-$C_{1-6}$-alkyl, $C_{1-6}$-alkylamino-$C_{1-6}$-alkyl or hydroxy-$C_{1-6}$-alkyl, —$C_{1-6}$-alkyl-$NR^{22}R^{23}$; or aryl, heteroaryl, aryl-$C_{1-6}$-alkyl, or heteroaryl-$C_{1-6}$-alkyl, wherein the aryl or heteroaryl part is optionally substituted with one or more substituents independently selected from $R^{24}$; or $C_{3-8}$-cycloalkyl, $C_{3-8}$-cycloalkenyl, $C_{3-8}$-cycloalkyl-$C_{1-6}$-alkyl, $C_{3-8}$-cycloalkenyl-$C_{1-6}$-alkyl;

$R^{22}$ and $R^{23}$ are independently selected from hydrogen, $C_{1-6}$-alkyl, carboxy-$C_{1-6}$-alkyl, $C_{1-6}$-alkyl-C(O)O—$C_{1-6}$-alkyl, —C(O)—O—$C_{1-6}$-alkyl, —$C_{1-6}$-alkyl-$S(O)_2$—$C_{1-6}$-alkyl, $C_{3-8}$-cycloalkyl, aryl, or heteroaryl; or $R^{22}$ and $R^{23}$ together with the nitrogen to which they are attached form a 3 to 8 membered heterocyclic ring with the said nitrogen atom, the heterocyclic ring optionally containing one or two further heteroatoms selected from nitrogen, oxygen and sulphur, the heterocyclic ring is optionally substituted with one or more substituents independently selected from $R^{24}$;

$R^{24}$ is halogen, nitro, cyano, hydroxy, carboxy, oxo, —$CF_3$, $C_{1-6}$-alkyl, hydroxy-$C_{1-6}$-alkyl, carboxy-$C_{1-6}$-alkyl, —C(O)—$C_{1-6}$-alkyl, —C(O)—$C_{3-8}$-cycloalkyl, —C(O)-aryl, —C(O)-heteroaryl, —C(O)—$C_{3-8}$-heterocyclyl-C(O)—O—$C_{1-6}$-alkyl, —$C_{1-6}$-alkyl-C(O)—O—$C_{1-6}$-alkyl, aryl, heteroaryl, aryl-$C_{1-6}$-alkyl, heteroaryl-$C_{1-6}$-alkyl, $C_{3-8}$-cycloalkyl, $C_{3-8}$-heterocyclyl, $C_{3-8}$-cycloalkyl-$C_{1-6}$-alkyl, $C_{3-8}$-heterocyclyl-$C_{1-6}$-alkyl, —$C_{1-6}$-alkyl-C(O)—$C_{3-8}$-heterocyclyl, —C(O)—O—$C_{1-6}$-alkyl-aryl, —NH—$S(O)_2R^{28}$, or —$S(O)_2R^{28}$, wherein each cyclic moiety is optionally substituted with one or more substituents independently selected from $R^{29}$;

$R^{25}$ and $R^{26}$ are independently $C_{1-6}$-alkyl, halogen, nitro, cyano, hydroxy, —C(O)—O—$C_{1-6}$-alkyl, carboxy, $C_{1-6}$-alkyl-C(O) O $C_{1-6}$-alkyl, carboxy-$C_{1-6}$-alkyl, —$CF_3$, —$S(O)_2CH_3$, or —$S(O)_2NH_2$;

$R^{28}$ is $C_{1-6}$-alkyl, carboxy-$C_{1-6}$-alkyl, —$C_{1-6}$-alkyl-C(O)—O—$C_{1-6}$-alkyl, $C_{3-8}$-cycloalkyl, aryl, aryl-$C_{1-6}$-alkyl, heteroaryl optionally substituted with $C_{1-6}$-alkyl, $NH_2$, or $N(CH_3)_2$;

$R^{29}$ is halogen, nitro, cyano, hydroxy, carboxy, oxo, —$CF_3$, $C_{1-6}$-alkyl, or $C_{1-6}$-alkoxy;

as well as any salt hereof with a pharmaceutically acceptable acid or base, or any optical isomer or mixture of optical isomers, racemic mixture, or tautomeric form thereof.]

[2. A compound according to claim 1, wherein $R^5$ and $R^{31}$ are independently selected from the group consisting of halogen, oxo, cyano, hydroxy, carboxy, —$CF_3$; or —$NR^{10}R^{11}$; or $C_{1-6}$-alkyl, $C_{2-6}$-alkenyl, $C_{3-8}$-cycloalkyl, $C_{3-8}$-cycloalkyl-$C_{1-6}$-alkyl, aryl, aryl-$C_{1-6}$-alkyl, $C_{1-6}$-alkoxy, $C_{3-6}$-cycloalkyl-$C_{1-6}$-alkoxy, aryl-$C_{1-6}$-alkoxy, $C_{1-6}$-alkylthio, arylthio, —C(O)—O—$C_{1-6}$-alkyl, or $C_{1-6}$-alkyl-C(O)—O—$C_{1-6}$-alkyl, each of which is optionally substituted with one or more substituents independently selected from $R^{12}$; or —C(O)—$R^{27}$, —$S(O)_2$—$R^{27}$, —C(O)—$NR^{13}R^{14}$, —$S(O)_2$—$NR^{13}R^{14}$, —$C_{1-6}$-alkyl-C(O)—$NR^{13}R^{14}$; or two substituents selected from $R^3$, $R^4$, $R^5$ and $R^6$ or $R^{30}$, $R^{31}$, $R^{32}$ and $R^{33}$ attached to the same or adjacent atoms together form a radical —O—$(CH_2)_{1-3}$—O—.]

[3. A compound according to claim 2, wherein $R^5$ and $R^{31}$ are independently selected from the group consisting of halogen, oxo, —$CF_3$; or $NR^{10}R^{11}$; or $C_{1-6}$-alkyl, $C_{3-8}$-cycloalkyl, $C_{1-6}$-alkoxy, $C_{1-6}$-alkylthio, aryl, aryl-$C_{1-6}$-alkyl, arylthio, —C(O)—O—$C_{1-6}$-alkyl, or $C_{1-6}$-alkyl-C(O)—O—$C_{1-6}$-alkyl, each of which is optionally substituted with one or more substituents independently selected from $R^{12}$; or —C(O)—$R^{27}$, —$S(O)_2$—$NR^{13}R^{14}$ or —$S(O)_2$—$R^{27}$; or two substituents selected from $R^3$, $R^4$, $R^5$ and $R^6$ or $R^{30}$, $R^{31}$, $R^{32}$ and $R^{33}$ attached to the same or adjacent atoms together form a radical O $(CH_2)_{1-3}$ O.]

[4. A compound according to claim 3, wherein $R^5$ and $R^{31}$ are independently selected from the group consisting of halogen, —$CF_3$; or methyl, ethyl, propyl, isopropyl, butyl, tert-butyl, cyclopropyl, cyclobutyl, cyclopentyl, cyclohexyl, phenyl, naphtyl, benzyl, phenyl-ethyl, methoxy, ethoxy. propoxy, phenylthio, —C(O)—O—$CH_3$, or —C(O)—O—$CH_2CH_3$, each of which is optionally substituted with one or more substituents independently selected from $R^{12}$; or —C(O)—$R^{27}$, —$S(O)_2$—$NR^{13}R^{14}$ or —$S(O)_2$—$R^{27}$; or two substituents selected from $R^3$, $R^4$, $R^5$ and $R^6$ or $R^{30}$, $R^{31}$, $R^{32}$ and $R^{33}$ attached to the same or adjacent atoms together form a radical —O—$(CH_2)_{1-3}$—O—.]

[5. A compound according to claim 4, wherein $R^5$ and $R^{31}$ are independently selected from the group consisting of halogen, —$CF_3$; or methyl, ethyl, propyl, isopropyl, butyl, tert-butyl, cyclopropyl, cyclobutyl, cyclopentyl, cyclohexyl, phenyl, naphtyl, benzyl, phenyl-ethyl, methoxy, ethoxy, propoxy, phenylthio, —C(O)—O—$CH_3$, or —C(O)—O—$CH_2CH_3$, each of which is optionally substituted with one or more substituents independently selected from $R^{12}$; or —C(O)—$R^{27}$, -—$S(O)_2$—$NR^{13}R^{14}$ or —$S(O)_2$—$R^{27}$.]

[6. A compound according to claim 5, wherein $R^5$ and $R^{31}$ are independently selected from the group consisting of F, Cl, —$CF_3$, methyl, ethyl, propyl, isopropyl, butyl, tert-butyl, methoxy, ethoxy, propoxy, —C(O)—$R^{27}$, —$S(O)_2$—$NR^{13}R^{14}$ or —$S(O)_2$—$R^{27}$.]

[7. A compound according to claim 3, wherein $R^5$ and $R^{31}$ are independently selected from $C_{1-6}$-alkyl, $C_{1-6}$-alkoxy, —$S(O)_2$—$R^{27}$ or —C(O)—$R^{27}$.]

[8. A compound according to claim 1, wherein $R^{10}$ and $R^{11}$ independently represent hydrogen, methyl, ethyl, propyl, —C(O)—$CH_3$, —C(O)—$CH_2CH_3$, —$CH_2$—C(O)OH, —$CH_2CH_2$C(O)OH, —C(O)—$CH_2$C(O)OH, —C(O)—$CH_2CH_2$—C(O)OH, $S(O)_2CH_3$, or phenyl.]

[9. A compound according to claim 8, wherein $R^{10}$ and $R^{11}$ independently represent hydrogen, methyl, ethyl, —C(O)—$CH_3$, —$CH_2$C(O)OH, —C(O)—$CH_2$—C(O)OH, —$S(O)_2CH_3$, or phenyl.]

[10. A compound according to claim 9, wherein $R^{10}$ and $R^{11}$ independently represent hydrogen, methyl, ethyl, or phenyl.]

[11. A compound according to claim 1, wherein $R^{27}$ is $C_{1-6}$-alkyl, $C_{1-6}$-alkoxy, $C_{2-6}$-alkenyl, $C_{2-6}$-alkynyl, $C_{3-8}$-cycloalkyl, $C_{3-8}$-cycloalkyl-$C_{1-6}$-alkyl, aryl, aryl-$C_{1-6}$-alkyl, aryl-$C_{2-6}$-alkenyl, heteroaryl, heteroaryl-$C_{1-6}$-alkyl, carboxy-$C_{1-6}$-alkyl, $C_{1-6}$-alkoxy-$C_{1-6}$-alkyl, $C_{1-6}$-alkthio-$C_{1-6}$-alkyl, $R^{10}$HN—$C_{1-6}$-alkyl, $R^{10}R^{11}$N—$C_{1-6}$-alkyl, $R^{10}R^{11}$N—$S(O)_2$—$C_{1-6}$-alkyl, or $R^{10}R^{11}$N—C(O)—$C_{1-6}$-alkyl, each of which is optionally substituted with one or more substituents independently selected from $R^{12}$.]

[12. A compound according to claim 11, wherein $R^{27}$ is $C_{1-6}$-alkyl, $C_{1-6}$-alkoxy, $C_{3-8}$-cycloalkyl, $C_{3-8}$cycloalkyl-$C_{1-6}$-alkyl, aryl-$C_{2-6}$-alkenyl, aryl, heteroaryl, heteroaryl-$C_{1-6}$-alkyl, carboxy-$C_{1-6}$-alkyl, carboxy-$C_{1-6}$-alkyl, $C_{1-6}$-alkoxy-$C_{1-6}$-alkyl, $R^{10}$HN—$C_{1-6}$-alkyl, $R^{10}R^{11}$N—$C_{1-6}$-alkyl, $R^{10}R^{11}N(O)_2$—$C_{1-6}$-alkyl, or $R^{10}R^{11}$N(O)—$C_{1-6}$-alkyl, each of which is optionally substituted with one or more substituents independently selected from $R^{12}$.]

[13. A compound according to claim 12, wherein $R^{27}$ is $C_{1-6}$-alkyl, $C_{1-6}$-alkoxy, $C_{3-8}$-cycloalkyl, $C_{3-8}$-cycloalkyl-$C_{1-6}$alkyl, aryl, heteroaryl-$C_{1-6}$-alkyl, aryl-$C_{1-6}$-alkyl, $C_{1-6}$-alkoxy-$C_{1-6}$-alkyl, carboxy-$C_{1-6}$-alkyl, or heteroaryl, each of which is optionally substituted with one or more substituents independently selected from $R^{12}$.]

[14. A compound according to claim 13, wherein $R^{27}$ is methyl, ethyl, propyl, n-butyl, isobutyl, 1,1,1-trifluoroethyl, cyclopropyl, cyclopentyl, cyclopropylmethyl, phenyl, pyridyl, thiophene, imidazole, or thiazole, each of which is optionally substituted with one or more substituents independently selected from $R^{12}$.]

[15. A compound according to claim 14, wherein $R^{27}$ is methyl, ethyl, propyl, n-butyl, isobutyl, 1,1,1-trifluoroethyl, cyclopropyl, cyclopentyl, cyclopropylmethyl, phenyl, or pyridyl, thiophene, imidazole, or thiazole.]

[16. A compound according to claim 1, wherein $R^{12}$ is halogen, cyano, hydroxy, carboxy, —$CF_3$, or $C_{1-6}$-alkyl.]

[17. A compound according to claim 16, wherein $R^{12}$ is halogen, cyano, hydroxy, carboxy, —$CF_3$, methoxy, methyl, ethyl or propyl.]

[18. A compound according to claim 17, wherein $R^{12}$ is halogen, carboxy, methyl, ethyl or propyl.]

[19. A compound according to claim 1, wherein $R^{13}$ and $R^{14}$ are independently selected from the group consisting of hydrogen, $C_{1-6}$-alkyl, hydroxy-$C_{1-6}$-alkyl, carboxy-$C_{1-6}$-alkyl, phenyl, or naphtyl, each of which is optionally substituted with one or more substituents independently selected from $R^{15}$; or $R^{13\ 3}$ and $R^{14}$ together with the nitrogen to which they are attached form a 3- to 8-membered heterocyclic ring with the said nitrogen atom, the heterocyclic ring optionally containing one or two further heteroatoms selected from nitrogen, oxygen and sulphur.]

[20. A compound according to claim 19, wherein $R^{13}$ and $R^{14}$ are independently selected from the group consisting of hydrogen, methyl, ethyl, propyl, hydroxy-methyl, hydroxy-ethyl, carboxy-methyl, carboxy-ethyl, phenyl, or naphtyl, each of which is optionally substituted with one or more substituents independently selected from $R^{15}$; or $R^{13}$ and $R^{14}$ together with the nitrogen to which they are attached form a 3- to 8-membered heterocyclic ring with the said nitrogen atom, the heterocyclic ring optionally containing one or two further heteroatoms selected from nitrogen, oxygen and sulphur.]

[21. A compound according to claim 20, wherein $R^{13}$ and $R^{14}$ are independently selected from the group consisting of hydrogen, methyl, ethyl, propyl, or phenyl, each of which is optionally substituted with one or more substituents independently selected from $R^{15}$.]

[22. A compound according to claim 1, wherein $R^{15}$ is halogen, cyano, hydroxy, carboxy, —$CF_3$, methyl, ethyl, or propyl.]

[23. A compound according to claim 22, wherein $R^{15}$ is halogen, hydroxy, carboxy, —$CF_3$, methyl, or ethyl.]

[24. A compound according to claim 1, wherein $R^8$ is selected from halogen, carboxy, cyano, nitro, hydroxy, —$CF_3$, —SCN; or $C_{1-6}$-alkyl, $C_{2-6}$-alkenyl, $C_{1-6}$-alkoxy, $C_{1-6}$-alkylthio, $C_{1-6}$-alkylamino, $C_{1-6}$-alkylsulfenyl, —C(O)—O—$C_{1-6}$-alkyl, NH C(O) $C_{1-6}$-alkyl, $C_{1-6}$-alkoxy-$C_{1-6}$-alkyl, —$C_{1-6}$-alkyl-S—$C_{1-6}$-alkyl, $C_{3-8}$-cycloalkyl-$C_{1-6}$-alkyl, $C_{3-6}$-cycloalkyl-$C_{1-6}$-alkoxy, $C_{3-6}$-cycloalkyl-$C_{1-6}$-alkylthio each of which is optionally substituted with one or more substituents independently selected from $R^{16}$; or aryl, heteroaryl, aryl-$C_{1-6}$-alkyl, heteroaryl-$C_{1-6}$-alkyl, aryl-$C_{1-6}$-alkoxy, heteroaryl-$C_{1-6}$-alkoxy, heteroaryl-thio-$C_{1-6}$-alkyl, aryloxy, heteroaryloxy, heteroarylthio, each of which is optionally substituted on the aryl or heteroaryl part with one or more substituents independently selected from $R^{17}$; or $C_{3-8}$-cycloalkyl, $C_{3-8}$-cycloalkenyl, $C_{3-8}$-cycloalkenyl-$C_{1-6}$-alkyl, each of which is optionally substituted on the cycloalkyl part with one or more substituents independently selected from $R^{18}$; or $C_{3-8}$-heterocyclyl, $C_{3-8}$-heterocyclyl-$C_{1-6}$-alkyl, $C_{3-8}$-heterocyclylthio, or —C(O)—$C_{3-8}$-heterocyclyl, each of which is optionally substituted with one or more substituents independently selected from $R^{16}$; or $NR^{19}R^{20}$, $C_{1-6}$-alkyl-$NR^{19}R^{20}$, $C_{1-6}$-alkyl-S $R^{21}$, —$C_{1-6}$-alkyl-S(O)—$R^{21}$, —$C_{1-6}$-alkyl-$S(O)_2$—$R^{21}$, $S(O)_2$ $R^{21}$ or $S(O)_2$ $NR^{19}R^{20}$, wherein each alkyl part may be substituted with one or more substituents independently selected from $R^{25}$; or —C(O)$NR^{22}R^{23}$, —$C_{1-6}$-alkyl-C(O)$NR^{22}R^{23}$ optionally substituted with one or more substituents independently selected from $R^{26}$.]

[25. A compound according to claim 24, wherein $R^8$ is selected from halogen, carboxy, cyano, or —$CF_3$; or $C_{1-6}$-alkyl, $C_{2-6}$-alkenyl, $C_{1-6}$-alkoxy, $C_{1-6}$-alkylthio, —C(O)—$C_{1-6}$-alkyl, —$C_{1-6}$-alkyl-C(O)—O—$C_{1-6}$-alkyl, —$C_{1-6}$-alkoxy-$C_{1-6}$-alkyl, $C_{3-8}$-cycloalkyl-$C_{1-6}$-alkyl, each of which is optionally substituted with one or more substituents independently selected from $R^{16}$; or aryl, heteroaryl, aryl-$C_{1-6}$-alkyl, heteroaryl-$C_{1-6}$-alkyl, each of which is optionally substituted on the aryl or heteroaryl part with one or more substituents independently selected from $R^{17}$; or $C_{3-8}$-cycloalkyl, $C_{3-8}$cycloalkyl-$C_{1-6}$-alkyl, each of which is optionally substituted on the cycloalkyl part with one or more substituents independently selected from $R^{18}$; or $C_{3-8}$-heterocyclyl, $C_{3-8}$-heterocyclyl-$C_{1-6}$-alkyl, or —C(O)—$C_{3-8}$-heterocyclyl, each of which is optionally substituted with one or more substituents independently selected from $R^{16}$; or $NR^{19}R^{20}$, —$C_{1-6}$-alkyl-$NR^{19}R^{20}$, —$S(O)_2$—$R^{21}$ or —$S(O)_2$—$NR^{19}R^{20}$, wherein each alkyl part may be substituted with one or more substituents independently selected from $R^{25}$; or —C(O)$NR^{22}R^{23}$, —$C_{1-6}$-alkyl-C(O)$NR^{22}R^{23}$ optionally substituted with one or more substituents independently selected from $R^{26}$.]

[26. A compound according to claim 25, wherein $R^8$ is selected from halogen, carboxy or —$CF_3$; or $C_{1-6}$-alkyl, $C_{1-6}$-alkoxy, $C_{1-6}$-alkylthio, —$C_{1-6}$-alkyl-C(O)—O—$C_{1-6}$-alkyl, —$C_{1-6}$-alkyl-O—C(O)—$C_{1-6}$-alkyl or —C(O)—O—$C_{1-6}$-alkyl, each of which is optionally substituted with one or more substituents independently selected from $R^{16}$; or phenyl, benzyl, or heteroarylthio, wherein heteroaryl is pyridyl or imidazolyl, and wherein each aryl or heteroaryl is optionally substituted on the aryl or heteroaryl part with one or more substituents independently selected from $R^{17}$; or cyclopropyl, cyclobutyl, cyclopentyl, or cyclohexyl, each of which is optionally substituted on the cycloalkyl part with one or more substituents independently selected from $R^{18}$; or pyrrolidinyl, piperidyl, piperazinyl, or morpholinyl, each of which is optionally substituted with one or more substituents independently selected from $R^{16}$; or —C(O)$NR^{22}R^{23}$, —$S(O)_2$—$R^{21}$ or —$S(O)_2$—$NR^{19}R^{20}$.]

[27. A compound according to claim 26, wherein $R^8$ is selected from halogen, carboxy, —$CF_3$, —S—$CH_3$, —S—$CH_2CH_3$, —S—$CH_2CH_2CH_3$, methyl, ethyl, propyl, isopropyl, butyl, tert-butyl, methoxy, ethoxy, $CH_2$ C (O)—O—$CH_3$, —$CH_2$—C(O)—O—$CH_2CH_3$, —$CH_2CH_2$—C(O)—O—$CH_3$, —$CH_2CH_2$—C(O)—O—$CH_2CH_3$, —$CH_2$—O—C(O)—$CH_3$, —$CH_2$—O—C(O)—$CH_2CH_3$, —$CH_2CH_2$—O—C(O)—$CH_3$, —$CH_2CH_2$—O—C(O)—$CH_2CH_3$, —C(O)—O—$CH_3$, —C(O)—O—$CH_2CH_3$, each of which is optionally substituted with one or more substituents independently selected from $R^{16}$; or heteroarylthio, wherein heteroaryl is pyridyl or imidazolyl, each optionally substituted on the heteroaryl part with one or more substituents independently selected from $R^{17}$, or pyrrolidinyl, piperidyl, piperazinyl, or morpholinyl, each of which is optionally substituted with one or more substituents independently selected from $R^{16}$, or —$S(O)_2$—$R^{21}$.]

[28. A compound according to claim 27, wherein $R^8$ is selected from Cl, F, Br, —$CF_3$, —S—$CH_3$, —S—$CH_2CH_3$, —S—$CH_2CH_2CH_3$, methyl, ethyl, methoxy, ethoxy, —$CH_2$—C(O)—O—$CH_2CH_3$, —C(O)—O—$CH_3$, or —C(O)—O—$CH_2CH_3$, each of which is optionally substituted with one or more substituents independently selected from $R^{16}$; or heteroarylthio, wherein heteroaryl is pyridyl or imidazolyl, each optionally substituted on the heteroaryl part with one or more substituents independently selected from $R^{17}$, or pyrrolidinyl, piperidyl, piperazinyl, or morpholinyl, each of which is optionally substituted with one or more substituents independently selected from $R^{16}$.]

[29. A compound according to claim 1, wherein $R^{16}$, $R^{17}$, and $R^{18}$ are independently $C_{1-6}$-alkyl, halogen, hydroxy, oxo, carboxy, —$CF_3$, carboxy-$C_{1-6}$-alkyl, hydroxy-$C_{1-6}$-alkyl, —$C_{1-6}$-alkyl-C(O)—O—$C_{1-6}$-alkyl, —C(O)—O—$C_{1-6}$-alkyl, —$NR^{19}R^{20}$, —C(O)$NR^{19}R^{20}$ or —$S(O)_2$—$C_{1-6}$-alkyl.]

[30. A compound according to claim 29, wherein $R^{16}$, $R^{17}$, and $R^{18}$ are independently methyl, ethyl, propyl, halogen, hydroxy, oxo, carboxy, $CF_3$, carboxy-methyl, carboxy-ethyl, carboxy-propyl, hydroxy-methyl, hydroxy-ethyl, hydroxy-propyl, —$CH_2$—C(O)—O—$CH_3$, —$CH_2$—C (O)—O—$CH_2CH_3$, —$CH_2CH_2$—C(O)—O—$CH_3$, —$CH_2CH_2$—C(O)—O—$CH_2CH_3$, —C(O)—O—$CH_3$, —C(O)—O—$CH_2CH_3$, —C(O)—O—$CH_2CH_2CH_3$, or —$S(O)_2CH_3$.]

[31. A compound according to claim 30, wherein $R^{16}$, $R^{17}$, and $R^{18}$ are independently methyl, ethyl, propyl, halogen, oxo, carboxy, carboxy-methyl, carboxy-ethyl, carboxy-propyl, hydroxy-methyl, hydroxy-ethyl, hydroxy-propyl, $CH_2$ C(O) O $CH_3$, $CH_2$ C(O) O $CH_2CH_3$, —$CH_2CH_2$—C(O)—O—$CH_3$, —$CH_2CH_2$—C(O)—O—$CH_2CH_3$, —C(O)—O—$CH_3$, —C(O)—O—$CH_2CH_3$, —C(O)—O—$CH_2CH_2CH_3$, or —$S(O)_2CH_3$.]

[32. A compound according to claim 29, wherein $R^{16}$, $R^{17}$, and $R^{18}$ are independently $C_{1-6}$-alkyl, carboxy, —$NR^{19}R^{20}$, —C(O)—O—$C_{1-6}$-alkyl or —C(O)$NR^{19}R^{20}$.]

[33. A compound according to claim 1, wherein $R^{19}$ and $R^{20}$ independently represent hydrogen, $C_{1-6}$-alkyl, hydroxy-$C_{1-6}$-alkyl, carboxy-$C_{1-6}$-alkyl, phenyl, naphtyl, $C_{3-8}$-heterocyclyl, phenyl-$C_{1-6}$-alkyl, $C_{3-8}$-heterocyclyl-$C_{1-6}$-alkyl, —C(O)—O—$C_{1-6}$-alkyl, —$C_{1-6}$-alkyl-C(O)—O—$C_{1-6}$-alkyl, —$C_{1-6}$-alkyl-$NR^{22}R^{23}$ or —$S(O)_2$—$C_{1-6}$-alkyl, each of which is optionally substituted with one or more substituents independently selected from $R^{24}$; or $R^{19}$ and $R^{20}$ together with the nitrogen to which they are attached form a 3- to 8-membered heterocyclic ring with the said nitrogen atom, the heterocyclic ring optionally containing one or two further heteroatoms selected from nitrogen, oxygen and sulphur, the heterocyclic ring is optionally substituted with one or more substituents independently selected from $R^{24}$.]

[34. A compound according to claim 33, wherein $R^{19}$ and $R^{20}$ independently represent hydrogen, methyl, ethyl, propyl, carboxy-methyl, carboxy-ethyl, carboxy-propyl, hydroxy-methyl, hydroxy-ethyl, hydroxy-propyl, phenyl, phenyl-$C_{1-6}$-alkyl, $C_{3-8}$-heterocyclyl-$C_{1-6}$-alkyl, —C(O)—O—$C_{1-6}$-alkyl, —$C_{1-6}$-alkyl-C(O)—O—$C_{1-6}$-alkyl, —$C_{1-6}$-alkyl- $NR^{22}R^{23}$, or naphtyl, or $R^{19}$ and $R^{20}$ together with the nitrogen to which they are attached form a 3- to 8-membered heterocyclic ring with the said nitrogen atom, the heterocyclic ring optionally containing one or two further heteroatoms selected from nitrogen, oxygen and sulphur, the heterocyclic ring is optionally substituted with one or more substituents independently selected from $R^{24}$.]

[35. A compound according to claim 33, wherein $R^{19}$ and $R^{20}$ independently represent hydrogen, $C_{1-6}$-alkyl, or $R^{19}$ and $R^{20}$ together with the nitrogen to which they are attached form a 3- to 8-membered heterocyclic ring with the said nitrogen atom, the heterocyclic ring optionally containing one or two further heteroatoms selected from nitrogen, oxygen and sulphur, the heterocyclic ring is optionally substituted with one or more substituents independently selected from $R^{24}$.]

[36. A compound according to claim 35, wherein $R^{19}$ and $R^{20}$ independently represent hydrogen, methyl, ethyl, or propyl, or $R^{19}$ and $R^{20}$ together with the nitrogen to which they are attached form a 3- to 8-membered heterocyclic ring with the said nitrogen atom, wherein the heterocyclic ring is pyrrolidyl, piperidyl, piperazinyl, homopiperazinyl, or morpholinyl, the heterocyclic ring is optionally substituted with one or more substituents independently selected from $R^{24}$.]

[37. A compound according to claim 1, wherein $R^{21}$ is selected from $C_{1-6}$-alkyl, carboxy-$C_{1-6}$-alkyl, —$C_{1-6}$-alkyl-$NR^{22}R^{23}$ or hydroxy-$C_{1-6}$-alkyl; or phenyl, naphtyl, or pheny-$C_{1-6}$-alkyl, wherein the aryl part is optionally substituted with one or more substituents independently selected from $R^{24}$; or $C_{3-8}$-cycloalkyl, or $C_{3-8}$-cycloalkyl-$C_{1-6}$-alkyl.]

[38. A compound according to claim 37, wherein $R^{21}$ is selected from methyl, ethyl, propyl, carboxy-methyl, carboxy-ethyl, carboxy-propyl, hydroxy-methyl, hydroxy-ethyl, hydroxy-propyl; or phenyl, naphtyl, or phenyl-$C_{1-6}$-alkyl, wherein the aryl part is optionally substituted with one or more substituents independently selected from $R^{24}$; or $C_{3-8}$-cycloalkyl, or $C_{3-8}$-cycloalkyl-$C_{1-6}$-alkyl.]

[39. A compound according to claim 38, wherein $R^{21}$ is selected from methyl, ethyl, carboxy-methyl, carboxy-ethyl, carboxy-propyl; or phenyl, naphtyl, or phenyl-$C_{1-6}$-alkyl, wherein the aryl part is optionally substituted with one or more substituents independently selected from $R^{24}$.]

[40. A compound according to claim 1, wherein $R^{22}$ and $R^{23}$ are independently selected from hydrogen, $C_{1-6}$-alkyl, carboxy-$C_{1-6}$-alkyl, —$C_{1-6}$-alkyl-C(O)—O—$C_{1-6}$-alkyl, —C(O)—O—$C_{1-6}$-alkyl, $C_{3-8}$-cycloalkyl, phenyl, naphtyl, or $R^{22}$ and $R^{23}$ together with the nitrogen to which they are attached form a 3- to 8-membered heterocyclic ring with the said nitrogen atom, the heterocyclic ring optionally containing one or two further heteroatoms selected from nitrogen, oxygen and sulphur, the heterocyclic ring is optionally substituted with one or more substituents independently selected from $R^{24}$.]

[41. A compound according to claim 40, wherein $R^{22}$ and $R^{23}$ are independently selected from hydrogen, methyl, ethyl, propyl, butyl, carboxymethyl, carboxyethyl, carboxypropyl, cyclopropyl, cyclobutyl, cyclopentyl, cyclohexyl, cycloheptyl, phenyl, naphtyl, or $R^{22}$ and $R^{23}$ together with the nitrogen to which they are attached form a 3- to 8-membered heterocyclic ring with the said nitrogen atom, wherein the heterocyclic ring is pyrrolidyl, piperidyl, piperazinyl, homopiperazinyl, or morpholinyl, the heterocyclic ring is optionally substituted with one or more substituents independently selected from $R^{24}$.]

[42. A compound according to claim 41, wherein $R^{22}$ and $R^{23}$ together with the nitrogen to which they are attached form a 3- to 8-membered heterocyclic ring with the said nitrogen atom, wherein the heterocyclic ring is pyrrolidyl, piperidyl, piperazinyl, homopiperazinyl, or morpholinyl, the heterocyclic ring is optionally substituted with one or more substituents independently selected from $R^{24}$.]

[43. A compound according to claim 1, wherein $R^{24}$ is halogen, hydroxy, carboxy, oxo, —$CF_3$, $C_{1-6}$-alkyl, hydroxy-$C_{1-6}$-alkyl, carboxy-$C_{1-6}$-alkyl, C(O) $C_{1-6}$-alkyl, —C(O)—O—$C_{1-6}$-alkyl, —$C_{1-6}$-alkyl-C(O)—O—$C_{1-6}$-alkyl, aryl, heteroaryl, aryl-$C_{1-6}$-alkyl, heteroaryl-$C_{1-6}$-alkyl, $C_{3-8}$-cycloalkyl, $C_{3-8}$-heterocyclyl, $C_{3-8}$-cycloalkyl-$C_{1-6}$-alkyl, $C_{3-8}$-heterocyclyl-$C_{1-6}$-alkyl, —C(O)—O—$C_{1-6}$-alkyl-aryl, or —$S(O)_2R^{28}$, wherein aryl is phenyl or naphtyl, and heteroaryl is pyridyl or pyrimidyl, and wherein each cyclic moiety is optionally substituted with one or more substituents independently selected from $R^{29}$.]

[44. A compound according to claim 43, wherein $R^{24}$ is halogen, hydroxy, carboxy, oxo, —$CF_3$, $C_{1-6}$-alkyl, hydroxy-$C_{1-6}$-alkyl, carboxy-$C_{1-6}$-alkyl, C(O) $C_{1-6}$-alkyl, —C(O)—O—$C_{1-6}$-alkyl, aryl, heteroaryl, aryl-$C_{1-6}$-alkyl, heteroaryl-$C_{1-6}$-alkyl, $C_{3-8}$-cycloalkyl, $C_{3-8}$-heterocyclyl, $C_{3-8}$-cycloalkyl-$C_{1-6}$-alkyl, $C_{3-8}$-heterocyclyl-$C_{1-6}$-alkyl, or —$S(O)_2R^{28}$, wherein aryl is phenyl or naphtyl, or heteroaryl is pyridyl or pyrimidyl, and wherein each cyclic moiety is optionally substituted with one or more substituents independently selected from $R^{29}$.]

[45. A compound according to claim 44, wherein $R^{24}$ is halogen, carboxy, oxo, —$CF_3$, $C_{1-6}$-alkyl, carboxy-$C_{1-6}$-alkyl, —C(O)—$C_{1-6}$-alkyl, —C(O)—O—$C_{1-6}$-alkyl, aryl, aryl-$C_{1-6}$-alkyl, $C_{3-8}$-cycloalkyl, $C_{3-8}$-heterocyclyl, $C_{3-8}$-heterocyclyl-$C_{1-6}$-alkyl, or —$S(O)_2R^{28}$, wherein aryl is phenyl or naphtyl, and wherein each cyclic moiety is optionally substituted with one or more substituents independently selected from $R^{29}$.]

[46. A compound according to claim 45, wherein $R^{24}$ is carboxy, oxo, $C_{1-6}$-alkyl, carboxy-$C_{1-6}$-alkyl, C(O) O $C_{1-6}$-alkyl, aryl, aryl-$C_{1-6}$-alkyl, $C_{3-8}$-cycloalkyl, $C_{3-8}$-heterocyclyl, $C_{3-8}$-heterocyclyl-$C_{1-6}$-alkyl, or —$S(O)_2R^{28}$, wherein aryl is phenyl or naphtyl, and wherein each cyclic moiety is optionally substituted with one or more substituents independently selected from $R^{29}$.]

[47. A compound according to claim 1, wherein $R^{25}$ and $R^{26}$ are independently $C_{1-6}$-alkyl, halogen, hydroxy, carboxy, or —$CF_3$.]

[48. A compound according to claim 47, wherein $R^{25}$ and $R^{26}$ are independently methyl, ethyl, propyl, halogen, hydroxy, carboxy, or —$CF_3$.]

[49. A compound according to claim 1, wherein $R^{28}$ is $C_{1-6}$-alkyl, —$C_{1-6}$-alkyl-C(O)—O—$C_{1-6}$-alkyl, phenyl, phenyl-$C_{1-6}$-alkyl, heteroaryl optionally substituted with $C_{1-6}$-alkyl or —$N(CH_3)_2$, wherein heteroaryl is imidazolyl, pyridyl or pyrimidyl.]

[50. A compound according to claim 49, wherein $R^{28}$ is $C_{1-6}$-alkyl, —$C_{1-6}$-alkyl-C(O)—O—$C_{1-6}$-alkyl, or $N(CH_3)_2$.]

[51. A compound according to claim 1, wherein $R^{29}$ is halogen, carboxy, —$CF_3$, $C_{1-6}$-alkyl, or $C_{1-6}$-alkoxy.]

*52. 1-(1-Acetyl-piperidin-4-yl)-3-(5-chloro-thiazol-2-yl)-1-(4-methyl-cyclohexyl)-urea or a pharmaceutically acceptable salt thereof.*

* * * * *